(12) United States Patent
Jobling et al.

(10) Patent No.: US 12,071,629 B2
(45) Date of Patent: Aug. 27, 2024

(54) WHEAT HAVING HIGH LEVELS OF BETA-GLUCAN

(71) Applicant: Commonwealth Scientific and Industrial Research Organisation, Australia Capital Territory (AU)

(72) Inventors: Stephen Alan Jobling, Australian Capital Territory (AU); Damien Paul Belobrajdic, South Australia (AU); Anthony Richard Bird, South Australia (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 14/910,577

(22) PCT Filed: Aug. 6, 2014

(86) PCT No.: PCT/AU2014/050173
§ 371 (c)(1),
(2) Date: Feb. 5, 2016

(87) PCT Pub. No.: WO2015/017901
PCT Pub. Date: Feb. 12, 2015

(65) Prior Publication Data
US 2016/0251670 A1 Sep. 1, 2016

(30) Foreign Application Priority Data

Aug. 6, 2013 (AU) ............... 2013902937
Jun. 12, 2014 (AU) ............... 2014902241

(51) Int. Cl.
*C12N 15/82* (2006.01)
*A01H 6/46* (2018.01)
*A23L 7/10* (2016.01)
*C12Q 1/6895* (2018.01)

(52) U.S. Cl.
CPC ............ *C12N 15/8245* (2013.01); *A23L 7/10* (2016.08); *A23L 7/198* (2016.08); *C12Q 1/6895* (2013.01); *A23V 2002/00* (2013.01); *C12Q 2600/13* (2013.01)

(58) Field of Classification Search
None
See application file for complete search history.

(56) References Cited

U.S. PATENT DOCUMENTS

| 2006/0064780 A1 | 3/2006 | Munck et al. | |
| 2011/0107467 A1* | 5/2011 | Doblin ................. | C12N 9/1051 |
| | | | 800/298 |

FOREIGN PATENT DOCUMENTS

WO    WO 2009/079714 A1    7/2009

OTHER PUBLICATIONS

Burton et al, 2011, Plant Biotechnology Journal, 9:117-135.*
Pins et al, 2006, Cereal Foods World, 51:8-11.*
Khoury et al, 2012, Journal of Nutrition & Metabolism, 1-28.*
Nemeth et al, 2010, Plant Physiology, 152:1209-1218.*
Cseh et al, 2013, Ann. Appl. Biol., 163:142-150.*
International Preliminary Report on Patentability, dated Feb. 9, 2016 in connection with PCT International Application No. PCT/AU2014/050173, filed Aug. 6, 2014.
Cseh et al., "Expression of HvCslF9 and HvCslF6 barley genes in the genetic background of wheat and their influence on the wheat β-glucan content", Annals of Applied Biology, 2013, vol. 163, pp. 142-150.
Nemeth et al., "Down-regulation of the CSLF6 gene results in decreased (1,3; 1,4)-beta-D-glucan in endosperm of wheat", Plant Physiology, 2010, vol. 152, pp. 1209-1218.
International Search Report, dated Oct. 22, 2014 in connection with PCT International Application No. PCT/AU2014/050,173, filed Aug. 6, 2014.
May 22, 2019 Response to the Communication Pursuant to Article 94(3) EPC dated Nov. 12, 2018, filed in connection with corresponding European Patent Application No. 14834859.2.
Burton et al., "The Genetics and Transcriptional Profiles of the Cellulose Synthase-Like HvCsIF Gene Family in Barely", *Plant Physiology*, 2008, vol. 149, pp. 1821-1833.
Comino et al, Food Hydrocolloids (2014) 41:219-226.
Jul. 4, 2017 Extended European search report issued in connection with European Application No. 14834859.2.
Mar. 6, 2017 Partial supplementary European search report issued in connection with European Application No. 14834859.2.
Nov. 12, 2018 Communication Pursuant to Article 94(3) EPC issued in connection with corresponding European Patent Application No. 14834859.2.
Nov. 1, 2021 Response to Jun. 25, 2020 Communication Pursuant to Article 94 (3) EPC issued in connection with corresponding European Patent Application No. 14834859.2.
Sep. 24, 2021 Office Action issued in connection with Canadian Application No. 2,920,310.

* cited by examiner

*Primary Examiner* — Jason Deveau Rosen
(74) *Attorney, Agent, or Firm* — Gary J. Gershik

(57) ABSTRACT

The present invention provides wheat grain comprising (1,3;1,4)-β-D-glucan (BG). The wheat grain is characterised by one or more of the following features; a BG content of at least 3% (w/w); the BG of the grain has a DP3/DP4 ratio between about 1.0 and about 2.0 or between about 1.0 and 2.3; and the BG is partially water soluble such that between 8.0% and about 25% or between about 10% and about 25% of the BG of the grain is water soluble. The present invention also provides uses of this grain.

25 Claims, 16 Drawing Sheets
Specification includes a Sequence Listing.

WHEAT HAVING HIGH LEVELS OF BETA-GLUCAN

CROSS-REFERENCE TO RELATED APPLICATIONS

This application is a § 371 national stage of PCT International Application No. PCT/AU2014/050,173, filed Aug. 6, 2014, claiming the priority of Australian Patent Application No. 2014902241, filed Jun. 12, 2014 and Australian Patent Application No. 2013902937, filed Aug. 6, 2013, the contents of each of which are hereby incorporated by reference in their entirety.

REFERENCE TO A SEQUENCE LISTING

This application incorporates-by-reference nucleotide and/or amino acid sequences which are present in the file named "180116 88361 Substitute Sequence Listing DH.txt," which is 414 kilobytes in size, and which was created Jan. 16, 2018 in the IBM-PC machine format, having an operating system compatibility with MS-Windows, which is contained in the text file filed Jan. 16, 2018 as part of this application.

FIELD OF THE INVENTION

The present invention relates to transformed wheat having high levels of beta-glucan and the use of this wheat.

BACKGROUND OF THE INVENTION

The cell wall polysaccharides of cereal grains are an important dietary component in human nutrition, being a significant source of dietary fibre (Topping, 2007). Consumption of whole grain cereals, of which cell wall polysaccharides comprise about 10% by dry weight, is associated with a reduced risk of developing diseases such as type 2 diabetes, cardiovascular disease and colorectal cancer, as well as with other health benefits such as improved gastrointestinal health (reviewed in Jonnalagadda et al., 2011). Whole grains also have a relatively low glycaemic index and are a rich source of other dietary components including vitamins, antioxidants and minerals, as well as starch as an energy source.

The cell walls of grasses (Poaceae) including cereal grains are characterised by the presence of mixed linkage (1,3;1,4)-β-D-glucan (hereinafter abbreviated as BG) (Trethewey et al., 2005). BG is found in cereals predominantly in cell walls along with other polysaccharides such as arabino-(1,4)-β-D-xylan (hereinafter AX). The structure of BG is unique among cell wall polymers in that it consists of a linear polymer of glucose residues linked covalently by 1-3 and 1-4 linkages, arranged in a non repeating but non random fashion (Fincher, 2009a, b). It can be considered to be a polymer of mainly β-1-4 linked cellotriosyl (each with 3 glucose residues) and cellotetrosyl (each with 4 glucose residues) units linked by single β-1-3 linkages. The polysaccharide from barley grain also has approximately 10% longer β-1-4 linked cellodextrin units (Fincher and Stone, 2004). The conformational asymmetry of the molecule enables the polymer to form a viscous porous gel like structure in the matrix of the plant cell wall. BGs are found at low levels in most vegetative tissues (Trethewey and Harris, 2002) and at higher levels in elongating cells such as the growing coleoptile (Carpita et al., 2001; Gibeaut et al., 2005). In contrast to cells of vegetative tissues, the endosperm cell walls of most cereal grains contain very little cellulose and the major cell wall components are AX and/or BG, although rice and other cereal grains also contain other cell wall polysaccharides. (Stone, 2006).

The BG content of grains varies considerably amongst the cereals, with barley, oats and rye having the highest amounts and wheat, maize and rice having relatively low levels (Fincher and Stone, 2004). In wheat endosperm, cell walls comprise about 70% AX and 15-25% BG, along with about 4% cellulose ((1,4)-β-D-glucan) and about 7% (1,4)-β-D-glucomannans. In contrast, barley endosperm cell walls have about 20% AX and 70% BG. Rice grain cell walls also have significant levels of cellulose (20%). The higher levels of BG in barley and oats have benefits in reducing coronary heart disease, but it is not known if wheat BG provides the same benefits. It is clear, therefore, that the properties of cell wall polysaccharides in one cereal cannot be generalized readily to other cereals.

The water solubility of BG also varies within cereals. Oat BG is more soluble than BG from barley and wheat which have relatively low water solubility (Aman and Graham, 1987; Beresford and Stone, 1983; Lazaridou and Biliaderis, 2007). BG from each cereal grain has a characteristic and different fine structure as indicated by digestion with lichenase and separation of the oligosaccharides by HPLC (Lazaridou and Biliaderis, 2007). Lichenase specifically cleaves BG at a (β,1-4) linkage after a (β,1-3) linkage releasing mainly oligosaccharides of degree of polymerisation (DP3 and DP4, having 3 and 4 glucosyl units, respectively). Oat BG has the lowest DP3/DP4 ratio amongst cereal grain BGs, generally being in the range of 1.5-2.3, while barley BG has a DP3/DP4 ratio in the range of 2.3-3.2 (Lazaridou and Biliaderis, 2007). As BG levels in wheat grain are very low (<1.0%) and in wheat endosperm even lower, the BG structure has not been characterised in detail. Wheat bran BG has been reported as having a DP3/DP4 ratio of 3.7-4.5 (Cui et al., 2000; Li et al., 2006) whereas BG from wheat wholemeal has a DP3/DP4 ratio of 3.0-3.8 (Wood et al., 1991) when measured with a lichenase assay. A more recent report, using a different method, gave lower values of 2.3 to 2.5 for wheat flour BG (Nemeth et al., 2010).

The biosynthesis of the individual cell wall polymers is not well understood. The enzymes involved are integral membrane proteins and while some can be assayed biochemically (Buckeridge et al., 2004; Tsuchiya et al., 2005) none have been purified to homogeneity and isolation of the encoded genes has involved a genetic approach or heterologous expression. Thus the cellulose synthase (CesA) and cellulose synthase-like (Csl) gene families have been shown to encode enzymes that make β-linked polysaccharides. The CesA genes encode cellulose synthase enzymes and there are nine Csl gene families designated CslA-J (Fincher, 2009a; Hazen et al., 2002). Some members of the CslA genes encode β-mannan and glucomannan synthases, (Dhugga et al., 2004; Liepman et al., 2007) and the CslC genes encode an enzyme that is believed to synthesise the (1,4)-β-D-glucan backbone of xyloglucan (Cocuron et al., 2007). The CslB and CslG families are restricted to dicotyledenous plants whereas the CslF and CslH families have so far been reported only in graminaceous monocotyledons. In the fully sequenced genome of rice there are nine CslF genes and three CslH genes, whereas in barley at least seven CslF genes and a single CslH gene have been characterised (Burton et al., 2008; Doblin et al., 2009).

Some of the genes involved in BG biosynthesis have recently been identified as belonging to the cellulose-synthase-like CslF and CslH gene families. Heterologous expression of rice OsCslF2, or OsCslF4 in transgenic *Arabidopsis* plants produced BG which could be detected immunologically although the absolute amounts produced were very low (Burton et al., 2006). In other work, Doblin et al., (2009) showed that overexpression of barley CslH led to low levels of BG synthesis in transgenic *Arabidopsis*. This indicated that multiple Csl genes might encode BG synthesizing enzymes, and perhaps that different cereals used different, or multiple, Csl activities to synthesize BG. EST counts from cDNA libraries indicate that, in wheat, there are at least seven expressed CslF genes, corresponding to rice CslF1, CslF2, CslF3, CslF4, CslF6, CslF8 and CslF9 genes (Nemeth et al., 2010).

Overexpression of the endogenous barley HvCslF6 gene in an endosperm specific manner was shown to increase BG levels by up to 80% in transgenic barley (Burton et al., 2011). In contrast, endosperm specific over-expression of HvCslF3, HvCslF4, HvCslF8 or HvCslF9 genes had no noticeable effect on BG levels. These results suggested that, in barley, individual CslF or CslH genes could have different effects on the level of BG synthesised in endosperm. Nemeth et al., (2010) showed that the down-regulation of CslF6 gene expression in wheat by RNAi methods reduced the BG levels in endosperm by between 30% and 52%, indicating that CslF6 was expressed in wheat grain and contributed to BG synthesis in that cereal. That is, wheat contains an endogenous CslF6 gene that is functional. However, it is not known which genes might be needed to be expressed in order to increase BG levels in wheat. Additionally, it is unknown which gene or combinations of genes might provide sufficient levels of BG with an optimum structure for nutritional functionality.

The reasons why wheat grain has relatively low BG levels, much lower than barley or oats, and why wheat BG has a different structure than other cereal BGs are unknown. This could be due to the lack of one or more Csl genes or to some other class of gene, the presence of other structural features, or any combination thereof.

There is need for wheat with increased levels of BG, in particular with increased levels of water-extractable (soluble) BG, for improved nutritional functionality.

SUMMARY OF THE INVENTION

In a first aspect, the present invention provides wheat grain comprising (1,3;1,4)-β-D-glucan (BG), which is characterised by one or more or all of the features:

(a) wherein the BG content of the grain is at least 3% (w/w);
(b) wherein the BG of the grain has a DP3/DP4 ratio between about 1.0 and about 2.0 or between about 1.0 and 2.3; and
(c) wherein the BG is partially water soluble such that between 8.0% and about 25%, between 8.0% and about 50%, between about 10% and 50%, or between about 10% and about 25% of the BG of the grain is water soluble.

In embodiments, the wheat grain comprises features (a) and (b), or features (a) and (c), or (b) and (c). In these embodiments, the third feature is optionally present. In an embodiment when the BG content is less than 3% (w/w), the BG content is increased relative to a wild-type wheat grain, and/or the solubility of the BG is increased relative to wild-type wheat grain. The grain may also comprise additional features as described below.

In a second aspect, the present invention provides wheat grain comprising (1,3;1,4)-β-D-glucan (BG) and a CslF6 polypeptide which comprises an amino acid other than isoleucine (I) at position 756 with reference to SEQ ID NO:18 or the corresponding amino acid position in other CslF6 polypeptides, and more preferably has a leucine (L) at that position. In an embodiment, the BG has a water solubility which is increased relative to the water solubility of the BG in a wild-type wheat grain, such as, for example, between 8.0% and about 25%, between 8.0% and about 50%, between about 10% and 50%, or between about 10% and about 25% of the BG that is water soluble. In a preferred embodiment, the BG content of the grain is at least 3% (w/w) and/or the BG of the grain has a DP3/DP4 ratio between about 1.0 and about 2.0 or between about 1.0 and 2.3.

In embodiments of these aspects, the wheat grain comprises features (a) and (b), or features (a) and (c), or (b) and (c). In these embodiments, the third feature is optionally present. In an embodiment when the BG content is less than 3% (w/w), the BG content is increased relative to a wild-type wheat grain, and/or the solubility of the BG is increased relative to wild-type wheat grain. The grain may also comprise additional features as described below.

In certain embodiments of the present invention, the BG content of the wheat grain (feature (a)) is at least 4% (w/w), at least 5% (w/w), or at least 6% (w/w). In combination with these minimum levels, the BG content of the wheat grain of the invention may have a maximum of about 10% (w/w) or 12% (w/w). In embodiments, the BG content is between 3% (w/w) and about 8% (w/w), between about 4% (w/w) and about 8% (w/w), between about 5% (w/w) and about 8% (w/w), about 3% (w/w), about 4% (w/w), about 5% (w/w), about 6% (w/w), about 7% (w/w), or about 8% (w/w). The BG content of the grain is typically measured on wholemeal flour obtained from the grain, which wholemeal flour is representative of the entire grain with regard to BG content and other components such as grain proteins, starch and DNA. Preferably, the BG content is measured as described in Example 1.

In embodiments, the BG of the grain has a DP3/DP4 ratio (feature (b)) of less than about 2.5, preferably less than about 2.4, less than about 2.3, less than about 2.2, less than about 2.1, less than about 2.0, less than about 1.9, less than about 1.8, about 2.5, about 2.4, about 2.3, about 2.2, about 2.1, about 2.0, about 1.9, about 1.8, or between about 1.8 and about 2.5. In these embodiments, the DP3/DP4 ratio may have a minimum of about 1.0. Preferably, the DP3/DP4 ratio is measured as described in Example 1.

In embodiments, the BG of the wheat grain comprises an increased proportion of water-soluble BG (feature (c)) relative to a corresponding wild-type grain as determined by, or determinable by, a method that comprises treatment of a sample of wholemeal flour obtained from the grain with (i) 80% ethanol for 1 hour at 80° C., followed by (ii) solubilisation of BG in aqueous buffer for about 2 hours at 37° C., and (iii) determination of the level of BG solubilised from the sample. It is preferred that at least 6%, preferably at least 8%, at least 10%, at least 12%, at least 14%, at least 16%, at least 18%, about 6%, about 8%, about 10%, about 12%, about 14%, about 16% or about 18% of the BG content of the grain is water-soluble as determined by, or determinable by, such a method. In these embodiments, the proportion of water-soluble BG may have a maximum value of about 30% or about 40% or about 50%. It would be understood that the proportion of water-soluble BG is relative to the total BG content of the grain which is defined in the preceding paragraph.

In embodiments, the BG is characterised by having a molecular weight of at least 10 kDa, preferably at least 100 kDa or 500 kDa, or between about 500 kDa and 5000 kDa, as determined by the position of the peak molecular weight following size-exclusion chromatography. The peak molecular weight may be, or not less than, about $0.5 \times 10^6$ Da, or about $1.0 \times 10^6$ Da, or about $2.0 \times 10^6$ Da. In preferred embodiments, the molecular weight is of the BG is predominantly (i.e. at least 50% of the BG) in the range of about $0.5 \times 10^6$ to about $2.0 \times 10^6$ Da.

In a preferred form of the invention, the grain is transgenic i.e. comprises one or more exogenous polynucleotides. In embodiments, the polynucleotides encode one or more Csl polypeptides, preferably including a CslF6 polypeptide, more preferably a CslF6 polypeptide other than a barley CslF6 polypeptide, and/or encode an exogenous polypeptide other than a Csl polypeptide such as a herbicide tolerance polypeptide, or a silencing RNA molecule. In an embodiment, the silencing RNA molecule is capable of reducing expression of one or more endogenous wheat genes in wheat plants of the invention, such as in the developing seed or endosperm of the plant. The exogenous polynucleotide may be operably linked to a promoter that is preferentially expressed in the developing seed or endosperm of the plant.

In an embodiment, the wheat grain comprises CslF6 genes in their native positions in the A, B and D genomes and is lacking exogenous CslF6 genes elsewhere in the genome. In a preferred embodiment, one or more of the CslF6 genes in their native positions each encode a variant CslF6 polypeptide which comprises an amino acid substitution relative to the corresponding wild-type CslF6 polypeptide. In a more preferred embodiment, the amino acid substitution is at amino acid position 756 with reference to SEQ ID NO:18 or the corresponding amino acid position in other CslF6 polypeptides. In a most preferred embodiment, the amino acid substitution is an I756L substitution with reference to SEQ ID NO:18 or an identical amino acid substitution at the corresponding amino acid in other CslF6 polypeptides.

In preferred forms, the grain comprises an exogenous CslF6 polypeptide. The amino acid sequence of the exogenous CslF6 polypeptide is preferably at least 95% identical, more preferably at least 99% identical, to the amino acid sequence of a CslF6 polypeptide from a plant, i.e. to a naturally occurring CslF6 polypeptide. Said plant may be a cereal plant or a plant in the family Poaceae. In an embodiment, the exogenous polypeptide is a CslF6 polypeptide other than a barley CslF6 polypeptide, HvCslF6, which corresponds to amino acids 12-958 of SEQ ID NO: 43 or a polypeptide which is at least 99% identical to amino acids 12-958 of SEQ ID NO: 43. In preferred embodiments, the exogenous CslF6 polypeptide is an oat (AsCslF6), maize (ZmCslF6), sorghum (SbCslF6) or rice (OsCslF6) CslF6 polypeptide. The exogenous CslF6 polypeptide may also be from a plant whose grain BG has a DP3/DP4 ratio of less than 2.3, or less than 2.1, or be a CslF6 polypeptide which is expressed in a plant most highly in a tissue other than grain. The amino acid sequence of the CslF6 polypeptide may be identical to the amino acid sequence of a naturally occurring plant CslF6 polypeptide such as an oat, maize, sorghum or rice CslF6 polypeptide, or may differ therefrom by no more than 10 conservative amino acids substitutions, preferably no more than 5 conservative amino acid substitutions, such as when compared to an oat, maize, sorghum or rice CslF6 polypeptide. See for example SEQ ID NOs 18-20, 55-57, 59 and 61. In a preferred embodiment, the CslF6 polypeptide comprises an amino acid other than isoleucine (I) at position 756 with reference to SEQ ID NO:18 or the corresponding amino acid position in other CslF6 polypeptides, and more preferably has a leucine (L) at that position.

In embodiments, the grain further comprises an exogenous CslH polypeptide. The amino acid sequence of the exogenous CslH polypeptide is preferably at least 95% identical to the amino acid sequence of a CslH polypeptide from a plant, preferably a cereal plant or a plant in the family Poaceae. See for example SEQ ID NOs 37-39, and 50.

The grain of the present invention may be further characterised by one or more of the following features, and all of the possible combinations of these features are contemplated. The grain is preferably non-shrunken and/or has a weight of at least 25 mg or at least 28 mg, preferably at least 30 mg, at least 35 mg, or at least 40 mg. Typically, the grain weight is between 25 mg and 40 mg, between 25 mg and 45 mg, between 25 mg and 50 mg, between 25 mg and 55 mg, between 25 mg and 60 mg, between 35 mg and 55 mg, between 35 mg and 60 mg, about 30 mg, about 35 mg, about 40 mg, about 45 mg, about 50 mg, or about 55 mg. Grain weight is preferably measured on a sample of at least 100 grains, in which case the grain weight is expressed as an average grain weight. The grain preferably has a moisture content of between about 8% and about 14%, more preferably about 10%. In embodiments, the grain is capable of producing a wheat plant which is male and female fertile, or a wheat plant which is essentially the same in morphology as a corresponding wild-type plant. For example, the wheat plant produced from the grain is green in colour, has the same seedling vigour, and/or produces pollen which has the same viability as a corresponding wild-type plant. It is desired that the germination rate of the grain is similar to, or essentially the same as, that of wild-type grain. In certain embodiments, the grain of the present invention has a germination rate of about 70% to about 90%, or about 90% to about 100%, relative to the germination rate of a corresponding wild-type grain. Typically this is measured at 7-10 days after imbibition at room temperature under low light conditions (e.g. in the dark), or as the percentage of grains that give rise to emerged seedlings after sowing in the field.

The wheat grain of the invention further comprises starch. It is preferred that the starch content of the grain is at least 30%, more preferably at least 35%, or at least 40% as a percentage of the total grain weight. In combination with these minimums, the maximum starch content of the grain may be about 60% or even 70%, as for wild-type grain. In an embodiment, the amylose content of the starch of the grain is at least 50% (w/w), at least 60% (w/w), at least 67% (w/w), or at least 70% (w/w) as a proportion of the extractable starch of the grain. The starch of the grain of the present invention is typically characterised by one or more of properties selected from the group consisting of:

comprising at least 2% resistant starch;
comprising a glycaemic index (GI) of less than 55;
comprising less than 20% amylopectin as a proportion of the starch content of the grain;
comprised in starch granules which have an altered morphology relative to wild-type wheat starch granules;
comprised in starch granules that exhibit reduced granule birefringence under polarised light relative to wild-type wheat starch granules;
when the grain is milled to flour, such flour exhibits reduced swelling volume;
modified chain length distribution and/or branching frequency relative to wild-type wheat starch;

delayed end of gelatinisation temperature and higher peak temperature;

reduced viscosity (peak viscosity, pasting temperature);

increased molecular weight of amylopectin;

modified percentage of crystalline starch; and modified percentage of A-type or B-type crystalline starch, in each case relative to wild-type wheat starch granules, flour or starch.

In an embodiment, the grain is also preferably free of any exogenous nucleic acid that encodes an RNA which reduces expression of an endogenous CslF gene.

Preferably the grain is from hexaploid wheat, preferably *Triticum aestivum* L., or from tetraploid wheat such as *T. durum*.

In certain forms of the present invention, the grain is processed so that it is no longer capable of germinating. Such processed grain includes kibbled, cracked, roasted, boiled, par-boiled, rolled, pearled, milled or ground grain.

The present invention is also directed to a wheat plant, preferably *Triticum aestivum* L. or *T. durum*, comprising the grain or that is capable of producing the grain of the present invention, and to plants produced from such grain. It is preferred that the wheat plant is male and female fertile. In an embodiment, the wheat plant is of a cultivar other than Bob White 26. The wheat plant may be of a winter or spring type, and is preferably semi-dwarf in height, such as a wheat plant comprising a mutant allele of an Rht gene that provides for a semi-dwarf height. The plant may be growing in a glasshouse or in the field. The plant may be one of a population of at least 1000 genetically identical or essentially identical wheat plants growing in the field.

The present invention also extends to wheat flour, such as wholemeal wheat flour, or other processed products obtained from the grain such as semolina, isolated wheat starch granules, isolated wheat starch or wheat bran produced from the grain of the invention. The BG content of the wholemeal flour is essentially the same as for the wheat grain, as described above. In an embodiment, the flour or other processed product comprises one or more exogenous CslF polypeptides, preferably including a CslF6 polypeptide, more preferably an oat, maize, sorghum or rice CslF6 polypeptide, which polypeptide is derived from the grain of the invention. In a preferred embodiment, the CslF6 polypeptide in the flour or processed product comprises an amino acid other than isoleucine (I) at position 756 with reference to SEQ ID NO:18 or the corresponding amino acid position in other CslF6 polypeptides, and more preferably has a leucine (L) at that position. The polypeptide is detectable by any method known in the art such as an immunological method e.g. ELISA or Western blot analysis, or mass spectrometry. The flour or processed product may also comprise one or more exogenous polynucleotides encoding the CslF polypeptide(s), derived from the grain. Said polynucleotides may be detectable by PCR. In an embodiment, the flour is wheat endosperm flour (white flour) comprising BG and one or more exogenous Csl polypeptides, wherein the BG content of the flour is between 0.3% and about 3% (w/w). The white flour has a lower bran content than the wholemeal flour from which it is obtained. The flour or bran may have been stabilised by heat treatment.

The present invention provides a variant CslF6 polypeptide which comprises an amino acid substitution at position 756 with reference to SEQ ID NO:18 or the corresponding amino acid position in other CslF6 polypeptides, wherein the amino acid present at position 756 is other than isoleucine (I) and more preferably is leucine (L). Such a polypeptide is preferably non-naturally occurring and/or is present in a cell which does not naturally comprise the polypeptide. In an embodiment, the polypeptide comprises amino acids whose sequence is set forth as SEQ ID NO: 178. In a preferred embodiment, the variant CslF6 polypeptide is capable of producing an increased amount of BG or producing BG which has a water solubility which is increased relative to BG produced by the wild-type CslF6 polypeptide, such as, for example, having a water solubility of between 8.0% and about 25%, between 8.0% and about 50%, between about 10% and 50%, or between about 10% and about 25% of the BG that is water soluble. In a preferred embodiment, the BG produced by the variant CslF6 polypeptide has a DP3/DP4 ratio between about 1.0 and about 2.0 or between about 1.0 and 2.3. The variant polypeptide may be an isolated polypeptide or it may be in a cell such as a wheat cell. The present invention also provides a CslF6 polynucleotide which encodes the variant CslF6 polypeptide and cells comprising such CslF6 polynucleotides, and methods of producing or using these.

The present invention also extends to isolated wheat BG produced from the grain of the present invention. Typically the BG is isolated together with wheat AX, and the invention therefore provides a composition comprising the BG and AX. In an embodiment, less than 50% of the AX in the composition is feruloylated. Preferably, at least 50% of the carbohydrate in the composition on a weight basis is BG or AX or the combination thereof. In an embodiment, the isolated BG has one or more of the features of the BG as defined above in the context of the wheat grain.

The present invention also provides for the use of the wheat grain, or the flour, or the BG of the present invention for use in the production of a product to increase the level of BG in said product, to decrease the DP3/DP4 ratio of the total BG in the product and/or to increase the solubility of the total BG in the product. The increased level of BG, or decreased DP3/DP4 ratio or solubility, is relative to use of an equivalent amount of wild-type wheat grain, flour or BG therefrom, respectively.

The present invention also provides a food ingredient that comprises the grain, flour, isolated BG or composition comprising BG and AX of the invention, or a drink ingredient comprising the isolated BG or composition comprising BG and AX of the invention. It is preferred that the food or drink ingredient is packaged ready for sale. The food or drink ingredient may be incorporated into a mixture with another food or drink ingredient, such as, for example, a cake mix, a pancake mix or a dough. The food ingredient may be used in a food product at a level of at least 1%, preferably at least 10%, on a dry weight basis, and the drink ingredient may be used in a drink product at a level of at least 0.1% on a weight basis. If the food product is a breakfast cereal, bread, cake or other farinaceous product, higher incorporation rates are preferred, such as at a level of at least 20% or at least 30%. Up to 100% of the ingredient (grain, flour such as wholemeal flour etc) in the food product may be an ingredient of the invention. Preferably, the food or drink product, when ready for consumption, comprises the BG derived from the food or drink ingredient in essentially unaltered form.

The food or drink product of the invention may be used in altering one or more physiological parameters in an animal, preferably a human. The physiological parameter may be, for example, of metabolic health, bowel health or cardiovascular health, or of preventing or reducing the severity or incidence of metabolic, bowel or cardiovascular disease in an animal. The human may be a child or an adult human, male or female. Alternatively, the animal may be a livestock animal such as pigs, cattle or sheep, a pet animal such as dogs or cats, or farmed animals such as fish, poultry such as chickens, ducks or turkeys.

The grain of the present invention and the ingredients obtained therefrom may be blended with essentially wild-type grain or other ingredients. The invention therefore provides a composition comprising non-modified wheat grain or an ingredient obtained therefrom, the non-modified wheat grain having a level of BG of less than 2% (w/w), in addition to the wheat grain of the invention or an ingredient obtained therefrom. In such compositions, it is preferred that the grain of the present invention and/or the ingredient obtained therefrom comprises at least 10% by weight of the composition. The non-modified ingredient may be, for example, flour such as wholemeal flour, semolina, a starch-containing ingredient, purified starch or bran.

The present invention also provides a method of producing a wheat plant that produces grain of the present invention. In an embodiment, the method comprises the steps of (i) introducing one or more exogenous polynucleotides which encode one or more Csl polypeptides, preferably including a CslF polypeptide such as a CslF6 polypeptide, into a progenitor wheat cell, and (ii) producing a transgenic wheat plant from the wheat cell of (i). Preferred CslF6 polypeptides are oat, maize, sorghum or rice CslF6 polypeptides or variants thereof. In a preferred embodiment, the CslF6 polypeptide in the cell comprises an amino acid other than isoleucine (I) at position 756 with reference to SEQ ID NO:18 or the corresponding amino acid position in other CslF6 polypeptides, and more preferably has a leucine (L) at that position. The exogenous polynucleotide may be operably linked to a promoter sequence which is preferentially expressed in the developing seed of a wheat plant relative to another tissue or organ of the wheat plant, such as in the leaves. The promoter sequence may be preferentially expressed in the endosperm of the wheat plant. The method may further comprise a step of obtaining grain from the transgenic wheat plant produced in step (ii), or additionally of producing progeny plants from the transgenic wheat plant or crossing a transgenic wheat plant with a second wheat plant. Progeny plants to the third or subsequent generations may be produced. The method will also typically involve a step of determining the expression level of the exogenous polynucleotide in the transgenic wheat plant or its progeny, the level of the Csl polypeptide in the grain of the wheat plant or its progeny, or the amount or type of the BG in the grain of the wheat plant or its progeny. The method may include a step of identifying a transgenic wheat plant with a desirable level of BG in its grain, from a plurality of wheat plants produced according to steps (i) and (ii), and/or of identifying a progeny plant which is homozygous for the exogenous polynucleotide(s). The method may comprise a selection step in which a transgenic wheat plant producing grain having the desired properties is selected from a plurality of candidates. The determination, identification or selection step may be carried out occur after growing one or more progeny transgenic wheat plants in a glasshouse or in the field (field trial).

In an embodiment, invention provides a method which comprises the steps of (i) introducing into a CslF6 gene of a progenitor wheat cell a nucleotide variation such that the variant gene encodes a variant CslF6 polypeptide, and (ii) producing a wheat plant from the wheat cell of (i). In a preferred embodiment, the variant CslF6 polypeptide comprises an amino acid other than isoleucine (I) at position 756 with reference to SEQ ID NO:18 or the corresponding amino acid position in other CslF6 polypeptides, and more preferably has a leucine (L) at that position. The method may further comprise a step of obtaining grain from the wheat plant produced in step (ii), or additionally of producing progeny plants from the wheat plant or crossing the wheat plant with a second wheat plant. Progeny plants to the third or subsequent generations may be produced. The method will also typically involve a step of determining the expression level of the polynucleotide in the wheat plant or its progeny, the level of the CslF6 polypeptide in the grain of the wheat plant or its progeny, or the amount or type of the BG in the grain of the wheat plant or its progeny, such as measuring the water solubility of the BG. The method may include a step of identifying a wheat cell or plant derived therefrom with a desirable level of BG in its grain, from a plurality of wheat cells or plants produced according to steps (i) and (ii), and/or of identifying a progeny plant which is homozygous for the variant CslF6 gene. The method may comprise a selection step in which a wheat plant producing grain having the desired properties is selected from a plurality of candidates. The determination, identification or selection step may be carried out occur after growing one or more progeny wheat plants in a glasshouse or in the field (field trial).

The present invention also provides a method of producing a wheat plant that produces grain of the present invention, the method comprising the steps of (i) crossing a first wheat plant which comprises one or more exogenous polynucleotides or variant CslF6 genes which encode one or more Csl polypeptides, preferably including a CslF polypeptide such as a CslF6 polypeptide, with a second wheat plant, and (ii) selecting a progeny wheat plant from the cross of (i) which produces the grain of the present invention. The method may comprise a determination, identification or selection step as described in the previous paragraph.

The present invention also provides a method of identifying or selecting a wheat plant, the method comprising (i) determining the amount of BG in grain obtained from each of at least two wheat plants, and (ii) selecting a plant from (i) which produces grain comprising BG, wherein the grain is grain of the invention, preferably grain having a BG content of at least 3% (w/w). The method may comprise a determination step as described in the previous paragraphs.

The present invention further provides a method of producing grain of the present invention, comprising the steps of i) harvesting wheat grain from a plant of the invention, and ii) optionally, processing the grain. The method may further comprise a step of cultivating the wheat plant prior to step i), thereby obtaining the wheat plant. The wheat plant may be growing in a field, preferably as part of a population of at least 1000 wheat plants which are essentially the same genetically. Preferably, the grain is harvested using a mechanical harvester.

The present invention also provides a method of producing bins of wheat grain comprising:
 a) reaping wheat stalks comprising wheat grain of the invention;
 b) threshing and/or winnowing the stalks to separate the grain from the chaff; and
 c) sifting and/or sorting the grain separated in step b), and loading the sifted and/or sorted grain into bins, thereby producing bins of wheat grain.

As will be understood, the wheat grain of the present invention may be traded for pecuniary gain. In addition, the methods of the present invention will generally involve cultivating a wheat plant of the invention, or harvesting the wheat grain, storing the wheat grain and/or transporting the wheat grain to a different location.

The present invention also provides a method of identifying a container comprising wheat grain of the present invention, the method comprising (i) determining the amount and/or properties of BG in a sample of wheat grain from the container, or determining the amount of a Csl polypeptide present in the sample, or determining the presence of a polynucleotide which encodes a Csl polypeptide in the sample, and (ii) if the amount and/or properties of the BG in the sample is as described above, or the Csl polypeptide or polynucleotide is present in a desired amount, thereby having identified the container from which the grain sample came.

The grain of the present invention may also be milled to produce a milled wheat product. This will typically involve obtaining wheat grain, milling the grain to produce flour, and optionally, separating any bran from the flour. Milling the grain may be by dry milling or wet milling. The grain may be conditioned to having a desirable moisture content prior to milling, preferably about 10% or about 14% on a weight basis, or the milled product such as flour or bran may be processed by treatment with heat to stabilize the milled product. As will be understood, the BG content of the milled product corresponds to the BG content in the wheat grain or the component of the wheat grain which is represented in the milled product.

BG, a composition comprising BG plus AX, starch granules or starch may also be extracted from the grain of the present invention to produce BG, BG plus AX, starch granules or starch, and the invention therefore provides a method of producing these. The extraction process typically comprises obtaining a milled product from the grain, and may comprise a water-soluble extraction of the milled product, which extraction may be under neutral (pH about 6-8) or alkaline conditions. The extracted product may comprise AX. The starch may be characterized by one or more properties as described for the starch in the grain of the invention. The BG, starch granules or starch produced by the method are preferably at least 60% pure, more preferably at least 90% pure on a dry weight basis. If BG is extracted by water-solubilisation, the extracted composition preferably comprises at least 60% BG plus AX, more preferably at least 90% pure BG plus AX on a dry weight basis. The BG or BG plus AX may be extracted from the grain of the invention as a secondary product in a process to extract gluten or starch from the grain.

The present invention also provides a method of producing a product comprising BG, or BG plus AX, wherein the method comprises (i) obtaining or producing a wheat grain of the present invention, or flour therefrom, and (ii) processing the wheat grain or flour therefrom to produce the product. This method may further comprise a step of assessing the level or type of BG in the wheat grain or flour of step (i) or in the product of step (ii), or a step of adding a processed wheat grain or flour from step (ii) to another food or drink ingredient, thereby producing the product comprising BG. The product may be a food or drink product or a pharmaceutical composition, or isolated BG, or isolated BG plus AX. Preferred food products include bread, breakfast cereals, biscuits, muffins, muesli bars, noodles.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

The present invention also provides a use of the BG or BG plus AX compositions isolated from wheat grain of the invention, which may be used as a low calorie food additive, a bulking agent, a dietary fibre, a texturizing agent, a preservative, a probiotic agent or any combination of these uses. Preferably, these uses are embodied in food products of the invention, by incorporating the BG or BG plus AX in the food product. The present invention therefore also provides a product, preferably a food product, which comprises the BG or BG plus AX which has been incorporated for the aforesaid use.

The present invention also provides a method of altering one or more physiological parameters in an animal, or of preventing or reducing the severity or incidence of a disease, the method comprising providing to the animal the grain of the present invention, or a food or drink product made therefrom, wherein the altered physiological parameter or reduced severity or incidence of disease is relative to providing to the animal the same amount of a corresponding wild-type grain or food or drink product made therefrom. It is preferred that the physiological parameter is a parameter of metabolic health, bowel health or cardiovascular health, such as a reduced incidence or severity of diabetes, bowel disease, obesity, hypertension, constipation, osteoporosis, cancer or cardiovascular disease. The physiological parameter may be one or more of: an increased number of beneficial intestinal bacteria, a reduced number of aberrant crypt foci in the bowel, an increased mineral absorption from the bowel, a reduced level of insulin in the blood, a reduced glycaemic index response, a reduced glycaemic load response, a reduced blood glucose level, a reduced blood pressure, a reduced body weight, a reduced blood cholesterol level or LDL cholesterol level, increased blood HDL cholesterol level, an increased bone density, or more frequent bowel movement.

It is preferred that the animal is a human, and the amount of grain, or food or drink produced therefrom, provided to the human is at least 10 g per day of the grain or grain equivalent.

DETAILED DESCRIPTION OF THE INVENTION

Figure 1:
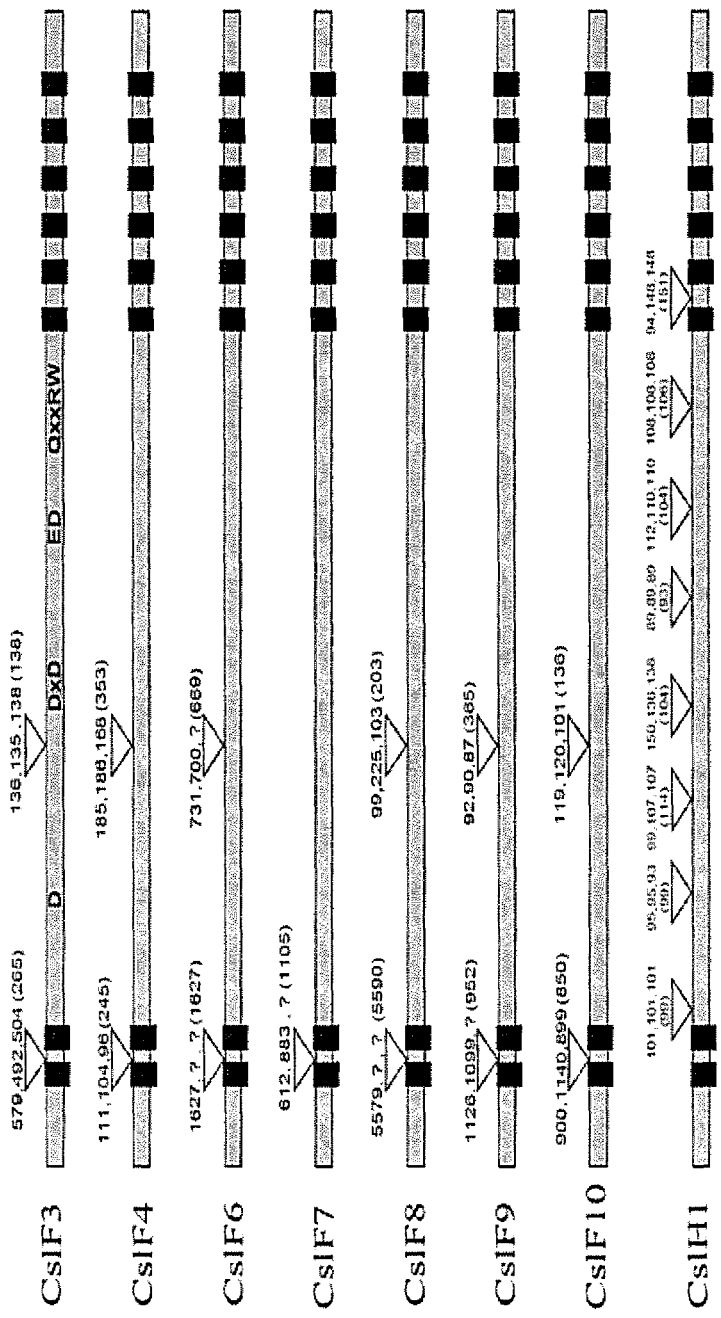
FIG. 1. Schematic representation of the structure of wheat TaCslF and TaCslH gene open reading frames. The long bars represent the open reading frames of the TaCslF and TaCslH genes from the ATG translation start codons to the stop codons, and the short black bars indicate the positions of the sequences encoding the predicted transmembrane domains in the proteins. The approximate positions of the sequences encoding the conserved D, DxD, ED and QxxRW motifs in the proteins are indicated only in the large central domain of CslF3 although they occur in all of the illustrated open reading frames. The triangles show the position of the introns with the length in nucleotides of each of the three wheat genomes (A, B and D) shown above (a question mark indicates the intron has not been isolated or determined). The length of the corresponding intron from barley is shown in brackets.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

As used in the subject specification, the singular forms "a", "an" and "the" include plural aspects unless the context clearly dictates otherwise. Thus, for example, reference to "a" includes a single as well as two or more; reference to "an" includes a single as well as two or more; reference to "the" includes a single as well as two or more and so forth.

The present invention is based on the experiments described herein that demonstrate that substantially increased BG levels can be produced in wheat grain, to much higher levels than could have been expected from experiments in other cereals, and that increased levels of BG can be produced having modified properties relative to the BG produced in wild-type wheat. Preferably the BG is modified relative to native wheat grain BG by having greater solubility in aqueous medium and/or a decreased DP3/DP4 ratio.

The cell walls of grasses (Poaceae) including cereals are complex and dynamic structures composed of a variety of polysaccharides such as cellulose, xyloglucans, pectin (rich in galacturonic acid residues), callose (1,3-β-D-glucan), arabinoxylans (arabino-(1,4)-β-D-xylan, hereinafter AX) and BG, as well as polyphenolics such as lignin. In cell walls of the grasses and some other monocot plants, glucurono-arabinoxylans and BG predominate and the levels of pectic polysaccharides, glucomannans and xyloglucans are relatively low (Carpita et al., 1993). These polysaccharides are synthesized by a large number of diverse polysaccharide synthases and glycosyltranferases, with at least 70 gene families present in plants and in many cases, multiple members of gene families.

As used herein, the term "(1,3;1,4)-β-D-glucan", also referred to as "β-glucan" and abbreviated herein as "BG", refers to an essentially linear polymer of unsubstituted and essentially unbranched β-glucopyranosyl monomers covalently linked mostly through (1,4)-linkages with some (1,3)-linkages. The glucopyranosyl residues, joined by (1-3)- and (1-4)-linkages, are arranged in a non repeating but non random fashion—i.e. the (1,4)- and (1,3)-linkages are not arranged randomly, but equally they are not arranged in regular, repeating sequences (Fincher, 2009a, b). Most (about 90%) of the (1-3)-linked residues follow 2 or 3 (1-4)-linked residues in oat and barley BG. BG can therefore be considered to be a chain of mainly β-1-4 linked cellotriosyl (each with 3 glucopyranosyl residues) and cellotetrosyl (each with 4 glucopyranosyl residues) units linked together by single β-1-3 linkages with approximately 10% longer β-1-4 linked cellodextrin units of 4 to about 10 (1-4)-linked glucopyranosyl residues (Fincher and Stone, 2004). Typically, the BG polymers have at least 1000 glycosyl residues and adopt an extended conformation in aqueous media. The ratio of tri- to tetra-saccharide units (DP3/DP4 ratio) varies among species and therefore is characteristic of BG from a species. However, it should be noted that most of the structural studies were done with barley grain or oat grain BG, not with BG from other cereals.

In wild-type cereal grains, BG levels are greater in the whole grain than in the endosperm, except in barley grain in which BG is present in similar concentrations in whole grain and endosperm (Henry, 1987). BG content of wild-type whole wheat grain was about 0.6% on a weight basis, compared to about 4.2% for barley, 3.9% for oats and 2.5% for rye (Henry 1987). It would be understood that there is natural variation in the sequences of CslF and CslH genes from different wheat varieties. The homologous genes are readily recognizable by the skilled artisan on the basis of sequence identity. The degree of sequence identity between homologous CslF genes or the proteins is thought to be at least 90%, similarly for CslH genes or proteins.

As used herein, the term "by weight" or "on a weight basis" refers to the weight of a substance, for example, BG, as a percentage of the weight of the material or item comprising the substance. This is abbreviated herein as "w/w". Typically, the weight of BG is determined as a percentage of the weight of the wheat wholemeal flour, assuming that wholemeal flour has a moisture content of 10%. This determination is according to the Megazyme kit for measuring BG.

Plants The terms "plant(s)" and "wheat plant(s)" as used herein as a noun generally refer to whole plants, but when "plant" or "wheat" is used as an adjective, the terms refer to any substance which is present in, obtained from, derived from, or related to a plant or a wheat plant, such as for example, plant organs (e.g. leaves, stems, roots, flowers), single cells (e.g. pollen), seeds or grain, plant cells including for example tissue cultured cells, products produced from the plant such as "wheat flour", "wheat grain", "wheat starch", "wheat starch granules" and the like. Plantlets and germinated seeds from which roots and shoots have emerged are also included within the meaning of "plant". The term "plant parts" as used herein refers to one or more plant tissues or organs which are obtained from a whole plant, preferably a wheat plant. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. The term "plant cell" as used herein refers to a cell obtained from a plant or in a plant, preferably a wheat plant, and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, pollen, and various forms of aggregations of plant cells in culture, such as calli. Plant tissues in or from seeds such as wheat grain are seed coat, endosperm, scutellum, aleurone layer and embryo. Wheat bran is the seed coat, aleurone layer and embryo, mixed together, when removed from the grain.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum* (also referred to as durum wheat or *Triticum turgidum* ssp. *durum*), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat plant or grain of the present invention may belong to, but is not limited to, any of the above-listed species. Also encompassed are plants that are produced by conventional techniques using *Triticum* sp. as a parent in a sexual cross with a non-*Triticum* species, such as rye *Secale cereale*, including but not limited to Triticale. Preferably the wheat plant is suitable for commercial production of grain, such as commercial varieties of hexaploid wheat or durum wheat, having suitable agronomic characteristics which are known to those skilled in the art. More preferably the wheat is *Triticum aestivum* ssp. *aestivum* or *Triticum turgidum* ssp. *durum*, and most preferably the wheat is *Triticum aestivum* ssp. *aestivum*, herein also referred to as "breadwheat".

As is understood in the art, hexaploid wheats such as bread wheat comprise three genomes which are commonly designated the A, B and D genomes, while tetraploid wheats such as durum wheat comprise two genomes commonly designated the A and B genomes. Each genome comprises 7 pairs of chromosomes which may be observed by cytological methods during meiosis and thus identified, as is well known in the art.

The wheat plants of the invention may be crossed with other wheat plants containing a more desirable genetic background. Further rounds of back-crossing to a recurrent parent variety with selection for the high BG phenotype may be carried out to recover the desired genetic background, as is known in the art. The desired genetic background may include a suitable combination of genes providing commercial yield and other characteristics such as agronomic performance or abiotic stress resistance. The genetic background might also include other altered starch biosynthesis or modification genes, for example genes from other wheat lines. The genetic background may comprise one or more transgenes such as, for example, a gene that confers tolerance to a herbicide such as glyphosate. The desired genetic background of the wheat plant will include considerations of agronomic yield and other characteristics. Such characteristics might include whether it is desired to have a winter or spring types, agronomic performance, disease resistance and abiotic stress resistance. For Australian use, one might want to cross the altered starch trait of the wheat plant of the invention into wheat cultivars such as Baxter, Kennedy, Janz, Frame, Rosella, Cadoux, Diamondbird or other commonly grown varieties. Other varieties will be suited for other growing regions.

It is preferred that the wheat plant of the invention provide a grain yield of at least 70% or at least 80% relative to the yield of the corresponding wild-type variety in at least some growing regions, more preferably a grain yield of at least 85% or at least 90%, and even more preferably at least 95% relative to a wild-type variety having about the same genetic background, grown under the same conditions. Most preferably, the grain yield of the wheat plant of the invention is at least as great as the yield of the wild-type wheat plant having about the same genetic background, grown under the same conditions. "Same conditions" as used herein in this context includes growing the plants at the same planting density as well as water availability, temperature, light conditions etc. The yield can readily be measured in controlled field trials, or in simulated field trials in the greenhouse, preferably in the field. Grain yield is typically expressed as tonnes/hectare or as grams/plant.

Marker assisted selection is a well recognised method of selecting for heterozygous plants obtained when backcrossing with a recurrent parent in a classical breeding program. The population of plants in each backcross generation will be heterozygous for the gene(s) of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Procedures such as crossing wheat plants, self-fertilising wheat plants or marker-assisted selection are standard procedures and well known in the art. Transferring alleles from tetraploid wheat such as durum wheat to a hexaploid, or other forms of hybridisation, is more difficult but is also known in the art.

To identify the desired phenotypic characteristic, wheat plants that are transformed with CslF and/or CslH genes and possess other desired genes are typically compared to control plants. When evaluating a phenotypic characteristic associated with enzyme activity such as BG content in the grain, the plants to be tested and control plants are grown under growth chamber, greenhouse, open top chamber and/ or field conditions. Identification of a particular phenotypic trait and comparison to controls is based on routine statistical analysis and scoring. Statistical differences between plants lines can be assessed by comparing enzyme activity between plant lines within each tissue type expressing the enzyme. Expression and activity are compared to growth, development and yield parameters which include plant part morphology, colour, number of heads, tillers or grains, grain weight, size, dimensions, dry and wet plant weight, ripening duration, above- and below-ground biomass ratios, and timing, rates and duration of various stages of growth through senescence, including vegetative growth, fruiting, flowering, and soluble carbohydrate content including sucrose, glucose, fructose and starch levels as well as endogenous starch levels. Preferably, the wheat plants of the invention differ from wild-type plants in one or more of these parameters by less than 50%, more preferably less than 40%, less than 30%, less than 20%, less than 15%, less than 10%, less than 5%, less than 2% or less than 1% when grown under the same conditions.

As used herein, the term "linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). The term "genetically linked" as used herein is narrower, only used in relation to where a marker locus and a second locus being sufficiently close on a chromosome that they will be inherited together in more than 50% of meioses. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait in the wheat plants of the invention. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al., 2001; Langridge et al., 2001; Sharp et al., 2001).

The terms "transgenic plant" and "transgenic wheat plant" as used herein refer to a plant that contains a gene construct ("transgene") not found in a wild-type plant of the same species, variety or cultivar, and includes the so-called intragenic and cisgenic plants. That is, transgenic plants (transformed plants) contain genetic material that they did not contain prior to the transformation. A "transgene" as referred to herein has the normal meaning in the art of biotechnology and refers to a genetic sequence which has been produced or altered by recombinant DNA or RNA technology and which has been introduced into the plant cell. The transgene may include genetic sequences obtained from or derived from a plant cell, or plant cell other than wheat, or a non-plant source, or a synthetic sequence. Typically, the transgene has been introduced into the wheat plant by human manipulation such as, for example, by transformation but any method can be used as one of skill in the art recognizes. The genetic material is typically stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". Transgenic plants as defined herein include all progeny of an initial transformed and regenerated plant (designated herein as a T0 plant) which has been genetically modified using recombinant techniques, where the progeny comprise the transgene. Such progeny may be obtained by self-fertilisation of the primary transgenic plant or by crossing such plants with another plant of the same species. In an embodiment, the transgenic plants are homozygous for each and every gene that has been introduced (transgene) so that their progeny do not segregate for the desired phenotype. Preferably, the transgene(s) in the transgenic plant are present at only a single genetic locus so that they are inherited together in all progeny. Transgenic plant parts include all parts and cells of said plants which comprise the transgene(s) such as, for example, grain, cultured tissues, callus and protoplasts. A "non-transgenic plant", preferably a non-transgenic wheat plant, is one which has not been genetically modified by the introduction of genetic material by recombinant DNA techniques.

As used herein, the term "corresponding non-transgenic plant" refers to a plant which is the same or similar in most characteristics, which is preferably an isogenic or near-isogenic relative of the transgenic plant, but without the transgene(s) of interest. Preferably, the corresponding non-transgenic plant is of the same cultivar or variety as the progenitor of the transgenic plant of interest, or a sibling plant line which lacks the construct, often termed a "null segregant", or a plant of the same cultivar or variety transformed with an "empty vector" construct, and may be a non-transgenic plant. "Wild-type", as used herein, refers to a cell, tissue, grain or plant that has not been modified according to the invention, or products derived therefrom such as flour etc. Wild-type wheat cells, tissue, grain or plants known in the art may be used as controls to compare levels of expression of an exogenous nucleic acid or the extent and nature of trait modification with wheat cells, tissue, grain or plants modified as described herein. As used herein, "wild-type wheat grain" means a corresponding non-mutagenized, non-transgenic wheat grain, and a "wild-type wheat plant" means a corresponding non-mutagenized, non-transgenic wheat plant. Specific wild-type wheat grains or plants as used herein include but are not limited to those of cultivars Westonia, Sunstate and Cadoux, each of which is commercially available.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. An alternative method to confirm a positive transformant is by Southern blot hybridization, well known in the art. Wheat plants which are transformed may also be identified i.e. distinguished from non-transformed or wild-type wheat plants by their phenotype, for example conferred by the presence of a selectable marker gene, or by immunoassays that detect or quantify the expression of an enzyme encoded by the transgene, or any other phenotype conferred by the transgene(s).

The wheat plants of the present invention may be grown or harvested for grain, primarily for use as food for human consumption or as animal feed, or for fermentation or industrial feedstock production such as ethanol production, among other uses. Preferably, the wheat grain is processed into a food ingredient such as, for example, flour (including wholemeal) or wheat bran that may be used as an ingredient in food manufacture. Alternatively, the wheat plants may be used directly as feed such as, for example, to be grazed by animals, or to produce hay or straw as feed. The plant and grain of the present invention is preferably useful for food production and in particular for commercial food production. Such food production might include the making of flour, dough, semolina or other products from the grain that might be an ingredient in commercial food production. The wheat plants or grain of the invention have uses other than uses for food or animal feed, for example uses in research or breeding.

In seed propagated crops such as wheat, the plants can be self-crossed to produce a plant which is homozygous for the desired genes, or haploid tissues such as developing germ cells can be induced to double the chromosome complement to produce a homozygous plant. These seeds can be grown to produce plants that would have the selected phenotype such as, for example, high levels of BG.

As used herein, the phrase "which is capable of producing a plant which produces grain whose BG content comprises" or variations thereof means that the wheat plant produced from the grain of the invention has the capacity to produce the BG in its grain with the defined components when grown under optimal conditions, for instance in greenhouse conditions such as those referred to in the Examples. When in possession of grain from a plant, it is routine to grow a progeny plant from at least one of the grains under suitable greenhouse conditions and test the BG content in the progeny grain using standard procedures such as those described herein. Accordingly, as the skilled person would understand whilst grain grown in a field may not meet all of the requirements defined herein due to unfavourable conditions in a particular year such heat, cold, drought, flooding, frost, pest stresses etc, such grain are nonetheless encompassed by the present invention if the grain comprises the transgene(s) according to the invention and is capable of producing a progeny plant which produces the defined BG content or composition when grown under more favourable conditions.

Grain As used herein, the term "grain" generally refers to mature, harvested seed of a plant but can also refer to grain after imbibition or germination, or after processing such as by grinding or milling, according to the context. Wheat grain is typically harvested when the wheat plant has senesced and lost all green colour and the grain has dried and hardened. Mature cereal grain such as wheat commonly has a moisture content of less than about 18% by weight. In an embodiment, grain of the invention has a moisture content of between about 8% and about 14%, and is preferably about 10% or about 12%. As used herein, the term "seed" means harvested seed as well as seed which is developing in the plant post anthesis and mature seed comprised in the plant prior to harvest.

As used herein, "germination" refers to the emergence of the root tip from the seed coat after imbibition. "Germination rate" refers to the percentage of seeds in a population which have germinated over a period of time, for example 7 or 10 days, after imbibition. Germination rates can be calculated using techniques known in the art. For example, a population of seeds can be assessed daily over several days to determine the germination percentage over time. Germination is typically measured at room temperature and in the dark by placing the grain between moistened filter papers. With regard to grain of the present invention, as used herein the term "germination rate which is substantially the same" means that the germination rate of the grain is at least 70% relative to the germination rate of a corresponding wild-type grain. This may be determined at a time point between 4 and 7 days. In an embodiment, the grain of the invention has been processed so that it is no longer able to germinate, such as, for example, that the embryo has been removed by milling, or by heat treatment to stablise the grain.

The invention also provides flour, meal or other products produced from the wheat grain. These may be unprocessed or processed, for example by fractionation or bleaching, or heat treated to stabilise the product such as flour. The invention includes methods of producing flour, meal, starch granules, starch or isolated BG from the grain or from an intermediate product such as flour. Such methods include, for example, milling, grinding, rolling, flaking or cracking the grain. The invention also provides starch from grain of the exemplified wheat plants comprising increased amounts of dietary fibre, which may be measured by the methods described herein. In preferred embodiments, these products comprise an elevated level of BG such as at least 3%, at least 4%, or between about 4% to about 10% by weight. In an embodiment, the soluble fibre content in the flour is increased by at least 50%, preferably by at least 100%, relative to wild-type flour produced in the same manner. Alternatively, or in combination with the increased soluble fibre, the insoluble fibre content is increased by at least 20%, preferably by at least 40%, relative to the wild-type flour. Furthermore, each of the soluble NNSP and insoluble NNSP contents may be increased by at least 20%, preferably at least 40% relative to the wild-type flour.

The term "dietary fibre" as used herein includes the carbohydrate and carbohydrate digestion products which are not absorbed in the small intestine of healthy humans but which enter the large bowel. This includes resistant starch and other soluble and insoluble carbohydrate polymers. It is intended to comprise that portion of carbohydrates that are fermentable, at least partially, in the large bowel by the resident microflora. The dietary fibre content may be measured as described herein.

The wheat grain or other plant parts of the invention can be processed to produce a food ingredient, food or non-food product using any technique known in the art. In one embodiment, the product is whole grain flour (wholemeal) such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to produce a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Whilst the invention may be particularly useful in the treatment or prophylaxis of humans, it is to be understood that the invention is also applicable to non-human subjects including but not limited to agricultural animals such as cows, sheep, pigs, poultry such as chickens and the like, domestic animals such as dogs or cats, laboratory animals such as rabbits or rodents such as mice, rats, hamsters, or animals that might be used for sport such as horses.

The method of treating the subject, particularly humans, may comprise the step of administering altered wheat grain, flour, starch, isolated BG or a composition comprising BG and AX, or a food or drink product as defined herein to the subject, in one or more doses, in an amount and for a period of time whereby a physiological parameter is modified. For example, the level of cholesterol uptake in the large intestine of the subject is reduced, which leads to decreased cholesterol levels in the bloodstream of the subject.

Dosages may vary depending on the condition being treated or prevented but are envisaged for humans as being the BG in at least 1 g of wheat grain or flour of the invention per day, more preferably at least 2 g per day, preferably at least 10 g or at least 20 g per day. Administration of greater than about 100 grams of grain or flour per day may require considerable volumes of delivery and reduce compliance. Most preferably the dosage for a human is between 0.2 g and 5 g of BG, which may be in the form of a food product containing grain or flour of the invention, which is equivalent to between about 5 g and about 60 g of wheat grain or flour per day, or for adults between about 5 g and 100 g per day.

It will be understood that one benefit of the present invention is that it provides for products such as bread that are of particular nutritional benefit, and moreover it does so without the need to post-harvest modify the constituents of the wheat grain.

Polypeptides The terms "polypeptide" and "protein" are generally used interchangeably herein. The terms "proteins" and "polypeptides" as used herein also include variants, mutants, modifications and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 60% free, more preferably at least 75% free, and more preferably at least 90% free from other components with which it is naturally associated. By "recombinant polypeptide" is meant a polypeptide made using recombinant techniques, i.e., through the expression of a recombinant polynucleotide in a cell, preferably a plant cell and more preferably a wheat cell. The terms "foreign polypeptide" or "exogenous polypeptide" or "heterologous polypeptide" and the like refer to any polypeptide which is produced in a cell, preferably a wheat cell, by expression (transcription and translation) of an exogenous polynucleotide in that cell. In a preferred embodiment, the exogenous polypeptide is a 0-glucan synthase such as a CslF or CslH polypeptide, more preferably an exogenous CslF6 polypeptide, most preferably a CslF6 polypeptide from a plant species other than wheat. In an embodiment, the wheat cell comprises two or more exogenous polypeptides such as, for example, an exognenous CslF6 polypeptide and an exogenous CslH polypeptide.

As used herein a "biologically active" fragment is a portion of a polypeptide of the invention which maintains a defined activity of the full-length polypeptide. In a particularly preferred embodiment, the biologically active fragment has β-glucan synthase (BG synthesizing) enzyme activity. Biologically active fragments can be any size as long as they maintain the defined activity, but are preferably at least 700 or 800 amino acid residues long, such as for CslH and CslF polypeptides, respectively.

The % identity of a polypeptide relative to another polypeptide can be determined by GAP (Needleman and Wunsch, 1970) analysis (GCG program) with a gap creation penalty=5, and a gap extension penalty=0.3. The query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. When comparing amino acid sequences to determine the percentage identity for example by Blastp, the full length sequences should be compared, and gaps in a sequence counted as amino acid differences.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention or by mutagenesis in vivo such as by chemical or radiation treatment, provided they retain β-glucan synthase enzyme activity. Such mutants include, for example, deletions, insertions or substitutions of residues within the amino acid sequence. The polynucleotides of the invention may be subjected to DNA shuffling techniques as described by Harayama, 1998 or other in vitro methods to produce altered polynucleotides which encode polypeptide variants. The enzyme activity can readily be tested in a system such as the *N. benthamiana* leaf transient expression system described herein.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites other than those identified as the active site(s). To retain activity, residues in Csl polypeptides obtained from various strains or species which are identical i.e. conserved amino acids, are generally to be retained. These positions may be important for biological activity. Other residues may be substituted, preferably with conservative amino acid substitutions.

Polypeptide variants may be generated by a process of directed evolution. In directed evolution, random mutagenesis is applied to a protein, and a selection regime is used to pick out variants that have the desired qualities, for example, increased β-glucan synthase enzyme activity. Further rounds of mutation and selection are then applied. A typical directed evolution strategy involves three steps:

Diversification. The gene encoding the protein of interest is mutated and/or recombined at random to create a large library of gene variants. Variant gene libraries can be constructed through error prone PCR (see, for example, Leung, 1989; Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al., 2002, Coco, 2002) or from mixtures of both, or even from undigested parental templates (Zhao et al., 1998; Eggert et al., 2005; Jezequel et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E. coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

Selection. The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity.

Amplification. The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

In an embodiment, an exogenous or recombinant polypeptide of the invention has β-glucan synthase (BG-synthesizing) enzyme activity when produced in a wheat cell and comprises amino acids having a sequence as provided in any one of SEQ ID NOs: 2, 9, 10, 11, 18, 19, 20, 23, 30, 37, 38, 39, 41, 43, 45, 47, 50, 55, 56, 57, 59, 61, a biologically active fragment thereof, or an amino acid sequence which is at least 40% identical, or at least 70% identical, or at least 90% identical or at least 95% identical or at least 98.2% identical to any one or more of SEQ ID NOs: NOs: 2, 9, 10, 11, 18, 19, 20, 23, 30, 37, 38, 39, 41, 43, 45, 47, 50, 55, 56, 57, 59, 61. Preferably, the exogenous or recombinant polypeptide comprises amino acids having a sequence as provided in any one of SEQ ID NOs: 18, 19, 20, 55, 56, 57, 59 or 61, a biologically active fragment thereof, or an amino acid sequence which is at least 40% identical, or at least 70% identical, or at least 90% identical or at least 95% identical or at least 98.2% identical to any one or more of SEQ ID NOs: NOs: 18, 19, 20, 55, 56, 57, 59 or 61. In a preferred embodiment, the exogenous polypeptide is a CslF6 polypeptide whose length is about 940-952 amino acid residues, more preferably of 943, 944 or 950 amino acid residues, such lengths including a signal sequence of about 90 amino acid residues. In an embodiment, the exogenous polypeptide is a CslF6 polypeptide whose length, including its signal sequence of 90 amino acids, is not 947 amino acids. In an embodiment, the exogenous CslF6 polypeptide has κ predicted transmembrane domains, including, for example, one or more of the transmembrane domains described in the Listing of Sequence ID NOs for any one or more of SEQ ID NOs: 55, 56, 57, 59 or 61. The CslF polypeptide preferably comprises the amino acids known to be critical for activity as described herein for one or more of SEQ ID NOs: 55, 56, 57, 59 or 61 such as the D228, DxD (430-432), D636 and QxxRW (674-678) amino acid motifs in SEQ ID NO: 55 or the corresponding amino acid positions in the other SEQ ID NOs. In preferred embodiments, the exogenous CslF6 polypeptide is an oat (AsCslF6), maize (ZmCslF6), sorghum (SbCslF6) or rice (OsCslF6) CslF6 polypeptide. As used herein, an oat CslF6 polypeptide is defined as a polypeptide whose amino acid sequence is set forth as SEQ ID NOs: 55-57 or which is at least 95% identical, preferably at least 98% identical, thereto. In an embodiment, the oat CslF6 polypeptide is encoded by a polynucleotide whose nucleotide sequence is set forth as any one of SEQ ID NOs: 51-54 or a protein coding region thereof or a polynucleotide which encodes the same polypeptide as any one of SEQ ID NOs: 51-54. As used herein, a rice CslF6 polypeptide is defined as a polypeptide whose amino acid sequence is set forth as SEQ ID NO: 61 or which is at least 95% identical, preferably at least 98% identical, thereto. In an embodiment, the rice CslF6 polypeptide is encoded by a polynucleotide whose nucleotide sequence is set forth as SEQ ID NO: 60 or a protein coding region thereof or a polynucleotide which encodes the same polypeptide as SEQ ID NO: 60. As used herein, a *Brachypodium* CslF6 polypeptide is defined as a polypeptide whose amino acid sequence is set forth as SEQ ID NO: 59 or which is at least 95% identical, preferably at least 98% identical, thereto. In an embodiment, the *Brachypodium* CslF6 polypeptide is encoded by a polynucleotide whose nucleotide sequence is set forth as SEQ ID NO: 58 or a protein coding region thereof or a polynucleotide which encodes the same polypeptide as SEQ ID NO: 58. As used herein, a barley CslF6 polypeptide is defined as a polypeptide whose amino acid sequence is set forth as SEQ ID NO: 175 or which is a naturally occurring variant thereof in barley. Such variants are at least 99% identical in amino acid sequence to SEQ ID NO:175. In an embodiment, the exogenous polypeptide is a CslF6 polypeptide other than a barley CslF6 polypeptide.

Polynucleotides The present invention refers to various polynucleotides. As used herein, a "polynucleotide" or "nucleic acid" or "nucleic acid molecule" means a polymer of nucleotides, which may be DNA or RNA or a combination thereof, for example a heteroduplex of DNA and RNA, and includes for example mRNA, cRNA, cDNA, tRNA, siRNA, shRNA, hpRNA, and single or double-stranded DNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein. Preferably the polynucleotide is solely DNA or solely RNA as occurs in a cell, and some bases may be methylated or otherwise modified as occurs in a wheat cell. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs in an RNA molecule. "Complementary" means two polynucleotides are capable of basepairing along part of their lengths, or along the full length of one or both.

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state or in a cell. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence to be transcribed in the cell.

The present invention refers to use of oligonucleotides which may be used as "probes" or "primers". As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length, typically comprised of 10-30 or 15-25 nucleotides which are identical to, or complementary to, part of an CslF or CslH gene or cDNA corresponding to an CslF or CslH gene. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Polynucleotides used as a probe are typically conjugated with a detectable label such as a radioisotope, an enzyme, biotin, a fluorescent molecule or a chemiluminescent molecule. Oligonucleotides and probes of the invention are useful in methods of detecting an allele of a CslF, CslH or other gene associated with a trait of interest. Such methods employ nucleic acid hybridization and in many instances include oligonucleotide primer extension by a suitable polymerase, for example as used in PCR for detection or identification of wild-type or mutant alleles. Preferred oligonucleotide pairs are those that span one or more introns, or a part of an intron and therefore may be used to amplify an intron sequence in a PCR reaction. Numerous examples are provided in the Examples herein.

The terms "polynucleotide variant" and "variant" and the like refer to polynucleotides displaying substantial sequence identity with a reference polynucleotide sequence and which are able to function in an analogous manner to, or with the same activity as, the reference sequence. These terms also encompass polynucleotides that are distinguished from a reference polynucleotide by the addition, deletion or substitution of at least one nucleotide, or that have, when compared to naturally occurring molecules, one or more mutations. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. The terms "polynucleotide variant" and "variant" also include naturally occurring allelic variants. Mutants can be either naturally occurring (that is to say, isolated from a natural source) or synthetic (for example, by performing site-directed mutagenesis on the nucleic acid). Preferably, a polynucleotide variant of the invention which encodes a polypeptide with enzyme activity is greater than 400, more preferably greater than 500, more preferably greater than 600, more preferably greater than 700, more preferably greater than 800, more preferably greater than 900, and even more preferably greater than 1,000 nucleotides in length, up to the full length of the gene.

A variant of an oligonucleotide of the invention includes molecules of varying sizes which are capable of hybridising, for example, to the wheat genome at a position close to that of the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close (for example, but not limited to, within 50 nucleotides) to the region of the plant genome where the specific oligonucleotides defined herein hybridise.

By "corresponds to" or "corresponding to" in the context of polynucleotides or polypeptides is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a defined minimum number of nucleotides or amino acid residues or preferably over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, 500 or 600 nucleotides in each case. Reference also may be made to the BLAST family of programs as for example disclosed by Altschul et al., 1997. A detailed discussion of sequence analysis can be found in Unit 19.3 of Ausubel et al., 1994-1998, Chapter 15.

Nucleotide or amino acid sequences are indicated as "essentially similar" when such sequences have a sequence identity of at least about 95%, particularly at least about 98%, more particularly at least about 98.5%, quite particularly about 99%, especially about 99.5%, more especially about 100%, quite especially are identical. It is clear that when RNA sequences are described as essentially similar to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In some embodiments, the present invention refers to the stringency of hybridization conditions to define the extent of complementarity of two polynucleotides. "Stringency" as used herein, refers to the temperature and ionic strength conditions, and presence or absence of certain organic solvents, during hybridization. The higher the stringency, the higher will be the degree of complementarity between a target nucleotide sequence and the labelled polynucleotide sequence. "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, herein incorporated by reference. Specific hybridization conditions referred to herein are as follows: 1) low stringency hybridization conditions in 6× sodium chloride/sodium citrate (SSC) at about 45° C., followed by two washes in 0.2×SSC, 0.1% SDS at 50-55° C.; 2) medium stringency hybridization conditions in 6×SSC at about 45° C., followed by one or more washes in 0.2×SSC, 0.1% SDS at 60° C.; 3) high stringency hybridization conditions in 6× SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

Genes In some embodiments, the present invention involves modification of gene activity, particularly of CslF gene activity, combinations of mutant genes, and the construction and use of chimeric genes. As used herein, the term "gene" includes any deoxyribonucleotide sequence which includes a protein coding region or which is transcribed in a cell but not translated, together with associated non-coding and regulatory regions. Such associated regions are typically located adjacent to the coding region on both the 5' and 3' ends for a distance of about 2 kb on either side. In this regard, the gene includes control signals such as promoters, enhancers, transcription termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. The term "gene" includes synthetic or fusion molecules encoding the proteins of the invention described herein. Genes are ordinarily present in the wheat genome as double-stranded DNA. A chimeric gene may be introduced into an appropriate vector for extrachromosomal maintenance in a cell or for integration into the host genome.

Examples of sequences of Cslgenes, or of protein coding regions of genes encoding Csl polypeptides, include SEQ ID NOs 1-8, 12-17, 21, 22, 24-29, 31-36, 40-42, 44, 46, 48, 49, 51-54, 58 and 60.

A genomic form or clone of a gene containing the coding region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide.

As used herein, a "chimeric gene" or "genetic construct" refers to any gene that is not a native gene in its native location i.e. it has been artificially manipulated, including a chimeric gene or genetic construct which is integrated into the wheat genome. Typically a chimeric gene or genetic construct comprises regulatory and transcribed or protein coding sequences that are not found together in nature. Accordingly, a chimeric gene or genetic construct may comprise regulatory sequences and coding sequences that are derived from different sources, or regulatory sequences and coding sequences derived from the same source, but arranged in a manner different than that found in nature. The term "endogenous" is used herein to refer to a substance that is normally produced in an unmodified plant at the same developmental stage as the plant under investigation, preferably a wheat plant. An "endogenous gene" refers to a native gene in its natural location in the genome of an organism, preferably a wheat plant. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations, preferably the wheat genome, but which does not naturally occur in the cell. These include modified forms of gene sequences found in that cell so long as the introduced gene contains some modification, e.g. an introduced mutation or the presence of a selectable marker gene, relative to the naturally-occurring gene. Foreign or exogenous genes may be genes found in nature that are inserted into a non-native organism, native genes introduced into a new location within the native host, or chimeric genes or genetic constructs. A "transgene" is a gene that has been introduced into the genome by a transformation procedure. The term "genetically modified" includes introducing genes into cells, mutating genes in cells and altering or modulating the regulation of a gene in a cell or organisms to which these acts have been done or their progeny.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides which regulates the expression of the genetic sequence. This may be a naturally occurring cis-acting sequence in its native context, for example regulating a wheat CslF or CslH gene, or a sequence in a genetic construct which when positioned appropriately relative to an expressible genetic sequence, regulates its expression. Such a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence, such as a promoter. The presence of an intron in the 5'-leader (UTR) of genes has been shown to enhance expression of genes in monocotyledonous plants such as wheat (Tanaka et al., 1990). Another type of cis-acting sequence is a matrix attachment region (MAR) which may influence gene expression by anchoring active chromatin domains to the nuclear matrix.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e., the gene from which the promoter is derived. As is known in the art, some variation in this distance can be accommodated without loss of function.

Vectors The present invention makes use of vectors for production, manipulation or transfer of chimeric genes or genetic constructs. By "vector" is meant a nucleic acid molecule, preferably a DNA molecule derived, for example, from a plasmid, bacteriophage or plant virus, into which a nucleic acid sequence may be inserted. A vector preferably contains one or more unique restriction sites and may be capable of autonomous replication in a defined host cell including a target cell or tissue or a progenitor cell or tissue thereof, or be integrable into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants, or sequences that enhance transformation of prokaryotic or eukaryotic (especially wheat) cells such as T-DNA or P-DNA sequences. Examples of such resistance genes and sequences are well known to those of skill in the art.

By "marker gene" is meant a gene that imparts a distinct phenotype to cells expressing the marker gene and thus allows such transformed cells to be distinguished from cells that do not have the marker. A "selectable marker gene" confers a trait for which one can 'select' based on resistance to a selective agent (e.g., a herbicide, antibiotic, radiation, heat, or other treatment damaging to untransformed cells) or based on a growth advantage in the presence of a metabolizable substrate. A screenable marker gene (or reporter gene) confers a trait that one can identify through observation or testing, i.e., by 'screening' (e.g., β-glucuronidase, luciferase, GFP or other enzyme activity not present in untransformed cells). The marker gene and the nucleotide sequence of interest do not have to be linked.

Examples of bacterial selectable markers are markers that confer antibiotic resistance such as ampicillin, kanamycin, erythromycin, chloramphenicol or tetracycline resistance. Exemplary selectable markers for selection of plant transformants include, but are not limited to, a hyg gene which confers hygromycin B resistance; a neomycin phosphotransferase (npt) gene conferring resistance to kanamycin, paromomycin, G418 and the like as, for example, described by Potrykus et al., 1985; a glutathione-S-transferase gene from rat liver conferring resistance to glutathione derived herbicides as, for example, described in EP-A-256223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A-275957, a gene encoding a 5-enolshikimate-3-phosphate synthase (EPSPS) conferring tolerance to N-phosphonomethylglycine as, for example, described by Hinchee et al., 1988, a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al, 1988); a mutant acetolactate synthase gene (ALS), which confers resistance to imidazolinone, sulfonylurea or other ALS-inhibiting chemicals (EP-A-154204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (GFP, Niedz et al., 1995) or one of its variants; a luciferase (luc) gene (Ow et al., 1986), which allows for bioluminescence detection, and others known in the art.

In some embodiments, the level of endogenous enzyme activity is modulated by decreasing the level of expression of genes encoding proteins involved in BG production in the wheat plant, or increasing the level of expression of a nucleotide sequence that codes for the enzyme involved in BG synthesis in a wheat plant. Increasing expression can be achieved at the level of transcription by using promoters of different strengths or inducible promoters, which are capable of controlling the level of transcript expressed from the coding sequence. Heterologous sequences may be introduced which encode transcription factors that modulate or enhance expression of genes whose products down regulate starch branching. The level of expression of the gene may be modulated by altering the copy number per cell of a construct comprising the coding sequence and a transcriptional control element that is operably connected thereto and that is functional in the cell. Alternatively, a plurality of transformants may be selected, and screened for those with a favourable level and/or specificity of transgene expression arising from influences of endogenous sequences in the vicinity of the transgene integration site. A favourable level and pattern of transgene expression is one which results in a substantial increase in BG content in the wheat plant. This may be detected by simple testing of transformants.

Reducing gene expression Reducing gene expression may be achieved through introduction and transcription of a "gene-silencing chimeric DNA" or a "gene-silencing chimeric nucleic acid" introduced into the wheat plant, or through the isolation of mutants which comprise mutations in a gene of interest that reduce the expression and/or activity of the gene relative to a wild-type gene. The gene-silencing chimeric DNA is an exogenous polynucleotide which is preferably introduced stably integrated into the wheat genome, preferably the wheat nuclear genome, so that it is stably inherited in progeny grain and plants as part of the wheat genome. As used herein "gene-silencing effect" refers to the reduction of expression of a target nucleic acid in a wheat cell, preferably a seed cell, more preferably an endosperm cell, which can be achieved by introduction of a silencing RNA. In a preferred embodiment, a gene-silencing chimeric DNA is introduced which encodes an RNA molecule which reduces expression of one or more endogenous genes. Such reduction may be the result of reduction of transcription, including via methylation of chromatin remodeling, or post-transcriptional modification of the RNA molecules transcribed from the endogenous gene, including via RNA degradation, or both. "Gene-silencing" as used herein includes a reduction in some but not all of the gene expression or activity—a partial reduction—as well as an abolishing of the expression of the target nucleic acid or gene. It is sufficient that the level of expression of the target nucleic acid in the presence of the silencing RNA is lower than in the absence thereof, for example in a corresponding cell lacking the gene-silencing chimeric DNA. The level of expression and/or the activity of the targeted gene may be reduced by at least about 40% or at least about 45% or at least about 50% or at least about 55% or at least about 60% or at least about 65% or at least about 70% or at least about 75% or at least about 80% or at least about 85% or at least about 90% or at least about 95% or effectively abolished to an essentially undetectable level.

Antisense. Antisense techniques may be used to reduce gene expression in wheat cells. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, 1999). Antisense methods are now a well established technique for manipulating gene expression in plants.

Antisense molecules typically include sequences that correspond to part of the transcribed region of a target gene or for sequences that effect control over the gene expression or splicing event. For example, the antisense sequence may correspond to the targeted protein coding region of the genes of the invention, or the 5'-untranslated region (UTR) or the 3'-UTR or combination of these, preferably only to exon sequences of the target gene. In view of the generally greater divergence between related genes of the UTRs, targeting these regions provides greater specificity of gene inhibition. The length of the antisense sequence should be at least 19 contiguous nucleotides, preferably at least 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Preferably, the antisense RNA is expressed preferentially in the endosperm of a wheat plant by use of an endosperm-specific promoter.

The term "ribozyme" refers to an RNA molecule which specifically recognizes a distinct substrate RNA and catalyzes its cleavage. Typically, the ribozyme contains an antisense sequence for specific recognition of a target nucleic acid, and an enzymatic region referred to herein as the "catalytic domain". The types of ribozymes that are particularly useful in this invention are the hammerhead ribozyme (Haseloff and Gerlach, 1988; Perriman et al., 1992) and the hairpin ribozyme (Shippy et al., 1999).

DsRNA. As used herein, "artificially introduced dsRNA molecule" refers to the introduction of double-stranded RNA (dsRNA) molecule, which preferably is synthesised in the wheat cell by transcription from a chimeric gene encoding such dsRNA molecule. RNA interference (RNAi) is particularly useful for specifically reducing the expression of a gene or inhibiting the production of a particular protein, also in wheat (Regina et al., 2006). This technology relies on the presence of dsRNA molecules that contain a sequence that is essentially identical to the mRNA of the gene of interest or part thereof, and its complement, thereby forming a dsRNA. Conveniently, the dsRNA can be produced from a single promoter in the host cell, where the sense and anti-sense sequences are transcribed to produce a hairpin RNA in which the sense and anti-sense sequences hybridize to form the dsRNA region with a related or unrelated sequence forming a loop structure, so the hairpin RNA comprises a stem-loop structure. The design and production of suitable dsRNA molecules for the present invention is well within the capacity of a person skilled in the art, particularly considering Waterhouse et al., 1998; Smith et al., 2000; WO 99/32619; WO 99/53050; WO 99/49029; and WO 01/34815.

The DNA encoding the dsRNA typically comprises both sense and antisense sequences arranged as an inverted repeat. In a preferred embodiment, the sense and antisense sequences are separated by a spacer region that comprises an intron which, when transcribed into RNA, is spliced out. This arrangement has been shown to result in a higher efficiency of gene silencing (Smith et al., 2000). The double-stranded region may comprise one or two RNA molecules, transcribed from either one DNA region or two. The dsRNA may be classified as long hpRNA, having long, sense and antisense regions which can be largely complementary, but need not be entirely complementary (typically larger than about 200 bp, ranging between 200-1000 bp). hpRNA can also be rather small with the double-stranded portion ranging in size from about 30 to about 42 bp, but not much longer than 94 bp (see WO04/073390). The presence of the double stranded RNA region is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement for the overall sequence identity. The RNA molecule may of course comprise unrelated sequences which may function to stabilize the molecule. The promoter used to express the dsRNA-forming construct may be any type of promoter that is expressed in the cells which express the target gene.

Other silencing RNA may be "unpolyadenylated RNA" comprising at least 20 consecutive nucleotides having at least 95% sequence identity to the complement of a nucleotide sequence of an RNA transcript of the target gene, such as described in WO01/12824 or U.S. Pat. No. 6,423,885. Yet another type of silencing RNA is an RNA molecule as described in WO03/076619 (herein incorporated by reference) comprising at least 20 consecutive nucleotides having at least 95% sequence identity to the sequence of the target nucleic acid or the complement thereof, and further comprising a largely-double stranded region as described in WO03/076619.

As used herein, "silencing RNAs" are RNA molecules that have 21 to 24 contiguous nucleotides that are complementary to a region of the mRNA transcribed from the target gene. The sequence of the 21 to 24 nucleotides is preferably fully complementary to a sequence of 21 to 24 contiguous nucleotides of the mRNA i.e. identical to the complement of the 21 to 24 nucleotides of the region of the mRNA. However, miRNA sequences which have up to five mismatches in region of the mRNA may also be used (Palatnik et al., 2003), and basepairing may involve one or two G-U basepairs. When not all of the 21 to 24 nucleotides of the silencing RNA are able to basepair with the mRNA, it is preferred that there are only one or two mismatches between the 21 to 24 nucleotides of the silencing RNA and the region of the mRNA. With respect to the miRNAs, it is preferred that any mismatches, up to the maximum of five, are found towards the 3' end of the miRNA. In a preferred embodiment, there are not more than one or two mismatches between the sequences of the silencing RNA and its target mRNA.

Silencing RNAs derive from longer RNA molecules that are encoded by the chimeric DNAs of the invention. The longer RNA molecules, also referred to herein as "precursor RNAs", are the initial products produced by transcription from the chimeric DNAs in the wheat cells and have partially double-stranded character formed by intra-molecular basepairing between complementary regions. The precursor RNAs are processed by a specialized class of RNAses, commonly called "Dicer(s)", into the silencing RNAs, typically of 21 to 24 nucleotides long. Silencing RNAs as used herein include short interfering RNAs (siRNAs) and microRNAs (miRNAs), which differ in their biosynthesis. SiRNAs derive from fully or partially double-stranded RNAs having at least 21 contiguous basepairs, including possible G-U basepairs, without mismatches or non-basepaired nucleotides bulging out from the double-stranded region. These double-stranded RNAs are formed from either a single, self-complementary transcript which forms by folding back on itself and forming a stem-loop structure, referred to herein as a "hairpin RNA", or from two separate RNAs which are at least partly complementary and that hybridize to form a double-stranded RNA region. MiRNAs are produced by processing of longer, single-stranded transcripts that include complementary regions that are not fully complementary and so form an imperfectly basepaired structure, so having mismatched or non-basepaired nucleotides within the partly double-stranded structure. The base-paired structure may also include G-U basepairs. Processing of the precursor RNAs to form miRNAs leads to the preferential accumulation of one distinct, small RNA having a specific sequence, the miRNA. It is derived from one strand of the precursor RNA, typically the "antisense" strand of the precursor RNA, whereas processing of the long complementary precursor RNA to form siRNAs produces a population of siRNAs which are not uniform in sequence but correspond to many portions and from both strands of the precursor.

MiRNA. MiRNAs were first discovered as a small regulatory RNA controlling the lin-4 gene in *C. elegans* (Lee et al., 1993). Since then, large numbers of other naturally occurring miRNAs have been reported to be involved in regulation of gene function in animals and plants. MiRNA precursor RNAs of the invention, also termed herein as "artificial miRNA precursors", are typically derived from naturally occurring miRNA precursors by altering the nucleotide sequence of the miRNA portion of the naturally-occurring precursor so that it is complementary, preferably fully complementary, to the 21 to 24 nucleotide region of the target mRNA, and altering the nucleotide sequence of the complementary region of the miRNA precursor that base-pairs to the miRNA sequence to maintain basepairing. The remainder of the miRNA precursor RNA may be unaltered and so have the same sequence as the naturally occurring miRNA precursor, or it may also be altered in sequence by nucleotide substitutions, nucleotide insertions, or preferably nucleotide deletions, or any combination thereof. The remainder of the miRNA precursor RNA is thought to be involved in recognition of the structure by the Dicer enzyme called Dicer-like 1 (DCL1), and therefore it is preferred that few if any changes are made to the remainder of the structure. For example, basepaired nucleotides may be substituted for other basepaired nucleotides without major change to the overall structure. The naturally occurring miRNA precursor from which the artificial miRNA precursor of the invention is derived may be from wheat, another plant such as another cereal plant, or from non-plant sources. Examples of such precursor RNAs are the rice mi395 precursor, the *Arabidopsis* mi159b precursor, or the mi172 precursor.

Artificial miRNAs have been demonstrated in plants, for example Alvarez et al., 2006; Parizotto et al., 2004; Schwab et al., 2006.

Co-suppression. Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

Transformation A number of techniques are available for the introduction of nucleic acid molecules into a wheat cell, well known to workers in the art. The term "transformation" as used herein means alteration of the genotype of a cell, for example a bacterium or a plant, particularly a wheat plant, by the introduction of a foreign or exogenous nucleic acid. By "transformant" is meant an organism so altered. Introduction of DNA into a wheat plant by crossing parental plants or by mutagenesis per se is not included in transformation. As used herein the term "transgenic" refers to a genetically modified plant in which the endogenous genome is supplemented or modified by the random or site-directed integration, or stable maintenance in a replicable non-integrated form, of an introduced foreign or exogenous gene or sequence. By "transgene" is meant a foreign or exogenous gene or sequence that is introduced into a plant. The nucleic acid molecule may be replicated as an extrachromosomal element or is preferably stably integrated into the genome of the plant. By "genome" is meant the total inherited genetic complement of the cell, plant or plant part, and includes chromosomal DNA, plastid DNA, mitochondrial DNA and extrachromosomal DNA molecules. In an embodiment, a transgene is integrated in the wheat nuclear genome which in hexaploid wheat includes the A, B and D subgenomes, herein referred to as the A, B and D "genomes".

The most commonly used methods to produce fertile, transgenic wheat plants comprise two steps: the delivery of DNA into regenerable wheat cells and plant regeneration through in vitro tissue culture. Two methods are commonly used to deliver the DNA: T-DNA transfer using *Agrobacterium tumefaciens* or related bacteria and direct introduction of DNA via particle bombardment, although other methods have been used to integrate DNA sequences into wheat or other cereals. It will be apparent to the skilled person that the particular choice of a transformation system to introduce a nucleic acid construct into plant cells is not essential to or a limitation of the invention, provided it achieves an acceptable level of nucleic acid transfer. Such techniques for wheat are well known in the art.

Transformed wheat plants can be produced by introducing a nucleic acid construct according to the invention into a recipient cell and growing a new plant that comprises and expresses a polynucleotide according to the invention. The process of growing a new plant from a transformed cell which is in cell culture is referred to herein as "regeneration". Regenerable wheat cells include cells of mature embryos, meristematic tissue such as the mesophyll cells of the leaf base, or preferably from the scutella of immature embryos, obtained 12-20 days post-anthesis, or callus derived from any of these. The most commonly used route to recover regenerated wheat plants is somatic embryogenesis using media such as MS-agar supplemented with an auxin such as 2,4-D and a low level of cytokinin, see Sparks and Jones, 2004).

*Agrobacterium*-mediated transformation of wheat may be performed by the methods of Cheng et al., 1997; Weir et al., 2001; Kanna and Daggard, 2003 or Wu et al., 2003. Any *Agrobacterium* strain with sufficient virulence may be used, preferably strains having additional virulence gene functions such as LBA4404, AGL0 or AGL1 (Lazo et al., 1991) or versions of C58. Bacteria related to *Agrobacterium* may also be used. The DNA that is transferred (T-DNA) from the *Agrobacterium* to the recipient wheat cells is comprised in a genetic construct (chimeric plasmid) that contains one or two border regions of a T-DNA region of a wild-type Ti plasmid flanking the nucleic acid to be transferred. The genetic construct may contain two or more T-DNAs, for example where one T-DNA contains the gene of interest and a second T-DNA contains a selectable marker gene, providing for independent insertion of the two T-DNAs and possible segregation of the selectable marker gene away from the transgene of interest.

Any wheat type that is regenerable may be used; varieties Bob White, Fielder, Veery-5, Cadenza and Florida have been reported with success. Transformation events in one of these more readily regenerable varieties may be transferred to any other wheat cultivars including elite varieties by standard backcrossing. An alternative method using *Agrobacterium* makes use of an in vivo inoculation method followed by regeneration and selection of transformed plants using tissue culture and has proven to be efficient, see WO00/63398. Other methods involving the use of *Agrobacterium* include: co-cultivation of *Agrobacterium* with cultured isolated protoplasts; transformation of seeds, apices or meristems with *Agrobacterium*, or inoculation in planta such as the floral-dip method for *Arabidopsis* as described by Bechtold et al., 1993. This latter approach is based on the vacuum infiltration of a suspension of *Agrobacterium* cells. Alternatively, the chimeric construct may be introduced using root-inducing (Ri) plasmids of *Agrobacterium* as vectors.

Another method commonly used for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al., 1987. This method has been adapted for wheat (Vasil, 1990). Microprojectile bombardment to induce wounding followed by co-cultivation with *Agrobacterium* may be used (EP-A-486233). The genetic construct can also be introduced into plant cells by electroporation as, for example, described by Fromm et al., 1985 and Shimamoto et al., 1989. Alternatively, the nucleic acid construct can be introduced into a wheat cell such as a pollen cell by contacting the cell with the nucleic acid using mechanical or chemical means.

Preferred selectable marker genes for use in the transformation of wheat include the Streptomyces hygroscopicus bar gene or pat gene in conjunction with selection using the herbicide glufosinate ammonium, the hpt gene in conjunction with the antibiotic hygromycin, or the nptII gene with kanamycin or G418. Alternatively, positively selectable markers such as the manA gene encoding phosphomannose isomerase (PMI) with the sugar mannose-6-phosphate as sole C source may be used.

Mutagenesis Procedures Techniques for generating mutant plant lines are known in the art. Examples of mutagens that can be used for generating mutant plants include irradiation and chemical mutagenesis. Mutants may also be produced by techniques such as T-DNA insertion and transposon-induced mutagenesis. The mutagenesis procedure may be performed on any parental cell of a wheat plant, for example a seed or a parental cell in tissue culture. A preferred method of mutagenesis is heavy ion bombardment or another irradiation method, or the use of zinc finger nucleases or TAL effectors, as known in the art.

Chemical mutagens are classifiable by chemical properties, e.g., alkylating agents, cross-linking agents, etc. Useful chemical mutagens include, but are not limited to, N-ethyl-N-nitrosourea (ENU); N-methyl-N-nitrosourea (MNU); procarbazine hydrochloride; chlorambucil; cyclophosphamide; methyl methanesulfonate (MMS); ethyl methanesulfonate (EMS); diethyl sulfate; acrylamide monomer; triethylene melamine (TEM); melphalan; nitrogen mustard; vincristine; dimethylnitrosamine; N-methyl-N'-nitro-Nitrosoguani-dine (MNNG); 7,12 dimethylbenzanthracene (DMBA); ethylene oxide; hexamethylphosphoramide; and bisulfan.

An example of suitable irradiation to induce mutations is by gamma radiation, such as that supplied by a Cesium 137 source. The gamma radiation preferably is supplied to the plant cells in a dosage of approximately 60 to 200 Krad., and most preferably in a dosage of approximately 60 to 90 Krad.

Plants are typically exposed to a mutagen for a sufficient duration to accomplish the desired genetic modification but insufficient to completely destroy the viability of the cells and their ability to be regenerated into a plant.

Mutations can also be introduced into wheat plants of the invention using the process known as TILLING (Targeting Induced Local Lesions IN Genomes) for detection of mutations in genes other than the exogenous polynucleotide. In a first step, introduced mutations such as novel single base pair changes are induced in a population of plants by treating seeds or pollen with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms.

Having generally described the invention, the same will be more readily understood by reference to the following examples, which are provided by way of illustration and are not intended as limiting.

EXAMPLES OF THE INVENTION

Example 1. Materials and Methods

Plant Material and Growth Conditions

Plants of barley (Hordeum vulgare) cultivar Himalaya and wheat (Triticum aestivum sp. aestivum) cultivar Bob White26, including both untransformed (wild-type) and transgenic derivatives, or cultivar Westonia were grown in 15 cm pots under standard glasshouse conditions with natural daylight and a temperature regime of 25° C. maximum during the day and 15° C. minimum at night. To provide barley leaf tissue for gene expression studies, grain was germinated in the lab in vermiculite and the first leaf was harvested after 7 days. The corresponding wheat leaves were harvested from plants after 9 days. For the grain development gene expression studies, heads of greenhouse grown plants were tagged at anthesis and grain was harvested every 4 days post anthesis (DPA). The whole caryopsis was used at 0 and 4 days post anthesis and the embryo and pericarp were removed from all other samples except the 28 day sample from which the pericarp could not be removed. For the coleoptile gene expression studies, grain was germinated in water in the dark on vermiculite and the coleoptile was harvested at 3, 4, 5, 6 and 7 days post imbibition. Mature coleoptiles were harvested from grain germinated in the light following emergence of the first leaf. In contrast to the dark grown coleoptiles, the mature coleoptiles were shorter and green.

DNA, RNA Isolation and cDNA Synthesis

Plant DNA was isolated from fully expanded leaf tissue using a CTAB based method according to Murray and Thompson (1980). Briefly, one gram of tissue frozen and ground in liquid nitrogen was extracted for one hour with 5 ml of CTAB extraction buffer at 60° C., followed by extraction with 5 ml of chloroform, inverted for 3 minutes and centrifugation at 5,000 g for 10 minutes. The supernatant was removed and DNA was precipitated by adding 2/3 volume of isopropanol followed by centrifugation at 2,000 g for 5 minutes. The pellet was washed with 70% ethanol and air dried before resuspension in 0.5 ml of 10 mM Tris, 1 mM EDTA pH 8.0 with 20 µg/ml RNAse A. The concentration and integrity of the DNA was determined by agarose gel electrophoresis and staining with ethidium bromide.

Total RNA was isolated from vegetative tissues using an RNAeasy kit (Qiagen, catalog number 74904) according to the manufacturer's instructions. RNA was isolated from developing endosperm using a phenol-SDS extraction solution and precipitation of RNA from the aqueous phase using LiCl according to Clarke et al., (2008). The RNA concentration in the preparations was determined spectrophotometrically and the integrity of the RNA was determined by agarose gel electrophoresis and staining with ethidium bromide. RNA was treated with DNAse using a "DNA-free" kit (Ambion, catalogue number 1906) to remove any residual DNA in the preparations, and then cDNA was synthesised from the RNA template using SuperscriptIII reverse transcriptase (Invitrogen, catalogue number 18080-044) according to the manufacturer's instructions.

Milling of Wheat Flour

The moisture content of wheat grain was measured by NIR using a FOSS 5000 machine according to the manufacturer's instruction and then conditioned to 14% moisture by mixing with the required amount of water overnight and then milled on a Brabender Quadrumat Junior mill into white flour and bran fractions. The fractions were combined and then sieved through 300 µm and 150 µm screens. Material collected on the 300 µm screen was considered bran and that retained by the 150 µm screen was pollard and was discarded while material passing through the 150 µm screen was considered white flour (endosperm). A wholemeal wheat flour was prepared by milling conditioned grain on a cylcone mill fitted with a 1 mm screen.

Analysis of the BG Content in Cereal Grains

Since milled whole grain flour was derived from and representative of the whole grain, the BG content of the grain was measured by assaying the BG content of the milled whole grain flour (w/w), as follows. Single grains were ground to a fine wholemeal flour with a single ball bearing in a dentists amalgam mixer (WIG-L-BUG, Dentsply). Such flour from mature single grains was analysed for BG content using a scaled down version of the lichenase enzymatic method (AACC Method 32-33, Megazyme assay kit, McCleary and Glennie-Holmes 1985). Briefly, 20 mg of flour in a 2 ml screw cap Eppendorf tube was resuspended in 1 ml of sodium phosphate buffer and incubated at 90° C. for one hour with shaking. The sample was cooled to 42° C. and 40 µl of lichenase (50 U/ml) was added and the sample incubated for one hour with occasional shaking. Following centrifugation at 13,000 g for 5 min, triplicate 10 µl samples (or 20 µl for low BG samples such as wheat) of the supernatant were transferred to a 96 well microtitre plate. One sample in each triplicate was treated as a blank by adding 10 µl of sodium acetate buffer, while the other two were each treated with 10 µl of betaglucosidase (2 U/ml) for 15 min at 42° C. The amount of released glucose in each sample was measured by adding 200 µl of GOPOD reagent, then colour development was allowed to take place at 42° C. for 20 minutes and the absorbance was measured at 510 nm. The amount of BG was calculated by reference to glucose standards and normalised against the barley reference standard supplied with the Megazyme assay kit. The BG contents are expressed as a weight percentage (w/w) of the milled whole grain flour, on a dry weight basis using the formula given in the Megazyme kit.

Analysis of the Structure of BG

The fine structure of the BG was examined by lichenase digestion and fluorescent labelling of the oligosaccharides followed by separation by capillary electrophoresis. This method was more sensitive than the traditional HPAEC method (Wood et al., 1991) and had the added advantage of being quantitative. In the lichenase/fluorescent labelling method, each oligosaccharide was labelled with only one fluorescent tag at the reducing end, so the signal strength was independent of oligosaccharide length and the molar ratio of the oligosaccharides was therefore directly proportional to the fluorescence signal.

After wheat flours were treated with the lichenase digestion in the Megazyme assay as described above, samples were centrifuged for one minute at 10,000 g. Samples of 100 µl of supernatant were dried in a Speedivac. The oligosaccharides were then fluorescently labelled by reductive amination with 8-amino-1,3,6-pyrenetrisulfonic acid (APTS) and separated by fluorophore-assisted-capillary electrophoresis (FACE) with laser induced fluorescence detection as described in O'Shea et al., 1998. The fluorescent signal in each of the peaks corresponding to the DP3 and DP4 oligosaccharides was integrated, and the ratio of these areas calculated to provide the DP3/DP4 ratio. (DP3 divided by DP4). As determined by this fluorescence method, this ratio is a molar ratio, not a weight/weight ratio. This method has also been used for the analysis of oat BG structure (Colleoni-Sirghie et al., 2003).

Water Solubility of BG in Flour Samples

In a first method, water solubility of BG in flour samples was determined using a method that included a heat inactivation step to inactivate endogenous enzymes, as follows. Samples of 100 mg flour were heated at 80° C. in 1.8 ml of 80% ethanol in screw capped tubes with shaking for 1 hour in an Eppendorf Thermomixer. This step inactivated any endogenous enzymes which would break down polymeric cell wall material in the subsequent steps, while the ethanolic nature of the solvent prevented any polymers from being solubilised and removed. However, sugars and other ethanol-soluble oligosaccharides would be removed from the flour samples in this ethanolic treatment step. Following centrifugation at 10,000 g for 1 min, the pelleted flour was resuspended in 1 ml of 20 mM sodium phosphate buffer pH 6.5 and incubated at 37° C. for 2 hours with shaking to extract water soluble components. The sample was spun again and the supernatant removed and collected—this water fraction contained the water-soluble (water-extractable) BG. The pellet (water insoluble fraction) was resuspended in 1 ml of the same buffer. Aliquots of both fractions, water-soluble and water-insoluble, were taken for assay of BG content using the scaled down Megazyme assay described above. Duplicate samples were assayed. Soluble and insoluble BG contents were calculated as % of dry weight of the flour, i.e. a BG content of 1% dry weight is equivalent to 10 mg of BG per gram dry weight of flour. In the calculation, flour was assumed to contain 10% (w/w) moisture—the moisture content of several flour samples from well dried grain was determined by near-infrared (NIR) spectroscopy and found to be about 10% (w/w). Total BG was calculated as the sum of the soluble and insoluble BG.

In a second method, used less often, water solubility of BG in flour samples was determined as described by Aman et al., (1987). This method does not use the heat inactivation step.

Dietary Fibre Determination

Total and soluble dietary fibre of the cereal flours were determined by the AOAC Official method 991.43 with minor modifications (Lee et al., 1992). The modifications were the use of 25 ml hexane in total for lipid extraction (not 25 ml per gram), the use of 80% and absolute ethanol for washing residues instead of 78% and 95% ethanol solutions and washing residues at 60° C. instead of 70° C. as stated in the AOAC method.

Determination of physicochemical and nutritional properties of wheat comprising elevated BG.

The nutritional composition of the fibre-enhanced wheat flour, including fibre content and composition, levels of macronutrients, antioxidant capacity and other relevant attributes are determined using standardised analytical procedures (Official Methods of Analysis of AOAC International (AOAC; 2002). Levels of lipid are determined gravimetrically after extraction with a mixture of chloroform:methanol (1:1, v/v), using the method of Daugherty (1983), (AOAC method 983.23). The total nitrogen level is determined by the Dumas oxidation technique using the method of Kirsten et al (1984) with a Carlo Erba nitrogen analyser. Following complete and instantaneous oxidation of the sample, the resulting gases are passed through a reduction furnace and a series of scrubbing columns prior to the nitrogen being measured using a thermal conductivity detector. The protein value is calculated by applying a multiplication factor of 6.25. For neutral NSP (NNSP), a modified version of the GC method of Theander et al., (1995; AOAC method 994.13) is used which employs a scaled-down procedure using a 2-hour hydrolysis with dilute sulphuric acid (1 M) followed by centrifugation for the insoluble NNSP, and a further hydrolysis using 2M trifluoroacetic acid for the soluble NNSP. Total starch was determined according to the enzymatic method of McCleary et al (1994) using a commercial assay kit (K-TSTA, Megazyme International Ireland Ltd., Bray, Ireland). The ash content was determined by igniting approximately 1 to 4 g of freeze dried sample in a muffle furnace for 15 h at 540° C. as outlined in the AOAC method 923.03 (1923). The weight of the ash was determined by difference. Simple sugars are extracted using method 982.14 of the Association of Official Analytical Chemists and quantified by HPLC using appropriate standards. Total starch was analysed as free glucose after α-amylase & amyloglucosidase digestion using a commercial procedure (Total Starch Assay Kit, Megazyme Ltd, Melbourne, Australia) that was based on the method of McCleary et al. (1994). Resistant starch (RS) content and glycemic index (GI) were predicted using an in vitro incubation system which modeled the buccal, gastric and pancreatic phases of food digestion as occurs in the human upper gut (Bird, Usher, Klingner, Topping and Morell, see WO2006/069422). Duplicate samples of the test flour and relevant reference foods are placed in a flask and mixed with artificial saliva (250 U/mL of α-amylase) at pH 7.0. After 15-20 s, the mixture is incubated with acidified (0.02M HCl) pepsin (1 mg/mL) at 37° C. for 30 min. The solution is then adjusted to pH 6.0 and the sample treated with pancreatin (2 mg/mL) and amyloglucosidase (28 U/mL) at 37° C. in 0.2M acetate buffer (pH 6.0) in a shaking water bath. For glycemic index (GI), aliquots of supernatant are sampled at designated time points for up to 5 h and glucose concentration determined using an automated electrochemical procedure. The predicted GI of the sample is calculated as the percentage of available carbohydrate converted to glucose and released during the time course of the incubation. For resistant starch (RS), the incubation period is extended for several more hours and the amount of starch remaining in the sample at that time determined using conventional enzymatic and spectrophotometric techniques. The predicted RS content of the sample is calculated as the amount of starch remaining in the digest as a percentage of sample weight.

Example 2. Cloning of Wheat CslF and CslH Genes

Introduction. The (1,3;1,4)-β-D-glucan (herein BG) content of cereal grains varies amongst the cereal species with barley, oats and rye having the highest amounts and wheat, maize and rice have relatively low levels (Fincher and Stone, 2004). For example, wild-type barley normally has about 4% BG with some barley lines having considerably more BG, whereas wheat grain typically has less than 1% BG, normally about 0.5-0.8%, on a dry weight basis. In barley, BG forms the main component of cell walls in both developing endosperm and mature endosperm (Izydorczyk and Dexter, 2008). In contrast, BG is the main cell-wall component of wheat endosperm only at early grain development stages whereas arabinoxylans accumulate at the beginning of cell differentiation and by grain maturity form 70-80% of the endosperm cell-walls (Philippe et al., 2006a, 2006b).

The CslF6 gene in barley was shown to encode an active BG synthase (Burton et al., 2008). More recently, Doblin et al., (2009) have shown that the barley CslH gene also encodes a BG synthase, and the authors concluded that both the CslF and CslH gene families contributed to BG synthesis in barley. In barley, overexpression of HvCslF6 led to an increase in the BG levels in transgenic grain by up to about 80% (Burton et al., 2011). In wheat, in contrast, overexpression of CslH in the developing endosperm resulted in an increase of about 100% of the BG level in mature grain, from about 0.69% of grain weight to a maximum of 1.9% (WO2009/079714). The authors commented that this level of BG had never been seen before in wheat. Nemeth et al. (2010) showed that the endogenous CslF6 gene was expressed in wheat and was required for production of normal levels of BG that is present in wild-type wheat endosperm. However, they did not over-express CslF6 in wheat and there was no indication whether the level of CslF6 expression in wheat was limiting the BG accumulation or whether other genes were limiting in wheat.

At the beginning of this study, it was not known whether genes other than CslH would increase BG levels when expressed from a transgene in wheat endosperm, and the present inventors therefore tested several CslF genes, in particular the CslF4, CslF6, CslF7 and CslF9 genes in transgenic wheat. The inventors therefore first cloned candidate wheat Csl genes and determined their expression patterns in wheat plants, as follows.

Isolation of cDNA Clones Corresponding to TaCslF and TaCslH Genes.

Total RNA was isolated from one week old leaf and seedling tissue of wheat cultivar Saratovskaya29 using an RNAeasy kit. This was used for SMART cDNA library construction. RNA was also isolated from developing grain of wheat cultivar Westonia by a phenol/SDS method using LiCl precipitation of RNA as described in Example 1 and used for cDNA synthesis. Complementary DNA (cDNA) was synthesised using Superscript III reverse transcriptase at 50° C. according to the manufacturers instructions (Invitrogen) and 5' and 3' SMART RACE was performed as described (Burton et al., 2008).

Expressed sequence tag sequences and corresponding consensus sequences were identified from NCBI and TIGR databases by BLAST searches using the available CslF and CslH sequences from barley (Burton et al., 2008). Wheat ESTs TC276200 and TC261037 were homologous to the 3' half of CslF3, TC244207 and TC256381 to the 3' half of CslF4 and TC275889 and TC250370 were homologous to the 5' and 3' ends of CslF6. Singleton TC255929 corresponded to the 3' end of CslH and BJ280995 to the central portion of CslF8. There were no EST sequences homologous to HvCslF7 in the databases. Sense primers were designed based on the barley sequences around the initiating methionine codon (SJ114, SJ115, SJ116, SJ117, SJ118, SJ30 and SJ163 for CslF3, CslF4, CslF6, CslF7, CslF8, CslF9 and CslH respectively, see Table 1 for sequences), in order to isolate cDNAs corresponding to these genes. To isolate the full length cDNA including 5'- and 3'-UTRs, the 5' end of the cDNA encoding wheat CslF10 was isolated by 5'RACE using nested primer pairs UPM-SJ150 and NUP-SJ155. Nested primer pairs for isolation of the 3' ends of the cDNAs by 3'RACE were: UPM-SJ60 and NUP-SJ14 for CslF4, UPM-SJ113 and NUP-SJ48 for CslF6, UPM-SJ61 and NUP-SJ56 for CslF8, and UPM-SJ113 and NUP-SJ03 for CslF9 (primer sequences in Table 1). Annealing was performed at 55° C. for all primers. Sense and antisense primers were designed to the consensus sequence or 3'RACE sequence and used for isolation of genomic and cDNA fragments to enable a full length protein coding consensus sequence to be assembled for each gene.

Full length cDNAs were isolated from wheat cultivar Westonia endosperm cDNA (4 days post anthesis) using primer pairs SJ116-SJ156 (CslF6), SJ118-SJ158 (CslF8), SJ165-SJ166 (CslF10) and SJ163-SJ164 (CslH).

No wheat sequences or ESTs corresponding to the rice CslF1, CslF2 or CslF5 genes were found in databases.
Isolation of Genomic Clones for TaCslF and TaCslH Genes.

Amplification was performed on DNA isolated from leaves from wheat plants of cultivar Chinese Spring in order to isolate genomic CslF and CslH sequences, including their introns. Cloning of genes from bread wheat was complicated by the fact that *Triticum aestivum* is a hexaploid with three subgenomes, commonly designated the A, B and D genomes. However, genomic clones including the full-length protein coding regions were successfully isolated from the wheat cultivar Chinese Spring using primer pairs SJ162-SJ156 for CslF6, SJ278-SJ147 for CslF7, and SJ163-SJ164 for CslH. Full length cDNA and genomic clones were obtained from each of the three genomes for most but not all of the CslF and CslH genes. The position and size of the introns were determined for each gene by comparing the cDNA and genomic sequences. The position and size of the introns in comparison to the corresponding barley genes are shown schematically in FIG. 1.

A CslF3 consensus nucleotide sequence was assembled from the nucleotide sequences from the cDNA (amplified with primer pair SJ114-SJ38) and genomic sequences (amplified with primer pairs SJ114-139 and SJ44-SJ31). A TaCslF3 cDNA sequence is provided as SEQ ID NO:1, and a TaCslF3 polypeptide amino acid sequence is provided as SEQ ID NO:2. A CslF4 consensus nucleotide sequence was assembled from the sequences of cDNAs (amplified with primer pairs SJ115-SJ13 and SJ14-NUP) and genomic sequences (amplified with primer pairs SJ115-SJ140 and SJ115-SJ157). cDNA sequences corresponding to the three wheat CslF4 genes are given in SEQ ID NOs: 3-5, the corresponding CslF4 genomic sequences including two introns each as SEQ ID NOs: 6-8, and the encoded CslF4 amino acid sequences as SEQ ID NOs: 9-11. cDNA sequences corresponding to the three wheat CslF6 genes are given in SEQ ID NOs: 12-14, the corresponding CslF6 genomic sequences including introns (where isolated) each as SEQ ID NOs: 15-17, and the encoded CslF6 amino acid sequences as SEQ ID NOs: 18-20. These probably represent, in order, the CslF6 genes from the A, B and D genomes. SEQ ID NOs: 21, 22 and 23 are the nucleotide sequence of a cDNA encoding CslF7, a genomic (partial length) clone and the encoded amino acid sequence, respectively. The CslF9 consensus nucleotide sequence was assembled from the sequences of cDNAs (amplified with primer pairs SJ30-5J135 and SJ03-NUP) and genomic sequences (amplified with primer pairs SJ30-101 and SJ152-SJ37). Partial length or full-length cDNA sequences corresponding to the three wheat CslF9 genes are given in SEQ ID NOs: 24-26, the corresponding CslF9 genomic sequences including introns (where isolated) each as SEQ ID NOs: 27-29, and an encoded CslF9 amino acid sequences as SEQ ID NO: 30. cDNA sequences corresponding to the three wheat CslH genes are given in SEQ ID NOs: 31-33, the corresponding CslH genomic sequences including introns (where isolated) each as SEQ ID NOs: 34-36, and the encoded CslH amino acid sequences as SEQ ID NOs: 37-39. These probably represent, in order, the CslH genes from the A, B and D genomes.
Discussion of the Wheat Genes and Polypeptides.

Like barley, each genome of hexaploid wheat had seven CslF genes (CslF3, CslF4, CSlF6, CslF7, CslF8, CslF9 and CslF10) and a single CslH gene. The positions of introns and splice junction (GT . . . AG) sequences were conserved in wheat and barley. In general, the sizes of the introns were similar between corresponding wheat and barley genes and some of the difference could be explained by the presence or absence of repetitive or transposon sequences. For instance, the second intron of the barley HvCslF9 gene had an Islay MITE insertion compared to the wheat sequence and the first intron of wheat TaCslF3 was slightly larger than the corresponding gene in barley and had a 30 bp sequence which was found in other barley genes. The first intron of both the wheat and barley CslF8 genes was much larger than all the other introns due in part to the presence of retrotransposons—in wheat of a sequence with homology to a Stowaway MITE from *Aegilops tauschii* and in barley to a Stowaway MITE Hades. The differences in intron sequences did not appear to affect splicing of the introns. cDNA sequences were obtained for all genes that corresponded to correctly spliced mRNAs. However, it was not determined whether the intron splicing efficiency was the same for the wheat genes relative to the corresponding barley genes.

All of the wheat genes encoded proteins of similar size to the corresponding barley proteins (Table 2) and all had the same number of predicted transmembrane domains, two towards the amino terminus and six towards the carboxy terminus for a total of eight per polypeptide (FIG. 1). All of the amino acids reported to be necessary for glycosyltransferase activity, namely D, DxD, ED and QxxRW amino acids (Pear et al., 1996), were conserved in the wheat proteins. Analogous to the barley HvCslF6 protein, the wheat TaCslF6 protein had an extended loop of about 50 additional amino acids compared to the other CslF proteins. The 50 additional amino acids were amino acids 517-566, 513-561 and 516-565 of the A, B and D genome encoded CslF6 proteins, respectively. All of the polypeptides have a signal sequence that directs them to the Golgi membrane system, but this sequence is not cleaved off.

The wheat TaCslH gene had eight introns, the same number of introns as the rice OsCslH1 gene and one more than the HvCslH gene isolated from the barley cultivar Golden Promise (Doblin et al., 2009) which lacked the penultimate intron. Isolation of the HvCslH gene from the hulless barley cultivar Himalaya confirmed that it had eight introns like the wheat and rice genes (FIG. 1).

Example 3. Analysis of Expression of CslF and CslH Genes in Wheat

For analysis of endogenous gene expression, semi-quantitative RT-PCR was performed with HotStar Taq (Qiagen) DNA polymerase. In order to not saturate the amplifications, the number of cycles in each PCR reaction was adjusted in the range of 28-35 for Csl and CesA genes, and 24 cycles for the α-tubulin gene used as a control for quantitation of RNA loading. Real time PCR, which was more quantitative, was performed on a Rotorgene6000 (Qiagen) with Platinum Taq and SyBR green. The machine software was used to calculate expression differences based on comparative quantitation. Nucleotide sequences of the primers used are given in Table 1.

Expression Analysis of CslF and CslH Genes in Wheat—Coleoptile and Leaf Tissue

Figure 2:
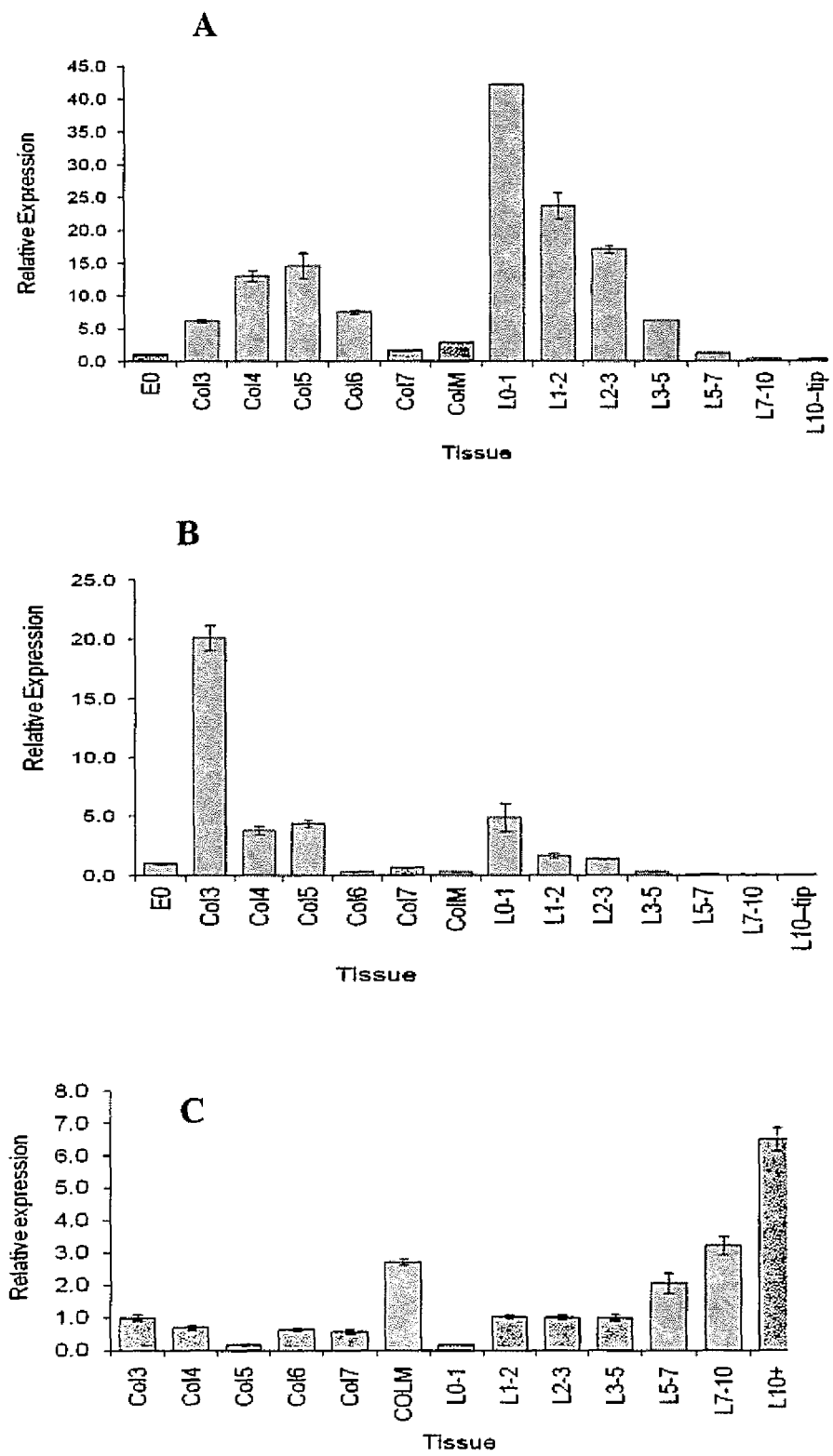
FIG. 2. Expression profiles of endogenous wheat TaCslF6 (panel A), TaCslF9 (panel B) and TaCslH (panel C) genes in coleoptile and leaf tissues. Expression was analysed by Real-time PCR in the indicated tissues (Col3, coleoptile 3 days post germination etc, ColM mature coleoptile. L0-1 leaf tissue 0-1 cm from base, E0 wheat endosperm 0 DPA). E0 samples were not analysed for CslH in this experiment but in other experiments the expression of CslH in E0 was approximately 0.25 the level in the Col3 sample. Expression is shown relevant to the first sample (E0 or Col3). Error bars show standard deviation of triplicate measurements.

Based on the semi-quantitative RT-PCR results, the expression of the more highly-expressed wheat CslF genes, namely TaCslF6 and TaCslF9, and the TaCslH gene was examined using Real-time PCR. Data are shown in FIG. 2 for the expression of these genes along an elongating leaf and over a time-course in coleoptile tissue (3-7 days post-germination) and in mature coleoptile. Of these genes, the wheat TaCslF6 gene was by far the most highly expressed TaCslF gene in all vegetative tissues examined, expression being higher in leaf than coleoptile. TaCslF6 expression was high in elongating tissues, young coleoptiles and lower leaf sections and declined in mature coleoptiles and towards the leaf tip. Expression was also lower in young endosperm tissue (FIG. 2A). The wheat TaCslF9 gene was expressed maximally in elongating tissues in the youngest coleoptile and lowest leaf section (FIG. 2B) and was lower in the leaf than the coleoptile and lower still in the developing grain. In contrast, the wheat TaCslH gene was expressed at highest levels in mature tissues that had completed elongation such as the mature coleoptile and leaf tip (FIG. 2C).

Expression of CslF and CslH Genes in Developing Wheat and Barley Grain

Figure 3:
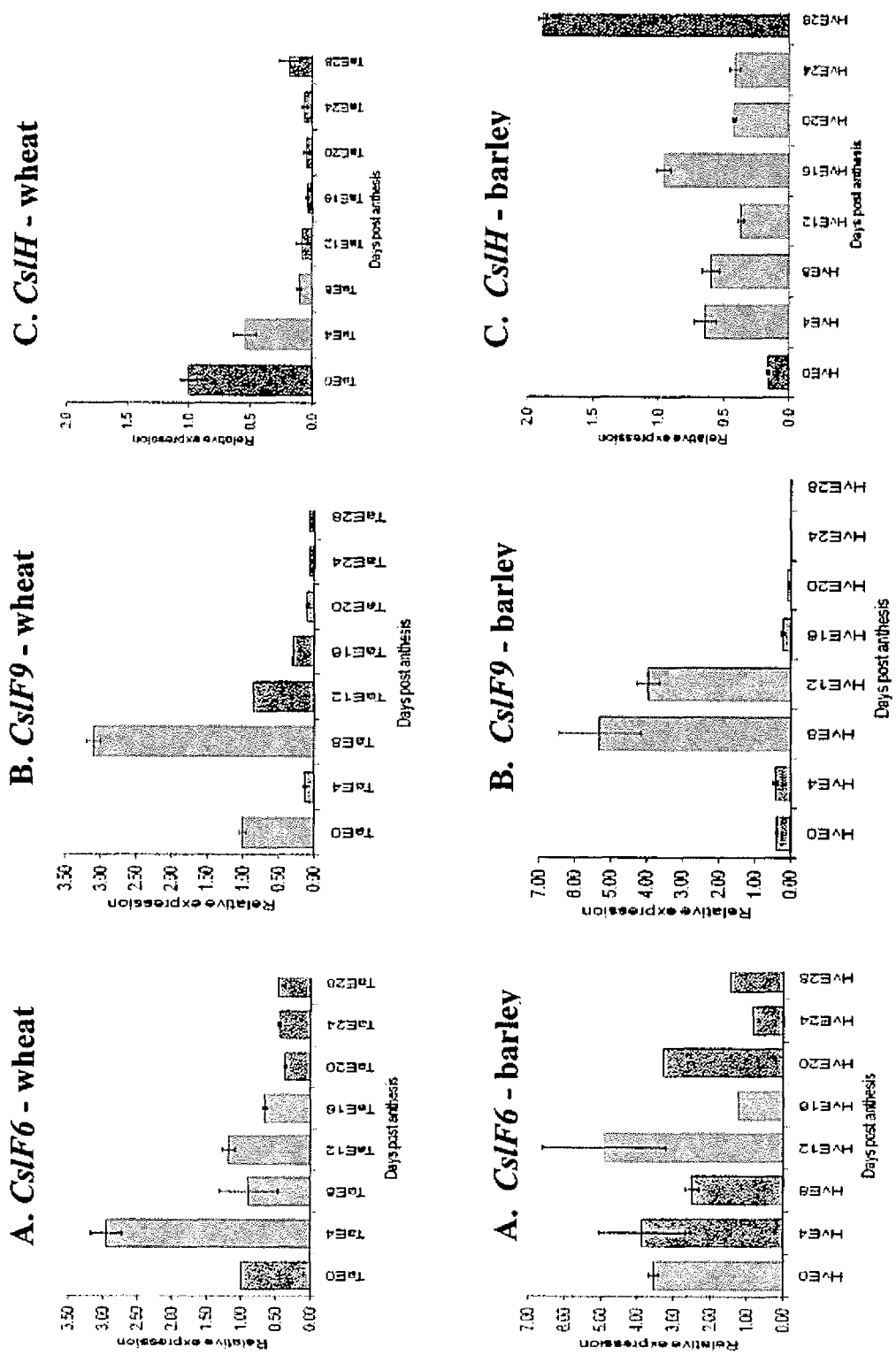
FIG. 3. Expression profiles of CslF6 (panel A), CslF9 (panel B) and CslH (panel C) genes in developing wheat and barley endosperm tissues. Expression was analysed by Real-time PCR in the indicated tissues (Ta=wheat; Hv=barley; TaE0=wheat endosperm at 0 DPA etc, HvE0=barley endosperm at 0 DPA etc). Expression is shown relative to the first sample (TaE0) in each panel. Error bars show standard deviation of triplicate measurements.

To investigate gene expression during grain development and to compare the expression in wheat and barley, Real-time PCR was performed on cDNA made from RNA extracted from wheat and barley endosperm at 4 day intervals from the day of anthesis (labelled TaE0, HvE0, respectively) up to 28 days post anthesis, and using the primers listed in Table 1. The data are shown in FIG. 3, showing the expression level relative to the E0 samples (E0=endosperm at 0 DPA), where the data was normalised against the amount of input RNA rather than against the expression of a control endogenous gene due to the large differences in developmental stages between the tissues. Levels of mRNA expressed from housekeeping genes such as sucrose synthase 1 and α-tubulin were also assayed and were greatest early in seed development at about 4-12 DPA. These profiles were reproducible and reflected the metabolic state of the developing grain as it proceeded through the development phases from (i) cellularisation and division early on (0-14 DPA), followed by (ii) a differentiation phase (14-28 DPA) with maximal starch and cell wall synthesis and then (iii) a slower maturation and dessication phase (28 days and following). The wheat TaCslF6 gene was the most highly expressed gene in the developing grain and was expressed at high levels throughout development (FIG. 3A), with the greatest expression in the sample 4 days post anthesis. The barley HvCslF6 gene was expressed at similar although slightly higher maximum levels at about 1.5-fold greater levels than for the wheat TaCslF6 gene, and expression also declined at late stages of grain development (FIG. 3A). The next most highly expressed gene, TaCslF9 peaked around 8 DPA in wheat and expression fell off dramatically after this (FIG. 3B). The barley HvCslF9 gene showed a similar expression level and pattern although expression at 12 DPA was higher than in wheat (FIG. 3B). Expression of the other HvCslF genes in developing barley grain was ten to a hundred fold lower, near the limit of reproducible detection and no distinct pattern of expression could be discerned (Burton et al., 2008). This was also the case in wheat and no consistent differences could be detected. In summary, the individual CslF genes in developing wheat grain were expressed in a similar pattern to the barley CslF genes, and it was considered that the substantial difference in BG content between wheat and barley grain was not likely to be due to differences in CslF gene expression during grain development.

The major difference observed between developing wheat and barley grain was the expression of the CslH gene (FIG. 3C). In barley, expression of the HvCslH gene was lowest in the youngest stage and expression increased during development, peaking at 28 DPA. In contrast in wheat, expression of TaCslH gene was highest in the youngest tissue and from 8 DPA and subsequent stages, expression was very low, such that the expression level in wheat endosperm was observed at about 10-fold lower levels than in barley at later stages of development (FIG. 3C). The expression profile of the TaCslH gene was therefore the opposite of the HvCslH gene, and this gene was therefore considered the likely cause to explain the differences in BG accumulation in grain between these species.

Discussion Wheat has much lower levels of BG in the endosperm compared to barley and some other cereals. The experiments described above set out to determine a possible reason for this. A comparative analysis of the CslF and CslH genes in wheat and barley was undertaken including isolation of the wheat genes (Example 2) and an analysis of gene expression in both vegetative tissues and developing grain (Example 3). This showed that wheat had a full complement of CslF and CslH genes, each of which are expressed, so the lower level of BG in wheat relative to barley was not caused by lack of a particular CslF or CslH gene or expression of a particular gene. The full length genes that were isolated from wheat all encoded proteins of similar length to the barley orthologs. Although there were some amino acid differences between the species, none of these were in completely conserved residues such that they were likely to affect enzymatic activity of the encoded proteins.

The expression of the most abundant wheat CslF and CslH genes in vegetative tissues also appeared to be similar to that of barley. The TaCslF6 gene was constitutively expressed at high levels, although expression was much lower in the upper half of the leaf and especially low in the leaf tip. The TaCslF9 gene was expressed at highest levels in elongating tissues such as the base of leaf and young coleoptile while the reverse was true for TaCslH, which was highest in differentiated tissues such as mature coleoptiles and leaf tips. In the developing endosperm, the TaCslF6 and TaCslF9 genes showed the same expression pattern as the barley homologues although at slightly lower levels but probably not different enough to explain the large difference in BG composition of the endosperm between the species. In contrast to expression in vegetative tissues, in developing endosperm the TaCslH gene was expressed in a different manner compared to the barley HvCslH gene in both temporal pattern and abundance. Whereas the HvCslH gene increased in expression as the endosperm matured and reached a maximum at 28 DPA, the TaCslH gene was maximally expressed at 0 and 4 DPA and expression declined steeply after that, so that at 28 DPA there was about a 10 fold lower expression of the TaCslH gene. In barley, BG biosynthesis predominantly occurred in the later stages of development after about 19 days (Coles, 1979; Seefeldt et al., 2009) so this difference in expression of the CslH gene between wheat and barley suggested a role for the CslH gene in controlling BG levels of the grain.

In Examples 2 and 3, the genes in the wheat CslF and CslH gene families were isolated and their expression profiles compared to those of the barley genes. It was found that wheat has a full complement of CslF and CslH genes and that a lower level of CslH during late endosperm development was hypothesized to explain the low levels of BG in the grain. This was tested as described in the following Example.

Example 4. Expression of a Chimeric Gene Encoding Barley HyCslH in Wheat Endosperm To test whether the observed differences in expression pattern, namely the lower level and altered timing, of the TaCslH gene in developing wheat grain compared to the HvCslH gene in barley contributed to the much lower levels of BG in the mature wheat grain, a construct was designed and made to over-express the barley HvCslH protein in transgenic wheat grain using an endosperm specific promoter, as follows. A genomic HvCslH sequence (SEQ ID NO:49) was used in case there were any regulatory sequences contained in the introns of the barley gene that might affect expression of the gene and contribute to the difference in expression.

Vector Construction and Plant Transformation

A full length cDNA sequence of the HvCslH gene was described in WO2009/079714. A chimeric gene comprising the protein coding region of HvCslH was isolated from genomic DNA and used to transform wheat plants. Based on the cDNA sequence, oligonucleotide primers SJ91 and SJ85 (Table 1) were designed for the 5' and 3' ends, respectively, of the protein coding sequence of the gene. These were used to amplify a DNA fragment including 3203 bp of barley DNA using genomic DNA obtained from barley plants of cultivar Himalaya as the template sequence in the amplification reaction. The fragment was inserted into the plasmid vector pCRBluntII TOPO (Invitrogen). The nucleotide sequence of this fragment plus flanking 12 bp nucleotide sequences from the vector, as an EcoRI fragment, is given in SEQ ID NO: 49. The introns in the gene correspond to nucleotides 339-437, 769-867, 994-1107, 1228-1331, 1545-1637, 1759-1817, 2048-2081, 2505-2655 in SEQ ID NO:49. The genomic HvCslH sequence was excised from the vector and inserted as an EcoRI fragment between a 1.9 kb fragment of the high molecular weight glutenin Bx17 promoter (pBx17) and the nos3' polyadenylation/terminator region in pZLBx17nosCas vector. The pBx17 promoter was used in the construct because it was known to confer high level and preferential expression in developing endosperm ("endosperm-specific promoter", Reddy and Appels, 1993). The resultant chimeric DNA construct was used to transform wheat plants of the Bob White 26 cultivar using the biolistics method of Pellegrineschi et al., (2004) using 50 mg/L G418 as the selection agent to select for transformed cells. To do this, the expression vector encoding HvCslH and a second plasmid (pCMSTSL2neo) comprising a NPTII selectable marker gene under the control of a CaMV 35S promoter sequence were mixed in equimolar amounts and co-bombarded into the scutella of immature embryos of Bob White 26 plants. Regenerated plants were screened for the presence of the transgene by PCR assays using DNA extracted from young leaf tissue with the RedExtractnAmp™ kit from Sigma.

Fourteen independently-transformed wheat plants were generated following antibiotic selection and were grown in a glasshouse to produce seed after self-fertilisation. Eleven of these plants were confirmed to be transgenic by PCR for the expression construct encoding the barley HvCslH protein. All of the transformed lines appeared phenotypically normal. Approximately fifteen days after anthesis, RNA was extracted from pools of three developing grains (T1 seeds) from each plant and expression of the introduced gene encoding barley HvCslH was monitored by real time PCR using primers specific for the HvCslH transgene (SJ183 and SJ85, Table 1). As a control gene for normalising expression levels of the introduced gene, expression of an endogenous α-tubulin was also assayed. At least five of the plants showed expression of the chimeric gene encoding barley HvCslH. The observed expression levels (Table 5) were several hundred-fold up to about 2000-fold greater than that of the lowest expressing PCR negative line, which was presumed to be a non-transformed line that had come through the transformation process. A full length cDNA clone of the barley HvCslH transgene transcript was isolated from line H1-5B with primers SJ163 and SJ164 (Table 1) and sequenced to show that the barley introns were correctly spliced in the transformed wheat plants.

Expression of the transgene was analysed by real-time PCR of cDNA from single or duplicate pooled T1 developing grain samples (approximately 15 DPA). The expression level was normalised against expression of a tubulin gene and is shown (Table 5) relative to the sample with the lowest level (Line H1-2) which represents the wild-type expression level. In addition, BG levels were determined on wholemeal flour from single mature T1 grains from the same plants. The BG content of grain from PCR negative plants i.e. non-transgenic plants, was up to a maximum of 1.0%. In contrast, two of the plants expressing the chimeric gene encoding HvCslH lines had several grains with 1.9% (w/w) BG, representing an increase of at least 90% in the BG level. On average, T1 grain from the PCR positive lines had a significantly higher BG content than the PCR negative lines (0.96 vs 0.69% (w/w) respectively). However, this analysis did not distinguish between homozygotes and heterozygotes for the introduced transgene.

Six to eight individual T1 plants of each line were grown, self-fertilised and T2 seed produced. The T2 seeds were PCR screened for the presence of the chimeric gene encoding HvCslH. Line 9 showed all PCR positive progeny, suggesting that this line was homozygous and this was confirmed in further generations. Other lines may also have been homozygous but the results of the first test were inconclusive.

At about the mid-point of grain development, three pooled T2 seed from each T1 plant were analysed for expression of the transgene, and at maturity 3-5 single seeds were analysed for BG content. Lines 6, 9 and 10 showed the highest transgene expression at levels between 4-fold and 6-fold greater than the RNA level expressed from the endogenous α-tubulin gene used as a control for quantitation. Most of the mature grains had increased BG content up to a maximum of 2.4%. Line H1-6A5 also appeared to be homozygous for the transgene as all grain from this line had increased BG levels.

Figure 4:
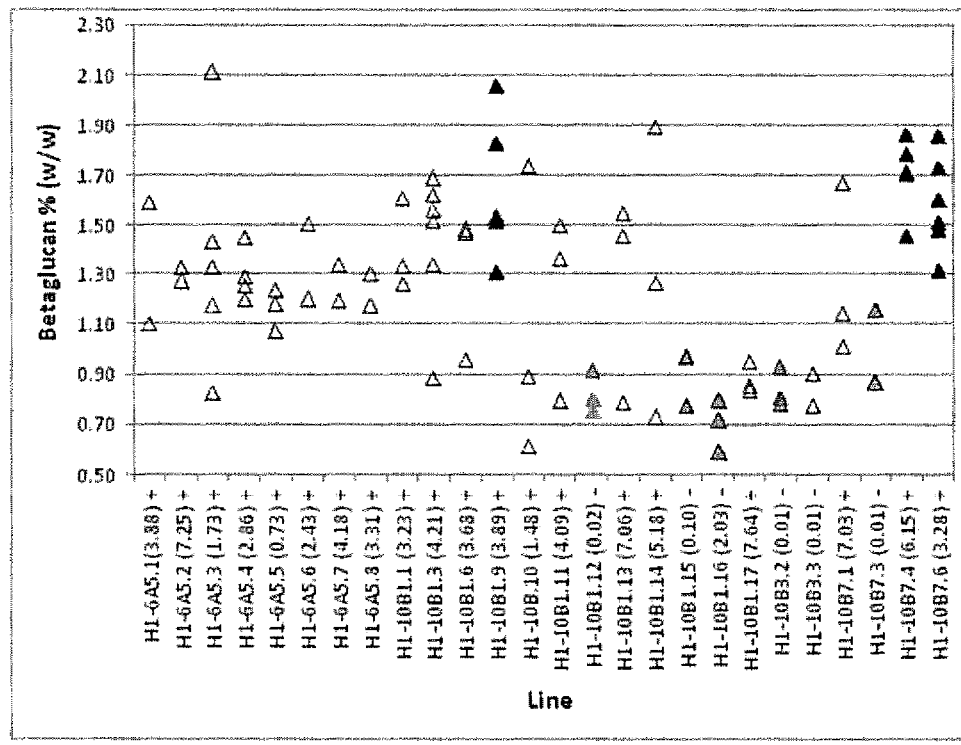
FIG. 4. BG content of single T3 wheat grains expressing a chimeric gene encoding HvCslH. The BG content of wholemeal flour from single T3 seeds of lines H1-6A5, H1-10B1, H1-10B3 and H1-10B7 was determined using the Megazyme kit. Lines are identified with the relative expression level of the HvCslH transgene in pooled T3 mid-development grain, normalised against a-tubulin shown in brackets. A plus or a minus indicates a PCR positive or PCR negative screen of the T2 seedling leaf stage. Gray filled triangles represent PCR negative lines, black filled triangles are potentially homozygous lines and unfilled triangles are segregating lines (mixed homozygotes/heterozygotes).

Based on the gene expression data and BG results, seeds of four T2 lines (Lines H1-6A5, H1-9B2, H1-10B1 and H1-10B7) were sown and the resultant plants self-fertilised to obtain homozygous T3 lines. The chimeric gene expression levels and BG levels of the T3 grain were assayed; the data are shown in FIG. 4. Wild-type BG levels were generally in the range 0.6% to about 1.0% as indicated for the PCR negative lines (gray filled triangles in FIG. 4). All except one T3 grain of line H1-6A5 had increased BG content. All T3 grain from lines H1-10B1.9 and H1-10B7.4 and H1-10B7.6 (dark filled triangles in FIG. 4) had increased BG content, suggesting homozygosity of the transgene in those grains. Screening of further generations confirmed homozygosity for all these lines. These lines together with line H1-10B7.3 as a negative segregant (i.e. wild-type) were bulked up to obtain more than 200 g of pooled T4 grain for further analysis, as described in Example 5.

Example 5. Analysis of BG Levels in Wheat Grain Transformed with an Exogenous Gene Encoding HvCslH The T4 grain from the HvCslH overexpressing lines looked phenotypically normal except for about an 18-20% decrease in average grain weight, from about 44 mg per wild-type grain to about 32-35 mg per transgenic grain, determined as an average weight of 100 grains. Samples of this grain were (i) ball milled to produce wholemeal flour or (ii) milled with a Buhler Quadrumat roller mill which separated the flaky bran from the white endosperm flour, thus producing endosperm flour ("white flour"), and each fraction was analysed for BG content as described in Example 1. This was done for T4 wheat grain from one negative segregant (H1-10B7.3 as a wild-type control) as well as for three homozygous HvCslH over-expressing lines. BG levels of duplicate samples were analysed with a Megazyme kit. Part of the lichenase digest from these samples was fluorescently labelled and analysed by FACE to determine the ratio of the DP3 and DP4 oligosaccharides. The dietary fibre levels of the white flour were determined according to enzymatic-gravimetric AOAC Official Method 991.43. The data are recorded in Table 6.

Wholemeal flour from the negative segregant grain (i.e. wild-type line H1-10B7.3) had 0.8% BG whereas the bran fraction had higher BG levels at 1.78%. The endosperm flour of this wild-type had a low BG content of 0.26% on a dry weight basis. In contrast, flour from plants expressing the chimeric HvCslH gene had increased BG content relative to the wild-type. The BG content of the wholemeal flour from the highest-expressing line had doubled to about 1.6% (w/w) (Table 6) and the endosperm flour had up to a 3.5-fold increase to 0.9% (w/w) compared to the control. The BG content of the bran also increased from 1.78% to 2.39% (w/w), probably due at least in part because of contamination with adhering endosperm fragments which were visible as white specks on the large bran flakes. This incomplete separation of the endosperm from the bran is often seen in small scale milling as these machines are less efficient than commercial mills.

As arabinoxylan (AX) is the major component of wheat endosperm cell walls, the pentosan content of the endosperm and bran fractions was also determined. This showed that there was a slight increase in the pentosan level of the endosperm in the high BG lines and there was a corresponding decrease in the pentosan levels of the bran from the same lines compared to the negative segregant control line.

Fine Structure and Water Solubility of BG in the Transgenic Grain

The structure of the BG isolated from the transgenic grain, isolated by the method described in Example 1, was examined after lichenase digestion and FACE analysis (O'Shea et al., 1998). BG from wholemeal wheat flour from the negative segregant grain had a DP3/DP4 ratio of about 2.4, while for BG from the bran the ratio was about 2.6. The ratio for BG from the endosperm flour was lower at about 1.9 (Table 6). The DP3/DP4 ratio of BG isolated from grain from the three wheat lines over-expressing HvCslH showed slight variation from each other, but overall the values were not significantly different to the ratios observed for wild-type wholemeal, bran and endosperm flours. The range in DP3/DP4 for BG from wholegrain was 2.30-2.44, while for BG from endosperm it was 1.89-1.99.

Figure 5:
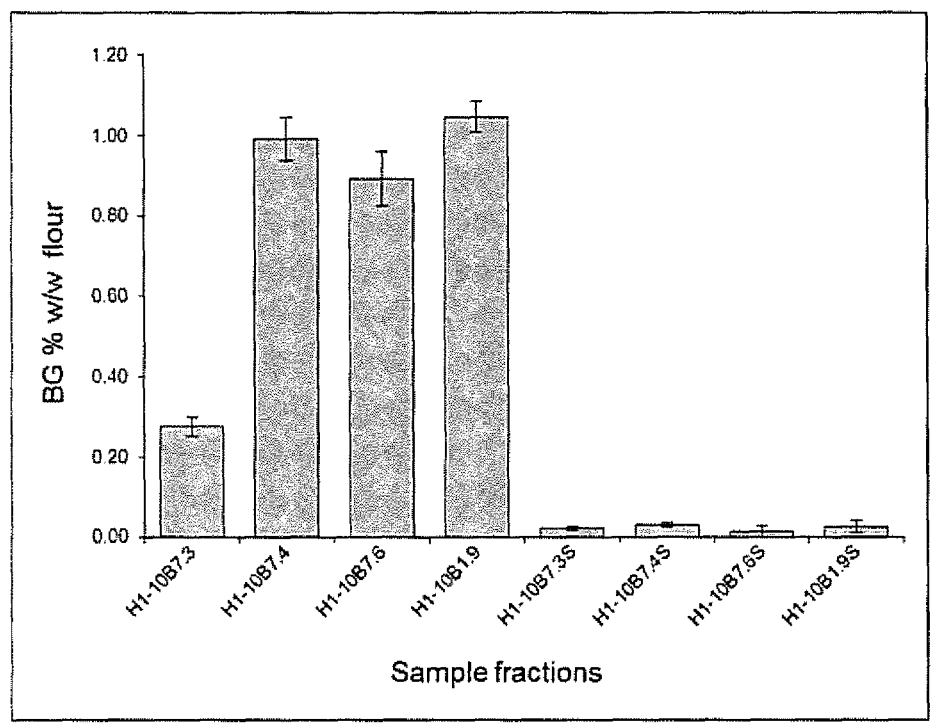
FIG. 5. Total BG content and soluble BG content in endosperm flour of T4 homozygous wheat HvCslH lines. The BG content of endosperm flour from three homozygous T4 lines H1-10B7.4, H1-10B7.6 and H1-10B1.9 and a negative segregant line H1-10B7.3 was determined using the Megazyme kit (first four bars). The amount of BG solubilised by an aqueous wash for 2 hours at 40° C. is also shown, indicated by an S after the sample name (bars 5-8). Error bars show standard deviation of triplicate measurements.

In wild-type wheat grain, very little BG is soluble (Beresford and Stone, 1983). The solubility of BG from wheat endosperm flour from the HsCslH transgenic grain was determined by extraction in aqueous buffer for 2 hours at 40° C. as described in Example 1. Under these conditions, about 7% of the BG in the control grain of line H1-10B7.3 was water-soluble (FIG. 5). Similar levels of water-soluble BG were found in the endosperm flours of the transgenic HvCslH grain although as a proportion this represented between 1 and 3% of the total BG in the grain.

It was concluded that although the BG content increased significantly in the HsCslH transgenic grain, the DP3/DP4 ratio in the BG and the amount of water-soluble BG had not changed.

Analysis of Dietary Fibre Levels in Endosperm Flour

While the proportion of soluble BG appeared not to have increased in the transgenic HvCslH grain, the levels of dietary fibre in white flour were also determined by the Prosky AOAC Official method 991.43 (Lee et al., 1992). This standard method uses high temperatures and thermostable starch hydrolysing and protease enzymes to simulate digestion of cooked foods in the human digestive tract. Analysis of the control endosperm flour confirmed that white flour had low levels of soluble and total dietary fibre at 0.7% and 2.4% of the dry weight, respectively (Table 6). In contrast, and unexpectedly, all three transgenic HvCslH lines showed large increases in both soluble and total dietary fibre in the white flour. Grain of line H1-10B1.9 showed more than a two fold increase with 1.8% soluble and 5.3% total dietary fibre.

Discussion When the low levels of endogenous TaCslH gene expression late in endosperm development were supplemented by introduction and expression of the chimeric gene encoding HvCslH, including the introns as found in the native barley gene, the BG content of the grain was increased substantially up to 2.1% (w/w) in transgenic grain compared to 0.6 to 1.0% in wild-type grain. Such a level of BG was unknown in non-transformed wheat or its wild progenitors (Pritchard et al., 2010). In bulked T4 grain from homozygous HvCslH transgenic lines, there was a two fold increase in BG content in wholemeal flour and a 3.5-fold increase from 0.26% to about 0.9% BG in white (endosperm) flour. Structural analysis of the BG after lichenase digestion showed that there were no changes in the DP3/DP4 ratio, indicating that the extra BG in the endosperm had a similar structure to the wild-type BG. There was also no change in the proportion of water soluble BG as both the wild-type and high BG lines showed only low levels of water soluble BG. Surprisingly, there were increases of about 2-fold in levels of soluble and total dietary fibre in the endosperm flour compared to the normal wheat flour. The difference in solubility between the two assays may be explained by the extraction conditions as the first step of the BG solubility assay involves heating the flour suspension in an 80% ethanol solution to inactivate endogenous enzymes, whereas the dietary fibre assay has no inactivation step and the endogenous hydrolytic enzymes could act on the cell wall and release more carbohydrate. The fibre assay also measured arabinoxylan and other fibre components.

Example 6. Isolation of Sequences Encoding Various HvCslF and CslH Proteins and Testing their Functionality in *Nicotiana benthamiana*

Several barley CslF genes are described in WO2007/014433. In order to prepare constructs for transformation of wheat for heterologous expression of the barley CslF proteins, the coding regions were isolated from either cDNA or genomic DNA and inserted in expression constructs as follows. Several of the constructs included, at the 5' end of the protein coding regions, a nucleotide sequence encoding a T7 epitope tag of 11 amino acids having the amino acid sequence MASMTGGQQMG (amino acids 1-11 of SEQ ID NO: 41), thereby adding the 11 amino acids to the N-terminus of the encoded proteins. This epitope was included to aid detection and quantitation by Western blot analysis of the protein expressed in transgenic grain, since commercial antibodies specific for this epitope were available. As shown below, addition of the T7 tag did not affect enzyme activity of the T7-added proteins compared to the wild-type proteins. Aside from the T7 tags, the encoded proteins were not modified in amino acid sequence relative to the wild-type barley proteins in cultivar Himalaya.

Cloning of cDNA Encoding HvCslF4

Total RNA was isolated from barley cultivar Himalaya leaf and seedling tissue using the RNAeasy kit (Qiagen). RNA samples were treated with RNAse-free DNAse (Ambion) before cDNA synthesis. Five micrograms of the RNA preparation was used to make cDNA using 10 pmol of the RoRidT17 primer and Superscript III reverse transcriptase (Invitrogen) for one hour at 50° C. in a 20 µl reaction according to the manufacturer's instructions. A full length cDNA corresponding to HvCslF4 was amplified from the leaf cDNA using primers SJ253 and SJ254 and Advantage 2 Taq DNA polymerase mix (Clontech Cat No 639201) according to the manufacturer's instructions. The amplification reaction used the green buffer with an initial cycle of 2 min at 94° C. followed by 30 cycles of 94° C. for 20 sec, 58° C. for 20 sec and 68° C. for 3 min. This amplification added the nucleotide sequence encoding the eleven amino acid T7 epitope tag in the same reading frame at the N-terminus of the HvCslF4 protein. The cDNA product was cloned into the pCR2.1-TOPO vector and sequenced. A sequencing error in the 3' end of the gene was corrected by replacing a SpeI-ClaI fragment from another HvCslF4 3'RACE construct cloned in the same orientation and vector.

Cloning of cDNAs Encoding HvCslF6

Two nucleic acid fragments each containing a full length protein coding region from cDNA corresponding to the HvCslF6 gene were amplified with (i) primers SJ116 and SJ77, or (ii) with primers SJ277 and SJ77. The 5' primer SJ277 included the nucleotide sequence encoding the T7 epitope tag (as above) while the 3' primer (5J77) was specific to the 3' untranslated region. The second amplification therefore included the T7 epitope tag sequence, whereas the first did not. The template nucleic acid was barley leaf cDNA prepared from RNA obtained from barley plants of cv. Himalaya (as above). The amplifications used Phusion DNA polymerase (New England Biolabs, catalogue number F-5305) with GC buffer and 3% DMSO according to manufacturer's instructions. The cycling conditions in the amplifications were: 98° C. for 30 sec, followed by 30 cycles of 98° C. for 7 sec, 15 sec at 63° C. and 72° C. for 1 min followed by a 5 min extension at 72° C. The use of GC buffer and DMSO was essential to amplify a full length coding region since, without this optimisation of PCR conditions all of the obtained clones had a deletion at the 5' end of the coding region. This may have been caused by the Taq polymerase skipping over a hairpin structure formed by a GC rich region near the 5' end of the barley CslF6 coding region. The approximately 3 kb PCR products were gel purified using an Illustra (GE Healthcare) kit and inserted into the pCRBluntII TOPO cloning vector (Invitrogen) and sequenced. One clone named HvCslF6_277-77 23 contained an intact open reading frame.

Cloning of a Genomic Region Encoding HvCslF7

A full length clone containing the protein coding region of the HvCslF7 gene (genomic clone) was amplified from barley cultivar Himalaya with primers SJ112 and SJ111. The amplifications used Phusion DNA polymerase with HF buffer according to manufacturer's instructions. The PCR reactions used initial denaturing conditions of 30 sec at 98° C. followed by 35 cycles of 98° C. for 7 sec, 57° C. for 15 sec and 72° C. for 2 min. The amplified fragments were dA tailed with HotStarTaq (Qiagen) according to the Invitrogen manual and cloned into the pCR2.1-TOPO vector (Invitrogen). The clone was designated HvCslF7g_112-111_1.

Cloning of a Genomic Region Encoding HvCslF9

A full length clone containing the protein coding region of the HvCslF9 gene (genomic clone) was also amplified from barley cultivar Himalaya with primers SJ30 and SJ99. The amplifications used Phusion polymerase with HF buffer according to manufacturer's instructions. The PCR reactions used initial denaturing conditions of 30 sec at 98° C. followed by 32 cycles of 98° C. for 7 sec, 56.5° C. for 15 sec and 72° C. for 2 min. The amplified fragments were dA tailed with HotStarTaq (Qiagen) according to the Invitrogen manual and cloned into the pCR2.1-TOPO vector (Invitrogen). The clone was designated HvCslF9g_30-99_2.

Expression of Full Length Coding Regions in Wheat

The full length HvCslF genes described above were expressed in wheat endosperm as described in detail in Example 7.

Isolation of Full Length cDNA for Expression in *Nicotiana benthamiana* Leaves

Full length CslF and CslH coding sequences were amplified from barley, wheat and oat seedling or 4DPA endosperm cDNA by using BDTaq or Phusion DNA polymerase with primers as detailed in Table 7. The amplified DNA fragments were inserted into TOPO vectors, sequenced and then inserted into the plant expression vector as described below. Cloning and functional analyses of the full length CslF6 coding sequences are described in Examples 2, 9 and 10.

Assessing the Functionality of Sequences Encoding Barley CslF Proteins by Transient Expression in *Nicotiana benthamiana* Leaves The functionality of the barley, wheat and oat CslF and CslH coding regions was initially assessed by transient expression of 35S-driven constructs in *Nicotiana benthamiana* leaves and analysis of the BG content in cell wall fractions from the leaves. Briefly, the full length CslF or CslH protein coding regions were excised from the TOPO vectors and ligated between the CaMV 35S promoter and the nos3' polyadenylation/terminator region in a binary expression vector pORE0235S which was a derivative of pORE02 with the CaMV 35S promoter inserted at the SfoI site at the 5' end of the polylinker (Wood et al., 2009). An example of such a plasmid is pSJ38.

The binary vector constructs were electroporated into *Agrobacterium tumefaciens* strain AGL1 and transformed colonies selected on media containing 100 mg/L kanamycin and 5 mg/L rifampicin. Transient expression in *N. benthamiana* leaves was carried out essentially as described in Wood et al., (2009). Agrobacterial cultures were used at an optical density (A600) of 0.4. They were mixed with an *Agrobacterium* strain pGV3101 containing a T-DNA for expression of the P19 viral silencing suppressor, included to reduce small RNA-induced gene silencing following transient introduction of the T-DNAs into the leaf tissue and thereby increasing the expression level and persistence of the transgenes. Each gene was under the control of the CaMV 35S promoter. Mixtures of the *Agrobacterium* cells were infiltrated into the underside of the top three fully expanded leaves of five week old *N. benthamiana* plants grown at 24° C. in a 16/8 light dark cycle. Leaves were harvested after five days and freeze dried.

The BG content of the inoculated leaf samples was assayed as follows. Firstly, dried leaf samples were ground to a powder and a crude cell wall preparation was made from 20 mg of ground leaf material by heating it for 30 min at 80° C. in 1.8 ml of 80% ethanol in a 2 ml tube with mixing. Each supernatant was removed after centrifugation at 10,000 rpm for 5 min and the pelleted residue was re-extracted in the same volume of 80% ethanol at 80° C. for 10 min. After centrifugation, the pellet was washed at room temperature for 10 min in 50% ethanol with a final 5 min wash in 20 mM sodium phosphate buffer pH 6.5. The pellet was resuspended in 0.5 ml of the same buffer and material was solubilised by heating at 90° C. for 30 min with mixing. The sample was cooled to 50° C. and BG was assayed with a Megazyme kit. Briefly, the sample was incubated for 2 hr with 20 µl (1 U) lichenase (Megazyme) to digest the BG, centrifuged at 10,000 rpm for 5 min and a sample was removed for BG assay by further digestion with β-glucosidase. The released glucose was quantitated spectrophotometrically against glucose standards as described in the Megazyme kit protocol.

Dicotyledonous plants do not ordinarily make BG so the presence of BG in the *N. benthamiana* leaves was also assayed by FACE detection of the released oligosaccharides in the lichenase digests (O'Shea et al., 1998). Lichenase cleaves only at a (1,4)-β-D-glucosidic linkage following a (1,3)-β-D-glucosidic linkage, releasing oligosaccharides with a degree of polymerisation (DP) of mainly DP3 and DP4 (G4G3G and G4G4G3G,) from BG (Lazaridou and Biliaderis, 2007). To determine the proportion of DP3 and DP4 oligosaccharides released by lichenase digestion, and thereby the DP3:DP4 ratio, 100 µl samples prepared as described in the previous paragraph but without the β-glucosidase digestion were dried in a Speedivac and the oligosaccharides in each sample fluorescently labelled by reductive amination with 8-amino-1,3,6-pyrenetrisulfonic acid (APTS). The labeled products were then separated by fluorophore-assisted-capillary electrophoresis (FACE) with laser induced fluorescence detection as described by O'Shea et al., (1998). The advantage of this method was that each oligosaccharide had a single fluorophore attached and the signal response from the detector was therefore independent of the oligosaccharide length, unlike in HPAEC methods with a pulsed amperometric detector where each oligosaccharide had a different response factor depending on the length. By this method, the oligosaccharides were readily quantitated.

In several independent experiments, the construct encoding the barley CslF6 protein directed the synthesis of considerable amounts of BG as measured by the Megazyme assay (Tables 8 and 9). In contrast, BG was not detected when constructs for expression of any of the cereal CslF polypeptides other than CslF6 were introduced. Control leaves always showed zero levels of BG in the Megazyme assay and no BG derived oligosaccharides (i.e. DP3 and DP4) could be detected after lichenase digestion or FACE analysis. In contrast, very small amounts of DP3 and DP4 oligosaccharides were detected from expression of the barley CslH coding sequence in *Nicotiana benthamiana* leaves but this was below the limit of detection by the Megazyme assay. To detect these oligosaccharides it was also necessary to concentrate the lichenase digest on graphitized carbon SPE cartridges before fluorophore labeling and FACE analysis.

Example 7. Production of Transgenic Wheat Plants Overexpressing the Barley CslF Genes in Developing Endosperm HvCslF9 Vector Construction The full length coding region for HvCslF9 from the pCR2.1 TOPO vector was inserted as an EcoRV-KpnI fragment into the BamHI-KpnI site of pZLBx17CasNK after treatment of the BamHI site with DNA polymerase I-Klenow fragment. The resultant plasmid was designated pSJ2. This introduced EcoRI sites between the Bx17 promoter and nos3' ends which were used for further cloning. The EcoRI HvCslF9 fragment of pSJ2 was excised and the vector religated to create pSJ5. This expression vector thereby had a 1.9 kb fragment comprising a high molecular weight glutenin Bx17 promoter and a nopaline synthase polyadenylation region/terminator (nos3') flanking a multiple cloning site (MCS), thus providing the regulatory regions for expression of any protein coding region in the developing endosperm of wheat. The MCS had BamHI, SmaI, KpnI, SacI and AflII sites. The Bx17 promoter is preferentially expressed and confers high level expression in developing endosperm tissue in cereals such as wheat (Reddy & Appels 1993). The expression cassette was flanked by XbaI, HindIII and NotI restriction sites so the entire cassette could be excised and inserted into other vectors.

HvCslF6 Vector Construction

The full length barley HvCslF6 coding region including the T7 epitope tag at the N-terminus was excised from the pCRBluntII TOPO vector as an EcoRI fragment and inserted into the EcoRI site of plasmid pSJ5. The resultant plasmid with the T7-HvCslF6 coding region was designated pSJ33.

HvCslF4-T7 Vector Construction

The DNA region encoding HvCslF4 with the N-terminal T7 tag was excised from the pCR2.1 TOPO vector as an AflII fragment and inserted into the same site of pSJ5 to create pSJ11.

HvCslF7 Vector Construction

The full length coding region for HvCslF7 was excised from the pCR2.1TOPO vector as an EcoRI fragment and cloned into the EcoRI site of pSJ2 to create pSJ3.

The length of each of the encoded polypeptides was as detailed in Table 10.

Production of Transgenic Wheat Plants Overexpressing HvCslF4, F6, F7 and F9

Each of the constructs for expression of the barley CslF proteins were used to produce transformed wheat plants of the cultivar Bob White 26 using the biolistic method (Pellegrineschi et al 2002) with 50 mg/L G418 as the selection agent, as described above for the HvCslH construct. For example, the HvCslF6 expression vector pSJ33 and a second plasmid with the CaMV 35S promoter driving expression of the NPTII selectable marker (pCMSTSL2neo) were mixed in equimolar amounts and co-bombarded into immature wheat embryos. Regenerated plants were screened for the presence of the transgenes by extracting DNA from young leaf tissue using the RedExtract-N-Amp™ kit (Sigma) and performing PCR reactions on the DNA preparations using a gene specific and a vector specific primer pair, followed by electrophoresis of the products on agarose gels. The appearance of the following sized sized DNA fragments on the gels indicated the presence of the transgene in the plants:

| Transgene | 5' primer | 3' primer | size (basepairs) |
|---|---|---|---|
| HvCslF4T7 | SJ244 | SJ81 | 599 |
| HvCslF6T7 | SJ242 | nosR | 268 |
| HvCslF7 | SJ123 | nosR | 680 |
| HvCslF9 | SJ217 | nosR | 289 |

Example 8. Analysis of Transgenic Wheat Plants Comprising HvCslF Genes

Expression Analysis of HvCslF Transgenes in Wheat by Real Time-PCR

In order to measure the expression level of the HvCslF transgenes in the transformed wheat lines, total RNA was isolated from three developing grains from each plant, collected approximately 15 days post anthesis (DPA). The RNA preparations were DNAse treated to remove any contaminating DNA, and RNA samples reverse transcribed with Superscript III according to the manufacturer's instructions (Invitrogen). PCR reactions were performed using Platinum Taq DNA polymerase. The cDNA was diluted and used in PCR reactions at a level equivalent to 1 ng of original RNA per microlitre. Quantitative Real time PCR was performed on triplicate samples on a Rotorgene6000 machine using Platinum Taq, SybrGreen and primers SJ242 and SJ77 (Table 1) for the HvCslF6 transgene and HvTUBF and HvTUBR primers for the endogenous alpha-tubulin reference gene (Accession number Y0840) and an annealing temperature of 60° C. Expression levels of the gene encoding HvCslF6 were calculated using the machine software and compared to the level of expression of the alpha-tubulin gene in the same sample. Cycling conditions were denaturation at 95° C. for 15 sec followed by 45 cycles of 94° C. for 20 sec, 60° C. for 20 sec, and 72° C. for 30 sec using Platinum Taq polymerase (Invitrogen Cat No. 10966-034) according to the manufacturer's instructions.

The 3' primer that was used in these PCR reactions (SJ77) was specific for the HvCslF6 transgene because it corresponded to a region in the 3' untranslated region of the transgene which was not conserved between wheat and barley, and therefore did not anneal to the endogenous wheat CslF6 genes or transcripts. Thus, any amplification products generated in the Real time PCR and therefore the output signals were specific for the transgene.

Fifteen, five and four PCR positive T0 wheat plants were obtained which were transformed with the HvCslF9, HvCslF4T7 and HvCslF7 constructs, respectively. Real time PCR of the HvCslF9 plants with primer pair SJ97 and SJ93, demonstrated that five of them were expressing the HvCslF9 transgene at high levels (2,000 to 10,000 times that of a PCR negative plant) in the developing endosperm at approximately 15 DPA. This expression level was stable in the T2 generation, but homozygous plants at the T3 generation had silenced the transgene and expression was at background levels. Analysis of BG content of single grains from any generation did not show any increase compared to the control or PCR negative lines. Similarly, the BG content of grain from HvCslF4T7 and HvCslF7 PCR positive lines showed no differences from the controls and these lines were not studied any further, nor were expression levels of the transgenes determined.

Generation of Wheat Plants Expressing HvCslF6 in the Grain

The full length barley HvCslF6 coding region with the T7 epitope tag at the N-terminus (HvCslF6_277-77_23) in pSJ33 was used to transform Bob White 26 wheat plants using the biolistics method. The HvCslF6 expression vector pSJ33 and a second plasmid with the CaMV 35S promoter driving expression of the NPTII selectable marker (pCMSTSL2neo) were mixed in equimolar amounts and co-bombarded into immature wheat embryos. Transgenic plants were screened for the presence of the transgene using young leaf tissue and the RedExtractnAmp™ kit (Sigma) and primers SJ242 and nosR. Five plants were confirmed to be transgenic by PCR for the HvCslF6-encoding transgene and the NPTII gene and were grown in the glasshouse to maturity along with PCR negative control plants from the transformation process. Complementary DNA was made from pooled T1 grain sampled at approximately 15 days post anthesis (DPA) and expression of the transgene was monitored by real time PCR and compared to the level of beta-tubulin. The endogenous wheat CslF6 gene expresses at about 0.005 the level of beta-tubulin and three of the primary transformants showed significantly increased levels of the HvCslF6 mRNA at 1.52, 0.92 and 0.22 that of tubulin (line F6-1, F6-6 and F6-21 respectively).

Analysis of the BG content in the T1 wheat grains was determined as described in Example 1 and expressed as a weight percentage (w/w) of the milled whole grain flour from the grain. That is 1% (w/w) was equivalent to 10 mg of BG per gram of material.

The BG content of single mature T1 grains showed that the PCR negative controls (i.e. equivalent to wild-type) and line F6-21 had BG levels of about 0.9% (w/w) whereas line F6-6 had increased levels up to about 1.7%. Moreover, six out of seven grains from line F6-1 had more than 3% BG up to a maximum of about 4.1%.

Figure 6:
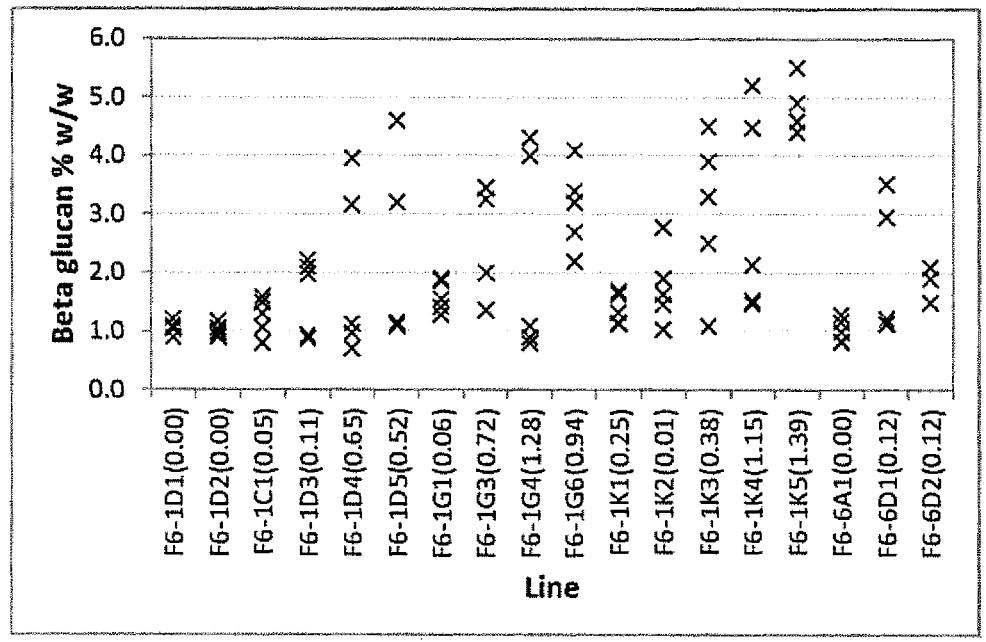
FIG. 6. BG levels in individual wheat T2 grains transformed with a chimeric gene for expression of HvCslF6. BG was determined in flour from five mature grains from each line as indicated. Expression of the HvCslF6 gene was measured by real time PCR from cDNA made from three pooled grain at approximately 15 DPA and is shown relative to the endogenous beta tubulin expression (in brackets after the line number). Lines F6-1D1 and F6-1D2 were PCR negative T1 plants (null segregants=wild-type). All other lines were expressing the HvCslF6 transgene.

A total of 24 T1 grains from lines F6-1, F6-6 and F6-21 were germinated and tested for the presence of the HvCslF6 transgene by PCR and grown as before in the glasshouse. Monitoring of transgene expression at mid maturity of T2 grain showed that line F6-21 no longer expressed the HvCslF6 gene whereas line F6-6 showed slightly decreased expression at 0.12-fold relative to that of tubulin. Most grains from line F6-1 had high levels of HvCslF6 expression at about 0.2-1.39-fold relative to tubulin, although some lines (for example, F6-1C1, F6-1D3 and F6-1K2) showed much lower levels of HvCslF6 expression (FIG. 6, numbers in brackets). It was noted that the transgene was still segregating in these lines. Both F6-1 and F6-6 showed an approximate 3:1 segregation ratio, and as only three grain were pooled to make cDNA, the expression levels were only an approximation of the expression level of the homozygous state. Analysis of the BG levels in mature single T2 grains from these plants did indeed show that most lines were still segregating with some grain having BG contents close to that of the PCR negative lines F6-1D1 and F6-1D2 (FIG. 6). In general, those lines that had high levels of HvCslF6 expression had the highest level of BG; F6-6 lines generally had lower expression than F6-1 lines and these had significantly higher BG levels with many having more than 4% BG and for line F6-1K5 all five grains had BG between 4.4 and a maximum of 5.5%.

Figure 7:
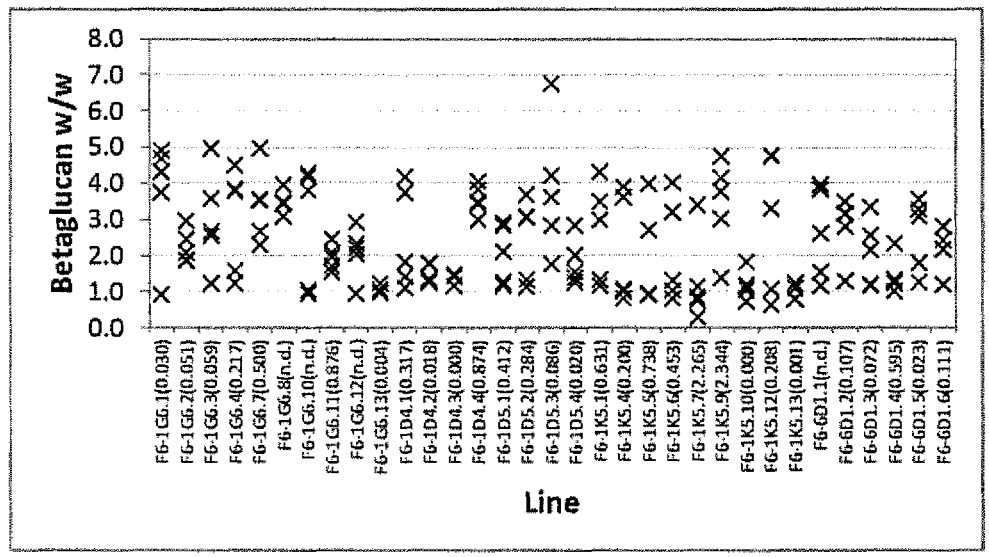
FIG. 7. BG levels in individual wheat T3 grains transformed with a chimeric gene for expression of HvCslF6. BG was determined in flour from five mature grains from each line as indicated. Expression of the HvCslF6 gene was measured by real time PCR from cDNA made from three pooled grain at approximately 15 DPA and is shown relative to the endogenous beta tubulin expression (in brackets after the line number). Lines F6-1G6.13 and F6-1K5.13 were PCR negative T1 plants and all other lines are expressing the HvCslF6 transgene.

In order to get homozygous lines expressing the transgene, between 5 and 10 T2 grains from each of twelve F6-1 and one F6-6 T1 plants were germinated, PCR tested and grown in the glasshouse. Transgene expression at mid grain development and the BG content of mature grain was assayed. Expression of the HvCslF6 transgene appeared to be stable as most of the lines continued to show high levels of expression, similar to or higher than the expression level of the endogenous tubulin gene. The BG content in the T3 grain of most of these T2 plants was between 3% and 5%, with an occasional grain showing BG of greater than 5% (FIG. 7). Most of these lines appeared to be still segregating as some grains had BG levels similar to four negative PCR lines. However, lines F6-1G6.2, F6-1G6.8 and F6-1D4.4 potentially were homozygous as all grain had high BG (FIG. 7) Again, F6-1 lines had higher mRNA levels and BG levels than F6-6 lines.

Phenotypic Appearance of Grain is Altered in Some Lines Expressing HvCslF6 at High Levels The original T0 plants had relatively poor seed set and reduced grain size as the plants were flowering at the hottest time of the year in the glasshouse although this was most obvious in those lines that showed expression of the transgene encoding HvCslF6. Many of the mature grains from plant F6-1 exhibited a reduced size and wrinkled appearance. This was most obvious for plant F6-1 and was also observed in many but not all high BG progeny of subsequent generations. All T3 grain of T2 plants F6-1D4.4 and F6-1G6.8 had a both a high BG content and a wrinkled and shrunken appearance whereas line F6-1G6.4 which was still segregating for low and high BG appeared morphologically normal, likewise the grain from the negative segregant line F6-1K3.2 which had wild-type levels of BG. The F6-6 grains and its progeny grains were not wrinkled or shrunken in morphology and the BG level in these grains was not as high as in F6-1 lines. Mature grain of negative segregants all had a normal appearance suggesting that the shrunken phenotype was linked to the HvCslF6 transgene in the F6-1 lines.

The BG Structure was Altered in the High BG HvCslF6 Lines

The fine structure of the BG was examined by lichenase digestion and fluorescent labelling of the oligosaccharides followed by separation by capillary electrophoresis. Lichenase digestion of wheat flour BG released oligosaccharides of mainly DP3 and DP4 (G4G3G and G4G4G3G), respectively with smaller amounts of longer oligosaccharides up to DP9. Calculating the molar ratio of the DP3 and DP4 peaks indicated that BG from an endosperm flour from wild-type wheat had a DP3/DP4 ratio of 2.5 which was slightly lower than that of the barley standard flour from Megazyme, while as expected, a wholegrain flour from oats had a lower ratio of 1.8. In the transgenic HvCslF6 wheat T2 single grain flours, the control negative segregants had a ratio of between 2.5 and 3, the same as the wild-type. However in those lines with increased BG levels, this ratio decreased to less than 2 in some cases (Table 9). Analysis of pooled (ten grains) flour from homozygous HvCslF6 wheat T3 lines clearly demonstrated that the high BG lines had low DP3/DP4 ratios, as low as 1.67 (Table 9), which was even lower than that of oat BG. This compared to the average DP3/DP4 ratio of 2.49 in the negative segregants and indicated that the BG structure was significantly different in the high BG lines.

Selection of Less Shrunken Grain with Increased BG Levels

Figure 8:
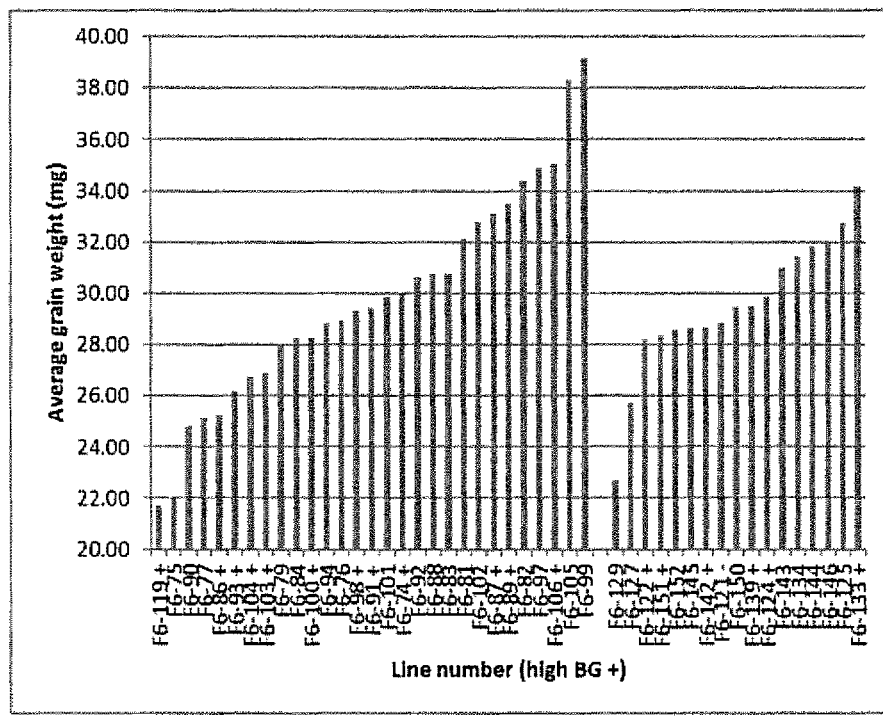
FIG. 8. Average T1 grain weights of T0 wheat lines with HvCslF6T7 and AsCslF6T7 genes. Average T1 grain weights of T0 lines. Lines F6-74 to F6-119 were transformed with HvCslF6T7 and lines F6-121 to F6-151 with AsCslF6T7. Lines showing increased BG in individual T1 grains are shown with a + after the line number. Line F6-121 is a PCR negative plant.

As noted before, grains of several of the homozygous HvCslF6 lines having high BG contents were shrunken and morphologically abnormal. As these were all derived from a single transformed line F6-1, further transformation experiments were undertaken with plasmid pSJ33 to determine if it was possible to get non-shrunken, normal grains having elevated levels of BG. Twenty nine new T0 HvCslF6 plants were generated of which fourteen showed individual T1 grains with increased BG content. While most high BG lines had lower than average grain weight, it was possible to obtain some high BG lines with high average grain weights e.g lines F6-87, F6-89 and F6-106 (FIG. 8). The maximum BG content of a single grain was 5.9% from line F6-90, 5.7% from F6-103 and 4.7% from line F6-87. These results demonstrated that it was possible to produce wheat grains containing high levels of BG and having a non-shrunken morphology.

Example 9. Cloning of CslF6 Genes from Other Species

Wheat CslF6

Two sequences were identified in available databases which encoded partial-length polypeptides which had similarity to barley CslF6, namely the ESTs TC275889 which appeared to include the 5' end of a wheat CslF6 and TC250370 which appeared to include the 3' end of a wheat CslF6. To isolate a full-length wheat sequence, total RNA was isolated from seedling tissue of plants of wheat cultivar Westonia using the RNAeasy kit (Qiagen). The RNA was treated with RNAse-free DNAse (Ambion) before cDNA synthesis. A 3'RACE library was made from the RNA using a Clontech SMART cDNA kit according to the manufacturer's instructions. The cDNA was then diluted to 100 microlitres with Tricine-EDTA and stored at 4° C. Subsequent PCR reactions were performed with Advantage 2 polymerase (Clontech) according to the manufacturer's instructions using the universal primer mix (UPM) and gene specific primer SJ113. The temperature cycling conditions were: denaturation for 1 min at 94° C., then 35 cycles of 94° C. for 30 sec, 30 sec at 55° C. and 72° C. for 2 min followed by a 5 min extension at 72° C. The resultant PCR reaction mixture was diluted 100-fold and used as template in a nested PCR using the nested universal primer (NUP) and a second internal gene specific primer (SJ123) with cycling conditions: denaturation for 1 min at 94° C., then 30 cycles of 94° C. for 30 sec, 30 sec at 58° C. and 72° C. for 90 sec followed by a 5 min extension at 72° C.

Several 3' RACE amplification products of about 800 bp were gel purified using an Illustra (GE Healthcare) kit and cloned into the pCR2.1 TOPO T/A cloning vector and sequenced. Three different sequence types were obtained.

These were presumed to correspond to the transcripts from each of the three wheat genomes (A, B and D). An antisense primer (SJ156) was designed in the 3' untranslated region that would match all three types and was used with a 5' primer (SJ162) to amplify cDNAs including the full-length protein coding regions corresponding to the transcripts for each of the three wheat genomes.

Five micrograms of seedling RNA was used to make cDNA using 10 pmol of the RoRidT17 primer and Superscript III reverse transcriptase (Invitrogen) for one hour at 50° C. in a 20 microlitre reaction according to the manufacturer's instructions. The cDNA was then diluted to 100 microlitres with Tricine EDTA and stored at 4° C. Full length cDNAs were amplified from first strand seedling cDNA using Phusion very high fidelity proofreading TaqPolymerase from Finnzymes (now available from NEB). One microlitre of diluted cDNA was amplified with primers SJ162 and SJ156 or SJ274 and SJ156 or SJ277 and SJ156 in 20 microlitre PCR reactions with GC buffer and 3% (w/v) DMSO according to the manufacturer's instructions. Cycling conditions were: 98° C. for 30 sec, followed by 35 cycles of 98° C. for 7 sec, 15 sec at 63° C. and 72° C. for 2 min followed by a 5 min extension at 72° C. PCR products around 3 kb in size were separated on a 1.0% TBE agarose gel, gel purified and cloned into the pCRBluntII II TOPO cloning vector and sequenced. Three clones named TaCslF6_277-156 23, TaCslF6_277-325 18 and TaCslF6_274-156_10 each contained an intact open reading frame encoding a wheat CslF6 polypeptide and corresponded to the CslF6 genes from the three wheat genomes. Their nucleotide sequences are given in SEQ ID NOs: 12-14 and the amino acid sequences in SEQ ID NOs: 18-20. They were used in functional expression studies in N. benthamiana and transgenic plants (below).

Oat CslF6

No sequences of oat CslF genes were identified in publically available databases so the genes were cloned using primers to conserved regions as follows. This used 5' and 3' RACE as well as conventional PCR. On the likelihood that CslF6 would be expressed in leaf tissue of oat seedlings, total RNA was isolated from the 2 cm regions of leaf tips of 12 day old oat seedlings (cultivar Matika) as well as whole 6-7 day old whole seedlings using RNAeasy columns (Qiagen) according to the manufacturer's instructions. The preparation was done without DNase treatment. Five micrograms of each RNA preparation was used to make cDNA using 10 pmol of the RoRidT17 primer and Superscript III reverse transcriptase in a 20 µl reaction. This involved annealing the primer with RNA at 70° C. for 10 min, cooling on ice before adding the remaining reagents and incubating at 50° C. for one hour. The reaction was terminated by heating at 70° C. for 10 min and the RNA template was degraded with 1.5 units of RNAseH at room temperature for 20 min. The cDNA was heated again at 70° C. for 10 min and then diluted to 100 µl with TE pH 8 and stored at 4° C.

PCR was performed with GoTaq polymerase (Promega) using one microlitre of oat seedling cDNA in a 20 µl PCR reaction, lx colourless buffer, 5 pmols of each primer, 0.2 mM dNTPs, 1.5 mM MgCl$_2$ and cycling conditions: denaturation for 2 min at 95° C., then 35 cycles of 95° C. for 30 sec, 30 sec at 58° C. and 72° C. for 2 min followed by a 5 min extension at 72° C. Primer pair SJ17 and SJ37 amplified several fragments around one kb in size as analysed by electrophoresis in a 1.0% TBE agarose gel. These fragments were gel purified and cloned into the pCRII TOPO T/A cloning vector and sequenced. One PCR product had a nucleotide sequence of 983 bp which had homology to wheat CslF6. From the region of homology, the sequence spanned the second and third exons of the oat CslF6 gene.

This sequence was extended using 5' and 3'RACE in order to clone a full-length oat CslF6 cDNA. The 5' and 3' RACE cDNA libraries were made from a mixture of RNAs from the leaf tip and seedling in a ten microlitre reaction using a Clontech SMART cDNA kit according to the manufacturer's instructions. The cDNA was then diluted to 1004 with Tricine-EDTA and stored at 4° C. Subsequent PCR reactions were performed with Advantage 2 polymerase (Clontech) according to the manufacturer's instructions using the universal primer mix (UPM) and a gene specific primer. Cycling conditions were: denaturation for 2 min at 95° C., then 35 cycles of 94° C. for 30 sec, 30 sec at 60° C. and 72° C. for 90 sec followed by a 10 min extension at 72° C. The resultant PCR mixture was diluted 100-fold and used as template in a nested PCR with the nested universal primer (NUP) and a second internal gene specific primer with cycling conditions: denaturation for 10 min at 95° C., then 35 cycles of 94° C. for 25 sec, 30 sec at 57° C. and 72° C. for 2 min followed by a 5 min extension at 72° C.

Alignment of the full length CslF6 cDNAs from barley, wheat and rice identified several regions which were conserved and sense and antisense primers, some degenerate, were designed to these regions. For 3'RACE, PCR with primer pairs SJ113-UPM and nested PCR with SJ123-NUP enabled amplification of an oat CslF6 3' RACE product of about 1000 bp in length. For 5' RACE, the same PCR conditions were used with primer pairs SJ37-UPM and nested PCR with SJ19-NUP. This enabled amplification of an oat CslF6 5' RACE product of about 600 bp in length. This RACE product did not contain the 5' end of the oat gene so additional rounds of 5'RACE were performed with new antisense primers designed specifically to the SJ19-NUP amplified fragment. Nested PCR with primers SJ265-UPM and SJ270-NUP extended the sequence to within approximately 30 bp of the predicted ATG methionine start of the full length gene. An additional antisense primer SJ272 was designed closer to the 5' end but this failed to extend the sequence any further despite repeated attempts. It was noted that the 5' region of the oat CslF6 gene was extremely GC rich and this was thought likely to produce significant secondary structure which could interfere with the extension of the Taq polymerase through this region. The 5'RACE procedure was repeated but with the inclusion of 3% DMSO to try and reduce the effect of the GC rich secondary structure. Additionally, the initial PCR protocol was modified by using a two-step PCR at a high annealing/extension temperature. PCR was performed with primer pair SJ265-UPM and cycling conditions: denaturation for 2 min at 95° C., seven cycles of 94° C. for 25 sec and 2 min at 72° C. then 32 cycles of 94° C. for 25 sec and 67° C. for 2 min followed by a 7 min extension at 67° C. Nested PCR was performed with primer pair SJ272-NUP with 3% DMSO and cycling conditions of denaturation for 1 min at 94° C., then 35 cycles of 94° C. for 25 sec, 25 sec at 60° C. and 72° C. for 1 min followed by a 5 min extension at 72° C. Sequencing of the cloned PCR products showed that these clones contained the 5' end of the oat CslF6 gene as stop codons were present upstream of the predicted initiating ATG methionine codon. The longest clone had more than 370 bp of the 5' untranslated leader sequence. Cloned PCR products contained sequences of the CslF6 gene from the three oat genomes. Shortly after identifying the full length oat CslF6 gene, a partial length oat CslF6 cDNA sequence was deposited in Genbank. This sequence (Accession number ACX85725) encodes a polypeptide of 891 amino acids and is missing 53 amino acids from the true N-terminus of the protein, further demonstrating the difficulty in isolating a full length oat CslF6 gene due to the very GC rich nature of the 5' end of the gene which was 73-75% GC in a region of more than 300 bp.

Based on this 5' sequence, new primers were designed to the sequence surrounding the initiating methionine codon, namely SJ116 and SJ277, the latter primer including an additional 33 bases encoding the 11 amino acid T7epitope tag MASMTGGQQMG (amino acids 1-11 of SEQ ID NO: 41) immediately upstream of the ATG. These were used with a primer in the 3' untranslated region (5J243) to amplify approximately 3 kb cDNAs containing the full-length oat CslF6 open reading frame of either 943 or 944 amino acids. The oat seedling cDNAs were amplified using Advantage 2 polymerase (Clontech) according to the manufacturer's instructions with 3% DMSO and cycling conditions of denaturation for 2 min at 94° C., then 35 cycles of 94° C. for 25 sec, 25 sec at 58° C. and 72° C. for 3 min followed by a 5 min extension at 72° C. PCR products around 3 kb in size were separated on a 1.0% TBE agarose gel, gel purified and cloned into the pCR2.1 TOPO T/A cloning vector and sequenced. Several of the full length cDNAs appeared to contain PCR-introduced single base changes. Therefore additional full length cDNAs were amplified from first strand seedling cDNA using the Phusion TaqPolymerase. One microlitre of diluted seedling cDNA was amplified with primers SJ277 and SJ243 in a 204 PCR reaction with HF buffer and 3% (w/v) DMSO according to the manufacturer's instructions with cycling conditions of 98° C. for 30 sec, followed by 30 cycles of 98° C. for 7 sec, 15 sec at 63° C. and 72° C. for 1 min followed by a 5 min extension at 72° C. Inclusion of DMSO improved both the yield and specificity of the reaction products. PCR products of about 3 kb in size were separated on a 1.0% TBE agarose gel, gel purified and cloned into the pCRBluntII II TOPO cloning vector and sequenced. Two sequenced clones designated AsCslF6_277-243 28 and AsCslF6_277-243 29 each contained an intact open reading frame and were subsequently shown by transient expression in *Nicotiana benthamiana* leaves to encode functional Csl polypeptides (see below).

The sequences of all the cloned oat CslF6 fragments were manually aligned in the Bioedit software program. Three consensus cDNA sequences were produced corresponding to the three genome variants of the hexaploid oat genome and these were designated as AsCslF6-1, AsCslF6-2 and AsCslF6-3. Each cDNA had a long open reading frame encoding a polypeptide of 944, 943 and 944 amino acids, respectively. The AsCslF6-2 protein sequence had a deletion of one amino acid relative to the other two, approximately 20 amino acids from the N-terminus within the signal peptide domain.

A full length genomic clone of AsCslF6 was isolated as follows. Genomic DNA was isolated from seedling tissue using a CTAB method (Murray and Thompson, 1980). Approximately 100 ng of diluted genomic DNA was used as template DNA in a 20 µl amplification reaction with Phusion polymerase, primers SJ274 and SJ243, HF buffer and 3% (w/v) DMSO according to the manufacturer's instructions with cycling conditions of 98° C. for 30 sec, followed by 35 cycles of 98° C. for 7 sec, 15 sec at 63° C. and 72° C. for 2 min followed by a 5 min extension at 72° C. The largest PCR product of about 5.2 kb in size was separated on a 1.0% TBE agarose gel, gel purified and cloned into the pCR-BluntII II TOPO cloning vector and sequenced. One clone designated AsCslF6_274-243_11 was sequenced; it contained a sequence of 5244 bp. Comparison with the cDNA sequences showed that there were two introns in the gene, the first of 1627 nucleotides and the second of 691 nucleotides. The nucleotide sequence of the exons was identical to the nucleotide sequence of the cDNA from AsCslF6-2. The nucleotide sequences and encoded amino acid sequences for the oat genes are given in SEQ ID NOs: 51-57.

Rice (*Oryzae sativa*)

RNA was isolated from approximately 100 mg tissue from one week old seedlings of *Oryzae sativa* cv. Nipponbare using a Nucleospin RNA Plant extraction kit according to the manufacturer's instructions (Macherey-Nagel). Five micrograms of RNA, without DNAse treatment, was reverse transcribed in a 20 µl reaction for one hour at 55° C. using 5 pmol of the RoRidT17 primer and a rice gene specific 3' primer SJ321 with Superscript III reverse transcriptase. Following heat inactivation at 70° C. for 15 min, the RNA strands were removed by digestion for 15 minutes at 37° C. with 1.5 units of RNAseH. The reaction was diluted with TE to 100 µl. One microlitre of this diluted seedling cDNA was amplified with Phusion polymerase, primers SJ69 and SJ324 with HF buffer and 7% (w/v) DMSO with cycling conditions of 98° C. for 30 sec, followed by 35 cycles of 98° C. for 10 sec, 15 sec at 62° C. and 72° C. for 90 secs followed by a 5 min extension at 72° C. Inclusion of at least 5% DMSO was essential for specific amplification as no full length PCR product was formed with even 3% DMSO. Optimum amplification occurred with DMSO concentration of between 7 and 10% (w/v). PCR products of about 3 kb in size were separated on a 1.0% TBE agarose gel, gel purified and cloned into the pCRBluntII II TOPO cloning vector and sequenced. One cDNA clone designated OsCslF6_69-324_15 was sequenced, its nucleotide sequence (SEQ ID No: 60) corresponded exactly to the sequence of the OsCslF6 gene in the published rice genome, and encoded a polypeptide having the amino acid sequence of SEQ ID NO: 61.

*Brachypodium distachyon*

RNA was isolated from approximately 100 mg of tissue from one week old seedlings of *Brachypodium distachyon* BD21 using a Nucleospin RNA Plant extraction kit. cDNA was prepared as described above for rice. Two microlitres of the seedling cDNA was used in a PCR with primers SJ116 and SJ357 or SJ277 and SJ357 using Phusion Hot Start polymerase. The PCR reaction including 7% (w/v) DMSO with cycling conditions of 98° C. for 30 sec, followed by 36 cycles of 98° C. for 7 sec, 15 sec at 62° C. and 72° C. for 90 secs followed by a 5 min extension at 72° C. PCR products around 3 kb in size were separated on a 1.0% TBE agarose gel, gel purified and cloned into the pCRBluntII II TOPO cloning vector and sequenced. Two clones designated BdCslF6_116-357_1 BdCslF6_277-357_10 were sequenced. The nucleotide sequences corresponded exactly to the sequences of the BdCslF6 genes in the published genome sequence. One nucleotide sequence is given as SEQ ID NO: 58 and the polypeptide amino acid sequence as SEQ ID NO: 59.

Example 10. Assessing the Functionality of Sequences Encoding Wheat, Oat, Rice and *Brachypodium* CslF6 Proteins by Transient Expression in *Nicotiana benthamiana* Leaves The functionality of the CslF6 coding regions from wheat, oat, rice and *Brachypodium* was initially assessed by transient expression of 35S-driven constructs in *Nicotiana benthamiana* leaves and analysis of the BG content in cell wall fractions from the leaves. The methods used were as described in Examples 1 and 6.

The constructs made and used are listed in Table 10. The presence of BG in the *N. benthamiana* leaves following the transient expression of the chimeric CslF6 genes was also assayed by lichenase digestion of the crude cell wall preparations and detection of the released oligosaccharides by FACE (O'Shea et al., 1998).

In several independent experiments, the constructs encoding the wheat, oat, rice and *Brachypodium* CslF6 protein directed the synthesis of significant amounts of BG as measured by the Megazyme assay (Tables 11 and 12). These chimeric genes were also compared to the barley CslF6 gene.

The amount of BG produced varied somewhat between experiments with the genes encoding the oat CslF6 proteins producing the least amount. The amount of BG produced in these transient assays did not correlate well with the BG levels in the corresponding grain, for example rice grain has low endogenous levels of about 0.02%, yet the chimeric gene was efficient at BG synthesis, while *Brachypodium* has relatively high levels of around 40% (Guillon et al., 2011) but the gene was only slightly more efficient than the others in producing BG. Therefore, the amounts observed in the transient assays (Table 12) may have reflected the efficiency of transcription and/or translation of the messenger RNA from each chimeric gene. Closer examination of the oat CslF6 sequences cloned in the plasmids revealed, however, that these PCR products were from more than one oat genome (pSJ79) or had one PCR error (pSJ78, which changes an amino acid C to Y at position 445) compared to the consensus sequences and that this may have an effect on the amount of BG produced.

The addition of the T7 epitope tag at the N-terminus of the wheat and *Brachypodium* CslF6 proteins had no apparent effect on activity of the proteins.

It was clear that the CslF6 gene from each species produced a BG with a particular structure as evidenced by the different DP3/DP4 oligosaccharide ratios. *Brachypodium* CslF6 produced BG with the highest DP3/DP4 ratio (1.6-1.7), followed by wheat (1.5-1.6) then barley (1.37) whereas oat and rice both produce BG with very lowDP3/DP4 ratios of about 1.0. The capillary electrophoresis system used to analyse these oligosaccharides was both very sensitive and accurate (see standard deviations in Table 12) giving high confidence that each chimeric CslF6 transgene produced a BG with a distinct DP3/DP4 ratio.

The DP3/DP4 ratios of the BG produced in *N. benthamiana* leaves were also well below those of native BG found in cereal grains. By the FACE analysis, barley and wheat enzymes yielded BG having a DP3/DP4 ratio of 2.55, the oat enzyme produced BG having a significantly lower ratio of about 1.9, whereas the *Brachypodium* enzyme produced BG having a high DP3/DP4 ratio of about 8.0. A large survey of BG structure studies has shown a typical range of DP3/DP4 ratio 1.7-3.8 in barley, wheat and oats (Lazaridou and Biliaderis, 2007). Some studies have shown DP3/DP4 ratios outside of this range and this can be affected by the method of analysis (eg HPLC, HPAEC or FACE), calculation of molar ratios, differences in the detection response of oligosaccharides of different lengths or whether whole grain or subfractions (eg bran or white flour) were used as well as the extraction methods used (water, alkali temperature etc) in the analysis.

Figure 9:
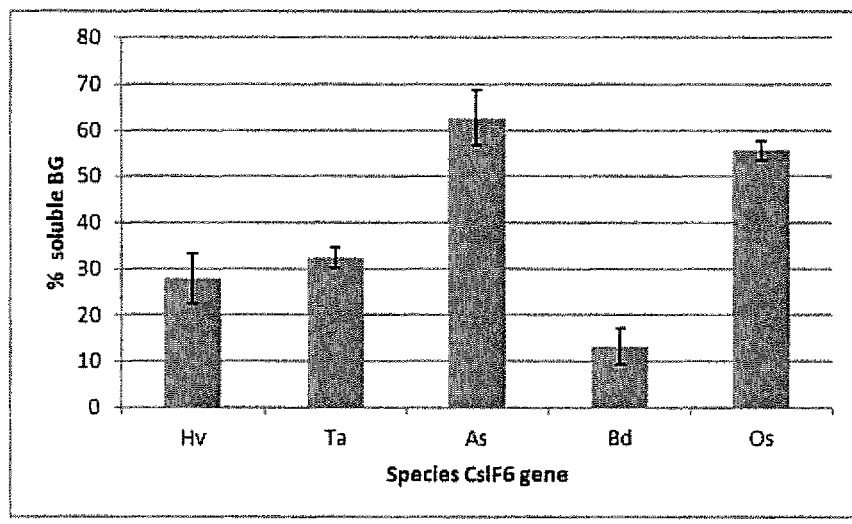
FIG. 9. Solubility of BG from N. benthamiana leaves expressing chimeric genes encoding exogenous cereal CslF6 polypeptides. Solubility was determined by a 2 hour aqueous extraction at 37° C. The graph shows the percentage of the total BG which was solubilised. The exogenous CslF6 polypeptides were: Hv (barley), Ta (wheat), As (oat), Bd (Brachypodium) and Os (rice).

The inventors considered that the large observed differences in fine structure of the BG produced from each CslF6 gene in the *N. benthamiana* leaf would affect the physical properties of the polymer considerably, in particular the viscosity and solubility. There is evidence that consecutive runs of cellotriosyl units causes helices or junction zones to form between polymer chains resulting in aggregation and insolubility (Tosh et al., 2004). Oat grain BG was more soluble than barley grain BG under the extraction conditions used (enzyme inactivation at 80° C. in 80% ethanol for one hour followed by extraction in 20 mM sodium phosphate buffer (pH 6.5) for 2 hours at 37° C.). Approximately 50% and 27% of the wild-type oat and barley grain BG was extractable, respectively, whereas little (2-5%) wheat grain BG or *Brachypodium* grain BG was soluble under the same conditions. There was an inverse relationship between the DP3/DP4 ratio and BG solubility i.e. the most soluble BG had the lowest DP3/DP4 ratio. The order of solubility of BG produced in *N. benthamiana* leaves from expression of the different CslF6 genes was the same as the order observed in the wild-type grain BG (FIG. 9). The *Brachypodium* CslF6 gene produced the least soluble BG and this had the highest DP3/DP4 ratio (1.6), the barley and wheat CslF6 genes had an intermediate solubility and DP3/DP4 ratios (1.4-1.5), whereas the oat and rice CslF6 genes produced the most warm water soluble BG and these had the lowest DP3/DP4 ratio of 1.0.

Example 11. Manipulation of BG Levels and Structure in Wheat Grain by Overexpression of CslF6 Genes The observation that different CslF6 polypeptides could produce a BG with a distinct structure when expressed heterologously opened up the opportunity for manipulating the BG structure and amount in transgenic plants by overexpression of a chimeric gene for expression of a particular, selected CslF6.

Generation of Wheat Plants Expressing Genetic Constructs Encoding Oat AsCslF6 in the Grain The full-length cDNA encoding oat CslF6 with the T7 epitope tag at the N-terminus (AsCslF6_277-243_29) and a full-length oat genomic coding region (AsCslF6_274_243_11) were each excised from the pCRBluntII-based clones EcoRI fragments and inserted between a 1.9 kb fragment of the high molecular weight glutenin Bx17 promoter and the nopaline synthase (nos3') polyadenylation region/transcription terminator to create genetic constructs pSJ127 and pSJ124, respectively. These constructs were used to transform immature embryos of Bob White 26 plants using the biolistics method. Transgenic plants were screened for the presence of the transgenes by extracting DNA from young leaf tissue using a RedExtractnAmp' kit (Sigma) and PCR reactions using primers SJ242 and nosR.

Twenty seven regenerated plants (T0 plants) were confirmed to be transgenic for an AsCslF6-encoding transgene and were grown in the glasshouse to maturity along with a non-transformed control plant (F6-121) from the transformation process. Complementary DNA was made from pooled, developing T1 grain sampled at approximately 15 days post anthesis (DPA) from each plant, and expression of the transgene in the developing grain monitored by Realtime PCR with primers SJ242 and SJ243. The transgene expression level in each transformed line was compared to the level of expression of an endogenous tubulin gene. Eleven of the primary transformants showed significant levels of expression of the AsCslF6 transgene, in extent from about 0.01-fold up to about 1.9-fold relative to the level of tubulin gene expression (Table 13). Analysis of the BG content of wholemeal flour obtained from single mature grains from the transformants indicated that most of the expressing lines had increased BG levels in the grain, up to about 4.4%. One plant from the transformation with pSJ124 containing the oat genomic AsCslF6 sequence showed expression of the transgene and increased BG levels (Table 13, last line). The grain weights of the grains expressing the AsCslF6 construct were also measured and some high BG lines (F6-124, F6-133 and F6-139) had average grain weights equal to or greater than the PCR negative line F6-121 (FIG. 8). The highest BG content of these single grains was from line F6-142 (4.4%) and line F6-139 (4.0%). In T2 grains, the AsCslF6 line F6-122.8 had an average BG content of 4.11% with an average grain size of 28 mg (Table 14). The level of (endogenous) BG in the non-transformed control grains (F6-121) were 0.7-1.4% in this experiment.

As expected, the T1 grains appeared to be segregating for both the transgene and the observed phenotype of the elevated BG content. That is, the T1 grains were a mixture of homozygotes and heterozygotes for the transgene, or null segregants.

Figure 10:
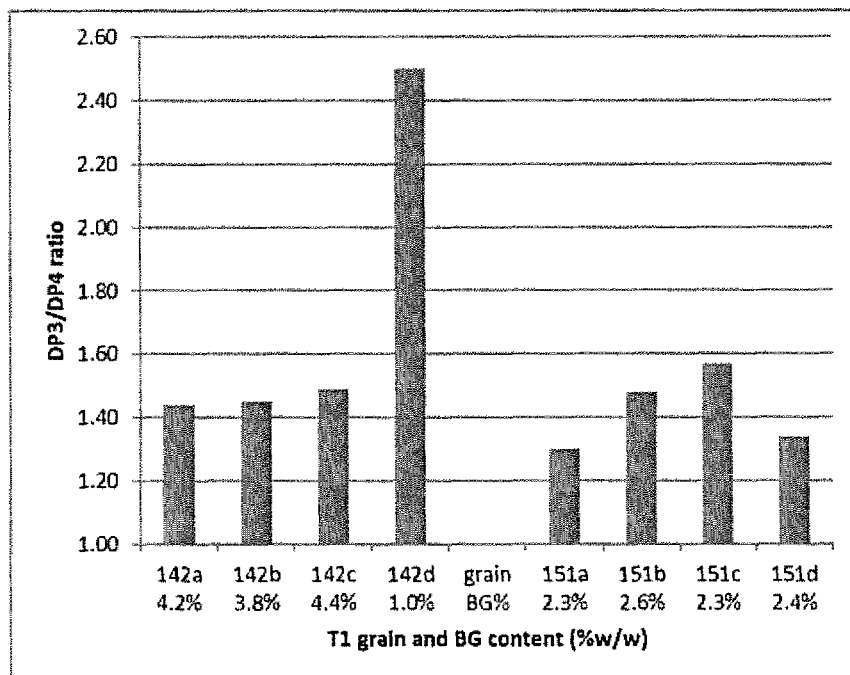
FIG. 10. DP3/DP4 ratio of BG in individual T1 wheat grain transformed with the chimeric gene for expression of exogenous AsCslF6. The DP3/DP4 ratio of BG extracted from individual mature grains of two lines (142 and 151) is shown. The BG content of each grain is shown below each bar. Grain from line 142d was a negative segregant (wild type) having BG with a high DP3/DP4 ratio. All of the other grains had increased BG content with reduced DP3/DP4 ratios.

The fine structure of the BG in single seeds from two plants transformed with the AsCslF6 construct was examined by lichenase digestion and fluorescent labelling of the oligosaccharides followed by separation by capillary electrophoresis. FIG. 10 shows the observed DP3/DP4 ratios. The wheat seed designated F6-142d had both a normal BG level (1.0%) and structure (DP3/DP4 ratio of 2.5), similar to that of the non-transformed control; it was a null segregant. In contrast, other grains from F6-142 had a BG content of at least 4%. In those grains, the DP3/DP4 ratio had decreased dramatically to as low as about 1.30. A wheat BG, with such a low DP3/DP4 ratio has never been reported previously.

Seeds from two AsCslF6 plants (F6-122 and F6-124) were sown and the resultant plants were grown in the glasshouse. AsCslF6-PCR positive lines were grown to maturity. Ten T2 grains from several of the progeny plants were pooled and each pool ground to a flour. The BG content and DP3/DP4 ratio was determined for each pool (Table 14). All pools showed a high BG content, up to about 4.11%, and low DP3/DP4 ratios of about 1.4 to 1.5 which was significantly lower than the wild type barley control flour provided with the Megazyme kit (Table 14). This demonstrated that the high BG trait was stably inherited.

Example 12. Solubility of the BG from Transgenic Wheat Grains

There are several methods described in the literature for determining BG solubility, some involving water extraction and some with other aqueous solvents such as containing sodium carbonate or alkali solutions. In addition different temperatures and times of extraction can be used, either with or without refluxing in ethanolic solutions at high temperature. The different methods don't all give the same solubility values. It was therefore important to define the solubilisation conditions for meaningful measurements to be made. The method used for determining BG solubility of grain samples in the inventors' experiments was as follows. Each 100 mg sample of flour—in this case wholemeal flour ball milled from pooled grain from each line—was heated at 80° C. in 1.8 ml of 80% ethanol in a screw capped tube shaking at 1000 rpm for 1 hour in an Eppendorf Thermomixer (or similar). This step inactivated any endogenous enzymes which could otherwise breakdown polymeric cell wall material, while the ethanolic nature of the solvent prevented any polymers from being solubilised and removed. Mono- and di-saccharides and oligosaccharides would however be removed from the flour samples in this ethanolic treatment step. Following centrifugation at 10,000 g for 1 min and decantation of the supernatant, the pelleted flour was resuspended in 1 ml of 20 mM sodium phosphate buffer (pH 6.5) and the suspensions incubated at 37° C. for 2 hours with shaking at 1000 rpm to extract water soluble components. The sample was spun at 10,000 g for 1 min and the supernatant carefully removed with a pipette and collected—this aqueous fraction contained the water-soluble (water-extractable) BG. The pellet containing the water-insoluble BG fraction was resuspended in 1 ml of the same buffer. Aliquots of both fractions, water-soluble and water-insoluble, were taken for assay of BG content using the scaled down Megazyme assay described above. Duplicate samples were assayed. Soluble and insoluble BG contents were calculated as a percentage of dry weight of the flour.

In wild-type barley and oat grain, a significant fraction of the BG content was reported to be water soluble whereas in wheat, little BG was soluble (Beresford and Stone, 1983). When measured without an ethanolic heat inactivation step, 80% of oat BG was soluble compared to 50% of barley BG, for about 21 different varieties, when solubilised in 38° C. water for 2 hours (Aman and Graham, 1987). When measured by the inventors' method described above, water-soluble levels of 50% and 27% for non-transformed oat (cultivar Mitika) and barley BG, respectively, were obtained. Therefore, the method used by Aman and Graham over-estimated the true water-soluble BG levels and the inventors' method using inactivation of endogenous enzymes by the ethanol treatment avoided that over-estimation.

Using the assay method including a heat inactivation step (Example 1), about 7% of the BG in the endosperm flour of control wheat of line H1-10B7.3 was water-soluble. Similar low levels of water-soluble BG were found in the endosperm flours of the homozygous transgenic HvCslH expressing lines H1-10B7.4, 7.6 and 1.9, although as a proportion this represented between 1 and 3% of the total BG in the endosperm flour. It was concluded that although the BG content increased significantly in the transgenic grain expressing the HvCslH construct, the DP3/DP4 ratio of the BG and the proportion of water-soluble BG had not increased. This conclusion was significant.

In wild-type wheat wholegrain flour, less than about 5% of the BG content is water soluble—considering that about 0.6% to about 1% of the dry weight of wheat flour is BG, the amount of water soluble BG in wheat flour is very low. Furthermore, the BG assay which requires conversion of the BG to glucose, involves subtraction of background glucose values from the glucose released by β-glucosidase treatment of lichenase-derived BG oligosaccharides, so small variations in the background can compound the uncertainty of BG values at this very low level.

Table 15 shows the percentage solubility of the BG content of the flours from a number of transformed and control wheat grains. The control grain F6-1K3.2 had a BG content of 0.91% of which about 5% was soluble, similar to that of PCR negative line F6-121 which had a slightly higher, but still low, percentage solubility. The insoluble BG from these grains had a normal DP3/DP4 ratio of 2.45 while the soluble BG had a lower ratio of around 2.15. Grain from homozygous transformed lines F6-1G6.1.8 and F6-1K5.9 had a shrunken appearance and had a high BG content of around 4%. The percentage solubility of BG from these lines was similar to the controls even though both the insoluble and the soluble BG had a lower DP3/DP4 ratio than the controls (Table 15). T1 grain from HvCslF6 line F6-87 had a normal appearance and an increased BG content of about 3% with a low DP3/DP4 ratio of 2.1. This line showed an increased percentage of soluble BG to about 10% even though the DP3/DP4 ratio was similar to line F6-1K5.9. This could be explained by the increased ratio of endosperm BG to bran BG in this non shrunken grain as endosperm BG is known to be more soluble than bran BG (Izydorczyk and Dexter, 2008). In contrast, the AsCslF6 expressing lines exhibited an increased percentage of soluble BG, to at least 15% with the best line having 18.5% soluble BG. In the next generation of the transgenic grain, milled flour from ten T2 pooled grains of lines F6-124.1 and F6-124.2 had BG contents around 3.8% of which up to 20.55% was water soluble. These grains were not uniformly homozygous for the transgenes, so further increases in BG content are expected. Wheat grain with this level of soluble BG has never been reported before.

Example 13. Manipulation of BG Levels and Structure in Wheat Grain by Over-Expression of Chimeric Genes Encoding Rice OsCslF6 and *Brachypodium* BdCslF6

As the rice OsCslF6 gene produced a BG in *N. benthamiana* leaves with a low DP3/DP4 ratio and the *Brachypodium* BdCslF6 gene produced BG with the highest ratio of about 1.6, chimeric genes encoding these enzymes were expressed in wheat endosperm to determine if further manipulation of BG levels or composition was possible. The full length OsCslF6 gene (OsCslF6_69-324_15) and the BdCslF6T7 gene (BdCslF6_277-357_10) were excised from the pCRBluntII vector as EcoRI fragments and inserted between a 1.9 kb fragment of the high molecular weight glutenin Bx17 promoter and the nopaline synthase terminator to create plasmid pSJ148 and pSJ149 respectively. The promoter-CslF6 coding regions-nos terminator/polyadenylation region as expression cassettes were then cloned as NotI fragments into the NotI site of the *Agrobacterium* vector pVecDRB to create plasmids pSJ151 and pSJ152, respectively. These constructs were then used to transform wheat by *Agrobacterium*-mediated methods.

Transformed plants were selected on G418 and plants were screened by PCR with primers SJ242 and nosR. BG content and DP3/DP4 ratio was determined on pooled T1 grain as described in the preceding examples and plants showing increased levels of BG were grown to obtain homozygous plants for further bulk up, grain compositional analysis and nutritional trials. The pooled T1 grain transformed with the construcy expressing OsCslF6 showed increased BG in 15 of 43 transformed lines. One line showed 3.32% BG (w/w) on a dry weight basis, with a DP3/DP4 ratio in the range 1.66-1.75. In T1 grain transformed with the construct expressing BdCslF6T7, 42 of 54 transformed lines showed increased BG content, with one line showing 4.9% BG (w/w) on a dry weight basis.

Example 14. Analysis of Dietary Fibre Levels in Endosperm Flour from HvCslH T4 Grain and CslF6 Grain Total and soluble dietary fibre levels of endosperm flour were determined by the Prosky AOAC Official method 991.43 (Lee et al., 1992) with minor modifications as described in Example 1. This method used high temperatures and thermostable starch hydrolysing and protease enzymes to simulate digestion of cooked foods in the human digestive tract. Analysis of the control endosperm flour confirmed that white flour had low levels of soluble and total dietary fibre at 0.7% and 2.4% of the dry weight (Table 6). In contrast and unexpectedly given that the solubility of the increased BG had not changed, all three transgenic HvCslH lines (H1-10B7.4, 7.6 and 1.9) showed large increases in both soluble and total dietary fibre in the endosperm flour. Endosperm flour from grain of line H1-10B1.9 showed more than a 2-fold increase with 1.8% soluble and 5.3% total dietary fibre. The difference in the percentage solubility of the BG and the amount of DF as measured in the assays may be explained by the extraction conditions as the first step of the BG solubility assay involved heating the flour suspension in an 80% ethanol solution to inactivate endogenous enzymes whereas the dietary fibre assay had no such inactivation step. Therefore, the endogenous hydrolytic enzymes could act on the cell wall and release more carbohydrate in the DF assay. The fibre assay also measured arabinoxylan and other fibre components. Given the increase in DF of the HvCslF6 grain, the inventors expected greater increases in the level of DF of the higher BG lines, especially of the soluble DF in those lines that contained high levels of soluble BG.

Progeny plants derived from the transformed line F6-1 (Example 8) were propagated in the glasshouse to provide grain of the T4 generation. These included lines that were homozygous for the transgene expressing HvCslF6T7 (including the T7 epitope tag at the N-terminus) and lines that were negative segregants for the transgene and therefore the same as wild-type. The lines F6-1G and F6-1K and their sub-lines were derived from different heads of the same initial transformed plant F6-1. Pooled grain of line F6-1G6.1.8 had an average grain weight of 29.7 mg, was much darker in colour (brown) and slightly wrinked in external appearance, and showed 4.36% (w/w) BG of which about 7% was soluble (determined with an ethanolic heat treatment step). Pooled T3 grain of line F6-1K5.9 had an average grain weight of 28.8 mg, was normal on colour and non-shrunken in appearance, and showed 4.03% BG, of which 6.2% was soluble. Pooled T3 grain of line F6-1G6.7 had an average seed weight of 36.5 mg and had 1.8% BG, of which about 7% was soluble. Negative segregant line F6-1K3.2 had an average grain weight of 34.7 mg and 0.77% BG, of which 2% was soluble. Grain from line F6-124.4 which was transformed with the transgene expressing the oat F6 protein had 3% BG, of which about 20% was soluble.

Fibre and fibre components were determined for flour obtained from these grains and a subsequent T5 generation for line F6-1K5.9, after milling on a cyclone mill with a 1 mm screen, providing a fine flour. Starch content, protein content and sugar content was also determined. The data are shown in Table 16. Each of the parameters, namely soluble fibre, insoluble fibre, neutral non-starch polysaccharides (soluble NNSP and insoluble NNSP) were increased, as well as fructan levels in some cases. These flours were used to prepare muffins for the animal feeding trial as described in Example 17.

Example 15. Alteration of BG Structure by Crossing HvCslF6 and HvCslH Overexpressing Lines A more modified grain composition may be obtained by producing transgenic wheat plants that express both CslF6 and CslH-encoding transgenes in the endosperm, for example the CslF6 and CslH from barley. Transgenic lines expressing the HvCslH gene were therefore crossed to lines expressing the HvCslF6 gene and the progeny were screened by PCR for the presence of both transgenes as described in previous examples. Two lines were obtained that were homozygous for both the HvCslF6 and the HvCslH genes: F6H1-19.2.1 (H1-10B1.9 and F6-6D1 parents) and H1F6-6.2.9.7 (H1-10B7.4 and F6-6D1 parents). All grain from these lines were not shrunken but had an angular appearance, an increased BG content and lower DP3/DP4 ratio compared to the wild-type control and slightly less of the BG was water soluble according to the inventors method (Table 17). Another cross F6H1-17 (parents H1-10B1.9 and F6-1G6.3) was still segregating and the results from analysis of flour milled from ten pooled grains of the negative segregant (F6H1-17.1.18), an HvCslF6 segregating line (F6H1-17.1.23) and one line with both HvCslF6 and HvCslH (F6H1-17.1.16) are also shown in Table 17.

Discussion The inventors were not aware of any reported examples where a CslF6 gene from one species had been used to alter BG levels or structure in another species of cereal grain. Burton et al., (2006) showed that heterologous expression of some members of the rice CslF gene family (OsCslF2 and/or OsCslF4 and OsCslF9) in vegetative tissues of Arabidopsis could produce very small amounts (considerably less than 0.1% w/w) of BG. Similar experiments over-expressing HvCslH in Arabidopsis leaves also produced very low levels of BG, estimated to be maximally 0.016% of the cell wall (Doblin et al., 2009). Those experiments demonstrated that some CslF and CslH genes can make BG but also the difficulty in making substantial levels of BG such as described herein.

Given that the endogenous CslF and CslH genes are expressed in wheat, yet wheat grain has only relatively low levels of BG, it was not known if heterologous expression of the HvCslF6 gene in wheat would give increased BG levels as it was possible that some other gene function was missing or limiting in these grains.

The inventors have demonstrated that it was possible to approximately double the amount of BG in wheat grain by over-expression of a gene encoding HvCslH. Furthermore, over-expression of HvCslF6 in wheat grain increased the amount of BG synthesised considerably more, by more than 6-fold, which was a much greater increase than in barley grain transformed with a HvCslF6 construct. When similar experiments were conducted in rice grain, it was determined that HvCslH over-expression does not increase BG levels. Furthermore, in at least one transformed wheat line, high levels of HvCslF6 expression appeared to be deleterious to endosperm development as many of the grains with the highest BG levels from that transgenic line were shrunken. Such grains appeared to develop normally at first but the central part of the endosperm then failed to develop and fill as normal and the grains collapsed upon drying down as they matured. The shrunken grains thus had a much lower endosperm/bran ratio. However, the inventors were able to select for wheat grains that had high levels of BG with minimal effects on grain size or morphology. This was done by generating a large number of additional new HvCslF6 transgenic wheat lines that looked relatively normal in size and or shape (i.e. were not shrunken) and growing these on, discarding those lines that showed severely shrunken grains.

Other CslF6 genes were also isolated and transformed into wheat in case this was a phenotype specific to the HvCslF6 gene. The oat AsCslF6 gene in fact produced high BG lines that were much less shrunken, although some lines did exhibit a shrunken phenotype and these were not studied further. Crossing the high expressing HvCslF6 lines to high expressing HvCslH lines also produced grain that had a high BG content and was not as shrunken as the original HvCslF6 lines, although this produced a BG with a different structure and solubility. However some non shrunken grains with only the HvCslF6 transgene (e.g Line F6H1-17.1.23) were produced by crossing and segregating away the HvCslH locus and this line not only had high BG but the BG was highly soluble at round 13% of the total BG. Thus, it is possible to create similar lines by crossing to other elite wheat varieties and selecting for those lines with the desirable BG and grain size characteristics.

The inventors also showed that AsCslF6 over-expression in wheat grain both increased BG levels and produced a BG structure with a low DP3/DP4 ratio of about 1.3, considerably lower than was seen with the HvCslF6 gene. Moreover, BG from the AsCslF6 expressing wheat grain was much more soluble than the BG from either the wild-type or the HvCslF6 expressing wheat grain. This grain is expected to provide considerable health benefits as the cholesterol lowering properties of BG is related to its water solubility and the ability to form viscous solutions in the gut (reviewed in Lazaridou and Biliaderis, 2007; Theuwissen and Mensink, 2008).

Example 16. Testing of Fermentation Parameters

The potential of the wheat comprising increased BG to produce large bowel fermentations patterns likely to improve human health and reduce the risk of several common chronic diseases is investigated using a high throughput, anaerobic batch culture system to simulate human colonic fermentation. A completely randomised experimental design is deployed to study the test substrates and fermentation standards (substrates). Human faeces is used as inoculum to simulate human large bowel fermentation. Freshly voided faeces will be sourced from three healthy adult subjects who are consuming their habitual diets and had not been on antibiotic mediations for the previous 6 months. After collection, faecal samples are homogenised and suspended at 10% w/v in sterile anaerobic phosphate buffered saline (PBS). Incubations are performed in quadruplicate in an anaerobic chamber for the test products, standard substrates and the controls (blanks). Briefly, standards and test flours are pre-weighed into sterile fermentation vessels and carbon-limited fermentation media comprising carbonate buffer and macro- and micronutrients added to achieve a set volume and a neutral pH. After equilibration, an aliquot of the 10% human faecal inoculum is added to each of the substrate suspensions, tubes capped, sealed and then incubated at 37° C. with continuous shaking. After designated intervals, ferments are sampled and frozen immediately at −20° C. to await bacterial enumeration using appropriate conventional and molecular methods (Abell et al., 2004; Bird et al., 2008 & 2009). DNA in digesta was extracted by repetitive bead beating and kit purification as described by Yu and Morrison (2004).

Example 17. Determination of the Potential of the Novel Wheat to Dampen Postprandial Glycemic Response in Rats An acute feeding trial was designed and carried out to evaluate the physiological functionality of the wheat to attenuate postprandial glycemia using the chronically cannulated, meal-fed rat model. The study also explored the mechanistic basis by which the β-glucan enriched wheat, as wholemeal or refined white flour, may help to slow glucose assimilation and promote better control of blood glucose levels.

Figure 11:
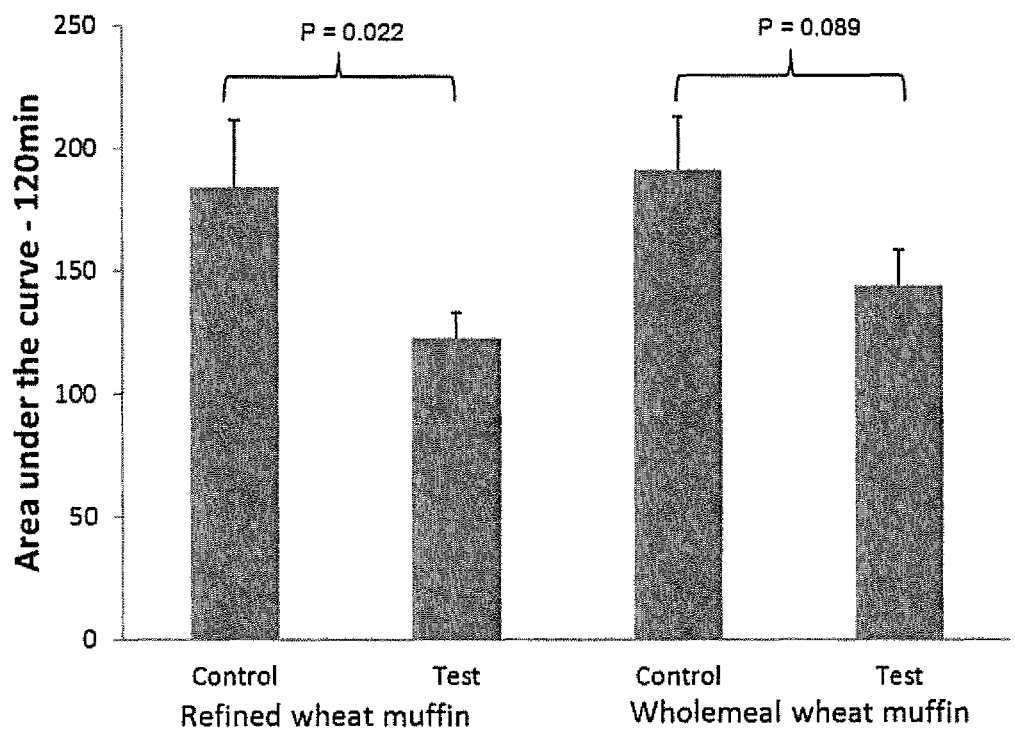
FIG. 11. Glycemic impact (GI, which is the area under the curve to 120 min after feeding) in rats fed either test muffins ("Test") made from either refined or wholemeal flours compared to rats fed muffins made with control, wild-type refined or wholemeal flours ("Control") as described in Example 17. 1-tailed t-tests were used to compare treatment effects; n=7-9 for each muffin type.
Figure 12:
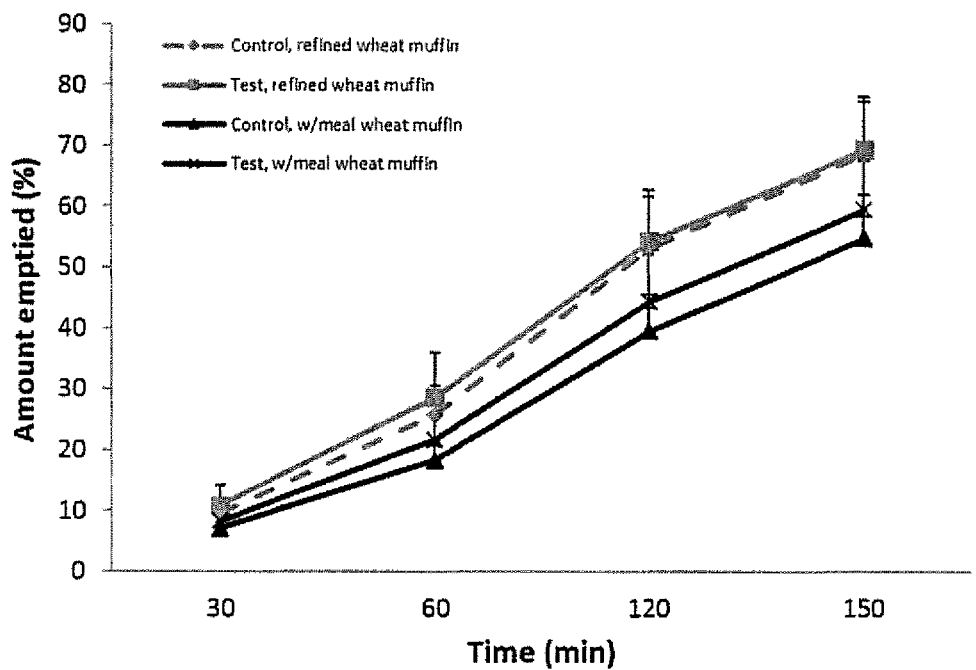
FIG. 12. Gastric emptying rate for rats fed the test or control muffins as described in Example 17. n=8-10 for each type of muffin.

The meal-fed rat model was used specifically to characterise the glycemic properties (blood glucose concentration, IAUC) of a prototype food manufactured from the wheat comprising increased BG. Wholemeal and refined white flour from the transgenic and conventional (control) wheats (composition shown in Table 18) were used to make test muffins which contained the following ingredients: 312 g flour, 100 g glucose powder, 310 g milk, 50 g egg and 90 g butter. 13C-octanoate salt (0.91 mg/g muffin) was also included in the formulation as a quantitation standard for determination of gastric emptying rates. The muffins were baked at 180° C. for 20 min and their composition is shown in Table 18. The four different muffins were tested in random order. The rats had free access to water and a standard commercial rat diet for 5 d before being given a standard AIN-93G diet for the remainder of the study. They were habituated to eating a prescribed amount of food within a set time. The superior vena cava of each rat was catheterised via the external left jugular vein under aseptic conditions and catheters flushed on a regular basis using sterile techniques. Following recovery from surgery and adaptation to the experimental regimen, a 10-mL breath sample was collected from each rat as the baseline measurement. Blood samples were also taken at that time. Each rat was then given a predetermined amount of the test and or control muffin and breath and blood samples collected at specified time points for up to 3 h after the rats finish eating their morning ration. The test and control muffins were investigated once each in any given animal. Blood glucose concentration was quantified using an automated blood glucose monitor. The remaining blood was collected into a tube containing anticoagulant, centrifuged (3000 rpm for 10 min) and the plasma supernatant removed and stored at −80° C. to await analysis for insulin, GLP-1, GIP and PYY using a gut hormone multiplex kit (Millipore, St. Charles, Mo., USA). The $^{13}C$ content of breath samples was analysed by mass spectrometry and the gastric emptying rate calculated. The results are shown in FIGS. 11 and 12. FIG. 11 shows that the glycemic index (GI), defined as the area under the blood glucose concentration curve to 120 minutes after feeding, was significantly lower in rats fed the muffins made with the wheat flours containing increased levels of BG and increased total dietary fibre (TDF) levels than the rats fed the control muffins made with wild-type flours. FIG. 12 shows that the gastric emptying rates for the rats fed the test muffins were not significantly different than for the rats fed the corresponding control muffins, showing that the reduced blood glucose concentrations and glycemic indices were not related to a difference in gastric emptying rates. As expected, there was a difference in gastric emptying rates when comparing the use of muffins made with refined wheat flour compared to wholemeal wheat flour (FIG. 12).

Example 18. Determination of the Potential of the Wheat to Improve Indices of Cardiometabolic Health in Lean and Obese Rats A 6-wk dietary intervention to determine whether foods made with the wheat comprising increased BG reduces live weight gain, reduces adiposity and has favourable effects on indices of metabolic health, such as for example increased insulin sensitivity, cardiovascular health such as for example lower blood pressure and reduced levels of LDL-cholesterol, and bowel health such as for example increased digesta mass, prebiosis and improved fermentation patterns. The physiological, biochemical and hormonal mechanisms mediating the cardiometabolic and other health benefits are also determined.

Briefly, adult obese Zucker rats and their lean counterparts will be maintained in groups in wire-bottomed cages in a room with controlled heating and lighting (23° C.; 12-h light/dark cycle) and have free access to food and water for drinking for the duration of the study. After a 7-day acclimation, the rats will be allocated randomly to one of four groups of about 12 animals each and fed one of two diets. The diets are based on AIN-93G formulation and will contain about 50% of wholemeal flour made from either the transgenic or a standard wheat. The diets are formulated to supply equal amounts of macronutrients, energy and starch. After 1 week on the experimental diets, the rats are transferred to metabolism cages for 4 days to determine intake of feed and water and fecal and urine excretion and then returned to their group cages. After 4 weeks on the experimental diets, the rats are anesthetized using 4% isoflourane in oxygen to allow blood from the abdominal aorta to be collected into vaccuette tubes (serum, EDTA-NaFl and EDTA-plasma with 10 uL/mL DPPIV inhibitor added) which are then centrifuged (3,000×g) and the supernatant removed and stored at −80° C. until analysed. Caecal and colonic digesta are then collected and weighed, and aliquots stored at −20° C. to await analysis of short-chain fatty acids (SCFA), pH, phenols, p-cresols and ammonia. The composition of the microbiota in large bowel digesta are determined using quantitative molecular microbiology techniques.

Plasma glucose, triglyceride, non-esterified free fatty acids and total cholesterol concentrations are measured using an automatic analyzer in conjunction with proprietary enzymatic kits (Roche Diagnostics Co, Indianapolis, Ind.). Plasma concentrations of various hormones including pancreatic polypeptide, GIP, GLP-1, PYY, insulin and leptin will be determined using the relevant gut hormone multiplex kit (Millipore, St. Charles, Mo., USA) (Belobrajdic et al., 2011).

Fecal, and cecal and colonic digesta samples will be analysed for the total and major individual SCFA (acetic, propionic and butyric acids) and other metabolites using published methods (Bird et al., 2007, 2008, 2009).

Example 19. Determination of the Glycemic Index of Prototype Foods Made with the Wheat The GI ranks carbohydrate-containing foods on a weight-for-weight basis according to their postprandial glycemic response. The transgenic wheat and a comparator (standard) wheat will be milled to produce wholemeal flours which are then made into a range of suitable prototype foods (bread, pasta, muffins, biscuits). The nutritional composition of the test foods is determined using the analytical methods described above. The available carbohydrate content of the tests foods is determined directly as the as the sum of the total starch and simple sugar contents. These constituents are assayed using standardised procedures (methods; AACC, 76-12 and AOAC, 982.14 respectively).

The standardised in vivo testing protocol (Australian Standard AS 4694-2007: Glycemic Index of Foods; International Standard ISO 26642) is used to determine the GI of the wheat-based test foods as described in more detail below.

The serving sizes of the foods used in the tests is based on 50 g of available carbohydrate, which is determined by direct analysis, as referred to earlier. The reference food to be used is glucose. All GI tests and associated laboratory analyses will be performed in the Clinical Research Unit at CSIRO Animal, Food and Health Sciences in Adelaide. For GI testing, about 12 participants fulfilling the selection criteria are to be recruited. Participants are not permitted to consume any food or beverages, other than water, for a minimum of 10 hours prior to each test. Volunteers are also required to refrain from undertaking vigorous exercise immediately prior to, or during the test. On the day of testing, two fasting blood samples are taken, by finger-prick, about 5 minutes apart, analysed for glucose and the average result used as the baseline blood glucose concentration. Each participant then consumes their assigned test meal, the serving of which contains the equivalent of 50 grams of available carbohydrate. Further finger-prick blood samples are taken at 15, 30, 45, 60, 90 and 120 minutes, starting immediately after the first mouthful of test food. The participants are also offered 250 mL of water to consume with the test foods.

For the reference food (glucose drink), 50 grams of anhydrous glucose powder is dissolved in 250 mL of water. This drink supplies exactly the same amount of available carbohydrate as the standard serving of the test food and will have been tested in each participant on three previous occasions within the immediate 3 month period prior to testing of the wheat breakfast cereals.

The glucose concentration in the blood samples will be assayed using an automated enzymatic and spectrophotometric technique which has an interassay coefficient variation of <3.0%. The GI will be determined as the glycemic response (measured as the incremental area under the blood glucose response curve) following consumption of the standard amount of the test food, expressed as a percentage of the average glycemic response (IAUC) to an identical amount of carbohydrate from the reference food (glucose drink) consumed by the same participant on a separate occasion. The GI of the test food equates to the mean GI of ≥10 subjects. Glycemic load (GL), which provides an indication of both the quality and quantity of carbohydrate in the test food, will be calculated according to the following formula:

GL=(GI×the amount of carbohydrate (grams)) divided by 100.

Example 20. Determination of the Cardiometabolic Health Benefits of the Novel Wheat in an 'at Risk' Population A medium-term, completely randomised, controlled parallel study will investigate the cardiometabolic health benefits of the novel wheat in free-living, mildly hypercholesterolemic but otherwise healthy adults (n=60). Volunteers will be recruited by public advertisement to participate in the 12-week study. Exclusion criteria include a history of cardiovascular, hepatic, peripheral vascular, respiratory, gut or renal disease or a malignancy. All study procedures will be approved by the Human Ethics Committee of the Commonwealth Scientific and Industrial Research Organisation.

About 60 volunteers will be randomised to one of three dietary groups to consume daily foods prepared from either the transgenic or conventional wheat (as wholemeal flours) or refined wheat. For the duration of the study volunteers will consume their habitual diet with modifications to accommodate the cereal-based study foods (the Study Dietician will help them in meeting this requirement). It is expected that about 100 g of the cereal flours will be eaten each day of the trial. Food records and other information as well as blood and faecal samples will be collected at baseline and at 3-week intervals thereafter for the remainder of study in order to assess changes in: plasma lipid profiles (total and LDL and HDL cholesterol, apo B and TAG) and glucose control (HbA1c and fasting blood glucose), TNF-alpha and homocysteine contents, food and energy intake, weight management, waist circumference, blood pressure, faecal mass, bacterial counts, bile acids and SCFA levels, insulin sensitivity (fasting insulin and homeostatic model assessment-insulin resistance) and circulating levels of selected hormones, including GLP-1 and glucose-dependent insulinotropic peptide (GIP). Volunteers will be asked to complete a 3-day food diary and a bowel habit, comfort and wellbeing questionnaire every three weeks as well. Faeces and blood will be analysed using standard methods described in the literature.

Example 21. Water Solubility of BG in Flour Samples without Ethanolic Heat Treatment A second BG water-solubility assay was developed which omitted the first ethanolic heat inactivation step as described in Example 1, as an indication of the solubility of BG in flour during normal food processing methods. A total BG assay on a 20 mg sample of flour was performed as described earlier using the scaled down Megazyme kit method and a second identical sample of flour was subjected to solubilisation in 1 ml of sodium phosphate buffer with shaking at 37 C for 2 hours. The insoluble material was pelleted by centrifugation at 10,000 g for 1 min, the supernatant was discarded, the pellet washed in 1 ml of phosphate buffer and then after a further centrifugation and discarding of the supernatant, the BG content of the pellet was determined as for the first sample to give the amount of insoluble BG in the flour. The soluble BG content of the sample was calculated by subtracting the insoluble BG value in the pellet from the total BG of the flour. Duplicate samples were measured.

Figure 13:
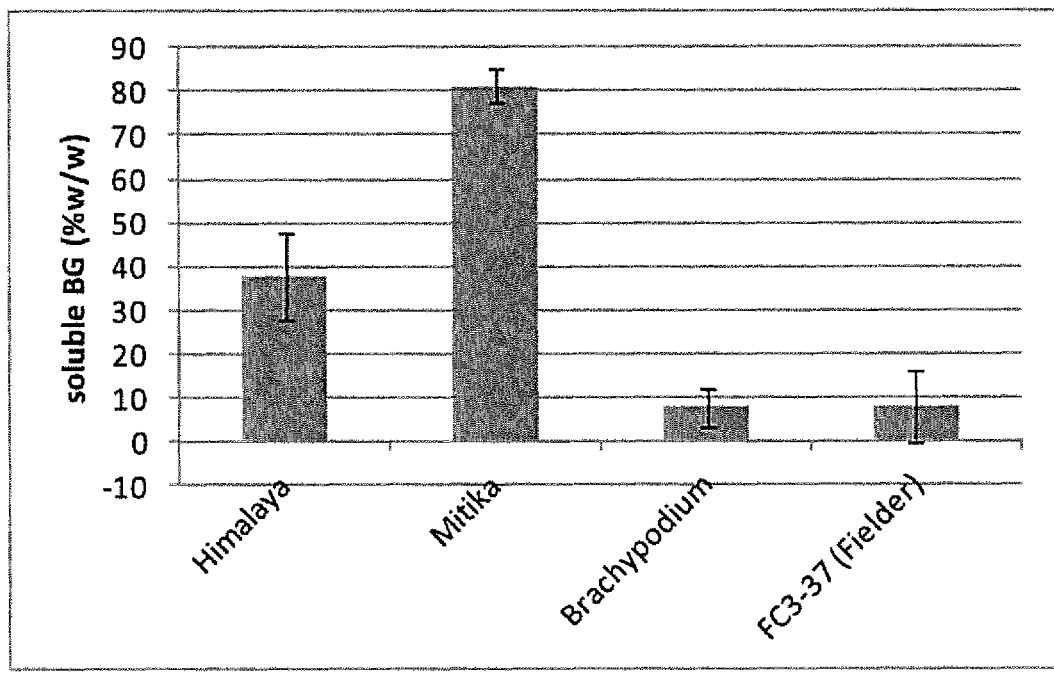
FIG. 13. Water-solubility of BG from wild-type flours from different grains, as determined by the method described in Example 21 (No heat-inactivation step).

Without the ethanolic heat inactivation step, oat and barley flours show an increased amount of BG solubilised with oat showing very high solubility of about 80% and barley just below 40% (FIG. 13), compared to levels of 50% and 27% respectively as described in Example 12. In comparison, both wheat and barley flours have low levels of water-soluble BG of about 8%. The inventors noted that grain of the wheat cultivar Fielder was regarded as "soft wheat" grain compared to the grain of the transformed lines which were derived from the "hard wheat" of the Bob White 26 cultivar.

The BG water-solubility of selected transgenic lines with increased BG levels was determined using the new assay and the results are shown in Table 19. Each set of samples included a negative segregant as a control with BG levels of approximately 0.7 to 0.8%. Half of the controls showed a BG solubility of around 20% whereas the other half had around 10% soluble BG. In the field grown samples, the HvCslF6 high BG lines showed increased BG solubility up to 40% compared to 10% in the negative segregant. The AsCslF6 expressing lines with increased BG content up to 3.9% also had dramatically increased BG solubilities ranging from 31% to more than 50%.

In contrast to the HvCslF6 lines, transgenic lines with higher BG levels as a result of expressing the HvCslH gene showed a reduced level of water-soluble BG (compare H1-10B7.3 with H1-10B1.9 and 7.4). The decreased solubility of BG in HvCslH expressing lines, was also visible in the HvCslF6×HvCslH crossed lines. Lines that had both HvCslF6 and HvCslH genes (F6H1-7.1.16 and F6H1-7.1.24) showed higher solubility of 17% and 23% than the negative segregant (F6H1-7.1.18, 11% soluble BG), but significantly lower than the line which contained only the HvCslF6 gene (F6H1-7.1.23) which had more than 50% soluble BG. As described earlier, this line was derived from one of the shrunken-grain HvCslF6 lines. However, with crossing and segregation from the HvCslH gene, grain from this line was no longer shrunken although it was slightly lighter than the wild type grain but still had a significantly increased BG content.

Thus, wheat grains with a large range of water-soluble BG content were produced by expressing different CslF and/or CslH genes or combination of genes in the developing wheat grain during plant growth.

Example 22. Determination of the Amino Acids within the CslF6 Protein that Control BG Structure and Solubility As described in Example 10, the CslF6 polypeptides from oat and rice, and also those maize and sorghum (see below), produced a BG with a low DP3/DP4 ratio of around 1 or less when expressed in the *Nicotiana benthamiana* leaf system. This BG had much higher solubility than that produced from expression of the barley, wheat or *Brachypodium* CslF6 polypeptides where the DP3/DP4 ratio was about 1.4 or higher. The CslF6 polypeptides that produced BG having the lower DP3/DP4 ratios also produced BG of higher solubility when the genes encoding those particular CslF6 polypeptides were expressed in the cereal grain. Therefore, chimeric gene constructs were made by joining part of a protein coding region from one gene (barley CslF6, higher DP3/DP4 ratio) with the other part of a second coding region (maize CslF6, lower DP3/DP4 ratio). These chimeric genes were expressed in the *N. benthamiana* system as described in Example 6 and the DP3/DP4 ratio of the BG that was produced determined, in order to determine the portion of the CslF6 polypeptide that controlled the ratio and therefore the BG structure. Using this approach and various such fusions as described below, it was concluded that a single amino acid difference in one of the eight predicted transmembrane domains of the CslF6 polypeptide controlled the BG structure and therefore the DP3/DP4 ratio.

Comparing the sequences of the CslF6 genes from different species, it was noted that there were several conserved restriction sites within the coding regions of the CslF6 cDNAs that could be used to swap regions of the CslF6 genes and thus express the chimeric polypeptides in plant cells. For example, there were conserved ApaI, BglII and SacI sites in both of the HvCslF6 gene and the ZmCslF6-2 gene.

Full length cDNAs corresponding to the barley CslF6 gene (HvCslF6, nucleotide sequence of cDNA is SEQ ID NO:169), maize CslF6 genes (ZmCslF6-1, SEQ ID NO:166; ZmCslF6-2, SEQ ID NO:167) and the sorghum CslF6 gene (SbCslF6, Sb07g004110; SEQ ID NO:168) were amplified using Phusion polymerase from seedling cDNA using the methods described in Example 13 and using primer pairs (forward and reverse) SJ116 and SJ77, SJ391 and SJ392, SJ393 and SJ392, and SJ387 and SJ389 respectively and cloned into the binary vector pCXSN as described in (Cheng et al 2009) to create plasmids pSJ226, pSJ192, pSJ195 and pSJ197. The sequences of the amplified cDNAs differed slightly from the published sequences (compare SEQ ID NOs: 164 and 165 with SEQ ID NOs: 166 and 167) in several positions, probably reflecting varietal differences. These differences were not within the region of the polypeptides that determined the DP3/DP4 ratio of the BG (see below). However the amino acid sequence of the ZmCslF6-1 polypeptide encoded by the isolated cDNA was found to have a 25 amino acid deletion in the coding sequence near the 5' end but this did not affect activity of the gene (see below). This deletion probably occurred as a result of the Phusion polymerase skipping over a secondary DNA loop structure due to the extreme GC richness of the 5' end of the CslF6 genes even though a high concentration of DMSO was used in the amplification reaction. This has been observed by the inventors with several other CslF6 genes.

TABLE 20

| Nucleotide sequences of primers | | | |
|---|---|---|---|
| Primer | Gene | Sequence | SEQ ID NO |
| SJ387 | SbCslF6 5' | GAGGGCGCAGCCGGCATTATGG | 179 |
| SJ388 | SbCslF6 3' | CTTCACGGCCAGTTGTAGGAGAGGTTG | 180 |
| SJ391 | ZmCslF6-1 5' | CCGCCAGGCAGGCAGAGAGG | 181 |
| SJ392 | ZmCslF6-2 5' | TCACGGCCAGAGGTAGTAGCCGT | 182 |
| SJ393 | ZmCslF6 3' | GCCAGGCAGGCAGGCATTATGG | 183 |

Figure 14:
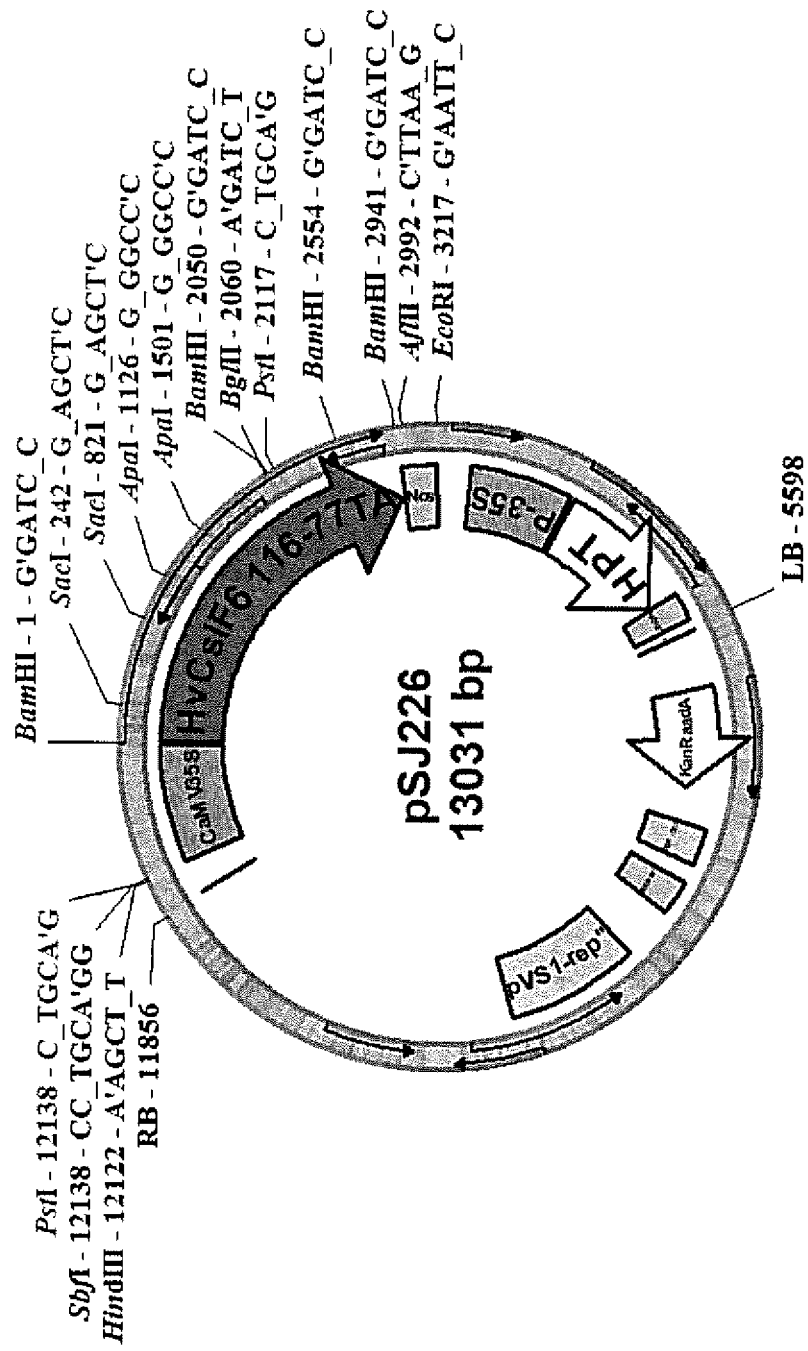
FIG. 14. Plasmid map of pSJ226 showing relevant restriction sites.
Figure 15:
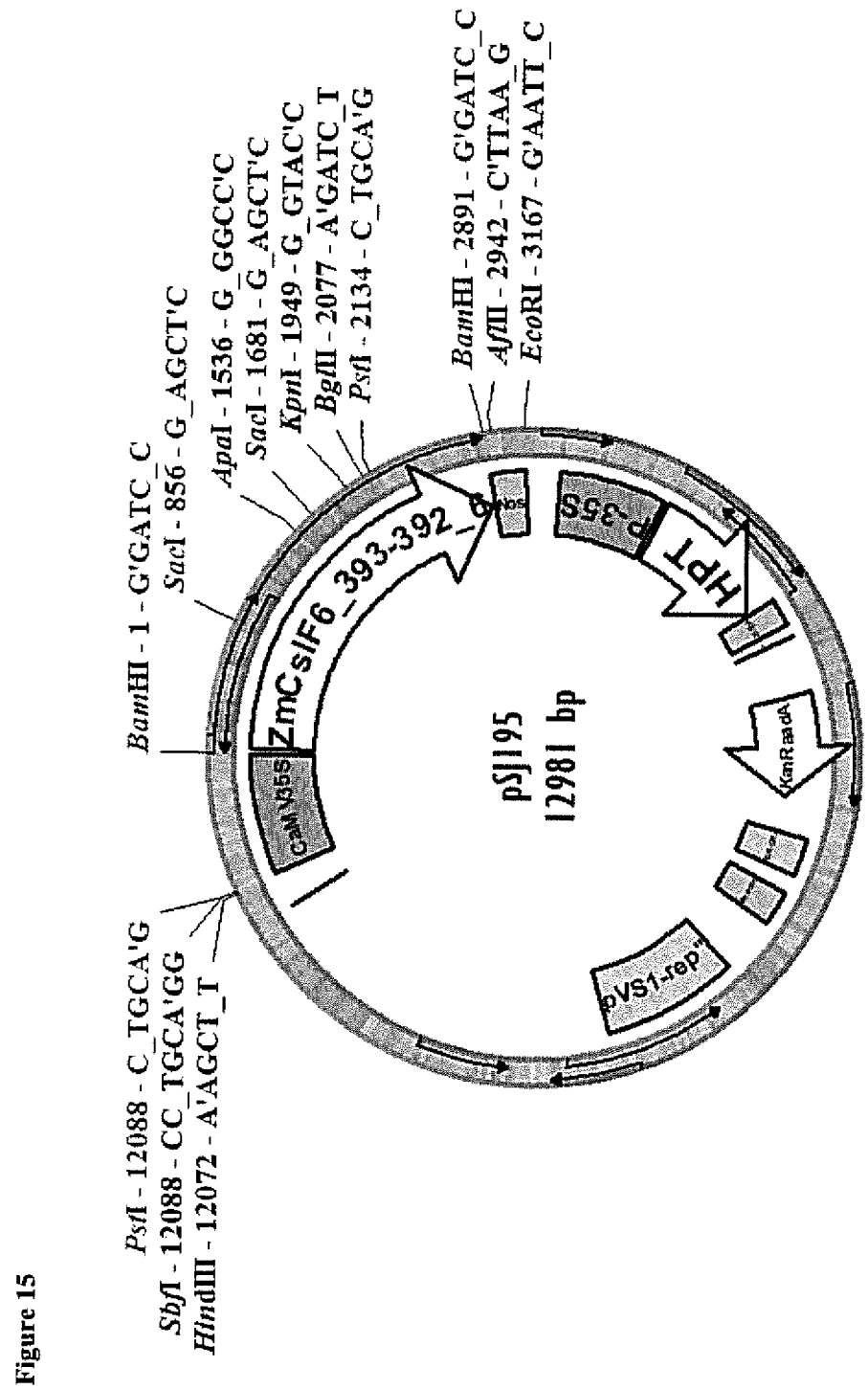
FIG. 15. Plasmid map of pSJ195 showing relevant restriction sites.

In the first instance, chimeric genes were made using the HvCslF6 and ZmCslF6-2 derived plasmids pSJ226 and pSJ195 as these had the most restriction sites in common (FIG. 14). The sites for the restriction enzymes SacI (nucleotide positions 821 and 856), ApaI (1501 and 1536) and BglII (2060 and 2077) occurred at the same positions within the coding sequences of the barley and maize genes.

Figure 16:
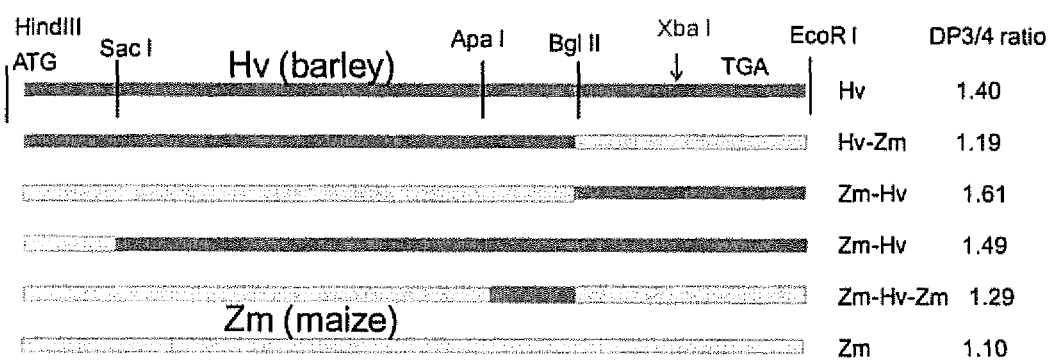
FIG. 16. Schematic of HvCslF6 and ZmCslF6-2 chimeric genes. HvCslF6 regions are shown in filled bars and ZmCslF6-2 regions in open bars. Restriction sites used in cloning are indicated. The HindIII and EcoRI sites are upstream and downstream of the CaMV 35S promoter and Nos polyA sites in the vector. The DP3/DP4 ratio of the BG produced by these constructs in the N. benthamiana leaves is shown on the right hand side.

Therefore a first set of chimeric genes were made using those sites and the unique HindIII and EcoRI sites which were 5' and 3' of the CaMV35S promoter and Nos polyadenylation regions, respectively. A schematic diagram of the constructs and summary of the results of the DP3/DP4 ratio of the BG produced after expression in *N. benthamiana* are shown in FIG. 16.

The parental HvCslF6 polypeptide produced a BG with a relatively high DP3/DP4 ratio of about 1.4 when expressed in the *N. benthamiana* cells whereas the parental ZmCslF6-2 polypeptide yielded a relatively low DP3/DP4 ratio of about 1.1. The standard deviations for the data from the assays were in the range 0.01-0.02 so the observed differences were significant even though the absolute values varied slightly from experiment to experiment depending on the plant age. These experiments were repeated many times and the differences between the two polypeptides were consistent. When the BglII-EcoRI fragment was exchanged between the HvCslF6 and ZmCslF6-2 genes, the DP3/DP4 ratio was changed—the Hv-ZmCslF6-2 polypeptide had a lower ratio similar to that conferred by the ZmCslF6-2 polypeptide whereas the Zm-HvCslF6-2 chimeric polypeptide yielded a higher ratio like the HvCSlF6 polypeptide. It was concluded that the BglII-EcoRI region (i.e. 3' region) of the genes conferred the characteristic DP3/DP4 ratio produced by the encoded polypeptides. When other regions of the genes were exchanged such as the 5' regions, there was no affect on the DP3/DP4 ratio of the BG, although the SacI-ApaI fragment exchange produced a DP3/DP4 ratio that was intermediate between the HvCslF6 and ZmCslF6-2 genes suggesting that this region might also exert some influence on the BG structure in this particular chimeric protein context.

To confirm these results, the BglII-EcoRI fragment was exchanged between the other CslF6 genes as shown in Table 21. The BglII site was conserved in all of the listed CslF6 genes. The native BdCslF6 and HvCslF6 polypeptides both produced a BG with a relatively high DP3/DP4 ratio of about 1.4 and about 1.74, respectively, whereas the AsCslF6, ZmCslF6-2 and SbCslF6 polypeptides produced a BG with a relatively low DP3/DP4 ratio of about 0.9 to about 1.09. When the BglII-EcoRI fragment was exchanged between these genes, the DP3/DP4 ratio and therefore the structure of the BG corresponded to the source of that fragment—if it was from a gene that produced a low DP3/DP4 ratio then the chimeric gene also yielded a low DP3/DP4 ratio and vice versa for the high DP3/DP4 ratio CslF6 genes. Exchanging the BglII-EcoRI fragments within a DP3/DP4 ratio class e.g. between the Bd and Hv CslF6 genes or between the As and Zm CslF6 genes had no effect on the BG structure as the DP3/DP4 ratio remained high or low, respectively. Therefore this region of the CslF6 polypeptides was shown conclusively to control the DP3/DP4 ratio of the BG.

This carboxy terminal region of the CslF6 polypeptides contains a small portion of the predicted cytoplasmic region and six predicted transmembrane domains which form part of a membrane channel as predicted by comparison to the recently published 3D crystal structure of the related bacterial cellulose synthase protein (Morgan et al., 2013). To further define the region controlling the DP3/DP4 ratio, an XbaI site was introduced into the middle of this region encoding the TM5 and TM6 transmembrane domains of the HvCslF6 and ZmCslF6 polypeptides (plasmids pSJ245 and pSJ246, respectively). This was achieved by a nucleotide change which would not change the amino acid sequence of the polypeptides, using a synthetic gBlock method (IDT, USA). This allowed the exchange of the BglII-XbaI and XbaI-EcoRI fragments between the HvCslF6 and ZmCslF6 genes. When expressed in the plant cells, these chimeric genes produced BG from which it was determined that the BglII-XbaI region of each gene determined the DP3/DP4 ratio (Table 22).

The amino acid sequences for the carboxy terminal half of the HvCslF6 and ZmCslF6 polypeptides and those for the cellulose synthase proteins CesA were aligned. The differences between the HvCSlF6 and ZmCslF6 polypeptides in the region encoded by the BglII-XbaI region were identified. There were twelve amino acid differences in this region, the majority of which were predicted to lie in the TM3-TM6 domains.

Synthetic BglII-XbaI gBlock DNA fragments were designed to create chimeric Hv-ZmCslF6 polypeptides fused just upstream of a PvuII position in the ZmCslF sequence as this separated in half the differences in the two polypeptides in that region—the N-terminal half of the region containing the TM3 and TM4 transmembrane domains and the C-terminal half containing the TM5 and TM6 domains. Expression of these chimeric Hv-ZmCslF6 polypeptides in the *N. benthamiana* cells thereby defined the region controlling the DP3/DP4 ratio of the BG to the N-terminal half of this region (compare pSJ253, pSJ254, pSJ255 and pSJ256, Table 21). This region included the TM3 and TM4 domains as well as two amino acid differences in the central cytoplasmic domain of the CslF6 polypeptides between the BglII site and the PstI sites. The latter two differences had no affect on the DP3/DP4 ratio as an exchange of the PstI fragments between the HvCslF6 and ZmCslF6 genes in plasmids pSJ226 and pSJ195 had no affect on the BG structure (pSJ252, Table 23). Therefore, it was concluded that the four amino acid differences in the TM4 transmembrane domain determined the difference in the DP3/DP4 ratio of BG produced by the HvCslF6 and ZmCSlF6 polypeptides. The region of the genes that encoded that domain lay between the PstI and XbaI sites of the CslF6 genes.

To simplify further cloning, the PstI site upstream of the CaMV 35S promoter in pSJ226 and pSJ195 was destroyed by cutting with SbfI and repairing the ends with T4-DNA polymerase, thus leaving the PstI site in the CslF6 coding sequence as a unique PstI site and enabling the gBlock fragments to be cloned into the PstI-XbaI sites of pSJ257 and pSJ258 (encoding HvCslF6 and ZmCslF6-2, respectively). Cloning of the PstI-XbaI fragments from plasmids pSJ254 and pSJ255 into pSJ257 and pSJ258 generated CslF6 genes that differed only in the PstI-XbaI region and expression of these genes (pSJ259 and pSJ260) in *N. benthamiana* cells confirmed that this region alone determined the DP3/DP4 ratio of the BG (Table 22).

There were four single amino acid differences in the TM4 domain between the HvCslF6 and ZmCslF6-2 polypeptides. To determine which of these four amino acid changes determined the BG structure and the DP3/DP4 ratio, four synthetic PstI-XbaI gBlock fragments each containing only one amino acid difference relative to the HvCslF6 polypeptide (G748A, S752A, V756I and I757L with reference to SEQ ID NO:175, single letter amino acid codes) were designed and tested. This experiment was designed to show whether any of these single amino acid changes by themselves could affect the DP3/DP4 ratio of the BG produced by HvCSlF6 polypeptide and essentially convert it into a polypeptide with the properties of the ZmCslF6 polypeptide. When these mutant HvCslF6 genes were expressed in *N. benthamiana* leaves, only the I757L (isoleucine for leucine) substitution affected the DP3/DP4 ratio producing a BG with a structure similar to that of the ZmCslF6 polypeptide (Table 24). This finding is very surprising as the amino acid substitution is a very conservative substitution; I for L. It was surprising this seemingly minor change had such a substantial effect.

This amino acid substitution is introduced into the endogenous CslF6 gene of barley and into one or more of the three wheat CslF6 genes by genome editing techniques to produce barley grain or wheat grain whose BG was an altered DP3/DP4 ratio and therefore an increased solubility of BG in the grain or flour or wholemeal obtained therefrom. This provides food ingredients and food products with increased soluble dietary fibre.

LISTING OF SEQUENCE ID NOS

SEQ ID NO: 1, TaCslF3 type B cDNA, 2618 nt's. Initiating methionine ATG is nucleotides 7-9, the translation stop codon TAG is nucleotides 2560-2562.

SEQ ID NO: 2, TaCslF3 type B polypeptide, 851aa's. Signal sequence is amino acids 1-57, predicted transmembrane domains are amino acids 72-93, 101-120, 630-651, 664-686, 701-721, 752-774, 791-813 and 822-841. Amino acids known to be critical for activity are D195, DxD (395-397), D556 and QxxRW motifs (594-598).

SEQ ID NO: 3, TaCslF4 type1 cDNA 2726 nt's. Initiating methionine ATG is nucleotides 1-3, the translation stop codon TAG is nucleotides 2608-2610

SEQ ID NO: 4, TaCslF4 type2 cDNA 2725 nt's. Initiating methionine ATG is nucleotides 1-3, the stop codon TAG is nucleotides 2608-2610.

SEQ ID NO: 5, TaCslF4 type3 cDNA 2728 nt's. Initiating methionine ATG is nucleotides 1-3, the translation stop codon TAG is nucleotides 2608-2610.

SEQ ID NO: 6, TaCslF4 type1 gene 3022 nt's. Initiating methionine ATG is nucleotides 1-3, the translation stop codon TAG is nucleotides 2904-2906. Intron sequences (GT . . . AG) are nucleotides 246-356, 1804-1268.

SEQ ID NO: 7, TaCslF4 type2 gene 3015 nt's. Initiating methionine ATG is nucleotides 1-3, the translation stop codon is nucleotides 2898-2900. Intron sequences are nucleotides 246-349 and 1077-1262.

SEQ ID NO: 8, TaCslF4 type3 gene 2992 nt's. Initiating methionine ATG is nucleotides 1-3, the translation stop codon TAG is nucleotides 2872-2874. Intron sequences are nucleotides 246-341 and 1069-1236.

SEQ ID NO: 9, TaCslF4 type1 polypeptide, 869aa's. Signal sequence is amino acids 1-62, predicted transmembrane domains are 79-101, 108-127, 635-656, 669-691, 706-726, 757-779, 794-816 and 825-845. Amino acids known to be critical for activity are D198, DxD (398-400), D561 and QxxRW motifs (599-603).

SEQ ID NO: 10, TaCslF4 type2 polypeptide, 869 aa's. Signal sequence, predicted transmembrane domains and D, DxD, D and QxxRW motifs are at the same positions as for SEQ ID NO: 8.

SEQ ID NO: 11, TaCslF4 type3 polypeptide, 869 aa's. Signal sequence, predicted transmembrane domains and D, DxD, D and QxxRW motifs are at the same positions as for SEQ ID NO: 8.

SEQ ID NO: 12, TaCslF6 typeA cDNA 3082 nt's. Initiating methionine ATG is nucleotides 2-4, the translation stop codon TGA is nucleotides 2837-2839.

SEQ ID NO: 13, TaCslF6 typeB cDNA 3156 nt's. Initiating methionine ATG is 97-99, the translation stop codon TGA is nucleotides 2920-2922.

SEQ ID NO: 14, TaCslF6 typeD cDNA 3193 nt's. Initiating methionine ATG is nucleotides 101-103, the translation stop codon TGA is nucleotides 2933-2935.

SEQ ID NO: 15, TaCslF6 type A gene 3813 nt's. Initiating ATG start codon is nucleotides 2-4, translation stop codon TGA is nucleotides 3568-3570. The first intron was not isolated and is not present in this sequence. The second intron sequence is nucleotides 1070-1800.

SEQ ID NO: 16, TaCslF6 type B gene without the first intron and the 3' part of the second intron from primer SJ180 to the splice site, 3741 nt's. Initiating methionine ATG start codon is nucleotides 97-99. Intron sequence is nucleotides 1153-1737.

SEQ ID NO: 17, TaCslF6 type D gene 5520 nt's. ATG start codon is nucleotides 101-103, translation stop codon TGA is nucleotides 5260-5262. Intron sequences are nucleotides 421-2047 and 2793-3492.

SEQ ID NO: 18, TaCslF6 type A polypeptide, 945 aa's. Signal sequence is amino acids 1-91, predicted transmembrane domains are amino acids 105-126, 134-153, 707-728, 741-763, 778-798, 831-852, 865-887 and 894-915. Amino acids known to be critical for activity are D228, DxD (430-432), D633 and QxxRW motifs (671-675).

SEQ ID NO: 19, TaCslF6 type B polypeptide 941 aa's. Signal sequence is amino acids 1-87, predicted transmembrane domains are amino acids 101-122, 130-149, 703-724, 737-759, 774-794, 827-848, 861-883 and 890-911. Amino acids known to be critical for activity are D224, DxD (426-428), D629 and QxxRW motifs (667-671).

SEQ ID NO: 20, TaCslF6 type D polypeptide, 944 aa's. Signal sequence is amino acids 1-90, predicted transmembrane domains are amino acids 104-125, 133-152, 706-727, 740-762, 777-797, 830-851, 864-886 and 893-914. Amino acids known to be critical for activity are D227, DxD (429-431), D632 and QxxRW motifs (670-674).

SEQ ID NO: 21, TaCslF7 type 3 cDNA sequence 2444 nt's. ATG start codon is nucleotides 11-13, translation stop codon TAA is nucleotides 2435-2437.

SEQ ID NO: 22, TaCslF7 type 3 gene, 3327 nt's partial sequence. Initiating ATG start codon is nucleotides 11-13. Intron sequence is nucleotides 157-1039.

SEQ ID NO: 23, TaCslF7 Type 3 polypeptide, 808 aa's. Signal sequence is amino acids 1-32, predicted transmembrane domains are amino acids 46-67, 81-101, 590-612, 631-653, 667-688, 723-745, 755-777 and 783-805. Amino acids known to be critical for activity are D168, DxD (342-344), D447 and QxxRW motifs (555-559).

SEQ ID NO: 24, TaCslF9 type A cDNA 2162 nt's, partial length—3' end not isolated. Initiating ATG methionine is at nucleotides 41-43.

SEQ ID NO: 25, TaCslF9 type B cDNA sequence, 2159 nt's. partial length-3' end not isolated. Initiating ATG methionine codon is nucleotides 41-43.

SEQ ID NO: 26, TaCslF9 type D cDNA 2760 nt's. ATG start codon is nucleotides 41-43, translation stop codon TAA is nucleotides 2612-2614.

SEQ ID NO: 27, TaCslF9 type A gene, 3370 nt's, partial length—3' end not isolated. ATG start codon is nucleotides 41-43. Intron sequences are nucleotides 1223-1375 and 2130-2211.

SEQ ID NO: 28, TaCslF9 type B gene, 3348 nt's, partial length—3' end not isolated. ATG start codon is nucleotides 41-43. Intron sequence is nucleotides 253-1351.

SEQ ID NO: 29, TaCslF9 type D gene, 2847nt, first intron not present. ATG start codon nucleotides 41-43, translation stop codon TAA is nucleotides 2699-2701. Intron sequence is 1004-1090.

SEQ ID NO: 30, TaCslF9 type D polypeptide, 857 aa's. Signal sequence is amino acids 1-51, predicted transmembrane domains are amino acids 67-89, 96-115, 634-655, 668-690, 793-815 and 822-844. Amino acids known to be critical for activity are D190, DxD (395-397), D560, and QxxRW motifs (598-602).

SEQ ID NO: 31, TaCslH type A cDNA, 2284 nt's. Initiating ATG start codon is nucleotides 19-21, translation stop codon TAA is nucleotides 2275-2277.

SEQ ID NO: 32, TaCslH type B cDNA, 2421 nt's. Initiating ATG start codon is nucleotides 156-158, translation stop codon TAA is nucleotides 2412-2414.

SEQ ID NO: 33, TaCslH type 3 cDNA, 2284 nt's. Initiating methionine ATG is nucleotides 19-21, the translation stop codon is nucleotides 2275-2277.

SEQ ID NO: 34, TaCslH type A gene, 3236 nt's. ATG start codon is nucleotides 141-143, translation stop codon TAA is nucleotides 3227-3229. Intron sequences are nucleotides 392-492, 824-918, 1045-1143, 1264-1337, 1627-1715, 1837-1948, 2134-2165 and 2595-2668.

SEQ ID NO: 35, TaCslH type B gene, 3316 nt's. ATG start codon is nucleotides 156-158, translation stop codon is nucleotides 3307-3309. Intron sequences are in corresponding positions relative to SEQ ID NO: 33

SEQ ID NO: 36, TaCslH type 3 gene, 3181 nt's. Initiating methionine ATG is nucleotides 19-21, the translation stop codon TAA is nucleotides 3172-3174. Intron sequences are in corresponding positions relative to SEQ ID NO: 33.

SEQ ID NO: 37, TaCslH type A polypeptide, 752 aa's. Signal sequence is amino acids 1-9, predicted transmembrane domains are amino acids 17-37, 44-66, 530-553, 572-596, 666-687 and 701-721. Amino acids known to be critical for activity are D133, DxD (293-295), D460, and QxxRW motifs (498-502).

SEQ ID NO: 38, TaCslH type B polypeptide, 752 aa's. Signal sequence, predicted transmembrane domains and amino acid D, DxD, D and QxxRW motifs are in the corresponding positions relative to SEQ ID NO: 36.

SEQ ID NO: 39, TaCslH type 3, polypeptide 752 aa's. Signal sequence, predicted transmembrane domains and amino acid D, DxD, D and QxxRW motifs are in the corresponding positions relative to SEQ ID NO: 36.

SEQ ID NO: 40. Chimeric HvCslF4T7 gene in pSJ11, AflII fragment, 2888nt. Initiating methionine ATG of the T7 tag amino acids is nucleotides 7-9, the ATG of the CslF4 polypeptide is nucleotides 34-36, the translation stop codon TAG is nucleotides 2653-2655.

SEQ ID NO: 41, Chimeric HvCslF4T7 polypeptide encoded by pSJ11, 882aa's. T7 tag consists of amino acids 1-11, signal peptide sequence is amino acids 10-70, predicted transmembrane domains are amino acids 89-110, 118-137, 648-669, 682-704, 718-739, 770-792, 807-829 and 836-858. Amino acids known to be critical for activity are D211, DxD (411-413), D574, and QxxRW motifs (612-616).

SEQ ID NO: 42 Chimeric HvCslF6T7 gene in pSJ33, AflII, 2977nt fragment, Initiating methionine of the T7 tag is nucleotides 6-9, the ATG of the CslF6 polypeptide is nucleotides 34-36, the translation stop codon TGA is nucleotides 2884-2886.

SEQ ID NO: 43, Chimeric HvCslF6T7 polypeptide encoded by pSJ33, 958aa's. T7 tag is amino acids 1-11, signal sequence is amino acids 12-101, predicted transmembrane domains are amino acids 117-138, 146-165, 719-740, 753-775, 789-810, 842-864, 877-899 and 906-927. Amino acids known to be critical for activity are D240, DxD (442-444), D645, and QxxRW motifs (683-687).

SEQ ID NO: 44, HvCslF9 genomic fragment in pSJ2, EcoRI fragment, 3984nt. ATG start codon is nucleotides 54-56, translation stop codon TAA is nucleotides 3942-3944. Intron sequences are nucleotides 269-1220 and 1972-2336.

SEQ ID NO: 45, HvCslF9 polypeptide, 857 aa's's. Signal sequence is amino acids 1-52, predicted transmembrane domains are amino acids 69-90, 98-117, 634-655, 668-690, 704-726, 757-778, 793-815 and 822-844. Amino acids known to be critical for activity are D192, DxD (396-398), D560, and QxxRW motifs (598-602).

SEQ ID NO: 46, Chimeric HvCslF7 genomic fragment in pSJ3, EcoRI fragment, 3620nt's. ATG start codon is nucleotides 35-37, translation stop codon TAA is nucleotides 3570-3572. Intron sequence is nucleotides 181-1285.

SEQ ID NO: 47, HvCslF7 polypeptide encoded in pSJ3, 810 aa's's. Signal sequence is amino acids 1-32, predicted transmembrane domains are amino acids 46-66, 82-101, 590-612, 631-654, 668-689, 725-747, 757-780 and 786-806. Amino acids known to be critical for activity are D168, DxD (343-345), D517, and QxxRW motifs (555-559).

SEQ ID NO: 48, HvCslH full length cDNA (2333 nt) ATG start codon is nucleotides 76-78, translation stop codon TAA is 2329-2331.

SEQ ID NO: 49, HvCslH genomic EcoRI fragment in pSJ6, 3227nt's. Initiating ATG start codon is nucleotides 88-90, translation stop codon TAA is nucleotides 3211-3213. Intron sequences are nucleotides: 339-437, 769-867, 994-1107, 1228-1331, 1545-1637, 1759-1817, 2048-2081, 2505-2655.

SEQ ID NO: 50, HvCslH polypeptide encoded by pSJ6, 751 aa's's. Signal sequence is amino acids 1-10, predicted transmembrane domains are amino acids 17-38, 44-66, 530-553, 572-595, 608-630, 665-688, 700-721 and 726-748. Amino acids known to be critical for activity are D133, DxD (293-295), D460, and QxxRW motifs (498-502).

SEQ ID NO: 51, Oats AsCslF6 type1 cDNA, 3002 nt's. Initiating methionine ATG is nucleotides 1-3, the translation stop codon TGA is nucleotides 2833-2835.

SEQ ID NO: 52, Oats AsCslF6 type 2 cDNA, 3424 nt's. Initiating methionine ATG is nucleotides 347-349, the translation stop codon TGA is nucleotides 3175-3177.

SEQ ID NO: 53, Oats AsCslF6 type 3 cDNA, 3269 nt's. Initiating methionine ATG is nucleotides 178-180, the translation stop codon TGA is nucleotides 3010-3012.

SEQ ID NO: 54, Oats AsCslF6 type2 genomic fragment AsCslF6_274 243_11, 5244 nt's. ATG start codon highlighted is nucleotides 18-20, translation stop codon is nucleotides 5165-5167. Intron sequences are nucleotides 338-1964 and 2710-3400

SEQ ID NO: 55, Oats AsCslF6 type 1 polypeptide amino acid sequence, 944 aa's. Signal sequence is amino acids 1-91, predicted transmembrane domains are amino acids 105-126, 134-153, 708-731, 744-766, 780-801, 834-853, 868-890 and 897-918. Amino acids known to be critical for activity are D228, DxD (430-432), D636 and QxxRW motifs (674-678).

SEQ ID NO: 56, Oats AsCslF6 type 2 polypeptide, 943 aa's. Signal sequence is amino acids 1-90, predicted transmembrane domains are amino acids 104-125, 133-152, 707-730, 743-765, 779-800, 833-852, 867-889 and 896-917. Amino acids known to be critical for activity are D227, DxD (429-431), D635 and QxxRW motifs (673-677).

SEQ ID NO: 57, Oats AsCslF6 type 3 polypeptide, 944 aa's. Motifs as for SEQ ID NO: 55.

SEQ ID NO: 58, BdCslF6_277-357_10 cDNA, 2933 nt's. The first 12 nucleotides and last 12 nucleotides are vector sequences from pCR BluntII. The T7 epitope tag sequence is nucleotides 16-48, and the translation stop codon TGA is nucleotides 2866-2868.

SEQ ID NO: 59, BdCslF6T7 polypeptide, 950 aa's. T7tag is amino acids 1-11. Signal sequence is amino acids 12-93, predicted transmembrane domains are amino acids 107-128, 135-155, 713-735, 747-769, 783-804, 837-856, 871-893 and 900-920. Amino acids known to be critical for activity are D230, DxD (433-435), D639 and QxxRW motifs (677-681).

SEQ ID NO: 60, Rice OsCslF6_69-324_15 cDNA 3115 nt's. The first 12 nucleotides and last 12 nucleotides are vector sequences from pCR BluntII. The initiating methionine ATG is nucleotides 244-246, the translation stop codon TGA is nucleotides 3100-3102.

SEQ ID NO: 61, Rice OsCslF6 polypeptide, 952 aa's. Signal sequence is amino acids 1-90, predicted transmembrane domains are amino acids 104-125, 132-152, 712-732, 744-766, 780-801, 834-853, 868-890 and 897-918. Amino acids known to be critical for activity are D227, DxD (429-431), D636 and QxxRW motifs (674-678).

SEQ ID NOs: 62-163. Oligonucleotide primers (Table 1).

SEQ ID NO:164 *Zea mays* cDNA corresponding to ZmCslF6-1 GRMZM2G110145

SEQ ID NO:165 *Zea mays* cDNA corresponding to ZmCslF6-2 GRMZM2G122277-T01

SEQ ID NO:166 *Zea mays* cDNA corresponding to ZmCslF6-1_391-392_14

SEQ ID NO:167 *Zea mays* cDNA corresponding to ZmCslF6-2 393-392_6

SEQ ID NO:168 *Sorghum biclor* cDNA corresponding to SbCslF6 Sb07g0041101Sb07g004110.1

SEQ ID NO:169 HvCslF6_116-77 (pSJ226)

SEQ ID NO:170 Amino acid sequence of *Zea mays* CslF6 polypeptide GRMZM2G110145_T01pro SEQ ID NO:171 Amino acid sequence of *Zea mays* CslF6 polypeptide -GRMZM2G122277-T01pro SEQ ID NO:172 Amino acid sequence of *Zea mays* CslF6 polypeptide ZmCslF6-1 391-392_14pro SEQ ID NO:173 Amino acid sequence of *Zea mays* CslF6 polypeptide *Zea mays* CslF6 ZmCslF6-2 393-392_6pro SEQ ID NO:174 Amino acid sequence of *Sorghum bicolor* CslF6 polypeptide-*Sorghum bicolor*|Sb07g004110|Sb07g004110.1

SEQ ID NO:175 Amino acid sequence of *Hordeum vulgare* CslF6 polypeptide HvCslF6 (pSJ226). Signal sequence is amino acids 1-90, predicted transmembrane domains are amino acids 105-127, 134-153, 714-736, 743-765, 778-800, 830-852, 867-889 and 896-918.

SEQ ID NO:176 Amino acid sequence of native HvCslF6 TM4

SEQ ID NO:177 Amino acid sequence of native ZmCslF6 TM4

SEQ ID NO:178 Amino acid sequence of HvCslF6 TM4 amino acid substitution mutant

SEQ ID NOs: 179-183. Oligonucleotide primers (Table 20).

TABLE 1

Nucleotide sequences of primers used in cloning CslF and CslH sequences and in RT-PCR experiments

| Primer ID | Gene | Nucleotide sequence (5' to 3') | Location in gene | SEQ ID NO |
|---|---|---|---|---|
| SJ85 | HvCslH | GGTTAGTTCCTTGTGCAGAGGT | 5' end FL | 62 |
| SJ91 | HvCslH | GAGCTGTGTTCGTGGAGCTTAG | a/s 3' end | 63 |
| SJ163 | HvCslH | CTGCTCTCGGCCACGGCCAT | 5'end FL | 64 |
| SJ164 | HvCslH | CCGCCGGTTAGTTCCTTGTGCAGA | a/s 3'end | 65 |
| SJ253 | HvCslF4T7 | AAGATGGCTAGCATGACTGGTGGACAGCAAATGGGTGCCCCGGCAGTCACT | 5' + T7 | 66 |
| SJ254 | HvCslF4 | AAGAGGAGTGGCACACAATGAC | a/s 3' | 67 |
| SJ77 | HvCslF6 | GATGGATGCATGCACTGACT | a/s 3' | 68 |
| SJ112 | HvCslF7 | ATAGCGCTTGGCCAGTGGAAGC | 5'end FL | 69 |
| SJ111 | HvCSlF7 | CATTTGAAATTTCACTCGTCGTCCA | a/s 3' end | 70 |
| SJ147 | HvCSlF7 | AGGCATGTTAAAGCATATGCAAATG | a/s 3' end | 71 |
| SJ114 | TaCslF3 | GGAGACATGGCGTCGGC | 5' end FL | 72 |
| SJ115 | TaCslF4 | ATGGCCCCGGCAGTCACTC | 5' end FL | 73 |
| SJ116 | TaCslF6 | CATGGCGCCAGCGGTGG | 5' end FL | 74 |
| SJ117 | TaCslF7 | AGAAGTCGGCCAATGTCGAGA | 5' end FL | 75 |
| SJ118 | TaCslF8 | GGGACATGGGTTCTTTGGC | 5' end FL | 76 |
| SJ158 | TaCSlF8 | ACAGCCTATATATGATTCACACCA | a/s 3' end | 77 |
| SJ30 | TaCslF9 | AAGAACAGGCTCTGCTACT | 5' end FL | 78 |
| SJ99 | TaCslF9 | CAGGTTTTGCAGCATTACTTGAC | a/s 3'utl | 79 |
| SJ150 | TaCslF10 | GACGGACATCATCCAAAACCACAT | a/s 5' RACE | 80 |
| SJ155 | TaCslF10 | CAGGATGATATTCTTGACTCTCCTG | a/s 5' RACE | 81 |
| SJ165 | TaCslF10 | CCTCAGGCAATGACGACG | 5'FL | 82 |
| SJ166 | TaCslF10 | GTCCATAGAAAAGTATGCTAAGGTACT | a/s 3' end | 83 |
| SJ14 | TaCslF4 | CATCGCGACGGAGGACGTGG | a/s 3' RACE | 84 |
| SJ60 | TaCslF4 | ATGACCTGGCTACCCTGATG | a/s 3' RACE | 85 |
| SJ48 | TaCslF6 | AAAGGATCCGGTACCAACGAGCAGTTCTACATCATCG | a/s 3' RACE | 86 |
| SJ113 | TaCslF6 | GACCACTACGTCAACAACTC | a/s 3' RACE | 87 |
| SJ61 | TaCslF8 | GACTGAATGGGGCAGAGAAG | a/s 3' RACE | 88 |
| SJ56 | TaCslF8 | CATTGCAACTGAGGATGTGG | a/s 3' RACE | 89 |

TABLE 1-continued

Nucleotide sequences of primers used in cloning CslF and CslH sequences and in RT-PCR experiments

| Primer ID | Gene | Nucleotide sequence (5' to 3') | Location in gene | SEQ ID NO |
|---|---|---|---|---|
| SJ03 | TaCslF9 | ACCACAACCGCATGTTCTTC | a/s 3' RACE | 90 |
| SJ156 | TaCslF6 | GCACTGTTCAGTGGATGACTTGTTG | a/s 3' end | 91 |
| SJ278 | TaCslF7 | CAGTGGGAGCATGTCAATGA | 5' end FL | 92 |
| SJ147 | TaCslF7 | AGGCATGTTAAAGCATATGCAAATG | a/s 3' end | 93 |
| SJ162 | TaCslF6 | GCCTGAGCGTGGAGAGCTAC | 5' end genomic | 94 |
| SJ38 | TaCslF3 | CGGCGGAACATGCAAC | a/s 3' partial cDNA | 95 |
| SJ139 | TaCslF3 | GCACATCAGTGCTGGCGAAGT | a/s 3' partial genomic | 96 |
| SJ44 | TaCslF3 | CGGAAATCCATAGGAAAGG | 5' partial genomic | 97 |
| SJ31 | TaCslF3 | GCTCCCAGCTTACTACAGA | a/s 3' partial genomic | 98 |
| SJ13 | TaCslF4 | CCACGTCCTCCGTCGCGATG | a/s 3' partial cDNA | 99 |
| SJI40 | TaCslF4 | GCGTCGCCGGAGTGGTCC | a/s 3' partial genomic | 100 |
| SJ157 | TaCslF4 | GTAGAGGAGTGGCACACAATGAC | a/s 3' partial genomic | 101 |
| SJ135 | TaCslF9 | ACCGGGTACGAGTAGTACATGC | a/s 3' partial cDNA | 102 |
| SJ101 | TaCslF9 | TTGGCCCAGAAGTAGCTCT | a/s 3' partial genomic | 103 |
| SJ152 | TaCSlF9 | GTGTGCAAATGCTACCTGGATG | 5' partial genomic | 104 |
| SJ37 | TaCSlF9 | GAGTTGTTGACGTAGTGGTC | a/s 3' partial genomic | 105 |
| SJ17 | AsCslF6 | ATCGCCGGSGAGCTCTGGTT | 5' | 106 |
| SJ19 | AsCslF6 | TTSCGGCAGAASGGCACCCA | a/s 3' | 107 |
| SJ37 | AsCslF6 | GAGTTGTTGACGTAGTGGTC | a/s 3' | 108 |
| SJ69 | OsCslF6 | TCCCCCACGTACTTTACGAC | 5' utl FL | 109 |
| SJ113 | AsCslF6 | GACCACTACGTCAACAACTC | 3' RACE | 110 |
| SJ123 | AsCslF6 | GCCATGGTGGCCGTGCTGGA | 3' RACE | 111 |
| SJ156 | TaCslF6 | GCACTGTTCAGTGGATGACTTGTTG | a/s 3' utl | 112 |
| SJ162 | TaCslF6 | GCCTGAGCGTGGAGAGCTAC | 5' utl | 113 |
| SJ243 | AsCslF6 | ACAGCTCAGCGGAAGACTTG | a/s 3' utl | 114 |
| SJ265 | AsCslF6 | GCGACTTGAGCTCGAAGTAGCTCT | a/s 5' RACE | 115 |
| SJ270 | AsCslF6 | GGTAGAGAAGGACGGCCTTAATC | a/s 5' RACE | 116 |
| SJ272 | AsCslF6 | TGCACGCGCACACCTGGAA | a/s 5' RACE | 117 |
| SJ274 | TaCslF6 | CATTGAGGACGACGGCCAT | 5' utl FL | 118 |
| SJ277 | Hv, Ta CslF6 | AAGATGGCTAGCATGACTGGTGGAC AGCAAATGGGTATGGCGCCAGCGGT | #NAME? | 119 |

TABLE 1-continued

Nucleotide sequences of primers used in cloning CslF and CslH sequences and in RT-PCR experiments

| Primer ID | Gene | Nucleotide sequence (5' to 3') | Location in gene | SEQ ID NO |
|---|---|---|---|---|
| SJ321 | OsCslF6 | CGTGTAGTAGAACGTACTCATCTC | a/s 3' utl | 120 |
| SJ324 | OsCslF6 | CTCATGGCCAGGCGTAGGTGAA | a/s 3' utl | 121 |
| SJ325 | TaCslF6 | GTCTCAGGTCGTCCTGTCCGG | a/s 3' utl | 122 |
| SJ357 | BdCslF6 | GTCGATCTTCTTCGTCCCGAT | a/s 3'utl | 123 |
| RoRidT17 | | CCAGTGAGCAGAGTGACGAGGACTCGAGCTCAAGCTTTTTTTTTTTTTTTTT | cDNA synthesis | 124 |
| NUP | RACE | AAGCAGTGGTATCAACGCAGAGT | Nested universal primer | 125 |
| UPM | RACE | CTAATACGACTCACTATAGGGC | Universal primer mix | 126 |
| SJ44 | HvCslF3 | CGGAAATCCATAGGAAAGG | RT-PCR | 97 |
| SJ38 | HvCslF3 | CGGCGGAACATGCAAC | RT-PCR | 95 |
| SJ94 | HvCslF4 | GATGCGTACAACTCGAGCAA | RT-PCR | 127 |
| SJ95 | HvCslF4 | CGTTGCTGAAGTCAAGTGGA | RT-PCR | 128 |
| SJ76 | HvCslF6 | AACATCCCCCACATGCATAC | RT-PCR | 129 |
| SJ77 | HvCslF6 | GATGGATGCATGCACTGACT | RT-PCR | 68 |
| SJ96 | HvCslF8 | GGATTGACCCAGCTGAAAAC | RT-PCR | 130 |
| SJ37 | HvCslFS | GAGTTGTTGACGTAGTGGTC | RT-PCR | 131 |
| SJ97 | HvCslF9 | CGCTGCAAACGAGAAAGAAGG | RT-PCR | 132 |
| SJ93 | HvCslF9 | GGCGCTGAAATCCAGAGG | RT-PCR | 133 |
| SJ54 | HvCslF10 | GGAAGATGGGCCAAGAGAAC | RT-PCR. | 134 |
| SJ120 | HvCslF10 | TGATCCATAGAAAAGTGTGCTAGGT | RT-PCR | 135 |
| SJ72 | HvCslH | CAGCCGTGATGACCAACG | RT-PCR | 136 |
| SJ74 | HvCslH | CAAAATGTCTTCTGTCATTGATCC | RT-PCR | 137 |
| HvTUB2F1 | α-tubulin | AATGCTGTTGGAGGTGGAAC | RT-PCR | 138 |
| HvTUBR | α-tubulin | CAAACCTCAGGGAAGCAGTCA | RT-PCR | 139 |
| HvCesA2F | HvCesA2 | GGCAGGCACTGTACGGTTATG | RT-PCR | 140 |
| HvCesA2R | HvCesA2 | ACCAGCCTTCTGAGTTTCAGCTC | RT-PCR | 141 |
| HvCesA4F | HvCesA4 | GTACGAGCTGGAGGAGATCG | RT-PCR | 142 |
| HvCesA4R | HvCesA4 | CGTCAGGATGTCCTCTGTCA | RT-PCR | 143 |
| HvTUBF | α-tubulin | AGTGTCCTGTCCACCCACTC | real time PCR | 144 |
| HvTUBR | α-tubulin | CAAACCTCAGGGAAGCAGTCA | real time PCR | 145 |
| SJ193 | HvSUS1 | AGTGCTGCTTGCTGGTTCAT | real time PCR | 146 |
| SJ94 | HvSUS1 | CCAACTTCAAAGGCACACAG | real time PCR | 147 |
| SJ199 | TaSUS1 | GCGTGTATGGGTTCTGGAAG | real time PCR | 148 |

TABLE 1-continued

Nucleotide sequences of primers used in cloning CslF and CslH sequences and in RT-PCR experiments

| Primer ID | Gene | Nucleotide sequence (5' to 3') | Location in gene | SEQ ID NO |
|---|---|---|---|---|
| SJ200 | TaSUS1 | GTCAACTGCCAATGGAACTG | real time PCR | 149 |
| SJ242 | HvCslF6 | GGGCATTCACCTTCGTCATC | real time PCR | 150 |
| SJ77 | HvCslF6 | GATGGATGCATGCACTGACT | real time PCR | 68 |
| SJ217 | HvCslF9 | GAGCAAGAGGCCCTACATCC | real time PCR | 151 |
| SJ99 | HvCslF9 | CAGGTTTTGCAGCATTACTTGAC | real time PCR | 152 |
| SJ183 | HvCslH | GGAGAGTTCGTGTGCTGTGG | real time PCR | 153 |
| SJ85 | HvCslH | GGTTAGTTCCTTGTGCAGAGGT | real time PCR | 62 |
| SJ242 | TaCslF6 | GGGCATTCACCTTCGTCATC | real time PCR | 150 |
| SJ156 | TaCslF6 | GCACTGTTCAGTGGATGACTTGTTG | real time PCR | 91 |
| SJ224 | TaCslF9 | CTCTTCGTCGTCATCGTCATC | real time PCR | 154 |
| SJ189 | TaCslF9 | CGATGATGTAGAACTGCTCGTTG | real time PCR | 155 |
| SJ97 | HvCslF9 | CGCTGCAAACGAGAAAGAAGG | real time KR | 156 |
| SJ93 | HvCslF9 | GGCGCTGAAATCCAGAGG | real time PCR | 157 |
| SJ183 | TaCslH | GGAGAGTTCGTGTGCTGTGG | real time PCR | 158 |
| SJ164 | TaCslH | CCGCCGGTTAGTTCCTTGTGCAGA | real time PCR | 65 |
| SJ244 | Bx17 5'utl | CGAGCACCCCAATCTACAGA | transgene PCR | 159 |
| SJ242 | HvCslF6T7 | GGGCATTCACCTTCGTCATC | transgene PCR | 150 |
| SJ123 | HvCslF7 | GCCATGGTGGCCGTGCTGGA | transgene PCR | 160 |
| SJ217 | HvCslF9 | GAGCAAGAGGCCCTACATCC | transgene PCR | 161 |
| SJ81 | HvCslF4T7 | CGGTGGTGACGAAGATGTCGATG | transgene PCR | 162 |
| nosR | NOS | GATAATCATCGCAAGACCGGCAACAGG | transgene PCR | 163 |

TABLE 2

Length of CslF and CslH polypeptides from barley and wheat (number of amino acids)

|  | CslF3 | CslF4 | CslF6 | CslF7 | CslF8 | CslF9 | CslF10 | CslH |
|---|---|---|---|---|---|---|---|---|
| Barley | 851 | 870 | 947 | 810 | 897 | 857 | 879 | 751 |
| Wheat | n/a | 869 | 945 | n/a | 897 | n/a | 878 | 752 |
| Wheat | 851 | 869 | 941 | 808 | 897 | n/a | n/a | 752 |
| Wheat | 847 | 869 | 944 | 808 | 897 | 857 | n/a | 752 | n/a full length cDNA not available.

TABLE 3

Percentage nucleotide sequence identity between barley and wheat CslF genes. Full length or near full length DNA sequences were aligned with Muscle software. Where more than one wheat full length gene was available, the range of % identity is shown.

|  | TaCslF3 | TaCslF4 | TaCslF6 | TaCslF7 | TaCslF8 | TaCslF9 | TaCslF10 |
|---|---|---|---|---|---|---|---|
| HvCslF3 | 89.8-90.4 | 60.5-60.6 | 48.7-55.7 | 49.6 | 61.3-62.0 | 65.5-60.5 | 64.5-70.8 |
| HvCslF4 | 60.3-60.6 | 91.2-91.7 | 53.6-61.4 | 56.2 | 60.6-62.1 | 65.1-69.2 | 57.1-62.2 |
| HvCslF6 | 48.8-49.0 | 53.9-54.5 | 84.6-92.9 | 50.8 | 52.1-52.8 | 55.3-60.3 | 47.2-52.8 |
| HvCslF7 | 48.7-49.1 | 55.8-56.2 | 49.9-50.2 | 89.3 | 50.9-51.0 | 55.2-56.0 | 46.1-49.7 |
| HvCslF8 | 60.8-61.2 | 62.3-62.5 | 51.5-57.7 | 51.4 | 95.6-96.0 | 64.2-66.9 | 58.1-64.1 |
| HvCslF9 | 57.5-57.9 | 66.0-66.8 | 54.7-59.8 | 55.5 | 64.2-64.3 | 89.8-93.6 | 56.5-59.3 |
| HvCslF10 | 62.5-62.6 | 56.3-56.7 | 46.2-53.1 | 46.5 | 58.0-58.2 | 53.7-56.8 | 83.2-93.1 |

TABLE 4

Percentage amino acid sequence identity between barley and wheat CslF genes. Full length polypetides were aligned with Muscle software. Where more than one wheat ORF was available, the range of identity is shown.

|  | TaCslF3 | TaCslF4 | TaCslF6 | TaCslF7 | TaCslF8 | TaCslF9 | TaCslF10 |
|---|---|---|---|---|---|---|---|
| HvCslF3 | 95.1-95.2 | 57.0-57.4 | 46.1-46.3 | 40.5 | 56.4 | 55.2 | 63 |
| HvCslF4 | 57.6-58.2 | 92.5 | 45.9-46.1 | 42.2 | 58.3-58.4 | 57.2 | 52.7 |
| HvCslF6 | 45.8-45.9 | 45.3-45.4 | 97.6-98.1 | 39.7 | 44.2-44.6 | 42.4 | 42.4 |
| HvCslF7 | 41.4-41.5 | 43.1-43.2 | 39.5-39.7 | 87.6 | 40.4-40.6 | 42.5 | 37 |
| HvCslF8 | 56.8-56.9 | 59.2-59.6 | 41.9-45.1 | 40.2 | 97.3-97.7 | 63.5 | 52 |
| HvCslF9 | 55.7-55.7 | 58.2-58.6 | 43.0-43.0 | 41.4 | 63.6-63.8 | 95.2 | 50.4 |
| HvCslF10 | 62.0-62.8 | 51.9 | 41.5-41.6 | 36.5 | 51.6-51.9 | 49.9 | 92.5 |

TABLE 5

Relative transgene expression levels in T1 developing grain (single or duplicate pooled T1 grain samples approximately 15 DPA) and BG levels in mature grain from wheat plants transformed with chimeric gene encoding HvCslH

| Line | Relative HvCslH Expression Level | Average BG level (% w/w) | Standard deviation | Maximum BG level (% w/w) |
|---|---|---|---|---|
| H1-1 | 234, 113 | 0.81 | 0.08 | 0.8 |
| H1-2 | 1 | 0.68 | 0.02 | 0.7 |
| H1-3 | 103 | 0.89 | 0.05 | 0.9 |
| H1-4 | 310, 248, 122 | 0.82 | 0.05 | 0.8 |
| H1-5 | 150, 205 | 0.83 | 0.21 | 1.1 |
| H1-6 | 476 | 0.91 | 0.09 | 1.0 |
| H1-7 | 32 | 0.65 | 0.05 | 0.7 |
| H1-8 | 70, 115 | 0.87 | 0.15 | 1.1 |
| H1-9 | 886 | 1.17 | 0.33 | 1.9 |
| H1-10 | 2198, 2026 | 1.12 | 0.39 | 1.9 |
| H1-11 | 3, 13 | 0.82 | 0.14 | 1.0 |
| H1-12 | 5, 515 | 1.23 | 0.26 | 1.7 |
| H1-14 | 176, 507 | 0.99 | 0.19 | 1.4 |
| H1-15 | 5 | 0.60 | 0.26 | 0.8 |
| average of PCR− (2, 7, 11) |  | 0.69 | 0.10 | 1.0 |
| average of PCR+ (rest) |  | 0.96 | 0.12 | 1.9 |

TABLE 6

BG and fibre analysis of wheat flour from T4 grain transformed with construct encoding HvCslH.
Standard deviations are shown below each value.

| | Wholegrain | | Bran | | Endosperm | | Endosperm | | |
|---|---|---|---|---|---|---|---|---|---|
| | BG | DP3/4 | BG | DP3/4 | BC | DP3/4 | Dietary Fibre (% w/w) | | |
| Line | level | ratio | level | ratio | level | ratio | Soluble | Insoluble | Total |
| H1-10B7.3 (control) | 0.80 ± 0.03 | 2.41 ± 0.06 | 1.78 ± 0.05 | 2.63 ± 0.00 | 0.26 ± 0.01 | 1.89 ± 0.02 | 0.7 | 1.7 | 2.4 |
| H1-10B7.4 | 1.58 ± 0.17 | 2.35 ± 0.01 | 2.24 ± 0.07 | 2.52 ± 0.01 | 0.84 ± 0.03 | 1.95 ± 0.01 | 1.2 | 2.8 | 3.9 |
| H1-10B7.6 | 1.49 ± 0.09 | 2.44 ± 0.01 | 2.39 ± 0.15 | 2.60 ± 0.02 | 0.72 ± 0.02 | 1.99 ± 0.02 | 1.7 | 2.7 | 4.5 |
| H1-10B1.9 | 1.59 ± 0.19 | 2.30 ± 0.01 | 2.34 ± 0.05 | 2.47 ± 0.01 | 0.90 ± 0.04 | 1.96 ± 0.01 | 1.8 | 3.5 | 5.3 |

TABLE 7

Primers used in cloning cereal CslF and CslH genes

| Plant Expression Plasmid | Gene/primers | PCR vector | Restriction sites |
|---|---|---|---|
| pSJ21 | HvCslF4T7_253-254 | pCR2.1 | XbaI-SacI |
| pSJ27 | HvCslF7_112-147 | pCRBluntII | EcoRI |
| pSJ26 | HvCslH_91-85 | pCRBluntII | EcoRI |
| pSJ23 | TaCslF8_118-158 | pCR2.1 | EcoRI |
| pSJ40 | TaCslF9_30-NUP | pCR2.1 | EcoRI |
| pSJ25 | TaCslF10_165-166 | pCRBluntII | EcoRI |
| pSJ45 | TaCslH_163-164 | pCRBluntII | EcoRI |
| pSJ18 | AsCslF3_251-250 | pCR2.1 | XbaI-SacI |
| pSJ20 | AsCSlF4_115-247 | pCR2.1 | XbaI-KpnI |
| pSJ19 | AsCslF8_248-249 | pCR2.1 | HindIII-XhoI |
| pSJ22 | AsCslF9_234-235 | pCR2.1 | EcoRI |
| pSJ117 | AsCslH_236-233 | pCR2.1 | EcoRI |

TABLE 8

HvCslF6 wheat T2 grain with increased BG content has an altered structure with a lower DP3/DP4 ratio.

| Line | BG content w/w | DP3/DP4 ratio |
|---|---|---|
| F6-1G4a | 0.9 | 2.53 |
| F6-1G4b | 1.1 | 3.05 |
| F6-1G4c | 4.0 | 2.17 |
| F6-1G4d | 4.3 | 1.98 |
| F6-1G4e | 0.8 | 2.46 |
| Wheat | 0.82 | 2.45, 2.37 |
| Oat | 4.45 | 1.75, 1.8 |
| Barley | 4.2 | 2.59, 2.59 |

TABLE 9

DP3/DP4 ratio of BG from pooled HvCslF6 wheat T3 wholemeal flour

| Line description | | DP3/DP4 ratio |
|---|---|---|
| F6-1G3.7 | neg seg | 2.41 ± 0.09 |
| F6-1K3.2 | neg seg | 2.54 ± 0.01 |
| F6-1D4.3 | neg seg | 2.51 ± 0.04 |
| F6-1G6.8 | homozygous | 1.74 ± 0.01 |
| F6-1D4.4 | homozygous | 1.80 ± 0.04 |
| F6-1K5.9 | homozygous | 1.67 ± 0.05 |

TABLE 10

Summary of binary vectors for transient expression of Csl proteins in *N. benthamiana* leaves

| Plasmid | Gene source | Sequence designation of Csl-encoding region | T7 Tag at N-terminus | Length of protein (including T7 tag if present) |
|---|---|---|---|---|
| pSJ21 | Barley HvCslF4 | HvCslF4_253-254_21 | Yes | 882 |
| pSJ38 | Barley HvCslF6 | HvCslF6_277-77_23 | Yes | 958 |
| pSJ27 | Barley HvCslF7 | HvCslF7_112-147_2 | No | 810 |
| pSJ46 | Wheat | TaCslF6_274-156_10 | No | 941 |
| pSJ104 | Wheat | TaCslF6_277-325_18 | Yes | 956 |
| pSJ106 | Wheat | TaCslF6_277-156_23 | Yes | 955 |
| pSJ78 | Oat | AsCslF6_277-243_28 | Yes | 954 |
| pSJ79 | Oat | AsCslF6_277-243_29 | Yes | 955 |
| pSJ134 | *Brachypodium* | BdCslF6_116-357_01 | No | 939 |
| pSJ135 | *Brachypodium* | BdCslF6_277-357_10 | Yes | 950 |
| pSJ129 | Rice | OsCslF6_69-324_15 | No | 951 |

TABLE 11

Amount and structure of BG from heterologous CslF6 genes expressed transiently in *N. benthamiana* leaves.

| | Construct | | | | | |
|---|---|---|---|---|---|---|
| | Expt 1 | | Expt 2 | | Expt 3 | |
| | BG % (w/w) | DP3/DP4 ratio | BG % (w/w) | DP3/DP4 ratio | BG % (w/w) | DP3/DP4 ratio |
| pSJ38 (HvCslF6T7) | 2.6 | 1.35 | 0.7 | 1.32 | 1.14 | 1.38 |
| pSJ46 (TaCslF6) | 1.7 | 1.65 | | | | |
| pSJ104 (TaCslF6T7) | 0.3 | 1.52 | | | | |
| pSJ106 (TaCslF6T7) | 2.8 | 1.53 | | | 1.2 | 1.43 |
| pSJ78 (AsCslF6T7) | 0.3 | 1.03 | | | | |
| pSJ79 (AsCslF6T7) | 0.6 | 0.95 | | | 0.2 | 0.80 |
| pSJ134 (BdCslF6) | | | 2.4 | 1.63 | | |
| pSJ135 (BdCslF6T7) | | | 4.1 | 1.52 | | |
| pSJ129 (OsCslF6) | | | | | 1.76 | 0.90 |

TABLE 12

Amount and structure of BG from CslF6 genes expressed in N. benthamiana leaves (average of 4 biological replicates per construct, (+/− s.d.).

| Construct | BG % (w/w) | DP3/DP4 ratio |
|---|---|---|
| pSJ38 (HvCslF6T7) | 0.32 (+/−0.01) | 1.37 (+/−0.01) |
| pSJ46 (TaCslF6) | 2.06 (+/−0.28) | 1.60 (+/−0.03) |
| pSJ79 (AsCslF6T7) | 0.14 (+/−0.02) | 1.01 (+/−0.04) |
| pSJ134 (BdCslF6) | 2.55 (+/−0.40) | 1.72 (+/−0.03) |
| pSJ129 (OsCslF6) | 2.52 (+/−0.39) | 1.03 (+/−0.01) |

TABLE 13

PCR analysis of regenerated wheat plants and AsCslF6 transgene expression and BG content in T1 grains

| T0 line | F6 PCR | construct | CslF6/tub ratio | single seed BG content (% dry wt) | | | |
|---|---|---|---|---|---|---|---|
| F6-121 | − | pSJ127 | 0.010 | 0.7 | 0.7 | 1.3 | 1.4 |
| F6-122 | + | pSJ127 | 1.250 | 2.3 | 2.3 | 3.1 | 3.2 |
| F6-124 | + | pSJ127 | 1.901 | 2.5 | 2.5 | 2.3 | 2.3 |
| F6-125 | + | pSJ127 | 1.288 | 1.0 | 0.7 | 0.7 | 0.8 |
| F6-127 | + | pSJ127 | 0.318 | 2.7 | 4.0 | 1.9 | 3.0 |
| F6-129 | + | pSJ127 | 0.210 | 1.6 | 1.8 | 2.6 | 2.1 |
| F6-133 | + | pSJ127 | 1.091 | 1.1 | 2.3 | 1.0 | 1.5 |
| F6-134 | + | pSJ127 | 0.012 | 1.2 | 1.1 | 1.3 | |
| F6-139 | + | pSJ127 | 0.525 | 3.1 | 2.4 | 4.0 | 2.9 |
| F6-142 | + | pSJ127 | 0.898 | 4.2 | 3.8 | 4.4 | 1.0 |
| F6-143 | + | pSJ127 | 0.009 | | | | |
| F6-144 | + | pSJ127 | 0.214 | 1.4 | 1.0 | 1.3 | 1.0 |
| F6-145 | + | pSJ127 | 0.006 | 1.4 | 1.3 | 1.3 | |
| F6-146 | + | pSJ127 | 0.198 | 1.3 | 1.1 | 0.8 | 1.5 |
| F6-151 | + | pSJ124 | 1.781 | 2.3 | 2.6 | 2.3 | 2.4 |

TABLE 14

BG content, DP3/DP4 ratio and average grain weight of T2 wheat grain expressing AsCslF6

| Flour | BG content (% w/w) | DP3/DP4 ratio | average grain weight (mg) |
|---|---|---|---|
| Barley Std | 4.10 | 2.58 | n/a |
| F6-122.1pool | 3.10 | 1.60 | 20.30 |
| F6-122.2pool | 3.40 | 1.55 | 22.02 |
| F6-122.4pool | 2.16 | 1.55 | 25.65 |
| F6-122.6pool | 1.57 | 1.43 | 27.75 |
| F6-122.7pool | 3.58 | 1.42 | 28.68 |
| F6-122.8pool | 4.11 | 1.51 | 28.07 |
| F6-124.1pool | 3.89 | 1.45 | 23.34 |
| F6-124.2pool | 3.67 | 1.49 | 25.84 |
| F6-124.3pool | 3.27 | 1.43 | 31.09 |
| F6-124.4pool | 3.53 | 1.47 | 28.37 |
| F6-124.5pool | 3.24 | 1.45 | 20.28 |
| F6-124.6pool | 3.33 | 1.73 | 24.45 |
| F6-124.7pool | 3.50 | 1.42 | 23.55 |
| F6-124.8pool | 2.92 | 1.39 | 21.67 |

TABLE 15

Solubility of BG from HvCslF6 and AsCslF6 wholegrain flour

| Line | plasmid | Gen | F6 PCR | total BG content (% dry wt) | % soluble BG | DP3/DP4 insol | DP3/DP4 sol |
|---|---|---|---|---|---|---|---|
| F6-1K3.2 | neg seg | T4 | − | 0.91 | 5.18 | 2.43 | 2.17 |
| F6-121 | pSJ127 | T0 | − | 0.91 | 6.40 | 2.45 | 2.13 |
| F6-1G6.1.8 | pSJ33 | T5 homo | +Hv | 3.99 | 3.89 | 1.94 | 1.86 |
| F6-1K5.9 | pSJ33 | T4 homo | +Hv | 3.91 | 6.29 | 2.15 | 2.01 |
| F6-87 | pSJ33 | T0 | +Hv | 3.07 | 9.52 | 2.10 | 2.01 |
| F6-139 | pSJ127 | T0 | +As | 2.34 | 18.49 | 1.47 | 1.35 |
| F6-142 | pSJ127 | T0 | +As | 2.10 | 14.89 | 1.48 | 1.31 |
| F6-124 | pSJ127 | T0 | +As | 2.32 | 15.32 | 1.45 | 1.37 |
| F6-151 | pSJ124 | T0 | +As | 1.69 | 15.18 | 1.61 | 1.33 |
| F6-124.1 | pSJ127 | T1 | +As | 3.84 | 20.55 | n.d | n.d |
| F6124.2 | pSJ127 | T1 | +As | 3.79 | 17.00 | n.d | n.d |

TABLE 16

Fibre and fibre components (% w/w = g/100 g) in flour from wheat grain transformed with constructs to express HvCslF6 or AsCslF6

| Sample Description | Protein | Total Starch | Total Sugars | Soluble Fibre | Insoluble Fibre | Soluble NNSP | Insoluble NNSP | β-Glucan | Fructans |
|---|---|---|---|---|---|---|---|---|---|
| F6-1K3.2 T4 (negative segregant control) | 11.1 | 59.3 | 1.3 | 1.6 | 10.7 | 2.4 | 3.6 | 0.9 | 1.9 |
| F6 1K5.9 T4 (HvCslF6) | 15.3 | 41.9 | 1.1 | 4.3 | 15.3 | 5.1 | 7.2 | 3.6 | 5.0 |
| F6-124.4 T3 (oat CslF6) | 9.9 | 55.7 | 1.6 | 3.2 | 12.3 | 4.8 | 4.3 | 3.2 | 2.9 |
| F6-1G6.7 T4 | 13.3 | 55.3 | 1.7 | 2.4 | 11.0 | 2.8 | 3.3 | 1.5 | 2.2 |
| F6-1K5.9 T5 | 13.7 | 46.6 | 4.2 | 4.2 | 14.4 | 5.5 | 4.7 | 3.7 | 5.0 |

TABLE 17

Composition of grains transformed with both CslF6 and CslH constructs

| Line | HvCslF6 | HvCslH1 | % BG | DP3/DP4 ratio | % soluble BG |
|---|---|---|---|---|---|
| Control average | − | − | 1.08 | 2.49 | 6.0 |
| F6H1-19.2.1 | + | + | 4.33 | 2.04 | 4.3 |
| H1F6-6.2.9.7 | + | + | 3.56 | 2.07 | 3.9 |
| F6H1-17.1.16 | + | + | 4.69 | n.d | 6.0 |
| F6H1-17.1.18 | − | − | 0.67 | n.d | 4.9 |
| F6H1-17.1.23 | + | − | 3.25 | n.d | 14.2 |

TABLE 18

Composition of wheat flours and muffins made with wheat grain transformed with a construct expressing HvCslH

| Flour or muffin type | Wheat flour (g/100 g flour) | | | | Muffin (g/100 g muffin, as eaten) | | |
|---|---|---|---|---|---|---|---|
| | β-glucan | soluble fibre | insoluble fibre | TDF | CHO | β-glucan | TDF |
| Control refined wheat | 0.21 | 0.8 | 1.4 | 2.2 | 38.4 | 0.08 | 0.8 |
| Test refined wheat | 0.87 | 1.0 | 2.9 | 3.9 | 38.3 | 0.31 | 1.4 |
| Control w/meal wheat | 0.64 | 1.4 | 9.2 | 10.6 | 34.7 | 0.23 | 3.8 |
| Test w/meal wheat | 1.5 | 1.9 | 11.5 | 13.4 | 33.5 | 0.54 | 4.9 |

TABLE 19

Water-solubility of BG in transgenic wheat flours made from grain transformed with constructs to express CslF6 polypeptides from barley or oats, as determined without a heat inactivation step (Example 21).

| Line | Growth | Transgene | BG content (% w/w) | Water-solubility (%) | Std deviation |
|---|---|---|---|---|---|
| F6-1K3.2 | Field grown | Neg seg | 0.7 | 10.5 | 0.2 |
| F6-1K5.9 | Field grown | HvCslF6 | 2.7 | 40.5 | 11.2 |
| F6-1G6.1.8 | Field grown | HvCslF6 | 3.5 | 31.7 | 6.1 |
| H1-10B7.3 | Field grown | Neg seg | 0.7 | 20.2 | 11.3 |
| H1-10B1.9 | Field grown | Hv CslH | 1.4 | 11.6 | 4.3 |
| H1-10B7.4 | Field grown | HvCslH | 1.2 | 4.3 | 3.8 |
| F6H1-7.1.18 | F6xH cross | Neg seg | 0.7 | 11.0 | 6.7 |
| F6H1-7.1.16 | F6xH cross | HvCslF6 + HvCslH | 2.4 | 23.2 | 8.8 |
| F6H1-7.1.23 | F6xH cross | HvCslF6 | 3.2 | 51.4 | 1.6 |
| F6H1-7.1.24 | F6xH cross | HvCslF6 + HvCslH | 1.0 | 16.9 | 2.4 |
| F6-133.6 | T2 new lines | Neg seg | 0.8 | 22.4 | 5.6 |
| F6-139.3 | | AsCslF6 | 3.6 | 37.9 | 12.0 |
| F6-139.7 | | AsCslF6 | 3.1 | 38.6 | 4.5 |
| F6-139.8 | | AsCslF6 | 3.4 | 39.4 | 1.8 |
| F6-127.1 | T2 new lines | Neg seg | 0.7 | 22.4 | 2.1 |
| F6-122.8 | | AsCslF6 | 3.9 | 52.7 | 10.3 |
| F6-142.2 | | AsCslF6 | 3.0 | 33.3 | 4.7 |
| F6-142.7 | | AsCslF6 | 3.0 | 40.1 | 4.9 |
| F6-127.1 | T4 new lines | Neg seg | 0.9 | 12.0 | 2.5 |
| F6-122.2 | | AsCslF6 | 3.1 | 48.3 | 1.6 |
| F6-122.8 | | AsCslF6 | 2.5 | 31.3 | 5.5 |
| F6-124.2 | | AsCslF6 | 2.8 | 46.2 | 3.9 |
| F6-124.4 | | AsCslF6 | 2.8 | 40.9 | 1.9 |

TABLE 21

DP3/DP4 ratio of BG produced by chimaeric CslF6 genes (BglII-EcoRI fragments)

| plasmid | Gene or BglII-EcoRI fusion | DP3/DP4 | St. dev. |
|---|---|---|---|
| pSJ226 | Hv CslF6 wt | 1.40 | 0.01 |
| pSJ195 | Zm CslF6 wt | 1.07 | 0.01 |
| pSJ197 | Sb CslF6 wt | 0.90 | 0.01 |
| pSJ175 | As CslF6 wt | 1.09 | 0.00 |
| pSJ135 | Bd CslF6 wt | 1.74 | 0.01 |
| pSJ227 | Hv-Zm CslF6 | 1.11 | 0.01 |
| pSJ228 | Zm-Hv CslF6 | 1.48 | 0.00 |
| pSJ237 | Sb-Bd CslF6 | 1.32 | 0.01 |
| pSJ238 | As-Hv CslF6 | 1.44 | 0.01 |
| pSJ239 | As-Bd CslF6 | 1.54 | 0.01 |
| pSJ240 | Bd-Zm CslF6 | 1.18 | 0.01 |
| pSJ241 | Bd-Hv CslF6 | 1.51 | 0.01 |
| pSJ242 | Zm-Bd CslF6 | 1.46 | 0.00 |
| pSJ243 | As-Zm CslF6 | 1.18 | 0.01 |

TABLE 22

DP3/DP4 ratio of BG produced by chimeric CslF6 genes (BglII-XbaI or XbaI-EcoRI fragments)

| Plasmid | Gene fusion | DP3/DP4 | St dev |
|---|---|---|---|
| pSJ226 | HvCslF6 wt | 1.41 | 0.01 |
| pSJ227 | Hv/Zm CslF6 BglII-EcoRI | 1.09 | 0.05 |
| pSJ247 | Hv/Zm CslF6 XbaI-EcoRI | 1.44 | 0.08 |
| pSJ249 | Hv/Zm/Hv CslF6 BglII-XbaI | 1.03 | 0.04 |
| pSJ195 | ZmCslF6-2 wt | 1.10 | 0.01 |
| pSJ228 | Zm/Hv CslF6 BglII-EcoRI | 1.47 | 0.08 |
| pSJ248 | Zm/Hv CslF6 XbaI-EcoRI | 1.12 | 0.01 |
| pSJ250 | Zm/Hv/Zm CslF6 BglII-XbaI | 1.45 | 0.04 |
| — | Barley flour | 2.51 | 0.01 |

TABLE 23

DP3/DP4 ratio of BG produced by chimeric CslF6 genes (BglII-XbaI gBlock fragments).

| plasmid | gene fusion | DP3/DP4 | St. dev. |
|---|---|---|---|
| pSJ195 | ZmCslF6-2 wt | 1.04 | 0.05 |
| pSJ226 | HvCSlF6 wt | 1.39 | 0.01 |
| pSJ253 | HvCslF6 + HvZmbx | 1.24 | 0.03 |
| pSJ254 | HvCslF6 + ZmHvbx | 1.10 | 0.02 |
| pSJ255 | ZmCslF6-2 + HvZmbx | 1.35 | 0.01 |

TABLE 23-continued

DP3/DP4 ratio of BG produced by chimeric CslF6 genes
(BglII-XbaI gBlock fragments).

| plasmid | gene fusion | DP3/DP4 | St. dev. |
|---|---|---|---|
| pSJ256 | ZmCslF6-2 + ZmHvbx | 1.09 | 0.04 |
| pSJ245 | HvCslF6 + XbaI | 1.37 | 0.01 |
| pSJ246 | ZmCslF6-2 + XbaI | 1.06 | 0.01 |
| pSJ252 | HvZmCslF6 PstI swap | 1.02 | 0.00 |
| std | barley flour | 2.55 | 0.01 |

TABLE 24

DP3/DP4 ratio of BG produced by chimeric CslF6 genes
(PstI-XbaI gBlock fragments).

| plasmid | gene | fusion | DP3/DP4 | std dev | BG % |
|---|---|---|---|---|---|
| pSJ245 | HvCslF6 | wt | 1.37 | 0.02 | 0.95 |
| pSJ246 | ZmCslF6 | wt | 1.09 | 0.01 | 1.40 |
| pSJ259 | HvZmCslF6 | 5'Half PstI-XbaI | 1.06 | 0.02 | 1.33 |
| pSJ260 | ZmHvCslF6 | 5' Half PstI-XbaI | 1.36 | 0.02 | 0.63 |
| pSJ265 | HvCslF6 | G-A | 1.41 | 0.00 | 1.01 |
| pSJ266 | HvCslF6 | S-A | 1.35 | 0.01 | 0.70 |
| pSJ267 | HvCslF6 | V-I | 1.39 | 0.02 | 1.36 |
| pSJ268 | HvCslF6 | I-L | 1.13 | 0.01 | 1.47 |
| pSJ269 | HvCslF6 | GS-AA | 1.38 | 0.01 | 0.73 |
| std | Barley flour | | 2.58 | 0.02 | 4.10 |

REFERENCES

Abell et al. (2004). *Br J Nutr* 105: 1480-1485.
Alvarez et al., (2006). *Plant Cell* 18: 1134-1151.
Aman et al. (1987). *Journal of Agricultural and Food Chemistry* 35: 704-709.
Bechtold et al., (1993). *C.R. Acad. Sci. Paris*, 316: 1194-1199.
Beresford et al. (1983). *Journal of Cereal Science* 1: 111-114.
Bird et al. (2007) *Br J Nutr* 97: 134-144.
Bird et al. (2008). *Br J Nutr* 99: 1032-1040.
Bird et al. (2009). *Digestive Diseases and Sciences* 54: 947-954.
Buckeridge et al. (2004). *Cereal Chemistry* 81: 115-127.
Burton et al., (2011). *Plant Biotechnol J* 9: 117-135.
Burton et al., (2008). *Plant Physiology* 146: 1821-1833.
Burton et al. (2006). *Science* 311: 1940-1942.
Cadwell and Joyce (1992) *PCR Methods Appl.* 2: 28-33.
Carpita et al., (2007). *Proc Nat Acad of Sci USA* 104: 8550-8555.
Chen et al., (2009) *Plant Physiology* 150: 1111-1121.
Cheng et al., (1997). *Plant Physiol* 115: 971-980.
Clarke et al., (2008). *Funct Integr Genomics* 8: 211-221.
Coco et al. (2001) *Nature Biotechnology* 19: 354-359.
Coco et al. (2002) *Nature Biotechnology* 20: 1246-1250.
Coles. (1979). *Carlsberg Research Communications* 44: 439-453.
Colleoni-Sirghie et al., (2003). *Carbohydrate Polymers* 54: 237-249.
Crameri et al. (1998) *Nature* 391: 288-291.
Cui et al. (2000). *Carbohydrate Polymers* 41: 249-258.
Dhugga et al. (2004). *Science* 303: 363-366.
Doblin et al. (2009). *Proc Nat Acad of Sci USA* 106: 5996-6001.
Eagles et al. (2001). *Aust J Agric Res.* 52: 1349-1356.
Eggert et al. (2005) *Chembiochem* 6: 1062-1067.
Fincher and Stone. (2004). In: Wrigley C, Corke H, Walker C, eds. *Encyclopedia of Grain Science* Vol. 1. Oxford: Elsevier Academic Press, pp 206-223.
Fincher. (2009a). *Current Opinion in Plant Biology* 12: 140-147.
Fincher. (2009b). *Plant Physiology* 149: 27-37.
Fromm et al., (1985). *Proc. Natl. Acad. Sci., U.S.A,* 82: 5824-5828.
Gibeaut et al. (2005). *Planta* 221: 729-738.
Guillon et al. (2011). *Journal of Experimental Botany* 62: 1001-1015.
Harayama (1998) *Trends Biotechnol.* 16: 76-82.
Hartmann and Endres, (1999). Manual of Antisense Methodology, Kluwer
Haseloff and Gerlach (1988). *Nature* 334: 585-591.
Hazen et al. (2002). *Plant Physiology* 128: 336-340.
Hellinga (1997) *Proc. Natl. Acad. Sci. USA* 94: 10015-10017.
Henikoff et al. (2004) *Plant Physiol.* 135: 630-636.
Henry (1987). *J. Cereal Science* 6: 253-258.
Hinchee et al. (1988) *Biotech.* 6: 915-922.
Izydorczyk and Dexter (2008). *Food Res Internat* 41: 850-868.
Jézéquel et al. (2008) *Biotechniques* 45: 523-532.
Jonnalagadda et al. (2011). *Journal of Nutrition* 141: 1011S-1022S.
Kanna and Daggard (2003). *Plant Cell Rep* 21: 429-436.
Klein et al., (1987). *Nature* 327: 70-73.
Kirsten et al., (1984). *J Agric. Food. Chem.* 32: 279-284.
Langridge et al., (2001) *Aust J Agric Res* 52: 1043-1077
Lazaridou et al. (2007). *Journal of Cereal Science* 46: 101-118.
Lazo et al., (1991). *Biotechnology* (N Y). 9: 963-967.
Lee et al. (1992). *Journal of AOAC International* 75: 395-416.
Leung et al. (1989) *Technique* 1: 11-15.
Liepman et al. (2007). *Plant Physiology* 143: 1881-1893.
McCleary et al. (1985). *J. Inst. Brew.* 91: 285-295.
McCleary et al., (1994). *J. Cereal Science* 20: 51-58.
Morgan et al. (2013) *Nature* 493: 181-187.
Murray et al. (1980). *Nucleic Acids Res* 8: 4321-4325.
Needleman and Wunsch (1970). *J Mol Biol.* 48: 443-453.
Nemeth et al. (2010). *Plant Physiology* 152: 1209-1218.
Ness et al. (2002) *Nature Biotechnology* 20: 1251-1255.
Niedz et al. (1995) *Plant Cell Reports* 14: 403-406.
O'Shea et al. (1998). *Carbohydrate Research* 307: 1-12.
Ostermeier et al. (1999) *Nature Biotechnology* 17: 1205-1209.
Ow et al. (1986) *Science* 234: 856-859.
Palatnik et al., (2003). *Nature* 425: 257-263.
Parizotto et al., (2004). *Genes Dev* 18: 2237-2242.
Pellegrineschi et al. (2004). *Genome* 47: 493-500.
Perriman et al. (1992) *Gene* 113: 157-163.
Philippe et al. (2006a). *Journal of Agricultural and Food Chemistry* 54: 2303-2308.
Philippe et al. (2006b). *Planta* 224: 449-461.
Prasher et al. (1985) *Biochem. Biophys. Res. Comm.* 126: 1259-1268.
Reddy and Appels. (1993). *Theoretical and Applied Genetics* 85: 616-624.
Regina et al. (2006). *Proc Natl Acd Sci USA* 103: 3546-3551.
Schwab et al., (2006). *Plant Cell* 18: 1121-1133.
Seefeldt et al. (2009). *Journal of Cereal Science* 49: 24-31.
Sharp et al (2001). *Aust J Agric. Res.* 52: 1357-1366.
Shimamoto et al., (1989). *Nature* 338: 274-276.
Shippy et al., (1999) *Mol. Biotech.* 12: 117-129.
Sieber et al. (2001) *Nature Biotechnology* 19: 456-460.

Slade and Knauf (2005) *Transgenic Res.* 14: 109-115.
Smith et al. (2000). *Nature* 407: 319-320.
Sparks and Jones (2004). In *Transgenic Crops of the World—Essential protocols*, Ed. IP Curtis, Kluwer Academic Publishers, Dordrecht, Netherlands, pp 19-34.
Stemmer (1994a) *Proc. Natl. Acad. Sci. USA* 91: 10747-10751.
Stemmer (1994b) *Nature* 370: 389-391.
Stone B A. (2006). *Cereal Foods World* 51: 62-65.
Tanaka et al. (1990). *Nucl Acids Res.* 18: 6767-6770.
Theander et al., (1995). *J of AOAC International.* 78: 1030-1044.
Topping D. (2007). *Journal of Cereal Science* 46: 220-229.
Tosh et al. (2004). *Carbohydrate Polymers* 57: 249-259.
Trethewey et al. (2005). *American Journal of Botany* 92: 1660-1674.
Trethewey and Harris. (2002). *New Phytologist* 154: 347-358.
Tsuchiya et al. (2005). *Physiologia Plantarum* 125: 181-191.
Vasil et al. (1990). *Bio/Technol* 8: 429-434.
Volkov et al. (1999) *Nucleic Acids Research* 27: e18.
Waterhouse et al. (1998). *Proc. Natl. Acad. Sci. USA* 95: 13959-13964.
Weir et al., (2001). *Aust J Plant Physiol* 28: 807-818.
Wood et al. (2009). *Plant Biotechnology Journal* 7: 914-924.
Wood et al. (1991). *Cereal Chemistry* 68: 31-39.
Wu et al., (2003). *Plant Cell Rep* 21: 659-668.
Yu and Morrison (2004). *BioTechniques* 36: 808-812.
Zhao et al. (1998) *Nature Biotechnology* 16: 258-261.

The invention claimed is:

1. Transgenic wheat grain comprising an exogenous polynucleotide which encodes a CslF6 polypeptide, and comprising between 3% and 8% (w/w) (1,3;1,4)-β-D-glucan (BG) which is characterised by one or both of:
   a) a DP3/DP4 ratio between 1.0 and 2.3; and
   b) partial water solubility such that between 8.0% and 25% of the BG of the grain is water soluble, as determined by a method that comprises treatment of a sample of wholemeal flour obtained from the grain with (i) 80% ethanol for 1 hour at 80° C., followed by (ii) solubilisation of BG in aqueous buffer for 2 hours at 37° C., and (iii) determination of the level of BG solubilised from the sample.

2. The grain of claim 1, wherein the BG of the grain has a DP3/DP4 ratio of less than 2.0.

3. The grain of claim 1 comprising one or more exogenous polynucleotides which encode a CslH polypeptide, a herbicide tolerance gene, or a polynucleotide which encodes a silencing RNA molecule.

4. The grain of claim 1, further comprising an exogenous CslH polypeptide.

5. The grain of claim 1 which is non-shrunken and/or has a weight of between 30 mg and 50 mg.

6. The grain of claim 1 which is capable of producing a wheat plant:
   a) which is male and female fertile,
   b) which is green in colour, has the same seedling vigour, or produces pollen which has the same viability as a corresponding wild-type plant, and/or
   c) which has a growth rate that differs from the growth rate of a corresponding wild-type plant by less than 30% when grown under the same conditions.

7. The grain of claim 1 comprising starch, wherein the starch of the grain has an amylose content of at least 60% (w/w) as a proportion of the extractable starch of the grain.

8. The grain of claim 1, wherein the starch content of the grain is at least 30% as a percentage of the total grain weight.

9. The grain of claim 1, wherein the plant is hexaploid wheat.

10. The grain of claim 1, wherein the starch of the grain is characterised by one or more of properties selected from the group consisting of:
   a. comprising at least 2% resistant starch;
   b. comprising a glycaemic index (GI) of less than 55;
   c. comprising less than 20% amylopectin as a proportion of the starch content of the grain;
   d. comprised in starch granules which have an altered morphology relative to wild-type wheat starch granules;
   e. comprised in starch granules that exhibit reduced granule birefringence under polarised light relative to wild-type wheat starch granules;
   f. when the grain is milled to flour, such flour exhibits reduced swelling volume relative to flour from wild-type wheat grain;
   g. modified chain length distribution and/or branching frequency relative to wild-type wheat starch;
   h. delayed end of gelatinisation temperature and higher peak temperature relative to starch of wild-type wheat starch granules;
   i. reduced viscosity (peak viscosity, pasting temperature) relative to starch of wild-type wheat starch granules;
   j. increased molecular weight of amylopectin relative to starch of wild-type wheat starch granules; and
   k. modified % crystallinity or % A-type or B-type starch, relative to wild-type wheat starch granules or starch.

11. The grain of claim 1 which is processed so that it is no longer capable of germinating.

12. A wheat plant which is capable of producing the grain of claim 1, which comprises an exogenous polynucleotide which encodes a CslF6 polypeptide.

13. A composition comprising isolated wheat BG and arabinoxylan (AX) produced from the grain of claim 1, the BG and AX being soluble in aqueous media, and the BG having a DP3/DP4 ratio of less than 2.0 and predominantly a molecular weight of at least about 100 kDa.

14. A food ingredient that comprises the grain of claim 1 for sale.

15. A method of producing a wheat plant that produces grain according to claim 1 comprising the steps of (i) introducing an exogenous polynucleotide which encodes a CslF6 polypeptide into a progenitor wheat cell, and (ii) producing a wheat plant from the wheat cell of (i), thereby producing a wheat plant that produces grain according to claim 1.

16. A method of selecting a wheat plant, the method comprising (i) determining the amount of BG in grain obtained from each of at least two wheat plants, and (ii) selecting a plant from (i) which produces grain according to claim 1.

17. A method of producing at least partially purified BG or starch, comprising the steps of i) obtaining wheat grain according to claim 1, and ii) extracting the BG or starch from the grain, thereby producing the at least partially purified BG or starch.

18. The grain of claim 1 wherein the BG of the grain has a DP3/DP4 ratio between 1.0 and 2.0.

19. The grain of claim 1 which is mature grain.

20. The grain of claim 1 wherein the grain has a moisture content of between 8% and 14% by weight.

21. The grain of claim 9, wherein the plant is *Triticum aestivum*.

22. The processed grain of claim 11 wherein the grain is kibbled, cracked, par-boiled, rolled, pearled, milled or ground grain.

23. A food product comprising the grain of claim 1 or comprising flour produced from such grain.

24. Transgenic wheat grain comprising an exogenous polynucleotide which encodes a CslF6 polypeptide, which is non-shrunken and comprises between 3% and 8% (w/w) (1,3;1,4)-β-D-glucan (BG) which is characterised by:
   a) a DP3/DP4 ratio between 1.0 and 2.3; and
   b) partial water solubility such that between 8.0% and 25% of the BG of the grain is water soluble, as determined by a method that comprises treatment of a sample of wholemeal flour obtained from the grain with (i) 80% ethanol for 1 hour at 80° C., followed by (ii) solubilisation of BG in aqueous buffer for 2 hours at 37° C., and (iii) determination of the level of BG solubilised from the sample.

25. Transgenic wheat grain comprising an exogenous polynucleotide which encodes a CslF6 polypeptide, which has a weight of between 30 mg and 50 mg and comprises between 3% and 8% (w/w) (1,3;1,4)-β-D-glucan (BG) which is characterised by:
   a) a DP3/DP4 ratio between 1.0 and 2.3; and
   b) partial water solubility such that between 8.0% and 25% of the BG of the grain is water soluble, as determined by a method that comprises treatment of a sample of wholemeal flour obtained from the grain with (i) 80% ethanol for 1 hour at 80° C., followed by (ii) solubilisation of BG in aqueous buffer for 2 hours at 37° C., and (iii) determination of the level of BG solubilised from the sample.

* * * * *

SEQUENCE LISTING

```
<160> NUMBER OF SEQ ID NOS: 183

<210> SEQ ID NO 1
<211> LENGTH: 2618
<212> TYPE: DNA
<213> ORGANISM: artificial
<220> FEATURE:
<223> OTHER INFORMATION: synthetic

<400> SEQUENCE: 1
ggagacatgg cgtcggcggt cggtgctggt ggggcaaatg ccggcctcgc cgacccgctg      60
ctggcgagcc gcgacggcgg tgccaagaag ccggtcggcg ccaagggcaa gcactgggtg     120
gccgccgaca aagaccagcg ccgggccgcc aaggagagcg gcggcgagga gggcaggccg     180
ttgctgttcc ggacgtacaa ggtcaaaggc accctcctgc atccctacag ggcgctgatc     240
ttcattcgct taattgccgt cctcctattc ttcgtatggc gcatcaagca caacaaatct     300
gatatcatgt ggttttggac aatgtcagtt gtcggggacg tatggttcgg gttctcgtgg     360
ctgctcaacc aactcccaaa gtttaacccc gtcaaaacca tacctgatat ggtcgccctt     420
aggcgacaat acgatctccc agatgggaca tctacacttc ctggcataga tgtctttgtc     480
accactgctg acccaatcga tgagccgata ctatacacca tgaattgtgt tctctctata     540
cttgcttctg actatcctgt tgatgggtgt gcatgctatc tctcagatga tagtggcgca     600
ttgatccaat atgaggcctt gattgagact gcaaagtttg ctactttgtg ggtcccattt     660
tgtcggaagc attgcatcga gccaagagcc ccagaaagct actttgaact agaggcacta     720
ttgtacactg gaagtgcacc agaggagttc aagaatgatc atagcagtgt acatagagag     780
tatgacgagt tcaaagggcg cttagactca ctatctagtg ctatttccaa gcgttctgat     840
gcttacaaca gcatgaagac tggggaagga gatgcaaagg ccacttggat ggcaaatggg     900
acacaatggc caggatcatg gattgacaca acggaaatcc ataggaaagg gcatcatgcc     960
ggaattgtta aggttgtgtt ggaccatttg gtccgtgggc ataatcttgg ttcacaagca    1020
agcacccaca acctcaactt cgccaacact gatgtgcgcc tcccgatgct tgtatatatc    1080
tctcgcggaa agaacccaag ctatgaccac aacaagaaag ctggtgcctt gaatgcgcaa    1140
ttgcgtgcct ctgcactact ctccaacgcg caattcatca tcaacttcga ctgcgaccac    1200
tacatcaaca actctcaagc cctacgtgca gctatgtgct tcatgctaga tcaacggcaa    1260
ggtgatagca ctgccttcgt tcaattccct caacgcttcg acaatgttga tccatcggac    1320
cgatatggca accacaaccg tgtcttcttc gatggcacaa tgctcgccct caatggtctc    1380
caaggtccat cttaccttgg cactggttgc atgttccgcc gcatagccct ttatggcatt    1440
```

```
gacccacctg agtggagaca tgacaacatc gtagttgatg ataaaaggtt tggtagctcc    1500
atacccttcc tagattccgt atcaaaagcc ataaaccaag aaagatctac catacctccc    1560
cccattagtg aaacattagt ggctaagatg gaaagggttg tgtcagcttc acatgataaa    1620
gccactgggt ggggaaaggg tgttgggtac atatatgaca tagccacaga ggatatagtg    1680
actggttttc gcatccacgg tcaaggttgg cgttccatgt attgtacaat ggagcgtgac    1740
gccttctgtg gcattgcacc aatcaaccta accgagcgcc tccaccaaat tgtgcgttgg    1800
tcaggtggat ctttagagat gttcttctca ctaaataacc cactcatagg cggtcgtcgg    1860
atccaatccc ttcagcgtgt ctcctacctc aacatgacag tttacccagt cacatcactc    1920
tttatcctac tctatgctct cagcccagtg atgtggctta ccctgatga agtatacatt     1980 cagaggccat tcaccaaata tgttgtgttc cttctcgtga tcattctgat gatccatgtt    2040
attgggtggc tcgagataaa atgggcgggg gtcacatggt tggattactg gaggaatgaa    2100
cagttcttca tgatcgggtc gacgagtgca tacccagcag ccgtgcttca catggtggtg    2160
aatctcctta caaagaaggg tattcacttc agagttactt cgaagcaaac agcggcagac    2220
accaatgaca agtttgccga cttgtatgac atgcgatggg tgccaatgtt aatacctaca    2280
acagtagtgc tgattgccaa tgttggtgca atcggtgtag ccatgggtaa aacgatagta    2340
tacatgggag catggacaat tgcacagaag acacatgccg cattgggtct gctcttcaat    2400
gtgtggatca tggtgctgct ctatccgttt gcattggcga tcatgggacg gtgggcaaag    2460
aggccagtca tcctgctggt cttgttgccg gttgcctta caatagtttg ccttgtatat    2520
gttgctgttc atatcttact tcttagttat cttacatttt agccaagtga tatagtagaa    2580
accattgtat tgtttagctt ctgtagtaag ctgggagc                            2618
```

<210> SEQ ID NO 2
<211> LENGTH: 851
<212> TYPE: PRT
<213> ORGANISM: Triticum aestivum

<400> SEQUENCE: 2

```
Met Ala Ser Ala Val Gly Ala Gly Gly Ala Asn Ala Gly Leu Ala Asp
1               5                   10                  15

Pro Leu Ala Ser Arg Asp Gly Gly Ala Lys Lys Pro Val Gly Ala
            20                  25                  30

Lys Gly Lys His Trp Val Ala Ala Asp Lys Asp Gln Arg Arg Ala Ala
        35                  40                  45

Lys Glu Ser Gly Gly Glu Glu Gly Arg Pro Leu Leu Phe Arg Thr Tyr
    50                  55                  60

Lys Val Lys Gly Thr Leu Leu His Pro Tyr Arg Ala Leu Ile Phe Ile
65                  70                  75                  80

Arg Leu Ile Ala Val Leu Leu Phe Phe Val Trp Arg Ile Lys His Asn
                85                  90                  95

Lys Ser Asp Ile Met Trp Phe Trp Thr Met Ser Val Gly Asp Val
            100                 105                 110

Trp Phe Gly Phe Ser Trp Leu Leu Asn Gln Leu Pro Lys Phe Asn Pro
        115                 120                 125

Val Lys Thr Ile Pro Asp Met Val Ala Leu Arg Arg Gln Tyr Asp Leu
    130                 135                 140

Pro Asp Gly Thr Ser Thr Leu Pro Gly Ile Asp Val Phe Val Thr Thr
145                 150                 155                 160
```

```
Ala Asp Pro Ile Asp Glu Pro Ile Leu Tyr Thr Met Asn Cys Val Leu
            165                 170                 175

Ser Ile Leu Ala Ser Asp Tyr Pro Val Asp Gly Cys Ala Cys Tyr Leu
        180                 185                 190

Ser Asp Asp Ser Gly Ala Leu Ile Gln Tyr Glu Ala Leu Ile Glu Thr
    195                 200                 205

Ala Lys Phe Ala Thr Leu Trp Val Pro Phe Cys Arg Lys His Cys Ile
210                 215                 220

Glu Pro Arg Ala Pro Glu Ser Tyr Phe Glu Leu Glu Ala Leu Leu Tyr
225                 230                 235                 240

Thr Gly Ser Ala Pro Glu Glu Phe Lys Asn Asp His Ser Ser Val His
                245                 250                 255

Arg Glu Tyr Asp Glu Phe Lys Gly Arg Leu Asp Ser Leu Ser Ser Ala
            260                 265                 270

Ile Ser Lys Arg Ser Asp Ala Tyr Asn Ser Met Lys Thr Gly Glu Gly
        275                 280                 285

Asp Ala Lys Ala Thr Trp Met Ala Asn Gly Thr Gln Trp Pro Gly Ser
    290                 295                 300

Trp Ile Asp Thr Thr Glu Ile His Arg Lys Gly His His Ala Gly Ile
305                 310                 315                 320

Val Lys Val Val Leu Asp His Leu Val Arg Gly His Asn Leu Gly Ser
                325                 330                 335

Gln Ala Ser Thr His Asn Leu Asn Phe Ala Asn Thr Asp Val Arg Leu
            340                 345                 350

Pro Met Leu Val Tyr Ile Ser Arg Gly Lys Asn Pro Ser Tyr Asp His
        355                 360                 365

Asn Lys Lys Ala Gly Ala Leu Asn Ala Gln Leu Arg Ala Ser Ala Leu
    370                 375                 380

Leu Ser Asn Ala Gln Phe Ile Ile Asn Phe Asp Cys Asp His Tyr Ile
385                 390                 395                 400

Asn Asn Ser Gln Ala Leu Arg Ala Ala Met Cys Phe Met Leu Asp Gln
                405                 410                 415

Arg Gln Gly Asp Ser Thr Ala Phe Val Gln Phe Pro Gln Arg Phe Asp
            420                 425                 430

Asn Val Asp Pro Ser Asp Arg Tyr Gly Asn His Asn Arg Val Phe Phe
        435                 440                 445

Asp Gly Thr Met Leu Ala Leu Asn Gly Leu Gln Gly Pro Ser Tyr Leu
    450                 455                 460

Gly Thr Gly Cys Met Phe Arg Arg Ile Ala Leu Tyr Gly Ile Asp Pro
465                 470                 475                 480

Pro Glu Trp Arg His Asp Asn Ile Val Val Asp Asp Lys Arg Phe Gly
                485                 490                 495

Ser Ser Ile Pro Phe Leu Asp Ser Val Ser Lys Ala Ile Asn Gln Glu
            500                 505                 510

Arg Ser Thr Ile Pro Pro Ile Ser Glu Thr Leu Val Ala Lys Met
        515                 520                 525

Glu Arg Val Val Ser Ala Ser His Asp Lys Ala Thr Gly Trp Gly Lys
530                 535                 540

Gly Val Gly Tyr Ile Tyr Asp Ile Ala Thr Glu Asp Ile Val Thr Gly
545                 550                 555                 560

Phe Arg Ile His Gly Gln Gly Trp Arg Ser Met Tyr Cys Thr Met Glu
                565                 570                 575

Arg Asp Ala Phe Cys Gly Ile Ala Pro Ile Asn Leu Thr Glu Arg Leu
```

```
                    580             585             590
His Gln Ile Val Arg Trp Ser Gly Gly Ser Leu Glu Met Phe Phe Ser
            595                 600             605
Leu Asn Asn Pro Leu Ile Gly Gly Arg Arg Ile Gln Ser Leu Gln Arg
        610                 615                 620
Val Ser Tyr Leu Asn Met Thr Val Tyr Pro Val Ser Leu Phe Ile
625                 630                 635                 640
Leu Leu Tyr Ala Leu Ser Pro Val Met Trp Leu Ile Pro Asp Glu Val
                645                 650                 655
Tyr Ile Gln Arg Pro Phe Thr Lys Tyr Val Val Phe Leu Leu Val Ile
            660                 665                 670
Ile Leu Met Ile His Val Ile Gly Trp Leu Glu Ile Lys Trp Ala Gly
        675                 680                 685
Val Thr Trp Leu Asp Tyr Trp Arg Asn Glu Gln Phe Phe Met Ile Gly
    690                 695                 700
Ser Thr Ser Ala Tyr Pro Ala Ala Val Leu His Met Val Val Asn Leu
705                 710                 715                 720
Leu Thr Lys Lys Gly Ile His Phe Arg Val Thr Ser Lys Gln Thr Ala
                725                 730                 735
Ala Asp Thr Asn Asp Lys Phe Ala Asp Leu Tyr Asp Met Arg Trp Val
            740                 745                 750
Pro Met Leu Ile Pro Thr Thr Val Val Leu Ile Ala Asn Val Gly Ala
        755                 760                 765
Ile Gly Val Ala Met Gly Lys Thr Ile Val Tyr Met Gly Ala Trp Thr
    770                 775                 780
Ile Ala Gln Lys Thr His Ala Ala Leu Gly Leu Leu Phe Asn Val Trp
785                 790                 795                 800
Ile Met Val Leu Leu Tyr Pro Phe Ala Leu Ala Ile Met Gly Arg Trp
                805                 810                 815
Ala Lys Arg Pro Val Ile Leu Leu Val Leu Leu Pro Val Ala Phe Thr
            820                 825                 830
Ile Val Cys Leu Val Tyr Val Ala Val His Ile Leu Leu Leu Ser Tyr
        835                 840                 845
Leu Thr Phe
    850

<210> SEQ ID NO 3
<211> LENGTH: 2726
<212> TYPE: DNA
<213> ORGANISM: artificial
<220> FEATURE:
<223> OTHER INFORMATION: synthetic

<400> SEQUENCE: 3
atggccccgg cagtcactcg ccgagccaac gccctccgcg tcgaggcccc ggacggcaac      60
gccgagagcg gcgcgccag cctagcagca gactccccg ccgccaagcg ggctgccgac      120
gccaaggacg acgtgtgggt ggccgcggac gagggagaca cgtcgggagc catcgccggc      180
gacggcaacc gaccgccgct gttccggacc ttcaaggtca agggaagcat cctgcatcct      240
tacaggttca tgatcctcgt ccgcttggtc gccatcgtcg ctttcttcgc gtggcgcgtg      300
aagcacaaga accatgacgg cgtgtggctg tgggccacgt ccatggtcgc cgacgtctgg      360
ttcggcttct cgtggctcct caaccagctg cccaagctca accccgtcaa gcgcgtcccc      420
gacctggccg ccctcgcgga ccactccggc gacgccaacc tgccgggcat cgacatcttc      480
```

```
gtcaccaccg tcgacccegt cgacgaaccc ctcttgtaca ccgtcaacac catcctctcc     540
atcctcgcca ccgactaccc cgtcgacaag tacgcctgct acctctcgga cgacggcggc     600
acgctggtgc actacgaggc gatgatcgaa gttgccaatt tcgctgtgct gtgggttcct     660
ttttgtcgga agtactgtgt agagccaaga tcccccgaga actattttgg gatgaaaacg     720
cagcagtacg ccgggagtat ggccggagag ttcatgaggg atcataggcg tgtgcgcaga     780
gagtatgatg agttcaaggt gagggtagac tcccttttcca ccaccatccg ccaacgatct     840
gatgcgtata actcgagcaa aaagggagat ggtgtacgtg caacctggat ggctgatggg     900
acacaatggc ctggtacatg gatcgagcag gttgacaacc accggagagg acaacatgct     960
ggaattgttc aggtgatact aggccatcca agttgtaaac cacaactggg atcgccggcg    1020
agcgccgaca tccactcga cttcagcaac gttgacacga ggctccccat gctcgtatac    1080
atgtcccggg agaagcgacc cggttataac caccaaaaga aggcaggcgc catgaacgtg    1140
atgctccgtg tctcggcgtt gctctccaac gcgcccttcg tcgtcaactt tgacggcgac    1200
cactacatca caactcgca agctctccgc gccctatgt gcttcatgct cgaccctcgc    1260
gacggtcaga acacggcctt tgtccagttt cctcagcgct tcgacgacgt cgacccgacg    1320
gaccgctacg ccaatcacaa ccgtgtcttc ttcgacggca ccatgctctc cctcaacggc    1380
ctccaagggc cttcctacct tggcaccggc accatgttcc gccgtgtcgc gctctatggc    1440
atggagccac cacgttacag agcggagaac atcaagcttg caggtaaggt caatgagttc    1500
ggtagctcga cgtcgttcat aaactcgatg ccggatgggg caatccagga gcggtctatc    1560
acgccggtgt tggtcgacga ggcactcagc aatgacctgg ctaccctgat gacgtgcgcc    1620
tacgaggatg gaagttcatg ggggagagac gtcgggtggg tgtacaacat cgcgacggag    1680
gacgtggtga ccggattccg catgcaccgg caagggtggc gctccatgta ttgctccatg    1740
gagccggccg ccttccgcgg aacggctccg attaacctca ccgagcgcct ctaccaggtg    1800
ctccggtggt cggcggctc cctcgagatg ttccttctcc acagcaatgc tctcatggcc    1860
ggtcgccggc tccaccctct ccagcgcatc gcctacctca acatgtcaac ctacccgatc    1920
gtcacgtgt tcatcctggc ctacaacctc ttccccgtcc tctggctctt ctcagagcag    1980
ttctacatcc agaggccgtt cggcacgtac atcatgtacc tcgtcgccgt catatccatc    2040
attcacgtga tcggcatgtt cgaggtgaaa tgggcgggga tcacgctgct cgactggtgc    2100
cgcaacgagc agttctacat gatcggggcc acgggcgtgt acccgacggc ggtgctttac    2160
atggcgctca gctcgtcac cgggaagggg atatacttca ggctcacgtc caagcagacg    2220
gacgcctgct ccaatgacaa gttcgccgac ctgtacaccg tgcggtgggt gccgctgctg    2280
ctcccgacca tcgtggtgct cgtcgtgaac gtcgcggccg tcggggcagc gataggcaag    2340
gcggcggcat gggggttctt cacggaccag gcgcggcacg tgctgctcgg gatgctgttc    2400
aacgtgtgga tcatcgtgct cctctacccg tttgcgctcg ggatcatggg gaaatggggg    2460
aagaggcccg tcatcctgtt cgtcatgttg gtcatggcca ttggcgccgt cgcgctcgtg    2520
tatgtcacct tccatgctcc gtacccagct gatttttcag aagctgcagc ttctcttggt    2580
gaagcatcgg tgaccggacc atctgggtag acacgtacgg ctcattcttt ttacaagtac    2640
agtcacagtc actactgcaa taatttgagt gtgtgtattc gtgtctatat agcatgagaa    2700
ctggtcattg tgtgccactc ctctac                                         2726
```

<210> SEQ ID NO 4
<211> LENGTH: 2725

```
<212> TYPE: DNA
<213> ORGANISM: artificial
<220> FEATURE:
<223> OTHER INFORMATION: synthetic

<400> SEQUENCE: 4
atggccccgg cagtcactcg cagagccaac gccctccgcg ccgaggcccc ggacgggaac      60
gccgagagcg gccgcgccag cctagcagca gactcccccg ccgccaagcg ggctgtcgac     120
gccaaggacg acgtgtgggt ggccgcggac gagggagaca cgtcgggagc catcgccggc     180
gacggcaacc ggccgccgct gttccggacc ttcaaggtca agggaagcat cctgcatcct     240
tacaggttca tgatcctcgt ccgcttggtc gccatcgtcg ccttcttcgc gtggcgcgtg     300
aagcacaaga accatgacgg cgtgtggctg tgggccacgt ccatggtcgc cgacgtctgg     360
ttcggcttct cgtggctcct caaccagctg cccaagctca accccgtcaa gcgcgtcccc     420
gacctggccg ccctcgcgga ccactccggc gacgccaacc tgccgggcat cgacatattc     480
gtcaccacag tcgaccccgt ggacgaaccc ctcttgtaca ccgtgaacac catcctctct     540
atcctggcca ccgactaccc cgtcgacaag tacgcctgct acctctcgga cgacggcgga     600
acgctggtgc actacgaggc gatgatcgaa gttgccaatt cgctgtcct gtgggtccct     660
ttttgtcgga agtactgtgt agagccaaga tcccccgaga actattttgg gatgaagacg     720
cagccgtacg ccgggagcat ggctggaaaa ttcatgaggg atcataggcg tgtgcgcaga     780
gagtatgatg agttcaaggt gagggtagac tcccttttcca ccaccatccg ccaacgatct     840
gatgcgtaca actcgagcaa gaaaggagat ggtgtacgtg caacctggat ggctgatggg     900
acacaatggc ctggtacatg gatcgagcag gttgagaacc accggagagg acaacatgct     960
ggaattgttc aggtcatact aggccatcca agttgtaaac cacaactggg atcgccggcg    1020
agcgccgaca atccacttga cttcagcaac gttgacacga ggctccccat gctcgtctac    1080
atgtcccggg agaagcgccc cggttataac caccaaaaga aggcgggcgc catgaacgtg    1140
atgctccgtg tctcggctat gctctccaac gcgcccttcg tcgtcaactt tgacggcgac    1200
cactacatca caactcgca agctctccgc gcccctatgt gcttcatgct cgacccacgc    1260
gacggtcaga acacggcctt cgtccagttc ccgcagcgct tcgacgacgt cgacccgacg    1320
gaccgctacg ccaaccacaa ccgtgtcttc ttcgacggca ccatgctctc cctcaacggc    1380
ctccaagggc cttcctacct cggcaccggc accatgttcc gccgtgtcgc gctctatggc    1440
atggagccac cacgttacag agcggagaac atcaagcttg caggtaaggt caatgagttc    1500
ggtagctcga cgtcgttcat aaactcgatg ccggatgggg caatccagga gcggtctatc    1560
acgcccgtgt ggtcgacga ggcactcagc aatgacctgg ctaccctgat gacgtgcgcc    1620
tacgaggacg ggagttcatg gggcagagac gtcgggtggg tgtacaacat cgcgacggag    1680
gacgtggtga ccggatttcg catgcaccgg caagggtggc gctccatgta ttgctccatg    1740
gagccggccg ccttccgcgg aacgctcccc atcaacctca ccgagcgcct ctaccaggtg    1800
ctccggtggt cgggcggctc cctcgagatg ttcttctccc acagcaatgc tctcatggcc    1860
ggtcgccggc tccaccctct ccagcgcatc gcctacctca acatgtcaac ctacccgatc    1920
gtcacggtgt tcatcctggc ctacaacctc ttccccgtcc tctggctctt ctcagagcag    1980
ttctacatcc agaggccgtt cggcacgtac atcatgtacc tcgtcgccgt catatccatc    2040
attcacgtga tcggcatgtt cgaggtgaaa tgggcgggga tcacgctgct cgactggtgc    2100
cgcaacgagc agttctacat gatcggggcc acgggcgtgt acccgacggc ggtgctttac    2160
```

| atggcgctca agctcgtcac cgggaagggg atatacttca ggctcacgtc caagcagacg | 2220 |
| dacgcctgct ccaatgacaa gttcgccgac ctgtacaccg tgcggtgggt gccgctgctg | 2280 |
| ctcccgacca tcgtggtgct cgtcgtgaac gtcgcggccg tcggggcagc gataggcaag | 2340 |
| gcggcggcat gggggttctt cacgaccag gcgcggcacg tgctgctcgg gatgctgttc | 2400 |
| aacgtgtgga tcatcgtgct cctctacccg tttgcgctcg ggatcatggg gaaatggggg | 2460 |
| aagaggcccg tcatcctgtt cgtcatgttg gtcatggcca ttggcgccgt cgcgctcgtg | 2520 |
| tatgtcacct ccatgctcc gtacccagct gattttcag aagctgcagc ttctcttggt | 2580 |
| gaagcatcgg tgaccggacc atctgggtag acacgtacgg ctcattcttt ttacaagtac | 2640 |
| agtcacagtc actactgcaa taatttgagt gtgtgtattc gtgtctatat agcatgagaa | 2700 |
| ctggtcattg tgtgccactc ctcta | 2725 |

<210> SEQ ID NO 5
<211> LENGTH: 2728
<212> TYPE: DNA
<213> ORGANISM: artificial
<220> FEATURE:
<223> OTHER INFORMATION: synthetic

<400> SEQUENCE: 5

| atggccccgg cagtcactcg cagagccaac gccctccgcg tcgaggcccc ggatgggaac | 60 |
| accgagagcg ggcgcgccag cctagcagcc gactcccccg tcgccaagcg ggctgtcgac | 120 |
| gccaaggacg acgtgtgggt ggccgcggac gagggagaag cgtcgggatc catcgccggc | 180 |
| gacggcaacc ggacgccgct gttccggacc ttcaaggtca agggaagcat cctgcatcct | 240 |
| tacaggttca tgattctcgt ccgcttggtc gccatcgtcg ccttcttcgc atggcgcgtg | 300 |
| aagcacaaga accatgacgg cgtgtggctg tgggccacgt ccatggtcgc cgacgtctgg | 360 |
| ttcggcttct cgtggctcct caaccagctg cccaagctca ccccgtcaa gcgcgtcccc | 420 |
| gacctggccg ccctcgcgga ccactccggc gacgccaacc tgccgggcat cgacatcttc | 480 |
| gtcaccaccg tcgaccccgt ggacgaaccc ctcttgtaca ccgtgaacac catcctctcc | 540 |
| atcctcgcca ccgactaccc cgtcgacaag tacgcctgct acctctcgga cgacggcggc | 600 |
| acgttggtgc actacgaggc gatgatcgaa gttgccaatt cgctgtctt gtgggtcccc | 660 |
| ttttgtcgga agtactgtgt agagccaaga tcccccgaga actattttgg gatgaaaacg | 720 |
| cagccgtatg ccgggagtat ggcgggagaa ttcatgaggg atcataggcg tgtgcgcaga | 780 |
| gagtatgatg agttcaaggt gagggtagac tcccttttcca ccaccatccg ccaacgatct | 840 |
| gatgcgtata actcgagcac caaggagat ggtgtacgtg ctacctggat ggctgatggg | 900 |
| acacaatggc ctggtacatg gatcgagcag gttgagaacc acggagagg acaacatgct | 960 |
| ggaattgttc aggtcatact aggccatcca agttgtaaac cgcaactggg atcgccggcg | 1020 |
| agcagcgaca atccacttga cttcagcaat gttgacacga ggctccccat gctcgtctac | 1080 |
| atgtcccggg agaagcgccc tggttataac accaaaaga aggcaggcgc catgaacgtg | 1140 |
| atgctccgtg tctcggcgtt gctctccaac gcgcccttcg tcgtcaactt tgacggcgac | 1200 |
| cactacatca caattcgca agcccttcgt gccctatgt gcttcatgct cgaccctcac | 1260 |
| gacggtcaga acacggcctt cgtccagttc ccgcagcgct tcgacgatgt cgacccgacg | 1320 |
| gaccgatatg ccaaccacaa ccgtgtcttc ttcgacggca ccatgctctc cctcaacggc | 1380 |
| ctccaagggc cttcttacct tggcaccggc accatgttcc gtcgtgtcgc gctctatggc | 1440 |
| atggagccac cacgttacag agcggagaac atcaagcttg caggtaaggt caatgagttc | 1500 |

| | |
|---|---:|
| ggtagctcga cgtcgttcat aaattcgatg ccggatggtg caatccagga gcggtctatc | 1560 |
| acgccggtgt tggtcgacga ggcactcagc aatgacctgg ctaccctgat gacgtgtgcc | 1620 |
| tacgaggatg gaagttcatg ggggagagac gtcgggtggg tgtacaacat cgcgacggag | 1680 |
| gacgtggtga ccggattccg catgcaccgg caagggtggc gttccatgta ttgctccatg | 1740 |
| gagccggccg ccttccgcgg aacggctccg atcaacctca ccgagcgcct ctaccaggtg | 1800 |
| ctccggtggt cgggcggctc cctggagatg ttcttctccc acagcaatgc tctcatggcc | 1860 |
| ggccgccggc tccacccact gcagcgcatc gcctacctca acatgtcgac ctacccgatc | 1920 |
| gtcacggtgt tcattctggc ctacaacctc ttccccgtcc tctggctctt ctcagagcag | 1980 |
| ttctacatcc agaggccgtt cggcacgtac atcatgtacc tcgtcgccgt cataggcatg | 2040 |
| attcatgtga tcggcatgtt cgaggtgaaa tgggcgggga tcacgctgct cgactggtgc | 2100 |
| cgcaacgagc agttttacat gatcggggcc acgggcgtgt acccgacggc ggtgctttac | 2160 |
| atggcgctca agctcgtcac cgggaagggg atatacttca ggctcacgtc caagcagacg | 2220 |
| gacgcctgct ccaatgacaa gttcgccgac ctttacaccg tgcggtgggt gccgctgctg | 2280 |
| ctcccgacca tcgtggtgct cgtcgtgaac gtcgcggccg tcggggcagc gataggcaag | 2340 |
| gcggcggcat gggggttctt cacggaccag gcgcggcacg tgctgctcgg gatgttgttc | 2400 |
| aacgtgtgga tcctcgtgct cctctacccg tttgcgctcg ggatcatggg gaaatggggg | 2460 |
| aagaggcccg tcatcctgtt cgtcatgttg gtcatggccg ttggcgcagt cgggctcttg | 2520 |
| tatgtcgcct tccatgctcc gtacccagct gatttttcag aagttgcagc ttctcttggt | 2580 |
| gaagcatcgc tgaccgggcc atctgggtag acacgtatac ggctcatttt ttttacaagt | 2640 |
| acagtcacag tcactactgc aataatttga gtgtgtgtat tcacgtcaat acagcatgag | 2700 |
| aactggtcat tgtgtgccac tcctctac | 2728 |

<210> SEQ ID NO 6
<211> LENGTH: 3022
<212> TYPE: DNA
<213> ORGANISM: artificial
<220> FEATURE:
<223> OTHER INFORMATION: synthetic

<400> SEQUENCE: 6

| | |
|---|---:|
| atggccccgg cagtcactcg ccgagccaac gccctccgcg tcgaggcccc ggacggcaac | 60 |
| gccgagagcg ggcgcgccag cctagcagca gactcccccg ccgccaagcg ggctgccgac | 120 |
| gccaaggacg acgtgtgggt ggccgcggac gagggagaca cgtcgggagc catcgccggc | 180 |
| gacggcaacc gaccgccgct gttccggacc ttcaaggtca agggaagcat cctgcatcct | 240 |
| tacaggtccg tccgcgctgc gcgccattct agcctgcctg catgcatgca tgctgttctc | 300 |
| gtacgtacgt accgctacgc ttctgaaatc tgaatacggc tgtcgttctg taccaggttc | 360 |
| atgatcctcg tccgcttggt cgccatcgtc gctttcttcg cgtggcgcgt gaagcacaag | 420 |
| aaccatgacg gcgtgtggct gtgggccacg tccatggtcg ccgacgtctg gttcggcttc | 480 |
| tcgtggctcc tcaaccagct gcccaagctc aaccccgtca gcgcgtcccc gacctggcc | 540 |
| gccctcgcga ccactccggc gacgccaac ctgccgggca tcgacatctt cgtcaccacc | 600 |
| gtcgaccccg tcgacgaacc cctcttgtac accgtcaaca ccatcctctc catcctcgcc | 660 |
| accgactacc ccgtcgacaa gtacgcctgc tacctctcgg acgacggcgg cacgctggtg | 720 |
| cactacgagg cgatgatcga agttgccaat ttcgctgtgc tgtgggttcc tttttgtcgg | 780 |

```
aagtactgtg tagagccaag atcccccgag aactattttg ggatgaaaac gcagcagtac    840
gccgggagta tggccggaga gttcatgagg gatcataggc gtgtgcgcag agagtatgat    900
gagttcaagg tgagggtaga ctcccttttcc accaccatcc gccaacgatc tgatgcgtat    960
aactcgagca aaaagggaga tggtgtacgt gcaacctgga tggctgatgg gacacaatgg   1020
cctggtacat ggatcgagca ggttgacaac caccggagag gacaacatgc tggaattgtt   1080
caggtaagag ttgtgagttg cacctttcga ttagtcaatt cctcttaatt tatgagtcta   1140
gtgagagatc tctgtcttaa agctcagtcg acgaaatttg ttcgttggat agtgatttgg   1200
cggcttaaaa ggaaaaggaa aggagaccaa tttctcaaat ttattggatt aacgtgtttt   1260
tctcacaggt gatactaggc catccaagtt gtaaaccaca actgggatcg ccggcgagcg   1320
ccgacaatcc actcgacttc agcaacgttg acacgaggct ccccatgctc gtatacatgt   1380
cccgggagaa gcgacccggt tataaccacc aaaagaaggc aggcgccatg aacgtgatgc   1440
tccgtgtctc ggcgttgctc tccaacgcgc ccttcgtcgt caactttgac ggcgaccact   1500
acatcaacaa ctcgcaagct ctccgcgccc ctatgtgctt catgctcgac cctcgcgacg   1560
gtcagaacac ggccttttgtc cagtttcctc agcgcttcga cgacgtcgac ccgacggacc   1620
gctacgccaa tcacaaccgt gtcttcttcg acggcaccat gctctcccte aacggcctcc   1680
aagggccttc ctaccttggc accggcacca tgttccgccg tgtcgcgctc tatggcatgg   1740
agccaccacg ttacagagcg gagaacatca agcttgcagg taaggtcaat gagttcggta   1800
gctcgacgtc gttcataaac tcgatgccgg atggggcaat ccaggagcgg tctatcacgc   1860
cggtgttggt cgacgaggca ctcagcaatg acctggctac cctgatgacg tgcgcctacg   1920
aggatggaag ttcatgggggg agagacgtcg ggtgggtgta caacatcgcg acggaggacg   1980
tggtgaccgg attccgcatg caccggcaag ggtggcgctc catgtattgc tccatggagc   2040
cggccgcctt ccgcggaacg gctccgatta acctcaccga gcgcctctac caggtgctcc   2100
ggtggtcggg cggctcccte gagatgttct tctcccacag caatgctctc atggccggtc   2160
gccggctcca ccctctccag cgcatcgcct acctcaacat gtcaacctac ccgatcgtca   2220
cggtgttcat cctggcctac aacctcttcc ccgtcctctg gctcttctca gagcagttct   2280
acatccagag gccgttcggc acgtacatca tgtacctcgt cgccgtcata tccatcattc   2340
acgtgatcgg catgttcgag gtgaaatggg cggggatcac gctgctcgac tggtgccgca   2400
acgagcagtt ctacatgatc ggggccacgg gcgtgtaccc gacggcggtg ctttacatgg   2460
cgctcaagct cgtcaccggg aaggggatat acttcaggct cacgtccaag cagacggacg   2520
cctgctccaa tgacaagttc gccgacctgt acaccgtgcg gtgggtgccg ctgctgctcc   2580
cgaccatcgt ggtgctcgtc gtgaacgtcg cggccgtcgg ggcagcgata ggcaaggcgg   2640
cggcatgggg gttcttcacg gaccaggcgc ggcacgtgct gctcgggatg ctgttcaacg   2700
tgtggatcat cgtgctcctc tacccgtttg cgctcgggat catggggaaa tgggggaaga   2760
ggcccgtcat cctgttcgtc atgttggtca tggccattgg cgccgtcgcg ctcgtgtatg   2820
tcaccttcca tgctccgtac ccagctgatt tttcagaagc tgcagcttct cttggtgaag   2880
catcggtgac cggaccatct gggtagacac gtacggctca ttcttttttac aagtacagtc   2940
acagtcacta ctgcaataat ttgagtgtgt gtattcgtgt ctatatagca tgagaactgg   3000
tcattgtgtg ccactcctct ac                                            3022
```

<210> SEQ ID NO 7
<211> LENGTH: 3015

```
<212> TYPE: DNA
<213> ORGANISM: artificial
<220> FEATURE:
<223> OTHER INFORMATION: synthetic

<400> SEQUENCE: 7
atggccccgg cagtcactcg cagagccaac gccctccgcg ccgaggcccc ggacgggaac    60
gccgagagcg gccgcgccag cctagcagca gactcccccg ccgccaagcg ggctgtcgac   120
gccaaggacg acgtgtgggt ggccgcggac gagggagaca cgtcgggagc catcgccggc   180
gacggcaacc ggccgccgct gttccggacc ttcaaggtca agggaagcat cctgcatcct   240
tacaggtccg tctgcgctgc gcgccattct agcctgcatg catgcatgca tgcatgctgt   300
tctcgtgcgt gccgctgcgc ttctgaacac ggctgtcgtt ctgtaccagg ttcatgatcc   360
tcgtccgctt ggtcgccatc gtcgccttct tcgcgtggcg cgtgaagcac aagaaccatg   420
acggcgtgtg gctgtgggcc acgtccatgg tcgccgacgt ctggttcggc ttctcgtggc   480
tcctcaacca gctgcccaag ctcaaccccg tcaagcgcgt ccccgacctg gccgccctcg   540
cggaccactc cggcgacgcc aacctgccgg gcatcgacat attcgtcacc acagtcgacc   600
ccgtggacga accctcttg tacaccgtga acaccatcct ctctatcctg gccaccgact   660
accccgtcga caagtacgcc tgctacctct cggacgacgg cggaacgctg gtgcactacg   720
aggcgatgat cgaagttgcc aatttcgctg tcctgtgggt cccttttgt cggaagtact   780
gtgtagagcc aagatccccc gagaactatt tgggatgaa gacgcagccg tacgccggga   840
gcatggctgg agaattcatg agggatcata ggcgtgtgcg cagagagtat gatgagttca   900
aggtgagggt agactcccct tccaccacca tccgccaacg atctgatgcg tacaactcga   960
gcaagaaagg agatggtgta cgtgcaacct ggatggctga tgggacacaa tggcctggta  1020
catggatcga gcaggttgag aaccaccgga gaggacaaca tgctggaatt gttcaggtaa  1080
aagttgtcaa ttcctcttaa tttatgatga gtcagtgag agatctctgt cttaaagctc  1140
agtcgacgaa atttgttcgt tggatagtga tttggcggct taaaaggaaa aggaaaggat  1200
accaatttcc caaatttata ttcaattaaa acaagctttg aattaacgcg tttttctcac  1260
aggtcatact aggccatcca agttgtaaac cacaactggg atcgccggcg agcgccgaca  1320
atccacttga cttcagcaac gttgacacga ggctccccat gctcgtctac atgtcccggg  1380
agaagcgccc cggttataac caccaaaaga aggcgggcgc catgaacgtg atgctccgtg  1440
tctcggctat gctctccaac gcgcccttcg tcgtcaactt tgacggcgac cactacatca  1500
acaactcgca agctctccgc gcccctatgt gcttcatgct cgacccacgc gacggtcaga  1560
acacggcctt cgtccagttc ccgcagcgct tcgacgacgt cgacccgacg gaccgctacg  1620
ccaaccacaa ccgtgtcttc ttcgacggca ccatgctctc cctcaacggc tccaagggc   1680
cttcctacct cggcaccggc accatgttcc gccgtgtcgc gctctatggc atggagccac  1740
cacgttacag agcggagaac atcaagcttg caggtaaggt caatgagttc ggtagctcga  1800
cgtcgttcat aaaactcgatg ccggatgggg caatccagga gcggtctatc acgcccgtgt  1860
tggtcgacga ggcactcagc aatgacctgg ctaccctgat gacgtgcgcc tacgaggacg  1920
ggagttcatg gggcagagac gtcgggtggg tgtacaacat cgcgacggag gacgtggtga  1980
ccggatttcg catgcaccgg caagggtggc gctccatgta ttgctccatg gagccggccg  2040
ccttccgcgg aacggctccc atcaacctca ccgagcgcct ctaccaggtg ctccggtggt  2100
cgggcggctc cctcgagatg ttcttctccc acagcaatgc tctcatggcc ggtcgccggc  2160
```

```
tccaccctct ccagcgcatc gcctacctca acatgtcaac ctacccgatc gtcacggtgt    2220
tcatcctggc ctacaacctc ttccccgtcc tctggctctt ctcagagcag ttctacatcc    2280
agaggccgtt cggcacgtac atcatgtacc tcgtcgccgt catatccatc attcacgtga    2340
tcggcatgtt cgaggtgaaa tgggcgggga tcacgctgct cgactggtgc cgcaacgagc    2400
agttctacat gatcggggcc acgggcgtgt acccgacggc ggtgctttac atggcgctca    2460
agctcgtcac cgggaagggg atatacttca ggctcacgtc caagcagacg gacgcctgct    2520
ccaatgacaa gttcgccgac ctgtacaccg tgcggtgggt gccgctgctg ctcccgacca    2580
tcgtggtgct cgtcgtgaac gtcgcggccg tcggggcagc gataggcaag gcggcggcat    2640
gggggttctt cacggaccag gcgcggcacg tgctgctcgg gatgctgttc aacgtgtgga    2700
tcatcgtgct cctctacccg tttgcgctcg ggatcatggg gaaatggggg aagaggcccg    2760
tcatcctgtt cgtcatgttg gtcatggcca ttggcgccgt cgcgctcgtg tatgtcacct    2820
tccatgctcc gtaccagct gattttcag aagctgcagc ttctcttggt gaagcatcgg    2880
tgaccggacc atctgggtag acacgtacgg ctcattcttt ttacaagtac agtcacagtc    2940
actactgcaa taatttgagt gtgtgtattc gtgtctatat agcatgagaa ctggtcattg    3000
tgtgccactc ctcta                                                    3015

<210> SEQ ID NO 8
<211> LENGTH: 2992
<212> TYPE: DNA
<213> ORGANISM: artificial
<220> FEATURE:
<223> OTHER INFORMATION: synthetic

<400> SEQUENCE: 8
atggccccgg cagtcactcg cagagccaac gccctccgcg tcgaggcccc ggatgggaac      60
accgagagcg ggcgcgccag cctagcagcc gactcccccg tcgccaagcg ggctgtcgac     120
gccaaggacg acgtgtgggt ggccgcggac gaggagaag cgtcgggatc catcgccggc      180
gacggcaacc ggacgccgct gttccggacc ttcaaggtca agggaagcat cctgcatcct     240
tacaggtccg tctgcgctgc gcgccattct agcctgtctg catgcatgct gttctcgtac     300
gtaccgctac agttctgaac acgactgtcg ttctgtacca ggttcatgat tctcgtccgc     360
ttggtcgcca tctcgccctt cttcgcatgg cgcgtgaagc acaagaacca tgacggcgtg     420
tggctgtggg ccacgtccat ggtcgccgac gtctggttcg gcttctcgtg gctcctcaac     480
cagctgccca agctcaaccc cgtcaagcgc gtccccgacc tggccgccct cgcggaccac     540
tccggcgacg ccaacctgcc gggcatcgac atcttcgtca ccaccgtcga ccccgtggac     600
gaacccctct tgtacaccgt gaacaccatc ctctccatcc tcgccaccga ctaccccgtc     660
gacaagtacg cctgctacct ctcggacgac ggcggcacgt tggtgcacta cgaggcgatg     720
atcgaagttg ccaatttcgc tgtcttgtgg gtccccttt gtcggaagta ctgtgtagag      780
ccaagatccc ccgagaacta ttttgggatg aaaacgcagc cgtatgccgg gagtatggcg     840
ggagaattca tgagggatca taggcgtgtg cgcagagagt atgatgagtt caaggtgagg     900
gtagactccc tttccaccac catccgccaa cgatctgatg cgtataactc gagcaccaaa     960
ggagatggtg tacgtgctac ctggatggct gatgggacac aatggcctgg tacatggatc    1020
gagcaggttc agaaccacag gagaggacaa catgctggaa ttgttcaggt aaaagttgtg    1080
agttgcacct ttcgattagt ctagtgagag atcagtcaac gaaatttgtt cgttggatag    1140
tgatttggcg gcttaaaagg aaaaggaaag gataccaact tctcaaattt atagtagatt    1200
```

```
aaaacaagct tgaattaac gtgttttcc tcacaggtca tactaggcca tccaagttgt    1260
aaaccgcaac tgggatcgcc ggcgagcagc gacaatccac ttgacttcag caatgttgac    1320
acgaggctcc ccatgctcgt ctacatgtcc cgggagaagc gccctggtta taaccaccaa    1380
aagaaggcag cgccatgaa cgtgatgctc cgtgtctcgg cgttgctctc caacgcgccc    1440
ttcgtcgtca actttgacgg cgaccactac atcaacaatt cgcaagccct tcgtgcccct    1500
atgtgcttca tgctcgaccc tcacgacggt cagaacacgg cctttcgtcca gttcccgcag    1560
cgcttcgacg atgtcgaccc gacggaccga tatgccaacc acaaccgtgt cttcttcgac    1620
ggcaccatgc tctccctcaa cggcctccaa gggccttctt accttggcac cggcaccatg    1680
ttccgtcgtg tcgcgctcta tggcatggag ccaccacgtt acagagcgga gaacatcaag    1740
cttgcaggta aggtcaatga gttcggtagc tcgacgtcgt tcataaaattc gatgccggat    1800
ggtgcaatcc aggagcggtc tatcacgccg gtgttggtcg acgaggcact cagcaatgac    1860
ctggctaccc tgatgacgtg tgcctacgag gatggaagtt catggggag agacgtcggg    1920
tgggtgtaca acatcgcgac ggaggacgtg gtgaccggat ccgcatgca ccggcaaggg    1980
tggcgttcca tgtattgctc catggagccg gccgccttcc gcggaacggc tccgatcaac    2040
ctcaccgagc gcctctacca ggtgctccgg tggtcgggcg gctccctgga gatgttcttc    2100
tcccacagca atgctctcat ggccggccgc cggctccacc cactgcagcg catcgcctac    2160
ctcaacatgt cgacctaccc gatcgtcacg gtgttcattc tggcctacaa cctcttcccc    2220
gtcctctggc tcttctcaga gcagttctac atccagaggc cgttcggcac gtacatcatg    2280
tacctcgtcg ccgtcatagg catgattcat gtgatcggca tgttcgaggt gaaatgggcg    2340
gggatcacgc tgctcgactg gtgccgcaac gagcagtttt acatgatcgg ggccacgggc    2400
gtgtacccga cggcggtgct ttacatggcg ctcaagctcg tcaccgggaa ggggatatac    2460
ttcaggctca cgtccaagca gacggacgcc tgctccaatg acaagttcgc cgaccttac    2520
accgtgcggt gggtgccgct gctgctcccg accatcgtgg tgctcgtcgt gaacgtcgcg    2580
gccgtcgggg cagcgatagg caaggcggcg gcatgggggt tcttcacgga ccaggcgcgg    2640
cacgtgctgc tcgggatgtt gttcaacgtg tggatcctcg tgctcctcta cccgtttgcg    2700
ctcgggatca tggggaaatg ggggaagagg cccgtcatcc tgttcgtcat gttggtcatg    2760
gccgttggcg cagtcgggct cttgtatgtc gccttccatg ctccgtaccc agctgatttt    2820
tcagaagttg cagcttctct tggtgaagca tcgctgaccg ggccatctgg gtagacacgt    2880
atacggctca tttttttac aagtacagtc acagtcacta ctgcaataat ttgagtgtgt    2940
gtattcacgt caatacagca tgagaactgg tcattgtgtg ccactcctct ac           2992
```

<210> SEQ ID NO 9
<211> LENGTH: 869
<212> TYPE: PRT
<213> ORGANISM: Triticum aestivum

<400> SEQUENCE: 9

Met Ala Pro Ala Val Thr Arg Arg Ala Asn Ala Leu Arg Val Glu Ala
1               5                   10                  15

Pro Asp Gly Asn Ala Glu Ser Gly Arg Ala Ser Leu Ala Ala Asp Ser
            20                  25                  30

Pro Ala Ala Lys Arg Ala Ala Asp Ala Lys Asp Asp Val Trp Val Ala
        35                  40                  45

Ala Asp Glu Gly Asp Thr Ser Gly Ala Ile Ala Gly Asp Gly Asn Arg

```
            50                  55                  60
Pro Pro Leu Phe Arg Thr Phe Lys Val Lys Gly Ser Ile Leu His Pro
 65                  70                  75                  80

Tyr Arg Phe Met Ile Leu Val Arg Leu Val Ala Ile Val Ala Phe Phe
                     85                  90                  95

Ala Trp Arg Val Lys His Lys Asn His Asp Gly Val Trp Leu Trp Ala
                    100                 105                 110

Thr Ser Met Val Ala Asp Val Trp Phe Gly Phe Ser Trp Leu Leu Asn
                    115                 120                 125

Gln Leu Pro Lys Leu Asn Pro Val Lys Arg Val Pro Asp Leu Ala Ala
                130                 135                 140

Leu Ala Asp His Ser Gly Asp Ala Asn Leu Pro Gly Ile Asp Ile Phe
145                 150                 155                 160

Val Thr Thr Val Asp Pro Val Asp Glu Pro Leu Leu Tyr Thr Val Asn
                    165                 170                 175

Thr Ile Leu Ser Ile Leu Ala Thr Asp Tyr Pro Val Asp Lys Tyr Ala
                180                 185                 190

Cys Tyr Leu Ser Asp Asp Gly Gly Thr Leu Val His Tyr Glu Ala Met
                195                 200                 205

Ile Glu Val Ala Asn Phe Ala Val Leu Trp Val Pro Phe Cys Arg Lys
210                 215                 220

Tyr Cys Val Glu Pro Arg Ser Pro Glu Asn Tyr Phe Gly Met Lys Thr
225                 230                 235                 240

Gln Gln Tyr Ala Gly Ser Met Ala Gly Glu Phe Met Arg Asp His Arg
                    245                 250                 255

Arg Val Arg Arg Glu Tyr Asp Glu Phe Lys Val Arg Val Asp Ser Leu
                260                 265                 270

Ser Thr Thr Ile Arg Gln Arg Ser Asp Ala Tyr Asn Ser Ser Lys Lys
                275                 280                 285

Gly Asp Gly Val Arg Ala Thr Trp Met Ala Asp Gly Thr Gln Trp Pro
290                 295                 300

Gly Thr Trp Ile Glu Gln Val Asp Asn His Arg Arg Gly Gln His Ala
305                 310                 315                 320

Gly Ile Val Gln Val Ile Leu Gly His Pro Ser Cys Lys Pro Gln Leu
                    325                 330                 335

Gly Ser Pro Ala Ser Ala Asp Asn Pro Leu Asp Phe Ser Asn Val Asp
                340                 345                 350

Thr Arg Leu Pro Met Leu Val Tyr Met Ser Arg Glu Lys Arg Pro Gly
                355                 360                 365

Tyr Asn His Gln Lys Lys Ala Gly Ala Met Asn Val Met Leu Arg Val
                370                 375                 380

Ser Ala Leu Leu Ser Asn Ala Pro Phe Val Val Asn Phe Asp Gly Asp
385                 390                 395                 400

His Tyr Ile Asn Asn Ser Gln Ala Leu Arg Ala Pro Met Cys Phe Met
                    405                 410                 415

Leu Asp Pro Arg Asp Gly Gln Asn Thr Ala Phe Val Gln Phe Pro Gln
                420                 425                 430

Arg Phe Asp Asp Val Asp Pro Thr Asp Arg Tyr Ala Asn His Asn Arg
                435                 440                 445

Val Phe Phe Asp Gly Thr Met Leu Ser Leu Asn Gly Leu Gln Gly Pro
                450                 455                 460

Ser Tyr Leu Gly Thr Gly Thr Met Phe Arg Arg Val Ala Leu Tyr Gly
465                 470                 475                 480
```

```
Met Glu Pro Pro Arg Tyr Arg Ala Glu Asn Ile Lys Leu Ala Gly Lys
            485                 490                 495

Val Asn Glu Phe Gly Ser Ser Thr Ser Phe Ile Asn Ser Met Pro Asp
        500                 505                 510

Gly Ala Ile Gln Glu Arg Ser Ile Thr Pro Val Leu Val Asp Glu Ala
            515                 520                 525

Leu Ser Asn Asp Leu Ala Thr Leu Met Thr Cys Ala Tyr Glu Asp Gly
        530                 535                 540

Ser Ser Trp Gly Arg Asp Val Gly Trp Val Tyr Asn Ile Ala Thr Glu
545                 550                 555                 560

Asp Val Val Thr Gly Phe Arg Met His Arg Gln Gly Trp Arg Ser Met
            565                 570                 575

Tyr Cys Ser Met Glu Pro Ala Ala Phe Arg Gly Thr Ala Pro Ile Asn
        580                 585                 590

Leu Thr Glu Arg Leu Tyr Gln Val Leu Arg Trp Ser Gly Gly Ser Leu
            595                 600                 605

Glu Met Phe Phe Ser His Ser Asn Ala Leu Met Ala Gly Arg Arg Leu
        610                 615                 620

His Pro Leu Gln Arg Ile Ala Tyr Leu Asn Met Ser Thr Tyr Pro Ile
625                 630                 635                 640

Val Thr Val Phe Ile Leu Ala Tyr Asn Leu Phe Pro Val Leu Trp Leu
            645                 650                 655

Phe Ser Glu Gln Phe Tyr Ile Gln Arg Pro Phe Gly Thr Tyr Ile Met
        660                 665                 670

Tyr Leu Val Ala Val Ile Ser Ile Ile His Val Ile Gly Met Phe Glu
            675                 680                 685

Val Lys Trp Ala Gly Ile Thr Leu Leu Asp Trp Cys Arg Asn Glu Gln
        690                 695                 700

Phe Tyr Met Ile Gly Ala Thr Gly Val Tyr Pro Thr Ala Val Leu Tyr
705                 710                 715                 720

Met Ala Leu Lys Leu Val Thr Gly Lys Gly Ile Tyr Phe Arg Leu Thr
            725                 730                 735

Ser Lys Gln Thr Asp Ala Cys Ser Asn Asp Lys Phe Ala Asp Leu Tyr
        740                 745                 750

Thr Val Arg Trp Val Pro Leu Leu Pro Thr Ile Val Val Leu Val
            755                 760                 765

Val Asn Val Ala Ala Val Gly Ala Ile Gly Lys Ala Ala Trp
770                 775                 780

Gly Phe Phe Thr Asp Gln Ala Arg His Val Leu Leu Gly Met Leu Phe
785                 790                 795                 800

Asn Val Trp Ile Ile Val Leu Leu Tyr Pro Phe Ala Leu Gly Ile Met
            805                 810                 815

Gly Lys Trp Gly Lys Arg Pro Val Ile Leu Phe Val Met Leu Val Met
        820                 825                 830

Ala Ile Gly Ala Val Ala Leu Val Tyr Val Thr Phe His Ala Pro Tyr
            835                 840                 845

Pro Ala Asp Phe Ser Glu Ala Ala Ala Ser Leu Gly Glu Ala Ser Val
        850                 855                 860

Thr Gly Pro Ser Gly
865

<210> SEQ ID NO 10
<211> LENGTH: 869
```

<212> TYPE: PRT
<213> ORGANISM: Triticum aestivum

<400> SEQUENCE: 10

```
Met Ala Pro Ala Val Thr Arg Arg Ala Asn Ala Leu Arg Ala Glu Ala
1               5                   10                  15

Pro Asp Gly Asn Ala Glu Ser Gly Arg Ala Ser Leu Ala Ala Asp Ser
            20                  25                  30

Pro Ala Ala Lys Arg Ala Val Asp Ala Lys Asp Asp Val Trp Val Ala
        35                  40                  45

Ala Asp Glu Gly Asp Thr Ser Gly Ala Ile Ala Gly Asp Gly Asn Arg
50                  55                  60

Pro Pro Leu Phe Arg Thr Phe Lys Val Lys Gly Ser Ile Leu His Pro
65                  70                  75                  80

Tyr Arg Phe Met Ile Leu Val Arg Leu Val Ala Ile Val Ala Phe Phe
                85                  90                  95

Ala Trp Arg Val Lys His Lys Asn His Asp Gly Val Trp Leu Trp Ala
            100                 105                 110

Thr Ser Met Val Ala Asp Val Trp Phe Gly Phe Ser Trp Leu Leu Asn
        115                 120                 125

Gln Leu Pro Lys Leu Asn Pro Val Lys Arg Val Pro Asp Leu Ala Ala
130                 135                 140

Leu Ala Asp His Ser Gly Asp Ala Asn Leu Pro Gly Ile Asp Ile Phe
145                 150                 155                 160

Val Thr Thr Val Asp Pro Val Asp Glu Pro Leu Leu Tyr Thr Val Asn
                165                 170                 175

Thr Ile Leu Ser Ile Leu Ala Thr Asp Tyr Pro Val Asp Lys Tyr Ala
            180                 185                 190

Cys Tyr Leu Ser Asp Asp Gly Gly Thr Leu Val His Tyr Glu Ala Met
        195                 200                 205

Ile Glu Val Ala Asn Phe Ala Val Leu Trp Val Pro Phe Cys Arg Lys
210                 215                 220

Tyr Cys Val Glu Pro Arg Ser Pro Glu Asn Tyr Phe Gly Met Lys Thr
225                 230                 235                 240

Gln Pro Tyr Ala Gly Ser Met Ala Gly Glu Phe Met Arg Asp His Arg
                245                 250                 255

Arg Val Arg Arg Glu Tyr Asp Glu Phe Lys Val Arg Val Asp Ser Leu
            260                 265                 270

Ser Thr Thr Ile Arg Gln Arg Ser Asp Ala Tyr Asn Ser Ser Lys Lys
        275                 280                 285

Gly Asp Gly Val Arg Ala Thr Trp Met Ala Asp Gly Thr Gln Trp Pro
290                 295                 300

Gly Thr Trp Ile Glu Val Glu Asn His Arg Arg Gly Gln His Ala
305                 310                 315                 320

Gly Ile Val Gln Val Ile Leu Gly His Pro Ser Cys Lys Pro Gln Leu
                325                 330                 335

Gly Ser Pro Ala Ser Ala Asp Asn Pro Leu Asp Phe Ser Asn Val Asp
            340                 345                 350

Thr Arg Leu Pro Met Leu Val Tyr Met Ser Arg Glu Lys Arg Pro Gly
        355                 360                 365

Tyr Asn His Gln Lys Lys Ala Gly Ala Met Asn Val Met Leu Arg Val
370                 375                 380

Ser Ala Met Leu Ser Asn Ala Pro Phe Val Val Asn Phe Asp Gly Asp
385                 390                 395                 400
```

```
His Tyr Ile Asn Asn Ser Gln Ala Leu Arg Ala Pro Met Cys Phe Met
            405                 410                 415

Leu Asp Pro Arg Asp Gly Gln Asn Thr Ala Phe Val Gln Phe Pro Gln
        420                 425                 430

Arg Phe Asp Asp Val Asp Pro Thr Asp Arg Tyr Ala Asn His Asn Arg
        435                 440                 445

Val Phe Phe Asp Gly Thr Met Leu Ser Leu Asn Gly Leu Gln Gly Pro
    450                 455                 460

Ser Tyr Leu Gly Thr Gly Thr Met Phe Arg Arg Val Ala Leu Tyr Gly
465                 470                 475                 480

Met Glu Pro Pro Arg Tyr Arg Ala Glu Asn Ile Lys Leu Ala Gly Lys
                485                 490                 495

Val Asn Glu Phe Gly Ser Ser Thr Ser Phe Ile Asn Ser Met Pro Asp
                500                 505                 510

Gly Ala Ile Gln Glu Arg Ser Ile Thr Pro Val Leu Val Asp Glu Ala
            515                 520                 525

Leu Ser Asn Asp Leu Ala Thr Leu Met Thr Cys Ala Tyr Glu Asp Gly
    530                 535                 540

Ser Ser Trp Gly Arg Asp Val Gly Trp Val Tyr Asn Ile Ala Thr Glu
545                 550                 555                 560

Asp Val Val Thr Gly Phe Arg Met His Arg Gln Gly Trp Arg Ser Met
                565                 570                 575

Tyr Cys Ser Met Glu Pro Ala Ala Phe Arg Gly Thr Ala Pro Ile Asn
                580                 585                 590

Leu Thr Glu Arg Leu Tyr Gln Val Leu Arg Trp Ser Gly Gly Ser Leu
            595                 600                 605

Glu Met Phe Phe Ser His Ser Asn Ala Leu Met Ala Gly Arg Arg Leu
    610                 615                 620

His Pro Leu Gln Arg Ile Ala Tyr Leu Asn Met Ser Thr Tyr Pro Ile
625                 630                 635                 640

Val Thr Val Phe Ile Leu Ala Tyr Asn Leu Phe Pro Val Leu Trp Leu
                645                 650                 655

Phe Ser Glu Gln Phe Tyr Ile Gln Arg Pro Phe Gly Thr Tyr Ile Met
                660                 665                 670

Tyr Leu Val Ala Val Ile Ser Ile Ile His Val Ile Gly Met Phe Glu
            675                 680                 685

Val Lys Trp Ala Gly Ile Thr Leu Leu Asp Trp Cys Arg Asn Glu Gln
    690                 695                 700

Phe Tyr Met Ile Gly Ala Thr Gly Val Tyr Pro Thr Ala Val Leu Tyr
705                 710                 715                 720

Met Ala Leu Lys Leu Val Thr Gly Lys Gly Ile Tyr Phe Arg Leu Thr
                725                 730                 735

Ser Lys Gln Thr Asp Ala Cys Ser Asn Asp Lys Phe Ala Asp Leu Tyr
                740                 745                 750

Thr Val Arg Trp Val Pro Leu Leu Leu Pro Thr Ile Val Val Leu Val
            755                 760                 765

Val Asn Val Ala Ala Val Gly Ala Ala Ile Gly Lys Ala Ala Ala Trp
    770                 775                 780

Gly Phe Phe Thr Asp Gln Ala Arg His Val Leu Leu Gly Met Leu Phe
785                 790                 795                 800

Asn Val Trp Ile Ile Val Leu Leu Tyr Pro Phe Ala Leu Gly Ile Met
                805                 810                 815
```

```
Gly Lys Trp Gly Lys Arg Pro Val Ile Leu Phe Val Met Leu Val Met
            820                 825                 830

Ala Ile Gly Ala Val Ala Leu Val Tyr Val Thr Phe His Ala Pro Tyr
            835                 840                 845

Pro Ala Asp Phe Ser Glu Ala Ala Ser Leu Gly Glu Ala Ser Val
            850                 855                 860

Thr Gly Pro Ser Gly
865

<210> SEQ ID NO 11
<211> LENGTH: 869
<212> TYPE: PRT
<213> ORGANISM: Triticum aestivum

<400> SEQUENCE: 11

Met Ala Pro Ala Val Thr Arg Arg Ala Asn Ala Leu Arg Val Glu Ala
1               5                   10                  15

Pro Asp Gly Asn Thr Glu Ser Gly Arg Ala Ser Leu Ala Ala Asp Ser
                20                  25                  30

Pro Val Ala Lys Arg Ala Val Asp Ala Lys Asp Asp Val Trp Val Ala
            35                  40                  45

Ala Asp Glu Gly Glu Ala Ser Gly Ser Ile Ala Gly Asp Gly Asn Arg
        50                  55                  60

Thr Pro Leu Phe Arg Thr Phe Lys Val Lys Gly Ser Ile Leu His Pro
65                  70                  75                  80

Tyr Arg Phe Met Ile Leu Val Arg Leu Val Ala Ile Val Ala Phe Phe
                85                  90                  95

Ala Trp Arg Val Lys His Lys Asn His Asp Gly Val Trp Leu Trp Ala
            100                 105                 110

Thr Ser Met Val Ala Asp Val Trp Phe Gly Phe Ser Trp Leu Leu Asn
        115                 120                 125

Gln Leu Pro Lys Leu Asn Pro Val Lys Arg Val Pro Asp Leu Ala Ala
130                 135                 140

Leu Ala Asp His Ser Gly Asp Ala Asn Leu Pro Gly Ile Asp Ile Phe
145                 150                 155                 160

Val Thr Thr Val Asp Pro Val Asp Glu Pro Leu Leu Tyr Thr Val Asn
                165                 170                 175

Thr Ile Leu Ser Ile Leu Ala Thr Asp Tyr Pro Val Asp Lys Tyr Ala
            180                 185                 190

Cys Tyr Leu Ser Asp Asp Gly Gly Thr Leu Val His Tyr Glu Ala Met
        195                 200                 205

Ile Glu Val Ala Asn Phe Ala Val Leu Trp Val Pro Phe Cys Arg Lys
210                 215                 220

Tyr Cys Val Glu Pro Arg Ser Pro Glu Asn Tyr Phe Gly Met Lys Thr
225                 230                 235                 240

Gln Pro Tyr Ala Gly Ser Met Ala Gly Glu Phe Met Arg Asp His Arg
                245                 250                 255

Arg Val Arg Arg Glu Tyr Asp Glu Phe Lys Val Arg Val Asp Ser Leu
            260                 265                 270

Ser Thr Thr Ile Arg Gln Arg Ser Asp Ala Tyr Asn Ser Ser Thr Lys
        275                 280                 285

Gly Asp Gly Val Arg Ala Thr Trp Met Ala Asp Gly Thr Gln Trp Pro
290                 295                 300

Gly Thr Trp Ile Glu Gln Val Glu Asn His Arg Arg Gly Gln His Ala
305                 310                 315                 320
```

```
Gly Ile Val Gln Val Ile Leu Gly His Pro Ser Cys Lys Pro Gln Leu
            325                 330                 335

Gly Ser Pro Ala Ser Ser Asp Asn Pro Leu Asp Phe Ser Asn Val Asp
            340                 345                 350

Thr Arg Leu Pro Met Leu Val Tyr Met Ser Arg Glu Lys Arg Pro Gly
            355                 360                 365

Tyr Asn His Gln Lys Lys Ala Gly Ala Met Asn Val Met Leu Arg Val
            370                 375                 380

Ser Ala Leu Leu Ser Asn Ala Pro Phe Val Val Asn Phe Asp Gly Asp
385                 390                 395                 400

His Tyr Ile Asn Asn Ser Gln Ala Leu Arg Ala Pro Met Cys Phe Met
            405                 410                 415

Leu Asp Pro His Asp Gly Gln Asn Thr Ala Phe Val Gln Phe Pro Gln
            420                 425                 430

Arg Phe Asp Asp Val Asp Pro Thr Asp Arg Tyr Ala Asn His Asn Arg
            435                 440                 445

Val Phe Phe Asp Gly Thr Met Leu Ser Leu Asn Gly Leu Gln Gly Pro
            450                 455                 460

Ser Tyr Leu Gly Thr Gly Thr Met Phe Arg Arg Val Ala Leu Tyr Gly
465                 470                 475                 480

Met Glu Pro Pro Arg Tyr Arg Ala Glu Asn Ile Lys Leu Ala Gly Lys
            485                 490                 495

Val Asn Glu Phe Gly Ser Ser Thr Ser Phe Ile Asn Ser Met Pro Asp
            500                 505                 510

Gly Ala Ile Gln Glu Arg Ser Ile Thr Pro Val Leu Val Asp Glu Ala
            515                 520                 525

Leu Ser Asn Asp Leu Ala Thr Leu Met Thr Cys Ala Tyr Glu Asp Gly
            530                 535                 540

Ser Ser Trp Gly Arg Asp Val Gly Trp Val Tyr Asn Ile Ala Thr Glu
545                 550                 555                 560

Asp Val Val Thr Gly Phe Arg Met His Arg Gln Gly Trp Arg Ser Met
            565                 570                 575

Tyr Cys Ser Met Glu Pro Ala Ala Phe Arg Gly Thr Ala Pro Ile Asn
            580                 585                 590

Leu Thr Glu Arg Leu Tyr Gln Val Leu Arg Trp Ser Gly Gly Ser Leu
            595                 600                 605

Glu Met Phe Phe Ser His Ser Asn Ala Leu Met Ala Gly Arg Arg Leu
            610                 615                 620

His Pro Leu Gln Arg Ile Ala Tyr Leu Asn Met Ser Thr Tyr Pro Ile
625                 630                 635                 640

Val Thr Val Phe Ile Leu Ala Tyr Asn Leu Phe Pro Val Leu Trp Leu
            645                 650                 655

Phe Ser Glu Gln Phe Tyr Ile Gln Arg Pro Phe Gly Thr Tyr Ile Met
            660                 665                 670

Tyr Leu Val Ala Val Ile Gly Met Ile His Val Ile Gly Met Phe Glu
            675                 680                 685

Val Lys Trp Ala Gly Ile Thr Leu Leu Asp Trp Cys Arg Asn Glu Gln
            690                 695                 700

Phe Tyr Met Ile Gly Ala Thr Gly Val Tyr Pro Thr Ala Val Leu Tyr
705                 710                 715                 720

Met Ala Leu Lys Leu Val Thr Gly Lys Gly Ile Tyr Phe Arg Leu Thr
            725                 730                 735
```

```
Ser Lys Gln Thr Asp Ala Cys Ser Asn Asp Lys Phe Ala Asp Leu Tyr
            740                 745                 750

Thr Val Arg Trp Val Pro Leu Leu Leu Pro Thr Ile Val Val Leu Val
            755                 760                 765

Val Asn Val Ala Ala Val Gly Ala Ala Ile Gly Lys Ala Ala Ala Trp
        770                 775                 780

Gly Phe Phe Thr Asp Gln Ala Arg His Val Leu Leu Gly Met Leu Phe
785                 790                 795                 800

Asn Val Trp Ile Leu Val Leu Leu Tyr Pro Phe Ala Leu Gly Ile Met
                805                 810                 815

Gly Lys Trp Gly Lys Arg Pro Val Ile Leu Phe Val Met Leu Val Met
            820                 825                 830

Ala Val Gly Ala Val Gly Leu Leu Tyr Val Ala Phe His Ala Pro Tyr
            835                 840                 845

Pro Ala Asp Phe Ser Glu Val Ala Ala Ser Leu Gly Glu Ala Ser Leu
        850                 855                 860

Thr Gly Pro Ser Gly
865

<210> SEQ ID NO 12
<211> LENGTH: 3082
<212> TYPE: DNA
<213> ORGANISM: artificial
<220> FEATURE:
<223> OTHER INFORMATION: synthetic

<400> SEQUENCE: 12
catggcgcca gcggtggccg gaggaggccg cgtgcggagc aatgagccgg ctgctgccgc      60
ggcgccggcg gccgccagcg ggaagccctg cgtctgcggc ttccaggtgt gcgcctgcac     120
gggatcggcc gcggtggcgt ccgccgcctc ctcgctggac atggacatcg tggccatggg     180
ccagatcggc gccgtcaacg acgagagctg ggtgggcgtg gagctcggcg aagacggcga     240
gaccgacgaa agcggtgtcg ccgttgacga ccgccccgtc ttccgcaccg agaaaatcaa     300
gggtgtcctt ctccaccccct accgggtgct gatcttcgtt cggctgatcg ccttcaccct     360
gttcgtgatc tggcgtatct cccacaagaa ccctgacgcc atgtggctgt gggtgacatc     420
catctgcggc gagttctggt tcggcttctc ctggctgctg atcagctgc caagctgaa      480 ccccatcaac cgcgtgccgg acctggccgt gctgcggcag cgcttcgacc gccccgacgg     540
cacctccacc ctcccggggc tcgacatctt cgtcaccacg gccgacccca tcaaggagcc     600
catcctctcc accgccaact ccgtgctctc catcctcgcc gccgactacc cgtcgaccg      660 caacacatgc tacgtctctg acgacagtgg catgctgctc acctacgagg ccctggccga     720
gtcctccaag ttcgccaccc tctgggtgcc cttctgccgc aagcacggga tcgagcccag     780
gggcccggag agctacttcg agctcaagtc ccaccctac atggggagag cccaggacga     840
attcgtcaac gaccgccgcc gcgtccgcaa ggagtacgac gagttcaagg ccagaatcaa     900
cagcctggag cacgacatca gcagcgcaa cgacgggtac aacgccgcca acgcccaccg     960
ggaaggcgag ccccgaccca cctggatggc cgacggcacc cagtggcagg gcacctgggt    1020
ggacgcctcc gagaaccacc gcaggggcga ccacgccggc atcgtcctgg tgctgctgaa    1080
ccacccgagc caccgccggc agacgggccc gccggcgagc gctgacaacc cactggactt    1140
cagcggcgtg gatgtgcgtc tccccatgct ggtgtacgtg tcccgtgaga gcgccccgg     1200 acacgaccac cagaagaagg ccggcgccat gaacgcgctc acccgcgcct ccgcgctgct    1260
```

-continued

| | |
|---|---|
| ctccaactcc cccttcatcc tcaacctcga ctgcgaccat tacatcaaca actcccaggc | 1320 |
| cctccgcgcc ggcatctgct tcatggtggg acgcgacagc gacaccgtcg ccttcgtcca | 1380 |
| gttcccgcag cgcttcgagg gcgtcgaccc caccgacctc tacgccaacc acaaccgcat | 1440 |
| cttcttcgac ggcaccctcc gtgccctcga cggcatgcag ggccccatct acgtcggcac | 1500 |
| cggctgtctc ttccgccgca tcaccgtcta cggcttcgac ccgcccagga tcaacgtcgg | 1560 |
| cgggccctgc ttccccaggc tcgccgggct cttcgccaag accaagtacg agaagcccgg | 1620 |
| cctcgagatg accatggcca aggccaaggc cgcgccggtg cccgccaagg gcaagcacgg | 1680 |
| cttcctgcct ctgcccaaga gacgtacgg caagtcggac gccttcgtgg acagcatccc | 1740 |
| gcgcgcgtcg cacccgtcgc cttacgccgc ggcggctgag ggcatcgtgg ccgacgaggc | 1800 |
| gaccatcgtg gaggcggtga acgtgacggc cgcggcgttc gagaagaaga ccggctgggg | 1860 |
| caaagagatc ggctgggtgt acgacaccgt gacggaggac gtggtgaccg ggtaccggat | 1920 |
| gcatatcaag gggtggcggt cacgctactg ctccatctac ccacacgcct tcatcggcac | 1980 |
| cgcacccatc aacctcacgg agaggctctt ccaggtgctc cgctggtcca cgggctccct | 2040 |
| cgagatcttc ttctccaaga caaacccgct cttcggcagc acctacctcc acccgctgca | 2100 |
| gcgcgtcgcc tacatcaaca tcaccaccta ccccttcacc gccatcttcc tcatcttcta | 2160 |
| caccaccgtg ccggcgctct ccttcgtcac cggccacttc atcgtgcaac gccccaccac | 2220 |
| catgttctac gtctacctgg gcatcgtgct ctccacgctg ctcgtcatcg ccgtgctgga | 2280 |
| ggtcaagtgg gccggggtca ccgtcttcga gtggttcagg aacggccagt tctggatgac | 2340 |
| ggcaagttgc tccgcctacc tcgccgccgt gtgccaggtg ctgaccaagg tgatattccg | 2400 |
| gcgtgacatc tccttcaagc tcacatccaa gctaccgtcc ggagacgaga agaaggaccc | 2460 |
| ctacgccgac ctgtacgtgg tgcgctggac gccgctcatg atcacaccca tcatcatcat | 2520 |
| tttcgtcaac atcattgggt cggcggtggc cttcgccaag gtgctcgacg gcgagtggac | 2580 |
| gcactggctc aaggtcgccg gcggggtctt cttcaacttc tgggtgctgt ccacctcta | 2640 |
| cccgttcgcc aaggggatcc tggggaagca cggcaagacg ccagtcgtgg tgcccgtctg | 2700 |
| gtgggcattc accttcgtca tcaccgccgt gctctacatc aacatccccc acatgcatag | 2760 |
| ctcgggaggc aagcacacaa cggtgcatgg tcaccatggc aagaagttcg tcgacgcagg | 2820 |
| gtactacaac tggccatgag gtccctgttg acgactttgc cgccggacag gacgacctga | 2880 |
| gacaagaagc aacaagtcat ccactgaaca gtgcatgcat ccatctgatc gagaagcaga | 2940 |
| gcccgccaaa gtttgaattt tttaattttt tttcttcact tttcgcccg tttctttta | 3000 |
| gttttgtcca gaaaaagat ggtgttgatt tgatttagtt cttaattacc tgtggtaatt | 3060 |
| aattatgtac ttattataca tt | 3082 |

<210> SEQ ID NO 13
<211> LENGTH: 3156
<212> TYPE: DNA
<213> ORGANISM: artificial
<220> FEATURE:
<223> OTHER INFORMATION: synthetic

<400> SEQUENCE: 13

| | |
|---|---|
| gcctgagcgt ggagagctac cttgcctgcc tccctcccat tcttgctgct gctctccttg | 60 |
| tcgtaaagga gagtgcgtgc attgaggacc acggccatgg cgccagcggt ggccggagga | 120 |
| ggccgcgtgc ggagcaatga gcctgctgct gccgctgcca gcgacaagcc ctgcgtgtgc | 180 |
| ggcttccagg tgtgcgcctg cacgggatcg gccgcggtgg cgtccgccgc ctcctcgctg | 240 |

-continued

```
gacatggaca tcgtggccat ggggcagatc ggcgccgtca acgacgagag ctgggtgggc    300
gtggagctcg gcgaggacgg cgagaccgac gaaagcggtg ccgctgttga cgaccgcccc    360
gtcttccgca ccgagaaaat caagggtgtc ctcctccacc cctaccgggt gctgatcttc    420
gtccgtctca tcgccttcac cctgttcgtg atctggcgta tctcccacaa gaaccctgac    480
gccatgtggc tgtgggtgac atccatctgc ggcgagttct ggttcggctt ctcctggctg    540
ctggatcagc tccccaagct gaaccccatc aaccgcgtgc cggacctggc cgtgctgcgg    600
cagcgcttcg accgccccga cggcacctcc acgctccctg gctggacatc ttcgtcacc    660 acggccgacc ccatcaagga gcccatcctc tccaccgcca actcggtgct ctccatcctc    720
gccgccgact accccgtgga ccgcaacaca tgctacgtct ccgacgacag tggcatgctg    780
ctcacctacg aggccctggc tgagtcctcc aagttcgcca ccctctgggt gcccttctgc    840
cgcaagcacg ggattgagcc gaggggcccg agagctact tcgagctcaa gtcccacccc    900
tacatgggga gagcccagga cgagttcgtg aacgaccgcc gacgcgtccg caaggagtac    960
gacgagttca aggccaggat caacagcctg gagcatgaca tcaagcagcg caacgacggg   1020
tacaacgccc caacgctca ccgggaaggc gagccccgac ccacctggat ggccgacggc   1080
acccagtggg agggcacctg ggtcgacgcc tccgagaacc accgcagggg cgaccacgcc   1140
ggcatcgtcc gggtgctgct gaaccacccg agccaccggc ggcagacggg cccgccggcg   1200
agcgctgaca acccactgga cttcagcggc gtggatgcgc gtctccccat gctggtgtac   1260 gtttccccgtg agaagcgccc cggacacgac caccagaaga aggccggcgc catgaacgcg   1320
ctcacccgcg cctccgcgct gctctccaac tcccccttca tcctcaacct cgactgcgac   1380
cattacatca caactccca ggccctccgc gccggcatct gcttcatggt gggacgcgac   1440
agcgacaccg tcgccttcgt ccagttcccg cagcgcttcg agggcgtcga ccccaccgac   1500
ctctacgcca accacaaccg catcttcttc gacggcaccc tccgtgccct cgacggcatg   1560
cagggcccca tctacgtcgg caccgggtgt ctcttccgcc gcatcaccgt ctacggcttc   1620
gacccgccca ggatcaacgt cggcgggccc tgcttcccca ggctcgccgg gctcttcgcc   1680
aagaccaagt acgagaagcc gagcctcgag atgacaatgg ccaaggccaa ggccgcgccg   1740
gtgcccgcca aggggaagca cggcttcctg cctctgccca gaagacgta cggcaagtcg   1800 gacgccttcg tggacagcat cccgcgcgcg tcgcacccgt cgccttacgc ggcggcggct   1860
gagggcatcg tggccgacga ggcgaccatc gtggaggcgg tgaacgtgac ggcggcggcg   1920
ttcgagaaga gaccgggtg gggcaaagag atcgggtggg tgtacgacac ggtgacggag   1980
gacgtggtca ccgggtaccg gatgcatatc aaggggtggc ggtcacgcta ctgctccatc   2040
tacccacacg ccttcatcgg caccgcaccc atcaacctca cggagaggct cttccaggtg   2100
ctccgctggt ccacgggctc cctcgagatc ttcttctcca gaacaaccc gctcttcggc   2160 agcacctacc tccacccgct gcagcgcgtc gcctacatca acatcaccac ctacccttc   2220 accgccatct tcctcatctt ctacaccacc gtgccggcgc tctccttcgt caccggccac   2280
ttcatcgtgc agcgcccac caccatgttc tacgtctacc tgggcatcgt gctctccacg   2340
ctgctcgtca tcgccgtgct ggaggtcaag tgggccgggg tcaccgtctt cgagtggttc   2400
aggaacggcc agttctggat gacggcaagt tgctccgcct acctcgccgc cgtgtgccag   2460
gtgcttacca aggtgatatt ccggcgtgac atctccttca agctcacatc caagctaccg   2520
tcgggagacg agaagaagga cccctacgcc gacctctacg tggtccgctg gacgccgctg   2580
```

| | |
|---|---:|
| atgatcacac ccatcatcat cattttcgtc aacatcatcg gatccgcggt ggccttcgcc | 2640 |
| aaggtgctgg acggcgagtg gacgcactgg ctcaaggtcg ccggcggggt cttcttcaac | 2700 |
| ttctgggtgc tgttccacct ctacccgttc gccaagggca tcctggggaa gcacggcaag | 2760 |
| acgccagtcg tggtgctcgt ctggtgggca ttcaccttcg tcatcaccgc cgtgctctac | 2820 |
| atcaacatcc cccacatgca tagctcggga ggcaagcaca caacggtgca tggtcaccat | 2880 |
| ggcaagaagt tcgtcgacgc agggtactac aactggccgt gaggtccctg tccactgtcc | 2940 |
| acgactttgc cgccgcgcat ccggacaaga tgacctgaga catgaaacaa caagtcatcc | 3000 |
| actcaacagt gcatgcatca atctgatcga caagcagagc ccgccaaagt ttgcattttt | 3060 |
| taatttttt cttcactttt ttgcccgttt cttttagtt ttgtccagaa aaagatggt | 3120 |
| gttgatttga tttagttctt aattacctgt ggtaat | 3156 |

<210> SEQ ID NO 14
<211> LENGTH: 3193
<212> TYPE: DNA
<213> ORGANISM: artificial
<220> FEATURE:
<223> OTHER INFORMATION: synthetic

<400> SEQUENCE: 14

| | |
|---|---:|
| gcctgagcgt ggagagctac cttgcctgcc tccctgccat tgttcggctt gttctccttg | 60 |
| tcgtaaagga gagtgagtgc gtgcattgag gacgacggcc atggcgccag cggtggccgg | 120 |
| aggaggccgc gtgcggagca acgagccggc tgctgccgct accgcgcccg ccagcgggaa | 180 |
| gccctgcgtc tgcggcttcc agtgtgcgc ctgcacggga tcggccgcgg tggcgtctgc | 240 |
| cgcctcctcg ctcgacatgg acatcgtggc catggggcag ataggcgccg tcaacgacga | 300 |
| gagctgggtg ggcgtggagc tcggcgagga cggcagacc gacgaaagcg gtgccgccgt | 360 |
| tgacgaccgc cccgtcttcc gcaccgagaa aatcaagggt gtcctcctcc acccctaccg | 420 |
| ggtgctgatc ttcgtccgtc tcatcgcctt caccctgttc gtgatctggc gtatttccca | 480 |
| caagaaccct gacgccatgt ggctgtgggt gacatccatc tgcggcgagt tctggttcgg | 540 |
| tttctcctgg ctgctggatc agctccccaa gctgaacccc atcaaccgcg tgccggacct | 600 |
| ggccgtgctg cggcagcgct tcgaccgccc cgacggcacc tccaccctcc cggggctgga | 660 |
| catcttcgtc accacggccg acccccatca aggagcccatc ctctccactg ccaactcggt | 720 |
| gctctccatc ctcgccgccg actaccccgt cgaccgcaac acatgctacg tttctgacga | 780 |
| cagtggcatg ctgctcacct acgaggccct ggctgagtcc tccaagttcg ccaccctctg | 840 |
| ggtgcccttc tgccgcaagc acgggatcga gcccaggggc ccggagagct actttgagct | 900 |
| caagtcccac ccctacatgg ggagagccca ggacgagttc gtgaacgacc gtcgccgcgt | 960 |
| ccgcaaggag tacgacgagt tcaaggccag gatcaacagc ctggagcatg acatcaagca | 1020 |
| gcgcaacgac gggtacaacg ccgccaacg ccaccgggaa ggcgagcccc gacccacctg | 1080 |
| gatggccgac ggcacccagt ggggagggcac ctgggtcgac gcctccgaga accaccgcag | 1140 |
| gggcgaccac gccggcatcg tcctggtgct gctgaaccac ccgagccacc gccggcagac | 1200 |
| gggcccgccg gcgagtgctg acaacccact ggacttcagc ggcgtggatg tgcgtctccc | 1260 |
| catgctggtg tacgtgtccc gtgagaagcg ccccggacac gaccaccaga agaaggccgg | 1320 |
| cgccatgaac gcgctcaccc gcgcctccgc gctgctctcc aactcccct tcatcctcaa | 1380 |
| cctcgactgc gaccactaca tcaacaactc ccaggccctc cgcgccggca tctgcttcat | 1440 |
| ggtgggacgc gacagcgaca ccgtcgcctt cgtccagttc ccgcagcgct tcgagggcgt | 1500 |

```
cgaccccacc gacctctacg ccaaccacaa ccgcatcttc ttcgacggca ccctccgtgc    1560
cctcgacggc atgcagggcc ccatctacgt cggcaccggc tgtctcttcc gccgcatcac    1620
cgtctacggc ttcgacccgc ccaggatcaa cgtcggcggg ccctgcttcc ccaggctcgc    1680
cgggctcttc gccaagacca agtacgagaa gcctgggctc gagatgacca tggccaaggc    1740
caaggctgcg ccggtgcccg ccaagggcaa gcacggcttc ctgcctctgc caagaagac     1800 gtacggcaag tcgacgcct tcgtggacag catcccgcgc cgtcgcacc cgtcgcctta     1860 cgccgcggcg gctgagggca tcgtggccga cgaggcgacc atcgtggagg cggtgaacgt    1920
gacggcggcg gcgttcgaga agaagaccgg gtggggcaaa gagatcggct gggtgtacga    1980
caccgtgacg gaggacgtgg tgaccgggta ccggatgcat atcaagggt ggcggtcacg    2040 ctactgctcc atctacccac acgccttcat cggcaccgca cccatcaacc tcacggagag    2100
gctcttccag gtgcttcgct ggtccacggg ctccctcgag atcttcttct ccaagaacaa    2160
cccgctcttc ggcagcacct acctccaccc gctgcagcgc gtcgcctaca tcaacatcac    2220
cacctacccg ttcaccgcca tcttcctcat cttctacacc accgtgccgg cgctctcctt    2280
cgtcactggc cacttcatcg tgcagcgccc caccaccatg ttctacgtct acctgggcat    2340
cgtgctctcc acgctgctcg tcatcgccgt gctggaggtc aagtgggccg gggtcaccgt    2400
cttcgagtgg ttcaggaacg gccagttctg gatgacggca agttgctccg cctacctcgc    2460
cgccgtgtgc caggtgctca ccaaggtgat attccggcgt gacatctcct tcaagctcac    2520
atccaagcta ccgtcgggag acgagaagaa ggacccctac gccgacctct acgtggtgcg    2580
ctggacgccg ctcatgatca cacccatcat catcattttc gtcaacatca tcgggtcggc    2640
ggtggccttc gccaaggtgc tcgacggcga gtggacgcac tggctcaagg tcgccggcgg    2700
cgtcttcttc aacttctggg tgctcttcca cctctacccg ttcgccaagg gcatcctggg    2760
gaagcacggc aagacgccag tcgtggtgct cgtctggtgg gcattcacct tcgtcatcac    2820
cgccgtgctc tacatcaaca tcccccacat gcatagctcg ggaggcaagc acacaacggt    2880
gcatggtcac catggcaaga agttcgtcga cgcagggtac tacaactggc cgtgaggtcc    2940
ctgttgacga ctttgccgcc gcgcatccgg acaagacaac gacgacctgc gacaagaaac    3000
aacaagtcat ccactgaaca gtgcatgcat ccatctgatc gagaagcaga gcccgccaaa    3060 gttttgcattt tttaattttt ttcttcactt ttttgcccgt ttctttttag ttttgtccag    3120
aaaaaagatg gtgttgattt gatttagttc ttaattacct gtggtaatta attatgtact    3180
taattataca cta                                                      3193
```

<210> SEQ ID NO 15
<211> LENGTH: 3813
<212> TYPE: DNA
<213> ORGANISM: artificial
<220> FEATURE:
<223> OTHER INFORMATION: synthetic

<400> SEQUENCE: 15

```
catggcgcca gcggtggccg gaggaggccg cgtgcggagc aatgagccgg ctgctgccgc      60
ggcgccggcg gccgccagcg ggaagccctg cgtctgcggc ttccaggtgt gcgcctgcac     120
gggatcggcc gcggtggcgt ccgccgcctc ctcgctggac atggacatcg tggccatggg     180
ccagatcggc gccgtcaacg acgagagctg ggtgggcgtg gagctcggcg aagcggcga     240 gaccgacgaa agcggtgtcg ccgttgacga ccgccccgtc ttccgcaccg agaaaatcaa     300
```

```
gggtgtcctt ctccacccct accgggtgct gatcttcgtt cggctgatcg ccttcaccct    360
gttcgtgatc tggcgtatct cccacaagaa ccctgacgcc atgtggctgt gggtgacatc    420
catctgcggc gagttctggt tcggcttctc ctggctgctg gatcagctgc ccaagctgaa    480
ccccatcaac cgcgtgccgg acctggccgt gctgcggcag cgcttcgacc gccccgacgg    540
cacctccacc ctcccggggc tcgacatctt cgtcaccacg gccgacccca tcaaggagcc    600
catcctctcc accgccaact ccgtgctctc catcctcgcc gccgactacc ccgtcgaccg    660
caacacatgc tacgtctctg acgacagtgg catgctgctc acctacgagg ccctggccga    720
gtcctccaag ttcgccaccc tctgggtgcc cttctgccgc aagcacggga tcgagcccag    780
gggcccggag agctacttcg agctcaagtc ccacccctac atggggagag cccaggacga    840
attcgtcaac gaccgccgcc gcgtccgcaa ggagtacgac gagttcaagg ccagaatcaa    900
cagcctggag cacgacatca agcagcgcaa cgacgggtac aacgccgcca acgcccaccg    960
ggaaggcgag ccccgaccca cctggatggc cgacggcacc cagtggcagg gcacctgggt   1020
ggacgcctcc gagaaccacc gcaggggcga ccacgccggc atcgtcctgg tcagtactag   1080
ttgctatact tatcactagg actaccattt acttagggtc tctttcgtcc gtgcatgatg   1140
catgcatgct gctgttcttg gaatcttggt tagttagggc ctcgttatta gtggccatct   1200
gatgtgatgc ctgcctgcac tgcactgctg tgccgatcca agggagattt tgacagaatg   1260
gacgtggtga tggtcgagag tgcaaccacc ggccggccag ccaagcacac ttgtggacag   1320
acatggaaga aaacatgcat gcttctcttc tcgcctcgtc ctgtggccag caacgtgtgg   1380
ttccactcac tcacgctgtg acgaggaatg gtggttgggg tggtcctttc cccccgacag   1440
cactacagcg tccactttat gacccattta attcaattca ccggccctgc tttcttaact   1500
gcctcaatca ttcatcagtt tgtttactct gcccaactct taaccctgta ctgtagtata   1560
cttagtagta ctaataatta attactccaa ccactaatca ccttaaggta gtaatagtaa   1620
cactccagta agaatcattt gaccttttac tatggcgatc gagaagtaaa agtaacagct   1680
aaaattaacc gtgtcattca tttaaccttg ttttttttacc actatctacc taagctcaag   1740
ttgtgattgt actgcaagag gaatggagtg ctgacaatgg tgtgtgtgca atggatgcag   1800
gtgctgctga accacccgag ccaccgccgg cagacgggcc cgccggcgag cgctgacaac   1860
ccactggact tcagcggcgt ggatgtgcgt ctccccatgc tggtgtacgt gtcccgtgag   1920
aagcgccccg acacgaccac cagaagaag gccggcgcca tgaacgcgct cacccgcgcc   1980
tccgcgctgc tctccaactc cccctttcatc ctcaacctcg actgcgacca ttacatcaac   2040
aactcccagg ccctccgcgc cggcatctgc ttcatggtgg gacgcgacag cgacaccgtc   2100
gccttcgtcc agttcccgca gcgcttcgag ggcgtcgacc ccaccgacct ctacgccaac   2160
cacaaccgca tcttcttcga cggcacccctc cgtgccctcg acggcatgca gggccccatc   2220
tacgtcggca ccggctgtct cttccgccgc atcaccgtct acggcttcga cccgcccagg   2280
atcaacgtcg gcgggccctg cttccccagg ctcgccgggc tcttcgccaa gaccaagtac   2340
gagaagcccg gcctcgagat gaccatggcc aaggccaagg ccgcgccggt gcccgccaag   2400
ggcaagcacg gcttcctgcc tctgcccaag aagacgtacg gcaagtcgga cgccttcgtg   2460
gacagcatcc gcgcgcgtc gcacccgtcg ccttacgccg cggcggctga gggcatcgtg   2520
gccgacgagg cgaccatcgt ggaggcggtg aacgtgacgg ccgcggcgtt cgagaagaag   2580
accggctggg gcaaagagat cggctgggtg tacgacaccg tgacggagga cgtggtgacc   2640
gggtaccgga tgcatatcaa ggggtggcgg tcacgctact gctccatcta cccacacgcc   2700
```

```
ttcatcggca ccgcacccat caacctcacg gagaggctct tccaggtgct ccgctggtcc    2760
acgggctccc tcgagatctt cttctccaag aacaacccgc tcttcggcag cacctacctc    2820
cacccgctgc agcgcgtcgc ctacatcaac atcaccacct accccttcac cgccatcttc    2880
ctcatcttct acaccaccgt gccggcgctc tccttcgtca ccggccactt catcgtgcaa    2940
cgccccacca ccatgttcta cgtctacctg gcatcgtgc tctccacgct gctcgtcatc     3000
gccgtgctgg aggtcaagtg ggccggggtc accgtcttcg agtggttcag gaacggccag    3060
ttctggatga cggcaagttg ctccgcctac ctcgccgccg tgtgccaggt gctgaccaag    3120
gtgatattcc ggcgtgacat ctccttcaag ctcacatcca agctaccgtc cggagacgag    3180
aagaaggacc cctacgccga cctgtacgtg gtgcgctgga cgccgctcat gatcacaccc    3240
atcatcatca ttttcgtcaa catcattggg tcggcggtgg ccttcgccaa ggtgctcgac    3300
ggcgagtgga cgcactggct caaggtcgcc ggcggggtct tcttcaactt ctgggtgctg    3360
ttccacctct acccgttcgc caaggggatc ctggggaagc acggcaagac gccagtcgtg    3420
gtgcccgtct ggtgggcatt caccttcgtc atcaccgccg tgctctacat caacatcccc    3480
cacatgcata gctcgggagg caagcacaca acggtgcatg gtcaccatgg caagaagttc    3540
gtcgacgcag ggtactacaa ctggccatga ggtccctgtt gacgactttg ccgccggaca    3600
ggacgacctg agacaagaag caacaagtca tccactgaac agtgcatgca tccatctgat    3660
cgagaagcag agcccgccaa agtttgaatt ttttaatttt ttttcttcac ttttttcgccc    3720 gtttctttt agttttgtcc agaaaaaaga tggtgttgat ttgatttagt tcttaattac     3780
ctgtggtaat taattatgta cttattatac att                                 3813
```

<210> SEQ ID NO 16
<211> LENGTH: 3741
<212> TYPE: DNA
<213> ORGANISM: artificial
<220> FEATURE:
<223> OTHER INFORMATION: synthetic

<400> SEQUENCE: 16

```
gcctgagcgt ggagagctac cttgcctgcc tccctcccat tcttgctgct gctctccttg      60
tcgtaaagga gagtgcgtgc attgaggacc acggccatgg cgccagcggt ggccggagga     120
ggccgcgtgc ggagcaatga gcctgctgct gccgctgcca gcgacaagcc ctgcgtgtgc     180
ggcttccagg tgtgcgcctg cacgggatcg gccgcggtgg cgtccgccgc ctcctcgctg     240
gacatggaca tcgtggccat ggggcagatc ggcgccgtca acgacgagag ctgggtgggc     300
gtggagctcg gcgaggacgg cgagaccgac gaaagcggtg ccgctgttga cgaccgcccc    360
gtcttccgca ccgagaaaat caagggtgtc tcctccacc cctaccgggt gctgatcttc      420
gtccgtctca tcgccttcac cctgttcgtg atctggcgta tctcccacaa gaaccctgac    480
gccatgtggc tgtgggtgac atccatctgc ggcgagttct ggttcggctt ctcctggctg    540
ctggatcagc tccccaagct gaaccccatc aaccgcgtgc cggacctggc cgtgctgcgg    600
cagcgcttcg accgcccga cggcacctcc acgctccctg gctggacat cttcgtcacc     660 acggccgacc ccatcaagga gcccatcctc tccaccgcca actcggtgct ctccatcctc    720
gccgccgact accccgtgga ccgcaacaca tgctacgtct ccgacgacag tggcatgctg    780
ctcacctacg aggccctggc tgagtcctcc aagttcgcca cctctgggt gcccttctgc     840 cgcaagcacg ggattgagcc gaggggcccg gagagctact tcgagctcaa gtcccacccc    900
```

```
tacatgggga gagcccagga cgagttcgtg aacgaccgcc gacgcgtccg caaggagtac    960
gacgagttca aggccaggat caacagcctg gagcatgaca tcaagcagcg caacgacggg   1020
tacaacgccg ccaacgctca ccgggaaggc gagccccgac ccacctggat ggccgacggc   1080
acccagtggg agggcacctg ggtcgacgcc tccgagaacc accgcagggg cgaccacgcc   1140
ggcatcgtcc gggtcagtac ttactattct tattatcact accatttact tactcctact   1200
tactgtctct ttcctactag agtacatgtc tgcatgcatg catgctgctg ttgttggaat   1260
cttggttagt agttagggcc tcgttattag ggcatgtaca atgcatagcc ttaaggtgat   1320
gcctcgcatg ccatgtagga tcggatatga cgtaaagtag gttcgataga aagcgggat    1380 cctctccagg aggcgggtgc ttgaagagaa aatatgtggt ccagtgacaa aagctgaaaa   1440
ggttggagtg aaaaatagag atgcatgtat actagagtct ttattttta ttttttaatg     1500 aggcccacta gtgatagctt gcattgaaga gaaaaaatta atgtagatgc tttaaattac   1560
tttttgtcat gaggcatatg tattcatatg ccaccattgt acatgccctt agtggccatc   1620
tgatgtgatg cctgcctgca ctgctgtgcc gatccaaggg agattttgac agaatggacg   1680
tggtgatagt cgagagtgca accaccggcc ggccagccaa gcacacttgt ggacagagtg   1740
ctgctgaacc cccgagcca ccggcggcag acgggcccgc cggcgagcgc tgacaaccca    1800
ctggacttca gcggcgtgga tgcgcgtctc cccatgctgg tgtacgtttc ccgtgagaag   1860
cgccccggac acgaccacca gaagaaggcc ggcgccatga acgcgctcac ccgcgcctcc   1920
gcgctgctct ccaactcccc cttcatcctc aacctcgact gcgaccatta catcaacaac   1980
tcccaggccc tccgcgccgg catctgcttc atggtgggac cgacagcga caccgtcgcc    2040 ttcgtccagt tcccgcagcg cttcgagggc gtcgacccca ccgacctcta cgccaaccac   2100
aaccgcatct tcttcgacgg caccctccgt gccctcgacg gcatgcaggg ccccatctac   2160
gtcggcaccg ggtgtctctt ccgccgcatc accgtctacg gcttcgaccc gcccaggatc   2220
aacgtcggcg ggccctgctt ccccaggctc gccgggctct tcgccaagac caagtacgag   2280
aagccgagcc tcgagatgac aatggccaag gccaaggccg cgccggtgcc cgccaagggg   2340
aagcacggct tcctgcctct gcccaagaag acgtacggca agtcggacgc cttcgtggac   2400
agcatcccgc gcgcgtcgca cccgtcgcct tacgcggcgg cggctgaggg catcgtggcc   2460
gacgaggcga ccatcgtgga ggcggtgaac gtgacggcgg cggcgttcga gaagaagacc   2520
gggtggggca aagagatcgg gtgggtgtac gacacggtga cggaggacgt ggtcaccggg   2580
taccggatgc atatcaaggg gtggcggtca cgctactgct ccatctaccc acacgccttc   2640
atcggcaccg cacccatcaa cctcacggag aggctcttcc aggtgctccg ctggtccacg   2700 ggctcccctcg agatcttctt ctccaagaac aacccgctct tcggcagcac ctacctccac   2760
ccgctgcagc gcgtcgccta catcaacatc accacctacc ccttcaccgc catcttcctc   2820
atcttctaca ccaccgtgcc ggcgctctcc ttcgtcaccg gccacttcat cgtgcagcgc   2880
cccaccacca tgttctacgt ctacctgggc atcgtgctct ccacgctgct cgtcatcgcc   2940
gtgctggagg tcaagtgggc cggggtcacc gtcttcgagt ggttcaggaa cggccagttc   3000
tggatgacgc aagttgctcc cgcctacctc gccgccgtgt gccaggtgct taccaaggtg   3060
atattccggc gtgacatctc cttcaagctc acatccaagc taccgtcggg agacgagaag   3120 aaggaccccct acgccgacct ctacgtggtc cgctggacgc cgctgatgat cacacccatc   3180
atcatcattt tcgtcaacat catcggatcc gcggtggcct tcgccaaggt gctggacggc   3240
gagtggacgc actggctcaa ggtcgccggc ggggtcttct tcaacttctg ggtgctgttc   3300
```

| | |
|---|---:|
| cacctctacc cgttcgccaa gggcatcctg gggaagcacg gcaagacgcc agtcgtggtg | 3360 |
| ctcgtctggt gggcattcac cttcgtcatc accgccgtgc tctacatcaa catcccccac | 3420 |
| atgcatagct cggaggcaa gcacacaacg gtgcatggtc accatggcaa gaagttcgtc | 3480 |
| gacgcagggt actacaactg gccgtgaggt ccctgtccac tgtccacgac tttgccgccg | 3540 |
| cgcatccgga caagatgacc tgagacatga acaacaagt catccactca acagtgcatg | 3600 |
| catcaatctg atcgacaagc agagcccgcc aaagtttgca ttttttaatt tttttcttca | 3660 |
| cttttttgcc cgtttctttt tagttttgtc cagaaaaaag atggtgttga tttgatttag | 3720 |
| ttcttaatta cctgtggtaa t | 3741 |

<210> SEQ ID NO 17
<211> LENGTH: 5520
<212> TYPE: DNA
<213> ORGANISM: artificial
<220> FEATURE:
<223> OTHER INFORMATION: synthetic

<400> SEQUENCE: 17

| | |
|---|---:|
| gcctgagcgt ggagagctac cttgcctgcc tccctgccat tgttcggctt gttctccttg | 60 |
| tcgtaaagga gagtgagtgc gtgcattgag gacgacggcc atggcgccag cggtggccgg | 120 |
| aggaggccgc gtgcggagca acgagccggc tgctgccgct accgcccccg ccagcgggaa | 180 |
| gccctgcgtc tgcggcttcc aggtgtgcgc ctgcacggga tcggccgcgg tggcgtctgc | 240 |
| cgcctcctcg ctcgacatgg acatcgtggc catggggcag ataggcgccg tcaacgacga | 300 |
| gagctgggtg ggcgtggagc tcggcgagga cggcgagacc gacgaaagcg gtgccgccgt | 360 |
| tgacgaccgc cccgtcttcc gcaccgagaa aatcaagggt gtcctcctcc accccctaccg | 420 |
| gtacgtgcaa ctaaactccc tactatatct gcgtcacagt aacaattacg tatttcatac | 480 |
| ttactgtata agtatttatt attaccactc ttttgcacaa caagtctaaa atgattaagc | 540 |
| caacaagcac aacgccaagg ttgacagtca cgattatttg atcttgaccg gtggcgctag | 600 |
| tactcctagg actagtagta gcatggtctg gtcggtgtta atcacagtaa ttaatggagt | 660 |
| agttaattaa tgtaaacttg gattaaaatt tgacaagtcc gagacaggtg cacgttagag | 720 |
| gcggttcaat gatggctcga atccacccaa aacagcgcgt cccggtgtgg gctgtcggct | 780 |
| cggtgcggcg gggcgctggt tcttccattt tactagtagt cgtagtcact gctgcatggg | 840 |
| cccgcttgag gggacgttag ccgttgggcc tgcctggcag tgggccccgg tggccaccct | 900 |
| ggcggctaat aaatccttgc cactttagag ttaataaaat ctgggtgtgc aatagcaata | 960 |
| ggaatccgag gtgaaacgag atgacagtgg gcatggcttg cacgtgaatc aagccacat | 1020 |
| cattaaaagc ctcgtcgcca tcctccctgg ggacgtcgca gtgagaaagt tggttaaact | 1080 |
| tttggggttg ggacaagata taaaagcaag taacatgtcc tttttttgtca ctggagaaac | 1140 |
| gtatgcatgt atgtatggta tggtagtata tgagattttt cggcatctag tctagttata | 1200 |
| gatggagcct gtagtacgtt agttttttgtt cagccgtttt attggagaaa acgagaagaa | 1260 |
| gattatcatg ccatatcgtg tcatagaaag gaggagaaga aaagaagtg gtgccaccgc | 1320 |
| atgaatgcct ttttcccag aagaatgcgt gagtcatgtt ggcaccgaga aaagccatat | 1380 |
| taaagtggca gagttacaac tcagaagaaa tgcgcgtgct agataaacac tactagcata | 1440 |
| tgtcaagtgc actcggcaca acatcttcaa agtactgcaa agattaacaa gaaaaagatt | 1500 |
| actactactc caaagtacta ctcctactag tagtaacgat tagcaggaga aggttccaac | 1560 |

```
gactttttgg cgccaatagc ataaataaat aagaagaaga aaacttaacg agaaagagg   1620
cccattaatg gagcaaggaa tccagcggca ccacctctgg cggtcgcgtc catgccctcg   1680
tacgacgggt gagggagggg cccgggccta ctgacagccg aggcatgtcg gtgctcatac   1740
acggcgccgt ttgctgccaa gtgtgccagc tcacactcat tgacttgcca gcacccgcct   1800
tggctgtcaa tgcgaacatg atgcccttcc ctctcgcctt ttggcatttg caaaaaaatt   1860
aaaactagct gtctgatagg gaaaagaaat gcaaagggaa aagatgaaca tggcgcatgt   1920
tccctccaat aattgcaccc aatcatcgca ccaacatagc cagcactcga ttaatccaaa   1980
caattttac taagagtgag ttgatgatga actgtaactg acggtgaatg tgaataatgc    2040
aatgcagggt gctgatcttc gtccgtctca tcgccttcac cctgttcgtg atctggcgta   2100
tttcccacaa gaaccctgac gccatgtggc tgtgggtgac atccatctgc ggcgagttct   2160
ggttcggttt ctcctggctg ctggatcagc tccccaagct gaacccatc aaccgcgtgc    2220
cggacctggc cgtgctgcgg cagcgcttcg accgccccga cggcacctcc accctcccgg   2280
ggctggacat cttcgtcacc acggccgacc ccatcaagga gccatcctc tccactgcca    2340
actcggtgct ctccatcctc gccgccgact acccgtcga ccgcaacaca tgctacgttt    2400
ctgacgacag tggcatgctg ctcacctacg aggccctggc tgagtcctcc aagttcgcca   2460
ccctctgggt gcccttctgc cgcaagcacg ggatcgagcc caggggcccg gagagctact   2520
ttgagctcaa gtcccacccc tacatgggga gagcccagga cgagttcgtg aacgaccgtc   2580
gccgcgtccg caaggagtac gacgagttca aggccaggat caacagcctg gagcatgaca   2640
tcaagcagcg caacgacggg tacaacgccg ccaacgccca ccgggaaggc gagccccgac   2700
ccacctggat ggccgacggc acccagtggg agggcacctg ggtcgacgcc tccgagaacc   2760
accgcagggg cgaccacgcc ggcatcgtcc tggtcagtac tagctattct tatcactacc   2820
gtttactcct acttactgtt tctttcctac tacatgtctg cattgcatgc atgcatgctg   2880
ctgttcttgg aatcttggtt agttaggccc tcgttattag tggccatctg atgtgatgcc   2940
tgcctgcact gctgtgccga tccaagggag attttgacag aatggacgtg gtgatagtcg   3000
agagtgcaac caccggccgg ccagccaagc acacttgtgg acagacatgc aagaaaacat   3060
gcatgctcct cttctcgcgt cgtcctgtgg ccagcaacgt gtggttccac tcattcatgc   3120
cgtgacgagg aatggtggtt gggtggtcc tttcccccg acagcactac agcgtccact     3180
ttatgaccca tttaattcaa ttcaccggcc ctgctttctt aactgcctca atcattcatc   3240
agtttactct gcccaactct taaccctgta tagtagtaat aattaattac tccaaccact   3300
aatcaccta aggtaatagt aacactccag taagaatcat ttgaccttt actatggagc     3360
agcgaaaatt aaccatgtca ttcattaac cttgttttt taccactact gtatctacct     3420
atgctcaagt tgtgattgta ctagtgcaag aggaatggag tgctgacaat ggtgtctgtg   3480
caatggatgc aggtgctgct gaaccacccg agccaccgcc ggcagacggg cccgccggcg   3540
agtgctgaca acccactgga cttcagcggc gtggatgtgc gtctccccat gctggtgtac   3600
gtgtcccgtg agaagcgccc cggacacgac caccagaaga aggccggcgc catgaacgcg   3660
ctcaccgcg cctccgcgct gctctccaac tccccttca tcctcaacct cgactgcgac    3720
cactacatca acaactccca ggccctccgc gccggcatct gcttcatggt gggacgcgac   3780
agcgacaccg tcgccttcgt ccagttcccg cagcgcttcg agggcgtcga ccccaccgac   3840
ctctacgcca accacaaccg catcttcttc gacggcaccc tccgtgccct cgacggcatg   3900
cagggcccca tctacgtcgg caccggctgt ctcttccgcc gcatcaccgt ctacggcttc   3960
```

-continued

```
gacccgccca ggatcaacgt cggcgggccc tgcttcccca ggctcgccgg gctcttcgcc    4020
aagaccaagt acgagaagcc tgggctcgag atgaccatgg ccaaggccaa ggctgcgccg    4080
gtgcccgcca agggcaagca cggcttcctg cctctgccca gaagacgta cggcaagtcg     4140
gacgccttcg tggacagcat cccgcgcgcg tcgcacccgt cgccttacgc cgcggcggct    4200
gagggcatcg tggccgacga ggcgaccatc gtggaggcgg tgaacgtgac ggcggcggcg    4260
ttcgagaaga gaccgggtg gggcaaagag atcggctggg tgtacgacac cgtgacggag     4320
gacgtggtga ccgggtaccg gatgcatatc aaggggtggc ggtcacgcta ctgctccatc    4380
tacccacacg ccttcatcgg caccgcaccc atcaacctca cggagaggct cttccaggtg    4440
cttcgctggt ccacgggctc cctcgagatc ttcttctcca gaacaaccc gctcttcggc     4500
agcacctacc tccacccgct gcagcgcgtc gcctacatca acatcaccac ctacccgttc    4560
accgccatct tcctcatctt ctacaccacc gtgccggcgc tctccttcgt cactggccac    4620
ttcatcgtgc agcgccccac caccatgttc tacgtctacc tgggcatcgt gctctccacg    4680
ctgctcgtca tcgccgtgct ggaggtcaag tgggccgggg tcaccgtctt cgagtggttc    4740
aggaacggcc agttctggat gacggcaagt tgctccgcct acctcgccgc cgtgtgccag    4800
gtgctcacca aggtgatatt ccggcgtgac atctccttca agctcacatc caagctaccg    4860
tcgggagacg agaagaagga ccctacgcc gacctctacg tggtgcgctg gacgccgctc    4920
atgatcacac ccatcatcat catttcgtc aacatcatcg ggtcggcggt ggccttcgcc    4980
aaggtgctcg acggcgagtg gacgcactgg ctcaaggtcg ccggcggcgt cttcttcaac    5040
ttctgggtgc tcttccacct ctacccgttc gccaagggca tcctggggaa gcacggcaag    5100
acgccagtcg tggtgctcgt ctggtgggca ttcaccttcg tcatcaccgc cgtgctctac    5160
atcaacatcc cccacatgca tagctcggga ggcaagcaca caacggtgca tggtcaccat    5220
ggcaagaagt tcgtcgacgc agggtactac aactggccgt gaggtccctg ttgacgactt    5280
tgccgccgcg catccggaca agacaacgac gacctgcgac aagaaacaac aagtcatcca    5340
ctgaacagtg catgcatcca tctgatcgag aagcagagcc cgccaaagtt tgcatttttt    5400
aatttttttc ttcacttttt tgcccgtttc tttttagttt tgtccagaaa aaagatggtg    5460
ttgatttgat ttagttctta attacctgtg gtaattaatt atgtacttaa ttatacacta    5520
```

<210> SEQ ID NO 18
<211> LENGTH: 945
<212> TYPE: PRT
<213> ORGANISM: Triticum aestivum
<400> SEQUENCE: 18

```
Met Ala Pro Ala Val Ala Gly Gly Gly Arg Val Arg Ser Asn Glu Pro
1               5                   10                  15

Ala Ala Ala Ala Ala Pro Ala Ala Ala Ser Gly Lys Pro Cys Val Cys
            20                  25                  30

Gly Phe Gln Val Cys Ala Cys Thr Gly Ser Ala Ala Val Ala Ser Ala
        35                  40                  45

Ala Ser Ser Leu Asp Met Asp Ile Val Ala Met Gly Gln Ile Gly Ala
    50                  55                  60

Val Asn Asp Glu Ser Trp Val Gly Val Glu Leu Gly Glu Asp Gly Glu
65                  70                  75                  80

Thr Asp Glu Ser Gly Val Ala Val Asp Asp Arg Pro Val Phe Arg Thr
                85                  90                  95
```

```
Glu Lys Ile Lys Gly Val Leu Leu His Pro Tyr Arg Val Leu Ile Phe
            100                 105                 110

Val Arg Leu Ile Ala Phe Thr Leu Phe Val Ile Trp Arg Ile Ser His
        115                 120                 125

Lys Asn Pro Asp Ala Met Trp Leu Trp Val Thr Ser Ile Cys Gly Glu
    130                 135                 140

Phe Trp Phe Gly Phe Ser Trp Leu Leu Asp Gln Leu Pro Lys Leu Asn
145                 150                 155                 160

Pro Ile Asn Arg Val Pro Asp Leu Ala Val Leu Arg Gln Arg Phe Asp
                165                 170                 175

Arg Pro Asp Gly Thr Ser Thr Leu Pro Gly Leu Asp Ile Phe Val Thr
            180                 185                 190

Thr Ala Asp Pro Ile Lys Glu Pro Ile Leu Ser Thr Ala Asn Ser Val
        195                 200                 205

Leu Ser Ile Leu Ala Ala Asp Tyr Pro Val Asp Arg Asn Thr Cys Tyr
    210                 215                 220

Val Ser Asp Asp Ser Gly Met Leu Leu Thr Tyr Glu Ala Leu Ala Glu
225                 230                 235                 240

Ser Ser Lys Phe Ala Thr Leu Trp Val Pro Phe Cys Arg Lys His Gly
                245                 250                 255

Ile Glu Pro Arg Gly Pro Glu Ser Tyr Phe Glu Leu Lys Ser His Pro
            260                 265                 270

Tyr Met Gly Arg Ala Gln Asp Glu Phe Val Asn Asp Arg Arg Val
        275                 280                 285

Arg Lys Glu Tyr Asp Glu Phe Lys Ala Arg Ile Asn Ser Leu Glu His
    290                 295                 300

Asp Ile Lys Gln Arg Asn Asp Gly Tyr Asn Ala Ala Asn Ala His Arg
305                 310                 315                 320

Glu Gly Glu Pro Arg Pro Thr Trp Met Ala Asp Gly Thr Gln Trp Gln
                325                 330                 335

Gly Thr Trp Val Asp Ala Ser Glu Asn His Arg Arg Gly Asp His Ala
            340                 345                 350

Gly Ile Val Leu Val Leu Asn His Pro Ser His Arg Arg Gln Thr
        355                 360                 365

Gly Pro Pro Ala Ser Ala Asp Asn Pro Leu Asp Phe Ser Gly Val Asp
370                 375                 380

Val Arg Leu Pro Met Leu Val Tyr Val Ser Arg Glu Lys Arg Pro Gly
385                 390                 395                 400

His Asp His Gln Lys Lys Ala Gly Ala Met Asn Ala Leu Thr Arg Ala
                405                 410                 415

Ser Ala Leu Leu Ser Asn Ser Pro Phe Ile Leu Asn Leu Asp Cys Asp
            420                 425                 430

His Tyr Ile Asn Asn Ser Gln Ala Leu Arg Ala Gly Ile Cys Phe Met
        435                 440                 445

Val Gly Arg Asp Ser Asp Thr Val Ala Phe Val Gln Phe Pro Gln Arg
    450                 455                 460

Phe Glu Gly Val Asp Pro Thr Asp Leu Tyr Ala Asn His Asn Arg Ile
465                 470                 475                 480

Phe Phe Asp Gly Thr Leu Arg Ala Leu Asp Gly Met Gln Gly Pro Ile
                485                 490                 495

Tyr Val Gly Thr Gly Cys Leu Phe Arg Arg Ile Thr Val Tyr Gly Phe
            500                 505                 510

Asp Pro Pro Arg Ile Asn Val Gly Gly Pro Cys Phe Pro Arg Leu Ala
```

```
            515                 520                 525
Gly Leu Phe Ala Lys Thr Lys Tyr Glu Lys Pro Gly Leu Glu Met Thr
530                 535                 540

Met Ala Lys Ala Lys Ala Ala Pro Val Pro Ala Lys Gly Lys His Gly
545                 550                 555                 560

Phe Leu Pro Leu Pro Lys Lys Thr Tyr Gly Lys Ser Asp Ala Phe Val
                565                 570                 575

Asp Ser Ile Pro Arg Ala Ser His Pro Ser Pro Tyr Ala Ala Ala Ala
                580                 585                 590

Glu Gly Ile Val Ala Asp Glu Ala Thr Ile Val Glu Ala Val Asn Val
            595                 600                 605

Thr Ala Ala Ala Phe Glu Lys Lys Thr Gly Trp Gly Lys Glu Ile Gly
610                 615                 620

Trp Val Tyr Asp Thr Val Thr Glu Asp Val Val Thr Gly Tyr Arg Met
625                 630                 635                 640

His Ile Lys Gly Trp Arg Ser Arg Tyr Cys Ser Ile Tyr Pro His Ala
                645                 650                 655

Phe Ile Gly Thr Ala Pro Ile Asn Leu Thr Glu Arg Leu Phe Gln Val
                660                 665                 670

Leu Arg Trp Ser Thr Gly Ser Leu Glu Ile Phe Phe Ser Lys Asn Asn
            675                 680                 685

Pro Leu Phe Gly Ser Thr Tyr Leu His Pro Leu Gln Arg Val Ala Tyr
690                 695                 700

Ile Asn Ile Thr Thr Tyr Pro Phe Thr Ala Ile Phe Leu Ile Phe Tyr
705                 710                 715                 720

Thr Thr Val Pro Ala Leu Ser Phe Val Thr Gly His Phe Ile Val Gln
                725                 730                 735

Arg Pro Thr Thr Met Phe Tyr Val Tyr Leu Gly Ile Val Leu Ser Thr
                740                 745                 750

Leu Leu Val Ile Ala Val Leu Glu Val Lys Trp Ala Gly Val Thr Val
            755                 760                 765

Phe Glu Trp Phe Arg Asn Gly Gln Phe Trp Met Thr Ala Ser Cys Ser
770                 775                 780

Ala Tyr Leu Ala Ala Val Cys Gln Val Leu Thr Lys Val Ile Phe Arg
785                 790                 795                 800

Arg Asp Ile Ser Phe Lys Leu Thr Ser Lys Leu Pro Ser Gly Asp Glu
                805                 810                 815

Lys Lys Asp Pro Tyr Ala Asp Leu Tyr Val Val Arg Trp Thr Pro Leu
                820                 825                 830

Met Ile Thr Pro Ile Ile Ile Phe Val Asn Ile Ile Gly Ser Ala
            835                 840                 845

Val Ala Phe Ala Lys Val Leu Asp Gly Glu Trp Thr His Trp Leu Lys
850                 855                 860

Val Ala Gly Gly Val Phe Phe Asn Phe Trp Val Leu Phe His Leu Tyr
865                 870                 875                 880

Pro Phe Ala Lys Gly Ile Leu Gly Lys His Gly Lys Thr Pro Val Val
                885                 890                 895

Val Pro Val Trp Trp Ala Phe Thr Phe Val Ile Thr Ala Val Leu Tyr
                900                 905                 910

Ile Asn Ile Pro His Met His Ser Ser Gly Gly Lys His Thr Thr Val
            915                 920                 925

His Gly His His Gly Lys Lys Phe Val Asp Ala Gly Tyr Tyr Asn Trp
930                 935                 940
```

```
Pro
945

<210> SEQ ID NO 19
<211> LENGTH: 941
<212> TYPE: PRT
<213> ORGANISM: Triticum aestivum

<400> SEQUENCE: 19

Met Ala Pro Ala Val Ala Gly Gly Arg Val Arg Ser Asn Glu Pro
1               5                   10                  15

Ala Ala Ala Ala Ala Ser Asp Lys Pro Cys Val Cys Gly Phe Gln Val
                20                  25                  30

Cys Ala Cys Thr Gly Ser Ala Ala Val Ala Ser Ala Ala Ser Ser Leu
            35                  40                  45

Asp Met Asp Ile Val Ala Met Gly Gln Ile Gly Ala Val Asn Asp Glu
        50                  55                  60

Ser Trp Val Gly Val Glu Leu Gly Glu Asp Gly Glu Thr Asp Glu Ser
65                  70                  75                  80

Gly Ala Ala Val Asp Asp Arg Pro Val Phe Arg Thr Glu Lys Ile Lys
                85                  90                  95

Gly Val Leu Leu His Pro Tyr Arg Val Leu Ile Phe Val Arg Leu Ile
            100                 105                 110

Ala Phe Thr Leu Phe Val Ile Trp Arg Ile Ser His Lys Asn Pro Asp
        115                 120                 125

Ala Met Trp Leu Trp Val Thr Ser Ile Cys Gly Glu Phe Trp Phe Gly
    130                 135                 140

Phe Ser Trp Leu Leu Asp Gln Leu Pro Lys Leu Asn Pro Ile Asn Arg
145                 150                 155                 160

Val Pro Asp Leu Ala Val Leu Arg Gln Arg Phe Asp Arg Pro Asp Gly
                165                 170                 175

Thr Ser Thr Leu Pro Gly Leu Asp Ile Phe Val Thr Thr Ala Asp Pro
            180                 185                 190

Ile Lys Glu Pro Ile Leu Ser Thr Ala Asn Ser Val Leu Ser Ile Leu
        195                 200                 205

Ala Ala Asp Tyr Pro Val Asp Arg Asn Thr Cys Tyr Val Ser Asp Asp
    210                 215                 220

Ser Gly Met Leu Leu Thr Tyr Glu Ala Leu Ala Glu Ser Ser Lys Phe
225                 230                 235                 240

Ala Thr Leu Trp Val Pro Phe Cys Arg Lys His Gly Ile Glu Pro Arg
                245                 250                 255

Gly Pro Glu Ser Tyr Phe Glu Leu Lys Ser His Pro Tyr Met Gly Arg
            260                 265                 270

Ala Gln Asp Glu Phe Val Asn Asp Arg Arg Val Arg Lys Glu Tyr
        275                 280                 285

Asp Glu Phe Lys Ala Arg Ile Asn Ser Leu Glu His Asp Ile Lys Gln
    290                 295                 300

Arg Asn Asp Gly Tyr Asn Ala Ala Asn Ala His Arg Glu Gly Glu Pro
305                 310                 315                 320

Arg Pro Thr Trp Met Ala Asp Gly Thr Gln Trp Glu Gly Thr Trp Val
                325                 330                 335

Asp Ala Ser Glu Asn His Arg Arg Gly Asp His Ala Gly Ile Val Arg
            340                 345                 350

Val Leu Leu Asn His Pro Ser His Arg Arg Gln Thr Gly Pro Pro Ala
```

```
              355                 360                 365
Ser Ala Asp Asn Pro Leu Asp Phe Ser Gly Val Asp Ala Arg Leu Pro
    370                 375                 380
Met Leu Val Tyr Val Ser Arg Glu Lys Arg Pro Gly His Asp His Gln
385                 390                 395                 400
Lys Lys Ala Gly Ala Met Asn Ala Leu Thr Arg Ala Ser Ala Leu Leu
                405                 410                 415
Ser Asn Ser Pro Phe Ile Leu Asn Leu Asp Cys Asp His Tyr Ile Asn
            420                 425                 430
Asn Ser Gln Ala Leu Arg Ala Gly Ile Cys Phe Met Val Gly Arg Asp
        435                 440                 445
Ser Asp Thr Val Ala Phe Val Gln Phe Pro Gln Arg Phe Glu Gly Val
    450                 455                 460
Asp Pro Thr Asp Leu Tyr Ala Asn His Asn Arg Ile Phe Phe Asp Gly
465                 470                 475                 480
Thr Leu Arg Ala Leu Asp Gly Met Gln Gly Pro Ile Tyr Val Gly Thr
                485                 490                 495
Gly Cys Leu Phe Arg Arg Ile Thr Val Tyr Gly Phe Asp Pro Pro Arg
            500                 505                 510
Ile Asn Val Gly Gly Pro Cys Phe Pro Arg Leu Ala Gly Leu Phe Ala
        515                 520                 525
Lys Thr Lys Tyr Glu Lys Pro Ser Leu Glu Met Thr Met Ala Lys Ala
    530                 535                 540
Lys Ala Ala Pro Val Pro Ala Lys Gly Lys His Gly Phe Leu Pro Leu
545                 550                 555                 560
Pro Lys Lys Thr Tyr Gly Lys Ser Asp Ala Phe Val Asp Ser Ile Pro
                565                 570                 575
Arg Ala Ser His Pro Ser Pro Tyr Ala Ala Ala Glu Gly Ile Val
            580                 585                 590
Ala Asp Glu Ala Thr Ile Val Glu Ala Val Asn Val Thr Ala Ala Ala
        595                 600                 605
Phe Glu Lys Lys Thr Gly Trp Gly Lys Glu Ile Gly Trp Val Tyr Asp
    610                 615                 620
Thr Val Thr Glu Asp Val Val Thr Gly Tyr Arg Met His Ile Lys Gly
625                 630                 635                 640
Trp Arg Ser Arg Tyr Cys Ser Ile Tyr Pro His Ala Phe Ile Gly Thr
                645                 650                 655
Ala Pro Ile Asn Leu Thr Glu Arg Leu Phe Gln Val Leu Arg Trp Ser
            660                 665                 670
Thr Gly Ser Leu Glu Ile Phe Phe Ser Lys Asn Asn Pro Leu Phe Gly
        675                 680                 685
Ser Thr Tyr Leu His Pro Leu Gln Arg Val Ala Tyr Ile Asn Ile Thr
    690                 695                 700
Thr Tyr Pro Phe Thr Ala Ile Phe Leu Ile Phe Tyr Thr Thr Val Pro
705                 710                 715                 720
Ala Leu Ser Phe Val Thr Gly His Phe Ile Val Gln Arg Pro Thr Thr
                725                 730                 735
Met Phe Tyr Val Tyr Leu Gly Ile Val Leu Ser Thr Leu Leu Val Ile
            740                 745                 750
Ala Val Leu Glu Val Lys Trp Ala Gly Val Thr Val Phe Glu Trp Phe
        755                 760                 765
Arg Asn Gly Gln Phe Trp Met Thr Ala Ser Cys Ser Ala Tyr Leu Ala
    770                 775                 780
```

```
Ala Val Cys Gln Val Leu Thr Lys Val Ile Phe Arg Arg Asp Ile Ser
785                 790                 795                 800

Phe Lys Leu Thr Ser Lys Leu Pro Ser Gly Asp Glu Lys Lys Asp Pro
            805                 810                 815

Tyr Ala Asp Leu Tyr Val Val Arg Trp Thr Pro Leu Met Ile Thr Pro
        820                 825                 830

Ile Ile Ile Ile Phe Val Asn Ile Ile Gly Ser Ala Val Ala Phe Ala
            835                 840                 845

Lys Val Leu Asp Gly Glu Trp Thr His Trp Leu Lys Val Ala Gly Gly
        850                 855                 860

Val Phe Phe Asn Phe Trp Val Leu Phe His Leu Tyr Pro Phe Ala Lys
865                 870                 875                 880

Gly Ile Leu Gly Lys His Gly Lys Thr Pro Val Val Leu Val Trp
                885                 890                 895

Trp Ala Phe Thr Phe Val Ile Thr Ala Val Leu Tyr Ile Asn Ile Pro
                900                 905                 910

His Met His Ser Ser Gly Gly Lys His Thr Thr Val His Gly His His
                915                 920                 925

Gly Lys Lys Phe Val Asp Ala Gly Tyr Tyr Asn Trp Pro
    930                 935                 940

<210> SEQ ID NO 20
<211> LENGTH: 944
<212> TYPE: PRT
<213> ORGANISM: Triticum aestivum

<400> SEQUENCE: 20

Met Ala Pro Ala Val Ala Gly Gly Gly Arg Val Arg Ser Asn Glu Pro
1               5                   10                  15

Ala Ala Ala Ala Thr Ala Pro Ala Ser Gly Lys Pro Cys Val Cys Gly
            20                  25                  30

Phe Gln Val Cys Ala Cys Thr Gly Ser Ala Ala Val Ala Ser Ala Ala
        35                  40                  45

Ser Ser Leu Asp Met Asp Ile Val Ala Met Gly Gln Ile Gly Ala Val
50                  55                  60

Asn Asp Glu Ser Trp Val Gly Val Glu Leu Gly Glu Asp Gly Glu Thr
65                  70                  75                  80

Asp Glu Ser Gly Ala Ala Val Asp Asp Arg Pro Val Phe Arg Thr Glu
                85                  90                  95

Lys Ile Lys Gly Val Leu Leu His Pro Tyr Arg Val Leu Ile Phe Val
            100                 105                 110

Arg Leu Ile Ala Phe Thr Leu Phe Val Ile Trp Arg Ile Ser His Lys
        115                 120                 125

Asn Pro Asp Ala Met Trp Leu Trp Val Thr Ser Ile Cys Gly Glu Phe
    130                 135                 140

Trp Phe Gly Phe Ser Trp Leu Leu Asp Gln Leu Pro Lys Leu Asn Pro
145                 150                 155                 160

Ile Asn Arg Val Pro Asp Leu Ala Val Leu Arg Gln Arg Phe Asp Arg
                165                 170                 175

Pro Asp Gly Thr Ser Thr Leu Pro Gly Leu Asp Ile Phe Val Thr Thr
            180                 185                 190

Ala Asp Pro Ile Lys Glu Pro Ile Leu Ser Thr Ala Asn Ser Val Leu
        195                 200                 205

Ser Ile Leu Ala Ala Asp Tyr Pro Val Asp Arg Asn Thr Cys Tyr Val
```

-continued

```
                210                 215                 220
Ser Asp Asp Ser Gly Met Leu Leu Thr Tyr Glu Ala Leu Ala Glu Ser
225                 230                 235                 240

Ser Lys Phe Ala Thr Leu Trp Val Pro Phe Cys Arg Lys His Gly Ile
                245                 250                 255

Glu Pro Arg Gly Pro Glu Ser Tyr Phe Glu Leu Lys Ser His Pro Tyr
                260                 265                 270

Met Gly Arg Ala Gln Asp Glu Phe Val Asn Asp Arg Arg Val Arg
                275                 280                 285

Lys Glu Tyr Asp Glu Phe Lys Ala Arg Ile Asn Ser Leu Glu His Asp
    290                 295                 300

Ile Lys Gln Arg Asn Asp Gly Tyr Asn Ala Ala Asn Ala His Arg Glu
305                 310                 315                 320

Gly Glu Pro Arg Pro Thr Trp Met Ala Asp Gly Thr Gln Trp Glu Gly
                325                 330                 335

Thr Trp Val Asp Ala Ser Glu Asn His Arg Arg Gly Asp His Ala Gly
                340                 345                 350

Ile Val Leu Val Leu Leu Asn His Pro Ser His Arg Arg Gln Thr Gly
                355                 360                 365

Pro Pro Ala Ser Ala Asp Asn Pro Leu Asp Phe Ser Gly Val Asp Val
370                 375                 380

Arg Leu Pro Met Leu Val Tyr Val Ser Arg Glu Lys Arg Pro Gly His
385                 390                 395                 400

Asp His Gln Lys Lys Ala Gly Ala Met Asn Ala Leu Thr Arg Ala Ser
                405                 410                 415

Ala Leu Leu Ser Asn Ser Pro Phe Ile Leu Asn Leu Asp Cys Asp His
                420                 425                 430

Tyr Ile Asn Asn Ser Gln Ala Leu Arg Ala Gly Ile Cys Phe Met Val
                435                 440                 445

Gly Arg Asp Ser Asp Thr Val Ala Phe Val Gln Phe Pro Gln Arg Phe
450                 455                 460

Glu Gly Val Asp Pro Thr Asp Leu Tyr Ala Asn His Asn Arg Ile Phe
465                 470                 475                 480

Phe Asp Gly Thr Leu Arg Ala Leu Asp Gly Met Gln Gly Pro Ile Tyr
                485                 490                 495

Val Gly Thr Gly Cys Leu Phe Arg Arg Ile Thr Val Tyr Gly Phe Asp
                500                 505                 510

Pro Pro Arg Ile Asn Val Gly Gly Pro Cys Phe Pro Arg Leu Ala Gly
                515                 520                 525

Leu Phe Ala Lys Thr Lys Tyr Glu Lys Pro Gly Leu Glu Met Thr Met
530                 535                 540

Ala Lys Ala Lys Ala Pro Val Pro Ala Lys Gly Lys His Gly Phe
545                 550                 555                 560

Leu Pro Leu Pro Lys Lys Thr Tyr Gly Lys Ser Asp Ala Phe Val Asp
                565                 570                 575

Ser Ile Pro Arg Ala Ser His Pro Ser Pro Tyr Ala Ala Ala Glu
                580                 585                 590

Gly Ile Val Ala Asp Glu Ala Thr Ile Val Glu Ala Val Asn Val Thr
                595                 600                 605

Ala Ala Ala Phe Glu Lys Lys Thr Gly Trp Gly Lys Glu Ile Gly Trp
                610                 615                 620

Val Tyr Asp Thr Val Thr Glu Asp Val Val Thr Gly Tyr Arg Met His
625                 630                 635                 640
```

Ile Lys Gly Trp Arg Ser Arg Tyr Cys Ser Ile Tyr Pro His Ala Phe
            645                 650                 655

Ile Gly Thr Ala Pro Ile Asn Leu Thr Glu Arg Leu Phe Gln Val Leu
        660                 665                 670

Arg Trp Ser Thr Gly Ser Leu Glu Ile Phe Ser Lys Asn Asn Pro
    675                 680                 685

Leu Phe Gly Ser Thr Tyr Leu His Pro Leu Gln Arg Val Ala Tyr Ile
    690                 695                 700

Asn Ile Thr Thr Tyr Pro Phe Thr Ala Ile Phe Leu Ile Phe Tyr Thr
705                 710                 715                 720

Thr Val Pro Ala Leu Ser Phe Val Thr Gly His Phe Ile Val Gln Arg
                725                 730                 735

Pro Thr Thr Met Phe Tyr Val Tyr Leu Gly Ile Val Leu Ser Thr Leu
                740                 745                 750

Leu Val Ile Ala Val Leu Glu Val Lys Trp Ala Gly Val Thr Val Phe
            755                 760                 765

Glu Trp Phe Arg Asn Gly Gln Phe Trp Met Thr Ala Ser Cys Ser Ala
770                 775                 780

Tyr Leu Ala Ala Val Cys Gln Val Leu Thr Lys Val Ile Phe Arg Arg
785                 790                 795                 800

Asp Ile Ser Phe Lys Leu Thr Ser Lys Leu Pro Ser Gly Asp Glu Lys
                805                 810                 815

Lys Asp Pro Tyr Ala Asp Leu Tyr Val Val Arg Trp Thr Pro Leu Met
            820                 825                 830

Ile Thr Pro Ile Ile Ile Ile Phe Val Asn Ile Ile Gly Ser Ala Val
            835                 840                 845

Ala Phe Ala Lys Val Leu Asp Gly Glu Trp Thr His Trp Leu Lys Val
850                 855                 860

Ala Gly Gly Val Phe Phe Asn Phe Trp Val Leu Phe His Leu Tyr Pro
865                 870                 875                 880

Phe Ala Lys Gly Ile Leu Gly Lys His Gly Lys Thr Pro Val Val Val
                885                 890                 895

Leu Val Trp Trp Ala Phe Thr Phe Val Ile Thr Ala Val Leu Tyr Ile
            900                 905                 910

Asn Ile Pro His Met His Ser Ser Gly Gly Lys His Thr Thr Val His
            915                 920                 925

Gly His His Gly Lys Lys Phe Val Asp Ala Gly Tyr Tyr Asn Trp Pro
930                 935                 940

<210> SEQ ID NO 21
<211> LENGTH: 2444
<212> TYPE: DNA
<213> ORGANISM: artificial
<220> FEATURE:
<223> OTHER INFORMATION: synthetic

<400> SEQUENCE: 21
cagtgggagc atgtcaatga catatatcac caagaagcat gactatgctg caaccttgga      60
tgagaaggag ccgtccgagg atcagaagcc ggccagtgtc aagaacctgc ttgttcggac     120
cacgaaactt accacggtta ccatcaagtt gtacaggctc atggtatttg ttcggctgac     180
catcttcgtg ctgttcttca aatggcgagt cagcactgct cttacagtga tcagcgacgg     240
cacaactaca gctcgtgcaa tgtggaccat gtccatcgcc ggcgagctct ggttcgccct     300
gatgtgggtg ctggaccagc tgcccaagat gcagcctgtc cggcgcaccg tctacgtcac     360

```
ggcgctcgag gagccgcggc ttccgaccat ggatgtattt gtcaccacca ccgatcccga    420
gaaggagccg ccgctggtga ccgtgaacac tatcctctcc atcctcgccg cggactaccc    480
cccagacaaa ctcacgtgct acgtctcaga cgacggcggc gctctgctca cgcgcgaggc    540
ggtggcgcac gctgcctgct cgccagact gtgggtgccg ttctgccgga agcacggggt    600
cgagccgagg aacccagagg cctacttctg ccccggcgtc aaggcgaggg tggtgtcaag    660
ggctgactat atgggaaggt cgtggccgga gctggcacgg gaccggaggc gtgtgcgccg    720
ggagtacgaa gaactgcggc tgcggatcga cgcgctccac gccggagacg tgcggccaca    780
gcaatggtcg cgcggcacgg cggaaaatca tgccggagtt gttgaagtgc tagtcggtcc    840
tccgggcagt acgccagagc tcggcgtcag tgatcttctg gacctcagct ccgtcgacgt    900
gcgtgttcca gcggtcgtgt acatgtgccg ggagaagcgc cacggccgcg tgcaccaccg    960
gaaggcaggt gccatgaacg cgctgctccg cacctcggcc gtgctctcca acgcgccctt   1020
catcctcaac ctcgactgcg accactacgt caacaactcg caggccctcc gcgccggcgt   1080
ctgcctcatg ctcgaccgcg gcggcagcaa cgtggcgttc gtccagttcc gcagcgctt    1140 cgacggcgtc gaccccgccg accggtacgc caaccacaac cgcgtcttct tcgactgcac   1200
ggagctcggc ctcgacggcc tccagggacc catttacgtg ggcaccggct gcatgtttcg   1260
ccgtgcggcg ctatacaacg ccgacccgcc actctggaga ccacatggtg gtgaccgcga   1320
cgctggcaag gacgtcgcca cagaggctga caagtttggc atctcgacgc cgttccttgg   1380
ctcggtgcgt gcggcccttg gcttgaaccg gtcggagcaa tggaacacaa ctactaaacc   1440
gccgcgctcg ttcgacgggg ctgccgtcgg cgaggcaacc gcacttgtct cgtgcggcta   1500
cgaggacagg acggcgtggg gccgggacat cggctggata tacggcacag tgacagagga   1560
cgtggccacg ggcttctgca tgcaccggcg agggtggcgc tccgcctact gcgccaccgc   1620 gccgacgcg ttccgcggca ccgcgcccat caacctcaca gaccggctgc accaggtcct   1680
ccgctgggcg gcgggctccc tcgagatatt cttctcccgc aacaacgccc tcctcgccgg   1740
ggcccggctc caccegctgc agcgcctggc gtacctcaac acgacggtgt acccgttcac   1800
ctccatcttc ctcctgctct actgcctcct gccggcgatc ccgtcgtga cccggagcgc    1860 gagcgcgagc gccttctcag tcaccatgcc gccgtcgggc acgtacatgg gctttgtggc   1920
ggcgctgatg ctgacgctgg ccatggtggc cgtgctggga gtgcggtggt cgggcataac   1980
gctgggcgag tggtggcgga acgagcagtt ctggatggtg tccgccacga gcgcgtacgc   2040
ggccgcggtg gtgcaggtgg cgctcaaggt ttcggcgggg aaggagatag ccttcaagct   2100
gacgtccaag cagcgggcgt cgagccccgg tggcggtgta aaagagaggt tcgcagagct   2160
gtacgccgtg agatgacgg tgctgatggt tccgacggcc gtggtgctgg ccgtgaacgt   2220
gatgtccatg gcggcagcag tacaagaggg gcggtggagg aaaggccccg cggcggtgct   2280
cgcgatggcc ttcaacgcgt gggtggtggt gcatctccac cccttcgccc ttggtctcat   2340
gggccgttgg agcaagacgt tgagcccccct cctcttgctc gtcgtagggt tcacagttct   2400
atcactatgt tttgtcctcc atttgcatat gctttaacat gcct                    2444
```

<210> SEQ ID NO 22
<211> LENGTH: 3327
<212> TYPE: DNA
<213> ORGANISM: artificial
<220> FEATURE:
<223> OTHER INFORMATION: synthetic

<400> SEQUENCE: 22

```
cagtgggagc atgtcaatga catatatcac caagaagcat gactatgctg caaccttgga    60
tgagaaggag ccgtccgagg atcagaagcc ggccagtgtc aagaacctgc ttgttcggac   120
cacgaaactt accacggtta ccatcaagtt gtacaggtaa tcatcagcta tatatgcata   180
cttagttatt cgaacatgtt cgtgtttaag tataaaacct acaagttctt cacgataaaa   240
cttgtgaaca tatactactc catgtctcca tctatattga actcagaaac gaacttacat   300
taagttacac agatactccc tccattctaa ataagtgtc ttgagttgta ttagagctag    360
tacaaagttg agacacttat tgtgggacag agggagtagt acacaatatt gtgactcatg   420
agtagttcaa ctagttcata taaaatgcgc agagttaaaa tttgttaagt gcagctaaca   480
gggtttcatg ggaagtaaaa agaaagtaga acagttggat gtgattaaaa aatatttttg   540
actaattatt ttcccgtgtt tactttacaa cttgagacat atgttgaatc tgatatgaat   600
ttgttgcacc gaatgcttaa aaatgatgaa ttcttatagc ttttttcttt acagtttgtc   660
tacttcacat tagatgtttt ttaaggatgt cacaactaag ctcccataaa tatataatgc   720
agtcataaaa aacaaaaaaa ctaggaaaaa aatagatcgc aaatagagtg gacattattt   780
tagatgtgac ataactatgt cacatctaga tgtgtcctat acagacccct ttctttatcg   840
tgtcatgaaa tctaagtgct caaagtgaca ttttaaaatg tcgaaattca tcctccctt    900
ttaatagagt gaataggagt aagtatatag aggactcatg caattaaata ttactaaaaa   960
atatgtggaa aatgactaaa agcttatgtg tgacaaacat atttatgcaa tttagtagcg  1020
aaatccatgg tgtttgcagg ctcatggtat ttgttcggct gaccatcttc gtgctgttct  1080
tcaaatggcg agtcagcact gctcttacag tgatcagcga cggcacaact acagctcgtg  1140
caatgtggac catgtccatc gccggcgagc tctggttcgc cctgatgtgg gtgctggacc  1200
agctgcccaa gatgcagcct gtccggcgca ccgtctacgt cacggcgctc gaggagccgc  1260
ggcttccgac catggatgta tttgtcacca ccaccgatcc cgagaaggag ccgccgctgg  1320
tgaccgtgaa cactatcctc tccatcctcg ccgcggacta ccccccagac aaactcacgt  1380
gctacgtctc agacgacggc ggcgctctgc tcacgcgcga ggcggtggcg cacgctgcct  1440
gcttcgccag actgtgggtg ccgttctgcc ggaagcacgg ggtcgagccg aggaacccag  1500
aggcctactt ctgccccggc gtcaaggcga gggtggtgtc aagggctgac tatatgggaa  1560
ggtcgtggcc ggagctggca cgggaccgga ggcgtgtgcg ccgggagtac gaagaactgc  1620
ggctgcggat cgacgcgctc cacgccgag acgtgcggcc acagcaatgg tcgcgcggca  1680
cggcggaaaa tcatgccgga gttgttgaag tgctagtcgg tcctccgggc agtacgccag  1740
agctcggcgt cagtgatctt ctggacctca gctccgtcga cgtgcgtgtt ccagcggtcg  1800
tgtacatgtg ccgggagaag cgccacggcc gcgtgcacca ccgaaggca ggtgccatga    1860
acgcgctgct ccgcacctcg gccgtgctct ccaacgcgcc cttcatcctc aacctcgact  1920
gcgaccacta cgtcaacaac tcgcaggccc tccgcgccgg cgtctgcctc atgctcgacc  1980
gcggcggcag caacgtggcg ttcgtccagt tcccgcagcg cttcgacggc gtcgaccccg  2040
ccgaccggta cgccaaccac aaccgcgtct tcttcgactg cacggagctc ggcctcgacg  2100
gcctccaggg acccatttac gtgggcaccg gctgcatgtt tcgccgtgcg gcgctataca  2160
acgccgaccc gccactctgg agaccacatg tggtgaccg cgacgctggc aaggacgtcg  2220
ccacagaggc tgacaagttt ggcatctcga cgccgttcct tggctcggtg cgtgcggccc  2280
ttggcttgaa ccggtcggag caatggaaca caactactaa accgccgcgc tcgttcgacg  2340
```

```
gggctgccgt cggcgaggca accgcacttg tctcgtgcgg ctacgaggac aggacggcgt    2400
ggggccggga catcggctgg atatacggca cagtgacaga ggacgtggcc acgggcttct    2460
gcatgcaccg gcgagggtgg cgctccgcct actgcgccac cgcgccggac gcgttccgcg    2520
gcaccgcgcc catcaacctc acagaccggc tgcaccaggt cctccgctgg gcggcgggct    2580
ccctcgagat attcttctcc cgcaacaacg ccctcctcgc cggggcccgg ctccacccgc    2640
tgcagcgcct ggcgtacctc aacacgacgg tgtacccgtt cacctccatc ttcctcctgc    2700
tctactgcct cctgccggcg atcccgctcg tgcccggag cgcgagcgcg agcgccttct    2760
cagtcaccat gccgccgtcg ggcacgtaca tgggctttgt ggcggcgctg atgctgacgc    2820
tggccatggt ggccgtgctg gaggtgcggt ggtcgggcat aacgctgggc gagtggtggc    2880
ggaacgagca gttctggatg gtgtccgcca cgagcgcgta cgcggccgcg gtggtgcagg    2940
tggcgctcaa ggtttcggcg gggaaggaga tagccttcaa gctgacgtcc aagcagcggg    3000
cgtcgagccc cggtggcggt gtaaaagaga ggttcgcaga gctgtacgcc gtgagatgga    3060
cggtgctgat ggttccgacg gccgtggtgc tggccgtgaa cgtgatgtcc atggcggcag    3120
cagtacaaga ggggcggtgg aggaaaggcc ccgcggcggt gctcgcgatg gcgttcaacg    3180
cgtgggtggt ggtgcatctc caccccttcg cccttggtct catgggccgt ggagcaaga    3240
cgttgagccc cctcctcttg ctcgtcgtag ggttcacagt tctatcacta tgttttgtcc    3300
tccatttgca tatgctttaa catgcct                                        3327
```

<210> SEQ ID NO 23
<211> LENGTH: 808
<212> TYPE: PRT
<213> ORGANISM: Triticum aestivum

<400> SEQUENCE: 23

```
Met Ser Met Thr Tyr Ile Thr Lys Lys His Asp Tyr Ala Ala Thr Leu
1               5                   10                  15

Asp Glu Lys Glu Pro Ser Glu Asp Gln Lys Pro Ala Ser Val Lys Asn
            20                  25                  30

Leu Leu Val Arg Thr Thr Lys Leu Thr Thr Val Thr Ile Lys Leu Tyr
        35                  40                  45

Arg Leu Met Val Phe Val Arg Leu Thr Ile Phe Val Leu Phe Phe Lys
    50                  55                  60

Trp Arg Val Ser Thr Ala Leu Thr Val Ile Ser Asp Gly Thr Thr Thr
65                  70                  75                  80

Ala Arg Ala Met Trp Thr Met Ser Ile Ala Gly Glu Leu Trp Phe Ala
                85                  90                  95

Leu Met Trp Val Leu Asp Gln Leu Pro Lys Met Gln Pro Val Arg Arg
            100                 105                 110

Thr Val Tyr Val Thr Ala Leu Glu Glu Pro Arg Leu Pro Thr Met Asp
        115                 120                 125

Val Phe Val Thr Thr Thr Asp Pro Glu Lys Glu Pro Pro Leu Val Thr
    130                 135                 140

Val Asn Thr Ile Leu Ser Ile Leu Ala Ala Asp Tyr Pro Pro Asp Lys
145                 150                 155                 160

Leu Thr Cys Tyr Val Ser Asp Asp Gly Gly Ala Leu Leu Thr Arg Glu
                165                 170                 175

Ala Val Ala His Ala Ala Cys Phe Ala Arg Leu Trp Val Pro Phe Cys
            180                 185                 190
```

-continued

```
Arg Lys His Gly Val Glu Pro Arg Asn Pro Glu Ala Tyr Phe Cys Pro
        195                 200                 205
Gly Val Lys Ala Arg Val Val Ser Arg Ala Asp Tyr Met Gly Arg Ser
210                 215                 220
Trp Pro Glu Leu Ala Arg Asp Arg Arg Val Arg Arg Glu Tyr Glu
225                 230                 235                 240
Glu Leu Arg Leu Arg Ile Asp Ala Leu His Ala Gly Asp Val Arg Pro
                245                 250                 255
Gln Gln Trp Ser Arg Gly Thr Ala Glu Asn His Ala Gly Val Val Glu
            260                 265                 270
Val Leu Val Gly Pro Pro Gly Ser Thr Pro Glu Leu Gly Val Ser Asp
        275                 280                 285
Leu Leu Asp Leu Ser Ser Val Asp Val Arg Val Pro Ala Val Val Tyr
    290                 295                 300
Met Cys Arg Glu Lys Arg His Gly Arg Val His His Arg Lys Ala Gly
305                 310                 315                 320
Ala Met Asn Ala Leu Leu Arg Thr Ser Ala Val Leu Ser Asn Ala Pro
                325                 330                 335
Phe Ile Leu Asn Leu Asp Cys Asp His Tyr Val Asn Asn Ser Gln Ala
            340                 345                 350
Leu Arg Ala Gly Val Cys Leu Met Leu Asp Arg Gly Gly Ser Asn Val
        355                 360                 365
Ala Phe Val Gln Phe Pro Gln Arg Phe Asp Gly Val Asp Pro Ala Asp
    370                 375                 380
Arg Tyr Ala Asn His Asn Arg Val Phe Phe Asp Cys Thr Glu Leu Gly
385                 390                 395                 400
Leu Asp Gly Leu Gln Gly Pro Ile Tyr Val Gly Thr Gly Cys Met Phe
                405                 410                 415
Arg Arg Ala Ala Leu Tyr Asn Ala Asp Pro Pro Leu Trp Arg Pro His
            420                 425                 430
Gly Gly Asp Arg Asp Ala Gly Lys Asp Val Ala Thr Glu Ala Asp Lys
        435                 440                 445
Phe Gly Ile Ser Thr Pro Phe Leu Gly Ser Val Arg Ala Ala Leu Gly
    450                 455                 460
Leu Asn Arg Ser Glu Gln Trp Asn Thr Thr Thr Lys Pro Pro Arg Ser
465                 470                 475                 480
Phe Asp Gly Ala Ala Val Gly Glu Ala Thr Ala Leu Val Ser Cys Gly
                485                 490                 495
Tyr Glu Asp Arg Thr Ala Trp Gly Arg Asp Ile Gly Trp Ile Tyr Gly
            500                 505                 510
Thr Val Thr Glu Asp Val Ala Thr Gly Phe Cys Met His Arg Arg Gly
        515                 520                 525
Trp Arg Ser Ala Tyr Cys Ala Thr Ala Pro Asp Ala Phe Arg Gly Thr
    530                 535                 540
Ala Pro Ile Asn Leu Thr Asp Arg Leu His Gln Val Leu Arg Trp Ala
545                 550                 555                 560
Ala Gly Ser Leu Glu Ile Phe Phe Ser Arg Asn Asn Ala Leu Leu Ala
                565                 570                 575
Gly Ala Arg Leu His Pro Leu Gln Arg Leu Ala Tyr Leu Asn Thr Thr
            580                 585                 590
Val Tyr Pro Phe Thr Ser Ile Phe Leu Leu Leu Tyr Cys Leu Leu Pro
        595                 600                 605
Ala Ile Pro Leu Val Thr Arg Ser Ala Ser Ala Ser Ala Phe Ser Val
```

```
Thr Met Pro Pro Ser Gly Thr Tyr Met Gly Phe Val Ala Ala Leu Met
625                 630                 635                 640

Leu Thr Leu Ala Met Val Ala Val Leu Glu Val Arg Trp Ser Gly Ile
                645                 650                 655

Thr Leu Gly Glu Trp Trp Arg Asn Glu Gln Phe Trp Met Val Ser Ala
            660                 665                 670

Thr Ser Ala Tyr Ala Ala Val Val Gln Val Ala Leu Lys Val Ser
                675                 680                 685

Ala Gly Lys Glu Ile Ala Phe Lys Leu Thr Ser Lys Gln Arg Ala Ser
        690                 695                 700

Ser Pro Gly Gly Gly Val Lys Glu Arg Phe Ala Glu Leu Tyr Ala Val
705                 710                 715                 720

Arg Trp Thr Val Leu Met Val Pro Thr Ala Val Leu Ala Val Asn
                725                 730                 735

Val Met Ser Met Ala Ala Val Gln Glu Gly Arg Trp Arg Lys Gly
            740                 745                 750

Pro Ala Ala Val Leu Ala Met Ala Phe Asn Ala Trp Val Val Val His
                755                 760                 765

Leu His Pro Phe Ala Leu Gly Leu Met Gly Arg Trp Ser Lys Thr Leu
770                 775                 780

Ser Pro Leu Leu Leu Leu Val Val Gly Phe Thr Val Leu Ser Leu Cys
785                 790                 795                 800

Phe Val Leu His Leu His Met Leu
                805
```

<210> SEQ ID NO 24
<211> LENGTH: 3370
<212> TYPE: DNA
<213> ORGANISM: artificial
<220> FEATURE:
<223> OTHER INFORMATION: synthetic

<400> SEQUENCE: 24

```
aagaacaggc tctgctactt ggtaggcgga ccaaggtggc atggcttctc cggcggccgt    60
ccgcggggt cgtctagccg acccactgct ggccgccgac gtcgtcgttg cgccaaggga   120
caggtactgg gtgcccgccg acgagagaga gatcctggcg tcgcagaaga gcggcgccgg   180
cgaggacggc cgggtaccgc tgctctaccg cacgttcatg gtcaacggct tcctcatcaa   240
cctttacagg tgggagcatc gtctcggttc agttccttct tccccttgt ttcgcgccat    300
agatgtatgt tcccgaaggg cagtgccact tgatcgaact cttacgtttc ataggtagtc   360
taaatctaag caatgtacta gtactacagt agtttgtagt actagtattt cttgacagac   420
tactcatgaa ggggccccgc ccacggctcc attttatatg aacgaacgga accagatgat   480
acctgaatat aaatgtactg cctgaatttt gatgcacact gacggagtgt tagttaattg   540
attccaaggc agtaagtaca atcttaagaa acaaacagaa cgtgctgtga tctggaggca   600
cccaaagtgc agtgagagga cagcgtcaaa gtaggcaaaa gctgcaaacg atccaaatgg   660
tattgcattg cttattactg tgcggcacgg gcgtgccatt ggatattttg ataacaaag    720
aaagcaaaag gttggcaaaa aaaagcaaa aggagatgca ccgacgccag tacacgctca    780
agctataagg acgtgaccct tgtgacttg tagccggatc cggacggggg cacagtaaaa   840
gttatccgga cggagtacc tttttgtcgg taaatagtg ctaaaattaa cctgttcgct   900
gagggccagc tagttagttc catactgata ggcgaaattc gcttatttta gttttatatg   960
```

```
tttattagaa tttgacgctc aaaaaaaatg cattgttagc atgcggcgga atgtctaacc   1020
gctgagattg cggatctcaa cgctcagatc ctgatccgcc caagacattt taaaaacgat   1080
taaggcagaa atctagaatc tacactgtgc aaatattcac tctgcacatg cattcgcagg   1140
atcttaattt gtagccagtg ctcaaaatag taagtgtggt attttaatcc aagagcacgt   1200
gagctcaact acagttatta cagtggagat catataacta cgaaagcatg cgacttggca   1260
aactttgttc tattatagtt agagattcta taaccttgtc gttctgtact accaagactt   1320
taacctattt ccatcagcac atcatttcat ctgtccaaac gtaaccgcac tgcaggttat   1380
tgactctggt gagagtgata gtggtgattc tattcttcac gtggcgcatg aggcaccggg   1440
actcggacgc gatgtggctg tggtggatct cggtcgtcgg cgacctctgg ttcggactca   1500
cctggctgct caaccagatc accaagctca agcccaggaa atgcgtccca agcatctccg   1560
tcctcagaga ccagctcgac cagcccgacg gcggctccga cctcccccte ctggacgtgt   1620 tcatcaacac cgtcgacccg gtggacgagc cgatgctcta ccatgaac tccatcctct   1680 ccatcctggc caccgactac cccgtcgaca gtacgccac ctacttctcc gacgacggcg   1740
ggtcgctggt gcactacgag ggcctgcagc tggcggcgga gttcgccgcg tcctgggtcc   1800
ccttctgccg gaagcactgc gtcgagcccc ggcccggga gagctactc tgggccaaga   1860 tgcgcgggga gtacgccggc agcgcgccca aggagttcct tgacgaccat cggcggatgc   1920
gcgcggcgta tgaggagttc aaggcgaggc tggacgggct ttctgccgcc atcgagcagc   1980
ggtcggaggc gtgcaaccgt gccaacggga aagacaaaga ggagtgtgca aatgctactt   2040
ggatggctga tgggtgcacg caatggcagg ggacgtggat caaaccggca aagggccaca   2100
ggaaaggaca ccaccctgca attcttcagg tacaaattaa aataaaccag gtttttattt   2160
catgcgattt tttcatacaa aactgttgct aacatgtgat gatggttcaa ggtaatgctg   2220
gatcaaccga gcaaggatcc tgagctgggc atggcggcga gctccgacca ccctctggac   2280
ttcagcgccg tggacgcgcg cctcccgatg ctggtctaca tcgcccggga agcggccg   2340 ggctacgacc accagaagaa ggcgggcgcc atgaacgtgc agctgcgcgt ctccgcgctg   2400
ctctccaacg cgcctttcat catcaacttc gacggcgacc actacgtcaa caactcgcag   2460
gccttccgcg ccgccatgtg cttcatgctc gacccgcgcg acggcgccga cacggccttc   2520
gtccagttcc cgcagcgctt cgacgacgtc gaccccaccg accgctactg caaccacaac   2580
cgcatgttct tcgacgccac cctcctcggc ctcaacggca tccagggccc ctccttcgtc   2640
ggcactggct gcatgtttcg ccgtgtcgcc ctctacagcc tgaccctcc ccggtggcgc   2700 cccgacgacg ccaaggaggc caaggcctcg cactacaggc ccaacatgtt tggcaagtcc   2760
acgtccttca tcaactccat gccggcgcc gccaaccaag aacggtccgt cccgtcaccg   2820
ccgacggttg gagaggtgga gctcgccgac acgatgacgt gcgcctacga ggacggcacc   2880
gagtggggca acgacgtcgg gtgggtgtac aacatcgcga cggaggacgt ggtgaccggc   2940
ttccggctgc accgcacggg gtggcgctcc acgtactgcg ccatggagcc cgacgcgttc   3000
cgcggcacgg cgcccatcaa cctgacggag cggctctacc agatcctgcg ctggtcgggg   3060
ggatccctcg agatgttctt ctcccgcttc tgccgctcc tggccggccg gcggctccac   3120
cccatgcagc gcgtcgccta catcaacatg accacctacc cggtctccac cttcttcatc   3180
ctcatgtact acttctaccc ggtgatgtgg ctccttccagg gggagttcta catccagagg   3240
ccgttccaga cgttcacgct gttcgtcgtc gtcatcatcg ccacggtgga gctcatcggc   3300
```

```
atggtggaga tcaggtgggc cggcctcacg ctgctcgact gggtccgcaa cgagcagttc      3360
tacatcatcg                                                             3370

<210> SEQ ID NO 25
<211> LENGTH: 2159
<212> TYPE: DNA
<213> ORGANISM: artificial
<220> FEATURE:
<223> OTHER INFORMATION: synthetic

<400> SEQUENCE: 25
aagaacaggc tctgctactt ggtaggcgaa ccagggtggc atggcttctc cggcggccgg        60 cggcggggt cgtctagctg acccattgct ggccaccgac gtcgtcgtcg ccccaagga        120 taagtactgg gtacccgccg acgagagaga gatcttggcg tcgcacagga gcggcgccgg      180
cggcgatgac ggccgggcac cgctgctgta ccgcacgttc agggtcaagg gccccctcat      240
caacctttac aggttattga ctctggtcag agtgatagtg gttattctat tcttcacatg      300
gcgcatgagg caccgggact cggacgcgat gtggctgtgg tggatctcgg tggtaggcga      360
cctctggttc ggagtgacat ggctgctcaa ccagatcacc aagctcaggc ccaggaaatg      420
cgtcccgagc atctccgtcc tgagagagca gctcgaccag cccgacggcg gctccgacct      480 cccccctcctg gacgtgttca tcaacaccgt cgacccggtg gacgagccga tgctctacac      540
catgaactcc atcctctcca tcctggccac cgactacccg gtcgacaagt acgccaccta      600
cttctccgac gacggcgggt cgctggtgca ctacgagggg ctgcagctgg cggcggagtt      660
cgccgcgtcg tgggtgccgt tctgccggaa gcactgcgtc gagccccggg ccccggagag      720
ctatttctgg gccaagatgc gcggggagta cgcgggcacc gcgcccaagg agttccttga      780
cgaccatcgg cggatgcggg cggcgtacga ggagttcaag gtgaggctgg acgggctttc      840
tgccgccatc gagcagcggt cggaggcgtg caaccgtgcg aacgggaaag aggagggtgc      900
agatgctact tggatggctg atgggtccac gcaatggcag gggacgtgga tcaagccggc      960
aaagggccac cggaaaggac accaccctgc aattctacaa gttatgctgg atcaaccgag     1020
caaggatcct gagctgggca tggcggcgag ctccggccac cctctggact tgagcgccgt     1080
ggacgcgcgc ctcccgatgc tggtctacat cgcgcgggag aagcggccgg ggtacgacca     1140
ccagaagaag gcgggcgcca tgaacgtgca gctgcgcgtc tccgcgctgc tctccaacgc     1200
gcccttcatc atcaacttcg acggcgacca ctacgtcaac aactcgcagg ccttccgcgc     1260
cgccatgtgc ttcatgctcg acccgcgcga cggcgccgac accgccttcg tccagttccc     1320
gcagcgcttc gacgacgtcg accccaccga ccgctactgc aaccacaacc gcatgttctt     1380
cgacgccacc ctcctcggcc tcaacggcat ccagggcccc tccttcgtcg gcaccggctg     1440
catgttccgc cgcgtcgcgc tctactccgc cgaccctcct cgctggcgcc ccgacgacgc     1500
caaggaggcc aaggcctcgc gctacaggcc aacatgttcg gcaaatcca cgtccttcat     1560 caactcggtg ccggcggccg ccaaccaaga gcggtccgtc ccttcaccgg cgaccgtcgg     1620
cgaggcggag ctcgccgacg ccatgacgtg cgcctacgag acggcaccg agtggggcaa     1680 cgacgtcggg tgggtgtaca acatcgcgac ggaggacgtg gtgaccggct tccggctgca     1740
ccgcacgggg tggcgctcca cgtactgcgc catggagccc gacgcgttcc gcggcacggc     1800
gcccatcaac ctcacggagc ggctctacca gatcctgcgc tggtcggggg gatccctcga     1860
gatgttcttc tcccgcttct gcccgctcct cgccggccgc cgcctccacc ccatgcagcg     1920
catcgcctac atcaacatga ccacctaccc cgtctccacc ttcttcatct gcatgtatta     1980
```

```
cttctacccg gtgatgtggc tcttccaggg ggagttctac atccagaggc cgttccagac    2040
gttcgcgctc ttcgtcgtca tcgtcatcgc cacggtggag ctcatcggca tggtggagat    2100
caggtgggcc ggcctcacgc cgctcgactg gttccgcaac gagcagttct acatcatcg     2159
```

<210> SEQ ID NO 26
<211> LENGTH: 2760
<212> TYPE: DNA
<213> ORGANISM: artificial
<220> FEATURE:
<223> OTHER INFORMATION: synthetic

<400> SEQUENCE: 26

```
aagaacaggc tctgctactt ggtaggtgaa ccaaggtggc atgccttctc cggctgccgt      60 cggcggggt cgtctagccg acccattgct ggccgccgac gtcgtcgtcg cgccaaaga      120 caagtactgg gtacccgccg acgagagaga gatcttggcg tcgcagaaga gcggcgccgg    180
cgaggacggc cgggcaccgc tgctgtaccg cacgttcagg gtcaagggcc ccctcatcaa    240
cctttacagg ttattgactc tggtcagagt tatagtggtt attctattct tcacatggcg    300
catgaggcac cggactcgg acgcgatgtg gctgtggtgg atctcggtcg tgggcgacct     360
ctggttcgga gtgacctggc tgctcaacca gatcaccaag ctcaggccca gaaaatgcgt    420
cccgagcatc tccgtcctca gagaccatct cgaccagccc gacggcggct ccgacctccc    480
cctcctggac gtgttcatca acacggtcga cccggtggac gagccaatgc tctacaccat    540
gaactccatc ctctccatcc tggccaccga ctacccggtc gagaagtacg ccacctactt    600
ctccgacgac ggcgggtcgc tggtgcacta cgagggcctg cagctggcgg cggagttcgc    660
cgcgtcgtgg gtgccgttct gccggaagca ctgcgtcgag ccccgggccc cggagagcta    720
cttctgggcc aagatgcgcg gggagtatgc gggcagcgcg cccaaggagt tccttgacga    780
ccatcggagg atgcgtgcgg cgtacgagga gttcaaggcg aggctggacg ggctttctgc    840
tgccatcgag cagcggtcgg aggcgtgcaa ccgtgccaac gggaaagaca agaggagtg     900 tgcaaatgct acctggatgg ctgatgggtc cacgcaatgg caggggacat ggatcaagcc    960
ggcaaagggc cacaggaaag gacaccaccc tgcaattctt caggttatgc tggatcaacc    1020
gagcaaggat cctgagctgg gcatggcggc gagctccgac cacccctgg acttcagcgc    1080 cgtggacgcg cgcctcccga tgctggtcta catcgcccgg gagaagcggc cgggctacga    1140
ccaccagaag aaggcgggcg ccatgaacgt gcagctgcgc gtctccgcgc tgctctccaa    1200
cgcgcctttc atcatcaact tcgacggcga ccactacgtc aacaactcgc aggccttccg    1260
cgccgccatc tgcttcatgc tcgacccgcg cgacggcgcc gacaccgcct tcgtccagtt    1320
cccgcagcgc ttcgacgacg tcgacccccac cgaccgctac tgcaaccaca accgcatgtt    1380
cttcgacgcc accctgctcg gcctcaacgg catccagggg ccctccttcg tcggcaccgg    1440
ctgcatgttc cgccgcgtcg cgctctacag cgccgaccct cccgtggc gccccgacga      1500 cgccaaggag gccaaggcct cgcgctacag gcccaacatg ttcggcaaat ccacgtcctt    1560
catcaactcg atgccggcgg ccgccaacca agagcggtcc gtcccttcac cagcgaccgt    1620
cggcgaggcg gagctcgccg acgccatgac gtgcgcctac gaggacggca ccgagtgggg    1680
caacgacgtc gggtgggtgt acaacatcgc gacggaggac gtggtgaccg gcttccggct    1740
gcaccggacg gggtggcgct ccacgtactg cgccatggag cccgacgcgt ccgcggcac    1800 ggcgcccatc aacctcacgg agcggctcta ccagatcctg cgctggtcgg ggggatccct    1860
```

```
cgagatgttc ttctcccgct tctgcccgct cctggccggc cgccgcctcc accccatgca    1920
gcgcgtcgcc tacatcaaca tgaccaccta cccggtctcc accttcttca tctgcatgta    1980
ctacttgtac ccggtgatgt ggctcttcca gggggagttc tacatccaga ggccgttcca    2040
gacgttcgcg ctcttcgtcg tcgtcatcat cgccacggtg gagctcatcg gcatggtgga    2100
gatcaggtgg gccggcctca cgctgctcga ctgggtccgc aacgagcagt tctacatcat    2160
cggcaccacc ggcgtgtacc cgatggccat gctgcacatc ctcctcaggt ccctcggcat    2220 caaggggggtg tccttcaagc tcacggccaa gaagctcaca ggcggcgcga gggagaggct    2280
cgcggagctc tacgacgtgc agtgggtgcc gttgctggtg cccactgtgg tggtgatggc    2340
cgtgaacgtg gccgccatcg gcgcggcggc gggcaaggcg atcgttgggc ggtggtcggc    2400
tgcgcaggtc gcggggggcgg cgagcgggct cgtcttcaac gtgtggatac tgctgctgct    2460
ctacccgttc gcgctcggga taatggggcg ctggagcaag aggccataca tcctgttcat    2520
tgtgctggtg accgcggtcg ctgccaccgc gtccatgtat gtcgcgctcg ccggctccct    2580
gccgtacttg cattcgggga taaagctagt ttaaattttg tactcctaag taatgctgca    2640
aagcctgtaa gagctgtgag tcaaaatagt tcagattgca gcatgtaata agtttacct    2700 taaaggttat gttcgtccac cctcctcctt caaaataaaa agttagggt tactgtaaaa    2760
```

<210> SEQ ID NO 27
<211> LENGTH: 3370
<212> TYPE: DNA
<213> ORGANISM: artificial
<220> FEATURE:
<223> OTHER INFORMATION: synthetic

<400> SEQUENCE: 27

```
aagaacaggc tctgctactt ggtaggcgga ccaaggtggc atggcttctc cggcggccgt      60 ccgcggggt cgtctagccg acccactgct ggccgccgac gtcgtcgttg cgccaagga      120 caggtactgg gtgcccgccg acgagagaga tcctggcg tcgcagaaga gcggcgccgg     180
cgaggacggc cgggtaccgc tgctctaccg cacgttcatg gtcaacggct cctcatcaa     240 cctttacagg tgggagcatc gtctcggttc agttccttct tccccccttgt ttcgcgccat     300 agatgtatgt tcccgaaggg cagtgccact tgatcgaact cttacgtttc ataggtagtc     360
taaatctaag caatgtacta gtactacagt agtttgtagt actagtatttt cttgacagac     420 tactcatgaa ggggccccgc ccacggctcc attttatatg aacgaacgga accagatgat     480
acctgaatat aaatgtactg cctgaattttt gatgcacact gacggagtgt tagttaattg     540
attccaaggc agtaagtaca atcttaagaa acaaacagaa cgtgctgtga tctggaggca     600
cccaaagtgc agtgagagga cagcgtcaaa gtaggcaaaa gctgcaaacg atccaaatgg     660
tattgcattg cttattactg tgcggcacgg gcgtgccatt ggatattttg gataacaaag     720
aaagcaaaag gttggcaaaa aaaagcaaa aggagatgca ccgacgccag tacacgctca     780
agctataagg gacgtgacct ttgtgacttg tagccggatc cggacggggg cacagtaaaa     840
gttatccgga cgggagtacc tttttgtcgg taaaatagtg ctaaaattaa cctgttcgct     900
gagggccagc tagttagttc catactgata ggcgaaattc gcttatttta gtttatatg     960 tttattagaa tttgacgctc aaaaaaaatg cattgttagc atgcggcgga atgtctaacc    1020
gctgagattg cggatctcaa cgctcagatc ctgatccgcc caagacattt taaaaacgat    1080
taaggcagaa atctagaatc tacactgtgc aaatattcac tctgcacatg cattcgcagg    1140 atcttaatt tgtagccagtg ctcaaaatag taagtgtggt attttaatcc aagagcacgt    1200
```

```
gagctcaact acagttatta cagtggagat catataacta cgaaagcatg cgacttggca      1260
aactttgttc tattatagtt agagattcta taaccttgtc gttctgtact accaagactt      1320
taacctattt ccatcagcac atcatttcat ctgtccaaac gtaaccgcac tgcaggttat      1380
tgactctggt gagagtgata gtggtgattc tattcttcac gtggcgcatg aggcaccggg      1440
actcggacgc gatgtggctg tggtggatct cggtcgtcgg cgacctctgg ttcggactca      1500
cctggctgct caaccagatc accaagctca agcccaggaa atgcgtccca agcatctccg      1560
tcctcagaga ccagctcgac cagcccgacg gcggctccga cctcccccctc ctggacgtgt      1620 tcatcaacac cgtcgacccg gtggacgagc cgatgctcta ccatgaac tccatcctct      1680 ccatcctggc caccgactac cccgtcgaca gtacgccac ctacttctcc gacgacggcg      1740
ggtcgctggt gcactacgag ggcctgcagc tggcggcgga gttcgccgcg tcctgggtcc      1800
ccttctgccg gaagcactgc gtcgagcccc gggccccgga gagctacttc tgggccaaga      1860
tgcgcgggga gtacgccggc agcgcgccca aggagttcct tgacgaccat cggcggatgc      1920
gcgcggcgta tgaggagttc aaggcgaggc tggacgggct ttctgccgcc atcgagcagc      1980
ggtcggaggc gtgcaaccgt gccaacggga aagacaaaga ggagtgtgca aatgctactt      2040
ggatggctga tgggtgcacg caatggcagg ggacgtggat caaaccggca aagggccaca      2100
ggaaaggaca ccaccctgca attcttcagg tacaaattaa aataaaccag gtttttattt      2160
catgcgattt tttcatacaa aactgttgct aacatgtgat gatggttcaa ggtaatgctg      2220
gatcaaccga gcaaggatcc tgagctgggc atggcggcga gctccgacca ccctctggac      2280
ttcagcgccg tggacgcgcg cctcccgatg ctggtctaca tcgcccggga gaagcggccg      2340
ggctacgacc accagaagaa ggcgggcgcc atgaacgtgc agctgcgcgt ctccgcgctg      2400
ctctccaacg cgccttttcat catcaacttc gacggcgacc actacgtcaa caactcgcag      2460
gccttccgcg ccgccatgtg cttcatgctc gacccgcgcg acggcgccga cacggccttc      2520
gtccagttcc cgcagcgctt cgacgacgtc gaccccaccg accgctactg caaccacaac      2580
cgcatgttct tcgacgccac cctcctcggc ctcaacggca tccagggccc ctccttcgtc      2640
ggcactggct gcatgtttcg ccgtgtcgcc ctctacagcc tgacccctcc ccggtggcgc      2700
cccgacgacg ccaaggaggc caaggcctcg cactacaggc ccaacatgtt tggcaagtcc      2760
acgtccttca tcaactccat gccggcggcc gccaaccaag aacggtccgt cccgtcaccg      2820
ccgacggttg gagaggtgga gctcgccgac acgatgacgt gcgcctacga ggacggcacc      2880
gagtggggca acgacgtcgg gtgggtgtac aacatcgcga cggaggacgt ggtgaccggc      2940
ttccggctgc accgcacggg gtggcgctcc acgtactgcg ccatggagcc cgacgcgttc      3000
cgcggcacgg cgcccatcaa cctgacggag cggctctacc agatcctgcg ctggtcgggg      3060
ggatccctcg agatgttctt ctcccgcttc tgcccgctcc tggccggccg gcggctccac      3120
cccatgcagc gcgtcgccta catcaacatg accacctacc cggtctccac cttcttcatc      3180
ctcatgtact acttctaccc ggtgatgtgg ctcttccagg gggagttcta catccagagg      3240
ccgttccaga cgttcacgct gttcgtcgtc gtcatcatcg ccacggtgga gctcatcggc      3300
atggtgagag tcaggtgggc cggcctcacg ctgctcgact gggtccgcaa cgagcagttc      3360
tacatcatcg                                                             3370
```

<210> SEQ ID NO 28
<211> LENGTH: 3348
<212> TYPE: DNA

<213> ORGANISM: artificial
<220> FEATURE:
<223> OTHER INFORMATION: synthetic

<400> SEQUENCE: 28

```
aagaacaggc tctgctactt ggtaggcgaa ccagggtggc atggcttctc cggcggccgg        60
cggcggggt  cgtctagctg acccattgct ggccaccgac gtcgtcgtcg gccccaagga       120
taagtactgg gtacccgccg acgagagaga gatcttggcg tcgcacagga gcggcgccgg       180
cggcgatgac ggccgggcac cgctgctgta ccgcacgttc agggtcaagg gcccctcat        240
caacctttac aggtgtgagc atcgtctcag ttcagttcct tcctacctct cccttgttt        300
ttcgccatag atgtatgttc ccgaaggaca gtgccacttg atcgaaccct tacgtttcat       360
acgtactcta acccgaagga cggtgcttgc agtatttctt gacaaattaa acatgtttgc       420
ctgaatctaa tgctccattt tatataaaca aaccagatg  atacctgaat ctaaacagta       480
tgcttgcctg aattctgatg cacactgacg gagtattagt taattgcttc caaagcagca       540
agtacaatat taagaaacag aacgtgctgt gatctcgagg cacccaaagt gcactgagag       600
gacagcgtca aagtaggcaa aagctggaaa cgatccaaat ggcactgcat tgcttattac       660
tgtgcagcat gggcgtgcca ttggatattc ggataacgaa gcagatgcac cgacgccagc       720
acaggctcaa gctataggg  acgtgacctt tgtgacttgt ggccggatcc aacgggggc        780
acagtaaaag ttatccggac ggcagtacct ttttgtcggt caaatagtgc taaattaaac       840
tactagtagt tcgctgaggg ccagctagtt agttccatac tgataggcga aattagctta       900
ttttagtttt atatgtttat aatttgacgc tccaaatatg ctttgttagc atgcgccgga       960
atgtctaacc gctgagattg cggatctcga cgctcggatc ctgatccggc aagaaattt       1020
taaaaacatt taaggcagaa atctagaatc tatactgtgc aaatattcac tctgcacatg      1080
cattcgctgg atcttaattt gtagccagtg ctaaaaatag taagtgtagt attttaatcc      1140
aagagcacgt gagctcaact acaattatta cagtatactc atataactac gcatgcaact      1200
tggcaaactt tgttctatta ttatagtact agtagttaga gattctaacc ttgtcggact      1260
tgtcgttgta cttctaccaa gactagcttt aacctattct caccagtact acgtacatca      1320
tttcatttgt ccaaacgtaa ctgcactgca ggttattgac tctggtcaga gtgatagtgg      1380
ttattctatt cttcacatgg cgcatgaggc accgggactc ggacgcgatg tggctgtggt      1440
ggatctcggt ggtaggcgac ctctggttcg gagtgacatg gctgctcaac cagatcacca      1500
agctcaggcc caggaaatgc gtcccgagca tctccgtcct gagagagcag ctcgaccagc      1560
ccgacggcgg ctccgacctc cccctcctgg acgtgttcat caacaccgtc gacccggtgg      1620
acgagccgat gctctacacc atgaactcca tcctctccat cctggccacc gactacccgg      1680
tcgacaagta cgccacctac ttctccgacg acggcgggtc gctggtgcac tacgaggggc      1740
tgcagctggc ggcggagttc gccgcgtcgt gggtgccgtt ctgccggaag cactgcgtcg      1800
agccccgggc cccggagagc tatttctggg ccaagatgcg cggggagtac gcgggcaccg      1860
cgcccaagga gttccttgac gaccatcggc ggatgcgggc ggcgtacgag gagttcaagg      1920
tgaggctgga cgggctttct gccgccatcg agcagcggtc ggaggcgtgc aaccgtgcga      1980
acgggaaaga ggagggtgca gatgctactt ggatggctga tgggtccacg caatggcagg      2040
ggacgtggat caagccggca aagggccacc ggaaaggaca ccaccctgca attctacaag      2100
taaaaattaa aataaatcag attttctccc atgcgattta atataataaa actgttgcta      2160
acatgtgaat gtgatgatgg ttcttcaagg ttatgctgga tcaaccgagc aaggatcctg      2220
```

```
agctgggcat ggcggcgagc tccggccacc ctctggactt gagcgccgtg gacgcgcgcc   2280
tcccgatgct ggtctacatc gcgcgggaga agcggccggg gtacgaccac cagaagaagg   2340
cgggcgccat gaacgtgcag ctgcgcgtct ccgcgctgct ctccaacgcg cccttcatca   2400
tcaacttcga cggcgaccac tacgtcaaca actcgcaggc cttccgcgcc gccatgtgct   2460
tcatgctcga cccgcgcgac ggcgccgaca ccgccttcgt ccagttcccg cagcgcttcg   2520
acgacgtcga ccccaccgac cgctactgca accacaaccg catgttcttc gacgccaccc   2580
tcctcggcct caacggcatc cagggcccct ccttcgtcgg caccggctgc atgttccgcc   2640
gcgtcgcgct ctactccgcc gaccctcctc gctggcgccc cgacgacgcc aaggaggcca   2700
aggcctcgcg ctacaggccc aacatgttcg gcaaatccac gtccttcatc aactcggtgc   2760
cggcggccgc caaccaagag cggtccgtcc cttcaccggc gaccgtcggc gaggcggagc   2820
tcgccgacgc catgacgtgc gcctacgagg acggcaccga gtggggcaac gacgtcgggt   2880
gggtgtacaa catcgcgacg gaggacgtgg tgaccggctt ccggctgcac cgcacggggt   2940
ggcgctccac gtactgcgcc atggagcccg acgcgttccg cggcacggcg cccatcaacc   3000
tcacggagcg gctctaccag atcctgcgct ggtcggggggg atccctcgag atgttcttct   3060
cccgcttctg cccgctcctc gccggccgcc gcctccaccc catgcagcgc atcgcctaca   3120
tcaacatgac cacctacccc gtctccacct tcttcatctg catgtattac ttctacccgg   3180
tgatgtggct cttccagggg gagttctaca tccagaggcc gttccagacg ttcgcgctct   3240
tcgtcgtcat cgtcatcgcc acggtggagc tcatcggcat ggtggagatc aggtgggccg   3300
gcctcacgcc gctcgactgg ttccgcaacg agcagttcta catcatcg               3348
```

<210> SEQ ID NO 29
<211> LENGTH: 2847
<212> TYPE: DNA
<213> ORGANISM: artificial
<220> FEATURE:
<223> OTHER INFORMATION: synthetic

<400> SEQUENCE: 29

```
aagaacaggc tctgctactt ggtaggtgaa ccaaggtggc atgccttctc cggctgccgt     60 cggcggggggt cgtctagccg acccattgct ggccgccgac gtcgtcgtcg gcgccaaaga    120
caagtactgg gtacccgccg acgagagaga gatcttggcg tcgcagaaga gcggcgccgg    180
cgaggacggc cgggcaccgc tgctgtaccg cacgttcagg gtcaagggcc cctcatcaa    240 cctttacagg ttattgactc tggtcagagt tatagtggtt attctattct tcacatggcg    300
catgaggcac cgggactcgg acgcgatgtg gctgtggtgg atctcggtcg tgggcgacct    360
ctggttcgga gtgacctggc tgctcaacca gatcaccaag ctcaggccca gaaaatgcgt    420
cccgagcatc tccgtcctca gagaccatct cgaccagccc gacggcggct ccgacctccc    480
cctcctggac gtgttcatca acacggtcga cccggtggac gagccaatgc tctacaccat    540
gaactccatc ctctccatcc tggccaccga ctacccggtc gagaagtacg ccacctactt    600
ctccgacgac ggcgggtcgc tggtgcacta cgagggcctg cagctggcgg cggagttcgc    660
cgcgtcgtgg gtgccgttct gccggaagca ctgcgtcgag ccccgggccc cggagagcta    720
cttctgggcc aagatgcgcg gggagtatgc gggcagcgcg cccaaggagt tccttgacga    780
ccatcggagg atgcgtgcgg cgtacgagga gttcaaggcg aggctggacg gctttctgc    840 tgccatcgag cagcggtcgg aggcgtgcaa ccgtgccaac gggaaagaca aagaggagtg    900
```

-continued

```
tgcaaatgct aacctggatgg ctgatgggtc cacgcaatgg caggggacat ggatcaagcc    960
ggcaaagggc cacaggaaag gacaccaccc tgcaattctt caggtacaaa taaaataaac   1020
cagatttctt tcttcccatg cgatttaata taataaaact gttgctaaca tgtgatgacg   1080
atggttcaag gttatgctgg atcaaccgag caaggatcct gagctgggca tggcggcgag   1140
ctccgaccac ccctggact tcagcgccgt ggacgcgcgc ctcccgatgc tggtctacat   1200
cgcccgggag aagcggccgg gctacgacca ccagaagaag gcgggcgcca tgaacgtgca   1260
gctgcgcgtc tccgcgctgc tctccaacgc gcctttcatc atcaacttcg acggcgacca   1320
ctacgtcaac aactcgcagg ccttccgcgc cgccatctgc ttcatgctcg acccgcgcga   1380
cggcgccgac accgccttcg tccagttccc gcagcgcttc gacgacgtcg accccaccga   1440
ccgctactgc aaccacaacc gcatgttctt cgacgccacc ctgctcggcc tcaacggcat   1500
ccagggggccc tccttcgtcg gcaccggctg catgttccgc cgcgtcgcgc tctacagcgc   1560
cgaccctccc cggtggcgcc ccgacgacg caaggaggcc aaggcctcgc gctacaggcc   1620
caacatgttc ggcaaatcca cgtccttcat caactcgatg ccggcggccg ccaaccaaga   1680
gcggtccgtc ccttcaccag cgaccgtcgg cgaggcggag ctcgccgacg ccatgacgtg   1740
cgcctacgag gacggcaccg agtggggcaa cgacgtcggg tgggtgtaca acatcgcgac   1800
ggaggacgtg gtgaccggct tccggctgca ccggacgggg tggcgctcca cgtactgcgc   1860
catggagccc gacgcgttcc gcggcacggc gcccatcaac ctcacggagc ggctctacca   1920
gatcctgcgc tggtcggggg gatccctcga gatgttcttc tcccgcttct gcccgctcct   1980
ggccggccgc cgcctccacc ccatgcagcg cgtcgcctac atcaacatga ccacctaccc   2040
ggtctccacc ttcttcatct gcatgtacta cttgtacccg gtgatgtggc tcttccaggg   2100
ggagttctac atccagaggc cgttccgac gttcgcgctc ttcgtcgtcg tcatcatcgc   2160
cacggtggag ctcatcggca tggtggagat caggtgggcc ggcctcacgc tgctcgactg   2220
ggtccgcaac gagcagttct acatcatcgg caccaccggc gtgtaccga tggccatgct   2280
gcacatcctc ctcaggtccc tcggcatcaa ggggggtgtcc ttcaagctca cggccaagaa   2340
gctcacaggc ggcgcgaggg agaggctcgc ggagctctac gacgtgcagt gggtgccgtt   2400
gctggtgccc actgtggtgg tgatggccgt gaacgtggcc gccatcggcg cggcggcggg   2460
caaggcgatc gttgggcggt ggtcggctgc gcaggtcgcg ggggcggcga gcgggctcgt   2520
cttcaacgtg tggatactgc tgctgctcta cccgttcgcg ctcgggataa tggggcgctg   2580
gagcaagagg ccatacatcc tgttcattgt gctggtgacc gcggtcgctg ccaccgcgtc   2640
catgtatgtc gcgctcgccg gctccctgcc gtacttgcat tcggggataa agctagttta   2700
aattttgtac tcctaagtaa tgctgcaaag cctgtaagag ctgtgagtca aaatagttca   2760
gattgcagca tgtaataaag tttaccttaa aggttatgtt cgtccaccct cctccttcaa   2820
aataaaaaag ttagggttac tgtaaaa                                       2847
```

<210> SEQ ID NO 30  
<211> LENGTH: 857  
<212> TYPE: PRT  
<213> ORGANISM: Triticum aestivum

<400> SEQUENCE: 30

```
Met Pro Ser Pro Ala Ala Val Gly Gly Gly Arg Leu Ala Asp Pro Leu
1               5                   10                  15

Leu Ala Ala Asp Val Val Val Gly Ala Lys Asp Lys Tyr Trp Val Pro
            20                  25                  30
```

```
Ala Asp Glu Arg Glu Ile Leu Ala Ser Gln Lys Ser Gly Ala Gly Glu
        35                  40                  45

Asp Gly Arg Ala Pro Leu Leu Tyr Arg Thr Phe Arg Val Lys Gly Pro
    50                  55                  60

Leu Ile Asn Leu Tyr Arg Leu Leu Thr Leu Val Arg Val Ile Val Val
65                  70                  75                  80

Ile Leu Phe Phe Thr Trp Arg Met Arg His Arg Asp Ser Asp Ala Met
                85                  90                  95

Trp Leu Trp Trp Ile Ser Val Val Gly Asp Leu Trp Phe Gly Val Thr
                100                 105                 110

Trp Leu Leu Asn Gln Ile Thr Lys Leu Arg Pro Arg Lys Cys Val Pro
            115                 120                 125

Ser Ile Ser Val Leu Arg Asp His Leu Asp Gln Pro Asp Gly Gly Ser
    130                 135                 140

Asp Leu Pro Leu Leu Asp Val Phe Ile Asn Thr Val Asp Pro Val Asp
145                 150                 155                 160

Glu Pro Met Leu Tyr Thr Met Asn Ser Ile Leu Ser Ile Leu Ala Thr
                165                 170                 175

Asp Tyr Pro Val Glu Lys Tyr Ala Thr Tyr Phe Ser Asp Gly Gly
                180                 185                 190

Ser Leu Val His Tyr Glu Gly Leu Gln Leu Ala Ala Glu Phe Ala Ala
            195                 200                 205

Ser Trp Val Pro Phe Cys Arg Lys His Cys Val Glu Pro Arg Ala Pro
    210                 215                 220

Glu Ser Tyr Phe Trp Ala Lys Met Arg Gly Glu Tyr Ala Gly Ser Ala
225                 230                 235                 240

Pro Lys Glu Phe Leu Asp Asp His Arg Arg Met Arg Ala Ala Tyr Glu
                245                 250                 255

Glu Phe Lys Ala Arg Leu Asp Gly Leu Ser Ala Ala Ile Glu Gln Arg
                260                 265                 270

Ser Glu Ala Cys Asn Arg Ala Asn Gly Lys Asp Lys Glu Glu Cys Ala
    275                 280                 285

Asn Ala Thr Trp Met Ala Asp Gly Ser Thr Gln Trp Gln Gly Thr Trp
    290                 295                 300

Ile Lys Pro Ala Lys Gly His Arg Lys Gly His His Pro Ala Ile Leu
305                 310                 315                 320

Gln Val Met Leu Asp Gln Pro Ser Lys Asp Pro Glu Leu Gly Met Ala
                325                 330                 335

Ala Ser Ser Asp His Pro Leu Asp Phe Ser Ala Val Asp Ala Arg Leu
            340                 345                 350

Pro Met Leu Val Tyr Ile Ala Arg Glu Lys Arg Pro Gly Tyr Asp His
        355                 360                 365

Gln Lys Lys Ala Gly Ala Met Asn Val Gln Leu Arg Val Ser Ala Leu
    370                 375                 380

Leu Ser Asn Ala Pro Phe Ile Ile Asn Phe Asp Gly Asp His Tyr Val
385                 390                 395                 400

Asn Asn Ser Gln Ala Phe Arg Ala Ala Ile Cys Phe Met Leu Asp Pro
                405                 410                 415

Arg Asp Gly Ala Asp Thr Ala Phe Val Gln Phe Pro Gln Arg Phe Asp
                420                 425                 430

Asp Val Asp Pro Thr Asp Arg Tyr Cys Asn His Asn Arg Met Phe Phe
        435                 440                 445
```

```
Asp Ala Thr Leu Leu Gly Leu Asn Gly Ile Gln Gly Pro Ser Phe Val
    450                 455                 460
Gly Thr Gly Cys Met Phe Arg Val Ala Leu Tyr Ser Ala Asp Pro
465                 470                 475                 480
Pro Arg Trp Arg Pro Asp Asp Ala Lys Glu Ala Lys Ala Ser Arg Tyr
                485                 490                 495
Arg Pro Asn Met Phe Gly Lys Ser Thr Ser Phe Ile Asn Ser Met Pro
                500                 505                 510
Ala Ala Ala Asn Gln Glu Arg Ser Val Pro Ser Pro Ala Thr Val Gly
            515                 520                 525
Glu Ala Glu Leu Ala Asp Ala Met Thr Cys Ala Tyr Glu Asp Gly Thr
            530                 535                 540
Glu Trp Gly Asn Asp Val Gly Trp Val Tyr Asn Ile Ala Thr Glu Asp
545                 550                 555                 560
Val Val Thr Gly Phe Arg Leu His Arg Thr Gly Trp Arg Ser Thr Tyr
                565                 570                 575
Cys Ala Met Glu Pro Asp Ala Phe Arg Gly Thr Ala Pro Ile Asn Leu
                580                 585                 590
Thr Glu Arg Leu Tyr Gln Ile Leu Arg Trp Ser Gly Gly Ser Leu Glu
            595                 600                 605
Met Phe Phe Ser Arg Phe Cys Pro Leu Leu Ala Gly Arg Arg Leu His
            610                 615                 620
Pro Met Gln Arg Val Ala Tyr Ile Asn Met Thr Thr Tyr Pro Val Ser
625                 630                 635                 640
Thr Phe Phe Ile Cys Met Tyr Tyr Leu Tyr Pro Val Met Trp Leu Phe
                645                 650                 655
Gln Gly Glu Phe Tyr Ile Gln Arg Pro Phe Gln Thr Phe Ala Leu Phe
                660                 665                 670
Val Val Val Ile Ile Ala Thr Val Glu Leu Ile Gly Met Val Glu Ile
            675                 680                 685
Arg Trp Ala Gly Leu Thr Leu Leu Asp Trp Val Arg Asn Glu Gln Phe
            690                 695                 700
Tyr Ile Ile Gly Thr Thr Gly Val Tyr Pro Met Ala Met Leu His Ile
705                 710                 715                 720
Leu Leu Arg Ser Leu Gly Ile Lys Gly Val Ser Phe Lys Leu Thr Ala
                725                 730                 735
Lys Lys Leu Thr Gly Gly Ala Arg Glu Arg Leu Ala Glu Leu Tyr Asp
                740                 745                 750
Val Gln Trp Val Pro Leu Leu Val Pro Thr Val Val Met Ala Val
            755                 760                 765
Asn Val Ala Ala Ile Gly Ala Ala Ala Gly Lys Ala Ile Val Gly Arg
770                 775                 780
Trp Ser Ala Ala Gln Val Ala Gly Ala Ala Ser Gly Leu Val Phe Asn
785                 790                 795                 800
Val Trp Ile Leu Leu Leu Leu Tyr Pro Phe Ala Leu Gly Ile Met Gly
                805                 810                 815
Arg Trp Ser Lys Arg Pro Tyr Ile Leu Phe Ile Val Leu Val Thr Ala
                820                 825                 830
Val Ala Ala Thr Ala Ser Met Tyr Val Ala Leu Ala Gly Ser Leu Pro
            835                 840                 845
Tyr Leu His Ser Gly Ile Lys Leu Val
    850                 855
```

<210> SEQ ID NO 31
<211> LENGTH: 2284
<212> TYPE: DNA
<213> ORGANISM: artificial
<220> FEATURE:
<223> OTHER INFORMATION: synthetic

<400> SEQUENCE: 31

| | |
|---|---:|
| ctgctctcgg ccgcggccat ggcgggcggc aagaagctgc acgagagggt cgccctgggg | 60 |
| agaactgcgt ggatgctggc cgacttcgtg atcctcctcc tcctcctcgc cctcgtggcc | 120 |
| cgccgcgccg cgtcgctcgg ggagcgcggc gggacgtggc tggcggcgct cgtctgcgag | 180 |
| gcgtggttcg ccttcgtctg gatcctcaac atgaacggca gtggagccc cgtccggttc | 240 |
| gacacctacc ccgagaacct ctcccacagg ctggaggagc tcccggcggt ggacatgttc | 300 |
| gtcacgacgg cggaccccgg cgctggagcc ccgttgatca cggtgaacac ggtgctctcg | 360 |
| ctgctcgccc tggactaccc ggacgtcggc aagctggcgt gctacgtctc cgacgacggc | 420 |
| tgctccccgg tgacgtgcta cgcgctgcgc gaggccgcca gttcgccag cctctggatt | 480 |
| cccttctgca agaggtatga cgttggtgtg agggccccct tcatgtactt ctcttccgcg | 540 |
| ccggaggttg gcaccggtac agccgaccac gagttcctgg aaagctgggc actcatgaag | 600 |
| accgaatatg agaagctggc cagccggatc gagaacgccg acgaggtctc cattctgcgt | 660 |
| gacggcggcg aagagttcgc cgagttcatc gacgccgagc gcgggaacca tcctaccatc | 720 |
| gttaaggttc tctgggataa cagcaagagc aaagcagggg aaggattccc acatctggtg | 780 |
| tacctctctc gagagaaaag ccccagacat cgccacaact tcaaggccgg tgccatgaat | 840 |
| gttctgacaa gggtgtcggc cgtgatgacc aacgctccaa tcatgctgaa tgtggactgc | 900 |
| gacatgttcg ccaacaaccc gcaggtcgcc ctgcacgcga tgtgcctcct gttgggttc | 960 |
| gacgacgaga tccacagcgg gttcgtccag cgccacagaa gttctacgg tggcctcaag | 1020 |
| gatgacccct ttggcaacca gatgcaggtt ataaccaaga aaattggagg tgggctcgcc | 1080 |
| gggatccaag gcaccttcta cggcggcacg ggctgttttc accgcaggaa ggtcatctac | 1140 |
| ggcatgccgc ctccggacac cgtcaagcac gagacaagag gttcaccatc ttacaaggag | 1200 |
| ctgcaagcca gtttgggag ctcaaaggag ttgatcgaat catctaggaa catcatctca | 1260 |
| ggggacctgc tcgctagacc aaccgtagat atatcgagtc gtgtcgaaat ggcaaaacaa | 1320 |
| gtaggcgact gcaactatga ggctggcaca tgttggggcc aagagattgg gtgggtctat | 1380 |
| ggatcaatga cagaggacat tttgaccggt caacggatcc aggcggcggg ttgggaatcg | 1440 |
| gccttgttgg acaccgaccc accggcattc ctggatgtg ctccgaccgg tggaccagcc | 1500 |
| agcttgaccc agttcaagag atgggcaaca gggcttctgg agatactcat cagccggaac | 1560 |
| agccccatcc tcgcaccat cttcaagggc ctccaactcc ggcaatgcct tggctatctc | 1620 |
| atcgtagacg cgtggcccgt gagggcgcct ttcgagctgt gctatgcgct cttgggacct | 1680 |
| ttctgccttc tcacaaacca atccttctta ccaacggcat cagatgaagg ttttcacatc | 1740 |
| ccagcggctc tatttttgac ttacaacata taccacctga tggagtacaa ggagtgcggg | 1800 |
| ctctcggtcc gcgcctggtg gaacaaccat aggatgcaac gcatcacctc ggcctccgcc | 1860 |
| tggctcctcg ccttcctcac cgtcatcctc aagacgctag gctctccga ccgtgttc | 1920 |
| gaggtcaccc gcaaggagag cagcacgtca tccgatggcg gcgcgggcac cgacgatgcc | 1980 |
| gatcctgggt tgttcacctt tgactcgcg cccgttttca tcccagtgac ggcgctctca | 2040 |
| gtgttgaaca ttgtcgccct caccgtcgcg gcatggcgcg ccgtcgtcgg gacggtggcg | 2100 |

|       |       |       |       |       |      |
|-------|-------|-------|-------|-------|------|
| ggcgttcatg | gtggcccggg | cgtcggagag | ttcgtgtgct | gtggctggat | ggtgttgtgc | 2160 |
| ttctggccat | tcgtgagagg | gcttgtcagt | agtggaaagt | atgggatccc | gtggagtgtc | 2220 |
| agggtgaagg | ctgggttgat | tgtggctgcg | ttcgtgcacc | tctgcacaag | gaactaaccg | 2280 |
| gccg |  |  |  |  |  | 2284 |

<210> SEQ ID NO 32
<211> LENGTH: 2421
<212> TYPE: DNA
<213> ORGANISM: artificial
<220> FEATURE:
<223> OTHER INFORMATION: synthetic

<400> SEQUENCE: 32

|       |       |       |       |       |      |
|-------|-------|-------|-------|-------|------|
| tgtcccgatc | ggaaatgcac | cgaggagagg | atagtttatc | cggtctttat | aaatgcactc |   60 |
| tagcatttgt | tgcttgtgga | tgtgggtgga | gctgtggtgt | tgtgctgcta | gctagtctgc |  120 |
| tactgctagt | ggctagctac | ctctcggcca | cggccatggc | gggcggcaag | aagctgcagg |  180 |
| agagggtcgc | cctgggcagg | agcgcgtgga | tgctggccga | cttcgtgatc | ctcttcctcg |  240 |
| tcctcgccct | cgtggcccgc | cgcgccgcgt | cgctcgggga | gcgcggcggg | acgtggctgg |  300 |
| cagcgctcgt | ctgcgaggcg | tggttcgcct | tcgtgtggat | cctcaacatg | aacggcaagt |  360 |
| ggagccccgt | ccggttcgac | acctaccccg | agaacctctc | ccacaggatg | aaagagctcc |  420 |
| cggcggtgga | catgttcgtc | acgacggcgg | acccggcgct | ggagccgccg | ttgatcacgg |  480 |
| tgaacacggt | gctctcgctg | ctcgccctgg | actacccgca | cgtcggcaag | ctggcgtgct |  540 |
| acgtctccga | cgacgctgc | tccccttga | cgtgctactc | tctgcgcgag | gccgccaagt |  600 |
| cgccagcct | ctgggttccc | ttctgcaaga | ggcacgacgt | tggtgtgagg | gcccctttca |  660 |
| tgtacttctc | ttccgcgccg | gaggttgaca | ccggtacagt | cgaccacgag | ttcctggaaa |  720 |
| gctgggcact | catgaagagc | gaatatgaga | agctggccag | ccggatcgag | aacgccgacg |  780 |
| aggtctccat | tctgcgtgac | ggcggcgacg | agttcgccga | gttcatcgac | gccgagcgcg |  840 |
| ggaaccatcc | taccatcgtt | aaggttctct | gggataacag | caagaacaaa | acaggtgaag |  900 |
| gattcccaca | tctggtgtac | ctctcgagag | agaaaagccc | cagacatcgt | cacaacttta |  960 |
| aggccggtgc | catgaatgtt | ctgacaaggg | tgtcggccgt | gatgaccaac | gctccgatca | 1020 |
| tgctgaatgt | ggactgcgac | atgtttgcca | caacccgca | ggtcgcccta | cacgcgatgt | 1080 |
| gcctcctgtt | ggggttcgac | gacgagatcc | acagcgggtt | cgtccaggcg | ccacagaagt | 1140 |
| tctacggtgg | cctcaaggat | gacccctttg | caaccagat | gcaggttata | accaagaaaa | 1200 |
| ttggaggtgg | gctcgccggg | atccaaggca | cgttctacgg | cggcacgggc | tgttttcacc | 1260 |
| gcaggaaggt | catttacggc | atgccgcctc | cggacaccgt | caagcacgag | acaagaggtt | 1320 |
| caccatctta | caaggagctg | caagccaagt | ttgggagctc | aaaggagttg | atcgaatcat | 1380 |
| ctaggaacat | catctcagga | gacctgctcg | ctagaccaac | cgtagatata | tcaagtcggg | 1440 |
| tcgaaatggc | aaaacaagta | ggcgactgca | actatgaggc | tggcacatgt | tggggccaag | 1500 |
| agattgggtg | ggtctatgga | tcaatgacag | aggacatttt | gaccgggcaa | cggatccaag | 1560 |
| cggcgggttg | gaaatcggcc | ttgttggaca | ccgacccacc | ggcattcttg | ggatgtgctc | 1620 |
| cgacagggg | gccggctagc | ttgacccagt | tcaagagatg | ggcaacaggg | cttctggaga | 1680 |
| tactcatcag | ccggaacagc | cccatcctcg | gcaccatctt | caggcgcctc | caactccggc | 1740 |
| aatgccttgc | ctatctcatc | gtcaacgcgt | ggcccatgag | ggcaccttc | gagatgtgtt | 1800 |
| acgcgctatt | gggacctttc | tgccttctca | caaaccagtc | cttcttgcca | acgacatcta | 1860 |

-continued

| | |
|---|---|
| atgaaggttt tcgcatccca gcggctctat tcttgagtta ccacgtatac cacctgatgg | 1920 |
| agtacaagga gtgcgggctc tcggtccgcg cctggtggaa caaccacagg atgcaacgca | 1980 |
| tcacctcggc ctccgcctgg ctcctcgcct tcctcaccgt catcctcaag acgctagggc | 2040 |
| tctccgagac cgtgttcgag gtcacccgca aggagagcag cacgtcctcc gatggtggcg | 2100 |
| cgggcaccga cgaggccgat actgggctgt tcaccttcga ctcggcgccc gttttcatcc | 2160 |
| cggtgacggc gctctcaatg ctgaacattg tcgccctcgc cgtcgcggca tggcgcgccg | 2220 |
| ttgtcgggac ggcggcgggc gttcatggtg gcccgggagt cggagagttc gtgtgctgtg | 2280 |
| gctggatggt gctgtgcttc tggccgttca tgagagggct tgtcagcagt ggaaagtatg | 2340 |
| ggatcccgtg gagtgtcagg gtgaaggctg ggttgattgt ggctgcgttc gtgcacctct | 2400 |
| gcacaaggaa ctaaccggcg g | 2421 |

<210> SEQ ID NO 33
<211> LENGTH: 2284
<212> TYPE: DNA
<213> ORGANISM: artificial
<220> FEATURE:
<223> OTHER INFORMATION: synthetic

<400> SEQUENCE: 33

| | |
|---|---|
| ctgctctcgg ccacggccat ggcgggcggc aagaagctgc aggagagggt cgccctgggc | 60 |
| aggagtgcgt ggatgctggc cgacttcgtg atcctcttcc tcctcctcgc cctcgtggcc | 120 |
| cgccgcgccg cgtcgctcgg ggagcgcggc gggacgtggc tggcagcgct cgtctgcgag | 180 |
| gcgtggttcg ccttcgtgtg gatcctcaac atgaacggca agtggagccc cgtccggttc | 240 |
| gacacctacc ccgacaacct ctcccacagg atggaggagc tcccagcggt ggacatgttc | 300 |
| gtcacgacgg cggacccggc gctggagccg ccgttgatca cggtgaacac ggtgctctcg | 360 |
| ctgctcgccc tggactaccc gcacgtcggc aagctggcgt gctacgtctc cgacgacggc | 420 |
| tgctccccct tgacgtgcta cggtctgcac gaggccgcca agttcgccag cctctgggtt | 480 |
| cccttctgca agaggcacga cgttggtgtg agggcccctt tcatgtactt ctcttccgcg | 540 |
| ccggaggttg acaccggtac agtcgaccac gagttcctgg aaagctgggc actcatgaag | 600 |
| agcgaatatg agaagctggc cagccggatc gagaacgccg acgaggtctc cattctgcgt | 660 |
| gacggcggcg acgagttcgc cgagttcatc gacgccgagc gcgggaacca tcctaccatc | 720 |
| gttaaggttc tctgggataa cagcaagaac aaaacaggtg aaggattccc acatctggtg | 780 |
| tacctctcga gagagaaaag ccccagacat cgtcacaact ttaaggccgg tgccatgaat | 840 |
| gttctgacaa gggtgtcggc cgtgatgacc aacgctccga tcatgctgaa tgtggactgc | 900 |
| gacatgtttg ccaacaaccc gcaggtcgcc ctacacgcga tgtgcctcct gttgggttc | 960 |
| gacgacgaga tccacagcgg gttcgtccag gcgccacaga agttctacgg tggcctcaag | 1020 |
| gatgacccct ttggcaacca gatgcaggtt ataaccaaga aaattggagg tgggctcgcc | 1080 |
| gggatccaag gcacgttcta cggcggcacg ggctgttttc accgcaggaa ggtcatttac | 1140 |
| ggcatgccgc ctccggacac cgtcaagcac gagacaagag gttcaccatc ttacaaggag | 1200 |
| ctgcaagcca gtttgggag ctcaaaggag ttgatcgaat catctaggaa catcatctca | 1260 |
| ggagacctgc tcgctagacc aaccgtagat atatcaagtc gggtcgaaat ggcaaaacaa | 1320 |
| gtaggcgact gcaactatga ggctggcaca tattggggcc aagagattgg gtgggtctat | 1380 |
| ggatcaatga cagaggacat tttgaccggg caacggatcc aagcggcggg ttggaaatcg | 1440 |

| | |
|---|---|
| gccttgttgg acaccgaccc accggcattc ttgggatgtg ctccgacagg ggggccggct | 1500 |
| agcttgaccc agttcaagag atgggcaaca gggcttctgg agatactcat cagccggaac | 1560 |
| agccccatcc tcggcaccat cttcaggcgc ctccaactcc ggcaatgcct tgcctatctc | 1620 |
| atcgtcaacg cgtggcccat gagggcacct ttcgagatgt gttacgcgct attgggacct | 1680 |
| ttctgccttc tcacaaacca gtccttcttg ccaacgacat ctaatgaagg ttttcgcatc | 1740 |
| ccagcggctc tattcttgag ttaccacgta taccacctga tggagtacaa ggagtgcggg | 1800 |
| ctctcggtcc gcgcctggtg gaacaaccac aggatgcaac gcatcacctc ggcctccgcc | 1860 |
| tggctcctcg ccttcctcac cgtcatcctc aagacgctag gctctccga gaccgtgttc | 1920 |
| gaggtcaccc gcaaggagag cagcacgtcc tccgatggtg gcgcgggcac cgacgaggcc | 1980 |
| gatactgggc tgttcacctt cgactcggcg cccgttttca tcccggtgac ggcgctctca | 2040 |
| atgctgaaca ttgtcgccct cgccgtcgcg gcatggcgcg ccgttgtcgg gacggcggcg | 2100 |
| ggcgttcatg gtggcccggg agtcggagag ttcgtgtgct gtggctggat ggtgctgtgc | 2160 |
| ttctggccgt tcatgagagg gcttgtcagc agtggaaagt atgggatccc gtggagtgtc | 2220 |
| agggtgaagg ctgggttgat tgtggctgcg ttcgtgcacc tctgcacaag gaactaaccg | 2280 |
| gcgg | 2284 |

<210> SEQ ID NO 34
<211> LENGTH: 3236
<212> TYPE: DNA
<213> ORGANISM: artificial
<220> FEATURE:
<223> OTHER INFORMATION: synthetic

<400> SEQUENCE: 34

| | |
|---|---|
| tgtcccgatc ggaaatgcac cgaggagagg atagtttatc cggtctttat aaatgcactc | 60 |
| tagcactcgt ttgcttgtgg ttgtgggtgg agctgtggtg tcgtgctagc tagccagtct | 120 |
| gctacctctc ggccgcggcc atggcgggcg gcaagaagct gcacgagagg gtcgccctgg | 180 |
| ggagaactgc gtggatgctg gccgacttcg tgatcctcct cctcctcctc gccctcgtgg | 240 |
| cccgccgcgc cgcgtcgctc ggggagcgcg gcgggacgtg gctggcggcg ctcgtctgcg | 300 |
| aggcgtggtt cgccttcgtc tggatcctca acatgaacgg caagtggagc ccgtccggt | 360 |
| tcgacaccta ccccgagaac ctctcccaca ggtacgtacg ttcttgtgca cactaactgc | 420 |
| aaaataatgt tgacctacag cttcgtgcag cttcttcctt aaactgtgtc gtgtctgtga | 480 |
| tgattttgct aggctggagg agctcccggc ggtggacatg ttcgtcacga cggcggaccc | 540 |
| ggcgctggag ccgccgttga tcacggtgaa cacggtgctc tcgctgctcg ccctggacta | 600 |
| cccggacgtc ggcaagctgg cgtgctacgt ctccgacgac ggctgctccc cggtgacgtg | 660 |
| ctacgcgctg cgcgaggccg ccaagttcgc cagcctctgg attcccttct gcaagaggta | 720 |
| tgacgttggt gtgagggccc cttttcatgta cttctcttcc gcgccggagg ttggcaccgg | 780 |
| tacagccgac cacgagttcc tggaaagctg ggcactcatg aaggttaggc gccatggtga | 840 |
| ccatttcagt ttccataatg tttggtcgtc catcgtcgcc atgaccatgc atcttcctcg | 900 |
| tgtacgtgtg actttcagac cgaatatgag aagctggcca gccggatcga gaacgccgac | 960 |
| gaggtctcca ttctgcgtga cggcggcgaa gagttcgccg agttcatcga cgccgagcgc | 1020 |
| gggaaccatc ctaccatcgt taaggtcgcc gcactgacca tgtccatgta catcgtgtca | 1080 |
| tgccaaacgc gtagcaaatc cgtctcgtgc taatatcgtc acggttaacc tgtgtgagtt | 1140 |
| caggttctct gggataacag caagagcaaa gcaggggaag gattcccaca tctggtgtac | 1200 |

```
ctctctcgag agaaaagccc cagacatcgc cacaacttca aggccggtgc catgaatgtt    1260
ctggtgagca ctctcttgta cacaacagtg tttcactggt aatcagtgtg tcacacaaac    1320
agcacaataa gtggcagttg aaagttcaga catgtgtaca atgcgcttga taatttgcaa    1380
gcaaataatt aagctgagcg tttcgtggtg cagacaaggg tgtcggccgt gatgaccaac    1440
gctccaatca tgctgaatgt ggactgcgac atgttcgcca acaacccgca ggtcgccctg    1500
cacgcgatgt gcctcctgtt ggggttcgac gacgagatcc acagcgggtt cgtccaggcg    1560
ccacagaagt tctacggtgg cctcaaggat gaccccttg gcaaccagat gcaggttata    1620
accaaggtac tacatatgca tgtgcacaag tgctgttgtg gtagtgcacc actagggtag    1680
tgttacagtt gcactggttt ttctggcatg ttcagaaaat tggaggtggg ctcgccggga    1740
tccaaggcac cttctacggc ggcacgggct gttttcaccg caggaaggtc atctacggca    1800
tgccgcctcc ggacaccgtc aagcacgaga caagaggtaa taaaactggg cacgcacaag    1860
atgagatcat ccgacgtaaa ttgaagtatt tggtcagtgc atttcagttc gactagggca    1920
tatcaaatgg ctgttctgaa tttgccaggt tcaccatctt acaaggagct gcaagccaag    1980
tttgggagct caaggagtt gatcgaatca tctaggaaca tcatctcagg ggacctgctc    2040
gctagaccaa ccgtagatat atcgagtcgt gtcgaaatgg caaaacaagt aggcgactgc    2100
aactatgagg ctggcacatg ttggggccaa gaggtgtgct tagcttcgtt gccgtatttt    2160
tgcaggtttt gctacagtac ggccacatct acacaccttc tgcagtttct ctctattaca    2220
gtttcttcca tgtattttg cagattgggt gggtctatgg atcaatgaca gaggacattt    2280
tgaccggtca acggatccag gcggcgggtt gggaatcggc cttgttggac accgacccac    2340
cggcattcct gggatgtgct ccgaccggtg gaccagccag cttgacccag ttcaagagat    2400
gggcaacagg gcttctggag atactcatca gccggaacag ccccatcctc ggcaccatct    2460
tcaagggcct ccaactccgg caatgccttg gctatctcat cgtagacgcg tggcccgtga    2520
gggcgccttt cgagctgtgc tatgcgctct tgggacctt ctgccttctc acaaaccaat    2580
ccttcttacc aacggtacac acatttttgc catgacccat tactacattg ctcatagctg    2640
aaattttagt gcatttgccg ttttgcaggc atcagatgaa ggttttcaca tcccagcggc    2700 tctattttg acttacaaca tataccacct gatggagtac aaggagtgcg ggctctcggt    2760
ccgcgcctgg tggaacaacc ataggatgca acgcatcacc tcggcctccg cctggctcct    2820
cgccttcctc accgtcatcc tcaagacgct agggctctcc gagaccgtgt tcgaggtcac    2880
ccgcaaggag agcagcacgt catccgatgg cggcgcgggc accgacgatg ccgatcctgg    2940
gttgttcacc tttgactcgg cgcccgtttt catcccagtg acggcgctct cagtgttgaa    3000
cattgtcgcc ctcaccgtcg cggcatgcg cgccgtcgtc gggacggtgg cgggcgttca    3060
tggtggcccg ggcgtcggag agttcgtgtg ctgtggctgg atggtgttgt gcttctggcc    3120
attcgtgaga gggcttgtca gtagtggaaa gtatgggatc ccgtgagtg tcagggtgaa    3180 ggctggggttg attgtggctg cgttcgtgca cctctgcaca aggaactaac cggccg       3236
```

<210> SEQ ID NO 35
<211> LENGTH: 3316
<212> TYPE: DNA
<213> ORGANISM: artificial
<220> FEATURE:
<223> OTHER INFORMATION: synthetic

<400> SEQUENCE: 35

```
tgtcccgatc ggaaatgcac cgaggagagg atagtttatc cggtctttat aaatgcactc    60
tagcatttgt tgcttgtgga tgtgggtgga gctgtggtgt tgtgctgcta gctagtctgc   120
tactgctagt ggctagctac ctctcggcca cggccatggc gggcggcaag aagctgcagg   180
agagggtcgc cctgggcagg agcgcgtgga tgctggccga cttcgtgatc ctcttcctcg   240
tcctcgccct cgtggcccgc cgcgccgcgt cgctcgggga gcgcggcggg acgtggctgg   300
cagcgctcgt ctgcgaggcg tggttcgcct tcgtgtggat cctcaacatg aacggcaagt   360
ggagccccgt ccggttcgac acctaccccg agaacctctc ccacaggtac gtacgttctt   420
gtgcacacta actgcaaaat aatgttgacc tacagcttcg tgcaacttct tccttaagct   480
gtgtcgtgtc tgtgatgatt tgctaggat ggaagagctc ccggcggtgg acatgttcgt    540
cacgacggcg gacccggcgc tggagccgcc gttgatcacg gtgaacacgg tgctctcgct   600
gctcgccctg gactacccgc acgtcggcaa gctggcgtgc tacgtctccg acgacggctg   660
ctcccccttg acgtgctact ctctgcgcga ggccgccaag ttcgccagcc tctgggttcc   720
cttctgcaag aggcacgacg ttggtgtgag ggccccttc atgtacttct cttccgcgcc    780
ggaggttgac accggtacag tcgaccacga gttcctggaa agctgggcac tcatgaaggt   840
cagccgatga tgatgatgtc agtttccata atgtttggtc gtccatcatc gccatgacca   900
tgcatcttcc ttgtgtacgt gtgactttca gagcgaatat gagaagctgg ccagccggat   960
cgagaacgcc gacgaggtct ccattctgcg tgacggcggc gacgagttcg ccgagttcat  1020
cgacgccgag cgcgggaacc atcctaccat cgttaaggtc gctgcactga ccatatccac  1080
gtgtccatgt acatcgtgtc gtgccaaacg catagcgaat ccgtctcgtg ctaatatcgt  1140
cacggttaac ctgtctgagt tcaggttctc tgggataaca gcaagaacaa acaggtgaa   1200 ggattcccac atctggtgta cctctcgaga gagaaaagcc ccagacatcg tcacaacttt  1260
aaggccggtg ccatgaatgt tctggtgagc tctcttctac tcaatacagt gttgcactac  1320
taatcagtgt gtcacacaaa cagcaaaaag tggcagataa aagctcagac ggttgcacga  1380
cacatttgat actaattaag ctgagcattt cgtggtgcag acaagggtgt cggccgtgat  1440
gaccaacgct ccgatcatgc tgaatgtgga ctgcgacatg tttgccaaca cccgcaggt   1500 cgccctacac gcgatgtgcc tcctgttggg gttcgacgac gagatccaca gcgggttcgt  1560
ccaggcgcca cagaagttct acggtggcct caaggatgac ccctttggca accagatgca  1620
ggttataacc aaggtactac atatgcatgt gcacaagtgc tgttgtggta gtgcaccact  1680
agggtagtgt tacagttgca ctggtttttc tggcatgttc agaaaattgg aggtgggctc  1740
gccgggatcc aaggcacgtt ctacggcggc acgggctgtt ttcaccgcag gaaggtcatt  1800
tacggcatgc cgcctccgga caccgtcaag cacgagacaa gaggtaataa aactgggcac  1860
acaaaagatg aggcatccgg cgtaaattgg agtatttggc cagtgcattt cagttcgact  1920
agggcatatc aaatggcttt ctgaatttgc caggttcacc atcttacaag gagctgcaag  1980
ccaagtttgg gagctcaaag gagttgatcg aatcatctag gaacatcatc tcaggagacc  2040
tgctcgctag accaaccgta gatatatcaa gtcgggtcga aatggcaaaa caagtaggcg  2100
actgcaacta tgaggctggc acatgttggg gccaagaggt gtgcttagct tcgttgccgt  2160
atttttgcag gttttgctac agtacggcca catctacaaa ccttctgcag tttctctcta  2220
ttacagtttc ttccatctat ttttgcagat tgggtgggtc tatggatcaa tgacagagga  2280
cattttgacc gggcaacgga tccaagcggc gggttgaaa tcggccttgt tggacaccga   2340
cccaccggca ttcttgggat gtgctccgac aggggggccg gctagcttga cccagttcaa  2400
```

```
gagatgggca acagggcttc tggagatact catcagccgg aacagcccca tcctcggcac    2460
catcttcagg cgcctccaac tccggcaatg ccttgcctat ctcatcgtca acgcgtggcc    2520
catgagggca cctttcgaga tgtgttacgc gctattggga cctttctgcc ttctcacaaa    2580
ccagtccttc ttgccaacgg tacacacatt tttgccatga ccctttacta cattgctcat    2640
agctgaaatt tcagtacacg tggtgatgtg gaaacacaag tctatgcaac taaacaaaaa    2700
tgtttgtgta atttgtttga taagatttgt gcatttgctg ttttgcagac atctaatgaa    2760
ggttttcgca tcccagcggc tctattcttg agttaccacg tataccacct gatggagtac    2820
aaggagtgcg ggctctcggt ccgcgcctgg tggaacaacc acaggatgca acgcatcacc    2880
tcggcctccg cctggctcct cgccttcctc accgtcatcc tcaagacgct agggctctcc    2940
gagaccgtgt tcgaggtcac ccgcaaggag agcagcacgt cctccgatgg tggcgcgggc    3000
accgacgagg ccgatactgg gctgttcacc ttcgactcgg cgcccgtttt catcccggtg    3060
acggcgctct caatgctgaa cattgtcgcc ctcgccgtcg cggcatggcg cgccgttgtc    3120
gggacggcgg cgggcgttca tggtggcccg ggagtcggag agttcgtgtg ctgtggctgg    3180
atggtgctgt gcttctggcc gttcatgaga gggcttgtca gcagtggaaa gtatgggatc    3240
ccgtggagtg tcagggtgaa ggctgggttg attgtggctg cgttcgtgca cctctgcaca    3300
aggaactaac cggcgg                                                    3316

<210> SEQ ID NO 36
<211> LENGTH: 3181
<212> TYPE: DNA
<213> ORGANISM: artificial
<220> FEATURE:
<223> OTHER INFORMATION: synthetic

<400> SEQUENCE: 36
ctgctctcgg ccacggccat ggcgggcggc aagaagctgc aggagagggt cgccctgggc      60
aggagtgcgt ggatgctggc cgacttcgtg atcctcttcc tcctcctcgc cctcgtggcc     120
cgccgcgccg cgtcgctcgg ggagcgcggc gggacgtggc tggcagcgct cgtctgcgag     180
gcgtggttcg ccttcgtgtg gatcctcaac atgaacggca agtggagccc cgtccggttc     240
gacacctacc ccgacaacct ctcccacagg tacgtacgtt cttgtgcaca ctaactgcaa     300
aataatgttg acctacaact tcgtgcaact tcttccttaa actgtgtcgt gtctgtgatg     360
attttgctag gatggaggag ctcccagcgg tggacatgtt cgtcacgacg gcggacccgg     420
cgctggagcc gccgttgatc acggtgaaca cggtgctctc gctgctcgcc ctggactacc     480
cgcacgtcgg caagctggcg tgctacgtct ccgacgacgg ctgctccccc ttgacgtgct     540
acggtctgca cgaggccgcc aagttcgcca gcctctgggt tcccttctgc aagaggcacg     600
acgttggtgt gagggcccct ttcatgtact tctcttccgc gccggaggtt gacaccggta     660
cagtcgacca cgagttcctg gaaagctggg cactcatgaa ggtcagccga tgatgatgat     720 gtcagttttcc ataatgtttg gtcgtccatc atcgccatga ccatgcatct tcctcgtgta     780
cgtgtgactt tcagagcgaa tatgagaagc tggccagccg gatcgagaac gccgacgagg     840
tctccattct gcgtgacggc ggcgacgagt tcgccgagtt catcgacgcc gagcgcggga     900
accatcctac catcgttaag gtcgctgcac tgaccatatc cacgtgtcca tgtacatcgt     960
gtcgtgccaa acgcatagcg aatccgtctc gtgctaatat cgtcacggtt aacctgtctg    1020
agttcaggtt ctctgggata acagcaagaa caaaacaggt gaaggattcc cacatctggt    1080
```

```
gtacctctcg agagagaaaa gccccagaca tcgtcacaac tttaaggccg gtgccatgaa    1140
tgttctggtg agcactctct tctactcaat acagtgttgc actactaatc agtgtgtcac    1200
acaaacagca aaaagtggca gataaaagct cagacggttg cacgacacat ttgatactaa    1260
ttaagctgag catttcgtgg tgcagacaag ggtgtcggcc gtgatgacca acgctccgat    1320
catgctgaat gtggactgcg acatgtttgc caacaacccg caggtcgccc tacacgcgat    1380
gtgcctcctg ttggggttcg acgacgagat ccacagcggg ttcgtccagg cgccacagaa    1440
gttctacggt ggcctcaagg atgacccctt tggcaaccag atgcaggtta taaccaaggt    1500
actacatatg catgtgcaca agtgctgttg tggtagtgca ccactagggt agtgttacag    1560
ttgcactggt ttttctggca tgttcagaaa attggaggtg ggctcgccgg gatccaaggc    1620
acgttctacg gcggcacggg ctgttttcac cgcaggaagg tcatttacgg catgccgcct    1680
ccggacaccg tcaagcacga gacaagaggt aataaaactg ggcacacaaa agatgaggca    1740
tccggcgtaa attggagtat ttggccagtg catttcagtt cgactagggc atatcaaatg    1800
gctttctgaa tttgccaggt tcaccatctt acaaggagct gcaagccaag tttgggagct    1860
caaaggagtt gatcgaatca tctaggaaca tcatctcagg agacctgctc gctagaccaa    1920
ccgtagatat atcaagtcgg gtcgaaatgg caaaacaagt aggcgactgc aactatgagg    1980
ctggcacata ttggggccaa gaggtgtgct tagcttcgtt gccgtatttt tgcaggtttt    2040
gctacagtac ggccacatct acaaaccttc tgcagtttct ctctattaca gtttcttcca    2100
tctattttg cagattgggt gggtctatgg atcaatgaca gaggacattt tgaccgggca    2160
acggatccaa gcggcgggtt ggaaatcggc cttgttggac accgacccac cggcattctt    2220
gggatgtgct ccgacagggg ggccggctag cttgacccag ttcaagagat gggcaacagg    2280
gcttctggag atactcatca gccggaacag ccccatcctc ggcaccatct tcaggcgcct    2340
ccaactccgg caatgccttg cctatctcat cgtcaacgcg tggcccatga gggcaccttt    2400
cgagatgtgt tacgcgctat tgggaccttt ctgccttctc acaaaccagt ccttcttgcc    2460
aacggtacac acatttttgc catgacccct tactacattg ctcatagctg aaatttcagt    2520
acacgtggta atgtggaaac acaagtctat gcaactaaac aaaaatgttt gtgtaatttg    2580
tttgataaga tttgtgcatt tgctgttttg cagacatcta atgaaggttt tcgcatccca    2640
gcggctctat tcttgagtta ccacgtatac cacctgatgg agtacaagga gtgcgggctc    2700
tcggtccgcg cctggtggaa caaccacagg atgcaacgca tcacctcggc tccgcctgg    2760
ctcctcgcct tcctcaccgt catcctcaag acgctagggc tctccgagac cgtgttcgag    2820
gtcacccgca aggagagcag cacgtcctcc gatggtggcg cgggcaccga cgaggccgat    2880
actgggctgt tcaccttcga ctcggcgccc gttttcatcc cggtgacggc gctctcaatg    2940
ctgaacattg tcgccctcgc cgtcgcggca tggcgcgccg ttgtcgggac ggcggcgggc    3000
gttcatggtg gcccgggagt cggagagttc gtgtgctgtg gctggatggt gctgtgcttc    3060
tggccgttca tgagagggct tgtcagcagt ggaaagtatg ggatcccgtg gagtgtcagg    3120
gtgaaggctg ggttgattgt ggctgcgttc gtgcacctct gcacaaggaa ctaaccggcg    3180
g                                                                    3181
```

<210> SEQ ID NO 37
<211> LENGTH: 752
<212> TYPE: PRT
<213> ORGANISM: Triticum aestivum

<400> SEQUENCE: 37

```
Met Ala Gly Gly Lys Lys Leu His Glu Arg Val Ala Leu Gly Arg Thr
1               5                   10                  15
Ala Trp Met Leu Ala Asp Phe Val Ile Leu Leu Leu Leu Leu Ala Leu
            20                  25                  30
Val Ala Arg Arg Ala Ala Ser Leu Gly Glu Arg Gly Gly Thr Trp Leu
        35                  40                  45
Ala Ala Leu Val Cys Glu Ala Trp Phe Ala Phe Val Trp Ile Leu Asn
    50                  55                  60
Met Asn Gly Lys Trp Ser Pro Val Arg Phe Asp Thr Tyr Pro Glu Asn
65                  70                  75                  80
Leu Ser His Arg Leu Glu Glu Leu Pro Ala Val Asp Met Phe Val Thr
                85                  90                  95
Thr Ala Asp Pro Ala Leu Glu Pro Pro Leu Ile Thr Val Asn Thr Val
            100                 105                 110
Leu Ser Leu Leu Ala Leu Asp Tyr Pro Asp Val Gly Lys Leu Ala Cys
        115                 120                 125
Tyr Val Ser Asp Asp Gly Cys Ser Pro Val Thr Cys Tyr Ala Leu Arg
    130                 135                 140
Glu Ala Ala Lys Phe Ala Ser Leu Trp Ile Pro Phe Cys Lys Arg Tyr
145                 150                 155                 160
Asp Val Gly Val Arg Ala Pro Phe Met Tyr Phe Ser Ser Ala Pro Glu
                165                 170                 175
Val Gly Thr Gly Thr Ala Asp His Glu Phe Leu Glu Ser Trp Ala Leu
            180                 185                 190
Met Lys Thr Glu Tyr Glu Lys Leu Ala Ser Arg Ile Glu Asn Ala Asp
        195                 200                 205
Glu Val Ser Ile Leu Arg Asp Gly Gly Glu Gly Phe Ala Glu Phe Ile
    210                 215                 220
Asp Ala Glu Arg Gly Asn His Pro Thr Ile Val Lys Val Leu Trp Asp
225                 230                 235                 240
Asn Ser Lys Ser Lys Ala Gly Glu Gly Phe Pro His Leu Val Tyr Leu
                245                 250                 255
Ser Arg Glu Lys Ser Pro Arg His Arg His Asn Phe Lys Ala Gly Ala
            260                 265                 270
Met Asn Val Leu Thr Arg Val Ser Ala Val Met Thr Asn Ala Pro Ile
        275                 280                 285
Met Leu Asn Val Asp Cys Asp Met Phe Ala Asn Asn Pro Gln Val Ala
    290                 295                 300
Leu His Ala Met Cys Leu Leu Leu Gly Phe Asp Asp Glu Ile His Ser
305                 310                 315                 320
Gly Phe Val Gln Ala Pro Gln Lys Phe Tyr Gly Gly Leu Lys Asp Asp
                325                 330                 335
Pro Phe Gly Asn Gln Met Gln Val Ile Thr Lys Lys Ile Gly Gly Gly
            340                 345                 350
Leu Ala Gly Ile Gln Gly Thr Phe Tyr Gly Gly Thr Gly Cys Phe His
        355                 360                 365
Arg Arg Lys Val Ile Tyr Gly Met Pro Pro Asp Thr Val Lys His
    370                 375                 380
Glu Thr Arg Gly Ser Pro Ser Tyr Lys Glu Leu Gln Ala Lys Phe Gly
385                 390                 395                 400
Ser Ser Lys Glu Leu Ile Glu Ser Arg Asn Ile Ser Gly Asp
                405                 410                 415
```

-continued

```
Leu Leu Ala Arg Pro Thr Val Asp Ile Ser Ser Arg Val Glu Met Ala
            420                 425                 430

Lys Gln Val Gly Asp Cys Asn Tyr Glu Ala Gly Thr Cys Trp Gly Gln
        435                 440                 445

Glu Ile Gly Trp Val Tyr Gly Ser Met Thr Glu Asp Ile Leu Thr Gly
    450                 455                 460

Gln Arg Ile Gln Ala Ala Gly Trp Glu Ser Ala Leu Leu Asp Thr Asp
465                 470                 475                 480

Pro Pro Ala Phe Leu Gly Cys Ala Pro Thr Gly Pro Ala Ser Leu
                485                 490                 495

Thr Gln Phe Lys Arg Trp Ala Thr Gly Leu Leu Glu Ile Leu Ile Ser
        500                 505                 510

Arg Asn Ser Pro Ile Leu Gly Thr Ile Phe Lys Gly Leu Gln Leu Arg
    515                 520                 525

Gln Cys Leu Gly Tyr Leu Ile Val Asp Ala Trp Pro Val Arg Ala Pro
530                 535                 540

Phe Glu Leu Cys Tyr Ala Leu Leu Gly Pro Phe Cys Leu Leu Thr Asn
545                 550                 555                 560

Gln Ser Phe Leu Pro Thr Ala Ser Asp Glu Gly Phe His Ile Pro Ala
                565                 570                 575

Ala Leu Phe Leu Thr Tyr Asn Ile Tyr His Leu Met Glu Tyr Lys Glu
                580                 585                 590

Cys Gly Leu Ser Val Arg Ala Trp Asn Asn His Arg Met Gln Arg
                595                 600                 605

Ile Thr Ser Ala Ser Ala Trp Leu Leu Ala Phe Leu Thr Val Ile Leu
    610                 615                 620

Lys Thr Leu Gly Leu Ser Glu Thr Val Phe Glu Val Thr Arg Lys Glu
625                 630                 635                 640

Ser Ser Thr Ser Ser Asp Gly Ala Gly Thr Asp Asp Ala Asp Pro
                645                 650                 655

Gly Leu Phe Thr Phe Asp Ser Ala Pro Val Phe Ile Pro Val Thr Ala
                660                 665                 670

Leu Ser Val Leu Asn Ile Val Ala Leu Thr Val Ala Ala Trp Arg Ala
        675                 680                 685

Val Val Gly Thr Val Ala Gly Val His Gly Gly Pro Gly Val Gly Glu
    690                 695                 700

Phe Val Cys Cys Gly Trp Met Val Leu Cys Phe Trp Pro Phe Val Arg
705                 710                 715                 720

Gly Leu Val Ser Ser Gly Lys Tyr Gly Ile Pro Trp Ser Val Arg Val
                725                 730                 735

Lys Ala Gly Leu Ile Val Ala Ala Phe Val His Leu Cys Thr Arg Asn
                740                 745                 750
```

<210> SEQ ID NO 38
<211> LENGTH: 752
<212> TYPE: PRT
<213> ORGANISM: Triticum aestivum

<400> SEQUENCE: 38

```
Met Ala Gly Gly Lys Lys Leu Gln Glu Arg Val Ala Leu Gly Arg Ser
1               5                   10                  15

Ala Trp Met Leu Ala Asp Phe Val Ile Leu Phe Leu Val Leu Ala Leu
            20                  25                  30

Val Ala Arg Arg Ala Ala Ser Leu Gly Glu Arg Gly Gly Thr Trp Leu
        35                  40                  45
```

```
Ala Ala Leu Val Cys Glu Ala Trp Phe Ala Phe Val Trp Ile Leu Asn
        50                  55                  60

Met Asn Gly Lys Trp Ser Pro Val Arg Phe Asp Thr Tyr Pro Glu Asn
 65                  70                  75                  80

Leu Ser His Arg Met Glu Glu Leu Pro Ala Val Asp Met Phe Val Thr
                     85                  90                  95

Thr Ala Asp Pro Ala Leu Glu Pro Pro Leu Ile Thr Val Asn Thr Val
                100                 105                 110

Leu Ser Leu Leu Ala Leu Asp Tyr Pro His Val Gly Lys Leu Ala Cys
            115                 120                 125

Tyr Val Ser Asp Asp Gly Cys Ser Pro Leu Thr Cys Tyr Ser Leu Arg
        130                 135                 140

Glu Ala Ala Lys Phe Ala Ser Leu Trp Val Pro Phe Cys Lys Arg His
145                 150                 155                 160

Asp Val Gly Val Arg Ala Pro Phe Met Tyr Phe Ser Ser Ala Pro Glu
                165                 170                 175

Val Asp Thr Gly Thr Val Asp His Glu Phe Leu Glu Ser Trp Ala Leu
                180                 185                 190

Met Lys Ser Glu Tyr Glu Lys Leu Ala Ser Arg Ile Glu Asn Ala Asp
            195                 200                 205

Glu Val Ser Ile Leu Arg Asp Gly Asp Glu Phe Ala Glu Phe Ile
        210                 215                 220

Asp Ala Glu Arg Gly Asn His Pro Thr Ile Val Lys Val Leu Trp Asp
225                 230                 235                 240

Asn Ser Lys Asn Lys Thr Gly Glu Gly Phe Pro His Leu Val Tyr Leu
                245                 250                 255

Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
        275                 280                 285

Met Leu Asn Val Asp Cys Asp Met Phe Ala Asn Asn Pro Gln Val Ala
290                 295                 300

Leu His Ala Met Cys Leu Leu Leu Gly Phe Asp Asp Glu Ile His Ser
305                 310                 315                 320

Gly Phe Val Gln Ala Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
                340                 345                 350

Leu Ala Gly Ile Gln Gly Thr Phe Tyr Gly Gly Thr Gly Cys Phe His
            355                 360                 365

Arg Arg Lys Val Ile Tyr Gly Met Pro Pro Asp Thr Val Lys His
370                 375                 380

Glu Thr Arg Gly Ser Pro Ser Tyr Lys Glu Leu Gln Ala Lys Phe Gly
385                 390                 395                 400

Ser Ser Lys Glu Leu Ile Glu Ser Arg Asn Ile Ile Ser Gly Asp
                405                 410                 415

Leu Leu Ala Arg Pro Thr Val Asp Ile Ser Ser Arg Val Glu Met Ala
            420                 425                 430

Lys Gln Val Gly Asp Cys Asn Tyr Glu Ala Gly Thr Cys Trp Gly Gln
        435                 440                 445

Glu Ile Gly Trp Val Tyr Gly Ser Met Thr Glu Asp Ile Leu Thr Gly
450                 455                 460
```

```
Gln Arg Ile Gln Ala Ala Gly Trp Lys Ser Ala Leu Leu Asp Thr Asp
465                 470                 475                 480

Pro Pro Ala Phe Leu Gly Cys Ala Pro Thr Gly Gly Pro Ala Ser Leu
            485                 490                 495

Thr Gln Phe Lys Arg Trp Ala Thr Gly Leu Leu Glu Ile Leu Ile Ser
        500                 505                 510

Arg Asn Ser Pro Ile Leu Gly Thr Ile Phe Arg Arg Leu Gln Leu Arg
            515                 520                 525

Gln Cys Leu Ala Tyr Leu Ile Val Asn Ala Trp Pro Met Arg Ala Pro
        530                 535                 540

Phe Glu Met Cys Tyr Ala Leu Leu Gly Pro Phe Cys Leu Leu Thr Asn
545                 550                 555                 560

Gln Ser Phe Leu Pro Thr Thr Ser Asn Glu Gly Phe Arg Ile Pro Ala
            565                 570                 575

Ala Leu Phe Leu Ser Tyr His Val Tyr His Leu Met Glu Tyr Lys Glu
            580                 585                 590

Cys Gly Leu Ser Val Arg Ala Trp Trp Asn Asn His Arg Met Gln Arg
            595                 600                 605

Ile Thr Ser Ala Ser Ala Trp Leu Leu Ala Phe Leu Thr Val Ile Leu
        610                 615                 620

Lys Thr Leu Gly Leu Ser Glu Thr Val Phe Glu Val Thr Arg Lys Glu
625                 630                 635                 640

Ser Ser Thr Ser Ser Asp Gly Gly Ala Gly Thr Asp Glu Ala Asp Thr
                645                 650                 655

Gly Leu Phe Thr Phe Asp Ser Ala Pro Val Phe Ile Pro Val Thr Ala
            660                 665                 670

Leu Ser Met Leu Asn Ile Val Ala Leu Ala Val Ala Ala Trp Arg Ala
            675                 680                 685

Val Val Gly Thr Ala Ala Gly Val His Gly Gly Pro Gly Val Gly Glu
            690                 695                 700

Phe Val Cys Cys Gly Trp Met Val Leu Cys Phe Trp Pro Phe Met Arg
705                 710                 715                 720

Gly Leu Val Ser Ser Gly Lys Tyr Gly Ile Pro Trp Ser Val Arg Val
                725                 730                 735

Lys Ala Gly Leu Ile Val Ala Ala Phe Val His Leu Cys Thr Arg Asn
            740                 745                 750

<210> SEQ ID NO 39
<211> LENGTH: 752
<212> TYPE: PRT
<213> ORGANISM: Triticum aestivum

<400> SEQUENCE: 39

Met Ala Gly Gly Lys Lys Leu Gln Glu Arg Val Ala Leu Gly Arg Ser
1               5                   10                  15

Ala Trp Met Leu Ala Asp Phe Val Ile Leu Phe Leu Leu Leu Ala Leu
            20                  25                  30

Val Ala Arg Arg Ala Ala Ser Leu Gly Glu Arg Gly Gly Thr Trp Leu
        35                  40                  45

Ala Ala Leu Val Cys Glu Ala Trp Phe Ala Phe Val Trp Ile Leu Asn
    50                  55                  60

Met Asn Gly Lys Trp Ser Pro Val Arg Phe Asp Thr Tyr Pro Asp Asn
65              70                  75                  80

Leu Ser His Arg Met Glu Glu Leu Pro Ala Val Asp Met Phe Val Thr
            85                  90                  95
```

```
Thr Ala Asp Pro Ala Leu Glu Pro Leu Ile Thr Val Asn Thr Val
            100                 105                 110

Leu Ser Leu Leu Ala Leu Asp Tyr Pro His Val Gly Lys Leu Ala Cys
            115                 120                 125

Tyr Val Ser Asp Asp Gly Cys Ser Pro Leu Thr Cys Tyr Gly Leu His
    130                 135                 140

Glu Ala Ala Lys Phe Ala Ser Leu Trp Val Pro Phe Cys Lys Arg His
145                 150                 155                 160

Asp Val Gly Val Arg Ala Pro Phe Met Tyr Phe Ser Ser Ala Pro Glu
                165                 170                 175

Val Asp Thr Gly Thr Val Asp His Glu Phe Leu Glu Ser Trp Ala Leu
            180                 185                 190

Met Lys Ser Glu Tyr Glu Lys Leu Ala Ser Arg Ile Glu Asn Ala Asp
            195                 200                 205

Glu Val Ser Ile Leu Arg Asp Gly Gly Asp Glu Phe Ala Glu Phe Ile
    210                 215                 220

Asp Ala Glu Arg Gly Asn His Pro Thr Ile Val Lys Val Leu Trp Asp
225                 230                 235                 240

Asn Ser Lys Asn Lys Thr Gly Glu Gly Phe Pro His Leu Val Tyr Leu
                245                 250                 255

Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
            275                 280                 285

Met Leu Asn Val Asp Cys Asp Met Phe Ala Asn Asn Pro Gln Val Ala
290                 295                 300

Leu His Ala Met Cys Leu Leu Leu Gly Phe Asp Asp Glu Ile His Ser
305                 310                 315                 320

Gly Phe Val Gln Ala Pro Gln Lys Phe Tyr Gly Gly Leu Lys Asp Asp
                325                 330                 335

Pro Phe Gly Asn Gln Met Gln Val Ile Thr Lys Lys Ile Gly Gly Gly
            340                 345                 350

Leu Ala Gly Ile Gln Gly Thr Phe Tyr Gly Gly Thr Gly Cys Phe His
            355                 360                 365

Arg Arg Lys Val Ile Tyr Gly Met Pro Pro Asp Thr Val Lys His
    370                 375                 380

Glu Thr Arg Gly Ser Pro Ser Tyr Lys Glu Leu Gln Ala Lys Phe Gly
385                 390                 395                 400

Ser Ser Lys Glu Leu Ile Glu Ser Ser Arg Asn Ile Ile Ser Gly Asp
                405                 410                 415

Leu Leu Ala Arg Pro Thr Val Asp Ile Ser Ser Arg Val Glu Met Ala
            420                 425                 430

Lys Gln Val Gly Asp Cys Asn Tyr Glu Ala Gly Thr Tyr Trp Gly Gln
            435                 440                 445

Glu Ile Gly Trp Val Tyr Gly Ser Met Thr Glu Asp Ile Leu Thr Gly
            450                 455                 460

Gln Arg Ile Gln Ala Ala Gly Trp Lys Ser Ala Leu Leu Asp Thr Asp
465                 470                 475                 480

Pro Pro Ala Phe Leu Gly Cys Ala Pro Thr Gly Gly Pro Ala Ser Leu
                485                 490                 495

Thr Gln Phe Lys Arg Trp Ala Thr Gly Leu Leu Glu Ile Leu Ile Ser
            500                 505                 510
```

Arg Asn Ser Pro Ile Leu Gly Thr Ile Phe Arg Arg Leu Gln Leu Arg
            515                 520                 525

Gln Cys Leu Ala Tyr Leu Ile Val Asn Ala Trp Pro Met Arg Ala Pro
        530                 535                 540

Phe Glu Met Cys Tyr Ala Leu Leu Gly Pro Phe Cys Leu Leu Thr Asn
545                 550                 555                 560

Gln Ser Phe Leu Pro Thr Thr Ser Asn Glu Gly Phe Arg Ile Pro Ala
            565                 570                 575

Ala Leu Phe Leu Ser Tyr His Val Tyr His Leu Met Glu Tyr Lys Glu
            580                 585                 590

Cys Gly Leu Ser Val Arg Ala Trp Trp Asn Asn His Arg Met Gln Arg
        595                 600                 605

Ile Thr Ser Ala Ser Ala Trp Leu Leu Ala Phe Leu Thr Val Ile Leu
    610                 615                 620

Lys Thr Leu Gly Leu Ser Glu Thr Val Phe Glu Val Thr Arg Lys Glu
625                 630                 635                 640

Ser Ser Thr Ser Ser Asp Gly Gly Ala Gly Thr Asp Glu Ala Asp Thr
            645                 650                 655

Gly Leu Phe Thr Phe Asp Ser Ala Pro Val Phe Ile Pro Val Thr Ala
        660                 665                 670

Leu Ser Met Leu Asn Ile Val Ala Leu Ala Val Ala Ala Trp Arg Ala
    675                 680                 685

Val Val Gly Thr Ala Ala Gly Val His Gly Gly Pro Gly Val Gly Glu
        690                 695                 700

Phe Val Cys Cys Gly Trp Met Val Leu Cys Phe Trp Pro Phe Met Arg
705                 710                 715                 720

Gly Leu Val Ser Ser Gly Lys Tyr Gly Ile Pro Trp Ser Val Arg Val
            725                 730                 735

Lys Ala Gly Leu Ile Val Ala Ala Phe Val His Leu Cys Thr Arg Asn
            740                 745                 750

<210> SEQ ID NO 40
<211> LENGTH: 2888
<212> TYPE: DNA
<213> ORGANISM: artificial
<220> FEATURE:
<223> OTHER INFORMATION: synthetic

<400> SEQUENCE: 40

| | | | | | |
|---|---|---|---|---|---|
| cttaagatgg | ctagcatgac | tggtggacag | caaatgggtg | ccccggcagt | cactcgccga | 60 |
| gccaacgctc | tccgcgtcga | ggccccggac | ggcaatgccg | agagcgggcg | cgccagccta | 120 |
| gcagcagact | cccccgcggc | caagcgggcc | atcgatgcca | aggacgatgt | gtgggtggcc | 180 |
| gcggctgagg | gagacgcgtc | tggagccagc | gccggcaacg | cgaccggcc | gccgctgttc | 240 |
| cggaccatga | aggtcaaggg | aagcatcctc | catccttaca | ggttcatgat | cctcgtgcgc | 300 |
| ttggtcgccg | tcgtcgcgtt | cttcgcgtgg | cgcctgaagc | acaagaacca | cgacggcatg | 360 |
| tggctctggg | ccacgtccat | ggtcgccgac | gtctggttcg | gcttctcatg | gctcctcaac | 420 |
| cagctgccca | agctcaaccc | catcaagcgc | gtccccgacc | tggccgccct | cgccgaccag | 480 |
| tgcggctcct | ccgcgacgc | caacctgcca | ggcatcgaca | tcttcgtcac | caccgtggac | 540 |
| cccgtggacg | aacccatctt | gtacaccgtg | aacaccatac | tctccatcct | cgccaccgac | 600 |
| taccctgtcg | ataagtacgc | ctgctacctc | tcagacgacg | gcggcacgtt | ggtgcactac | 660 |
| gaggccatga | tcgaagtggc | caatttcgcg | gtgatgtggg | tcccttttg | ccggaagcac | 720 |

```
tgtgtcgagc caaggtcccc cgagaactac tttgggatga aaacgcagcc gtacgtcggg    780
agtatggctg gagaattcat gagggagcat aggcgtgtgc gcagagagta tgatgagttc    840
aaggtgagga tagactccct gtccaccacc atccgccaaa gatctgatgc gtacaactcg    900
agcaacaaag gagatggtgt gcgtgcaacc tggatggctg atgggacaca atggcctggt    960
acgtggattg agcaggttga gaaccaccgg agaggacaac atgctggaat tgttcaggtc   1020
atactaagcc atcctagttg caaaccgcaa ctggggtctc cggcgagcac tgacaatcca   1080
cttgacttca gcaacgttga cacgaggctg cccatgctcg tctacatgtc ccgggagaag   1140
cgccccggtt ataaccacca aaagaaggca ggcgccatga acgtgatgct ccgtgtctcg   1200
gcgttgctct ccaacgcgcc attcgtcgtc aattttgact gcgaccacta catcaacaac   1260
acgcaagctc tccgcgcccc tatgtgcttc atgctcgacc ctcgcgacgg tcagaacacg   1320
gccttcgtcc agtttccgca cgcgttcgac gacgtcgacc cgacggaccg ctacgccaac   1380
cacaaccgtg tcttcttcga cggtaccatg ctctccctca acggccttca agggccttcc   1440
tacctcggca ctggcaccat gttccgtcgt gtcacgctct atggcatgga gccaccacgt   1500
tatagagcgg agaacatcaa gcttgtaggt aagacctatg agttcggtag ctcgacgtct   1560
ttcatcaatt ccatgccgga cggcgcaatc caagagcggt ctatcacacc ggtgttggtc   1620
gacgaggcac tcagcaatga cctggctacc ctgatgacgt gtgcttacga ggacgggacc   1680
tcatggggga gagacgttgg gtgggtgtac aacatcgcga cggaggacgt ggtgaccgga   1740
ttccgcatgc accggcaggg gtggcgctcc atgtattgct ccatggagcc ggccgccttc   1800
cgcggaacag cgccgatcaa cctcaccgag cgcctttacc aggtgctccg gtggtcgggc   1860
ggctctctcg agatgttctt ctcccacagc aacgctctca tggccggccg ccgtatccac   1920
cctctgcagc gtgtcgcgta cctcaacatg tcgacctacc cgatcgtcac ggtgttcatc   1980
ctggcctaca acctcttccc cgtcatgtgg ctcttctccg agcagttcta catccagagg   2040
ccgttcggca cgtacatcat gtacctcgtc ggcgtcatag cgatgattca cgtgatcggc   2100
atgttcgagg tgaaatgggc ggggatcacg ctgctcgact ggtgccgcaa cgagcagttc   2160
tacatgatcg gggcgacggg cgtgtacccg acggcggtgc tttacatggc gctcaagctt   2220
gtcacgggga aggggatata cttcaggctc acatccaagc agacggacgc ttgctccaac   2280
gacaagttcg ccgacctgta cacggtgcgg tgggtgccgc tgctgttccc gacggtcgca   2340
gtgctcatcg tgaacgtcgc ggctgtcggg gcagcgatag gcaaggcagc agcgtggggc   2400
ttcttcacgg accaggcgcg gcacgtgctg ctcgggatgt gttcaacgt gtggatcctc   2460 gtgctcctct acccgtttgc gctcgggatc atggggaaat gggggaagag acccatcatc   2520
ctgttcgtca tgttgatcat ggccattggc gccgtcgggc tcgtgtatgt cgccttccat   2580
gatccctacc caactgattt ttcagaagtt gcagcttctc ttggtgaagc atcgctgacc   2640
gggccatctg ggtagacacg tacggctctt ttttttacaa gtacagccag agtcactgca   2700
ataatttgag tgtgtgtatt catgtctact tatatagcat gagaactggt cattgtgtgc   2760
cactcctcta ctctagtaga gtataaatgt acctatcttt tctttggaaa aaaactgaag   2820
tgcggcttgt gctcttttgg aaaaaaaaaa aaaaaaaaaa gtactctgcg ttgataccac   2880
tgcttaag                                                             2888
```

<210> SEQ ID NO 41
<211> LENGTH: 882
<212> TYPE: PRT
<213> ORGANISM: Hordeum vulgare

<400> SEQUENCE: 41

```
Met Ala Ser Met Thr Gly Gly Gln Gln Met Gly Ala Pro Ala Val Thr
1               5                   10                  15

Arg Arg Ala Asn Ala Leu Arg Val Glu Ala Pro Asp Gly Asn Ala Glu
            20                  25                  30

Ser Gly Arg Ala Ser Leu Ala Ala Asp Ser Pro Ala Ala Lys Arg Ala
        35                  40                  45

Ile Asp Ala Lys Asp Asp Val Trp Val Ala Ala Glu Gly Asp Ala
    50                  55                  60

Ser Gly Ala Ser Ala Gly Asn Gly Asp Arg Pro Pro Leu Phe Arg Thr
65                  70                  75                  80

Met Lys Val Lys Gly Ser Ile Leu His Pro Tyr Arg Phe Met Ile Leu
                85                  90                  95

Val Arg Leu Val Ala Val Ala Phe Phe Ala Trp Arg Leu Lys His
            100                 105                 110

Lys Asn His Asp Gly Met Trp Leu Trp Ala Thr Ser Met Val Ala Asp
            115                 120                 125

Val Trp Phe Gly Phe Ser Trp Leu Leu Asn Gln Leu Pro Lys Leu Asn
130                 135                 140

Pro Ile Lys Arg Val Pro Asp Leu Ala Ala Leu Ala Asp Gln Cys Gly
145                 150                 155                 160

Ser Ser Gly Asp Ala Asn Leu Pro Gly Ile Asp Ile Phe Val Thr Thr
            165                 170                 175

Val Asp Pro Val Asp Glu Pro Ile Leu Tyr Thr Val Asn Thr Ile Leu
            180                 185                 190

Ser Ile Leu Ala Thr Asp Tyr Pro Val Asp Lys Tyr Ala Cys Tyr Leu
        195                 200                 205

Ser Asp Asp Gly Gly Thr Leu Val His Tyr Glu Ala Met Ile Glu Val
        210                 215                 220

Ala Asn Phe Ala Val Met Trp Val Pro Phe Cys Arg Lys His Cys Val
225                 230                 235                 240

Glu Pro Arg Ser Pro Glu Asn Tyr Phe Gly Met Lys Thr Gln Pro Tyr
            245                 250                 255

Val Gly Ser Met Ala Gly Glu Phe Met Arg Glu His Arg Arg Val Arg
            260                 265                 270

Arg Glu Tyr Asp Glu Phe Lys Val Arg Ile Asp Ser Leu Ser Thr Thr
        275                 280                 285

Ile Arg Gln Arg Ser Asp Ala Tyr Asn Ser Ser Asn Lys Gly Asp Gly
    290                 295                 300

Val Arg Ala Thr Trp Met Ala Asp Gly Thr Gln Trp Pro Gly Thr Trp
305                 310                 315                 320

Ile Glu Gln Val Glu Asn His Arg Arg Gly Gln His Ala Gly Ile Val
                325                 330                 335

Gln Val Ile Leu Ser His Pro Ser Cys Lys Pro Gln Leu Gly Ser Pro
            340                 345                 350

Ala Ser Thr Asp Asn Pro Leu Asp Phe Ser Asn Val Asp Thr Arg Leu
        355                 360                 365

Pro Met Leu Val Tyr Met Ser Arg Glu Lys Arg Pro Gly Tyr Asn His
        370                 375                 380

Gln Lys Lys Ala Gly Ala Met Asn Val Met Leu Arg Val Ser Ala Leu
385                 390                 395                 400

Leu Ser Asn Ala Pro Phe Val Val Asn Phe Asp Cys Asp His Tyr Ile
```

-continued

```
                405                 410                 415
Asn Asn Thr Gln Ala Leu Arg Ala Pro Met Cys Phe Met Leu Asp Pro
            420                 425                 430
Arg Asp Gly Gln Asn Thr Ala Phe Val Gln Phe Pro Gln Arg Phe Asp
            435                 440                 445
Asp Val Asp Pro Thr Asp Arg Tyr Ala Asn His Asn Arg Val Phe Phe
            450                 455                 460
Asp Gly Thr Met Leu Ser Leu Asn Gly Leu Gln Gly Pro Ser Tyr Leu
465                 470                 475                 480
Gly Thr Gly Thr Met Phe Arg Arg Val Thr Leu Tyr Gly Met Glu Pro
                485                 490                 495
Pro Arg Tyr Arg Ala Glu Asn Ile Lys Leu Val Gly Lys Thr Tyr Glu
            500                 505                 510
Phe Gly Ser Ser Thr Ser Phe Ile Asn Ser Met Pro Asp Gly Ala Ile
            515                 520                 525
Gln Glu Arg Ser Ile Thr Pro Val Leu Val Asp Glu Ala Leu Ser Asn
            530                 535                 540
Asp Leu Ala Thr Leu Met Thr Cys Ala Tyr Glu Asp Gly Thr Ser Trp
545                 550                 555                 560
Gly Arg Asp Val Gly Trp Val Tyr Asn Ile Ala Thr Glu Asp Val Val
                565                 570                 575
Thr Gly Phe Arg Met His Arg Gln Gly Trp Arg Ser Met Tyr Cys Ser
            580                 585                 590
Met Glu Pro Ala Ala Phe Arg Gly Thr Ala Pro Ile Asn Leu Thr Glu
            595                 600                 605
Arg Leu Tyr Gln Val Leu Arg Trp Ser Gly Gly Ser Leu Glu Met Phe
610                 615                 620
Phe Ser His Ser Asn Ala Leu Met Ala Gly Arg Arg Ile His Pro Leu
625                 630                 635                 640
Gln Arg Val Ala Tyr Leu Asn Met Ser Thr Tyr Pro Ile Val Thr Val
            645                 650                 655
Phe Ile Leu Ala Tyr Asn Leu Phe Pro Val Met Trp Leu Phe Ser Glu
            660                 665                 670
Gln Phe Tyr Ile Gln Arg Pro Phe Gly Thr Tyr Ile Met Tyr Leu Val
            675                 680                 685
Gly Val Ile Ala Met Ile His Val Ile Gly Met Phe Glu Val Lys Trp
            690                 695                 700
Ala Gly Ile Thr Leu Leu Asp Trp Cys Arg Asn Glu Gln Phe Tyr Met
705                 710                 715                 720
Ile Gly Ala Thr Gly Val Tyr Pro Thr Ala Val Leu Tyr Met Ala Leu
                725                 730                 735
Lys Leu Val Thr Gly Lys Gly Ile Tyr Phe Arg Leu Thr Ser Lys Gln
            740                 745                 750
Thr Asp Ala Cys Ser Asn Asp Lys Phe Ala Asp Leu Tyr Thr Val Arg
            755                 760                 765
Trp Val Pro Leu Leu Phe Pro Thr Val Ala Val Leu Ile Val Asn Val
770                 775                 780
Ala Ala Val Gly Ala Ala Ile Gly Lys Ala Ala Ala Trp Gly Phe Phe
785                 790                 795                 800
Thr Asp Gln Ala Arg His Val Leu Leu Gly Met Val Phe Asn Val Trp
                805                 810                 815
Ile Leu Val Leu Leu Tyr Pro Phe Ala Leu Gly Ile Met Gly Lys Trp
            820                 825                 830
```

```
Gly Lys Arg Pro Ile Ile Leu Phe Val Met Leu Ile Met Ala Ile Gly
        835                 840                 845

Ala Val Gly Leu Val Tyr Val Ala Phe His Asp Pro Tyr Pro Thr Asp
    850                 855                 860

Phe Ser Glu Val Ala Ala Ser Leu Gly Glu Ala Ser Leu Thr Gly Pro
865                 870                 875                 880

Ser Gly

<210> SEQ ID NO 42
<211> LENGTH: 2977
<212> TYPE: DNA
<213> ORGANISM: artificial
<220> FEATURE:
<223> OTHER INFORMATION: synthetic

<400> SEQUENCE: 42
cttaagatgg ctagcatgac tggtggacag caaatgggta tggcgccagc ggtggccgga      60
ggggccgcg  tgcggagcaa tgagccggtt gctgctgctg ccgccgcgcc ggcggccagc     120
ggcaagccct gcgtgtgcgg cttccaggtt tgcgcctgca cggggtcggc cgcggtggcc     180
tccgccgcct cgtcgctgga catggacatc gtggccatgg gcagatcgg  cgccgtcaac     240
gacgagagct gggtgggcgt ggagctcggc gaagatggcg agaccgacga aagcggtgcc     300
gccgttgacg accgccccgt attccgcacc gagaagatca agggtgtcct cctccacccc     360
taccgggtgc tgattttcgt tcgtctgatc gccttcacgc tgttcgtgat ctggcgtatc     420
tcccacaaga acccagacgc gatgtggctg tgggtgacat ccatctgcgg cgagttctgg     480
ttcggtttct cgtggctgct ggatcagctg cccaagctga accccatcaa ccgcgtgccg     540
gacctggcgg tgctgcggca cgcttcgac  cgccccgacg gcacctccac gctcccgggg     600
ctggacatct tcgtcaccac ggccgacccc atcaaggagc ccatcctctc caccgccaac     660
tcggtgctct ccatcctggc cgccgactac cccgtggacc gcaacacatg ctacgtctcc     720
gacgacagtg gcatgctgct cacctacgag gccctggcag agtcctccaa gttcgccacg     780
ctctgggtgc ccttctgccg caagcacggg atcgagccca gggtccgga  gagctacttc     840
gagctcaagt cacacccctta catggggaga gccaggacg  agttcgtcaa cgaccgccgc     900
cgcgttcgca aggagtacga cgagttcaag gccaggatca cagcctgga  gcatgacatc     960
aagcagcgca acgacgggta caacgccgcc attgcccaca gccaaggcgt gccccggccc    1020
acctggatgg cggacggcac ccagtgggag ggcacatggg tcgacgcctc cgagaaccac    1080
cgcagggcg  accacgccgg catcgtactg gtgctgctga accacccgag ccaccgccgg    1140
cagacgggcc cgccggcgag cgctgacaac ccactggact tgagcggcgt ggatgtgcgt    1200
ctccccatgc tggtgtacgt gtcccgtgag aagcgccccg gcacgacca  ccagaagaag    1260
gccggtgcca tgaacgcgct acccgcgcc  tcggcgctgc tctccaactc ccccttcatc    1320
ctcaacctcg actgcgatca ttacatcaac aactcccagg cccttcgcgc cggcatctgc    1380
ttcatggtgg acgggacag  cgacacggtt gccttcgtcc agttcccgca gcgcttcgag    1440
ggcgtcgacc ccaccgacct ctacgccaac acaaccgca  tcttcttcga cggcacccto    1500
cgtgccctgg acggcatgca gggccccatc tacgtcggca ctgggtgtct cttccgccgc    1560
atcaccgtct acggcttcga cccgccgagg atcaacgtcg gcggtcctg  cttcccagg     1620
ctcgccgggc tcttcgccaa gaccaagtac gagaagcccg gctcgagat  gaccacggcc    1680
aaggccaagg ccgcgcccgt gccgccaag  ggtaagcacg gcttcttgcc actgcccaag    1740
```

```
aagacgtacg gcaagtcgga cgccttcgtg gacaccatcc cgcgcgcgtc gcacccgtcg    1800
ccctacgccg cggcggctga ggggatcgtg gccgacgagg cgaccatcgt cgaggcggtg    1860
aacgtgacgg ccgccgcgtt cgagaagaag accggctggg gcaaagagat cggctgggtg    1920
tacgacaccg tcacggagga cgtggtcacc ggctaccgga tgcatatcaa ggggtggcgg    1980
tcacgctact gctccatcta cccacacgcc ttcatcggca ccgcccccat caacctcacg    2040
gagaggctct tccaggtgct ccgctggtcc acgggatccc tcgagatctt cttctccaag    2100
aacaacccgc tcttcggcag cacataccct caccccgctgc agcgcgtcgc ctacatcaac    2160
atcaccactt acccctcac cgccatcttc ctcatcttct acaccaccgt gccggcgcta    2220
tccttcgtca ccggccactt catcgtgcag cgcccgacca ccatgttcta cgtctacctg    2280
ggcatcgtgc tatccacgct gctcgtcatc gccgtgctgg aggtcaagtg ggccggggtc    2340
acagtcttcg agtggttcag gaacggccag ttctggatga cagcaagttg ctccgcctac    2400
ctcgccgccg tctgccaggt gctgaccaag gtgatattcc ggcgggacat ctccttcaag    2460
ctcacatcca agctaccctc gggagacgag aagaaggacc cctacgccga cctctacgtg    2520
gtgcgctgga cgccgctcat gattacaccc atcatcatca tcttcgtcaa catcatcgga    2580
tccgccgtgg ccttcgccaa ggttctcgac ggcgagtgga cgcactggct caaggtcgcc    2640
ggcggcgtct tcttcaactt ctgggtgctc ttccacctct accccttcgc caagggcatc    2700
ctggggaagc acggaaagac gccagtcgtg gtgctcgtct ggtgggcatt caccttcgtc    2760
atcaccgccg tgctctacat caacatcccc cacatgcata cctcgggagg caagcacaca    2820
acggtgcatg gtcaccatgg caagaagttg gtcgacacag ggctctatgg ctggctccat    2880
tgatgacttt gcccggacaa gacgacctga gacaagaaac aactcatcca ctcaacagtc    2940
agtgcatgca tccatcaagg gcgaattcgc ccttaag                             2977
```

<210> SEQ ID NO 43
<211> LENGTH: 958
<212> TYPE: PRT
<213> ORGANISM: Hordeum vulgare

<400> SEQUENCE: 43

Met Ala Ser Met Thr Gly Gly Gln Gln Met Gly Met Ala Pro Ala Val
1               5                   10                  15

Ala Gly Gly Gly Arg Val Arg Ser Asn Glu Pro Val Ala Ala Ala
            20                  25                  30

Ala Ala Pro Ala Ala Ser Gly Lys Pro Cys Val Cys Gly Phe Gln Val
        35                  40                  45

Cys Ala Cys Thr Gly Ser Ala Ala Val Ala Ser Ala Ala Ser Ser Leu
    50                  55                  60

Asp Met Asp Ile Val Ala Met Gly Gln Ile Gly Ala Val Asn Asp Glu
65                  70                  75                  80

Ser Trp Val Gly Val Glu Leu Gly Glu Asp Gly Thr Asp Glu Ser
                85                  90                  95

Gly Ala Ala Val Asp Asp Arg Pro Val Phe Arg Thr Glu Lys Ile Lys
            100                 105                 110

Gly Val Leu Leu His Pro Tyr Arg Val Leu Ile Phe Val Arg Leu Ile
        115                 120                 125

Ala Phe Thr Leu Phe Val Ile Trp Arg Ile Ser His Lys Asn Pro Asp
    130                 135                 140

Ala Met Trp Leu Trp Val Thr Ser Ile Cys Gly Glu Phe Trp Phe Gly

```
            145                 150                 155                 160
        Phe Ser Trp Leu Leu Asp Gln Leu Pro Lys Leu Asn Pro Ile Asn Arg
                        165                 170                 175

Val Pro Asp Leu Ala Val Leu Arg Gln Arg Phe Asp Arg Pro Asp Gly
                        180                 185                 190

Thr Ser Thr Leu Pro Gly Leu Asp Ile Phe Val Thr Thr Ala Asp Pro
                        195                 200                 205

Ile Lys Glu Pro Ile Leu Ser Thr Ala Asn Ser Val Leu Ser Ile Leu
        210                 215                 220

Ala Ala Asp Tyr Pro Val Asp Arg Asn Thr Cys Tyr Val Ser Asp Asp
        225                 230                 235                 240

Ser Gly Met Leu Leu Thr Tyr Glu Ala Leu Ala Glu Ser Ser Lys Phe
                        245                 250                 255

Ala Thr Leu Trp Val Pro Phe Cys Arg Lys His Gly Ile Glu Pro Arg
                        260                 265                 270

Gly Pro Glu Ser Tyr Phe Glu Leu Lys Ser His Pro Tyr Met Gly Arg
                        275                 280                 285

Ala Gln Asp Glu Phe Val Asn Asp Arg Arg Val Arg Lys Glu Tyr
                        290                 295                 300

Asp Glu Phe Lys Ala Arg Ile Asn Ser Leu Glu His Asp Ile Lys Gln
        305                 310                 315                 320

Arg Asn Asp Gly Tyr Asn Ala Ala Ile Ala His Ser Gln Gly Val Pro
                        325                 330                 335

Arg Pro Thr Trp Met Ala Asp Gly Thr Gln Trp Glu Gly Thr Trp Val
                        340                 345                 350

Asp Ala Ser Glu Asn His Arg Arg Gly Asp His Ala Gly Ile Val Leu
                        355                 360                 365

Val Leu Leu Asn His Pro Ser His Arg Arg Gln Thr Gly Pro Pro Ala
                        370                 375                 380

Ser Ala Asp Asn Pro Leu Asp Leu Ser Gly Val Asp Val Arg Leu Pro
        385                 390                 395                 400

Met Leu Val Tyr Val Ser Arg Glu Lys Arg Pro Gly His Asp His Gln
                        405                 410                 415

Lys Lys Ala Gly Ala Met Asn Ala Leu Thr Arg Ala Ser Ala Leu Leu
                        420                 425                 430

Ser Asn Ser Pro Phe Ile Leu Asn Leu Asp Cys Asp His Tyr Ile Asn
                        435                 440                 445

Asn Ser Gln Ala Leu Arg Ala Gly Ile Cys Phe Met Val Gly Arg Asp
        450                 455                 460

Ser Asp Thr Val Ala Phe Val Gln Phe Pro Gln Arg Phe Glu Gly Val
        465                 470                 475                 480

Asp Pro Thr Asp Leu Tyr Ala Asn His Asn Arg Ile Phe Phe Asp Gly
                        485                 490                 495

Thr Leu Arg Ala Leu Asp Gly Met Gln Gly Pro Ile Tyr Val Gly Thr
                        500                 505                 510

Gly Cys Leu Phe Arg Arg Ile Thr Val Tyr Gly Phe Asp Pro Pro Arg
                        515                 520                 525

Ile Asn Val Gly Gly Pro Cys Phe Pro Arg Leu Ala Gly Leu Phe Ala
        530                 535                 540

Lys Thr Lys Tyr Glu Lys Pro Gly Leu Glu Met Thr Thr Ala Lys Ala
        545                 550                 555                 560

Lys Ala Ala Pro Val Pro Ala Lys Gly Lys His Gly Phe Leu Pro Leu
                        565                 570                 575
```

Pro Lys Lys Thr Tyr Gly Lys Ser Asp Ala Phe Val Asp Thr Ile Pro
               580                 585                 590

Arg Ala Ser His Pro Ser Pro Tyr Ala Ala Ala Glu Gly Ile Val
         595                 600                 605

Ala Asp Glu Ala Thr Ile Val Glu Ala Val Asn Val Thr Ala Ala
 610                 615                 620

Phe Glu Lys Lys Thr Gly Trp Gly Lys Glu Ile Gly Trp Val Tyr Asp
625                 630                 635                 640

Thr Val Thr Glu Asp Val Val Thr Gly Tyr Arg Met His Ile Lys Gly
                 645                 650                 655

Trp Arg Ser Arg Tyr Cys Ser Ile Tyr Pro His Ala Phe Ile Gly Thr
         660                 665                 670

Ala Pro Ile Asn Leu Thr Glu Arg Leu Phe Gln Val Leu Arg Trp Ser
     675                 680                 685

Thr Gly Ser Leu Glu Ile Phe Phe Ser Lys Asn Asn Pro Leu Phe Gly
 690                 695                 700

Ser Tyr Leu His Pro Leu Gln Arg Val Ala Tyr Ile Asn Ile Thr
705                 710                 715                 720

Thr Tyr Pro Phe Thr Ala Ile Phe Leu Ile Phe Tyr Thr Thr Val Pro
                 725                 730                 735

Ala Leu Ser Phe Val Thr Gly His Phe Ile Val Gln Arg Pro Thr Thr
         740                 745                 750

Met Phe Tyr Val Tyr Leu Gly Ile Val Leu Ser Thr Leu Leu Val Ile
     755                 760                 765

Ala Val Leu Glu Val Lys Trp Ala Gly Val Thr Val Phe Glu Trp Phe
 770                 775                 780

Arg Asn Gly Gln Phe Trp Met Thr Ala Ser Cys Ser Ala Tyr Leu Ala
785                 790                 795                 800

Ala Val Cys Gln Val Leu Thr Lys Val Ile Phe Arg Arg Asp Ile Ser
                 805                 810                 815

Phe Lys Leu Thr Ser Lys Leu Pro Ser Gly Asp Glu Lys Lys Asp Pro
         820                 825                 830

Tyr Ala Asp Leu Tyr Val Val Arg Trp Thr Pro Leu Met Ile Thr Pro
     835                 840                 845

Ile Ile Ile Ile Phe Val Asn Ile Ile Gly Ser Ala Val Ala Phe Ala
 850                 855                 860

Lys Val Leu Asp Gly Glu Trp Thr His Trp Leu Lys Val Ala Gly Gly
865                 870                 875                 880

Val Phe Phe Asn Phe Trp Val Leu Phe His Leu Tyr Pro Phe Ala Lys
                 885                 890                 895

Gly Ile Leu Gly Lys His Gly Lys Thr Pro Val Val Val Leu Val Trp
         900                 905                 910

Trp Ala Phe Thr Phe Val Ile Thr Ala Val Leu Tyr Ile Asn Ile Pro
     915                 920                 925

His Met His Thr Ser Gly Gly Lys His Thr Thr Val His Gly His His
 930                 935                 940

Gly Lys Lys Leu Val Asp Thr Gly Leu Tyr Gly Trp Leu His
945                 950                 955

<210> SEQ ID NO 44
<211> LENGTH: 3984
<212> TYPE: DNA
<213> ORGANISM: artificial
<220> FEATURE:

<223> OTHER INFORMATION: synthetic

<400> SEQUENCE: 44

```
gaattcgccc ttaagaacag gctctgctac ttggtaggcg gaccaaaggt ggcatggctt        60
ctccggcggc cgtcggcggg ggtcgtctag ccgacccact gctggccgcc gacgtcgtcg       120
tcgtcggcgc caaagacaag tactgggtgc ccgccgacga gagagagatc ctggcgtcgc       180
agagcagcgg cggcggtgaa caggacggcc gggcaccgct gctataccgc acgttcaggg       240
tcaagggctt cttcatcaac ctttacaggt gggagcattg tctcagactc tcagttcagt       300
tccttctccc cccttgtttt gcgccataga tttatgttcc ccacttgatc gaacccttac       360
ccttaggctt cgtacgtagt ctaaatctaa gcaatgtggt acgtactagt agtacttact       420
gcttgtagta tttcttgaca gattggatct aaatgttctt ctcgatcaga aggggccccg       480
cctccggctc cattttatat agacgaaacc agatgatacc tgaatctgaa tgtacacaac       540
aaacagtatg cttgcctgaa cgttgatgca cactgacaga gcattagtta attgatccaa       600
aggcagtaaa gtacaatctt aagaaacaga acgtgctgtg atctggaggc accgagagga       660
cagcgtcaaa gtagtcaaaa gctgcaaacg atccaaatag tacttgcatt gcttataaac       720
tgtgcggcac gggggatgca ccgacgccag ctcacgctca acggctcaag ccatagagga       780
catgaccttt gtgacttgtg tccggatccg gacgggagca cagtaaaagt aatctagctt       840
tatgtcggta aaacagtgct aagagtaaac tactactcca tgctgatagg cgaaattcac       900
ttatatttta gcattagcat gtggcggaat gtccgaccgc tgagatccat ttttagttg       960
ctgcgaatct caacgctcag atcctgatcc ggctaagaga ttttaaaagg attttaaggc      1020
aaaaatctag aatgtacact gtgcaagtat tcactttgca catgtatctg taggatcttg      1080
atctgtagcc agtgctaaaa atagtaagcg ctactagtat ctaaatccaa gagcacgtga      1140
gctcaaccac aattacagta tcatatgtaa tttgcatcag tacatcgttt catgattcat      1200
ctgtccaaac gtaactgcag gttattgact ctggtcagag ttatcgtggt tattctattc      1260
ttcacgtggc gcatgaggca ccgggactcg gacgcgatgt ggctgtggtg gatctcggtc      1320
gtgggcgacc tctggttcgg agtcacctgg ctgctcaacc agatcaccaa gctcaagccc      1380
aggaaatgcg tccccagcat ctccgtcctg agagagcagc tcgaccagcc cgacggcggc      1440
tccgacctgc cccttctcga cgtgttcatc aacaccgtcg acccggtgga cgagccgatg      1500
ctctacacca tgaactccat cctctccatc ctggccaccg actacccgt ccagaagtac       1560
gccacctatt tctccgatga cggcgggtcg ctggtgcact acgagggct gctgctgacg       1620
gcggagttcg ccgcgtcgtg ggtcccgttc tgccggaagc attgcgtcga gcctcgcgcc      1680
ccggagagct acttctgggc caagatgcgc ggggagtacg ccggcagcgc ggccaaggag      1740
ttccttgacg accatcggag gatgcgcgcg gcgtatgagg agttcaaggc gaggctggac      1800
gggctttctg ccgtcatcga gcagcggtcc gaggcgtgca accgcgctgc aaacgagaaa      1860
gaagggtgtg ggaacgcgac ttggatggcc gatgggtcga cgcaatggca ggggacgtgg      1920
atcaagccgg ccaagggcca ccggaaagga caccatcctg caattcttca ggtacaaatt      1980
aaatatacat atacttccac gcaaatgttt ttatacagaa aggtaaaact gttgctaagg      2040
ctttgtttgg tttcaaataa gtcatcaact tagaagttga aaattgtaaa aagtgactta      2100
ttttgtcaaa cagacccaac ttataagtca ccctaactta taagtcataa gttgctccac      2160
cccaacttga acttataagt cacccacttt tgcatgaaaa gctgacttat aagtcagatg      2220
acaaccaaac agacgacaac caaacagacg cgacttataa gtcactggtt ttaagtcacc      2280
```

```
tgacttatta aaccaaacaa ggcctaattc aacatgttat gtgatgattg ttacaggtta    2340
tgctggatca acctagcaag gatcctgagc tgggaatggc ggcgagctcc gaccaccctc    2400
tggatttcag cgccgtggac gtgcgcctcc cgatgctggt ctacattgcc cgggagaagc    2460
ggcctgggta tgaccaccag aagaaggcgg gcgccatgaa cgtgcagctg cgcgtgtccg    2520
cgctgctctc caacgcgccc ttcatcatca acttcgacgg cgaccactac atcaaccact    2580
cgcaggcctt ccgcgccgcc atgtgcttca tgctcgaccc gcgcgacggc gccgacaccg    2640
ccttcgtcca gttcccgcag cgcttcgacg acgtcgaccc caccgaccgc tactgcaacc    2700
acaaccgcat gttcttcgac gccaccctcc tcggcctcaa cggcatccag gcccctcct    2760
tcgtcggcac cggatgcatg ttccgccgcg tcgctctcta cagcgccgac cctccacggt    2820
ggcggtccga cgacgccaag gaggccaagg cctcgcacag gcccaacatg tttggcaagt    2880
ctacgtcctt catcaactca atgccggcgg ccgccaacca agaacggtcc gtcccgtcac    2940
cggcgacagt cggcgaggcg gagctcgcag acgcgatgac ttgcgcgtac gaggacggca    3000
ccgagtgggg caacgacgtt gggtgggtgt acaacatcgc gacggaggac gtggtgaccg    3060
gcttccggct gcaccggacg gggtggcgct ccacgtactg cgccatggag cccgacgcgt    3120
tccgcggcac ggcgcccatc aacctcaccg agcgcctgta ccagatcctg cgttggtcgg    3180
ggggatccct cgagatgttc ttctcccgct tctgcccgct cctggccggc cgccgcctcc    3240
accccatgca gcgcgtcgcc tacatcaaca tgaccaccta cccggtctcc accttcttca    3300
tcctcatgta ttacttctac ccggtcatgt ggctcttcca gggggagttc tacatccaga    3360
ggccgttcca gacgttcgcg ctcttcgtcg tcgtcgtcat cgccacggtg gagctcatcg    3420
gcatggtgga gatcaggtgg gcaggcctca cgctgctcga ctgggtccgc aacgagcagt    3480
tctacatcat cggcaccacc ggcgtgtacc cgatggccat gctgcacatc ctcctcaggt    3540
ccctcggcat aaaggggtg tccttcaagc tgacggccaa gaagctcacg gggggcgcca    3600
gggagaggct cgcggagctg tacgacgtgc agtgggtgcc gttgctggtg cccaccgtgg    3660
tggtcatggc cgtgaacgtg gccgccatcg gcgcggcggc gggcaaggcg atcgttgggc    3720
ggtggtcggc agcgcaggtc gcgggggcgg cgagcgggct tgttttcaac gtgtggatgc    3780
tgctgctgct ctacccgttc gcgctcggga taatggggca ctggagcaag aggccctaca    3840
tcctgttcct tgtgctggtg accgcggtcg ctgccaccgc gtccgtgtac gtcgcactcg    3900
cggggtcctt gctgtacttg cattcgggga taaaactagt ttaatttttg tcaagtaatg    3960
ctgcaaaacc tgaagggcga attc                                          3984
```

<210> SEQ ID NO 45
<211> LENGTH: 857
<212> TYPE: PRT
<213> ORGANISM: Hordeum vulgare

<400> SEQUENCE: 45

```
Met Ala Ser Pro Ala Ala Val Gly Gly Gly Arg Leu Ala Asp Pro Leu
1               5                   10                  15

Leu Ala Ala Asp Val Val Val Gly Ala Lys Asp Lys Tyr Trp Val
            20                  25                  30

Pro Ala Asp Glu Arg Glu Ile Leu Ala Ser Gln Ser Ser Gly Gly Gly
        35                  40                  45

Glu Gln Asp Gly Arg Ala Pro Leu Leu Tyr Arg Thr Phe Arg Val Lys
    50                  55                  60
```

```
Gly Phe Phe Ile Asn Leu Tyr Arg Leu Leu Thr Leu Val Arg Val Ile
 65                  70                  75                  80

Val Val Ile Leu Phe Phe Thr Trp Arg Met Arg His Arg Asp Ser Asp
                 85                  90                  95

Ala Met Trp Leu Trp Trp Ile Ser Val Val Gly Asp Leu Trp Phe Gly
            100                 105                 110

Val Thr Trp Leu Leu Asn Gln Ile Thr Lys Leu Lys Pro Arg Lys Cys
            115                 120                 125

Val Pro Ser Ile Ser Val Leu Arg Glu Gln Leu Asp Gln Pro Asp Gly
        130                 135                 140

Gly Ser Asp Leu Pro Leu Leu Asp Val Phe Ile Asn Thr Val Asp Pro
145                 150                 155                 160

Val Asp Glu Pro Met Leu Tyr Thr Met Asn Ser Ile Leu Ser Ile Leu
                165                 170                 175

Ala Thr Asp Tyr Pro Val Gln Lys Tyr Ala Thr Tyr Phe Ser Asp Asp
            180                 185                 190

Gly Gly Ser Leu Val His Tyr Glu Gly Leu Leu Leu Thr Ala Glu Phe
        195                 200                 205

Ala Ala Ser Trp Val Pro Phe Cys Arg Lys His Cys Val Glu Pro Arg
210                 215                 220

Ala Pro Glu Ser Tyr Phe Trp Ala Lys Met Arg Gly Glu Tyr Ala Gly
225                 230                 235                 240

Ser Ala Ala Lys Glu Phe Leu Asp Asp His Arg Arg Met Arg Ala Ala
                245                 250                 255

Tyr Glu Glu Phe Lys Ala Arg Leu Asp Gly Leu Ser Ala Val Ile Glu
            260                 265                 270

Gln Arg Ser Glu Ala Cys Asn Arg Ala Ala Asn Glu Lys Glu Gly Cys
        275                 280                 285

Gly Asn Ala Thr Trp Met Ala Asp Gly Ser Thr Gln Trp Gln Gly Thr
290                 295                 300

Trp Ile Lys Pro Ala Lys Gly His Arg Lys Gly His His Pro Ala Ile
305                 310                 315                 320

Leu Gln Val Met Leu Asp Gln Pro Ser Lys Asp Pro Glu Leu Gly Met
                325                 330                 335

Ala Ala Ser Ser Asp His Pro Leu Asp Phe Ser Ala Val Asp Val Arg
            340                 345                 350

Leu Pro Met Leu Val Tyr Ile Ala Arg Glu Lys Arg Pro Gly Tyr Asp
        355                 360                 365

His Gln Lys Lys Ala Gly Ala Met Asn Val Gln Leu Arg Val Ser Ala
370                 375                 380

Leu Leu Ser Asn Ala Pro Phe Ile Ile Asn Phe Asp Gly Asp His Tyr
385                 390                 395                 400

Ile Asn His Ser Gln Ala Phe Arg Ala Ala Met Cys Phe Met Leu Asp
                405                 410                 415

Pro Arg Asp Gly Ala Asp Thr Ala Phe Val Gln Phe Pro Gln Arg Phe
            420                 425                 430

Asp Asp Val Asp Pro Thr Asp Arg Tyr Cys Asn His Asn Arg Met Phe
        435                 440                 445

Phe Asp Ala Thr Leu Leu Gly Leu Asn Gly Ile Gln Gly Pro Ser Phe
450                 455                 460

Val Gly Thr Gly Cys Met Phe Arg Arg Val Ala Leu Tyr Ser Ala Asp
465                 470                 475                 480

Pro Pro Arg Trp Arg Ser Asp Asp Ala Lys Glu Ala Lys Ala Ser His
```

```
                    485                 490                 495
Arg Pro Asn Met Phe Gly Lys Ser Thr Ser Phe Ile Asn Ser Met Pro
                500                 505                 510

Ala Ala Ala Asn Gln Glu Arg Ser Val Pro Ser Pro Ala Thr Val Gly
            515                 520                 525

Glu Ala Glu Leu Ala Asp Ala Met Thr Cys Ala Tyr Glu Asp Gly Thr
        530                 535                 540

Glu Trp Gly Asn Asp Val Gly Trp Val Tyr Asn Ile Ala Thr Glu Asp
545                 550                 555                 560

Val Val Thr Gly Phe Arg Leu His Arg Thr Gly Trp Arg Ser Thr Tyr
                565                 570                 575

Cys Ala Met Glu Pro Asp Ala Phe Arg Gly Thr Ala Pro Ile Asn Leu
                580                 585                 590

Thr Glu Arg Leu Tyr Gln Ile Leu Arg Trp Ser Gly Gly Ser Leu Glu
                595                 600                 605

Met Phe Phe Ser Arg Phe Cys Pro Leu Leu Ala Gly Arg Arg Leu His
        610                 615                 620

Pro Met Gln Arg Val Ala Tyr Ile Asn Met Thr Thr Tyr Pro Val Ser
625                 630                 635                 640

Thr Phe Phe Ile Leu Met Tyr Tyr Phe Tyr Pro Val Met Trp Leu Phe
                645                 650                 655

Gln Gly Glu Phe Tyr Ile Gln Arg Pro Phe Gln Thr Phe Ala Leu Phe
                660                 665                 670

Val Val Val Val Ile Ala Thr Val Glu Leu Ile Gly Met Val Glu Ile
            675                 680                 685

Arg Trp Ala Gly Leu Thr Leu Leu Asp Trp Val Arg Asn Glu Gln Phe
        690                 695                 700

Tyr Ile Ile Gly Thr Thr Gly Val Tyr Pro Met Ala Met Leu His Ile
705                 710                 715                 720

Leu Leu Arg Ser Leu Gly Ile Lys Gly Val Ser Phe Lys Leu Thr Ala
                725                 730                 735

Lys Lys Leu Thr Gly Gly Ala Arg Glu Arg Leu Ala Glu Leu Tyr Asp
                740                 745                 750

Val Gln Trp Val Pro Leu Leu Val Pro Thr Val Val Met Ala Val
            755                 760                 765

Asn Val Ala Ala Ile Gly Ala Ala Gly Lys Ala Ile Val Gly Arg
        770                 775                 780

Trp Ser Ala Ala Gln Val Ala Gly Ala Ala Ser Gly Leu Val Phe Asn
785                 790                 795                 800

Val Trp Met Leu Leu Leu Leu Tyr Pro Phe Ala Leu Gly Ile Met Gly
                805                 810                 815

His Trp Ser Lys Arg Pro Tyr Ile Leu Phe Leu Val Leu Val Thr Ala
                820                 825                 830

Val Ala Ala Thr Ala Ser Val Tyr Val Ala Leu Ala Gly Ser Leu Leu
            835                 840                 845

Tyr Leu His Ser Gly Ile Lys Leu Val
    850                 855
```

<210> SEQ ID NO 46
<211> LENGTH: 3620
<212> TYPE: DNA
<213> ORGANISM: artificial
<220> FEATURE:
<223> OTHER INFORMATION: synthetic

<400> SEQUENCE: 46

```
gaattcgccc ttatagcgct tggccagtgg aagcatgtta atgacatata tcaccaagaa      60
gcatgactat gttgcaacct tggatgagaa ggagtcgccc gcggatgaga agtcggccaa     120
tgtcgagagg ttgcttgtcc ggaccacaaa acttacaaca gttaccatca agttgtacag     180
gtaatcatca gccatacaca tatatactta cttattcaaa catgttcgtg cttaattaca     240
agacctaaaa gttcttcatg ataaaacgtg tacccatata ctacgcaata tcgtgactca     300
tgagtagtat gcagggtttc aagggaagta tattgtatgt gatcgcagaa attatgtttg     360
accaattatt ttctataccg tgtttacttt acaaattgag acatatgcta atcgtatat     420
gaatttgttg caacaaatgc ttgcaaatga tgagttatta taaccttttt ctttaccgtg     480
tcatgaaatc tataatgccc agaaaaagtc aaaattcacc cttttaattg agcgaatagg     540
actatgtata tattaaagaa aaggtgtggt tagatctcag tcgactgaga tcgacaagtc     600
ccagtcaagt gataaggtat atatacagtt ttttcaacaa caaaaattaa gtgtcgattc     660
tccttaagaa tctgggaggc tgtcaaggct tggcttgatg cgcccaactg aatactcgga     720
gttggggaga catccgaacg gttacaagct gatgaatcgc aacggttcta cggcgtggtc     780
acagaaggaa ggccatctca tcgcttctcg tgctcatctg ttggaagttg tggaacgaaa     840
gaaatgcaag agttttttg gagcaaatct atcgtacgtg tccaccgttc tggttgacaa     900
catcatacta gaggcaagga attgggtcct tgcggggga acatttgag cactttaatg     960
ttgcaacagt aggatcttat cttttccatt tgttgaggtg taatggacct ggttaaactt    1020
tgttggttat tccttttta ttattaatga gataaagcaa agttttttgcc tccgttttaa    1080
aaaactgaat tttgtttgtt cgaatcatca tgcaaaatca agaaactgc aagatcaaag    1140
aatatagcat cggctgagac atagtcgact aagacttaac aaaaatgata gaaatatgac    1200
tagaaatcat gtggaaaaag actagaagtt tatgtgtgtg tgacaaacat atgcaattaa    1260
gtggcgaaag ccatggtgtt tgcaggctca tgatcgttgt tcggatggcc atcttcgtgc    1320
tgttcttcaa atggcgaatc agcactgctc ttgcgatgac cagcaacggc acaagtacag    1380
ctcgtgcaat gtggacggtg tccatcgccg gggagctctg gttcgcccta atgtgggtgc    1440
tggaccagct gcccaagatg cagcctgtcc ggcgcaccgt cttcgccacc gcgctggagg    1500
agtcgctgct tccgaccatg gatgtgttcg tcaccaccgc cgaccccgac aaggagccgc    1560
cgctggtgac cgtgaacact atcctctcca tccttgccgc cgactatccc ccagacaagc    1620
tcacatgcta cgtctcagac gacgcggcg ctctgctcac gcgcgaggct gtggtggagg    1680
ctgcccggtt cgccggactg tgggtgccgt tctgccggaa gcacggggtt gagccgagga    1740
acccagaggc ctacttcagc cacggcgtta aggtgagggt ggtgtcaagg gctgactata    1800
agggaagatc gtggccggaa ctggcacggg acagaaggcg tgtgcgccgg gagtacgaag    1860
aactgcggct gcgggtcgac gcgcttcacg ccggagacgt gcagcgcccg tggcggtcgc    1920
gcggcacgcc ggaagatcat gccggagttg ttgaggtgct agtggatcct cccagctgta    1980
cgccagagcc cggcgtcagt ggtaatctac tggacctcag ctccgtcgat gtgcgggttc    2040
cagcgctcgt gtacatgtgc cgggagaagc gccgcggccg cgcgcaccac cggaaggcag    2100
gtgccatgaa cgcgctgctc cggacctcgg ccgtgctctc caacgcgccc atcatcctca    2160
acctcgactg cgaccactac gtcaacaact cgcaggccct ccgcgcgggt gtctgcctca    2220
tgctcgaccg cggcggcagc gacgtggcgt ttgtccagtt cccgcagcgc ttcgacggcg    2280
tcgaccccgc cgaccggtac gccaaccaca accgcgtctt cttcgactgc acggagctcg    2340
```

```
gcctcgacgg cctccaggga cccatttacg tgggcaccgg ctgcatgttt cgccgtgcgg      2400
cgctatacag catcgacccg ccgctctggt ggtcacatgg cgacagcgac gccggcaagg      2460
acgtcgctgc agaggccgac aagtttggcg tttcgacgcc gttccttggc tcggtgcgtg      2520
cggccttgaa cttgaaccgg tcggagcaac ggaacacagg tacttcaccg ccgtgctcgt      2580
tcgacgcggc tgccgtcggc gaggccaccg cgctcgtctc gtgcggctac gaggacagga      2640
cggcatgggg cagggaaatc ggctggatat acgggacggt gacagaggac gtggccacgg      2700
gcttctgcat gcaccggcga gggtggcgct ccgcctactg cgccaccgcg ccggacgcgt      2760
tccgcggcac ggcgcccatc aacctcacag accggctgca ccaggtcctc cgctgggcgg      2820
cgggctccct cgagatattc ttctcccgca acaacgccct cctcgccggg ccccggctcc      2880
acccgctgca gcggctggcg tacctcaaca cgacggtgta cccgttcacc tccatcttcc      2940
tcctggtcta ctgcctcttg ccggcgatcc cgctcgtgac ccggagcgcg accatgagcg      3000
ccttctcaac caacatgccg ccgtcgtcca cgtacatcac gtttgtggcg cactgatgc       3060 tgacgctggc catggtggcc gcgctggagg tgaggtggtc gggcataacg ctgggcgagt      3120
ggtggcggaa cgagcagttc tggatggtgt cggccacgag cgcgtacgcg gccgcggtgg      3180
tgcaggtggc gctcaaggtt ttggtgggga aggaggtagc gttcaagctg acgtccaagc      3240
ggcgcgcgtc gggctccggc ggcggcggcg tagtaaaagg caggttcgcg gagctgtacg      3300
ccgtgagatg gacggtgcta atggttccga cggcggtggt gctggcggtg aacgtggcgt      3360
ccatggcagc ggcagtacag gagaggcggt ggaggaaggg ccccgcggcg gtgctcgcga      3420
cggcgttcaa cgcttgggtg gtggtgcatc tccacccctt cgcccttggg ctcatgggcc      3480
gttggagcaa gacgttgagc ccctgctctg tgcttgtcgt agcgttcaca attctatcac      3540
tatgttttct cctccatttg catatgcttt aacatgccta ttttggacga cgagtgaaat      3600
ttcaaatgaa gggcgaattc                                                  3620
```

<210> SEQ ID NO 47
<211> LENGTH: 810
<212> TYPE: PRT
<213> ORGANISM: Hordeum vulgare

<400> SEQUENCE: 47

Met Leu Met Thr Tyr Ile Thr Lys Lys His Asp Tyr Val Ala Thr Leu
1               5                   10                  15

Asp Glu Lys Glu Ser Pro Ala Asp Glu Lys Ser Ala Asn Val Glu Arg
            20                  25                  30

Leu Leu Val Arg Thr Thr Lys Leu Thr Thr Val Thr Ile Lys Leu Tyr
        35                  40                  45

Arg Leu Met Ile Val Val Arg Met Ala Ile Phe Val Leu Phe Phe Lys
    50                  55                  60

Trp Arg Ile Ser Thr Ala Leu Ala Met Thr Ser Asn Gly Thr Ser Thr
65                  70                  75                  80

Ala Arg Ala Met Trp Thr Val Ser Ile Ala Gly Glu Leu Trp Phe Ala
                85                  90                  95

Leu Met Trp Val Leu Asp Gln Leu Pro Lys Met Gln Pro Val Arg Arg
            100                 105                 110

Thr Val Phe Ala Thr Ala Leu Glu Glu Ser Leu Leu Pro Thr Met Asp
        115                 120                 125

Val Phe Val Thr Thr Ala Asp Pro Asp Lys Glu Pro Pro Leu Val Thr
    130                 135                 140

```
Val Asn Thr Ile Leu Ser Ile Leu Ala Ala Asp Tyr Pro Asp Lys
145                 150                 155                 160

Leu Thr Cys Tyr Val Ser Asp Asp Gly Gly Ala Leu Leu Thr Arg Glu
                165                 170                 175

Ala Val Val Glu Ala Ala Arg Phe Ala Gly Leu Trp Val Pro Phe Cys
                180                 185                 190

Arg Lys His Gly Val Glu Pro Arg Asn Pro Glu Ala Tyr Phe Ser His
                195                 200                 205

Gly Val Lys Val Arg Val Val Ser Arg Ala Asp Tyr Lys Gly Arg Ser
                210                 215                 220

Trp Pro Glu Leu Ala Arg Asp Arg Arg Val Arg Arg Glu Tyr Glu
225                 230                 235                 240

Glu Leu Arg Leu Arg Val Asp Ala Leu His Ala Gly Asp Val Gln Arg
                245                 250                 255

Pro Trp Arg Ser Arg Gly Thr Pro Glu Asp His Ala Gly Val Val Glu
                260                 265                 270

Val Leu Val Asp Pro Pro Ser Cys Thr Pro Glu Pro Gly Val Ser Gly
                275                 280                 285

Asn Leu Leu Asp Leu Ser Ser Val Asp Val Arg Val Pro Ala Leu Val
290                 295                 300

Tyr Met Cys Arg Glu Lys Arg Arg Gly Arg Ala His His Arg Lys Ala
305                 310                 315                 320

Gly Ala Met Asn Ala Leu Leu Arg Thr Ser Ala Val Leu Ser Asn Ala
                325                 330                 335

Pro Ile Ile Leu Asn Leu Asp Cys Asp His Tyr Val Asn Asn Ser Gln
                340                 345                 350

Ala Leu Arg Ala Gly Val Cys Leu Met Leu Asp Arg Gly Gly Ser Asp
                355                 360                 365

Val Ala Phe Val Gln Phe Pro Gln Arg Phe Asp Gly Val Asp Pro Ala
                370                 375                 380

Asp Arg Tyr Ala Asn His Asn Arg Val Phe Phe Asp Cys Thr Glu Leu
385                 390                 395                 400

Gly Leu Asp Gly Leu Gln Gly Pro Ile Tyr Val Gly Thr Gly Cys Met
                405                 410                 415

Phe Arg Arg Ala Ala Leu Tyr Ser Ile Asp Pro Pro Leu Trp Trp Ser
                420                 425                 430

His Gly Asp Ser Asp Ala Gly Lys Asp Val Ala Ala Glu Ala Asp Lys
                435                 440                 445

Phe Gly Val Ser Thr Pro Phe Leu Gly Ser Val Arg Ala Ala Leu Asn
                450                 455                 460

Leu Asn Arg Ser Glu Gln Arg Asn Thr Gly Thr Ser Pro Pro Cys Ser
465                 470                 475                 480

Phe Asp Ala Ala Ala Val Gly Glu Ala Thr Ala Leu Val Ser Cys Gly
                485                 490                 495

Tyr Glu Asp Arg Thr Ala Trp Gly Arg Glu Ile Gly Trp Ile Tyr Gly
                500                 505                 510

Thr Val Thr Glu Asp Val Ala Thr Gly Phe Cys Met His Arg Arg Gly
                515                 520                 525

Trp Arg Ser Ala Tyr Cys Ala Thr Ala Pro Asp Ala Phe Arg Gly Thr
                530                 535                 540

Ala Pro Ile Asn Leu Thr Asp Arg Leu His Gln Val Leu Arg Trp Ala
545                 550                 555                 560
```

```
Ala Gly Ser Leu Glu Ile Phe Phe Ser Arg Asn Asn Ala Leu Leu Ala
            565                 570                 575

Gly Pro Arg Leu His Pro Leu Gln Arg Leu Ala Tyr Leu Asn Thr Thr
        580                 585                 590

Val Tyr Pro Phe Thr Ser Ile Phe Leu Leu Val Tyr Cys Leu Leu Pro
    595                 600                 605

Ala Ile Pro Leu Val Thr Arg Ser Ala Thr Met Ser Ala Phe Ser Thr
610                 615                 620

Asn Met Pro Pro Ser Ser Thr Tyr Ile Thr Phe Val Ala Ala Leu Met
625                 630                 635                 640

Leu Thr Leu Ala Met Val Ala Ala Leu Glu Val Arg Trp Ser Gly Ile
                645                 650                 655

Thr Leu Gly Glu Trp Trp Arg Asn Glu Gln Phe Trp Met Val Ser Ala
            660                 665                 670

Thr Ser Ala Tyr Ala Ala Ala Val Val Gln Val Ala Leu Lys Val Leu
        675                 680                 685

Val Gly Lys Glu Val Ala Phe Lys Leu Thr Ser Lys Arg Arg Ala Ser
    690                 695                 700

Gly Ser Gly Gly Gly Gly Val Val Lys Gly Arg Phe Ala Glu Leu Tyr
705                 710                 715                 720

Ala Val Arg Trp Thr Val Leu Met Val Pro Thr Ala Val Val Leu Ala
                725                 730                 735

Val Asn Val Ala Ser Met Ala Ala Val Gln Glu Arg Arg Trp Arg
            740                 745                 750

Lys Gly Pro Ala Ala Val Leu Ala Thr Ala Phe Asn Ala Trp Val Val
        755                 760                 765

Val His Leu His Pro Phe Ala Leu Gly Leu Met Gly Arg Trp Ser Lys
    770                 775                 780

Thr Leu Ser Pro Leu Leu Leu Val Val Ala Phe Thr Ile Leu Ser
785                 790                 795                 800

Leu Cys Phe Leu Leu His Leu His Met Leu
                805                 810

<210> SEQ ID NO 48
<211> LENGTH: 2333
<212> TYPE: DNA
<213> ORGANISM: artificial
<220> FEATURE:
<223> OTHER INFORMATION: synthetic

<400> SEQUENCE: 48
gagctgtgtt cgtggagctt agctagtctg ctactgctac tgctggctag tggctacctg      60
ctctcggcca cggccatggc gggcggcaag aagctgcagg agagggtcgc cctggcgaga     120
accgcgtgga tgctggccga cttcgcgatc tcttcctcc tcctcgccat cgtggcccgc     180
cgcgccgcct cgctccggga gcgcggcggg acgtggttgg cggcgctcgt ctgcgaggcg     240
tggttcgcct tcgtgtggat cctcaacatg aacggcaagt ggagccccgt ccggttcgac     300
acctaccccg acaacctcgc caacaggatg gaggagctcc cggcggtgga catgttcgtc     360
acgaccgcgg acccggcgct ggagcctccg ttgatcacgg tgaacacggt gctctcgctg     420
ctcgccctgg actacccgga cgtcggcaag ctggcgtgct acgtctctga cgacggctgc     480
tccccggtga cgtgctacgc gctgcgtgag gccgccaagt cgccggcct ctgggtccct     540 ttctgcaaga ggcacgacgt tgctgtgagg gccccattca tgtacttctc ttccacgccg     600
gaggttggca caggcacagc cgaccacgag ttcctggaaa gctgggcgct catgaagagc     660
```

```
gaatatgaga gactagccag ccgaatcgag aacgccgatg agggctccat tatgcgtgac    720
agcggcgacg agttcgccga gttcatcgac gccgagcgcg ggaaccatcc taccatcgtt    780
aaggttctgt gggataacag caagagcaaa gtgggggaag gattcccaca tctggtgtac    840
ctctctcgag agaaaagccc cagacatcgc cacaacttca aggctggtgc catgaatgtt    900
ctgacaaggg tgtcagccgt gatgaccaac gctcccatca tgctgaatgt ggactgcgac    960
atgttcgcca caatccgca ggtcgcccta cacgcgatgt gcctcctatt ggggttcgac   1020
gacgagatcc acagcgggtt cgtccaagtg ccacagaagt tctacggtgg cctcaaggac   1080
gatccctttg caaccagat gcaggttata accaagaaaa ttggaggtgg aatcgccggg   1140
atccaaggca tgttctacgg cggcacgggc tgttttcacc gcaggaaagt catttacggc   1200
atgccgccac ctgacaccgt caaacacgag acaagaggtt caccatctta caaggagctg   1260
caagtcaggt ttgggagctc aaaggtgttg atcgaatcat ctaggaacat catctcagga   1320
gacctgctcg ctagaccaac cgttgatgta tcgagtcgca tcgaaatggc aaaacaagtc   1380
ggcgattgca actatgaggc tggcacgtgt tgggcaagg agattggttg ggtctatgga   1440
tcaatgacag aagacatttt gaccggacaa cggatccatg cggcgggttg gaaatcggcc   1500
ttgttggaca ccaacccacc ggcattcttg ggatgtgctc cgaccggggg accggccagc   1560
ttgacccagt tcaagagatg ggcaacaggg gttctggaga tactcatcag ccggaacagc   1620
cctatcctcg gcaccatctt ccaacgcctc caactccggc aatgccttgg ctatctcatc   1680
gtcgaggcgt ggcccgtgag ggcgcctttc gagctgtgct atgcactatt gggacctttc   1740
tgccttctca caaaccagtc cttcttgcca acggcatcgg atgaaggttt tcgcatccca   1800
gtagctctat tcttgagtta ccacatatac cacttgatgg agtacaagga gtgcgggctc   1860
tctgcccgcg cctggtggaa caaccacagg atgcaacgca tcacctcggc ctccgcctgg   1920
ctcctcgcct tcctcaccgt gatcctcaag acactagggc tctctgagac cgtgttcgag   1980
gtcacccgca aggaaagcag cacgtccgat ggcggcgccg gcaccgacga ggccgatcca   2040
ggactgttca cattcgactc ggcgcccgtt ttcatcccgg tgacggcgct ctcagtgttg   2100
aacattgtgg ccctcgccgt cggggcatgg cgcgccgtca tcgggactgc ggcggtcgtt   2160
catggtggcc cggcatcgg agagttcgtg tgctgtggct ggatggtgtt gtgcttctgg   2220
ccgttcgtga gagggcttgt cagcaggga aagcatgaa tcccgtggag cgtcaaggtg   2280
aaggctggtt tgattgtggc tgcgttcgtg cacctctgca caggaactaa acc         2333
```

<210> SEQ ID NO 49
<211> LENGTH: 3227
<212> TYPE: DNA
<213> ORGANISM: artificial
<220> FEATURE:
<223> OTHER INFORMATION: synthetic

<400> SEQUENCE: 49

```
gaattcgccc ttgagctgtg ttcgtggagc ttagctagtc tgctactgct actgctggct    60
agtggctacc tgctctcggc cacggccatg gcgggcggca agaagctgca ggagagggtc   120
gccctggcga gaaccgcgtg gatgctgccc gacttcgcga tcctcttcct cctcctcgcc   180
atcgtggccc gccgcgccgc ctcgctccgg gagcgcggcg ggacgtggtt ggcggcgctc   240
gtctgcgagg cgtggttcgc cttcgtgtgg atcctcaaca tgaacggcaa gtggagcccc   300
gtccggttcg acacctaccc cgacaacctc gccaacaggt actctacgta cgtacccacg   360
```

```
gcgacaagac ccaccatgct gacccctaca acttcctcaa attttgatct agctagtgtc    420
tgtgataatt ttgctaggat ggaggagctc ccggcggtgg acatgttcgt cacgaccgcg    480
gacccggcgc tggagcctcc gttgatcacg gtgaacacgg tgctctcgct gctcgccctg    540
gactacccgg acgtcggcaa gctggcgtgc tacgtctctg acgacggctg ctccccggtg    600
acgtgctacg cgctgcgtga ggccgccaag ttcgccggcc tctgggtccc tttctgcaag    660
aggcacgacg ttgctgtgag ggccccattc atgtacttct cttccacgcc ggaggttggc    720
acaggcacag ccgaccacga gttcctggaa agctgggcgc tcatgaaggt taggcgccaa    780
tggtgaccat gtcagtttac aaaataatgt ttggtcgtcc atcatcgcca tggccattca    840
tcttcctcgt gtacgtgtga cttcagagc gaatatgaga gactagccag ccgaatcgag     900
aacgccgatg agggctccat tatgcgtgac agcggcgacg agttcgccga gttcatcgac    960
gccgagcgcg ggaaccatcc taccatcgtt aaggtcgccg cactgaccat gtccatgcat   1020
gtgtccatga acatcgtgtc atgacaaacg catagcaaat ccgtgtctcg tgctaatatc   1080
gtcacggtta atttgggccg agttcaggtt ctgtgggata acagcaagag caaagtgggg   1140
gaaggattcc cacatctggt gtacctctct cgagagaaaa gccccagaca tcgccacaac   1200
ttcaaggctg gtgccatgaa tgttctggtg agcactctct ttcgctcaac acagtgttgc   1260
actgctaatc agtgtcacac aagcagcaca ccacatttta tactaattaa gctgatcatt   1320
tcgtggtgca gacaagggtg tcagccgtga tgaccaacgc tcccatcatg ctgaatgtgg   1380
actgcgacat gttcgccaac aatccgcagg tcgccctaca cgcgatgtgc ctcctattgg   1440
ggttcgacga cgagatccac agcggggttcg tccaagtgcc acagaagttc tacggtggcc   1500
tcaaggacga tccctttggc aaccagatgc aggttataac caaggtacta catatgcatg   1560
tgcacaagtg ctcttgtcgt cgtgctgtgc accactaggt agtgttacag ttgtactggt   1620
ttttgtggca tgttcagaaa attggaggtg gaatcgccgg gatccaaggc atgttctacg   1680
gcggcacggg ctgttttcac cgcaggaaag tcatttacgg catgccgcca cctgacaccg   1740
tcaaacacga gacaagaggt gaaactgggc acacaacaga tgtgatcatc aggcgtaaat   1800
tggagtatgc atttcagttc gactagggca tttcaaatgg ctaagtgttc ttaatttgcc   1860
aggttcacca tcttacaagg agctgcaagt caggtttggg agctcaaagg tgttgatcga   1920
atcatctagg aacatcatct caggagacct gctcgctaga ccaaccgttg atgtatcgag   1980
tcgcatcgaa atggcaaaac aagtcggcga ttgcaactat gaggctggca cgtgttgggg   2040
caaggaggta tgcttagcta cctgttgccg tattttttgca ggtttcgcta cagtacatct   2100
acaatctttt gcagttttc tctagttaca gtttcttcca tgtattttttg cagattggtt    2160 gggtctatgg atcaatgaca gaagacattt tgaccggaca acggatccat gcggcgggtt   2220
ggaaatcggc cttgttggac accaacccac cggcattctt gggatgtgct ccgaccgggg   2280
gaccggccag cttgacccag ttcaagagat gggcaacagg ggttctggag atactcatca   2340
gccggaacag ccctatcctc ggcaccatct tccaacgcct ccaactccgg caatgccttg   2400
gctatctcat cgtcgaggcg tggcccgtga gggcgccttt cgagctgtgc tatgcactat   2460
tgggaccttt ctgccttctc acaaaccagt ccttcttgcc aacggtacat acactttcgc   2520
ggttcgccaa gatacattat gcagctaaac aaaaatgctg tgtgatttgt ttgataatga   2580
agcaggacct agttggctaa tatgtatgta aattcagata ttttttttat gattggtaca   2640
tttgttgttt tgcaggcatc ggatgaaggt tttcgcatcc cagtagctct attcttgagt   2700
taccacatat accacttgat ggagtacaag gagtgcgggc tctctgcccg cgcctggtgg   2760
```

```
aacaaccaca ggatgcaacg catcacctcg gcctccgcct ggctcctcgc cttcctcacc    2820
gtgatcctca agacactagg gctctctgag accgtgttcg aggtcacccg caaggaaagc    2880
agcacgtccg atggcggcgc cggcaccgac gaggccgatc caggactgtt cacattcgac    2940
tcggcgcccg ttttcatccc ggtgacggcg ctctcagtgt tgaacattgt ggccctcgcc    3000
gtcggggcat ggcgcgccgt catcgggact gcggcggtcg ttcatggtgg cccgggcatc    3060
ggagagttcg tgtgctgtgg ctggatggtg ttgtgcttct ggccgttcgt gagagggctt    3120
gtcagcaggg gaaagcatgg aatcccgtgg agcgtcaagg tgaaggctgg tttgattgtg    3180
gctgcgttcg tgcacctctg cacaaggaac taaccaaggg cgaattc                  3227
```

<210> SEQ ID NO 50
<211> LENGTH: 751
<212> TYPE: PRT
<213> ORGANISM: Hordeum vulgare

<400> SEQUENCE: 50

```
Met Ala Gly Gly Lys Lys Leu Gln Glu Arg Val Ala Leu Ala Arg Thr
 1               5                  10                  15

Ala Trp Met Leu Ala Asp Phe Ala Ile Leu Phe Leu Leu Leu Ala Ile
            20                  25                  30

Val Ala Arg Arg Ala Ala Ser Leu Arg Glu Arg Gly Gly Thr Trp Leu
        35                  40                  45

Ala Ala Leu Val Cys Glu Ala Trp Phe Ala Phe Val Trp Ile Leu Asn
    50                  55                  60

Met Asn Gly Lys Trp Ser Pro Val Arg Phe Asp Thr Tyr Pro Asp Asn
65                  70                  75                  80

Leu Ala Asn Arg Met Glu Glu Leu Pro Ala Val Asp Met Phe Val Thr
                85                  90                  95

Thr Ala Asp Pro Ala Leu Glu Pro Pro Leu Ile Thr Val Asn Thr Val
            100                 105                 110

Leu Ser Leu Leu Ala Leu Asp Tyr Pro Asp Val Gly Lys Leu Ala Cys
        115                 120                 125

Tyr Val Ser Asp Asp Gly Cys Ser Pro Val Thr Cys Tyr Ala Leu Arg
    130                 135                 140

Glu Ala Ala Lys Phe Ala Gly Leu Trp Val Pro Phe Cys Lys Arg His
145                 150                 155                 160

Asp Val Ala Val Arg Ala Pro Phe Met Tyr Phe Ser Ser Thr Pro Glu
                165                 170                 175

Val Gly Thr Gly Thr Ala Asp His Glu Phe Leu Glu Ser Trp Ala Leu
            180                 185                 190

Met Lys Ser Glu Tyr Glu Arg Leu Ala Ser Arg Ile Glu Asn Ala Asp
        195                 200                 205

Glu Gly Ser Ile Met Arg Asp Ser Gly Asp Glu Phe Ala Glu Phe Ile
    210                 215                 220

Asp Ala Glu Arg Gly Asn His Pro Thr Ile Val Lys Val Leu Trp Asp
225                 230                 235                 240

Asn Ser Lys Ser Lys Val Gly Glu Gly Phe Pro His Leu Val Tyr Leu
                245                 250                 255

Ser Arg Glu Lys Ser Pro Arg His Arg His Asn Phe Lys Ala Gly Ala
            260                 265                 270

Met Asn Val Leu Thr Arg Val Ser Ala Val Met Thr Asn Ala Pro Ile
        275                 280                 285
```

```
Met Leu Asn Val Asp Cys Asp Met Phe Ala Asn Asn Pro Gln Val Ala
290                 295                 300
Leu His Ala Met Cys Leu Leu Gly Phe Asp Asp Glu Ile His Ser
305                 310                 315                 320
Gly Phe Val Gln Val Pro Gln Lys Phe Tyr Gly Gly Leu Lys Asp Asp
                    325                 330                 335
Pro Phe Gly Asn Gln Met Gln Val Ile Thr Lys Lys Ile Gly Gly Gly
                340                 345                 350
Ile Ala Gly Ile Gln Gly Met Phe Tyr Gly Thr Gly Cys Phe His
            355                 360                 365
Arg Arg Lys Val Ile Tyr Gly Met Pro Pro Asp Thr Val Lys His
370                 375                 380
Glu Thr Arg Gly Ser Pro Ser Tyr Lys Glu Leu Gln Val Arg Phe Gly
385                 390                 395                 400
Ser Ser Lys Val Leu Ile Glu Ser Ser Arg Asn Ile Ile Ser Gly Asp
                405                 410                 415
Leu Leu Ala Arg Pro Thr Val Asp Val Ser Ser Arg Ile Glu Met Ala
                420                 425                 430
Lys Gln Val Gly Asp Cys Asn Tyr Glu Ala Gly Thr Cys Trp Gly Lys
                435                 440                 445
Glu Ile Gly Trp Val Tyr Gly Ser Met Thr Glu Asp Ile Leu Thr Gly
                450                 455                 460
Gln Arg Ile His Ala Ala Gly Trp Lys Ser Ala Leu Leu Asp Thr Asn
465                 470                 475                 480
Pro Pro Ala Phe Leu Gly Cys Ala Pro Thr Gly Gly Pro Ala Ser Leu
                485                 490                 495
Thr Gln Phe Lys Arg Trp Ala Thr Gly Val Leu Glu Ile Leu Ile Ser
                500                 505                 510
Arg Asn Ser Pro Ile Leu Gly Thr Ile Phe Gln Arg Leu Gln Leu Arg
                515                 520                 525
Gln Cys Leu Gly Tyr Leu Ile Val Glu Ala Trp Pro Val Arg Ala Pro
530                 535                 540
Phe Glu Leu Cys Tyr Ala Leu Leu Gly Pro Phe Cys Leu Leu Thr Asn
545                 550                 555                 560
Gln Ser Phe Leu Pro Thr Ala Ser Asp Glu Gly Phe Arg Ile Pro Val
                565                 570                 575
Ala Leu Phe Leu Ser Tyr His Ile Tyr His Leu Met Glu Tyr Lys Glu
                580                 585                 590
Cys Gly Leu Ser Ala Arg Ala Trp Trp Asn Asn His Arg Met Gln Arg
                595                 600                 605
Ile Thr Ser Ala Ser Ala Trp Leu Leu Ala Phe Leu Thr Val Ile Leu
                610                 615                 620
Lys Thr Leu Gly Leu Ser Glu Thr Val Phe Glu Val Thr Arg Lys Glu
625                 630                 635                 640
Ser Ser Thr Ser Asp Gly Gly Ala Gly Thr Asp Glu Ala Asp Pro Gly
                645                 650                 655
Leu Phe Thr Phe Asp Ser Ala Pro Val Phe Ile Pro Val Thr Ala Leu
                660                 665                 670
Ser Val Leu Asn Ile Val Ala Leu Ala Val Gly Ala Trp Arg Ala Val
                675                 680                 685
Ile Gly Thr Ala Ala Val Val His Gly Pro Gly Ile Gly Glu Phe
                690                 695                 700
Val Cys Cys Gly Trp Met Val Leu Cys Phe Trp Pro Phe Val Arg Gly
```

| | | | | |
|---|---|---|---|---|
| Leu Val Ser Arg Gly Lys His Gly Ile Pro Trp Ser Val Lys Val Lys | | | | |
| 705 | 710 | 715 | | 720 |
| Ala Gly Leu Ile Val Ala Ala Phe Val His Leu Cys Thr Arg Asn | | | | |
| | 725 | | 730 | 735 |
| | 740 | | 745 | 750 |

<210> SEQ ID NO 51
<211> LENGTH: 3002
<212> TYPE: DNA
<213> ORGANISM: artificial
<220> FEATURE:
<223> OTHER INFORMATION: synthetic

<400> SEQUENCE: 51

| | | | | | |
|---|---|---|---|---|---|
| atggcgccag | cggtggccgg | cggaggccgc | gtgcggagca | atgaggcgcc | cgctgcttct | 60 |
| gctgcggcgg | cggcgaccgg | gaacccgtgc | gcgtgcgggt | tccaggtgtg | cgcgtgcacg | 120 |
| gggactgcgg | cggtggcatc | tgccgcgtcg | tccgtggaca | tggacatcat | ggcgacgggg | 180 |
| cggatcggcc | ccctcaacga | cgagagctgg | gtgggcgtgg | agctcggcga | agacggcgag | 240 |
| accgacgaga | gcggcgccgc | cgtcgacgac | cgcccegtct | tccgcaccga | gaagattaag | 300 |
| gccgtccttc | tctaccccta | ccgggtgctg | atcttcgttc | gtctgatcgc | cttcacgctg | 360 |
| ttcgtgatct | ggcgtatctc | gcacaagaat | cccgacgcca | tgtggctgtg | ggtgaccctc | 420 |
| atctgcggcg | agttctggtt | cggtttctcc | tggctgctgg | atcagctgcc | caagctgaac | 480 |
| cccatcaacc | gcgtcccgga | cctggccgtg | ctgcggcagc | gcttcgaccg | ccccgacggc | 540 |
| acctccacgc | tgccgggcct | cgacatcttc | gtcaccaccg | ccgatccatt | caaggagccc | 600 |
| atcctttcca | cggccaattc | agtgctctcc | atcctcgccg | ccgactaccc | ggtggaccgc | 660 |
| aacacctgct | acgtctccga | cgacagtggc | atgctgctga | cctacgaggc | cctggcggag | 720 |
| gcgtccaagt | tgccacgct | gtgggtgccc | ttctgccgca | agcacggcat | cgaacccagg | 780 |
| ggccccgaga | gctacttcga | gctcaagtcg | caccccttaca | tggggagagc | ccaggacgag | 840 |
| ttcgtgaacg | accgccgccg | cgtgcgcaag | gagtacgacg | agttcaaggc | aaggatcaac | 900 |
| tccctggatc | acgacatcag | gcagcgcaac | gacggctaca | cgccgccaa | cgcgcaccgg | 960 |
| gaaggcgagc | cccgcccgac | atggatggct | gatggcaccc | agtgggaggg | cacctgggtc | 1020 |
| gacgcctccg | agaaccaccg | caagggcgac | cacgccggca | tcgtcaaggt | gctgctgaac | 1080 |
| caccccgagcc | acagccggca | gtacggcccg | ccggcgagcg | ccgacaaccc | gctggacttc | 1140 |
| agcggcgtcg | acgtgcgtgt | ccccatgcta | gtctacgttt | ccgtgagaa | gcgcccggga | 1200 |
| cacaaccgcc | agaagaaggc | cggcgccatg | aacgcgctca | cccgcgcctc | cgcactgctc | 1260 |
| tccaacgccc | ccttcatcct | caacctcgac | tgcgaccact | acatcaacaa | ctcacaggcg | 1320 |
| ctccgctccg | gtatctgctt | catgctggga | cgcgacagcg | acacagtcgc | cttcgtccag | 1380 |
| ttcccgcagc | gcttcgaggg | agtcgacccc | accgacctct | acgccaacca | caaccgcatc | 1440 |
| ttcttcgacg | gctcgctccg | tgccctcgac | ggcatgcagg | gcctatcta | cgtcggcaca | 1500 |
| gggtgcctct | tccgccgcat | caccgtctat | gccttcgacc | cgcccaggat | caacgtcggc | 1560 |
| gggccctgct | tccgatgct | cggcgggatg | ttcgccaaga | ccaagtacca | gaagcctggg | 1620 |
| ctcgagatga | ccatggccaa | ggccaaggcg | gcgccggtgc | ctgccaaggg | gaagcacggc | 1680 |
| ttcctgcccc | tgcccaagaa | gacctacggc | aaatcggatg | cgttcgtgga | cagcatcccg | 1740 |
| ctcgcgtcgc | acccgtcccc | ttacgtcgct | gcttacaaca | ctgctgaggg | gatcgtcacc | 1800 |
| gacgaggcca | ctatggccga | ggctgtgaac | gtgacggcgg | cggcgttcga | agaagacc | 1860 |

```
ggctggggca aggagatcgg gtgggtgtac gacaccgtca cggaggacgt cgtcacaggc    1920
taccggatgc acatcaaggg gtggcgctca cgctactgct ccatctaccc gcacgccttc    1980
atcggcaccg cgcccatcaa cctgacggag aggctcttcc aggtgctccg ctggtccacg    2040
ggctccctcg agatcttctt ctccaagaac aacccgctct tcggcagcac ctacctccac    2100
ccgctgcagc gcatcgccta catcaacatc acaacctacc ccttcaccgc catcttcctc    2160
atcttctaca ccaccgtacc ggcgctctcc ttcgtcaccg gccacttcat cgtgcagcgc    2220
ccgaccacca tgttctacgt ctacctgggc atcgtgctca ccacgctgct catcatcgcc    2280
gtgctggagg tcaagtgggc aggggtcacc gtcttcgagt ggttcaggaa cggccagttc    2340
tggatgacgg cgagcatgtc cgcctaccta caggccgtgt gccaggtgct catcaaggtg    2400
atattccaaa aggacatctc cttcaagctc acatccaagc tgccggcggg agacgagaag    2460
aaggacccgt acgccgacct gtacgtcgtg cgatggacac cgctgatgat cgtgcccatt    2520
atcgtcatct tcgtcaacat cattggatcg gcggtggcct ttgctaaggt gctcgacggc    2580
gagtggacgc actggctcaa ggtggccggc ggcgtcttct tcaacttctg ggtgctcttc    2640
cacctctacc cgttcgccaa gggcatcctc gggaagcacg gaaagacgcc agtcgttgtg    2700
ctcgtctggt gggcattcac cttcgtcatc accgccgtgc tctacatcaa catcccccac    2760
atgcatagtc caggaggcaa gcacacaaag gtggcgcacg gtcaccatgg ccagaagttc    2820
ctcggctggc cgtgagctcg gttgacgacg tcgccgccgt gcgtccaaca agacgacatc    2880
agagaagaaa caagtcttcc gctgagctgt gcatgcatcg atctgatcaa gaagcagagc    2940
ccgccattta attttttat tttttcttc acttttttgc ccgtttcttt ttagttttgt     3000
cc                                                                 3002
```

<210> SEQ ID NO 52
<211> LENGTH: 3424
<212> TYPE: DNA
<213> ORGANISM: artificial
<220> FEATURE:
<223> OTHER INFORMATION: synthetic

<400> SEQUENCE: 52

```
gaccactgca gcagacactt ccaacccatt ggttgggtag ctcaagaaga caacccagct     60
gcccagctga gctgagctga gctgaaatcc tctaccgaca ctagcttgcc tgcaagtctc    120
ggcccataaa tccccacccc cacgtacttt actcgccatt gctcacagcc ctctccctcc    180 ctctctttc tctctctgct cgcacatgct aaaggctgct gcctcgccca ttgcctgagc    240
agggagagct accttgcctg ctctgccatt gttggtgtcc ttgagggacg taatctctcc    300
ttcttgtaaa ggagagcgcg cgtgcgggca ttgaggacga cggccatggc gccagcggtg    360
gccggcggag gccgcgtgcg gagcaatgag gcgcccgctg ctgctgctac ggcggcgacc    420
gggaacccgt gcgcgtgcgg gttccaggtg tgcgcgtgca cggggtcggc ggcggtggca    480
tccgccgcct cgtccgtgga catggacatc atggcgacgg ggcggatcgg ccccctcaac    540
gatgagagct gggtgggagt ggagctcggc gaagacggcg agaccgacga gagcggcgcc    600
gccgtcgacg accgccccgt cttccgcacc gagaagatta aggccgtcct tctctacccc    660
taccgggtgc tgatcttcgt tcgtctgatc gcgttcacgc tgtttgtgat atggcgtatc    720
tcgcacaaga atcccgacgc catgtggctg tgggtgacct ccatctgcgg cgagttctgg    780 ttcggttct cctggctgct ggatcagctg cccaagctga accccatcaa tcgcgtcccg    840
```

```
gacctggccg tgctgcggca gcgcttcgac cgccccgatg gcacctctac gctgccgggt    900
ctcgacatct tcgtcaccac cgccgatcct ttcaaggagc ccatcctttc cacggccaac    960
tccgtgctct ccatcctcgc cgccgactac ccagtggacc gcaacacctg ctacgtctct   1020
gacgacagtg gcatgctgct cacctacgag gcgctggccg aggcctccaa gttcgccacg   1080
ctctgggtgc ccttctgccg caagcacggc atcgaaccca ggggtccgga gagctacttc   1140
gagctcaagt cccacccctta catggggaga gcccaggacg agttcgtcaa cgaccgccgc   1200
cgcgtccgca aggagtacga cgagttcaag acgaggatca actccctgga tcacgacatc   1260
aggcagcgca acgacggcta caacgccgcc aacgcgcacc gggaaggcga gccccgcccg   1320
acatggatgg ccgatggcac ccagtgggag ggcacctggg tcgacgcctc cgagaaccac   1380
cgcaagggcg accacgccgg catcgtcagg gtgctggtga accacccgag ccacagccgg   1440
cagtatggcc cgccggcgag cgccgacaac cctctggact cagcggcgt cgacgtgcgt    1500
gtccccatgc tcgtctacat tcccgtgag aagcgcccgg acacaacca ccagaagaag    1560
gccggcgcca tgaacgcgct cacccgcgcc tccgcactgc tctcgaacgc cccctttatc   1620
ctcaacctcg actgcgacca ctacatcaac aactcccagg cgctccgctc cggtatctgc   1680
ttcatgctgg gacgcgacag cgacaccgtc gccttcgtgc agttcccgca gcgcttcgag   1740
ggcgtcgacc ccaccgacct ctacgccaac cacaaccgca tcttcttcga cggctccctc   1800
cgtgccctcg acggcatgca gggccctatc tacgtcggca cagggtgcct cttccgccgc   1860
atcaccgtct atgccttcga cccgcccagg atcaacgtcg gcgggccgtg cttcccgatg   1920
ctcggcggat tgttcgccaa gaccaagtac gagaagcctg ggctcgagat gaccttggcc   1980
aaggccaagg cgaccccggt gcctgccaag gggaagcacg gcttcctgcc cctgcccaag   2040
aagacctacg ggaaatcgga tgccttcgtg gacagcatcc cgcgcgcgtc gcacccgtcg   2100
ccttacaccg ctgcttacgc cgctgctgag ggggtcgtga ccgacgaggc gactatggtc   2160
gaggcggtga acgtcacggc ggcggcgttc gagaagaaga ccggctgggg caaggagatc   2220
gggtgggtgt acgacaccgt cacggaggac gtcgtcacag gctaccggat gcacatcaag   2280
gggtggcgct cacgctactg ctccatctac ccgcacgcct tcatcggcac cgcgcccatc   2340
aacctgactg agaggctctt ccaggtgctc cgatggtcca cgggctccct cgagatcttc   2400
ttctccaaga caacccgct cttcggcagc acctacctcc acccgctgca gcgcatcgcc    2460
tacatcaaca tcactaccta ccccttcacc gccatcttcc tcatcttcta caccaccgtg   2520
ccggcgctct cctttgtcac cggccacttc atcgtcagc gcccgaccac catgttctac    2580
gtctacctgg gcatcgtgct cgccacgctg ctcatcatcg ccgtgctgga ggtcaagtgg   2640
gcagggcgtca ccgtcttcga gtggttcaga acggccagt tctggatgac ggcgagcatg   2700
tccgcctacc tacaggccgt gtgccaggtg ctcatcaagg tgatattcca gaaggacatc   2760
tccttcaagc tcacatccaa gctgccggcg ggagacgaga agaaggaccc ctacgccgac   2820
ctgtacgtcg tgcggtggac gccgctcatg atcgtgccca ttatcgtcat cttcgtcaac   2880
atcattggat cggcggtggc ctttgctaag gtgctcgacg gcgagtggac gcactggctc   2940
aaggtggccg cgcgcgtctt cttcaacttc tgggtgctct ccacctcta cccgttcgcc    3000
aagggcatcc tcgggaagca cggcaagacg ccagtcgttg tgctcgtctg gtgggcattc   3060
accttcgtca tcaccgccgt gctctacatc aacatccccc acatgcatag tccaggaggc   3120
aagcacacaa aggtgacaca cggtcaccat ggccagaagt tcctcggctg ccatgagct    3180
cggatgacga cgtcgccgcc gtgcgtccag caagacgaca tatgagagaa gaaacaagtc   3240
```

```
ttccgctgag ctgtcatgca tgatctgatc aagaagcaga gctcgccatt taatttttta    3300 atttttctt cacttttttg cccgtttctt tttagttttg tccagagaaa agatggtgtt    3360
gatttgattt agttcttaat tacctgtggt aattaattat gtacttaaga aaaaaaaaa    3420 aaaa                                                                  3424

<210> SEQ ID NO 53
<211> LENGTH: 3269
<212> TYPE: DNA
<213> ORGANISM: artificial
<220> FEATURE:
<223> OTHER INFORMATION: synthetic

<400> SEQUENCE: 53
gattgctcac acagccccg cccctccct ctctttctct ctctgcacgc acatgctaaa      60
gcctgcctcg gccattgcct gagccgggag tgctaccttg cctgctctgc cattgttgag    120
gtaaatctct ccttctcgta aaggagagcg cgcgtgcgtg cattgaggac cacgccatg    180 gcgccagcgg tggccggcgg aggccgcgtg cggagcaatg aggcgcccgc tgcttctgct    240
gcggcggcgc cgaccgggaa cccgtgcgcg tgcgggttcc aggtgtgcgc gtgcacgggg    300
actgcggcgg tggcatctgc cgcgtcgtcc gtggacatgg acatcatggc gacggggcgg    360
atcggccccc tcaacgacga gagctgggta ggcgtggagc tcggcgaaga cggcgagacc    420
gacgagagcg gcgccgccgt cgacgaccgc cccgtcttcc gcaccgagaa gattaaggcc    480
gtccttctct acccctaccg ggtgctgatc ttcgttcgtc tgatcgcctt cacgctgttc    540
gtgatctggc gtatctcgca caagaatccc gacgccatgt ggctgtgggt gacctccatc    600
tgcggcgagt tctggttcgg tttctcctgg ctgctggatc agctgcccaa gctgaacccc    660
atcaaccgcg tcccggacct ggccgtgctg cggcagcgct tcgaccgccc cgacggcacc    720
tccacgctgc cgggcctcga catcttcgtc accaccgccg atccattcaa ggagcccatc    780 cttttccaccg ccaattcagt gctctccatc ctcgccgccg actacccggt ggaccgcaac    840
acctgctacg tctccgacga cagtggcatg ctgctgacct acgaggccct ggcggaggcg    900
tccaagtttg ccacgctgtg ggtgcccttc tgccgcaagc acggcatcga acccagggc    960 cccgagagct acttcgagct caagtcgcac ccttacatgg ggagagccca ggacgagttc   1020
gtgaacgacc gccgccgcgt gcgcaaggag tacgacgagt caaggcgag gatcaactcc   1080 ctggatcacg acatcaggca gcgcaacgac ggctacaacg ccgccaacgc gcaccgggaa   1140
ggcgagcccc gcccaacatg gatggccgat ggcacccagt ggagggcac ctgggtcgac   1200 gcctccgaga ccaccgcaa gggcgaccac gccggcatcg tcaaggtgct gctgaaccac   1260 ccagccaca gccggcagta cggcccgccg gcgagcgccg acaacccgct ggacttcagc   1320
ggcgtcgacg tgcgtgtccc catgctcgtc tacgtttccc gtgagaagcg cccgggacac   1380
aaccaccaga agaaggccgg cgccatgaac gcgctcaccc gcgcctccgc actgctctcc   1440 aacgcccct tcatcctcaa cctcgactgc gaccactaca tcaacaactc acaggcgctc   1500
cgctccggta tctgcttcat gctgggacgc gacagcgaca cagtcgcctt cgtccagttc   1560
ccgcagcgct tcgagggagt tcgaccccacc gacctctacg ccaaccacaa ccgcatcttc   1620
ttcgacggct cgctccgtgc cctcgacggc atgcagggcc ctatctacgt cggcacaggg   1680
tgcctcttcc gccgcatcac cgtctatgcc ttcgacccgc caggatcaa cgtcggcggg   1740 ccctgcttcc cgatgctcgg cgggatgttc gccaagacca agtaccagaa gcctgggctc   1800
```

```
gagatgacca tggccaaggc caaggcggcg ccggtgcctg ccaaggggaa gcacggcttc  1860
ctgcccctgc ccaagaagac ctacggcaaa tcggatgcgt tcgtggacag catcccgctc  1920
gcgtcgcacc cgtcccctta cgtcgctgct acaacactg ctgaggggat cgtcaccgac  1980
gaggccacta tggccgaggc tgtgaacgtg acggcggcgg cgttcgagaa gaagaccggc  2040
tggggcaagg agatcgggtg ggtgtacgac accgtcacgg aggacgtcgt cacaggctac  2100
cggatgcaca tcaaggggtg gcgctcacgc tactgctcca tctacccgca cgccttcatc  2160
ggcaccgcgc ccatcaacct gacggagagg ctcttccagg tgctccgctg gtccacgggc  2220
tccctcgaga tcttcttctc caagaacaac ccgctcttcg gcagcaccta cctccacccg  2280
ctgcagcgca tcgcctacat caacatcaca acctaccct tcaccgccat cttcctcatc  2340
ttctacacca ccgtgccggc gctctccttc gtcaccggcc acttcatcgt gcagcgcccg  2400
accaccatgt tctacgtcta cctgggcatc gtgctcgcca cgctgctcat catcgccgtg  2460
ctggaggtca gtgggcagg ggtcaccgtc ttcgagtggt tcaggaacgg ccagttctgg  2520
atgacggcga gcatgtccgc ctacctacag gccgtgtgcc aggtgctcat caaggtgata  2580
ttccagaagg acatctcctt caagctcaca tccaagctgc cggcgggaga cgagaagaag  2640
gacccgtacg ccgacctgta cgtcgtgcgg tggacaccgc tgatgatcgt gcccattatc  2700
gtcatcttcg tcaacatcat tggatcggcg gtggcctttg ctaaggtgct cgacggcgag  2760
tggacgcact ggctcaaggt ggccggcggc gtcttcttca acttctgggt gctcttccac  2820
ctctacccgt cgccaaggg catcctcggg aagcacggaa agacgccagt cgttgtgctc  2880
gtctggtggg cattcacctt cgtcatcacc gccgtgctct acatcaacat cccccacatg  2940
catagtccag gaggcaagca cacaaaggtg gcgcacggtc accatggcca gaagttcctc  3000
ggctggccgt gagctcggtt gacgacgtcg ccgccgtgcg tccaacaaga cgacatcaga  3060
gaagaaacaa gtcttccgct gagctgtgca tgcatcgatc tgatcaagaa gcagagcccg  3120
ccatttaatt ttttattt ttcttcact tttttgcccg tttcttttta gttttgtcca  3180
gagaaaagat ggtgttgatt tgatttagtt tttaattacc tgtggtaatt aattatgtat  3240
ttaattatac agtaccctta cccaacaag                                   3269

<210> SEQ ID NO 54
<211> LENGTH: 5244
<212> TYPE: DNA
<213> ORGANISM: artificial
<220> FEATURE:
<223> OTHER INFORMATION: synthetic

<400> SEQUENCE: 54
cattgaggac gacggccatg gcgccagcgg tggccggcgg aggccgcgtg cggagcaatg    60
aggcgcccgc tgctgctgct acggcggcga ccggaaccc gtgcgcgtgc gggttccagg   120
tgtgcgcgtg cacggggtcg gcggcggtgg catccgccgc ctcgtccgtg acatggaca   180 tcatggcgac ggggcggatc ggccccctca acgatgagag ctgggtggga gtggagctcg   240
gcgaagacgg cgagaccgac gagagcggcg ccgccgtcga cgaccgcccc gtcttccgca   300
ccgagaagat taaggccgtc cttctctacc cctaccggta cgtactcact ccaattatta   360
cccatcttat tattattaca tccaagaagg agtagtgaac aagtccttga ttaattacta   420
ctacactctt ctaatctagt aatttgctta aaccgaccag cagctcagca acaactgcat   480
gcattgcgca acagtttgtt tgacagtcag ttacacacct taattcgtgt tcatgagaaa   540
attgccagta ctcctaagct gctggcatga gtagtagtat ttacagtagt tagctaaaat   600
```

```
ttgagcgccc caagacaggc gcacgttaga ggcgggccaa tgatggctcg aatacgccca    660
agcgagcgcg tcccggtgtg ggctgtctgt tcggtgcggc gctggttctt ttctattctc    720
attagtcatc gttcgcgtta gtcactgctg cgtgggcccc tccctagagg ggacgttagc    780
cgttgggcct gcctgcctgc ctggcagatg ggcccttcag tacaccctgg cggctcataa    840
atctttacca ctttagagta aaaaaaaact ggccgtctgg ttttgccgct ttgcaatagg    900
gaatccgagg tgaaatgaaa tgaggagacg acagtgggcg gggcatggct tgcatgtgaa    960
tccaagacac attattaaaa gcctcccaca tccctatcct tccttactgc aagattagtt   1020
gggcacgtag ttgcagtgat aaaggtggtt aaacttttgg ggttcggaca agatgagaaa   1080
agctactaac atgttcttgt ttgtctctgg gaaaacgcat gctcgagatc tcagttcgca   1140
gtctagatgg gtgattgggt gtaggtagct tttgttgagt tggttcatgt agcataggag   1200
gaaaatttaa tggatgtcat atgtcagaca tagaaaaaag gaggagaaga aaaagggtac   1260
accgaaaaag aagcggtgcc gcagcatgaa tgtgtgactc atgttggcac cgagaaagag   1320
cttagtacaa aagtgggata gttacaactc agaatggagc gtgctaatat tgtactagca   1380
caaaattagc aagaaagatt tcgtacaaca ttttagtaag aaaatgcacc catttccaaa   1440
aataaaataa attatgtgaa cacttagcat tagtctaagt aacctatagt agtttagcag   1500
gagaaggttc caacatcctc cactaggcaa cagcaaaagg aaagaaaaaa agaggcacat   1560
attaatggag caacgaatcc agcgagacca ccgctagcac cagtggtggt ggtcgcatcc   1620
atatgccctc gcacgacgga cgtagggggc taccgacagc cgcagcatgt cggtgcgcac   1680
acgccgtgtt gtgctgctgc caagttccag ctcacactca ttgacttgcc agccccgcc    1740
ttcgctgtca atatgcgctt tcgcttttt ggcatttgca aaaataaat agctttattt      1800
atttataacg cggcaaaaaa atgcaaagat gaacctggcg catgttccct ccaataatta   1860
catccaatca tgaaaccaac acaccgccca attaacccaa taaacctaca gtagtatatt   1920
cgagtgtgat gattttact aataactgtg agtgaatgat gcagggtgct gatcttcgtt    1980
cgtctgatcg cgttcacgct gtttgtgata tggcgtatct cgcacaagaa tcccgacgcc   2040
atgtggctgt gggtgacctc catctgcggc gagttctggt tcggtttctc ctggctgctg   2100
gatcagctgc ccaagctgaa ccccatcaat cgcgtcccgg acctggccgt gctgcggcag   2160
cgcttcgacc gccccgatgg cacctctacg ctgccgggtc tcgacatctt cgtcaccacc   2220
gccgatcctt tcaaggagcc catccttttcc acggccaact ccgtgctctc catcctcgcc   2280
gccgactacc cagtggaccg caacacctgc tacgtctctg acgacagtgg catgctgctc   2340
acctacgagg cgctggccga ggcctccaag ttcgccacgc tctgggtgcc cttctgccgc   2400
aagcacggca tcgaacccag gggtccggag agctacttcg agctcaagtc ccacccttac   2460
atggggagag cccaggacga gttcgtcaac gaccgccgcc gcgtccgcaa ggagtacgac   2520
gagttcaaga cgaggatcaa ctcccctggat cacgacatca ggcagcgcaa cgacggctac   2580
aacgccgcca acgcgcaccg ggaaggcgag ccccgcccga catggatggc cgatggcacc   2640
cagtgggagg gcacctgggt cgacgcctcc gagaaccacc gcaagggcga ccacgccggc   2700
atcgtcaggg tcagtactag tactatttac agcctcgtcg ttcctactta catgcatgca   2760
tgccattgtt cattcatttc tgttcttgga attatgctgg ccggttagtt agggtctcgt   2820
tattagcggc catgtgatgt gatgcctgcc tgcctgccga tccatcggag atttgatgga   2880
atggacgtgg cgatagccga gagcgtaagc atcaggcaga caagcacact tgtagacaga   2940
```

```
catggaacaa agacatgcat gctctgctct cgtctggcca gcaatgcaat ggggtggtt    3000
ccattcattc atggtctgac gaggaatggt ggttggggtg gtccttttcc cccgacacca    3060
ctacagcatc cactttatga ctctttaatt caccgcctct gcattgttaa ctgcagtctc    3120
acctcaatca ttcattcatc ggactgatta atttggttgg tcatttagtt atactactct    3180
actagtacta gtacgtggta agtacaatta agatttaact ataattatcc catctcaaag    3240
tttaattaat caacgaccca aatttcacct tcatcaacta tgcatatcat tttgaccttt    3300
ttaccgttac cagctcaaat taacgatgtt tagccttgtt ttttactgga ttagttaccc    3360
atactgtaag agtgtggtcg ctgacagttt ttggatgcag gtgctggtga accacccgag    3420
ccacagccgg cagtatggcc cgccggcgag cgccgacaac cctctggact tcagcggcgt    3480
cgacgtgcgt gtccccatgc tcgtctacat ttcccgtgag aagcgcccgg acacaaacca    3540
ccagaagaag gccggcgcca tgaacgcgct caccgcgcc tccgcactgc tctcgaacgc    3600
cccctttatc ctcaacctcg actgcgacca ctacatcaac aactcccagg cgctccgctc    3660
cggtatctgc ttcatgctgg gacgcgacag cgacaccgtc gccttcgtgc agttcccgca    3720
gcgcttcgag ggcgtcgacc ccaccgacct ctacgccaac cacaaccgca tcttcttcga    3780
cggctccctc cgtgccctcg acggcatgca gggcccctatc tacgtcggca cagggtgcct    3840
cttccgccgc atcaccgtct atgccttcga cccgcccagg atcaacgtcg gcgggccgtg    3900
cttcccgatg ctcggcggat tgttcgccaa gaccaagtac gagaagcctg ggctcgagat    3960
gaccttggcc aaggccaagg cgaccccggt gcctgccaag gggaagcacg gcttcctgcc    4020
cctgccaag aagacctacg ggaaatcgga tgccttcgtg gacagcatcc cgcgcgcgtc    4080
gcacccgtcg ccttacaccg ctgcttacgc cgctgctgag ggggtcgtga ccgacgaggc    4140
gactatggtc gaggcggtga acgtcacggc ggcggcgttc gagaagaaga ccggctgggg    4200
caaggagatc gggtgggtgt acgacaccgt cacggaggac gtcgtcacag gctaccggat    4260
gcacatcaag gggtggcgct cacgctactg ctccatctac ccgcacgcct tcatcggcac    4320
cgcgcccatc aacctgactg agaggctctt ccaggtgctc cgatggtcca cgggctccct    4380
cgagatcttc ttctccaaga caacccgct cttcggcagc acctacctcc acccgctgca    4440
gcgcatcgcc tacatcaaca tcactaccta ccccttcacc gccatcttcc tcatcttcta    4500
caccaccgtg ccggcgctct cctttgtcac cggccacttc atcgtgcagc gcccgaccac    4560
catgttctac gtctacctgg gcatcgtgct cgccacgctg ctcatcatcg ccgtgctgga    4620
ggtcaagtgg gcaggggtca ccgtcttcga gtggttcaga aacggccagt tctgggatgac    4680
ggcgagcatg tccgcctacc tacaggccgt gtgccaggtg ctcatcaagg tgatattcca    4740
gaaggacatc tccttcaagc tcacatccaa gctgccggcg ggagcgaga agaaggaccc    4800
ctacgccgac ctgtacgtcg tgcggtggac gccgctcatg atcgtgccca ttatcgtcat    4860
cttcgtcaac atcattggat cggcggtggc cttttgctaag gtgctcgacg gcagtggac    4920
gcactggctc aaggtggccg gcggcgtctt cttcaacttc tgggtgctct ccacctcta    4980
cccgttcgcc aagggcatcc tcgggaagca cggcaagacg ccagtcgttg tgctcgtctg    5040
gtgggcattc accttcgtca tcaccgccgt gctctacatc aacatccccc acatgcatag    5100
tccaggaggc aagcacacaa aggtgacaca cggtcaccat ggccagaagt tcctcggctg    5160
gccatgagct cggatgacga cgtgccgcc gtgcgtccag caagacgaca tatgagagaa    5220
gaaacaagtc ttccgctgag ctgt                                          5244
```

```
<210> SEQ ID NO 55
<211> LENGTH: 944
<212> TYPE: PRT
<213> ORGANISM: Avena sativa

<400> SEQUENCE: 55
```

| | | | | | | | | | | | | | | |
|---|---|---|---|---|---|---|---|---|---|---|---|---|---|---|
| Met | Ala | Pro | Ala | Val | Ala | Gly | Gly | Arg | Val | Arg | Ser | Asn | Glu | Ala |
| 1 | | | | 5 | | | | | 10 | | | | | 15 |
| Pro | Ala | Ala | Ser | Ala | Ala | Ala | Ala | Thr | Gly | Asn | Pro | Cys | Ala | Cys |
| | | | 20 | | | | | 25 | | | | | 30 | |
| Gly | Phe | Gln | Val | Cys | Ala | Cys | Thr | Gly | Thr | Ala | Ala | Val | Ala | Ser | Ala |
| | | | 35 | | | | | 40 | | | | | 45 | |
| Ala | Ser | Ser | Val | Asp | Met | Asp | Ile | Met | Ala | Thr | Gly | Arg | Ile | Gly | Pro |
| | 50 | | | | | 55 | | | | | 60 | | | | |
| Leu | Asn | Asp | Glu | Ser | Trp | Val | Gly | Val | Glu | Leu | Gly | Glu | Asp | Gly | Glu |
| 65 | | | | | 70 | | | | | 75 | | | | | 80 |
| Thr | Asp | Glu | Ser | Gly | Ala | Ala | Val | Asp | Asp | Arg | Pro | Val | Phe | Arg | Thr |
| | | | | 85 | | | | | 90 | | | | | 95 | |
| Glu | Lys | Ile | Lys | Ala | Val | Leu | Leu | Tyr | Pro | Tyr | Arg | Val | Leu | Ile | Phe |
| | | | 100 | | | | | 105 | | | | | 110 | | |
| Val | Arg | Leu | Ile | Ala | Phe | Thr | Leu | Phe | Val | Ile | Trp | Arg | Ile | Ser | His |
| | | 115 | | | | | 120 | | | | | 125 | | | |
| Lys | Asn | Pro | Asp | Ala | Met | Trp | Leu | Trp | Val | Thr | Ser | Ile | Cys | Gly | Glu |
| | 130 | | | | | 135 | | | | | 140 | | | | |
| Phe | Trp | Phe | Gly | Phe | Ser | Trp | Leu | Leu | Asp | Gln | Leu | Pro | Lys | Leu | Asn |
| 145 | | | | | 150 | | | | | 155 | | | | | 160 |
| Pro | Ile | Asn | Arg | Val | Pro | Asp | Leu | Ala | Val | Leu | Arg | Gln | Arg | Phe | Asp |
| | | | | 165 | | | | | 170 | | | | | 175 | |
| Arg | Pro | Asp | Gly | Thr | Ser | Thr | Leu | Pro | Gly | Leu | Asp | Ile | Phe | Val | Thr |
| | | | 180 | | | | | 185 | | | | | 190 | | |
| Thr | Ala | Asp | Pro | Phe | Lys | Glu | Pro | Ile | Leu | Ser | Thr | Ala | Asn | Ser | Val |
| | | 195 | | | | | 200 | | | | | 205 | | | |
| Leu | Ser | Ile | Leu | Ala | Ala | Asp | Tyr | Pro | Val | Asp | Arg | Asn | Thr | Cys | Tyr |
| | 210 | | | | | 215 | | | | | 220 | | | | |
| Val | Ser | Asp | Asp | Ser | Gly | Met | Leu | Leu | Thr | Tyr | Glu | Ala | Leu | Ala | Glu |
| 225 | | | | | 230 | | | | | 235 | | | | | 240 |
| Ala | Ser | Lys | Phe | Ala | Thr | Leu | Trp | Val | Pro | Phe | Cys | Arg | Lys | His | Gly |
| | | | | 245 | | | | | 250 | | | | | 255 | |
| Ile | Glu | Pro | Arg | Gly | Pro | Glu | Ser | Tyr | Phe | Glu | Leu | Lys | Ser | His | Pro |
| | | | 260 | | | | | 265 | | | | | 270 | | |
| Tyr | Met | Gly | Arg | Ala | Gln | Asp | Glu | Phe | Val | Asn | Asp | Arg | Arg | Val |
| | | 275 | | | | | 280 | | | | | 285 | | | |
| Arg | Lys | Glu | Tyr | Asp | Glu | Phe | Lys | Ala | Arg | Ile | Asn | Ser | Leu | Asp | His |
| | 290 | | | | | 295 | | | | | 300 | | | | |
| Asp | Ile | Arg | Gln | Arg | Asn | Asp | Gly | Tyr | Asn | Ala | Ala | Asn | Ala | His | Arg |
| 305 | | | | | 310 | | | | | 315 | | | | | 320 |
| Glu | Gly | Glu | Pro | Arg | Pro | Thr | Trp | Met | Ala | Asp | Gly | Thr | Gln | Trp | Glu |
| | | | | 325 | | | | | 330 | | | | | 335 | |
| Gly | Thr | Trp | Val | Asp | Ala | Ser | Glu | Asn | His | Arg | Lys | Gly | Asp | His | Ala |
| | | | 340 | | | | | 345 | | | | | 350 | | |
| Gly | Ile | Val | Lys | Val | Leu | Leu | Asn | His | Pro | Ser | His | Ser | Arg | Gln | Tyr |
| | | 355 | | | | | 360 | | | | | 365 | | | |
| Gly | Pro | Pro | Ala | Ser | Ala | Asp | Asn | Pro | Leu | Asp | Phe | Ser | Gly | Val | Asp |
| | 370 | | | | | 375 | | | | | 380 | | | | |

Val Arg Val Pro Met Leu Val Tyr Val Ser Arg Glu Lys Arg Pro Gly
385                 390                 395                 400

His Asn His Gln Lys Lys Ala Gly Ala Met Asn Ala Leu Thr Arg Ala
            405                 410                 415

Ser Ala Leu Leu Ser Asn Ala Pro Phe Ile Leu Asn Leu Asp Cys Asp
        420                 425                 430

His Tyr Ile Asn Asn Ser Gln Ala Leu Arg Ser Gly Ile Cys Phe Met
        435                 440                 445

Leu Gly Arg Asp Ser Asp Thr Val Ala Phe Val Gln Phe Pro Gln Arg
        450                 455                 460

Phe Glu Gly Val Asp Pro Thr Asp Leu Tyr Ala Asn His Asn Arg Ile
465                 470                 475                 480

Phe Phe Asp Gly Ser Leu Arg Ala Leu Asp Gly Met Gln Gly Pro Ile
            485                 490                 495

Tyr Val Gly Thr Gly Cys Leu Phe Arg Arg Ile Thr Val Tyr Ala Phe
            500                 505                 510

Asp Pro Pro Arg Ile Asn Val Gly Gly Pro Cys Phe Pro Met Leu Gly
        515                 520                 525

Gly Met Phe Ala Lys Thr Lys Tyr Gln Lys Pro Gly Leu Glu Met Thr
        530                 535                 540

Met Ala Lys Ala Lys Ala Ala Pro Val Pro Ala Lys Gly Lys His Gly
545                 550                 555                 560

Phe Leu Pro Leu Pro Lys Lys Thr Tyr Gly Lys Ser Asp Ala Phe Val
            565                 570                 575

Asp Ser Ile Pro Leu Ala Ser His Pro Ser Pro Tyr Val Ala Ala Tyr
        580                 585                 590

Asn Thr Ala Glu Gly Ile Val Thr Asp Glu Ala Thr Met Ala Glu Ala
        595                 600                 605

Val Asn Val Thr Ala Ala Ala Phe Glu Lys Lys Thr Gly Trp Gly Lys
        610                 615                 620

Glu Ile Gly Trp Val Tyr Asp Thr Val Thr Glu Asp Val Val Thr Gly
625                 630                 635                 640

Tyr Arg Met His Ile Lys Gly Trp Arg Ser Arg Tyr Cys Ser Ile Tyr
            645                 650                 655

Pro His Ala Phe Ile Gly Thr Ala Pro Ile Asn Leu Thr Glu Arg Leu
            660                 665                 670

Phe Gln Val Leu Arg Trp Ser Thr Gly Ser Leu Glu Ile Phe Phe Ser
        675                 680                 685

Lys Asn Asn Pro Leu Phe Gly Ser Thr Tyr Leu His Pro Leu Gln Arg
690                 695                 700

Ile Ala Tyr Ile Asn Ile Thr Thr Tyr Pro Phe Thr Ala Ile Phe Leu
705                 710                 715                 720

Ile Phe Tyr Thr Thr Val Pro Ala Leu Ser Phe Val Thr Gly His Phe
            725                 730                 735

Ile Val Gln Arg Pro Thr Thr Met Phe Tyr Val Tyr Leu Gly Ile Val
            740                 745                 750

Leu Thr Thr Leu Leu Ile Ile Ala Val Leu Glu Val Lys Trp Ala Gly
        755                 760                 765

Val Thr Val Phe Glu Trp Phe Arg Asn Gly Gln Phe Trp Met Thr Ala
        770                 775                 780

Ser Met Ser Ala Tyr Leu Gln Ala Val Cys Gln Val Leu Ile Lys Val
785                 790                 795                 800

Ile Phe Gln Lys Asp Ile Ser Phe Lys Leu Thr Ser Lys Leu Pro Ala

```
            805                 810                 815
Gly Asp Glu Lys Lys Asp Pro Tyr Ala Asp Leu Tyr Val Val Arg Trp
            820                 825                 830

Thr Pro Leu Met Ile Val Pro Ile Ile Val Ile Phe Val Asn Ile Ile
            835                 840                 845

Gly Ser Ala Val Ala Phe Ala Lys Val Leu Asp Gly Glu Trp Thr His
            850                 855                 860

Trp Leu Lys Val Ala Gly Gly Val Phe Phe Asn Phe Trp Val Leu Phe
865                 870                 875                 880

His Leu Tyr Pro Phe Ala Lys Gly Ile Leu Gly Lys His Gly Lys Thr
                    885                 890                 895

Pro Val Val Val Leu Val Trp Trp Ala Phe Thr Phe Val Ile Thr Ala
            900                 905                 910

Val Leu Tyr Ile Asn Ile Pro His Met His Ser Pro Gly Gly Lys His
            915                 920                 925

Thr Lys Val Ala His Gly His His Gly Gln Lys Phe Leu Gly Trp Pro
930                 935                 940
```

<210> SEQ ID NO 56
<211> LENGTH: 943
<212> TYPE: PRT
<213> ORGANISM: Avena sativa

<400> SEQUENCE: 56

```
Met Ala Pro Ala Val Ala Gly Gly Arg Val Arg Ser Asn Glu Ala
1               5                   10                  15

Pro Ala Ala Ala Thr Ala Ala Thr Gly Asn Pro Cys Ala Cys Gly
                20                  25                  30

Phe Gln Val Cys Ala Cys Thr Gly Ser Ala Ala Val Ala Ser Ala Ala
            35                  40                  45

Ser Ser Val Asp Met Asp Ile Met Ala Thr Gly Arg Ile Gly Pro Leu
        50                  55                  60

Asn Asp Glu Ser Trp Val Gly Val Glu Leu Gly Glu Asp Gly Glu Thr
65                  70                  75                  80

Asp Glu Ser Gly Ala Ala Val Asp Asp Arg Pro Val Phe Arg Thr Glu
                85                  90                  95

Lys Ile Lys Ala Val Leu Leu Tyr Pro Tyr Arg Val Leu Ile Phe Val
            100                 105                 110

Arg Leu Ile Ala Phe Thr Leu Phe Val Ile Trp Arg Ile Ser His Lys
        115                 120                 125

Asn Pro Asp Ala Met Trp Leu Trp Val Thr Ser Ile Cys Gly Glu Phe
    130                 135                 140

Trp Phe Gly Phe Ser Trp Leu Leu Asp Gln Leu Pro Lys Leu Asn Pro
145                 150                 155                 160

Ile Asn Arg Val Pro Asp Leu Ala Val Leu Arg Gln Arg Phe Asp Arg
                165                 170                 175

Pro Asp Gly Thr Ser Thr Leu Pro Gly Leu Asp Ile Phe Val Thr Thr
            180                 185                 190

Ala Asp Pro Phe Lys Glu Pro Ile Leu Ser Thr Ala Asn Ser Val Leu
        195                 200                 205

Ser Ile Leu Ala Ala Asp Tyr Pro Val Asp Arg Asn Thr Cys Tyr Val
    210                 215                 220

Ser Asp Asp Ser Gly Met Leu Leu Thr Tyr Glu Ala Leu Ala Glu Ala
225                 230                 235                 240
```

```
Ser Lys Phe Ala Thr Leu Trp Val Pro Phe Cys Arg Lys His Gly Ile
            245                 250                 255

Glu Pro Arg Gly Pro Glu Ser Tyr Phe Glu Leu Lys Ser His Pro Tyr
        260                 265                 270

Met Gly Arg Ala Gln Asp Glu Phe Val Asn Asp Arg Arg Val Arg
        275                 280                 285

Lys Glu Tyr Asp Glu Phe Lys Thr Arg Ile Asn Ser Leu Asp His Asp
        290                 295                 300

Ile Arg Gln Arg Asn Asp Gly Tyr Asn Ala Asn Ala His Arg Glu
305                 310                 315                 320

Gly Glu Pro Arg Pro Thr Trp Met Ala Asp Gly Thr Gln Trp Glu Gly
            325                 330                 335

Thr Trp Val Asp Ala Ser Glu Asn His Arg Lys Gly Asp His Ala Gly
            340                 345                 350

Ile Val Arg Val Leu Val Asn His Pro Ser His Ser Arg Gln Tyr Gly
            355                 360                 365

Pro Pro Ala Ser Ala Asp Asn Pro Leu Asp Phe Ser Gly Val Asp Val
        370                 375                 380

Arg Val Pro Met Leu Val Tyr Ile Ser Arg Glu Lys Arg Pro Gly His
385                 390                 395                 400

Asn His Gln Lys Lys Ala Gly Ala Met Asn Ala Leu Thr Arg Ala Ser
            405                 410                 415

Ala Leu Leu Ser Asn Ala Pro Phe Ile Leu Asn Leu Asp Cys Asp His
            420                 425                 430

Tyr Ile Asn Asn Ser Gln Ala Leu Arg Ser Gly Ile Cys Phe Met Leu
        435                 440                 445

Gly Arg Asp Ser Asp Thr Val Ala Phe Val Gln Phe Pro Gln Arg Phe
        450                 455                 460

Glu Gly Val Asp Pro Thr Asp Leu Tyr Ala Asn His Asn Arg Ile Phe
465                 470                 475                 480

Phe Asp Gly Ser Leu Arg Ala Leu Asp Gly Met Gln Gly Pro Ile Tyr
            485                 490                 495

Val Gly Thr Gly Cys Leu Phe Arg Arg Ile Thr Val Tyr Ala Phe Asp
            500                 505                 510

Pro Pro Arg Ile Asn Val Gly Gly Pro Cys Phe Pro Met Leu Gly Gly
        515                 520                 525

Leu Phe Ala Lys Thr Lys Tyr Glu Lys Pro Gly Leu Glu Met Thr Leu
        530                 535                 540

Ala Lys Ala Lys Ala Thr Pro Val Pro Ala Lys Gly Lys His Gly Phe
545                 550                 555                 560

Leu Pro Leu Pro Lys Lys Thr Tyr Gly Lys Ser Asp Ala Phe Val Asp
            565                 570                 575

Ser Ile Pro Arg Ala Ser His Pro Ser Pro Tyr Thr Ala Ala Tyr Ala
        580                 585                 590

Ala Ala Glu Gly Val Val Thr Asp Glu Ala Thr Met Val Glu Ala Val
        595                 600                 605

Asn Val Thr Ala Ala Ala Phe Glu Lys Lys Thr Gly Trp Gly Lys Glu
        610                 615                 620

Ile Gly Trp Val Tyr Asp Thr Val Thr Glu Asp Val Val Thr Gly Tyr
625                 630                 635                 640

Arg Met His Ile Lys Gly Trp Arg Ser Arg Tyr Cys Ser Ile Tyr Pro
            645                 650                 655

His Ala Phe Ile Gly Thr Ala Pro Ile Asn Leu Thr Glu Arg Leu Phe
```

```
                   660                 665                 670
Gln Val Leu Arg Trp Ser Thr Gly Ser Leu Glu Ile Phe Phe Ser Lys
                675                 680                 685

Asn Asn Pro Leu Phe Gly Ser Thr Tyr Leu His Pro Leu Gln Arg Ile
            690                 695                 700

Ala Tyr Ile Asn Ile Thr Thr Tyr Pro Phe Thr Ala Ile Phe Leu Ile
705                 710                 715                 720

Phe Tyr Thr Thr Val Pro Ala Leu Ser Phe Val Thr Gly His Phe Ile
                725                 730                 735

Val Gln Arg Pro Thr Thr Met Phe Tyr Val Tyr Leu Gly Ile Val Leu
            740                 745                 750

Ala Thr Leu Leu Ile Ile Ala Val Leu Glu Val Lys Trp Ala Gly Val
        755                 760                 765

Thr Val Phe Glu Trp Phe Arg Asn Gly Gln Phe Trp Met Thr Ala Ser
    770                 775                 780

Met Ser Ala Tyr Leu Gln Ala Val Cys Gln Val Leu Ile Lys Val Ile
785                 790                 795                 800

Phe Gln Lys Asp Ile Ser Phe Lys Leu Thr Ser Lys Leu Pro Ala Gly
                805                 810                 815

Asp Glu Lys Lys Asp Pro Tyr Ala Asp Leu Tyr Val Val Arg Trp Thr
            820                 825                 830

Pro Leu Met Ile Val Pro Ile Ile Val Ile Phe Val Asn Ile Ile Gly
        835                 840                 845

Ser Ala Val Ala Phe Ala Lys Val Leu Asp Gly Glu Trp Thr His Trp
    850                 855                 860

Leu Lys Val Ala Gly Gly Val Phe Phe Asn Phe Trp Val Leu Phe His
865                 870                 875                 880

Leu Tyr Pro Phe Ala Lys Gly Ile Leu Gly Lys His Gly Lys Thr Pro
                885                 890                 895

Val Val Val Leu Val Trp Trp Ala Phe Thr Phe Val Ile Thr Ala Val
            900                 905                 910

Leu Tyr Ile Asn Ile Pro His Met His Ser Pro Gly Gly Lys His Thr
        915                 920                 925

Lys Val Thr His Gly His His Gly Gln Lys Phe Leu Gly Trp Pro
    930                 935                 940

<210> SEQ ID NO 57
<211> LENGTH: 944
<212> TYPE: PRT
<213> ORGANISM: Avena sativa

<400> SEQUENCE: 57

Met Ala Pro Ala Val Ala Gly Gly Gly Arg Val Arg Ser Asn Glu Ala
1               5                   10                  15

Pro Ala Ala Ser Ala Ala Ala Ala Thr Gly Asn Pro Cys Ala Cys
            20                  25                  30

Gly Phe Gln Val Cys Ala Cys Thr Gly Thr Ala Ala Ala Ser Ala
        35                  40                  45

Ala Ser Ser Val Asp Met Asp Ile Met Ala Thr Gly Arg Ile Gly Pro
    50                  55                  60

Leu Asn Asp Glu Ser Trp Val Gly Val Glu Leu Gly Glu Asp Gly Glu
65                  70                  75                  80

Thr Asp Glu Ser Gly Ala Ala Val Asp Asp Arg Pro Val Phe Arg Thr
                85                  90                  95
```

```
Glu Lys Ile Lys Ala Val Leu Leu Tyr Pro Tyr Arg Val Leu Ile Phe
                100                 105                 110

Val Arg Leu Ile Ala Phe Thr Leu Phe Val Ile Trp Arg Ile Ser His
        115                 120                 125

Lys Asn Pro Asp Ala Met Trp Leu Trp Val Thr Ser Ile Cys Gly Glu
    130                 135                 140

Phe Trp Phe Gly Phe Ser Trp Leu Leu Asp Gln Leu Pro Lys Leu Asn
145                 150                 155                 160

Pro Ile Asn Arg Val Pro Asp Leu Ala Val Leu Arg Gln Arg Phe Asp
                165                 170                 175

Arg Pro Asp Gly Thr Ser Thr Leu Pro Gly Leu Asp Ile Phe Val Thr
            180                 185                 190

Thr Ala Asp Pro Phe Lys Glu Pro Ile Leu Ser Thr Ala Asn Ser Val
        195                 200                 205

Leu Ser Ile Leu Ala Ala Asp Tyr Pro Val Asp Arg Asn Thr Cys Tyr
210                 215                 220

Val Ser Asp Asp Ser Gly Met Leu Leu Thr Tyr Glu Ala Leu Ala Glu
225                 230                 235                 240

Ala Ser Lys Phe Ala Thr Leu Trp Val Pro Phe Cys Arg Lys His Gly
                245                 250                 255

Ile Glu Pro Arg Gly Pro Glu Ser Tyr Phe Glu Leu Lys Ser His Pro
            260                 265                 270

Tyr Met Gly Arg Ala Gln Asp Glu Phe Val Asn Asp Arg Arg Val
        275                 280                 285

Arg Lys Glu Tyr Asp Glu Phe Lys Ala Arg Ile Asn Ser Leu Asp His
    290                 295                 300

Asp Ile Arg Gln Arg Asn Asp Gly Tyr Asn Ala Ala Asn Ala His Arg
305                 310                 315                 320

Glu Gly Glu Pro Arg Pro Thr Trp Met Ala Asp Gly Thr Gln Trp Glu
                325                 330                 335

Gly Thr Trp Val Asp Ala Ser Glu Asn His Arg Lys Gly Asp His Ala
            340                 345                 350

Gly Ile Val Lys Val Leu Leu Asn His Pro Ser His Ser Arg Gln Tyr
        355                 360                 365

Gly Pro Pro Ala Ser Ala Asp Asn Pro Leu Asp Phe Ser Gly Val Asp
    370                 375                 380

Val Arg Val Pro Met Leu Val Tyr Val Ser Arg Glu Lys Arg Pro Gly
385                 390                 395                 400

His Asn His Gln Lys Lys Ala Gly Ala Met Asn Ala Leu Thr Arg Ala
                405                 410                 415

Ser Ala Leu Leu Ser Asn Ala Pro Phe Ile Leu Asn Leu Asp Cys Asp
            420                 425                 430

His Tyr Ile Asn Asn Ser Gln Ala Leu Arg Ser Gly Ile Cys Phe Met
        435                 440                 445

Leu Gly Arg Asp Ser Asp Thr Val Ala Phe Val Gln Phe Pro Gln Arg
    450                 455                 460

Phe Glu Gly Val Asp Pro Thr Asp Leu Tyr Ala Asn His Asn Arg Ile
465                 470                 475                 480

Phe Phe Asp Gly Ser Leu Arg Ala Leu Asp Gly Met Gln Gly Pro Ile
                485                 490                 495

Tyr Val Gly Thr Gly Cys Leu Phe Arg Arg Ile Thr Val Tyr Ala Phe
            500                 505                 510

Asp Pro Pro Arg Ile Asn Val Gly Gly Pro Cys Phe Pro Met Leu Gly
```

```
            515                 520                 525
Gly Met Phe Ala Lys Thr Lys Tyr Gln Lys Pro Gly Leu Glu Met Thr
    530                 535                 540

Met Ala Lys Ala Lys Ala Ala Pro Val Pro Ala Lys Gly Lys His Gly
545                 550                 555                 560

Phe Leu Pro Leu Pro Lys Lys Thr Tyr Gly Lys Ser Asp Ala Phe Val
                565                 570                 575

Asp Ser Ile Pro Leu Ala Ser His Pro Ser Pro Tyr Val Ala Ala Tyr
                580                 585                 590

Asn Thr Ala Glu Gly Ile Val Thr Asp Glu Ala Thr Met Ala Glu Ala
            595                 600                 605

Val Asn Val Thr Ala Ala Ala Phe Glu Lys Lys Thr Gly Trp Gly Lys
        610                 615                 620

Glu Ile Gly Trp Val Tyr Asp Thr Val Thr Glu Asp Val Val Thr Gly
625                 630                 635                 640

Tyr Arg Met His Ile Lys Gly Trp Arg Ser Arg Tyr Cys Ser Ile Tyr
                645                 650                 655

Pro His Ala Phe Ile Gly Thr Ala Pro Ile Asn Leu Thr Glu Arg Leu
                660                 665                 670

Phe Gln Val Leu Arg Trp Ser Thr Gly Ser Leu Glu Ile Phe Phe Ser
            675                 680                 685

Lys Asn Asn Pro Leu Phe Gly Ser Thr Tyr Leu His Pro Leu Gln Arg
        690                 695                 700

Ile Ala Tyr Ile Asn Ile Thr Thr Tyr Pro Phe Thr Ala Ile Phe Leu
705                 710                 715                 720

Ile Phe Tyr Thr Thr Val Pro Ala Leu Ser Phe Val Thr Gly His Phe
                725                 730                 735

Ile Val Gln Arg Pro Thr Thr Met Phe Tyr Val Tyr Leu Gly Ile Val
                740                 745                 750

Leu Ala Thr Leu Leu Ile Ile Ala Val Leu Glu Val Lys Trp Ala Gly
            755                 760                 765

Val Thr Val Phe Glu Trp Phe Arg Asn Gly Gln Phe Trp Met Thr Ala
        770                 775                 780

Ser Met Ser Ala Tyr Leu Gln Ala Val Cys Gln Val Leu Ile Lys Val
785                 790                 795                 800

Ile Phe Gln Lys Asp Ile Ser Phe Lys Leu Thr Ser Lys Leu Pro Ala
                805                 810                 815

Gly Asp Glu Lys Lys Asp Pro Tyr Ala Asp Leu Tyr Val Val Arg Trp
                820                 825                 830

Thr Pro Leu Met Ile Pro Ile Ile Val Ile Phe Val Asn Ile Ile
            835                 840                 845

Gly Ser Ala Val Ala Phe Ala Lys Val Leu Asp Gly Glu Trp Thr His
        850                 855                 860

Trp Leu Lys Val Ala Gly Gly Val Phe Phe Asn Phe Trp Val Leu Phe
865                 870                 875                 880

His Leu Tyr Pro Phe Ala Lys Gly Ile Leu Gly Lys His Gly Lys Thr
                885                 890                 895

Pro Val Val Leu Val Trp Trp Ala Phe Thr Phe Val Ile Thr Ala
                900                 905                 910

Val Leu Tyr Ile Asn Ile Pro His Met His Ser Pro Gly Gly Lys His
            915                 920                 925

Thr Lys Val Ala His Gly His Gly Gln Lys Phe Leu Gly Trp Pro
        930                 935                 940
```

<210> SEQ ID NO 58
<211> LENGTH: 2933
<212> TYPE: DNA
<213> ORGANISM: artificial
<220> FEATURE:
<223> OTHER INFORMATION: synthetic

<400> SEQUENCE: 58

| | | | | | | |
|---|---|---|---|---|---|---|
| gaattcgccc | ttaagatggc | tagcatgact | ggtggacagc | aaatgggtat | ggcgccagcg | 60 |
| gtggccggcg | ggagcagccg | gggtgcaggg | tgtaagtgcg | ggttccaggt | gtgcgtgtgc | 120 |
| tctgggtcgg | cggcggtggc | gtcggcgggt | tcgtcgctgg | aggtggagag | agccatggcg | 180 |
| gtgacgccgg | tggaagggca | ggcggcgccg | gtggacggcg | agagctgggt | cggcgtcgag | 240 |
| ctcggccccg | acggcgtgga | gacggacgag | agcggcgccg | gcgtcgacga | ccgcccgtc | 300 |
| ttcaagaccg | agaagatcaa | gggcgtcctc | ctccaccct | acagggtgct | gatctttgtt | 360 |
| cgtctgatag | cgttcaccct | gttcgtgatc | tggcgtatct | cgcacaagaa | cccggacacg | 420 |
| atgtggctgt | gggtgaccte | catctgcggc | gagttctggt | tcggcttctc | ctggctgctg | 480 |
| gaccagcttc | caaagctcaa | cccgatcaac | cggatcccgg | acctcgccgt | gctccggcaa | 540 |
| cgcttcgacc | gcgccgacgg | gacatccaca | ttgccgggcc | tcgacatctt | cgtcaccacg | 600 |
| gccgacccca | tcaaggaacc | catcctgtcg | acggccaact | ccgtgctctc | catcctggcc | 660 |
| gccgactacc | cggtggaccg | caacacctgc | tacatctccg | acgacagcgg | catgctcatg | 720 |
| acctacgagg | ccatggcgga | gtcggccaag | ttcgccaccc | tctgggtgcc | attctgccgc | 780 |
| aagcacggca | tcgaaccacg | cgggccggag | agctacttcg | agctcaagtc | gcacccgtac | 840 |
| atggggagag | cgcacgacga | gttcgtcaat | gaccgccgcc | gggtgcgcaa | ggagtatgat | 900 |
| gacttcaagg | ccaagattaa | ctctctggag | actgatatcc | agcagaggaa | tgatctgcat | 960 |
| aacgctgccg | tgccgcagaa | tggggatggg | atccccaggc | ctacctggat | ggctgatgga | 1020 |
| gtccagtggc | aggggacttg | ggtcgagccg | tccgctaatc | accgcaaggg | agaccacgcc | 1080 |
| ggcatcgtcc | tggttctgat | tgaccacccg | agccacgacc | gccttcccgg | cgcgccggcg | 1140 |
| agcgccgaca | acgcgctgga | cttcagcggc | gtggacaccc | gcctcccgat | gctcgtctac | 1200 |
| atgtcccgcg | agaagcgccc | aggccacaac | accagaaga | aggccggcgc | catgaacgcg | 1260 |
| ctcaccaggg | cttccgcgct | gctctccaac | gcgcccttca | tcctcaacct | cgactgcgac | 1320 |
| cactacatca | caactccca | ggccctccgc | gccgggatct | gcttcatggt | cggccgggac | 1380 |
| agcgacaccg | tcgccttcgt | gcagttcccg | cagcggttcg | agggcgtcga | ccccacggac | 1440 |
| ctctacgcca | accacaaccg | catcttcttc | gacggcaccc | tcagggcgct | cgacggaatg | 1500 |
| caaggcccga | tctatgtcgg | cacgggatgc | ctcttccggc | gcatcaccgt | ctacggcttc | 1560 |
| gacccgccca | ggatcaacgt | cggcgggcca | tgcttccctg | ctctcggtgg | cctgttcgcc | 1620 |
| aagaccaagt | atgagaagcc | cagcatggag | atgaccatgg | cgagagccaa | ccaggccgtg | 1680 |
| gtgccggcca | tggccaaggg | gaagcacggc | ttcctgccgc | tccccaagaa | gacgtacggg | 1740 |
| aagtccgaca | agttcgtgga | caccatcccg | cgcgcgtccc | accgtcgcc | gtacgcggcg | 1800 |
| gaggggatcc | gcgtggtgga | ctccggcgcg | gagactctgg | ctgaggccgt | caaggtgacc | 1860 |
| ggatcggcat | tcgagcagaa | gaccggatgg | ggcagcgagc | tcggctgggt | ctacgacact | 1920 |
| gtcacagagg | acgtggtgac | tggctacagg | atgcacatca | agggctggag | gtcccgctac | 1980 |
| tgctccatct | acccgcacgc | cttcatcggc | accgccccga | tcaacctcac | ggagcggctc | 2040 |

-continued

```
ttccaggtgc tccgctggtc caccggctcc ctcgagatct tcttctccaa gaacaacccg    2100
ctcttcggca gcacctacct gcacccgctc cagcgcgtcg cctacatcaa catcaccaca    2160
tacccgttca ccgccatctt cctcatcttc tacaccaccg tgccggcgct ctccttcgtc    2220
accggccact tcatcgtgca cgcccgacg accatgttct acgtctacct ggggatcgtg     2280
ctggcgacgc tgctcatcat cgctgttctt gaggtcaagt gggctggagt gacagtgttc    2340
gagtggttca ggaacgggca gttctggatg acggctagct gctccgccta ccttgctgct    2400
gtgtgccagg tgctcaccaa ggtgatcttc aggagggaca tctcattcaa gctcacttcc    2460
aagctgcctg ctggggacga gaagaaggac ccctatgccg atctgtacgt ggtgcgttgg    2520
actccactca tgatcactcc aatcatcatc atcttcgtca acatcatcgg tcggcggtg    2580 gccttcgcca aggtgctgga cggcgagtgg acgcactggc tcaaggtggc gggaggagtc    2640
ttcttcaact tctgggtgct gttccactc tacccgttcg ccaagggtct cctggggaag     2700
catggcaaga cccccgtcgt cgtgctcgtc tggtgggcat tcaccttcgt catcaccgcc    2760
gtcctctaca tcaacatccc gcacatccat ggaggaggag gcaagcacag cgtggggcat    2820
gggatgcacc atggcaagaa gttcgacggc tactacctct ggccgtgagc gcgcgccgcg    2880
gggccggcgc gcggggtcg atcgggacga agaagatcga caagggcgaa ttc            2933
```

<210> SEQ ID NO 59
<211> LENGTH: 950
<212> TYPE: PRT
<213> ORGANISM: Brachypodium distachyon

<400> SEQUENCE: 59

```
Met Ala Ser Met Thr Gly Gly Gln Gln Met Gly Met Ala Pro Ala Val
1               5                   10                  15

Ala Gly Gly Ser Ser Arg Gly Ala Gly Cys Lys Cys Gly Phe Gln Val
            20                  25                  30

Cys Val Cys Ser Gly Ser Ala Ala Val Ala Ser Ala Gly Ser Ser Leu
        35                  40                  45

Glu Val Glu Arg Ala Met Ala Val Thr Pro Val Glu Gly Gln Ala Ala
    50                  55                  60

Pro Val Asp Gly Glu Ser Trp Val Gly Val Glu Leu Gly Pro Asp Gly
65                  70                  75                  80

Val Glu Thr Asp Glu Ser Gly Ala Gly Val Asp Asp Arg Pro Val Phe
                85                  90                  95

Lys Thr Glu Lys Ile Lys Gly Val Leu Leu His Pro Tyr Arg Val Leu
            100                 105                 110

Ile Phe Val Arg Leu Ile Ala Phe Thr Leu Phe Val Ile Trp Arg Ile
        115                 120                 125

Ser His Lys Asn Pro Asp Thr Met Trp Leu Trp Val Thr Ser Ile Cys
    130                 135                 140

Gly Glu Phe Trp Phe Gly Phe Ser Trp Leu Leu Asp Gln Leu Pro Lys
145                 150                 155                 160

Leu Asn Pro Ile Asn Arg Ile Pro Asp Leu Ala Val Leu Arg Gln Arg
                165                 170                 175

Phe Asp Arg Ala Asp Gly Thr Ser Thr Leu Pro Gly Leu Asp Ile Phe
            180                 185                 190

Val Thr Thr Ala Asp Pro Ile Lys Glu Pro Ile Leu Ser Thr Ala Asn
        195                 200                 205

Ser Val Leu Ser Ile Leu Ala Ala Asp Tyr Pro Val Asp Arg Asn Thr
    210                 215                 220
```

```
Cys Tyr Ile Ser Asp Asp Ser Gly Met Leu Met Thr Tyr Glu Ala Met
225                 230                 235                 240

Ala Glu Ser Ala Lys Phe Ala Thr Leu Trp Val Pro Phe Cys Arg Lys
            245                 250                 255

His Gly Ile Glu Pro Arg Gly Pro Glu Ser Tyr Phe Glu Leu Lys Ser
        260                 265                 270

His Pro Tyr Met Gly Arg Ala His Asp Glu Phe Val Asn Asp Arg Arg
    275                 280                 285

Arg Val Arg Lys Glu Tyr Asp Asp Phe Lys Ala Lys Ile Asn Ser Leu
290                 295                 300

Glu Thr Asp Ile Gln Gln Arg Asn Asp Leu His Asn Ala Ala Val Pro
305                 310                 315                 320

Gln Asn Gly Asp Gly Ile Pro Arg Pro Thr Trp Met Ala Asp Gly Val
                325                 330                 335

Gln Trp Gln Gly Thr Trp Val Glu Pro Ser Ala Asn His Arg Lys Gly
            340                 345                 350

Asp His Ala Gly Ile Val Leu Val Leu Ile Asp His Pro Ser His Asp
        355                 360                 365

Arg Leu Pro Gly Ala Pro Ala Ser Ala Asp Asn Ala Leu Asp Phe Ser
    370                 375                 380

Gly Val Asp Thr Arg Leu Pro Met Leu Val Tyr Met Ser Arg Glu Lys
385                 390                 395                 400

Arg Pro Gly His Asn His Gln Lys Lys Ala Gly Ala Met Asn Ala Leu
                405                 410                 415

Thr Arg Ala Ser Ala Leu Leu Ser Asn Ala Pro Phe Ile Leu Asn Leu
            420                 425                 430

Asp Cys Asp His Tyr Ile Asn Asn Ser Gln Ala Leu Arg Ala Gly Ile
        435                 440                 445

Cys Phe Met Val Gly Arg Asp Ser Asp Thr Val Ala Phe Val Gln Phe
    450                 455                 460

Pro Gln Arg Phe Glu Gly Val Asp Pro Thr Asp Leu Tyr Ala Asn His
465                 470                 475                 480

Asn Arg Ile Phe Phe Asp Gly Thr Leu Arg Ala Leu Asp Gly Met Gln
                485                 490                 495

Gly Pro Ile Tyr Val Gly Thr Gly Cys Leu Phe Arg Arg Ile Thr Val
            500                 505                 510

Tyr Gly Phe Asp Pro Pro Arg Ile Asn Val Gly Gly Pro Cys Phe Pro
        515                 520                 525

Ala Leu Gly Gly Leu Phe Ala Lys Thr Lys Tyr Glu Lys Pro Ser Met
    530                 535                 540

Glu Met Thr Met Ala Arg Ala Asn Gln Ala Val Val Pro Ala Met Ala
545                 550                 555                 560

Lys Gly Lys His Gly Phe Leu Pro Leu Pro Lys Lys Thr Tyr Gly Lys
                565                 570                 575

Ser Asp Lys Phe Val Asp Thr Ile Pro Arg Ala Ser His Pro Ser Pro
            580                 585                 590

Tyr Ala Ala Glu Gly Ile Arg Val Val Asp Ser Gly Ala Glu Thr Leu
        595                 600                 605

Ala Glu Ala Val Lys Val Thr Gly Ser Ala Phe Glu Gln Lys Thr Gly
    610                 615                 620

Trp Gly Ser Glu Leu Gly Trp Val Tyr Asp Thr Val Thr Glu Asp Val
625                 630                 635                 640
```

Val Thr Gly Tyr Arg Met His Ile Lys Gly Trp Arg Ser Arg Tyr Cys
            645                 650                 655

Ser Ile Tyr Pro His Ala Phe Ile Gly Thr Ala Pro Ile Asn Leu Thr
        660                 665                 670

Glu Arg Leu Phe Gln Val Leu Arg Trp Ser Thr Gly Ser Leu Glu Ile
            675                 680                 685

Phe Phe Ser Lys Asn Asn Pro Leu Phe Gly Ser Thr Tyr Leu His Pro
690                 695                 700

Leu Gln Arg Val Ala Tyr Ile Asn Ile Thr Thr Tyr Pro Phe Thr Ala
705                 710                 715                 720

Ile Phe Leu Ile Phe Tyr Thr Thr Val Pro Ala Leu Ser Phe Val Thr
                725                 730                 735

Gly His Phe Ile Val Gln Arg Pro Thr Thr Met Phe Tyr Val Tyr Leu
            740                 745                 750

Gly Ile Val Leu Ala Thr Leu Leu Ile Ala Val Leu Glu Val Lys
            755                 760                 765

Trp Ala Gly Val Thr Val Phe Glu Trp Phe Arg Asn Gly Gln Phe Trp
770                 775                 780

Met Thr Ala Ser Cys Ser Ala Tyr Leu Ala Ala Val Cys Gln Val Leu
785                 790                 795                 800

Thr Lys Val Ile Phe Arg Arg Asp Ile Ser Phe Lys Leu Thr Ser Lys
                805                 810                 815

Leu Pro Ala Gly Asp Glu Lys Lys Asp Pro Tyr Ala Asp Leu Tyr Val
            820                 825                 830

Val Arg Trp Thr Pro Leu Met Ile Thr Pro Ile Ile Ile Phe Val
            835                 840                 845

Asn Ile Ile Gly Ser Ala Val Ala Phe Ala Lys Val Leu Asp Gly Glu
850                 855                 860

Trp Thr His Trp Leu Lys Val Ala Gly Gly Val Phe Phe Asn Phe Trp
865                 870                 875                 880

Val Leu Phe His Leu Tyr Pro Phe Ala Lys Gly Leu Leu Gly Lys His
                885                 890                 895

Gly Lys Thr Pro Val Val Val Leu Val Trp Trp Ala Phe Thr Phe Val
            900                 905                 910

Ile Thr Ala Val Leu Tyr Ile Asn Ile Pro His Ile His Gly Gly Gly
            915                 920                 925

Gly Lys His Ser Val Gly His Gly Met His His Gly Lys Lys Phe Asp
            930                 935                 940

Gly Tyr Tyr Leu Trp Pro
945                 950

<210> SEQ ID NO 60
<211> LENGTH: 3115
<212> TYPE: DNA
<213> ORGANISM: artificial
<220> FEATURE:
<223> OTHER INFORMATION: synthetic

<400> SEQUENCE: 60
gaattcgccc tttcccccac gtactttacg acccatttct cacacccctc ttctcctcct      60
cctcttcttc tccaccacct ccattgctgc tcgcctctct cacctcctcc tcctcctctt     120
gtgtggagct cgtcggcgtc gaggtgtagc tagctagcta agcttgtttt gccattgttg     180
tgttcttggt gttcggagag ggagcttgcc tttgccttga ggggagaggc aaaggcatta     240
gcaatggcgc cagcggtggc cggcggcgga gggaggagga caatgaggg ggtgaacggg     300

```
aacgcggcgg cgccggcgtg cgtgtgcggg ttcccggtgt gcgcgtgcgc gggggcggcg    360
gcggtggcgt cggcggcgtc gtcggcggac atggacatcg tggcggcggg gcagatcggc    420
gccgtcaacg acgagagctg ggtcgccgtc gacctcagcg acagcgacga cgccccccgcc    480 gccggcgacg tccagggcgc cctcgacgac cgccccgtct tccgtaccga aagatcaag     540 ggcgtcctcc tccaccccta ccgggtgctg atctttgtga ggctgatcgc gttcacactg    600
ttcgtgatat ggcgtatcga gcacaagaac ccggacgcga tgtggctgtg ggtgacgtcg    660
atcgccggcg agttctggtt cgggttctcg tggctgctcg accagctccc caagctgaac    720
ccgatcaacc gcgtccccga cctcgccgtc ctccgccgcc gcttcgacca cgccgacggg    780
acctcctccc tcccggggct ggacatcttc gtcaccaccg ccgacccgat caaggagccc    840
atcctgtcga cggcgaactc catcctctcc atcctcgccg ccgactaccc cgtcgaccgc    900
aacacctgct acctctccga cgactctggg atgctcctca cctacgaggc catggcggag    960
gcggccaagt tcgcgacgct gtgggtgccc ttctgccgga agcacgccat cgagccgcgc   1020
gggcctgaga gctacttcga gctcaagtcc caccccataca tggggagggc gcaggaggag   1080
ttcgtcaacg accgccgccg cgtccgcaag gagtacgacg acttcaaggc caggatcaac   1140
ggcctcgagc acgacatcaa gcagaggtcc gactcctaca cgccgccgc cggcgtcaag    1200 gacgcgagc cccgcgccac ctggatggcc gacgggtcgc agtgggaggg cacctggatc    1260
gagcagtcgg agaaccaccg caagggcgac cacgccggca tcgtcctggt gttgctgaac    1320
cacccgagcc acgcacggca gctggggccg ccggcgagcg ccgacaaccc gctggacttc    1380
agcggcgtgg acgtgcggct gccgatgctg gtgtacgtcg cacgtgagaa gcgccccggg    1440
tgcaaccacc agaagaaggc cggcgccatg aacgcgctga cccgcgcctc cgccgtgctc    1500
tccaactccc ccttcatcct caacctcgac tgcgaccact acatcaacaa ctcccaggcg    1560
ctccgcgccg gcatctgctt catgctcggc cgcgacagcg acaccgtcgc gttcgtccag    1620
ttcccgcagc gcttcgaggg cgtcgacccc accgacctct atgctaacca caaccgtatc    1680
ttcttcgacg gcacgctccg tgccctcgac gggctgcagg ggcctatcta cgtcggcacc    1740
gggtgtctct tccgccgcat cacgctgtac gggttcgagc cgccgaggat caacgtcggc    1800
ggaccgtgct tcccgaggct cggtgggatg ttcgccaaga acaggtacca gaagcctggg    1860
ttcgagatga ccaagcctgg tgccaagccg gtggcgccgc cgccggcggc gacggtggcg    1920
aaggggaagc acgggttcct gccgatgccc aagaaggcgt acggcaagtc ggacgcgttc    1980
gccgacacca tcccgcgcgc gtcgcacccg tcgccgtacg cggcggaggc ggcggtggcg    2040
gccgacgagg cggcgatcgc ggaggccgtg atggtgacgg cggcggcgta cgagaagaag    2100
accggtgggg ggagcgacat cggtgggtg tacggcacgg tgacggagga cgtggtgacc    2160
ggctaccgga tgcacatcaa ggggtggagg tcgcgctact gctccatcta cccgcacgcg    2220
ttcatcggga cggcgccgat caacctgacg gagaggctgt tccaggtgct ccggtggtcg    2280
acgggttcgc tggagatctt cttctcgagg aacaacccgc tgttcgggag cacgttcctg    2340
cacccgctgc agcgcgtggc gtacatcaac atcaccacct acccgttcac ggcgctgttc    2400
ctcatcttct acaccaccgt gccggcgctg tcgttcgtga cggggcactt catcgtgcag    2460
aggccgacca ccatgttcta cgtctacctc gccatcgtgc tcgggacgct gctcatcctc    2520
gccgtgctgg aggtgaagtg ggcggggggtc accgtgttcg agtggttcag gaacgggcag    2580
ttctggatga cggccagctg ctccgcctac ctcgccgccg tgctgcaggt ggtcaccaag    2640
```

-continued

```
gtggtgttcc ggcgggacat ctcgttcaag ctcacctcca agctcccgc cggcgacgag  2700 aagaaggacc cctacgccga cctgtacgtg gtgcggtgga cgtggctcat gatcaccccc  2760
atcatcatca tcctcgtcaa catcatcggc tccgccgtcg ccttcgccaa ggtgctcgac  2820
ggcgagtgga cgcactggct caaggtcgcc ggcggcgtgt tcttcaactt ctgggtcctc  2880
ttccacctct acccttcgc caagggcatc ctcgggaagc acggcaagac gccggtggtg  2940
gtgctcgtct ggtgggcctt caccttcgtc atcaccgtcg tgctctacat caacatcccc  3000
cacatccatg gccccggccg ccacggcgcc gcctcaccat cccacggcca ccacagcgcc  3060
catggcacca agaagtacga cttcacctac gcctggccat gagaagggcg aattc        3115
```

<210> SEQ ID NO 61
<211> LENGTH: 952
<212> TYPE: PRT
<213> ORGANISM: Oryzae sativa

<400> SEQUENCE: 61

```
Met Ala Pro Ala Val Ala Gly Gly Gly Arg Arg Asn Asn Glu Gly
1               5                   10                  15

Val Asn Gly Asn Ala Ala Pro Ala Cys Val Cys Gly Phe Pro Val
                20                  25                  30

Cys Ala Cys Ala Gly Ala Ala Ala Val Ala Ser Ala Ala Ser Ser Ala
            35                  40                  45

Asp Met Asp Ile Val Ala Ala Gly Gln Ile Gly Ala Val Asn Asp Glu
        50                  55                  60

Ser Trp Val Ala Val Asp Leu Ser Asp Ser Asp Ala Pro Ala Ala
65              70                  75                  80

Gly Asp Val Gln Gly Ala Leu Asp Asp Arg Pro Val Phe Arg Thr Glu
                85                  90                  95

Lys Ile Lys Gly Val Leu Leu His Pro Tyr Arg Val Leu Ile Phe Val
                100                 105                 110

Arg Leu Ile Ala Phe Thr Leu Phe Val Ile Trp Arg Ile Glu His Lys
            115                 120                 125

Asn Pro Asp Ala Met Trp Leu Trp Val Thr Ser Ile Ala Gly Glu Phe
        130                 135                 140

Trp Phe Gly Phe Ser Trp Leu Leu Asp Gln Leu Pro Lys Leu Asn Pro
145             150                 155                 160

Ile Asn Arg Val Pro Asp Leu Ala Val Leu Arg Arg Phe Asp His
                165                 170                 175

Ala Asp Gly Thr Ser Ser Leu Pro Gly Leu Asp Ile Phe Val Thr Thr
            180                 185                 190

Ala Asp Pro Ile Lys Glu Pro Ile Leu Ser Thr Ala Asn Ser Ile Leu
        195                 200                 205

Ser Ile Leu Ala Ala Asp Tyr Pro Val Asp Arg Asn Thr Cys Tyr Leu
    210                 215                 220

Ser Asp Asp Ser Gly Met Leu Leu Thr Tyr Glu Ala Met Ala Glu Ala
225             230                 235                 240

Ala Lys Phe Ala Thr Leu Trp Val Pro Phe Cys Arg Lys His Ala Ile
                245                 250                 255

Glu Pro Arg Gly Pro Glu Ser Tyr Phe Glu Leu Lys Ser His Pro Tyr
            260                 265                 270

Met Gly Arg Ala Gln Glu Glu Phe Val Asn Asp Arg Arg Val Arg
        275                 280                 285

Lys Glu Tyr Asp Asp Phe Lys Ala Arg Ile Asn Gly Leu Glu His Asp
```

```
                290                 295                 300
Ile Lys Gln Arg Ser Asp Ser Tyr Asn Ala Ala Gly Val Lys Asp
305                 310                 315                 320

Gly Glu Pro Arg Ala Thr Trp Met Ala Asp Gly Ser Gln Trp Glu Gly
                325                 330                 335

Thr Trp Ile Glu Gln Ser Glu Asn His Arg Lys Gly Asp His Ala Gly
                340                 345                 350

Ile Val Leu Val Leu Leu Asn His Pro Ser His Ala Arg Gln Leu Gly
                355                 360                 365

Pro Pro Ala Ser Ala Asp Asn Pro Leu Asp Phe Ser Gly Val Asp Val
370                 375                 380

Arg Leu Pro Met Leu Val Tyr Val Ala Arg Glu Lys Arg Pro Gly Cys
385                 390                 395                 400

Asn His Gln Lys Lys Ala Gly Ala Met Asn Ala Leu Thr Arg Ala Ser
                405                 410                 415

Ala Val Leu Ser Asn Ser Pro Phe Ile Leu Asn Leu Asp Cys Asp His
                420                 425                 430

Tyr Ile Asn Asn Ser Gln Ala Leu Arg Ala Gly Ile Cys Phe Met Leu
                435                 440                 445

Gly Arg Asp Ser Asp Thr Val Ala Phe Val Gln Phe Pro Gln Arg Phe
                450                 455                 460

Glu Gly Val Asp Pro Thr Asp Leu Tyr Ala Asn His Asn Arg Ile Phe
465                 470                 475                 480

Phe Asp Gly Thr Leu Arg Ala Leu Asp Gly Leu Gln Gly Pro Ile Tyr
                485                 490                 495

Val Gly Thr Gly Cys Leu Phe Arg Arg Ile Thr Leu Tyr Gly Phe Glu
                500                 505                 510

Pro Pro Arg Ile Asn Val Gly Gly Pro Cys Phe Pro Arg Leu Gly Gly
                515                 520                 525

Met Phe Ala Lys Asn Arg Tyr Gln Lys Pro Gly Phe Glu Met Thr Lys
                530                 535                 540

Pro Gly Ala Lys Pro Val Ala Pro Pro Ala Ala Thr Val Ala Lys
545                 550                 555                 560

Gly Lys His Gly Phe Leu Pro Met Pro Lys Lys Ala Tyr Gly Lys Ser
                565                 570                 575

Asp Ala Phe Ala Asp Thr Ile Pro Arg Ala Ser His Pro Ser Pro Tyr
                580                 585                 590

Ala Ala Glu Ala Ala Val Ala Ala Asp Glu Ala Ala Ile Ala Glu Ala
                595                 600                 605

Val Met Val Thr Ala Ala Ala Tyr Glu Lys Lys Thr Gly Trp Gly Ser
                610                 615                 620

Asp Ile Gly Trp Val Tyr Gly Thr Val Thr Glu Asp Val Val Thr Gly
625                 630                 635                 640

Tyr Arg Met His Ile Lys Gly Trp Arg Ser Arg Tyr Cys Ser Ile Tyr
                645                 650                 655

Pro His Ala Phe Ile Gly Thr Ala Pro Ile Asn Leu Thr Glu Arg Leu
                660                 665                 670

Phe Gln Val Leu Arg Trp Ser Thr Gly Ser Leu Glu Ile Phe Phe Ser
                675                 680                 685

Arg Asn Asn Pro Leu Phe Gly Ser Thr Phe Leu His Pro Leu Gln Arg
                690                 695                 700

Val Ala Tyr Ile Asn Ile Thr Thr Tyr Pro Phe Thr Ala Leu Phe Leu
705                 710                 715                 720
```

```
Ile Phe Tyr Thr Thr Val Pro Ala Leu Ser Phe Val Thr Gly His Phe
                725                 730                 735

Ile Val Gln Arg Pro Thr Thr Met Phe Tyr Val Tyr Leu Ala Ile Val
            740                 745                 750

Leu Gly Thr Leu Leu Ile Leu Ala Val Leu Glu Val Lys Trp Ala Gly
        755                 760                 765

Val Thr Val Phe Glu Trp Phe Arg Asn Gly Gln Phe Trp Met Thr Ala
    770                 775                 780

Ser Cys Ser Ala Tyr Leu Ala Ala Val Leu Gln Val Val Thr Lys Val
785                 790                 795                 800

Val Phe Arg Arg Asp Ile Ser Phe Lys Leu Thr Ser Lys Leu Pro Ala
                805                 810                 815

Gly Asp Glu Lys Lys Asp Pro Tyr Ala Asp Leu Tyr Val Arg Trp
            820                 825                 830

Thr Trp Leu Met Ile Thr Pro Ile Ile Ile Leu Val Asn Ile Ile
        835                 840                 845

Gly Ser Ala Val Ala Phe Ala Lys Val Leu Asp Gly Glu Trp Thr His
    850                 855                 860

Trp Leu Lys Val Ala Gly Gly Val Phe Phe Asn Phe Trp Val Leu Phe
865                 870                 875                 880

His Leu Tyr Pro Phe Ala Lys Gly Ile Leu Gly Lys His Gly Lys Thr
                885                 890                 895

Pro Val Val Val Leu Val Trp Trp Ala Phe Thr Phe Val Ile Thr Val
            900                 905                 910

Val Leu Tyr Ile Asn Ile Pro His Ile His Gly Pro Gly Arg His Gly
        915                 920                 925

Ala Ala Ser Pro Ser His Gly His His Ser Ala His Gly Thr Lys Lys
    930                 935                 940

Tyr Asp Phe Thr Tyr Ala Trp Pro
945                 950

<210> SEQ ID NO 62
<211> LENGTH: 22
<212> TYPE: DNA
<213> ORGANISM: artificial
<220> FEATURE:
<223> OTHER INFORMATION: synthetic

<400> SEQUENCE: 62
ggttagttcc ttgtgcagag gt                                            22

<210> SEQ ID NO 63
<211> LENGTH: 22
<212> TYPE: DNA
<213> ORGANISM: artificial
<220> FEATURE:
<223> OTHER INFORMATION: synthetic

<400> SEQUENCE: 63
gagctgtgtt cgtggagctt ag                                            22

<210> SEQ ID NO 64
<211> LENGTH: 22
<212> TYPE: DNA
<213> ORGANISM: artificial
<220> FEATURE:
<223> OTHER INFORMATION: synthetic

<400> SEQUENCE: 64
```
gagctgtgtt cgtggagctt ag                                              22

<210> SEQ ID NO 65
<211> LENGTH: 24
<212> TYPE: DNA
<213> ORGANISM: artificial
<220> FEATURE:
<223> OTHER INFORMATION: synthetic

<400> SEQUENCE: 65
ccgccggtta gttccttgtg caga                                            24

<210> SEQ ID NO 66
<211> LENGTH: 51
<212> TYPE: DNA
<213> ORGANISM: artificial
<220> FEATURE:
<223> OTHER INFORMATION: synthetic

<400> SEQUENCE: 66
aagatggcta gcatgactgg tggacagcaa atgggtgccc cggcagtcac t              51

<210> SEQ ID NO 67
<211> LENGTH: 22
<212> TYPE: DNA
<213> ORGANISM: artificial
<220> FEATURE:
<223> OTHER INFORMATION: synthetic

<400> SEQUENCE: 67
aagaggagtg gcacacaatg ac                                              22

<210> SEQ ID NO 68
<211> LENGTH: 20
<212> TYPE: DNA
<213> ORGANISM: artificial
<220> FEATURE:
<223> OTHER INFORMATION: synthetic

<400> SEQUENCE: 68
gatggatgca tgcactgact                                                 20

<210> SEQ ID NO 69
<211> LENGTH: 22
<212> TYPE: DNA
<213> ORGANISM: artificial
<220> FEATURE:
<223> OTHER INFORMATION: synthetic

<400> SEQUENCE: 69
atagcgcttg gccagtggaa gc                                              22

<210> SEQ ID NO 70
<211> LENGTH: 25
<212> TYPE: DNA
<213> ORGANISM: artificial
<220> FEATURE:
<223> OTHER INFORMATION: synthetic

<400> SEQUENCE: 70
catttgaaat ttcactcgtc gtcca                                           25

<210> SEQ ID NO 71
<211> LENGTH: 25
<212> TYPE: DNA

```
<213> ORGANISM: artificial
<220> FEATURE:
<223> OTHER INFORMATION: synthetic

<400> SEQUENCE: 71
aggcatgtta aagcatatgc aaatg                                         25

<210> SEQ ID NO 72
<211> LENGTH: 17
<212> TYPE: DNA
<213> ORGANISM: artificial
<220> FEATURE:
<223> OTHER INFORMATION: synthetic

<400> SEQUENCE: 72
ggagacatgg cgtcggc                                                  17

<210> SEQ ID NO 73
<211> LENGTH: 19
<212> TYPE: DNA
<213> ORGANISM: artificial
<220> FEATURE:
<223> OTHER INFORMATION: synthetic

<400> SEQUENCE: 73
atggccccgg cagtcactc                                                19

<210> SEQ ID NO 74
<211> LENGTH: 17
<212> TYPE: DNA
<213> ORGANISM: artificial
<220> FEATURE:
<223> OTHER INFORMATION: synthetic

<400> SEQUENCE: 74
catggcgcca gcggtgg                                                  17

<210> SEQ ID NO 75
<211> LENGTH: 21
<212> TYPE: DNA
<213> ORGANISM: artificial
<220> FEATURE:
<223> OTHER INFORMATION: synthetic

<400> SEQUENCE: 75
agaagtcggc caatgtcgag a                                             21

<210> SEQ ID NO 76
<211> LENGTH: 19
<212> TYPE: DNA
<213> ORGANISM: artificial
<220> FEATURE:
<223> OTHER INFORMATION: synthetic

<400> SEQUENCE: 76
gggacatggg ttctttggc                                                19

<210> SEQ ID NO 77
<211> LENGTH: 24
<212> TYPE: DNA
<213> ORGANISM: artificial
<220> FEATURE:
<223> OTHER INFORMATION: synthetic

<400> SEQUENCE: 77
acagcctata tatgattcac acca                                          24
```

<210> SEQ ID NO 78
<211> LENGTH: 19
<212> TYPE: DNA
<213> ORGANISM: artificial
<220> FEATURE:
<223> OTHER INFORMATION: synthetic

<400> SEQUENCE: 78
aagaacaggc tctgctact                                               19

<210> SEQ ID NO 79
<211> LENGTH: 23
<212> TYPE: DNA
<213> ORGANISM: artificial
<220> FEATURE:
<223> OTHER INFORMATION: synthetic

<400> SEQUENCE: 79
caggttttgc agcattactt gac                                          23

<210> SEQ ID NO 80
<211> LENGTH: 24
<212> TYPE: DNA
<213> ORGANISM: artificial
<220> FEATURE:
<223> OTHER INFORMATION: synthetic

<400> SEQUENCE: 80
gacggacatc atccaaaacc acat                                         24

<210> SEQ ID NO 81
<211> LENGTH: 25
<212> TYPE: DNA
<213> ORGANISM: artificial
<220> FEATURE:
<223> OTHER INFORMATION: synthetic

<400> SEQUENCE: 81
caggatgata ttcttgactc tcctg                                        25

<210> SEQ ID NO 82
<211> LENGTH: 18
<212> TYPE: DNA
<213> ORGANISM: artificial
<220> FEATURE:
<223> OTHER INFORMATION: synthetic

<400> SEQUENCE: 82
cctcaggcaa tgacgacg                                                18

<210> SEQ ID NO 83
<211> LENGTH: 27
<212> TYPE: DNA
<213> ORGANISM: artificial
<220> FEATURE:
<223> OTHER INFORMATION: synthetic

<400> SEQUENCE: 83
gtccatagaa aagtatgcta aggtact                                      27

<210> SEQ ID NO 84
<211> LENGTH: 20
<212> TYPE: DNA
<213> ORGANISM: artificial
<220> FEATURE:

<223> OTHER INFORMATION: synthetic

<400> SEQUENCE: 84
catcgcgacg gaggacgtgg                                                     20

<210> SEQ ID NO 85
<211> LENGTH: 20
<212> TYPE: DNA
<213> ORGANISM: artificial
<220> FEATURE:
<223> OTHER INFORMATION: synthetic

<400> SEQUENCE: 85
atgacctggc taccctgatg                                                     20

<210> SEQ ID NO 86
<211> LENGTH: 37
<212> TYPE: DNA
<213> ORGANISM: artificial
<220> FEATURE:
<223> OTHER INFORMATION: synthetic

<400> SEQUENCE: 86
aaaggatccg gtaccaacga gcagttctac atcatcg                                  37

<210> SEQ ID NO 87
<211> LENGTH: 20
<212> TYPE: DNA
<213> ORGANISM: artificial
<220> FEATURE:
<223> OTHER INFORMATION: synthetic

<400> SEQUENCE: 87
gaccactacg tcaacaactc                                                     20

<210> SEQ ID NO 88
<211> LENGTH: 20
<212> TYPE: DNA
<213> ORGANISM: artificial
<220> FEATURE:
<223> OTHER INFORMATION: synthetic

<400> SEQUENCE: 88
gactgaatgg ggcagagaag                                                     20

<210> SEQ ID NO 89
<211> LENGTH: 20
<212> TYPE: DNA
<213> ORGANISM: artificial
<220> FEATURE:
<223> OTHER INFORMATION: synthetic

<400> SEQUENCE: 89
cattgcaact gaggatgtgg                                                     20

<210> SEQ ID NO 90
<211> LENGTH: 20
<212> TYPE: DNA
<213> ORGANISM: artificial
<220> FEATURE:
<223> OTHER INFORMATION: synthetic

<400> SEQUENCE: 90
accacaaccg catgttcttc                                                     20

```
<210> SEQ ID NO 91
<211> LENGTH: 25
<212> TYPE: DNA
<213> ORGANISM: artificial
<220> FEATURE:
<223> OTHER INFORMATION: synthetic

<400> SEQUENCE: 91
gcactgttca gtggatgact tgttg                                25

<210> SEQ ID NO 92
<211> LENGTH: 20
<212> TYPE: DNA
<213> ORGANISM: artificial
<220> FEATURE:
<223> OTHER INFORMATION: synthetic

<400> SEQUENCE: 92
cagtgggagc atgtcaatga                                     20

<210> SEQ ID NO 93
<211> LENGTH: 25
<212> TYPE: DNA
<213> ORGANISM: artificial
<220> FEATURE:
<223> OTHER INFORMATION: synthetic

<400> SEQUENCE: 93
aggcatgtta aagcatatgc aaatg                                25

<210> SEQ ID NO 94
<211> LENGTH: 20
<212> TYPE: DNA
<213> ORGANISM: artificial
<220> FEATURE:
<223> OTHER INFORMATION: synthetic

<400> SEQUENCE: 94
gcctgagcgt ggagagctac                                     20

<210> SEQ ID NO 95
<211> LENGTH: 16
<212> TYPE: DNA
<213> ORGANISM: artificial
<220> FEATURE:
<223> OTHER INFORMATION: synthetic

<400> SEQUENCE: 95
cggcggaaca tgcaac                                         16

<210> SEQ ID NO 96
<211> LENGTH: 21
<212> TYPE: DNA
<213> ORGANISM: artificial
<220> FEATURE:
<223> OTHER INFORMATION: synthetic

<400> SEQUENCE: 96
gcacatcagt gctggcgaag t                                   21

<210> SEQ ID NO 97
<211> LENGTH: 19
<212> TYPE: DNA
<213> ORGANISM: artificial
<220> FEATURE:
<223> OTHER INFORMATION: synthetic
```

<400> SEQUENCE: 97
cggaaatcca taggaaagg    19

<210> SEQ ID NO 98
<211> LENGTH: 19
<212> TYPE: DNA
<213> ORGANISM: artificial
<220> FEATURE:
<223> OTHER INFORMATION: synthetic

<400> SEQUENCE: 98
gctcccagct tactacaga    19

<210> SEQ ID NO 99
<211> LENGTH: 20
<212> TYPE: DNA
<213> ORGANISM: artificial
<220> FEATURE:
<223> OTHER INFORMATION: synthetic

<400> SEQUENCE: 99
ccacgtcctc cgtcgcgatg    20

<210> SEQ ID NO 100
<211> LENGTH: 18
<212> TYPE: DNA
<213> ORGANISM: artificial
<220> FEATURE:
<223> OTHER INFORMATION: synthetic

<400> SEQUENCE: 100
gcgtcgccgg agtggtcc    18

<210> SEQ ID NO 101
<211> LENGTH: 23
<212> TYPE: DNA
<213> ORGANISM: artificial
<220> FEATURE:
<223> OTHER INFORMATION: synthetic

<400> SEQUENCE: 101
gtagaggagt ggcacacaat gac    23

<210> SEQ ID NO 102
<211> LENGTH: 22
<212> TYPE: DNA
<213> ORGANISM: artificial
<220> FEATURE:
<223> OTHER INFORMATION: synthetic

<400> SEQUENCE: 102
accgggtacg agtagtacat gc    22

<210> SEQ ID NO 103
<211> LENGTH: 19
<212> TYPE: DNA
<213> ORGANISM: artificial
<220> FEATURE:
<223> OTHER INFORMATION: synthetic

<400> SEQUENCE: 103
ttggcccaga agtagctct    19

<210> SEQ ID NO 104
<211> LENGTH: 22

```
<212> TYPE: DNA
<213> ORGANISM: artificial
<220> FEATURE:
<223> OTHER INFORMATION: synthetic

<400> SEQUENCE: 104
gtgtgcaaat gctacctgga tg                                          22

<210> SEQ ID NO 105
<211> LENGTH: 20
<212> TYPE: DNA
<213> ORGANISM: artificial
<220> FEATURE:
<223> OTHER INFORMATION: synthetic

<400> SEQUENCE: 105
gagttgttga cgtagtggtc                                             20

<210> SEQ ID NO 106
<211> LENGTH: 20
<212> TYPE: DNA
<213> ORGANISM: artificial
<220> FEATURE:
<223> OTHER INFORMATION: synthetic

<400> SEQUENCE: 106
atcgccggsg agctctggtt                                             20

<210> SEQ ID NO 107
<211> LENGTH: 20
<212> TYPE: DNA
<213> ORGANISM: artificial
<220> FEATURE:
<223> OTHER INFORMATION: synthetic

<400> SEQUENCE: 107
ttscggcaga asggcaccca                                             20

<210> SEQ ID NO 108
<211> LENGTH: 20
<212> TYPE: DNA
<213> ORGANISM: artificial
<220> FEATURE:
<223> OTHER INFORMATION: synthetic

<400> SEQUENCE: 108
gagttgttga cgtagtggtc                                             20

<210> SEQ ID NO 109
<211> LENGTH: 20
<212> TYPE: DNA
<213> ORGANISM: artificial
<220> FEATURE:
<223> OTHER INFORMATION: synthetic

<400> SEQUENCE: 109
tcccccacgt actttacgac                                             20

<210> SEQ ID NO 110
<211> LENGTH: 20
<212> TYPE: DNA
<213> ORGANISM: artificial
<220> FEATURE:
<223> OTHER INFORMATION: synthetic

<400> SEQUENCE: 110
```
gaccactacg tcaacaactc                                                   20

<210> SEQ ID NO 111
<211> LENGTH: 20
<212> TYPE: DNA
<213> ORGANISM: artificial
<220> FEATURE:
<223> OTHER INFORMATION: synthetic

<400> SEQUENCE: 111
gccatggtgg ccgtgctgga                                                   20

<210> SEQ ID NO 112
<211> LENGTH: 25
<212> TYPE: DNA
<213> ORGANISM: artificial
<220> FEATURE:
<223> OTHER INFORMATION: synthetic

<400> SEQUENCE: 112
gcactgttca gtggatgact tgttg                                             25

<210> SEQ ID NO 113
<211> LENGTH: 20
<212> TYPE: DNA
<213> ORGANISM: artificial
<220> FEATURE:
<223> OTHER INFORMATION: synthetic

<400> SEQUENCE: 113
gcctgagcgt ggagagctac                                                   20

<210> SEQ ID NO 114
<211> LENGTH: 20
<212> TYPE: DNA
<213> ORGANISM: artificial
<220> FEATURE:
<223> OTHER INFORMATION: synthetic

<400> SEQUENCE: 114
acagctcagc ggaagacttg                                                   20

<210> SEQ ID NO 115
<211> LENGTH: 24
<212> TYPE: DNA
<213> ORGANISM: artificial
<220> FEATURE:
<223> OTHER INFORMATION: synthetic

<400> SEQUENCE: 115
gcgacttgag ctcgaagtag ctct                                              24

<210> SEQ ID NO 116
<211> LENGTH: 23
<212> TYPE: DNA
<213> ORGANISM: artificial
<220> FEATURE:
<223> OTHER INFORMATION: synthetic

<400> SEQUENCE: 116
ggtagagaag gacggcctta atc                                               23

<210> SEQ ID NO 117
<211> LENGTH: 19
<212> TYPE: DNA
<213> ORGANISM: artificial

```
<220> FEATURE:
<223> OTHER INFORMATION: synthetic

<400> SEQUENCE: 117
tgcacgcgca cacctggaa                                              19

<210> SEQ ID NO 118
<211> LENGTH: 19
<212> TYPE: DNA
<213> ORGANISM: artificial
<220> FEATURE:
<223> OTHER INFORMATION: synthetic

<400> SEQUENCE: 118
cattgaggac gacggccat                                              19

<210> SEQ ID NO 119
<211> LENGTH: 50
<212> TYPE: DNA
<213> ORGANISM: artificial
<220> FEATURE:
<223> OTHER INFORMATION: synthetic

<400> SEQUENCE: 119
aagatggcta gcatgactgg tggacagcaa atgggtatgg cgccagcggt            50

<210> SEQ ID NO 120
<211> LENGTH: 24
<212> TYPE: DNA
<213> ORGANISM: artificial
<220> FEATURE:
<223> OTHER INFORMATION: synthetic

<400> SEQUENCE: 120
cgtgtagtag aacgtactca tctc                                        24

<210> SEQ ID NO 121
<211> LENGTH: 22
<212> TYPE: DNA
<213> ORGANISM: artificial
<220> FEATURE:
<223> OTHER INFORMATION: synthetic

<400> SEQUENCE: 121
ctcatggcca ggcgtaggtg aa                                          22

<210> SEQ ID NO 122
<211> LENGTH: 21
<212> TYPE: DNA
<213> ORGANISM: artificial
<220> FEATURE:
<223> OTHER INFORMATION: synthetic

<400> SEQUENCE: 122
gtctcaggtc gtcctgtccg g                                           21

<210> SEQ ID NO 123
<211> LENGTH: 21
<212> TYPE: DNA
<213> ORGANISM: artificial
<220> FEATURE:
<223> OTHER INFORMATION: synthetic

<400> SEQUENCE: 123
gtcgatcttc ttcgtcccga t                                           21
```

<210> SEQ ID NO 124
<211> LENGTH: 52
<212> TYPE: DNA
<213> ORGANISM: artificial
<220> FEATURE:
<223> OTHER INFORMATION: synthetic

<400> SEQUENCE: 124
ccagtgagca gagtgacgag gactcgagct caagcttttt ttttttttt tt            52

<210> SEQ ID NO 125
<211> LENGTH: 23
<212> TYPE: DNA
<213> ORGANISM: artificial
<220> FEATURE:
<223> OTHER INFORMATION: synthetic

<400> SEQUENCE: 125
aagcagtggt atcaacgcag agt                                            23

<210> SEQ ID NO 126
<211> LENGTH: 22
<212> TYPE: DNA
<213> ORGANISM: artificial
<220> FEATURE:
<223> OTHER INFORMATION: synthetic

<400> SEQUENCE: 126
ctaatacgac tcactatagg gc                                             22

<210> SEQ ID NO 127
<211> LENGTH: 20
<212> TYPE: DNA
<213> ORGANISM: artificial
<220> FEATURE:
<223> OTHER INFORMATION: synthetic

<400> SEQUENCE: 127
gatgcgtaca actcgagcaa                                                20

<210> SEQ ID NO 128
<211> LENGTH: 20
<212> TYPE: DNA
<213> ORGANISM: artificial
<220> FEATURE:
<223> OTHER INFORMATION: synthetic

<400> SEQUENCE: 128
cgttgctgaa gtcaagtgga                                                20

<210> SEQ ID NO 129
<211> LENGTH: 20
<212> TYPE: DNA
<213> ORGANISM: artificial
<220> FEATURE:
<223> OTHER INFORMATION: synthetic

<400> SEQUENCE: 129
aacatccccc acatgcatac                                                20

<210> SEQ ID NO 130
<211> LENGTH: 20
<212> TYPE: DNA
<213> ORGANISM: artificial
<220> FEATURE:
<223> OTHER INFORMATION: synthetic

```
<400> SEQUENCE: 130
ggattgaccc agctgaaaac                                           20

<210> SEQ ID NO 131
<211> LENGTH: 20
<212> TYPE: DNA
<213> ORGANISM: artificial
<220> FEATURE:
<223> OTHER INFORMATION: synthetic

<400> SEQUENCE: 131
gagttgttga cgtagtggtc                                           20

<210> SEQ ID NO 132
<211> LENGTH: 21
<212> TYPE: DNA
<213> ORGANISM: artificial
<220> FEATURE:
<223> OTHER INFORMATION: synthetic

<400> SEQUENCE: 132
cgctgcaaac gagaaagaag g                                         21

<210> SEQ ID NO 133
<211> LENGTH: 18
<212> TYPE: DNA
<213> ORGANISM: artificial
<220> FEATURE:
<223> OTHER INFORMATION: synthetic

<400> SEQUENCE: 133
ggcgctgaaa tccagagg                                             18

<210> SEQ ID NO 134
<211> LENGTH: 20
<212> TYPE: DNA
<213> ORGANISM: artificial
<220> FEATURE:
<223> OTHER INFORMATION: synthetic

<400> SEQUENCE: 134
ggaagatggg ccaagagaac                                           20

<210> SEQ ID NO 135
<211> LENGTH: 25
<212> TYPE: DNA
<213> ORGANISM: artificial
<220> FEATURE:
<223> OTHER INFORMATION: synthetic

<400> SEQUENCE: 135
tgatccatag aaaagtgtgc taggt                                     25

<210> SEQ ID NO 136
<211> LENGTH: 18
<212> TYPE: DNA
<213> ORGANISM: artificial
<220> FEATURE:
<223> OTHER INFORMATION: synthetic

<400> SEQUENCE: 136
cagccgtgat gaccaacg                                             18

<210> SEQ ID NO 137
```

```
<211> LENGTH: 24
<212> TYPE: DNA
<213> ORGANISM: artificial
<220> FEATURE:
<223> OTHER INFORMATION: synthetic

<400> SEQUENCE: 137
caaaatgtct tctgtcattg atcc                                              24

<210> SEQ ID NO 138
<211> LENGTH: 20
<212> TYPE: DNA
<213> ORGANISM: artificial
<220> FEATURE:
<223> OTHER INFORMATION: synthetic

<400> SEQUENCE: 138
aatgctgttg gaggtggaac                                                   20

<210> SEQ ID NO 139
<211> LENGTH: 21
<212> TYPE: DNA
<213> ORGANISM: artificial
<220> FEATURE:
<223> OTHER INFORMATION: synthetic

<400> SEQUENCE: 139
caaacctcag ggaagcagtc a                                                 21

<210> SEQ ID NO 140
<211> LENGTH: 21
<212> TYPE: DNA
<213> ORGANISM: artificial
<220> FEATURE:
<223> OTHER INFORMATION: synthetic

<400> SEQUENCE: 140
ggcaggcact gtacggttat g                                                 21

<210> SEQ ID NO 141
<211> LENGTH: 23
<212> TYPE: DNA
<213> ORGANISM: artificial
<220> FEATURE:
<223> OTHER INFORMATION: synthetic

<400> SEQUENCE: 141
accagccttc tgagtttcag ctc                                               23

<210> SEQ ID NO 142
<211> LENGTH: 20
<212> TYPE: DNA
<213> ORGANISM: artificial
<220> FEATURE:
<223> OTHER INFORMATION: synthetic

<400> SEQUENCE: 142
gtacgagctg gaggagatcg                                                   20

<210> SEQ ID NO 143
<211> LENGTH: 20
<212> TYPE: DNA
<213> ORGANISM: artificial
<220> FEATURE:
<223> OTHER INFORMATION: synthetic

<400> SEQUENCE: 143
```
cgtcaggatg tcctctgtca                                              20

<210> SEQ ID NO 144
<211> LENGTH: 20
<212> TYPE: DNA
<213> ORGANISM: artificial
<220> FEATURE:
<223> OTHER INFORMATION: synthetic

<400> SEQUENCE: 144
agtgtcctgt ccacccactc                                              20

<210> SEQ ID NO 145
<211> LENGTH: 21
<212> TYPE: DNA
<213> ORGANISM: artificial
<220> FEATURE:
<223> OTHER INFORMATION: synthetic

<400> SEQUENCE: 145
caaacctcag ggaagcagtc a                                            21

<210> SEQ ID NO 146
<211> LENGTH: 20
<212> TYPE: DNA
<213> ORGANISM: artificial
<220> FEATURE:
<223> OTHER INFORMATION: synthetic

<400> SEQUENCE: 146
agtgctgctt gctggttcat                                              20

<210> SEQ ID NO 147
<211> LENGTH: 20
<212> TYPE: DNA
<213> ORGANISM: artificial
<220> FEATURE:
<223> OTHER INFORMATION: synthetic

<400> SEQUENCE: 147
ccaacttcaa aggcacacag                                              20

<210> SEQ ID NO 148
<211> LENGTH: 20
<212> TYPE: DNA
<213> ORGANISM: artificial
<220> FEATURE:
<223> OTHER INFORMATION: synthetic

<400> SEQUENCE: 148
gcgtgtatgg gttctggaag                                              20

<210> SEQ ID NO 149
<211> LENGTH: 20
<212> TYPE: DNA
<213> ORGANISM: artificial
<220> FEATURE:
<223> OTHER INFORMATION: synthetic

<400> SEQUENCE: 149
gtcaactgcc aatggaactg                                              20

<210> SEQ ID NO 150
<211> LENGTH: 20
<212> TYPE: DNA

```
<213> ORGANISM: artificial
<220> FEATURE:
<223> OTHER INFORMATION: synthetic

<400> SEQUENCE: 150
gggcattcac cttcgtcatc                                              20

<210> SEQ ID NO 151
<211> LENGTH: 20
<212> TYPE: DNA
<213> ORGANISM: artificial
<220> FEATURE:
<223> OTHER INFORMATION: synthetic

<400> SEQUENCE: 151
gagcaagagg ccctacatcc                                              20

<210> SEQ ID NO 152
<211> LENGTH: 23
<212> TYPE: DNA
<213> ORGANISM: artificial
<220> FEATURE:
<223> OTHER INFORMATION: synthetic

<400> SEQUENCE: 152
caggttttgc agcattactt gac                                          23

<210> SEQ ID NO 153
<211> LENGTH: 20
<212> TYPE: DNA
<213> ORGANISM: artificial
<220> FEATURE:
<223> OTHER INFORMATION: synthetic

<400> SEQUENCE: 153
ggagagttcg tgtgctgtgg                                              20

<210> SEQ ID NO 154
<211> LENGTH: 21
<212> TYPE: DNA
<213> ORGANISM: artificial
<220> FEATURE:
<223> OTHER INFORMATION: synthetic

<400> SEQUENCE: 154
ctcttcgtcg tcatcgtcat c                                            21

<210> SEQ ID NO 155
<211> LENGTH: 23
<212> TYPE: DNA
<213> ORGANISM: artificial
<220> FEATURE:
<223> OTHER INFORMATION: synthetic

<400> SEQUENCE: 155
cgatgatgta gaactgctcg ttg                                          23

<210> SEQ ID NO 156
<211> LENGTH: 21
<212> TYPE: DNA
<213> ORGANISM: artificial
<220> FEATURE:
<223> OTHER INFORMATION: synthetic

<400> SEQUENCE: 156
cgctgcaaac gagaaagaag g                                            21
```

<210> SEQ ID NO 157
<211> LENGTH: 18
<212> TYPE: DNA
<213> ORGANISM: artificial
<220> FEATURE:
<223> OTHER INFORMATION: synthetic

<400> SEQUENCE: 157
ggcgctgaaa tccagagg					18

<210> SEQ ID NO 158
<211> LENGTH: 20
<212> TYPE: DNA
<213> ORGANISM: artificial
<220> FEATURE:
<223> OTHER INFORMATION: synthetic

<400> SEQUENCE: 158
ggagagttcg tgtgctgtgg					20

<210> SEQ ID NO 159
<211> LENGTH: 20
<212> TYPE: DNA
<213> ORGANISM: artificial
<220> FEATURE:
<223> OTHER INFORMATION: synthetic

<400> SEQUENCE: 159
cgagcacccc aatctacaga					20

<210> SEQ ID NO 160
<211> LENGTH: 20
<212> TYPE: DNA
<213> ORGANISM: artificial
<220> FEATURE:
<223> OTHER INFORMATION: synthetic

<400> SEQUENCE: 160
gccatggtgg ccgtgctgga					20

<210> SEQ ID NO 161
<211> LENGTH: 20
<212> TYPE: DNA
<213> ORGANISM: artificial
<220> FEATURE:
<223> OTHER INFORMATION: synthetic

<400> SEQUENCE: 161
gagcaagagg ccctacatcc					20

<210> SEQ ID NO 162
<211> LENGTH: 23
<212> TYPE: DNA
<213> ORGANISM: artificial
<220> FEATURE:
<223> OTHER INFORMATION: synthetic

<400> SEQUENCE: 162
cggtggtgac gaagatgtcg atg					23

<210> SEQ ID NO 163
<211> LENGTH: 27
<212> TYPE: DNA
<213> ORGANISM: artificial
<220> FEATURE:

<223> OTHER INFORMATION: synthetic

<400> SEQUENCE: 163
gataatcatc gcaagaccgg caacagg    27

<210> SEQ ID NO 164
<211> LENGTH: 3602
<212> TYPE: DNA
<213> ORGANISM: Artificial
<220> FEATURE:
<223> OTHER INFORMATION: Synthetic

<400> SEQUENCE: 164

| | | | | | |
|---|---|---|---|---|---|
| cccgctcctc | ctctgtcttc | cactcatcct | cacacaacct | agaagagcag | acgaggcagc | 60 |
| tagcttcagg | ttcttggtct | ccgttgatcc | tctcctccca | cccagaccct | gctcggcctc | 120 |
| ttctctcttg | ccgagagaga | gagagagaga | gagagagaga | gatacagggg | agccagctac | 180 |
| ctccggccgc | cgccaggcag | gcagagaggg | agggcgcgcc | cggcattatg | gcggcggggc | 240 |
| agcagcaggc | gagcggcggc | gccaagcacg | ggtgcgtgtg | cggttcccc | gtgtgcgcgt | 300 |
| gcgccggcgc | cgcggcggtg | gcgtccgccg | cgtcctccgc | cgacatggac | cgcgtggccg | 360 |
| tggccgccac | cgagggccag | atcggcgccg | tcaacgacga | gagctggatc | gccgtcgacc | 420 |
| tcagcgacga | cggcctgtcc | gccgacggcg | ccgacccggg | cgtcgcgctc | gaggaccgcc | 480 |
| ccgtcttccg | caccgagaag | atcaaggcg | tcctcctcca | cccctacagg | gtgctgatct | 540 |
| tcgtccggct | gatcgcgttc | acgctgttcg | taatctggcg | catctcgcac | cgcaacccgg | 600 |
| acgcgctgtg | gctgtgggtg | acgtcgatcg | cgggcgagtt | ctggttcggc | ttctcgtggc | 660 |
| tgctggacca | gctgccgaag | ctgaacccga | tcaaccgcgt | gccggacctg | gcggcgctgc | 720 |
| ggcagcggtt | cgaccgcgcg | ggcggggcg | ccggcggagg | gacgtcgctg | ctgccggggc | 780 |
| tggacgtgtt | cgtgacgacg | gcggacccgt | tcaaggagcc | gatcctgagc | acggccaact | 840 |
| ccgtgctgtc | catcctggcc | gccgactacc | ccgtggagcc | caacacgtgc | tacctctccg | 900 |
| acgactccgg | gatgctgctc | acctacgagg | ccatggcgga | ggccgccaag | ttcgccaccg | 960 |
| tctgggtgcc | cttctgccgc | aagcacggca | tcgagccgcg | cggccccgag | agctacttcg | 1020 |
| acctcaagtc | ccacccttac | atgggccgct | cccaggagga | cttcgtcaac | gaccgccgcc | 1080 |
| gcgtgcgcaa | ggactacgac | gagttcaagg | cgcgcatcaa | cggcctcgac | acgacatca | 1140 |
| agcagaggtc | cgacgcgtac | aacgccgcca | gggggctcaa | ggacggcgag | cccagggcaa | 1200 |
| cctggatggc | cgacggcacc | cagtgggagg | gcacatgggt | tgagccctcc | gagaaccacc | 1260 |
| gcaagggaga | ccacgccggc | atcgtactgg | tgcttctgaa | ccacccgagc | cacagccgtc | 1320 |
| agctcggccc | gccggcgagc | gcggacaacc | cgctggactt | gagcatggtg | gacgtgcggc | 1380 |
| tcccgatgct | ggtgtacgtg | tcccgcgaga | gcggcccgg | gcacaaccac | cagaagaagg | 1440 |
| ccggcgccat | gaacgcgctg | acccggtgct | ccgcggtgct | gtccaactcg | cccttcatcc | 1500 |
| tcaacctgga | ctgcgaccac | tacatcaaca | actcgcaggc | gctgcgcgcg | ggcatctgct | 1560 |
| tcatgctcgg | ccgcgacagc | gacacggtgg | ccttcgtgca | gttcccgcag | cgcttcgagg | 1620 |
| gcgtggaccc | cacggacctg | tacgccaacc | acaaccgcat | cttcttcgac | ggcacgctca | 1680 |
| gggcgctgga | cggcatgcag | ggccccatct | acgtgggcac | gggctgcctg | ttccgccgca | 1740 |
| tcacgctcta | cggcttcgac | ccgcgcgga | tcaacgtggg | cgggccgtgc | ttccggcgc | 1800 |
| tgggcggcat | gttcgccaag | gccaagtacg | agaagcccgg | gctggagctc | accaccacca | 1860 |
| aggccgccgt | ggccaagggc | aagcacggct | tcctgcccat | gcccaagaag | tcgtacggca | 1920 |

```
agtcggacgc gttcgcggac accatcccga tggcgtcgca cccgtcgccg ttcgcggccg    1980
cctcggccgc ctccgtcgtg gcggacgagg cgaccatcgc cgaggccgtg gcggtgtgcg    2040
cggcggcgta cgagaagaag accgggtggg gcagcgacat cgggtgggtg tacggcacgg    2100
tgacggagga cgtggtgacg gggtaccgga tgcacatcaa ggggtggcgg tcccgctact    2160
gctccatcta cccgcacgcc ttcatcggca ccgcccccat caacctgacg gagcggctgt    2220
tccaggtgct ccgctggtcg acgggttccc tggagatctt cttctcccgg aacaacccgc    2280
tgttcgggag cacgttcctg cacccgctgc agcgcgtggc gtacatcaac atcacgacgt    2340
acccgttcac ggccatcttc ctcatcttct acacgacggt gccggcgctg tcgttcgtga    2400
cggggcactt catcgtgcag cggcccacca ccatgttcta cgtgtacctg gccatcgtgc    2460
tgggcacgct gctgatcctg gccgtcctgg aggtgaagtg ggcgggcgtg acggtgttcg    2520
agtggttcag gaacgggcag ttctggatga cggccagctg ctccgcgtac ctggccgcgg    2580
tgtgccaggt gctggtgaag gtggtgttca ggcgggacat ctcgttcaag ctgacgtcga    2640
agcagcccgc gggggacgag aagaaggacc cctacgcaga cctgtacgtg gtgcgctgga    2700
cctggctcat ggtgacgccc atcatcatca tcctcgtcaa catcatcggc tccgccgtgg    2760
ccttcgccaa ggtgctggac ggcgagtgga cgcactggct caaggtggcc ggcggcgtct    2820
tcttcaactt ctgggtgctc ttccacctct accctttcgc caagggcatc ctggggaggc    2880
acggcaagac ccccgtggtg gtgctcgtct ggtgggcctt caccttcgtc atcaccgccg    2940
tgctgtacat caacatcccc cacatccacg ggccaggcgg caagcacggc ggcgcgatcg    3000
gaaggcacgg cggcgacgca caccaccatg gcaagaagtt cgacggctac tacctctggc    3060
cgtgaagcgc cgagcagcca gcatcgtcat gcatgcacat ataccgcctg ccctgatggt    3120
gacgatggtg agccgccaag gtgaagactg aagagtacgt tcccgttcat ccatccatcg    3180
tctccttagt actgctgccc ggtgattagt cgatgaagag tgaaggtgaa ggctacccac    3240
acacacacat ttggtcgacg tacccgccaa aatttgaatt ttttttcttc cccttcttc     3300 cttctcattc ttttttcttt tagttttgtc cagaaatcga aaggtgtgtt gatttgattt    3360
agttttttta attaccgtgc cccgtggtaa ttaattatgt acgtacttat atatatatac    3420
attacgccga agaggaagga gcactttgta taagagagga atggggaacg tacttatggg    3480 tgggggccg gggtgtcagc gtctgcctgt ctgtactgta catggcttag aggagtcaca     3540
tgcagagagg gagggccctg gctttggggt ggtattcttt tggtacatgg atcaagaata    3600
aa                                                                  3602
```

<210> SEQ ID NO 165
<211> LENGTH: 3599
<212> TYPE: DNA
<213> ORGANISM: Artificial
<220> FEATURE:
<223> OTHER INFORMATION: Synthetic

<400> SEQUENCE: 165

```
catctcccca cgcacccggg cgcccgcgcc gcgccaccttc tctcccccc tcctcctcct     60 cctctctctc tctctctctc tctgccacac agcacaccag aagggcagca ggggaggtag    120
agagaggtag cttcgcattc tcggtttccc tccgcgcgtg tcctcccagc ctcgacagag    180
agaagggcca ccatcgtccc tgcctgattg cgcgccaggc aggcaggcat tatgcgccg     240 ggcggccggc gcagcaacgg cgagacgccg acaggacagc agcagcagca gcagcaggct    300
```

```
gacggcaggc gcgggtgcgc atgcggcggg ttccccgtgt gcgcgtgcgc cggcgcggcg    360
gcggtggcgt ccgccgcctc ctccgccgac atggaccgcg tggcggtggc cgccaccgag    420
ggccagatcg gcgccgtcaa cgacgagagc tgggtggcgg tcgacctcag cgacgacggc    480
ctctcctccg ccgccgaccc gggggccgtc gcgctcgagg aacgcccgt cttccgcacc     540 gagaagatca agggtgtcct cctccacccc tacagggtgc tcatcttcgt gcgcctgatc    600
gcgttcacgc tgttcgtgat ctggcgcatc tcgcaccgca acccggacgc gctgtggctg    660
tgggtgacgt cgatcgcggg cgagttctgg ttcggcttct cgtggctgct ggaccagctg    720
ccgaagctga acccgatcaa ccgcgtgccg gacctggggg cgctgcggca gcggttcgac    780
cgcgccgacg ggacgtcgcg gctgccgggg ctggacatct tcgtgaccac ggcggacccg    840
ttcaaggagc cgatcctgag cacggccaac tccatcctct ccatcctggc cgccgactac    900
cccgtggagc gcaacacgtg ctacctctcc gacgactcgg gcatgctgct cacgtacgag    960
gccatggcgg aggccgccaa gttcgccacc gtctgggtgc ccttctgccg caagcacggc    1020
atcgagccgc gcggccccga gagctacttc gagctcaagt cccaccccta catgggccgc    1080
tcccaggagg acttcgtcaa cgaccgccgc gcgtgcgca gggactacga cgagttcaag    1140
gcgcgcatca acgggctgga gaacgacatc aggcagcgct ccgacgccta caacgccgcc    1200 aggggggctca aggacggcga gcccagggct acgtggatgg ccgacggcac acagtgggag    1260
ggcacctggg ttgagccgtc cgagaaccac cgcaagggcg accatgccgg catcgtcctg    1320
gtgcttctga accacccgag ccacagccgt cagctcgggc cgccggcgag cgcggacaac    1380
ccgctggact tgagcatggt ggacgtgcgg ctccccatgc tggtgtacgt ctcccgcgag    1440
aagcggcccg ggcacaacca ccagaagaag gccggcgcca tgaacgcgct gacccggtgc    1500
tccgccgtgc tctccaactc gcccttcatc ctgaacctgg actgcgacca ctacatcaac    1560
aactcgcagg cgctgcgcgc gggcatctgc ttcatgctcg ggcgggacag cgacacggtg    1620
gcgttcgtcc agttcccgca cgcttcgag ggcgtggacc ccacggacct gtacgccaac    1680
cacaaccgca tcttcttcga cggcacgctc cgggcgctgg acggcatgca gggccccatc    1740
tacgtcggca cgggctgcct gttccgccgc atcacgctct acggcttcga cccgccgcgg    1800
atcaacgtgg gcgggccgtg cttcccgtcg ctgggcggca tgttcgccaa gaccaagtac    1860
gagaagcctg ggctggagct caccaccaag gccgccgtgg ccaagggcaa gcacggcttc    1920
ctgcccatgc ccaagaagtc gtacggcaag tcggacgcgt tcgcggacac catcccgatg    1980
gcgtcgcacc cgtcgccgtt cgcggccgcg ccgccgtcg tggcggaaga ggcgaccatc    2040
gccgaggcag tggcggtgtg cgcggcggcg tacgagaaga agaccgggtg gggcagcgac    2100
atcgggtggg tgtacggcac ggtgacggag acgtggtga cggggtaccg gatgcacatc    2160 aagggggtggc gctcccgcta ctgctccatc tacccgcacg ccttcatcgg caccgccccc    2220
atcaacctga cggagcggct gttccaggtg ctccgctggt ccacgggctc cctggagatc    2280
ttcttctccc ggaacaaccc gctgttcggg agcacgttcc tgcacccgct gcagcgcgtg    2340
gcgtacatca acatcaccac gtacccgttc acggcgatct tcctcatctt ctacaccacg    2400
gtgccggcgc tgtcgttcgt gacggggcac ttcatcgtgc agcggcccac caccatgttc    2460
tacgtgtacc tggccatcgt gctgggcacg ctgctgatcc tggccgtcct ggaggtgaag    2520
tgggcgggcg tgaccgtgtt cgagtggttc cggaacgggc agttctggat gacggccagc    2580
tgctccgcgt acctgccgc cgtgtgccag gtgctggtga aggtggtgtt ccggcgggac    2640
atctcgttca agctgacgtc gaagcagccc gcgggggacg agaagaagga cccctacgcc    2700
```

```
gacctgtacg tggtgcgctg gacctggctc atggtgacgc ccatcatcat catcctcgtc    2760
aacatcatcg gctccgccgt ggccttcgcc aaggtgctgg acggcgagtg gacgcactgg    2820
ctaaaggtgg ccggcggcgt cttcttcaac ttctgggtgc tgttccacct ctaccccttc    2880
gccaagggca tcctggggag gcacggcaag accccgtgg tggtgctcgt ctggtgggcc     2940
ttcaccttcg tcatcaccgc cgtgctgtac atcaacatac cccacatcca cggccccggc    3000
ggcaagcacg gcggcgcgat cggaaagcac ggcgccgccc accatggcaa gaagttcgac    3060
ggctactacc tctggccgtg aaggatcgat cgatcggagc agccaaccca gcatcgtcat    3120
gcatgcacat acctgccctg atgatgatat ggtgagccgc gaaggtgaag agtacgtt     3180 cccgttcatc catcgtcctt agtgatgccc ggtgattagt tgatgatgaa gagtgaagaa    3240
gactacacac caacccacac acatttgatc gacccagcga cgtacccgcc aattttttt    3300 cttcttcttt ccttttgcc cgccccttt tcttcattct tttttcttcta gttttgtcca    3360 gaaattgaaa gatgtgttaa gatgtgttga tttgatttag ttttttaatt accgtacccg    3420
tggtaattaa attatgtacc tacttatata tacattacgc cgaagaggaa ggatcacttt    3480
gtataagaaa agagagaaat gggggatgta ggagggggg ctagggccc ggctttgggg     3540 tggtattctt ttagcatatg gaacacaata aatttaattt cattcttgga aaaaagaa    3599
```

```
<210> SEQ ID NO 166
<211> LENGTH: 2792
<212> TYPE: DNA
<213> ORGANISM: Artificial
<220> FEATURE:
<223> OTHER INFORMATION: Synthetic

<400> SEQUENCE: 166
```

```
ccgccaggca ggcagagagg gagggcgcgc ccggcattat ggcggcggtg gcgtccgccg      60
cgtcctccgc cgacatggac cgcgtggccg tggccgccac cgagggccag atcggcgccg    120
tcaacgacga gagctggatc gccgtcgacc tcagcgacga cggcctgtcc gccgacggcg    180
ccgacccggg cgtcgcgctc gaggaccgcc ccgtcttccg caccgagaag atcaagggcg    240
tcctcctcca ccccctacagg gtgctgatct tcgtccggct gatcgcgttc acgctgttcg    300
tgatctggcg catctcgcac cgcaacccgg acgcgctgtg gctgtgggtg acgtcgatcg    360
cgggcgagtt ctggttcggc ttctcgtggc tgctggacca gctgccgaag ctgaacccga    420
tcaaccgcgt gccggacctg gcggcgctgc ggcagcggtt cgaccgcgcg ggcggggggcg    480 ccggcggagg gacgtcgctg ctgccggggc tggacgtgtt cgtgacgacg gcggacccgt    540
tcaaggagcc gatactgagc acggccaact ccgtgctgtc catcctggcc gccgactacc    600
ccgtggagcg caacacgtgc tacctctccg acgactccgg gatgctgctc acctacgagg    660
ccatggcgga ggccgccaag ttcgccaccg tctgggtgcc cttctgccgc aagcacggca    720
tcgagccgcg cggcccggag agctacttcg acctcaagtc ccaccettac atgggccgct    780 cccaggagga cttcgtcaac gaccgccgcc gcgtgcgcaa ggactacgac gagttcaagg    840
cgcgcatcaa cggcctcgac cacgacatca agcagaggtc cgacgcgtac aacgccgcca    900
gggggctcaa ggacggcgag cccagggcaa cctggatggc cgacggcacc cagtgggagg    960
gcacctgggt cgagccctcc gagaaccacc gcaagggaga ccacgccggc atcgtactgg   1020
tgcttctgaa ccaccgagc cacagccgtc agctcggccc gccggcgagc gctgacaacc   1080
cgctggactt gagcatggtg gacgtgcggc tcccgatgct ggtgtacgtg tcccgcgaga   1140
```

-continued

| | |
|---|---|
| agcggcccgg tcacaaccac cagaagaagg ccggcgccat gaacgcgctg acccggtgct | 1200 |
| ccgcggtgct gtccaactcg cccttcatcc tcaacctgga ctgcgaccac tacatcaaca | 1260 |
| actcgcaggc gctgcgcgcg ggcatctgct tcatgctcgg ccgcgacagc gacacggtgg | 1320 |
| ccttcgtgca gttcccgcag cgcttcgagg gcgtggaccc cacggacctg tacgccaacc | 1380 |
| acaaccgcat cttcttcgac ggcacgctca gggcgctgga cggcatgcag gccccatct | 1440 |
| acgtgggcac gggctgcctg ttccgccgca tcacgctcta cggcttcgac ccgccgcgga | 1500 |
| tcaacgtggg cgggccgtgc ttcccggcgc tgggcggcat gttcgccaag gccaagtacg | 1560 |
| agaagcccgg actggagctc accaccaagg ccgccgtggc caagggcaag cacggcttcc | 1620 |
| tgcccatgcc taagaagtcg tacggcaagt cggacgcgtt cgcggacacc atcccgatgg | 1680 |
| cgtcgcaccc gtcgccgttc gcggcggccg ccgccgccgt cgtcgtggcg gacgaggcga | 1740 |
| ccatcgccga ggcagtggcg gtgtgcgcgg cggcgtacga gaagaagacc gggtggggca | 1800 |
| gcgacatcgg atgggtgtac ggcacggtga cggaggacgt ggtgacgggg taccggatgc | 1860 |
| acatcaaggg gtggcggtcc cgctactgct ccatctaccc gcacgccttc atcggcaccg | 1920 |
| cccccatcaa cctgacggag cggctgttcc aggtgctccg ctggtccacg ggttccctgg | 1980 |
| agatcttctt ctcccggaac aacccgctgt tcgggagcac gttcctgcac ccgctgcagc | 2040 |
| gcgtggcgta catcaacatc acgacgtacc cgttcacggc catcttcctc atcttctaca | 2100 |
| cgacggtgcc ggcgctgtcg ttcgtgacgg ggcacttcat cgtgcagcgg cccaccacca | 2160 |
| tgttctacgt gtacctggcc atcgtgctgg gcacgctgct gatcctggcc gtcctggagg | 2220 |
| tgaagtgggc gggcgtgacg gtgttcgagt ggttcaggaa cgggcagttc tggatgacgg | 2280 |
| ccagctgctc cgcgtacctg gccgcggtgt gccaggtgct ggtgaaggtg gtgttcaggc | 2340 |
| gggacatctc gttcaagctg acgtcgaagc agcccgcggg ggacgagaag aaggaccct | 2400 |
| acgcagacct gtacgtggtg cgctggacct ggctcatggt gacgcccatc atcatcatcc | 2460 |
| tcgtcaacat catcggctcc gccgtggcct tcgccaaggt gctggacggc gagtggacgc | 2520 |
| actggctcaa ggtggccggc ggcgtcttct tcaacttctg ggtgctcttc cacctctacc | 2580 |
| ctttcgccaa gggcatcctg gggaggcacg gcaagacccc cgtggtggtg ctcgtctggt | 2640 |
| gggccttcac cttcgtcatc accgccgtgc tgtacatcaa catcccacac atccacgggc | 2700 |
| ccggcggcaa gcacggcggc gcgatcggaa ggcacggcgg cgacgcacac caccatggca | 2760 |
| agaagttcga cggctactac ctctggccgt ga | 2792 |

<210> SEQ ID NO 167
<211> LENGTH: 2859
<212> TYPE: DNA
<213> ORGANISM: Artificial
<220> FEATURE:
<223> OTHER INFORMATION: Synthetic

<400> SEQUENCE: 167

| | |
|---|---|
| gccaggcagg caggcattat ggcgccgggc ggccggcgca gcaacggcga gacgccgaca | 60 |
| ggacagcagc agcagcaggc tgacggcagg cgcgggtgcg cgtgcggcgg gttccccgtg | 120 |
| tgcgcgtgcg ccgcgccgc ggcggtggcg tccgccgcct cgtccgccga catgaccgc | 180 |
| gtggcggtgg ccgccaccga gggccagatc ggcgccgtca acgacgagag ctgggtggcg | 240 |
| gtcgacctca cgacgacgg cctctccgcc gccgacccgg gggccgtcgc gctcgaggaa | 300 |
| cgccccgtct tccgcaccga gaagatcaag ggcgtcctcc tccacccata cagggtgctc | 360 |
| atcttcgtgc gcctgatcgc gttcacgctg ttcgtgatct ggcgcatctc gcaccgcaac | 420 |

-continued

```
ccggacgcgc tgtggctgtg ggtgacgtcg atcgcgggcg agttctggtt cggcttctcg      480
tggctgctgg accagctgcc gaagctgaac ccgatcaacc gcgtgccgga cctggcggcg      540
ctgcggcagc ggttcgaccg cgccgacggg acgtcgcggc tgccggggct ggacatcttc      600
gtgaccacgg cggacccgtt caaggagccg atcctgagca cggccaactc catcctctcc      660
atcctggccg ccgactaccc cgtggagcgc aacacgtgct acctctccga cgactcgggc      720
atgctgctca cgtacgaggc catggcggag ccgccaagt tcgccaccgt ctgggtgccc       780
ttctgccgca agcacggcat cgagccgcgc ggccccgaga gctacttcga gctcaagtcc      840 caccccctaca tgggccgctc ccaggaggac ttcgtcaacg accgccgccg cgtgcgcagg     900
gactacgacg agttcaaggc gcgcatcaac gggctggaga cgacatcag gcagcgctcc      960 gacgcctaca cgccgccag ggggctcaag gacggcgagc ccagggccac gtggatggcc      1020
gacggcacac agtgggaggg cacctgggtt gagccgtccg agaaccaccg caagggcgac     1080
catgccggca tcgtactggt gcttctgaac caccccgagcc acagccgtca gctcggcccg    1140
ccggcgagcg cggacaaccc gctggacttg agcatggtgg acgtgcggct ccccatgctg     1200
gtgtacgtct cccgcgagaa gcggcccggg cacaaccacc agaagaaggc cggcgccatg     1260
aacgcgctga cccggtgctc cgccgtgctc tccaactcgc ccttcatcct gaacctggac     1320
tgcgaccact acatcaacaa ctcgcaggcg ctgcgcgcgg gcatctgctt catgctcggg     1380
cgggacagcg acacggtggc gttcgtccag ttcccgcagc gcttcgaggg cgtggacccc     1440
acggacctgt acgccaacca caaccgcatc ttcttcgacg gcacgctccg ggcgctggac     1500
ggcatgcagg gccccatcta cgtcggcacg ggctgcctgt ccgccgcat cacgctctac     1560 ggcttcgacc cgccgcggat caacgtgggc gggccgtgct cccgtcgct gggcggcatg     1620 ttcgccaaga ccaagtacga gaagcctggg ctggagctca ccaccaaggc cgccgtggcc     1680
aagggcaagc acggcttcct gcccatgccc aagaagtcgt acggcaagtc ggacgcgttc     1740
gcggacacca tcccgatggc gtcgcacccg tcgccgttcg cggccgcggc cgccgtcgtg     1800
gcggaagagg cgaccatcgc cgaggcattg gcggtgtgcg cggcggcgta cgagaagaag     1860
accgggtggg gcagcgacat cgggtgggtg tacggcacgg tgacggagga cgtggtgacg     1920
gggtaccgga tgcacatcaa ggggtggcgc tcccgctact gctccatcta cccgcacgcc     1980
ttcatcggca ccgcccccat caacctgacg gagcggctgt ccaggtgct ccgctggtcc      2040 acgggctccc tggagatctt cttctcccgg aacaacccgc tgttcgggag cacgttcctg     2100
cacccgctgc agcgcgtggc gtacatcaac atcaccacgt acccgttcac ggcgatcttc     2160
ctcatcttct acaccacggt gccggcgctg tcgttcgtga cggggcactt catcgtgcag     2220
cggcccacca ccatgttcta cgtgtacctg gccatcgtgc tgggcacgct gctgatcctg     2280
gccgtcctgg aggtgaagtg ggcgggcgtg accgtgttcg agtggttccg gaacgggcag     2340
ttctggatga cggccagctg ctccgcgtac ctggccgccg tgtgccaggt gctggtgaag     2400
gtggtgttcc ggcgggacat ctcgttcaag ctgacgtcga agcagcccgc ggggacgag     2460 aagaaggacc cctacgccga cctgtacgtg gtgcgctgga cctggctcat ggtgacgccc     2520
atcatcatca tcctcgtcaa catcatcggc tccgccgtgg ccttcgccaa ggttctagac     2580
ggcgagtgga cgcactggct aaaggtggcc ggcggcgtct tcttcaactt ctgggtgctg     2640
ttccacctct accccttcgc caagggcatc ctggggaggc acggcaagac ccccgtggtg     2700
gtgctcgtct ggtgggcctt caccttcgtc atcaccgccg tgctgtacat caacataccc     2760
```

| | | | |
|---|---|---|---|
| cacatccacg | gccccggcgg | caagcacggc ggcgcgatcg gaaagcacgg cgccgcccac | 2820 |
| catggcaaga | agttcgacgg | ctactacctc tggccgtga | 2859 |

<210> SEQ ID NO 168
<211> LENGTH: 3514
<212> TYPE: DNA
<213> ORGANISM: Artificial
<220> FEATURE:
<223> OTHER INFORMATION: Synthetic

<400> SEQUENCE: 168

| | | | | |
|---|---|---|---|---|
| atcatctctt | tctctctcac | aaaacacaca | gagtcggcgc gaggtttccc ccctgatta | 60 |
| cccatataaa | tcctgaggca | gggggtgctt | gccttccata actcaccagt ccaccacgca | 120 |
| tatccagctc | gctccctctc | actcacacgc | gcatagggac agaccagac gcgcacattt | 180 |
| gacagagcag | ctgagtgagt | agatacctat | acagctacag agtgtgaaga aaagacagag | 240 |
| agggacgtgt | acagacgcgt | acaaaaatac | agagggaact tagctagcct tgcaaaaaaa | 300 |
| aaaaaaaaaa | acccacccga | ccgacactcg | gctagtgaat tccggcccat attttctata | 360 |
| tatcccgtcc | ctcccccccac | gtactttact | cggcatctcc tctccccctc cctcctcgcc | 420 |
| cccgcgccac | caccaccacc | accttctctt | ccaccctcag cccctcccct tctcatacaa | 480 |
| accagaagag | cagaggaggc | agcagcagca | gcttcgcatt cctggtctcc gtcctccaat | 540 |
| cccacgctct | tctctcttgc | ctcgagagag | aagagccacc accgtcgtcc gacaagcaga | 600 |
| gagagggtgc | gagggcgcag | ccggcattat | ggcgccgggc ggcggagacg gccggcgcaa | 660 |
| cggcgaggga | cagcagcagg | cgaacggcaa | caacaacaac aacaacagca acgctaaggc | 720 |
| taagcacggg | tgcgtgtgcg | ggttccccgt | gtgcgcgtgc gccggcgcgg ccgcggtggc | 780 |
| gtccgcggcc | tcctccgccg | acatggaccg | cgtggccgcc gcgcagaccg agggccagat | 840 |
| cggcgccgtc | aacgacgaga | gctggatcgc | cgtcgacctg agcgacgacc tctccggcga | 900 |
| cggcggcggc | gccgaccccg | gcgtcgcgat | cgaggaccgc cccgtcttcc gcaccgagaa | 960 |
| gatcaagggc | atcctcctcc | acccctacag | ggtgctcatc ttcgtgcgcc tgatcgcgtt | 1020 |
| cacgctgttc | gtcatctggc | gtatctcgca | ccgcaacccg gacgcgatgt ggctgtgggt | 1080 |
| gacgtcgatc | gcgggcgagt | tctggttcgg | cttctcctgg ctgctggacc agctccccaa | 1140 |
| gctgaacccg | atcaaccgcg | tcccggacct | cgcggtgctc cggcagcggt tcgaccgcgc | 1200 |
| cgacggcacg | tcccgcctcc | cgggcctgga | catcttcgtc accacggcgg acccgttcaa | 1260 |
| ggagcccatc | ctgagcacgg | ccaactccat | cctctccatc cttgccgccg actacccgt | 1320 |
| ggagcgcaac | acgtgctacc | tctccgacga | ctccgggatg ctgctcacct acgaggccat | 1380 |
| ggcggaggcc | gccaagttcg | ccaccgtctg | ggtgcccttc tgccggaagc acggcatcga | 1440 |
| gcctcgtggc | cccgagagct | acttcgagct | caagtcgcac ccctacatgg ggaggtcgca | 1500 |
| ggaggacttc | gtcaacgacc | gccgccgtgt | ccgcaaggag tacgacgagt tcaaggcccg | 1560 |
| gatcaatggc | ctcgagcatg | atatcaagca | gaggtccgac gcgtttaacg ccgctagggg | 1620 |
| gcttaaggac | ggcgagccca | gagctacgtg | gatggccgac gggaaccagt gggagggcac | 1680 |
| atgggttgag | ccatcggaga | accaccgcaa | gggtgaccac gccggcatcg tctatgtgct | 1740 |
| tctgaaccac | ccgagccaca | gccgtcagct | cggcccgccg gcgagcgcgg acaacccgct | 1800 |
| ggacttcagc | atggtggacg | ttcgcctccc | catgctggtg tacgtctccc gtgagaagcg | 1860 |
| gcccgggttc | aaccacgaga | agaaggccgg | cgccatgaac gcgctgaccc gctgctccgc | 1920 |
| cgtgatctcc | aactcgccct | tcatcctcaa | cctggactgc gaccactaca tcaacaactc | 1980 |

```
gcaggcgctt cgcgccggca tctgcttcat gctcggccgg acagcgaca cggtggcgtt      2040 cgtgcagttc ccgcagcggt tcgagggcgt ggacccccacg gacctgtacg ccaaccacaa    2100
ccgcatcttc ttcgacggca cgctccgggc gctggacggc atgcagggcc ccatctacgt     2160
cggcaccggc tgcatgttcc gccgcatcac gctctacgtg ttcgacccgc cgaggatcaa     2220
cgtcggcggg ccgtgcttcc cgtcgctcgg cggcatgttc gccaagacca agtacgagaa     2280
gcccgggctg gagctcacca ccaaggccgc cgtcgccaag ggcaagcacg gcttcctccc     2340
gttgcccaag aagtcgtacg gcaagtcgga cgcgttcgtc gacaccatcc cgagggcgtc     2400
tcacccgtcg ccgttcctga cgcccgacga ggccgccgcc atcgtcgccg acgaggccat     2460
gatcaccgag gccgtggagg tgtgcacggc ggcgtacgag aagaagaccg gctggggcag     2520
cgacatcggc tgggtgtacg gcaccgtcac cgaggacgtg gtgacggggt accggatgca     2580
catcaagggg tggcggtctc gctactgctc catctacccg cacgccttca tcggcaccgc     2640
cccgatcaac ctgacggagc ggctgtacca ggtgctccgc tggtccacgg ggtcgctgga    2700
gatcttcttc tcccggaaca cccgctgttt cggcagcacg ttcctgcacc cgctgcagcg     2760
cgtggcgtac atcaacatca ccacctaccc gttcacggcg ctgttcctca tcttctacac     2820
caccgtgccg gcgctgtcgt tcgtgacggg gcacttcatc gtgcagcggc cgaccaccat     2880
gttctacgtg tacctggcca tcgtgctggg gacgctgctc atcctggccg tcctggaggt     2940
gaaatgggcg gcgtcaccg tcttcgagtg gttcaggaac gggcagttct ggatgacggc     3000
cagctgctcc gcgtacctgg ccgccgtgtg ccaggtgctg gtgaaagtgg tgttccggcg     3060
agacatctcc ttcaagctca catccaagca gcccgccggc gacgagaaga aggacccta     3120 cgccgacctg tacgtggtgc gctggacctg gctcatggtg acccccatca tcatcatcct     3180
cgtcaacatc atcggatccg ccgtggcgtt cgccaaggtg ctggacggcg agtggacgca     3240
ctggctcaag gtggccggcg gcgtcttctt caacttctgg gtgctgttcc acctctaccc     3300
gttcgccaag ggcctcctcg ggaggcacgg caagacccccg tggtggtgc tcgtctggtg     3360 ggcattcacc ttcgtcatca ccgccgtgct ctacatcaac atcccccaca tccatggccc     3420
cggcggcaag cacggcggcg cgatcggaaa gcacggcgcc gcccaccacg gcaagaagtt     3480
cgacctcgac aacctctcct acaactggcc gtga                                 3514

<210> SEQ ID NO 169
<211> LENGTH: 2918
<212> TYPE: DNA
<213> ORGANISM: Artificial
<220> FEATURE:
<223> OTHER INFORMATION: Synthetic

<400> SEQUENCE: 169
catggcgcca gcggtggccg gagggggccg cgtgcggagc aatgagccgg ttgctgctgc       60
tgccgccgcg ccggcggcca gcggcaagcc ctgcgtgtgc ggcttccagg tttgcgcctg     120
cacggggtcg gccgcggtgg cctccgccgc ctcgtcgctg acatggaca tcgtggccat     180 ggggcagatc ggcgccgtca acgacgagag ctgggtgggc gtggagctcg gcgaagatgg     240
cgagaccgac gaaagcggtg ccgccgttga cgaccgcccc gtattccgca ccgagaagat     300
caagggtgtc ctcctccacc cctaccgggt gctgattttc gttcgtctga tcgccttcac     360
gctgttcgtg atctggcgta tctccccacaa gaacccagac gcgatgtggc tgtgggtgac     420
atccatctgc ggcgagttct ggttcggttt ctcgtggctg ctagatcagc tgcccaagct     480
```

```
gaacccatc  aaccgcgtgc  cggacctggc  ggtgctgcgg  cagcgcttcg  accgccccga    540
cggcacctcc  acgctcccgg  ggctggacat  cttcgtcacc  acggccgacc  ccatcaagga    600
gcccatcctc  tccaccgcca  actcggtgct  ctccatcctg  gccgccgact  accccgtgga    660
ccgcaacaca  tgctacgtct  ccgacgacag  tggcatgctg  ctcacctacg  aggccctggc    720
agagtcctcc  aagttcgcca  cgctctgggt  gcccttctgc  cgcaagcacg  ggatcgagcc    780 cagggggtccg  gagagctact  tcgagctcaa  gtcacaccct  tacatgggga  gagcccagga    840
cgagttcgtc  aacgaccgcc  gccgcgttcg  caaggagtac  gacgagttca  aggccaggat    900
caacagcctg  gagcatgaca  tcaagcagcg  caacgacggg  tacaacgccg  ccattgccca    960
cagccaaggc  gtgccccggc  ccacctggat  ggcggacggc  acccagtggg  agggcacatg   1020
ggtcgacgcc  tccgagaacc  accgcagggg  cgaccacgcc  ggcatcgtac  tggtgctgct   1080
gaaccacccg  agccaccgcc  ggcagacggg  cccgccggcg  agcgctgaca  acccactgga   1140
cttgagcggc  gtggatgtgc  gtctcccccat  gctggtgtac  gtgtcccgtg  agaagcgccc   1200
cgggcacgac  caccagaaga  aggccggtgc  catgaacgcg  cttacccgcg  cctcggcgct   1260
gctctccaac  tcccccttca  tcctcaacct  cgactgcgat  cattacatca  acaactccca   1320
ggcccttcgc  gccggcatct  gcttcatggt  gggacggag   agcgacacgg  ttgccttcgt   1380
ccagttcccg  cagcgcttcg  agggcgtcga  ccccaccgac  ctctacgcca  accacaaccg   1440
catcttcttc  gacggcaccc  tccgtgccct  ggacggcatg  cagggcccca  tctacgtcgg   1500
cactgggtgt  ctcttccgcc  gcatcaccgt  ctacggcttc  gacccgccga  ggatcaacgt   1560
cggcggtccc  tgcttcccca  ggctcgccgg  gctcttcgcc  aagaccaagt  acgagaagcc   1620
cgggctcgag  atgaccacgg  ccaaggccaa  ggccgcgccc  gtgcccgcca  agggtaagca   1680
cggcttcttg  ccactgccca  agaagacgta  cggcaagtcg  gacgccttcg  tggacaccat   1740
cccgcgcgcg  tcgcacccgt  cgccctacgc  cgcggcggct  gagggatcg   tggccgacga   1800 ggcgaccatc  gtcgaggcgg  tgaacgtgac  ggccgccgcg  ttcgagaaga  agaccggctg   1860
gggcaaagag  atcggctggg  tgtacgacac  cgtcacggag  gacgtggtca  ccggctaccg   1920
gatgcatatc  aaggggtggc  ggtcacgcta  ctgctccatc  tacccacacg  ccttcatcgg   1980
caccgccccc  atcaacctca  cggagaggct  cttccaggtg  ctccgctggt  ccacgggatc   2040
cctcgagatc  ttcttctcca  gaacaaccc   gctcttcggc  agcacatacc  tccaccgct   2100 gcagcgcgtc  gcctacatca  acatcaccac  ttaccccttc  accgccatct  tcctcatctt   2160
ctacaccacc  gtgccggcgc  tatccttcgt  caccggccac  ttcatcgtgc  agcgcccgac   2220
caccatgttc  tacgtctacc  tgggcatcgt  gctatccacg  ctgctcgtca  tcgccgtgct   2280
ggaggtcaag  tgggccgggg  tcacagtctt  cgagtggttc  aggaacggcc  agttctggat   2340
gacagcaagt  tgctccgcct  acctcgccgc  cgtctgccag  gtgctgacca  aggtgatatt   2400
ccggcgggac  atctccttca  agctcacatc  caagctaccc  tcgggagacg  agaagaagga   2460
cccctacgcc  gacctctacg  tggtgcgctg  gacgccgctc  atgattacac  ccatcatcat   2520
catcttcgtc  aacatcatcg  gatccgccgt  ggccttcgcc  aaggttctcg  acggcgagtg   2580
gacgcactgg  ctcaaggtcg  ccggcggcgt  cttcttcaac  ttctgggtgc  tcttccacct   2640 ctacccccttc  gccaagggca  tcctggggaa  gcacggaaag  acgccagtcg  tggtgctcgt   2700
ctggtgggca  ttcaccttcg  tcatcaccgc  cgtgctctac  atcaacatcc  cccacatgca   2760
tacctcggga  ggcaagcaca  caacggtgca  tggtcaccat  ggcaagaagt  tggtcgacac   2820
agggctctat  ggctggctcc  attgatgact  ttgcccggac  aagacgacct  gagacaagaa   2880
```
acaactcatc cactcaacag tcagtgcatg catccatc 2918

<210> SEQ ID NO 170
<211> LENGTH: 945
<212> TYPE: PRT
<213> ORGANISM: Artificial
<220> FEATURE:
<223> OTHER INFORMATION: Synthetic

<400> SEQUENCE: 170

```
Met Ala Ala Gly Gln Gln Ala Ser Gly Ala Lys His Gly Cys
1               5                   10                  15

Val Cys Gly Phe Pro Val Cys Ala Cys Ala Gly Ala Ala Val Ala
                20                  25                  30

Ser Ala Ala Ser Ser Ala Asp Met Asp Arg Val Ala Val Ala Thr
            35                  40                  45

Glu Gly Gln Ile Gly Ala Val Asn Asp Glu Ser Trp Ile Ala Val Asp
        50                  55                  60

Leu Ser Asp Asp Gly Leu Ser Ala Asp Gly Ala Asp Pro Gly Val Ala
65                  70                  75                  80

Leu Glu Asp Arg Pro Val Phe Arg Thr Glu Lys Ile Lys Gly Val Leu
                85                  90                  95

Leu His Pro Tyr Arg Val Leu Ile Phe Val Arg Leu Ile Ala Phe Thr
            100                 105                 110

Leu Phe Val Ile Trp Arg Ile Ser His Arg Asn Pro Asp Ala Leu Trp
        115                 120                 125

Leu Trp Val Thr Ser Ile Ala Gly Glu Phe Trp Phe Gly Phe Ser Trp
    130                 135                 140

Leu Leu Asp Gln Leu Pro Lys Leu Asn Pro Ile Asn Arg Val Pro Asp
145                 150                 155                 160

Leu Ala Ala Leu Arg Gln Arg Phe Asp Arg Ala Gly Gly Ala Gly
                165                 170                 175

Gly Gly Thr Ser Leu Leu Pro Gly Leu Asp Val Phe Val Thr Thr Ala
            180                 185                 190

Asp Pro Phe Lys Glu Pro Ile Leu Ser Thr Ala Asn Ser Val Leu Ser
        195                 200                 205

Ile Leu Ala Ala Asp Tyr Pro Val Glu Arg Asn Thr Cys Tyr Leu Ser
    210                 215                 220

Asp Asp Ser Gly Met Leu Leu Thr Tyr Glu Ala Met Ala Glu Ala Ala
225                 230                 235                 240

Lys Phe Ala Thr Val Trp Val Pro Phe Cys Arg Lys His Gly Ile Glu
                245                 250                 255

Pro Arg Gly Pro Glu Ser Tyr Phe Asp Leu Lys Ser His Pro Tyr Met
            260                 265                 270

Gly Arg Ser Gln Glu Asp Phe Val Asn Asp Arg Arg Val Arg Lys
        275                 280                 285

Asp Tyr Asp Glu Phe Lys Ala Arg Ile Asn Gly Leu Asp His Asp Ile
    290                 295                 300

Lys Gln Arg Ser Asp Ala Tyr Asn Ala Ala Arg Gly Leu Lys Asp Gly
305                 310                 315                 320

Glu Pro Arg Ala Thr Trp Met Ala Asp Gly Thr Gln Trp Glu Gly Thr
                325                 330                 335

Trp Val Glu Pro Ser Glu Asn His Arg Lys Gly Asp His Ala Gly Ile
            340                 345                 350
```

-continued

Val Leu Val Leu Leu Asn His Pro Ser His Ser Arg Gln Leu Gly Pro
            355                 360                 365

Pro Ala Ser Ala Asp Asn Pro Leu Asp Leu Ser Met Val Asp Val Arg
370                 375                 380

Leu Pro Met Leu Val Tyr Val Ser Arg Glu Lys Arg Pro Gly His Asn
385                 390                 395                 400

His Gln Lys Lys Ala Gly Ala Met Asn Ala Leu Thr Arg Cys Ser Ala
            405                 410                 415

Val Leu Ser Asn Ser Pro Phe Ile Leu Asn Leu Asp Cys Asp His Tyr
            420                 425                 430

Ile Asn Asn Ser Gln Ala Leu Arg Ala Gly Ile Cys Phe Met Leu Gly
            435                 440                 445

Arg Asp Ser Asp Thr Val Ala Phe Val Gln Phe Pro Gln Arg Phe Glu
450                 455                 460

Gly Val Asp Pro Thr Asp Leu Tyr Ala Asn His Asn Arg Ile Phe Phe
465                 470                 475                 480

Asp Gly Thr Leu Arg Ala Leu Asp Gly Met Gln Gly Pro Ile Tyr Val
            485                 490                 495

Gly Thr Gly Cys Leu Phe Arg Arg Ile Thr Leu Tyr Gly Phe Asp Pro
            500                 505                 510

Pro Arg Ile Asn Val Gly Gly Pro Cys Phe Pro Ala Leu Gly Gly Met
            515                 520                 525

Phe Ala Lys Ala Lys Tyr Glu Lys Pro Gly Leu Glu Leu Thr Thr Thr
            530                 535                 540

Lys Ala Ala Val Ala Lys Gly Lys His Gly Phe Leu Pro Met Pro Lys
545                 550                 555                 560

Lys Ser Tyr Gly Lys Ser Asp Ala Phe Ala Asp Thr Ile Pro Met Ala
            565                 570                 575

Ser His Pro Ser Pro Phe Ala Ala Ala Ser Ala Ala Ser Val Val Ala
            580                 585                 590

Asp Glu Ala Thr Ile Ala Glu Ala Val Ala Val Cys Ala Ala Ala Tyr
            595                 600                 605

Glu Lys Lys Thr Gly Trp Gly Ser Asp Ile Gly Trp Val Tyr Gly Thr
610                 615                 620

Val Thr Glu Asp Val Val Thr Gly Tyr Arg Met His Ile Lys Gly Trp
625                 630                 635                 640

Arg Ser Arg Tyr Cys Ser Ile Tyr Pro His Ala Phe Ile Gly Thr Ala
            645                 650                 655

Pro Ile Asn Leu Thr Glu Arg Leu Phe Gln Val Leu Arg Trp Ser Thr
            660                 665                 670

Gly Ser Leu Glu Ile Phe Phe Ser Arg Asn Asn Pro Leu Phe Gly Ser
            675                 680                 685

Thr Phe Leu His Pro Leu Gln Arg Val Ala Tyr Ile Asn Ile Thr Thr
690                 695                 700

Tyr Pro Phe Thr Ala Ile Phe Leu Ile Phe Tyr Thr Thr Val Pro Ala
705                 710                 715                 720

Leu Ser Phe Val Thr Gly His Phe Ile Val Gln Arg Pro Thr Met Met
            725                 730                 735

Phe Tyr Val Tyr Leu Ala Ile Val Leu Gly Thr Leu Leu Ile Leu Ala
            740                 745                 750

Val Leu Glu Val Lys Trp Ala Gly Val Thr Val Phe Glu Trp Phe Arg
            755                 760                 765

Asn Gly Gln Phe Trp Met Thr Ala Ser Cys Ser Ala Tyr Leu Ala Ala

```
                        770                 775                 780
Val Cys Gln Val Leu Val Lys Val Val Phe Arg Arg Asp Ile Ser Phe
785                 790                 795                 800

Lys Leu Thr Ser Lys Gln Pro Ala Gly Asp Glu Lys Lys Asp Pro Tyr
                805                 810                 815

Ala Asp Leu Tyr Val Val Arg Trp Thr Trp Leu Met Val Thr Pro Ile
                820                 825                 830

Ile Ile Ile Leu Val Asn Ile Ile Gly Ser Ala Val Ala Phe Ala Lys
                835                 840                 845

Val Leu Asp Gly Glu Trp Thr His Trp Leu Lys Val Ala Gly Gly Val
                850                 855                 860

Phe Phe Asn Phe Trp Val Leu Phe His Leu Tyr Pro Phe Ala Lys Gly
865                 870                 875                 880

Ile Leu Gly Arg His Gly Lys Thr Pro Val Val Val Leu Val Trp Trp
                885                 890                 895

Ala Phe Thr Phe Val Ile Thr Ala Val Leu Tyr Ile Asn Ile Pro His
                900                 905                 910

Ile His Gly Pro Gly Gly Lys His Gly Gly Ala Ile Gly Arg His Gly
                915                 920                 925

Gly Asp Ala His His His Gly Lys Lys Phe Asp Gly Tyr Tyr Leu Trp
                930                 935                 940

Pro
945

<210> SEQ ID NO 171
<211> LENGTH: 949
<212> TYPE: PRT
<213> ORGANISM: Artificial
<220> FEATURE:
<223> OTHER INFORMATION: Synthetic

<400> SEQUENCE: 171

Met Ala Pro Gly Gly Arg Arg Ser Asn Gly Glu Thr Pro Thr Gly Gln
1               5                   10                  15

Gln Gln Gln Gln Gln Ala Asp Gly Arg Arg Gly Cys Ala Cys Gly
                20                  25                  30

Gly Phe Pro Val Cys Ala Cys Ala Gly Ala Ala Val Ala Ser Ala
                35                  40                  45

Ala Ser Ser Ala Asp Met Asp Arg Val Ala Val Ala Ala Thr Glu Gly
                50              55                  60

Gln Ile Gly Ala Val Asn Asp Glu Ser Trp Val Ala Val Asp Leu Ser
65                  70                  75                  80

Asp Asp Gly Leu Ser Ser Ala Ala Asp Pro Gly Ala Val Ala Leu Glu
                85                  90                  95

Glu Arg Pro Val Phe Arg Thr Glu Lys Ile Lys Gly Val Leu Leu His
                100                 105                 110

Pro Tyr Arg Val Leu Ile Phe Val Arg Leu Ile Ala Phe Thr Leu Phe
                115                 120                 125

Val Ile Trp Arg Ile Ser His Arg Asn Pro Asp Ala Leu Trp Leu Trp
130                 135                 140

Val Thr Ser Ile Ala Gly Glu Phe Trp Phe Gly Phe Ser Trp Leu Leu
145                 150                 155                 160

Asp Gln Leu Pro Lys Leu Asn Pro Ile Asn Arg Val Pro Asp Leu Gly
                165                 170                 175

Ala Leu Arg Gln Arg Phe Asp Arg Ala Asp Gly Thr Ser Arg Leu Pro
```

-continued

```
                180                 185                 190
Gly Leu Asp Ile Phe Val Thr Thr Ala Asp Pro Phe Lys Glu Pro Ile
            195                 200                 205
Leu Ser Thr Ala Asn Ser Ile Leu Ser Ile Leu Ala Ala Asp Tyr Pro
            210                 215                 220
Val Glu Arg Asn Thr Cys Tyr Leu Ser Asp Asp Ser Gly Met Leu Leu
225                 230                 235                 240
Thr Tyr Glu Ala Met Ala Glu Ala Ala Lys Phe Ala Thr Val Trp Val
            245                 250                 255
Pro Phe Cys Arg Lys His Gly Ile Glu Pro Arg Gly Pro Glu Ser Tyr
            260                 265                 270
Phe Glu Leu Lys Ser His Pro Tyr Met Gly Arg Ser Gln Glu Asp Phe
            275                 280                 285
Val Asn Asp Arg Arg Val Arg Arg Asp Tyr Asp Glu Phe Lys Ala
290                 295                 300
Arg Ile Asn Gly Leu Glu Asn Asp Ile Arg Gln Arg Ser Asp Ala Tyr
305                 310                 315                 320
Asn Ala Ala Arg Gly Leu Lys Asp Gly Glu Pro Arg Ala Thr Trp Met
            325                 330                 335
Ala Asp Gly Thr Gln Trp Glu Gly Thr Trp Val Glu Pro Ser Glu Asn
            340                 345                 350
His Arg Lys Gly Asp His Ala Gly Ile Val Leu Val Leu Leu Asn His
            355                 360                 365
Pro Ser His Ser Arg Gln Leu Gly Pro Pro Ala Ser Ala Asp Asn Pro
            370                 375                 380
Leu Asp Leu Ser Met Val Asp Val Arg Leu Pro Met Leu Val Tyr Val
385                 390                 395                 400
Ser Arg Glu Lys Arg Pro Gly His Asn His Gln Lys Lys Ala Gly Ala
            405                 410                 415
Met Asn Ala Leu Thr Arg Cys Ser Ala Val Leu Ser Asn Ser Pro Phe
            420                 425                 430
Ile Leu Asn Leu Asp Cys Asp His Tyr Ile Asn Asn Ser Gln Ala Leu
            435                 440                 445
Arg Ala Gly Ile Cys Phe Met Leu Gly Arg Asp Ser Asp Thr Val Ala
            450                 455                 460
Phe Val Gln Phe Pro Gln Arg Phe Glu Gly Val Asp Pro Thr Asp Leu
465                 470                 475                 480
Tyr Ala Asn His Asn Arg Ile Phe Phe Asp Gly Thr Leu Arg Ala Leu
            485                 490                 495
Asp Gly Met Gln Gly Pro Ile Tyr Val Gly Thr Gly Cys Leu Phe Arg
            500                 505                 510
Arg Ile Thr Leu Tyr Gly Phe Asp Pro Pro Arg Ile Asn Val Gly Gly
            515                 520                 525
Pro Cys Phe Pro Ser Leu Gly Gly Met Phe Ala Lys Thr Lys Tyr Glu
            530                 535                 540
Lys Pro Gly Leu Glu Leu Thr Thr Lys Ala Ala Val Ala Lys Gly Lys
545                 550                 555                 560
His Gly Phe Leu Pro Met Pro Lys Lys Ser Tyr Gly Lys Ser Asp Ala
            565                 570                 575
Phe Ala Asp Thr Ile Pro Met Ala Ser His Pro Ser Pro Phe Ala Ala
            580                 585                 590
Ala Ala Ala Val Val Ala Glu Glu Ala Thr Ile Ala Glu Ala Val Ala
            595                 600                 605
```

Val Cys Ala Ala Ala Tyr Glu Lys Lys Thr Gly Trp Gly Ser Asp Ile
610 615 620

Gly Trp Val Tyr Gly Thr Val Thr Glu Asp Val Val Thr Gly Tyr Arg
625 630 635 640

Met His Ile Lys Gly Trp Arg Ser Arg Tyr Cys Ser Ile Tyr Pro His
645 650 655

Ala Phe Ile Gly Thr Ala Pro Ile Asn Leu Thr Glu Arg Leu Phe Gln
660 665 670

Val Leu Arg Trp Ser Thr Gly Ser Leu Glu Ile Phe Phe Ser Arg Asn
675 680 685

Asn Pro Leu Phe Gly Ser Thr Phe Leu His Pro Leu Gln Arg Val Ala
690 695 700

Tyr Ile Asn Ile Thr Thr Tyr Pro Phe Thr Ala Ile Phe Leu Ile Phe
705 710 715 720

Tyr Thr Thr Val Pro Ala Leu Ser Phe Val Thr Gly His Phe Ile Val
725 730 735

Gln Arg Pro Thr Thr Met Phe Tyr Val Tyr Leu Ala Ile Val Leu Gly
740 745 750

Thr Leu Leu Ile Leu Ala Val Leu Glu Val Lys Trp Ala Gly Val Thr
755 760 765

Val Phe Glu Trp Phe Arg Asn Gly Gln Phe Trp Met Thr Ala Ser Cys
770 775 780

Ser Ala Tyr Leu Ala Ala Val Cys Gln Val Leu Val Lys Val Val Phe
785 790 795 800

Arg Arg Asp Ile Ser Phe Lys Leu Thr Ser Lys Gln Pro Ala Gly Asp
805 810 815

Glu Lys Lys Asp Pro Tyr Ala Asp Leu Tyr Val Val Arg Trp Thr Trp
820 825 830

Leu Met Val Thr Pro Ile Ile Ile Leu Val Asn Ile Ile Gly Ser
835 840 845

Ala Val Ala Phe Ala Lys Val Leu Asp Gly Glu Trp Thr His Trp Leu
850 855 860

Lys Val Ala Gly Gly Val Phe Phe Asn Phe Trp Val Leu Phe His Leu
865 870 875 880

Tyr Pro Phe Ala Lys Gly Ile Leu Gly Arg His Gly Lys Thr Pro Val
885 890 895

Val Val Leu Val Trp Trp Ala Phe Thr Phe Val Ile Thr Ala Val Leu
900 905 910

Tyr Ile Asn Ile Pro His Ile His Gly Pro Gly Lys His Gly Gly
915 920 925

Ala Ile Gly Lys His Gly Ala Ala His His Gly Lys Lys Phe Asp Gly
930 935 940

Tyr Tyr Leu Trp Pro
945

<210> SEQ ID NO 172
<211> LENGTH: 917
<212> TYPE: PRT
<213> ORGANISM: Artificial
<220> FEATURE:
<223> OTHER INFORMATION: Synthetic

<400> SEQUENCE: 172

Met Ala Ala Val Ala Ser Ala Ala Ser Ser Ala Asp Met Asp Arg Val
1 5 10 15

```
Ala Val Ala Ala Thr Glu Gly Gln Ile Gly Ala Val Asn Asp Glu Ser
         20                  25                  30

Trp Ile Ala Val Asp Leu Ser Asp Gly Leu Ser Ala Asp Gly Ala
         35                  40                  45

Asp Pro Gly Val Ala Leu Glu Asp Arg Pro Val Phe Arg Thr Glu Lys
 50                  55                  60

Ile Lys Gly Val Leu Leu His Pro Tyr Arg Val Leu Ile Phe Val Arg
 65                  70                  75                  80

Leu Ile Ala Phe Thr Leu Phe Val Ile Trp Arg Ile Ser His Arg Asn
             85                  90                  95

Pro Asp Ala Leu Trp Leu Trp Val Thr Ser Ile Ala Gly Glu Phe Trp
         100                 105                 110

Phe Gly Phe Ser Trp Leu Leu Asp Gln Leu Pro Lys Leu Asn Pro Ile
         115                 120                 125

Asn Arg Val Pro Asp Leu Ala Ala Leu Arg Gln Arg Phe Asp Arg Ala
 130                 135                 140

Gly Gly Gly Ala Gly Gly Gly Thr Ser Leu Leu Pro Gly Leu Asp Val
 145                 150                 155                 160

Phe Val Thr Thr Ala Asp Pro Phe Lys Glu Pro Ile Leu Ser Thr Ala
                 165                 170                 175

Asn Ser Val Leu Ser Ile Leu Ala Ala Asp Tyr Pro Val Glu Arg Asn
             180                 185                 190

Thr Cys Tyr Leu Ser Asp Asp Ser Gly Met Leu Leu Thr Tyr Glu Ala
         195                 200                 205

Met Ala Glu Ala Ala Lys Phe Ala Thr Val Trp Val Pro Phe Cys Arg
 210                 215                 220

Lys His Gly Ile Glu Pro Arg Gly Pro Glu Ser Tyr Phe Asp Leu Lys
 225                 230                 235                 240

Ser His Pro Tyr Met Gly Arg Ser Gln Glu Asp Phe Val Asn Asp Arg
             245                 250                 255

Arg Arg Val Arg Lys Asp Tyr Asp Glu Phe Lys Ala Arg Ile Asn Gly
         260                 265                 270

Leu Asp His Asp Ile Lys Gln Arg Ser Asp Ala Tyr Asn Ala Ala Arg
         275                 280                 285

Gly Leu Lys Asp Gly Glu Pro Arg Ala Thr Trp Met Ala Asp Gly Thr
 290                 295                 300

Gln Trp Glu Gly Thr Trp Val Glu Pro Ser Glu Asn His Arg Lys Gly
 305                 310                 315                 320

Asp His Ala Gly Ile Val Leu Val Leu Leu Asn His Pro Ser His Ser
             325                 330                 335

Arg Gln Leu Gly Pro Pro Ala Ser Ala Asp Asn Pro Leu Asp Leu Ser
         340                 345                 350

Met Val Asp Val Arg Leu Pro Met Leu Val Tyr Val Ser Arg Glu Lys
         355                 360                 365

Arg Pro Gly His Asn His Gln Lys Lys Ala Gly Ala Met Asn Ala Leu
 370                 375                 380

Thr Arg Cys Ser Ala Val Leu Ser Asn Ser Pro Phe Ile Leu Asn Leu
 385                 390                 395                 400

Asp Cys Asp His Tyr Ile Asn Asn Ser Gln Ala Leu Arg Ala Gly Ile
             405                 410                 415

Cys Phe Met Leu Gly Arg Asp Ser Asp Thr Val Ala Phe Val Gln Phe
         420                 425                 430
```

-continued

```
Pro Gln Arg Phe Glu Gly Val Asp Pro Thr Asp Leu Tyr Ala Asn His
        435                 440                 445
Asn Arg Ile Phe Phe Asp Gly Thr Leu Arg Ala Leu Asp Gly Met Gln
    450                 455                 460
Gly Pro Ile Tyr Val Gly Thr Gly Cys Leu Phe Arg Arg Ile Thr Leu
465                 470                 475                 480
Tyr Gly Phe Asp Pro Arg Ile Asn Val Gly Gly Pro Cys Phe Pro
                485                 490                 495
Ala Leu Gly Gly Met Phe Ala Lys Ala Lys Tyr Glu Lys Pro Gly Leu
                500                 505                 510
Glu Leu Thr Thr Lys Ala Ala Val Ala Lys Gly Lys His Gly Phe Leu
            515                 520                 525
Pro Met Pro Lys Lys Ser Tyr Gly Lys Ser Asp Ala Phe Ala Asp Thr
        530                 535                 540
Ile Pro Met Ala Ser His Pro Ser Pro Phe Ala Ala Ala Ala Ala
545                 550                 555                 560
Val Val Val Ala Asp Glu Ala Thr Ile Ala Glu Ala Val Ala Val Cys
                565                 570                 575
Ala Ala Ala Tyr Glu Lys Lys Thr Gly Trp Gly Ser Asp Ile Gly Trp
                580                 585                 590
Val Tyr Gly Thr Val Thr Glu Asp Val Val Thr Gly Tyr Arg Met His
            595                 600                 605
Ile Lys Gly Trp Arg Ser Arg Tyr Cys Ser Ile Tyr Pro His Ala Phe
        610                 615                 620
Ile Gly Thr Ala Pro Ile Asn Leu Thr Glu Arg Leu Phe Gln Val Leu
625                 630                 635                 640
Arg Trp Ser Thr Gly Ser Leu Glu Ile Phe Phe Ser Arg Asn Asn Pro
                645                 650                 655
Leu Phe Gly Ser Thr Phe Leu His Pro Leu Gln Arg Val Ala Tyr Ile
                660                 665                 670
Asn Ile Thr Thr Tyr Pro Phe Thr Ala Ile Phe Leu Ile Phe Tyr Thr
            675                 680                 685
Thr Val Pro Ala Leu Ser Phe Val Thr Gly His Phe Ile Val Gln Arg
        690                 695                 700
Pro Thr Thr Met Phe Tyr Val Tyr Leu Ala Ile Val Leu Gly Thr Leu
705                 710                 715                 720
Leu Ile Leu Ala Val Leu Glu Val Lys Trp Ala Gly Val Thr Val Phe
                725                 730                 735
Glu Trp Phe Arg Asn Gly Gln Phe Trp Met Thr Ala Ser Cys Ser Ala
                740                 745                 750
Tyr Leu Ala Ala Val Cys Gln Val Leu Val Lys Val Val Phe Arg Arg
            755                 760                 765
Asp Ile Ser Phe Lys Leu Thr Ser Lys Gln Pro Ala Gly Asp Glu Lys
        770                 775                 780
Lys Asp Pro Tyr Ala Asp Leu Tyr Val Val Arg Trp Thr Trp Leu Met
785                 790                 795                 800
Val Thr Pro Ile Ile Ile Leu Val Asn Ile Ile Gly Ser Ala Val
                805                 810                 815
Ala Phe Ala Lys Val Leu Asp Gly Glu Trp Thr His Trp Leu Lys Val
                820                 825                 830
Ala Gly Gly Val Phe Asn Phe Trp Val Leu Phe His Leu Tyr Pro
            835                 840                 845
Phe Ala Lys Gly Ile Leu Gly Arg His Gly Lys Thr Pro Val Val Val
```

```
                850             855             860
Leu Val Trp Trp Ala Phe Thr Phe Val Ile Thr Ala Val Leu Tyr Ile
865                 870             875                 880

Asn Ile Pro His Ile His Gly Pro Gly Gly Lys His Gly Gly Ala Ile
                885             890             895

Gly Arg His Gly Gly Asp Ala His His Gly Lys Lys Phe Asp Gly
            900             905             910

Tyr Tyr Leu Trp Pro
        915

<210> SEQ ID NO 173
<211> LENGTH: 946
<212> TYPE: PRT
<213> ORGANISM: Artificial
<220> FEATURE:
<223> OTHER INFORMATION: Synthetic

<400> SEQUENCE: 173

Met Ala Pro Gly Gly Arg Arg Ser Asn Gly Glu Thr Pro Thr Gly Gln
1               5                   10                  15

Gln Gln Gln Ala Asp Gly Arg Arg Gly Cys Ala Cys Gly Gly Phe
            20                  25                  30

Pro Val Cys Ala Cys Ala Gly Ala Ala Val Ala Ser Ala Ala Ser
        35                  40                  45

Ser Ala Asp Met Asp Arg Val Ala Val Ala Thr Glu Gly Gln Ile
    50                  55                  60

Gly Ala Val Asn Asp Glu Ser Trp Val Ala Val Asp Leu Ser Asp Asp
65                  70                  75                  80

Gly Leu Ser Ala Ala Asp Pro Gly Ala Val Ala Leu Glu Glu Arg Pro
                85                  90                  95

Val Phe Arg Thr Glu Lys Ile Lys Gly Val Leu Leu His Pro Tyr Arg
                100                 105                 110

Val Leu Ile Phe Val Arg Leu Ile Ala Phe Thr Leu Phe Val Ile Trp
            115                 120                 125

Arg Ile Ser His Arg Asn Pro Asp Ala Leu Trp Leu Trp Val Thr Ser
130                 135                 140

Ile Ala Gly Glu Phe Trp Phe Gly Phe Ser Trp Leu Leu Asp Gln Leu
145                 150                 155                 160

Pro Lys Leu Asn Pro Ile Asn Arg Val Pro Asp Leu Ala Ala Leu Arg
                165                 170                 175

Gln Arg Phe Asp Arg Ala Asp Gly Thr Ser Arg Leu Pro Gly Leu Asp
            180                 185                 190

Ile Phe Val Thr Thr Ala Asp Pro Phe Lys Glu Pro Ile Leu Ser Thr
        195                 200                 205

Ala Asn Ser Ile Leu Ser Ile Leu Ala Ala Asp Tyr Pro Val Glu Arg
    210                 215                 220

Asn Thr Cys Tyr Leu Ser Asp Asp Ser Gly Met Leu Leu Thr Tyr Glu
225                 230                 235                 240

Ala Met Ala Glu Ala Ala Lys Phe Ala Thr Val Trp Val Pro Phe Cys
                245                 250                 255

Arg Lys His Gly Ile Glu Pro Arg Gly Pro Ser Tyr Phe Glu Leu
            260                 265                 270

Lys Ser His Pro Tyr Met Gly Arg Ser Gln Glu Asp Phe Val Asn Asp
        275                 280                 285

Arg Arg Arg Val Arg Arg Asp Tyr Asp Glu Phe Lys Ala Arg Ile Asn
```

```
            290                 295                 300
Gly Leu Glu Asn Asp Ile Arg Gln Arg Ser Asp Ala Tyr Asn Ala Ala
305                 310                 315                 320

Arg Gly Leu Lys Asp Gly Glu Pro Arg Ala Thr Trp Met Ala Asp Gly
                325                 330                 335

Thr Gln Trp Glu Gly Thr Trp Val Glu Pro Ser Glu Asn His Arg Lys
            340                 345                 350

Gly Asp His Ala Gly Ile Val Leu Val Leu Asn His Pro Ser His
        355                 360                 365

Ser Arg Gln Leu Gly Pro Pro Ala Ser Ala Asp Asn Pro Leu Asp Leu
    370                 375                 380

Ser Met Val Asp Val Arg Leu Pro Met Leu Val Tyr Val Ser Arg Glu
385                 390                 395                 400

Lys Arg Pro Gly His Asn His Gln Lys Lys Ala Gly Ala Met Asn Ala
                405                 410                 415

Leu Thr Arg Cys Ser Ala Val Leu Ser Asn Ser Pro Phe Ile Leu Asn
                420                 425                 430

Leu Asp Cys Asp His Tyr Ile Asn Asn Ser Gln Ala Leu Arg Ala Gly
                435                 440                 445

Ile Cys Phe Met Leu Gly Arg Asp Ser Asp Thr Val Ala Phe Val Gln
        450                 455                 460

Phe Pro Gln Arg Phe Glu Gly Val Asp Pro Thr Asp Leu Tyr Ala Asn
465                 470                 475                 480

His Asn Arg Ile Phe Phe Asp Gly Thr Leu Arg Ala Leu Asp Gly Met
                485                 490                 495

Gln Gly Pro Ile Tyr Val Gly Thr Gly Cys Leu Phe Arg Arg Ile Thr
                500                 505                 510

Leu Tyr Gly Phe Asp Pro Pro Arg Ile Asn Val Gly Gly Pro Cys Phe
            515                 520                 525

Pro Ser Leu Gly Gly Met Phe Ala Lys Thr Lys Tyr Glu Lys Pro Gly
            530                 535                 540

Leu Glu Leu Thr Thr Lys Ala Ala Val Ala Lys Gly Lys His Gly Phe
545                 550                 555                 560

Leu Pro Met Pro Lys Lys Ser Tyr Gly Lys Ser Asp Ala Phe Ala Asp
                565                 570                 575

Thr Ile Pro Met Ala Ser His Pro Ser Pro Phe Ala Ala Ala Ala
                580                 585                 590

Val Val Ala Glu Glu Ala Thr Ile Ala Glu Ala Leu Ala Val Cys Ala
            595                 600                 605

Ala Ala Tyr Glu Lys Lys Thr Gly Trp Gly Ser Asp Ile Gly Trp Val
        610                 615                 620

Tyr Gly Thr Val Thr Glu Asp Val Val Thr Gly Tyr Arg Met His Ile
625                 630                 635                 640

Lys Gly Trp Arg Ser Arg Tyr Cys Ser Ile Tyr Pro His Ala Phe Ile
                645                 650                 655

Gly Thr Ala Pro Ile Asn Leu Thr Glu Arg Leu Phe Gln Val Leu Arg
            660                 665                 670

Trp Ser Thr Gly Ser Leu Glu Ile Phe Phe Ser Arg Asn Asn Pro Leu
        675                 680                 685

Phe Gly Ser Thr Phe Leu His Pro Leu Gln Arg Val Ala Tyr Ile Asn
    690                 695                 700

Ile Thr Thr Tyr Pro Phe Thr Ala Ile Phe Leu Ile Phe Tyr Thr Thr
705                 710                 715                 720
```

```
Val Pro Ala Leu Ser Phe Val Thr Gly His Phe Ile Val Gln Arg Pro
                725                 730                 735

Thr Thr Met Phe Tyr Val Tyr Leu Ala Ile Val Leu Gly Thr Leu Leu
            740                 745                 750

Ile Leu Ala Val Leu Glu Val Lys Trp Ala Gly Val Thr Val Phe Glu
            755                 760                 765

Trp Phe Arg Asn Gly Gln Phe Trp Met Thr Ala Ser Cys Ser Ala Tyr
770                 775                 780

Leu Ala Ala Val Cys Gln Val Leu Val Lys Val Val Phe Arg Arg Asp
785                 790                 795                 800

Ile Ser Phe Lys Leu Thr Ser Lys Gln Pro Ala Gly Asp Glu Lys Lys
                805                 810                 815

Asp Pro Tyr Ala Asp Leu Tyr Val Val Arg Trp Thr Trp Leu Met Val
                820                 825                 830

Thr Pro Ile Ile Ile Leu Val Asn Ile Ile Gly Ser Ala Val Ala
                835                 840                 845

Phe Ala Lys Val Leu Asp Gly Glu Trp Thr His Trp Leu Lys Val Ala
850                 855                 860

Gly Gly Val Phe Phe Asn Phe Trp Val Leu Phe His Leu Tyr Pro Phe
865                 870                 875                 880

Ala Lys Gly Ile Leu Gly Arg His Gly Lys Thr Pro Val Val Leu
                885                 890                 895

Val Trp Trp Ala Phe Thr Phe Val Ile Thr Ala Val Leu Tyr Ile Asn
                900                 905                 910

Ile Pro His Ile His Gly Pro Gly Gly Lys His Gly Ala Ile Gly
                915                 920                 925

Lys His Gly Ala Ala His His Gly Lys Lys Phe Asp Gly Tyr Tyr Leu
                930                 935                 940

Trp Pro
945

<210> SEQ ID NO 174
<211> LENGTH: 961
<212> TYPE: PRT
<213> ORGANISM: Artificial
<220> FEATURE:
<223> OTHER INFORMATION: Synthetic

<400> SEQUENCE: 174

Met Ala Pro Gly Gly Gly Asp Gly Arg Arg Asn Gly Glu Gly Gln Gln
1               5                   10                  15

Gln Ala Asn Gly Asn Asn Asn Asn Asn Ser Asn Ala Lys Ala Lys
                20                  25                  30

His Gly Cys Val Cys Gly Phe Pro Val Cys Ala Cys Gly Ala Ala
            35                  40                  45

Ala Val Ala Ser Ala Ala Ser Ser Ala Asp Met Asp Arg Val Ala Ala
            50                  55                  60

Ala Gln Thr Glu Gly Gln Ile Gly Ala Val Asn Asp Glu Ser Trp Ile
65                  70                  75                  80

Ala Val Asp Leu Ser Asp Asp Leu Ser Gly Asp Gly Gly Ala Asp
                85                  90                  95

Pro Gly Val Ala Ile Glu Asp Arg Pro Val Phe Arg Thr Glu Lys Ile
            100                 105                 110

Lys Gly Ile Leu Leu His Pro Tyr Arg Val Leu Ile Phe Val Arg Leu
            115                 120                 125
```

```
Ile Ala Phe Thr Leu Phe Val Ile Trp Arg Ile Ser His Arg Asn Pro
130                 135                 140

Asp Ala Met Trp Leu Trp Val Thr Ser Ile Ala Gly Glu Phe Trp Phe
145                 150                 155                 160

Gly Phe Ser Trp Leu Leu Asp Gln Leu Pro Lys Leu Asn Pro Ile Asn
                165                 170                 175

Arg Val Pro Asp Leu Ala Val Leu Arg Gln Arg Phe Asp Arg Ala Asp
                180                 185                 190

Gly Thr Ser Arg Leu Pro Gly Leu Asp Ile Phe Val Thr Thr Ala Asp
                195                 200                 205

Pro Phe Lys Glu Pro Ile Leu Ser Thr Ala Asn Ser Ile Leu Ser Ile
210                 215                 220

Leu Ala Ala Asp Tyr Pro Val Glu Arg Asn Thr Cys Tyr Leu Ser Asp
225                 230                 235                 240

Asp Ser Gly Met Leu Leu Thr Tyr Glu Ala Met Ala Glu Ala Ala Lys
                245                 250                 255

Phe Ala Thr Val Trp Val Pro Phe Cys Arg Lys His Gly Ile Glu Pro
                260                 265                 270

Arg Gly Pro Glu Ser Tyr Phe Glu Leu Lys Ser His Pro Tyr Met Gly
                275                 280                 285

Arg Ser Gln Glu Asp Phe Val Asn Asp Arg Arg Val Arg Lys Glu
290                 295                 300

Tyr Asp Glu Phe Lys Ala Arg Ile Asn Gly Leu Glu His Asp Ile Lys
305                 310                 315                 320

Gln Arg Ser Asp Ala Phe Asn Ala Ala Arg Gly Leu Lys Asp Gly Glu
                325                 330                 335

Pro Arg Ala Thr Trp Met Ala Asp Gly Asn Gln Trp Glu Gly Thr Trp
                340                 345                 350

Val Glu Pro Ser Glu Asn His Arg Lys Gly Asp His Ala Gly Ile Val
                355                 360                 365

Tyr Val Leu Leu Asn His Pro Ser His Ser Arg Gln Leu Gly Pro Pro
370                 375                 380

Ala Ser Ala Asp Asn Pro Leu Asp Phe Ser Met Val Asp Val Arg Leu
385                 390                 395                 400

Pro Met Leu Val Tyr Val Ser Arg Glu Lys Arg Pro Gly Phe Asn His
                405                 410                 415

Glu Lys Lys Ala Gly Ala Met Asn Ala Leu Thr Arg Cys Ser Ala Val
                420                 425                 430

Ile Ser Asn Ser Pro Phe Ile Leu Asn Leu Asp Cys Asp His Tyr Ile
                435                 440                 445

Asn Asn Ser Gln Ala Leu Arg Ala Gly Ile Cys Phe Met Leu Gly Arg
450                 455                 460

Asp Ser Asp Thr Val Ala Phe Val Gln Phe Pro Gln Arg Phe Glu Gly
465                 470                 475                 480

Val Asp Pro Thr Asp Leu Tyr Ala Asn His Asn Arg Ile Phe Phe Asp
                485                 490                 495

Gly Thr Leu Arg Ala Leu Asp Gly Met Gln Gly Pro Ile Tyr Val Gly
                500                 505                 510

Thr Gly Cys Met Phe Arg Arg Ile Thr Leu Tyr Gly Phe Asp Pro Pro
                515                 520                 525

Arg Ile Asn Val Gly Gly Pro Cys Phe Pro Ser Leu Gly Gly Met Phe
530                 535                 540
```

```
Ala Lys Thr Lys Tyr Glu Lys Pro Gly Leu Glu Leu Thr Thr Lys Ala
545                 550                 555                 560

Ala Val Ala Lys Gly Lys His Gly Phe Leu Pro Leu Pro Lys Lys Ser
            565                 570                 575

Tyr Gly Lys Ser Asp Ala Phe Val Asp Thr Ile Pro Arg Ala Ser His
        580                 585                 590

Pro Ser Pro Phe Leu Ser Ala Asp Glu Ala Ala Ile Val Ala Asp
    595                 600                 605

Glu Ala Met Ile Thr Glu Ala Val Glu Val Cys Thr Ala Ala Tyr Glu
    610                 615                 620

Lys Lys Thr Gly Trp Gly Ser Asp Ile Gly Trp Val Tyr Gly Thr Val
625                 630                 635                 640

Thr Glu Asp Val Val Thr Gly Tyr Arg Met His Ile Lys Gly Trp Arg
            645                 650                 655

Ser Arg Tyr Cys Ser Ile Tyr Pro His Ala Phe Ile Gly Thr Ala Pro
            660                 665                 670

Ile Asn Leu Thr Glu Arg Leu Tyr Gln Val Leu Arg Trp Ser Thr Gly
        675                 680                 685

Ser Leu Glu Ile Phe Phe Ser Arg Asn Asn Pro Leu Phe Gly Ser Thr
    690                 695                 700

Phe Leu His Pro Leu Gln Arg Val Ala Tyr Ile Asn Ile Thr Thr Tyr
705                 710                 715                 720

Pro Phe Thr Ala Leu Phe Leu Ile Phe Tyr Thr Thr Val Pro Ala Leu
            725                 730                 735

Ser Phe Val Thr Gly His Phe Ile Val Gln Arg Pro Thr Thr Met Phe
            740                 745                 750

Tyr Val Tyr Leu Ala Ile Val Leu Gly Thr Leu Leu Ile Leu Ala Val
        755                 760                 765

Leu Glu Val Lys Trp Ala Gly Val Thr Val Phe Glu Trp Phe Arg Asn
    770                 775                 780

Gly Gln Phe Trp Met Thr Ala Ser Cys Ser Ala Tyr Leu Ala Ala Val
785                 790                 795                 800

Cys Gln Val Leu Lys Val Val Phe Arg Arg Asp Ile Ser Phe Lys
            805                 810                 815

Leu Thr Ser Lys Gln Pro Ala Gly Asp Glu Lys Lys Asp Pro Tyr Ala
        820                 825                 830

Asp Leu Tyr Val Val Arg Trp Thr Trp Leu Met Val Thr Pro Ile Ile
            835                 840                 845

Ile Ile Leu Val Asn Ile Ile Gly Ser Ala Val Ala Phe Ala Lys Val
850                 855                 860

Leu Asp Gly Glu Trp Thr His Trp Leu Lys Val Ala Gly Gly Val Phe
865                 870                 875                 880

Phe Asn Phe Trp Val Leu Phe His Leu Tyr Pro Phe Ala Lys Gly Leu
            885                 890                 895

Leu Gly Arg His Gly Lys Thr Pro Val Val Leu Val Trp Trp Ala
            900                 905                 910

Phe Thr Phe Val Ile Thr Ala Val Leu Tyr Ile Asn Ile Pro His Ile
            915                 920                 925

His Gly Pro Gly Gly Lys His Gly Gly Ala Ile Gly Lys His Gly Ala
            930                 935                 940

Ala His His Gly Lys Lys Phe Asp Leu Asp Asn Leu Ser Tyr Asn Trp
945                 950                 955                 960

Pro
```

```
<210> SEQ ID NO 175
<211> LENGTH: 947
<212> TYPE: PRT
<213> ORGANISM: Artificial
<220> FEATURE:
<223> OTHER INFORMATION: Synthetic

<400> SEQUENCE: 175

Met Ala Pro Ala Val Ala Gly Gly Arg Val Arg Ser Asn Glu Pro
1               5                   10                  15

Val Ala Ala Ala Ala Ala Pro Ala Ser Gly Lys Pro Cys Val
            20                  25                  30

Cys Gly Phe Gln Val Cys Ala Cys Thr Gly Ser Ala Ala Val Ala Ser
            35                  40                  45

Ala Ala Ser Ser Leu Asp Met Asp Ile Val Ala Met Gly Gln Ile Gly
        50                  55                  60

Ala Val Asn Asp Glu Ser Trp Val Gly Val Glu Leu Gly Glu Asp Gly
65                  70                  75                  80

Glu Thr Asp Glu Ser Gly Ala Ala Val Asp Asp Arg Pro Val Phe Arg
                85                  90                  95

Thr Glu Lys Ile Lys Gly Val Leu Leu His Pro Tyr Arg Val Leu Ile
            100                 105                 110

Phe Val Arg Leu Ile Ala Phe Thr Leu Phe Val Ile Trp Arg Ile Ser
            115                 120                 125

His Lys Asn Pro Asp Ala Met Trp Leu Trp Val Thr Ser Ile Cys Gly
    130                 135                 140

Glu Phe Trp Phe Gly Phe Ser Trp Leu Leu Asp Gln Leu Pro Lys Leu
145                 150                 155                 160

Asn Pro Ile Asn Arg Val Pro Asp Leu Ala Val Leu Arg Gln Arg Phe
                165                 170                 175

Asp Arg Pro Asp Gly Thr Ser Thr Leu Pro Gly Leu Asp Ile Phe Val
            180                 185                 190

Thr Thr Ala Asp Pro Ile Lys Glu Pro Ile Leu Ser Thr Ala Asn Ser
        195                 200                 205

Val Leu Ser Ile Leu Ala Ala Asp Tyr Pro Val Asp Arg Asn Thr Cys
    210                 215                 220

Tyr Val Ser Asp Asp Ser Gly Met Leu Leu Thr Tyr Glu Ala Leu Ala
225                 230                 235                 240

Glu Ser Ser Lys Phe Ala Thr Leu Trp Val Pro Phe Cys Arg Lys His
                245                 250                 255

Gly Ile Glu Pro Arg Gly Pro Glu Ser Tyr Phe Glu Leu Lys Ser His
            260                 265                 270

Pro Tyr Met Gly Arg Ala Gln Asp Glu Phe Val Asn Asp Arg Arg Arg
        275                 280                 285

Val Arg Lys Glu Tyr Asp Glu Phe Lys Ala Arg Ile Asn Ser Leu Glu
    290                 295                 300

His Asp Ile Lys Gln Arg Asn Asp Gly Tyr Asn Ala Ala Ile Ala His
305                 310                 315                 320

Ser Gln Gly Val Pro Arg Pro Thr Trp Met Ala Asp Gly Thr Gln Trp
                325                 330                 335

Glu Gly Thr Trp Val Asp Ala Ser Glu Asn His Arg Arg Gly Asp His
            340                 345                 350

Ala Gly Ile Val Leu Val Leu Leu Asn His Pro Ser His Arg Arg Gln
        355                 360                 365
```

```
Thr Gly Pro Pro Ala Ser Ala Asp Asn Pro Leu Asp Leu Ser Gly Val
    370                 375                 380
Asp Val Arg Leu Pro Met Leu Val Tyr Val Ser Arg Glu Lys Arg Pro
385                 390                 395                 400
Gly His Asp His Gln Lys Lys Ala Gly Ala Met Asn Ala Leu Thr Arg
                405                 410                 415
Ala Ser Ala Leu Leu Ser Asn Ser Pro Phe Ile Leu Asn Leu Asp Cys
            420                 425                 430
Asp His Tyr Ile Asn Asn Ser Gln Ala Leu Arg Ala Gly Ile Cys Phe
        435                 440                 445
Met Val Gly Arg Asp Ser Asp Thr Val Ala Phe Val Gln Phe Pro Gln
450                 455                 460
Arg Phe Glu Gly Val Asp Pro Thr Asp Leu Tyr Ala Asn His Asn Arg
465                 470                 475                 480
Ile Phe Phe Asp Gly Thr Leu Arg Ala Leu Asp Gly Met Gln Gly Pro
            485                 490                 495
Ile Tyr Val Gly Thr Gly Cys Leu Phe Arg Arg Ile Thr Val Tyr Gly
        500                 505                 510
Phe Asp Pro Pro Arg Ile Asn Val Gly Gly Pro Cys Phe Pro Arg Leu
                515                 520                 525
Ala Gly Leu Phe Ala Lys Thr Lys Tyr Glu Lys Pro Gly Leu Glu Met
530                 535                 540
Thr Thr Ala Lys Ala Lys Ala Ala Pro Val Pro Ala Lys Gly Lys His
545                 550                 555                 560
Gly Phe Leu Pro Leu Pro Lys Lys Thr Tyr Gly Lys Ser Asp Ala Phe
                565                 570                 575
Val Asp Thr Ile Pro Arg Ala Ser His Pro Ser Pro Tyr Ala Ala Ala
            580                 585                 590
Ala Glu Gly Ile Val Ala Asp Glu Ala Thr Ile Val Glu Ala Val Asn
        595                 600                 605
Val Thr Ala Ala Ala Phe Glu Lys Lys Thr Gly Trp Gly Lys Glu Ile
610                 615                 620
Gly Trp Val Tyr Asp Thr Val Thr Glu Asp Val Val Thr Gly Tyr Arg
625                 630                 635                 640
Met His Ile Lys Gly Trp Arg Ser Arg Tyr Cys Ser Ile Tyr Pro His
                645                 650                 655
Ala Phe Ile Gly Thr Ala Pro Ile Asn Leu Thr Glu Arg Leu Phe Gln
            660                 665                 670
Val Leu Arg Trp Ser Thr Gly Ser Leu Glu Ile Phe Phe Ser Lys Asn
        675                 680                 685
Asn Pro Leu Phe Gly Ser Thr Tyr Leu His Pro Leu Gln Arg Val Ala
                690                 695                 700
Tyr Ile Asn Ile Thr Thr Tyr Pro Phe Thr Ala Ile Phe Leu Ile Phe
705                 710                 715                 720
Tyr Thr Thr Val Pro Ala Leu Ser Phe Val Thr Gly His Phe Ile Val
                725                 730                 735
Gln Arg Pro Thr Thr Met Phe Tyr Val Tyr Leu Gly Ile Val Leu Ser
            740                 745                 750
Thr Leu Leu Val Ile Ala Val Leu Glu Val Lys Trp Ala Gly Val Thr
        755                 760                 765
Val Phe Glu Trp Phe Arg Asn Gly Gln Phe Trp Met Thr Ala Ser Cys
770                 775                 780
```

```
Ser Ala Tyr Leu Ala Ala Val Cys Gln Val Leu Thr Lys Val Ile Phe
785                 790                 795                 800

Arg Arg Asp Ile Ser Phe Lys Leu Thr Ser Lys Leu Pro Ser Gly Asp
            805                 810                 815

Glu Lys Lys Asp Pro Tyr Ala Asp Leu Tyr Val Val Arg Trp Thr Pro
        820                 825                 830

Leu Met Ile Thr Pro Ile Ile Ile Phe Val Asn Ile Ile Gly Ser
            835                 840                 845

Ala Val Ala Phe Ala Lys Val Leu Asp Gly Glu Trp Thr His Trp Leu
    850                 855                 860

Lys Val Ala Gly Gly Val Phe Phe Asn Phe Trp Val Leu Phe His Leu
865                 870                 875                 880

Tyr Pro Phe Ala Lys Gly Ile Leu Gly Lys His Gly Lys Thr Pro Val
            885                 890                 895

Val Val Leu Val Trp Trp Ala Phe Thr Phe Val Ile Thr Ala Val Leu
                900                 905                 910

Tyr Ile Asn Ile Pro His Met His Thr Ser Gly Gly Lys His Thr Thr
            915                 920                 925

Val His Gly His His Gly Lys Lys Leu Val Asp Thr Gly Leu Tyr Gly
        930                 935                 940

Trp Leu His
945

<210> SEQ ID NO 176
<211> LENGTH: 22
<212> TYPE: PRT
<213> ORGANISM: Artificial
<220> FEATURE:
<223> OTHER INFORMATION: Synthetic

<400> SEQUENCE: 176

Val Tyr Leu Gly Ile Val Leu Ser Thr Leu Leu Val Ile Ala Val Leu
1               5                   10                  15

Glu Val Lys Trp Ala Gly
            20

<210> SEQ ID NO 177
<211> LENGTH: 22
<212> TYPE: PRT
<213> ORGANISM: Artificial
<220> FEATURE:
<223> OTHER INFORMATION: Synthetic

<400> SEQUENCE: 177

Val Tyr Leu Ala Ile Val Leu Gly Thr Leu Leu Ile Leu Ala Val Leu
1               5                   10                  15

Glu Val Lys Trp Ala Gly
            20

<210> SEQ ID NO 178
<211> LENGTH: 22
<212> TYPE: PRT
<213> ORGANISM: Artificial
<220> FEATURE:
<223> OTHER INFORMATION: Synthetic

<400> SEQUENCE: 178

Val Tyr Leu Gly Ile Val Leu Ser Thr Leu Leu Val Leu Ala Val Leu
1               5                   10                  15

Glu Val Lys Trp Ala Gly
```

```
<210> SEQ ID NO 179
<211> LENGTH: 22
<212> TYPE: DNA
<213> ORGANISM: artificial
<220> FEATURE:
<223> OTHER INFORMATION: synthetic

<400> SEQUENCE: 179
gagggcgcag ccggcattat gg                                              22

<210> SEQ ID NO 180
<211> LENGTH: 27
<212> TYPE: DNA
<213> ORGANISM: artificial
<220> FEATURE:
<223> OTHER INFORMATION: synthetic

<400> SEQUENCE: 180
cttcacggcc agttgtagga gaggttg                                         27

<210> SEQ ID NO 181
<211> LENGTH: 20
<212> TYPE: DNA
<213> ORGANISM: artificial
<220> FEATURE:
<223> OTHER INFORMATION: synthetic

<400> SEQUENCE: 181
ccgccaggca ggcagagagg                                                 20

<210> SEQ ID NO 182
<211> LENGTH: 23
<212> TYPE: DNA
<213> ORGANISM: artificial
<220> FEATURE:
<223> OTHER INFORMATION: synthetic

<400> SEQUENCE: 182
tcacggccag aggtagtagc cgt                                             23

<210> SEQ ID NO 183
<211> LENGTH: 22
<212> TYPE: DNA
<213> ORGANISM: artificial
<220> FEATURE:
<223> OTHER INFORMATION: synthetic

<400> SEQUENCE: 183
gccaggcagg caggcattat gg                                              22
```